(12) United States Patent
Han

(10) Patent No.: US 12,070,506 B2
(45) Date of Patent: Aug. 27, 2024

(54) STEROIDS AND ANTIBODY-CONJUGATES THEREOF

(71) Applicant: Regeneron Pharmaceuticals, Inc., Tarrytown, NY (US)

(72) Inventor: Amy Han, Hockessin, DE (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 834 days.

(21) Appl. No.: 16/243,020

(22) Filed: Jan. 8, 2019

(65) Prior Publication Data

US 2019/0209702 A1 Jul. 11, 2019

Related U.S. Application Data

(60) Provisional application No. 62/614,905, filed on Jan. 8, 2018.

(51) Int. Cl.
| | |
|---|---|
| A61K 47/68 | (2017.01) |
| A61K 31/58 | (2006.01) |
| A61K 31/685 | (2006.01) |
| A61K 31/7048 | (2006.01) |
| A61K 47/54 | (2017.01) |
| C07J 71/00 | (2006.01) |
| C07K 16/28 | (2006.01) |
| C07K 16/32 | (2006.01) |

(52) U.S. Cl.
CPC ......... *A61K 47/6803* (2017.08); *A61K 31/58* (2013.01); *A61K 31/685* (2013.01); *A61K 31/7048* (2013.01); *A61K 47/542* (2017.08); *A61K 47/545* (2017.08); *A61K 47/549* (2017.08); *A61K 47/6849* (2017.08); *A61K 47/6855* (2017.08); *A61K 47/6889* (2017.08); *C07J 71/0031* (2013.01); *C07K 16/2866* (2013.01); *C07K 16/2896* (2013.01); *C07K 16/32* (2013.01); *C07K 2317/41* (2013.01)

(58) Field of Classification Search
CPC .............. A61K 47/6803; A61K 47/545; C07J 71/0031; C07K 2317/41
See application file for complete search history.

(56) References Cited

U.S. PATENT DOCUMENTS

| | | | |
|---|---|---|---|
| 2,920,999 | A | 1/1960 | Agnello et al. |
| 3,007,923 | A | 11/1961 | Muller et al. |
| 3,020,275 | A | 2/1962 | Marx et al. |
| 3,033,873 | A | 5/1962 | Pinson et al. |
| 3,033,874 | A | 5/1962 | Pinson et al. |
| 3,047,468 | A | 7/1962 | Origoni et al. |
| 3,197,469 | A | 7/1965 | Fried |
| 3,232,839 | A | 2/1966 | Kieslich et al. |
| 3,383,394 | A | 5/1968 | Weber et al. |
| 3,723,484 | A | 3/1973 | Laurant et al. |
| 3,798,216 | A | 3/1974 | Boissier et al. |
| 3,886,145 | A | 5/1975 | Diamanti |
| 3,928,326 | A | 12/1975 | Brattsand et al. |
| 3,929,768 | A | 12/1975 | Brattsand et al. |
| 4,076,737 | A | 2/1978 | Anner et al. |
| 4,925,933 | A | 5/1990 | Jakupovic et al. |
| 5,116,829 | A | 5/1992 | Hori et al. |
| 5,183,815 | A | 2/1993 | Saari et al. |
| 5,208,020 | A | 5/1993 | Chari et al. |
| 5,500,362 | A | 3/1996 | Robinson et al. |
| 5,714,586 | A | 2/1998 | Kunstmann et al. |
| 5,821,337 | A | 10/1998 | Carter et al. |
| 5,837,698 | A | 11/1998 | Tjoeng et al. |
| 5,908,833 | A | 6/1999 | Brattsand et al. |
| 6,596,541 | B2 | 7/2003 | Murphy et al. |
| 6,908,934 | B2 | 6/2005 | Adams et al. |
| 7,750,116 | B1 | 7/2010 | Doronina et al. |
| 8,524,697 | B2 | 9/2013 | Anthes et al. |
| 8,703,714 | B2 | 4/2014 | Doronina et al. |
| 9,375,473 | B2 | 6/2016 | Latov et al. |
| 10,711,032 | B2 * | 7/2020 | Han ........................ A61P 29/00 |
| 11,129,903 | B2 | 9/2021 | Andreev et al. |
| 11,491,237 | B2 | 11/2022 | Han et al. |
| 11,578,135 | B2 | 2/2023 | Papadopoulos et al. |
| 11,760,775 | B2 | 9/2023 | Han et al. |
| 2003/0125357 | A1 | 7/2003 | Adams et al. |
| 2003/0199529 | A1 | 10/2003 | Garvey et al. |
| 2004/0077595 | A1 | 4/2004 | Cheng et al. |
| 2004/0157810 | A1 | 8/2004 | Teicher et al. |
| 2004/0192778 | A1 | 9/2004 | Jardien et al. |
| 2005/0009798 | A1 | 1/2005 | Currie et al. |
| 2005/0192257 | A1 | 9/2005 | Peyman |

(Continued)

FOREIGN PATENT DOCUMENTS

| | | |
|---|---|---|
| CN | 1414008 A | 4/2003 |
| CN | 101397328 A | 4/2009 |

(Continued)

OTHER PUBLICATIONS

Kern et al., Novel phosphate modified cathepsin B linkers: improving aqueous solubility and enhancing payload scope of ADCs, Bioconjugate Chem. 2016, 27, 2081-2088, Publication Date: Jul. 28, 2016 (Year: 2016).*

Lemke et al., Foye's Principles of Medicinal Chemistry, Chapter 44, pp. 1253, Publication Year: 2008 (Year: 2008).*

Svendsen et al., Antibody-Directed Glucocorticoid Targeting to CD163 in M2-type Macrophages Attenuates Fructose-Induced Liver Inflammatory Changes, Molecular Therapy: Methods & Clinical Development, vol. 4, 50-61, Publication Date: Mar. 2017 (Year: 2017).*

Dai et al., Regulation of MSR-1 and CD36 in macrophages by LOX-1 mediated through PPAR-c, Biochemical and Biophysical Research Communications, 431, 496-500, Publication Date: Jan. 16, 2013 (Year: 2013).*

(Continued)

*Primary Examiner* — Peter J Reddig
*Assistant Examiner* — Cheng Lu
(74) *Attorney, Agent, or Firm* — SQUIRE PATTON BOGGS (US)

(57) ABSTRACT

Described herein protein steroid conjugates that are useful, for example, for the target-specific delivery of glucocorticoids (GCs) to cells.

21 Claims, 4 Drawing Sheets

Figures 1A, 1B:
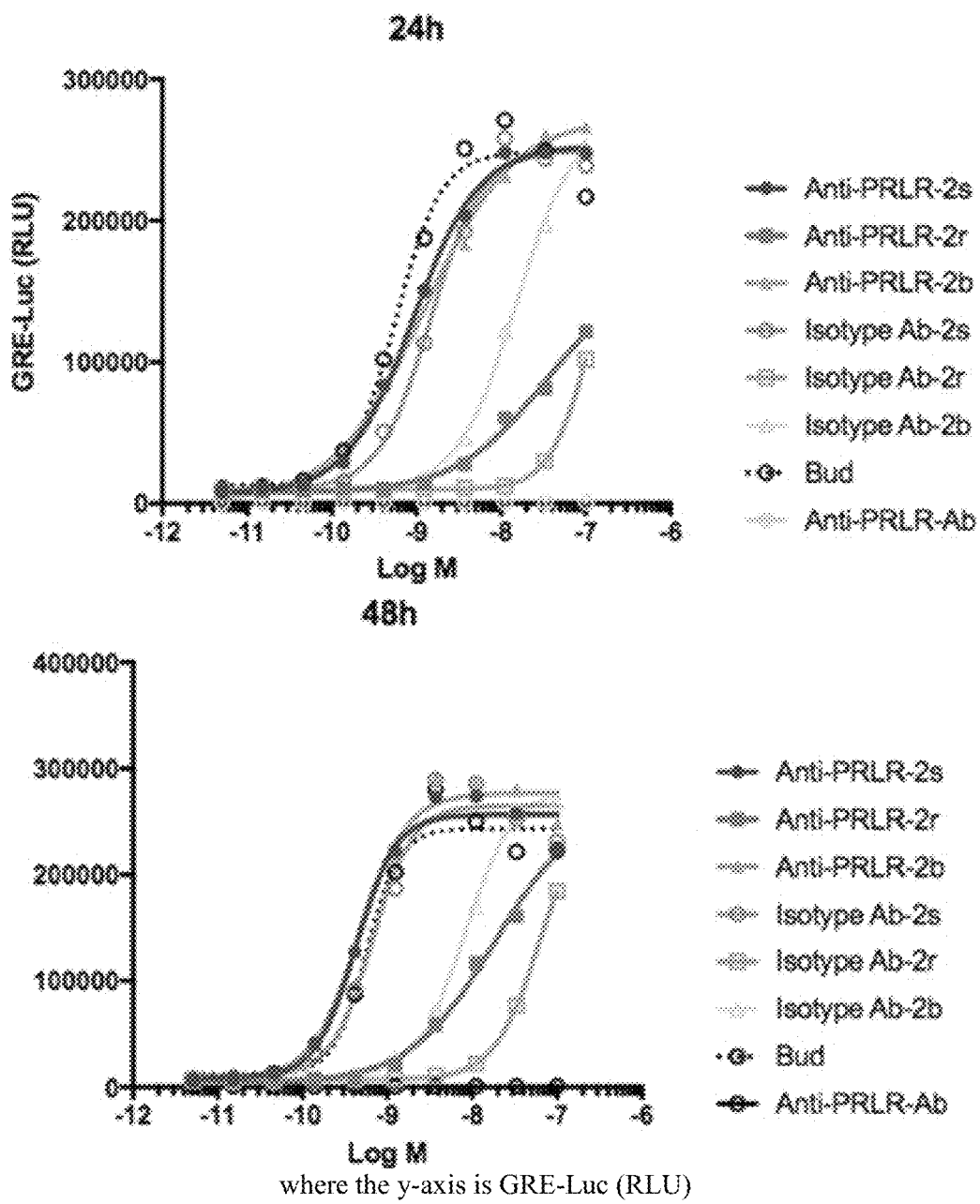

Specification includes a Sequence Listing.

(56) References Cited

U.S. PATENT DOCUMENTS

| | | | |
|---|---|---|---|
| 2005/0287155 A1 | 12/2005 | Santi et al. | |
| 2006/0046967 A1 | 3/2006 | Satyam | |
| 2006/0074008 A1 | 4/2006 | Senter et al. | |
| 2007/0258987 A1 | 11/2007 | Francisco et al. | |
| 2008/0171040 A1 | 7/2008 | Ebens et al. | |
| 2008/0305044 A1 | 12/2008 | McDonagh et al. | |
| 2008/0305497 A1 | 12/2008 | Kosmeder et al. | |
| 2009/0221543 A1 | 9/2009 | Soldato et al. | |
| 2009/0318396 A1 | 12/2009 | Baker et al. | |
| 2010/0041633 A1 | 2/2010 | Benedini et al. | |
| 2010/0093685 A1 | 4/2010 | Benedini et al. | |
| 2010/0129314 A1 | 5/2010 | Singh et al. | |
| 2010/0209508 A1 | 8/2010 | Baker et al. | |
| 2010/0226987 A1 | 9/2010 | Gnaim et al. | |
| 2010/0323973 A1 | 12/2010 | Leamon et al. | |
| 2011/0178287 A1 | 7/2011 | Glucksmann et al. | |
| 2011/0182828 A1 | 7/2011 | Anthes et al. | |
| 2011/0262368 A1 | 10/2011 | Anthes et al. | |
| 2012/0058892 A1 | 3/2012 | Braun et al. | |
| 2012/0059158 A1 | 3/2012 | Ishii | |
| 2012/0096572 A1 | 4/2012 | Macdonald et al. | |
| 2012/0258107 A1 | 10/2012 | Graversen et al. | |
| 2012/0276193 A1 | 11/2012 | Graversen et al. | |
| 2012/0302505 A1 | 11/2012 | Fetzer et al. | |
| 2013/0101546 A1 | 4/2013 | Yurkovetskiy et al. | |
| 2014/0227294 A1 | 8/2014 | Anderson et al. | |
| 2015/0056221 A1 | 2/2015 | Papadopoulos et al. | |
| 2015/0152187 A1 | 6/2015 | Sun et al. | |
| 2015/0165064 A1* | 6/2015 | Bregeon | A61K 47/6889 424/181.1 |
| 2015/0258203 A1 | 9/2015 | Vlahov et al. | |
| 2015/0290337 A1 | 10/2015 | Vetter et al. | |
| 2015/0291563 A1 | 10/2015 | Park et al. | |
| 2016/0082119 A1 | 3/2016 | Gonzalez et al. | |
| 2016/0158369 A1 | 6/2016 | Sato et al. | |
| 2016/0279054 A1 | 9/2016 | Rangaramanujam et al. | |
| 2016/0310612 A1 | 10/2016 | Lyon et al. | |
| 2016/0340445 A1 | 11/2016 | Bouckaert et al. | |
| 2017/0182181 A1 | 6/2017 | Garbaccio et al. | |
| 2018/0002372 A1 | 1/2018 | Tripathi et al. | |
| 2018/0104357 A1 | 4/2018 | Rudge et al. | |
| 2018/0126000 A1 | 5/2018 | Mcpherson et al. | |
| 2018/0155389 A1 | 6/2018 | Han et al. | |
| 2018/0333504 A1 | 11/2018 | Han et al. | |
| 2018/0334426 A1 | 11/2018 | Han et al. | |
| 2018/0360979 A1 | 12/2018 | Mejia Oneto et al. | |
| 2019/0030171 A1 | 1/2019 | Garbaccio et al. | |
| 2019/0134220 A1 | 5/2019 | Godwin | |
| 2019/0367631 A1 | 12/2019 | Gromada et al. | |
| 2020/0115326 A1* | 4/2020 | Tsuchikama | A61K 31/40 |
| 2020/0368361 A1 | 11/2020 | Nittoli et al. | |
| 2021/0040144 A1* | 2/2021 | Han | A61K 31/566 |
| 2023/0079407 A1* | 3/2023 | Gromada | A61K 47/60 |
| 2023/0119539 A1* | 4/2023 | Han | A61K 47/549 424/179.1 |

FOREIGN PATENT DOCUMENTS

| | | |
|---|---|---|
| CN | 103694375 A | 4/2014 |
| CN | 104302664 A | 1/2015 |
| CN | 107849131 A | 3/2018 |
| CN | 108 853 514 A | 11/2018 |
| CN | 109 106 951 A | 1/2019 |
| DE | 1165595 B | 3/1964 |
| EP | 1625854 A1 | 2/2006 |
| ES | 544825 A1 | 7/1985 |
| GB | 889766 | 2/1962 |
| GB | 898295 A | 6/1962 |
| GB | 1428416 | 3/1976 |
| IL | 73337 A | 9/1988 |
| WO | WO 94/22898 A1 | 10/1994 |
| WO | WO 97/41144 A1 | 11/1997 |
| WO | WO 2000/049993 A1 | 8/2000 |
| WO | WO 2002/080931 A1 | 10/2002 |
| WO | WO2004/022099 A2 | 3/2004 |
| WO | WO 2005/063777 A1 | 7/2005 |
| WO | WO 2005/079523 A2 | 9/2005 |
| WO | WO 2005/089808 A2 | 9/2005 |
| WO | WO 2005/119266 A1 | 12/2005 |
| WO | WO 2006/135371 A1 | 12/2006 |
| WO | WO 2008/122039 A2 | 10/2008 |
| WO | WO 2008/127347 A1 | 10/2008 |
| WO | WO 2010/010119 A1 | 1/2010 |
| WO | WO 2010/010324 A1 | 1/2010 |
| WO | WO 2010/126953 A1 | 11/2010 |
| WO | WO 2010/132743 A1 | 11/2010 |
| WO | WO 2011/018611 A1 | 2/2011 |
| WO | WO2011/020107 A2 | 2/2011 |
| WO | WO 2011/081937 A1 | 7/2011 |
| WO | WO 2011/103389 A1 | 8/2011 |
| WO | WO 2011/130598 | 10/2011 |
| WO | WO 2012/011591 A1 | 1/2012 |
| WO | WO 2012/058592 | 5/2012 |
| WO | WO 2012/166559 | 12/2012 |
| WO | WO 2013/053872 | 4/2013 |
| WO | WO 2013/053873 | 4/2013 |
| WO | WO 2013/055990 | 4/2013 |
| WO | WO 2013/055993 | 4/2013 |
| WO | WO 2013/068874 | 5/2013 |
| WO | WO 2013/085925 | 6/2013 |
| WO | WO 2013/093465 A2 | 6/2013 |
| WO | WO 2014/065661 | 5/2014 |
| WO | WO2014/165119 A1 | 10/2014 |
| WO | WO 2014/197854 | 12/2014 |
| WO | WO 2015/155998 A1 | 10/2015 |
| WO | WO2015/189478 A1 | 12/2015 |
| WO | WO 2016/090038 A1 | 6/2016 |
| WO | WO 2016/090040 A1 | 6/2016 |
| WO | WO 2016/094509 A1 | 6/2016 |
| WO | WO 2016/094517 A1 | 6/2016 |
| WO | WO 2016127081 A1 | 8/2016 |
| WO | WO 2017006279 A1 | 1/2017 |
| WO | WO 2017/062271 A2 | 4/2017 |
| WO | WO 2017/132103 A2 | 8/2017 |
| WO | WO 2017/147542 | 8/2017 |
| WO | WO 2017/165851 A1 | 9/2017 |
| WO | WO2017/199046 A1 | 11/2017 |
| WO | WO 2017/210471 A1 | 12/2017 |
| WO | WO 2017/214458 A2 | 12/2017 |
| WO | WO 2018/089373 A2 | 5/2018 |
| WO | WO 2018/089373 A9 | 5/2018 |
| WO | IWO 2018/213082 A1 | 11/2018 |
| WO | WO 2018/213077 A1 | 11/2018 |
| WO | WO 2019/094395 A2 | 5/2019 |
| WO | WO 2019/136487 A2 | 7/2019 |
| WO | WO 2020/146541 A2 | 7/2020 |

OTHER PUBLICATIONS

Patani et al., Bioisosterism: A Rational Approach in Drug Design, Chem. Rev. 96,3147-3176, 1996, Publication Year: 1996 (Year: 1996).*

Thalén et al., 6a-Fluoro- and 6a, 9a-difluoro-11b,21-dihydroxy-16a,17a-propylmethylenedioxypregn-4-ene-3,20-dione: Synthesis and evaluation of activity and kinetics, Steroids 63:37-43, 1998, Publication Year: 1998 (Year: 1998).*

Simons S. Jr. et al., "Alpha Keto Mesylate: A Reactive Thiol Specific Functional Group", Journal of Organic Chemistry, American Chemical Society, Washington, vol. 45, No. 15, Jan. 1, 1980, pp. 3084-3088, XP008100022.

Invitation to Pay Additional Fees and, Where Applicable, Protest Fee of PCT/US2019/012786 dated Apr. 24, 2019; 24 pages.

Agarwal et al., "A Pictet-Spengler ligation for protein chemical modification", PNAS, Jan. 2, 2013, vol. 110, No. 1, pp. 46-51.

Aherne et al., "A sensitive radioimmunoassay for budesonide in plasma", Journal of Steroid Biochemistry, vol. 17, No. 5, Nov. 1982, pp. 559-565.

Angal et al., "A Single Amino Acid Substitution Abolishes the Heterogeneity of Chimeric Mouse/Human (IgG4) Antibody", Molecular Immunology, Jan. 1993, vol. 30, No. 1, pp. 105-108.

(56) References Cited

OTHER PUBLICATIONS

Baskin et al., "Copper-free click chemistry for dynamic in vivo imaging", PNAS, Oct. 23, 2007, vol. 104, No. 43, pp. 16793-16797.
Beck et al., "Strategies and challenges for the next generation of antibody-drug conjugates", Nature Reviews/Drug Discovery, vol. 16, May 2017, pp. 315-337.
Berge et al., "Pharmaceutical Salts", Review Article, Jan. 1977, vol. 66, No. 1, pp. 1-19.
Berlin M., "Recent advances in the development of novel glucocorticoid receptor modulators", Review, Expert Opinion on Therapeutic Patents, 2010, 20(7), pp. 855-873.
Biju et al., "Synthesis of novel anti-inflammatory steroidal macrocycles using ring closing metathesis reaction", Tetrahedron Letters, Jan. 2015, vol. 56, No. 4, pp. 636-638.
Carrico et al., "Introducing genetically enclosed aldehydes into proteins", Nature Chemical Biology, Jun. 2007, vol. 3, No. 6, pp. 321-322.
CAS Registry Compounds, accessed Jul. 16, 2019; 355 pages.
CAS RN 2341-08-4 (entered into STN Nov. 16, 1984) (Year: 1984).
CAS RN 3859-14-1 (entered into STN Nov. 16, 1984) (Year: 1984).
CAS RN 57-86-3 (entered into STN Nov. 16, 1984) (Year: 1984).
Casati et al., "Unraveling Unidirectional Threading of α-Cyclodextrin in a [2]Rotaxane through Spin Labeling Approach", Journal of the American Chemical Society, Oct. 29, 2012, vol. 134, pp. 19108-19117.
Cho et al., "Regioselective Synthesis of Heterocycles Containing Nitrogen Neighboring an Aromatic Ring by Reductive Ring Expansion Using Diisobutylaluminum Hydride and Studies on the Reaction Mechanism", J. Org. Chem., 2010, vol. 75, pp. 627-636; published online Dec. 29, 2009.
Clynes et al., "Fc receptors are required in passive and active immunity to melanoma", Proc. Natl. Acad. Sci. USA, Jan. 1998, vol. 95, pp. 652-656.
Compounds from CAS Registry database, accessed May 20, 2019; 16 pages.
Compounds retrieved on Nov. 18, 2017 from SciFinder, Set 1; 4 pages.
Compounds retrieved on Nov. 18, 2017 from SciFinder, Set 2; 1 page.
Compounds retrieved on Nov. 18, 2017 from SciFinder, Set 3; 3 pages.
Dennler et al., "Transglutaminase-Based Chemo-Enzymatic Conjugation Approach Yields Homogeneous Antibody-Drug Conjugates", Bioconjugate Chem., Feb. 3, 2014, vol. 25, pp. 569-578.
Dubois-Camacho et al., "Glucocorticosteroid therapy in inflammatory bowel diseases: From clinical practice to molecular biology", World J Gastroenterol, Sep. 28, 2017, vol. 23(36), pp. 6628-6638.
Fellier et al., "Bindung von Cortisol, Fluocortolon und Difluocortolon a Humanplasmaproteine", J. Clin. Chem. Clin. Biochem., 1977, vol. 15, pp. 545-548.
Ferraboschi et al., "Estimation and characterisation of budesonide tablets impurities", Journal of Pharmaceutical and Biomedical Analysis, 2008, 47(3), pp. 636-640.
Graversen et al., "Targeting the Hemoglobin Scavenger receptor CD163 in Macrophages Highly Increases the Anti-inflammatory Potency of Dexamethasone", Molecular Therapy, vol. 20, No. 8, Aug. 2012, pp. 1550-1558.
Hamasaki et al., "Fluorescent sensors of molecular recognition. Modified cyclodextrins capable of exhibiting guest-responsive twisted intramolecular charge transfer fluorescence", J. Am. Chem. Soc., Jun. 1993, vol. 115, No. 12, pp. 5035-5040.
Hofer et al., "An engineered selenocysteine defines a unique class of antibody derivatives", PNAS, Aug. 26, 2008, vol. 105, No. 34, pp. 12451-12456.
Hollander et al., "Selection of Reaction Additives Used in the Preparetion of Monomeric Antibody-Calicheamicin Conjugates", Biooonjugate Chem., 2008, vol. 19, pp. 358-361; published on online Nov. 10, 2007.
Kapp et al., "Studies on the Pharmacology of 6alpha, 9-difluoro-11beta-hydroxy-16alpha-methyl-21-valeryloxy-1,4-pregnadiene-3,20-dione", Arzneimittel-Forschung Drug Reserch. 1976;26(7b):1463-1475; with an English abstract.
Kern et al., "Discovery of Pyrophosphate Diesters as Tunable, Soluble, and Bioorthogonal Linkers for Site-Specific Antibody-Drug Conjugates", J. Am. Chem. Soc. (JACS), Jan. 25, 2016, vol. 138, No. 4, pp. 1430-1445.
Kern et al., "Novel Phosphate Modified Cathepsin B Linkers: Improving Aqueous Solubility and Enhancing Payload Scope of ADCs", Bioconjugate Chem., Jul. 28, 2016, vol. 27, No. 9, pp. 2081-2088.
Krajcsi et al., "Novel Synthesis of 21-Aminopregnanes", J. Chem. Research (S), Nov. 1987, issue 11, pp. 382-383.
Kronkvist et al., "Determination of Drugs in Biosamples at Picomolar Concentrations Using Competitive Elisa With Electrochemical Detection: Application to Steroids", Journal of Pharmaceutical and Biomedical Analysis, vol. 11, No. 6, 1993, pp. 459-463.
Lichtenecker R. J., "Synthesis of aromatic $^{13}C/^{2}H$-α-ketoacid precursors to be used in selective phenylalanine and tyrosine protein labelling", Organic & Biomolecular Chemistry, Jul. 31, 2014, vol. 12, pp. 7551-7560.
Lu et al., "Linkers Having a Crucial Role in Antibody-Drug Conjugates", Int. J. Mol. Sci., Apr. 14, 2016, vol. 17, No. 561, 22 pages.
McCombs et al., "Antibody Drug Conjugates: Design and Selection of Linker, Payload and Conjugation Chemistry", The AAPS Journal, Mar. 2015, vol. 17, No. 2, pp. 339-351.
Muck et al., "High pressure liquid chromatography of some triamcinolone derivatives", Bollettino chimico farmaceutica, Italy, Apr. 1981, 120(4), pp. 240-247; with an English abstract.
Papachristos et al., "Antibody-drug conjugates: a mini-review. The synopsis of two approved medicines", Drug Delivery, 2016, vol. 23, No. 5, pp. 1662-1666; published online Jan. 27, 2015.
Paul-Clark et al., "Glucocorticoid Receptor Nitration Leads to Enhanced Anti-Inflammatory Effects of Novel Steroid Ligands", The Journal of Immunology, 2003, vol. 171, pp. 3245-3252; doi: 10.4049/jimmunol.171.6.3245.
Rabuka et al., "Site-specific chemical protein conjugation using genetically encoded aldehyde tags", Nat Protoc., vol. 7, No. 6, pp. 1052-1067, Dec. 1, 2012, doi:10.1038/nprot.2012.04.
Reggelin et al., "Asymmetric Synthesis of Highly Substituted Azapolycyclic Compounds via 2-Alkenyl Sulfoximines: Potential Scaffolds for Peptide Mimetics", J. American Chemical Society, Mar. 8, 2006, vol. 128, pp. 4023-4034.
Ryan et al., "Polyclonal Antibody Production Against Chito-Oligosaccharides", Food and Agricultural Immunology, 2001, vol. 13, pp. 127-130.
Samal et al., "The First Synthesis of Water-Soluble Cyclodextrinazafullerenes", Synthetic Communications, 2002, vol. 32, No. 21, pp. 3367-3372.
Sehgal et al., "Desoxymethasone: a new topical corticosteroid", International Journal of Dermatology, Dec. 1976, vol. 15, pp. 770-773; with an English abstract.
Shaunak et al., "Site-specific PEGylation of native disulfide bonds in therapeutic proteins", Nature Chemical Biology, Jun. 2006, vol. 2, No. 6, pp. 312-313.
Svendsen et al., "Antibody-Directed Glucocorticoid Targeting to CD163 M2-type Macrophages Attenuates Fructose-Induced Liver Inflammatory Changes", Molecular Therapy—Methods & Clinical Develop, vol. 4, Mar. 2017, pp. 50-61.
Taylor et al., "A transgenic mouse that expresses a diversity of human sequence heavy and light chain immunoglobulins", Nucleic Acids Research, 1992, vol. 20, No. 23, pp. 6287-6295.
Thalen et al., "Epimers of budesonide and related corticosteroids. I. Preparative resolution by chromatography on Sephadex LH-20", Acta Pharmaceutica Suecica, 1982, 19(4), pp. 247-266.
Thalen et al., "Synthesis and pharmacological properties of some 16α,17α-acetals of 16α hydroxyhydrocortisone, 16α-hydroxyprednisolone and fluorinated 16α-hydroxyprednisolones", Acta Pharmaceutica Suecica, 1984, 21(2), pp. 109-124.

(56) References Cited

OTHER PUBLICATIONS

Thalen, "Epimers of budesonide and related corticosteroids. II. Structure elucidation by mass spectrometry", Acta Pharmaceutica Suecica, 1982, 19(5), pp. 327-354.
Toth et al., "Amino-derivatives of 11,17,21-Trihydroxy-3,20-Dioxo-1,4-Pregnadiene", Nature 191, Aug. 5, 1961, p. 607.
Uekama et al., "$6^A$-O-[(4-Biphenylyl)acetyl]-α-, -β-, and -γ-cyclodextrins and 6 $^A$-Deoxy-6 $^A$-[[(4-biphenylyl) acetyl]amino]-α-, -β-, and -γ-cyclodextrins: Potential Prodrugs for Colon-Specific Delivery", J. Med. Chem., 1997, vol. 40, pp. 2755-2761.
Wikby et al., "Separation of epimers of budesonide and related corticosteroids by high-performance liquid chromatography. A comparison between straight- and reversed-phase systems", Journal of Chromatography, 1978, 157(1), pp. 65-74.
Wikby et al., "Separation of epimers of budesonide and related corticosteroids by reversed bonded-phase liquid chromatography", Journal of Chromatography, 1978, 157(1), pp. 51-64.
Romero-Hernández et al., "Diosgenin-based thio(seleno)ureas and triazolyl glycoconjugates as hybrid drugs, Antioxidant and antiproliferative profile", European Journal of Medicinal Chemistry, May 14, 2015, vol. 99, pp. 67-82.
Cannon et al., "The liver X receptor agonist AZ876 protects against pathological cardiac hypertrophy and fibrosis without lipogenic side effects", European Journal of Heart Failure, 2015, vol. 17, pp. 273-282.
Doi et al., "The Histidine Interruption of an α-Helical Coiled Coil Allosterically Mediates a pH-Dependent Ligand Dissociation From Macrophage Scavenger Receptors", The Journal of Biological Chemistry, vol. 269, No. 41, Oct. 14, 1994, pp. 25598-25604.
Mori et al., "Endocytic Pathway of Scavenger Receptors via Trans-Golgi System in Bovine Alveolar Macrophages", Laboratory Investigation, vol. 71, No. 3, 1994, pp. 409-417.
International Search Report and Written Opinion of the Interantional Searching Authority of PCT/US2019/012786 dated Aug. 9, 2019; 32 pages.
Database Registry [Online] Chemical Abstracts Service Retrieved from STN on Aug. 11, 2020; Compounds with CAS Registry No. of 23640-98-4 (Entered STN: Nov. 16, 1984); 23640-97-3 (Entered STN: Nov. 16, 1984); 6477-56-1 (Entered STN: Nov. 16, 1984); 5514-61-4 (Entered STN: Nov. 16, 1984); 2353-16-4 (Entered STN: Nov. 16, 1984).
Bajaj et al., "Topochemical model for prediction of anti-HIV activity of HEPT analogs", Bioorganic & Medicinal Chemistry Letters, vol. 15, No. 2, Jan. 17, 2005, pp. 467-469.
Bogan et al., "Liver X Receptor Modulation of Gene Expression Leading to Proluteolytic Effects in Primate Luteal Cells", Biology of Reproduction, (2012) 86(3):89, 1-9.
Cho et al., "The first preparation of alpha-functionalized benzylamine", Tetrahedron Letters, vol. 40, No. 47, Nov. 19, 1999, pp. 8215-8217; XP005024955.
Chuu, "Modulation of liver X receptor signaling as a prevention and therapy for colon cancer", Medical Hypotheses, 2011, vol. 76, pp. 697-699.
Czerkies et al., "An interplay between scavenger receptor A and CD14 during activation of J774 cells by high concentrations of LPS", Immunobiology, Apr. 12, 2013, vol. 218, pp. 1217-1226.
Doronina et al., "Novel Peptide Linkers for Highly Potent Antibody-Auristatin Conjugate", Bioconjugate Chem., 2008, vol. 19, No. 10, pp. 1960-1963.
Effenberger et al., "Trifluormethansulfonate van [alpha]-Hydroxycarbonsaureestern—Edukte zur racemisierungsfreien Synthese N-substituierter [alpha]-Aminosauren", Angewandte Chemie, vo 1, 95, No. 1, Jan. 1, 1983, p. 50.
Gidwani et al., "A Comprehensive Review on Cyclodextrin-Based Carriers for Delivery of Chemotherapeutic Cytotoxic Anticancer Drugs", Hindawi Publishing Corporation, BioMed Research International, vol. 2015, article ID 198268, 15 pages.
Hein et al., "The Synthesis of a Multiblock Osteotropic Polyrotaxane by Copper(I)-Catalyzed Huisgen 1,3-Dipolar Cycloaddition", Macromolecular Bioscience, Dec. 8, 2010, vol. 10, No. 12, pp. 1544-1556, XP055052204.
Jeger, Simon, "Site-specific conjugation of tumour-targeting, antibodies using transglutaminase", Ph.D. thesis, 2009, XP055208841, ETH Zurich, CH; 140 pages. DOI: 10.3929/ethz-a-005963273; pp. 41-46.
Kovtun et al., "Antibody-Maytansinoid Conjugates Designed to Bypass Multidrug Resistance", Cancer Research, vol. 70, No. 6, Mar. 15, 2010, pp. 2528-2537.
Lehar et al., "Novel antibody-antibiotic conjugate eliminates intracellular *S. aureus*", Nature, Nov. 19, 2015, vol. 527, No. 7578, pp. 323-328.
Lim et al., "Targeted Delivery of LXR Agonist Using a Site-Specific Antibody-Drug Conjugate", Bioconjugate Chemistry, 2015, vol. 26, No. 11, pp. 2216-2222.
Lyon et al., Reducing hydrophobicity of homogeneous antibody-drug conjugates improves pharmacokinetics and therapeutic index, Nature Biotechnology, Jul. 2015, vol. 33, No. 7, pp. 733-735.
Pufall "Glucocorticoids and Cancer", Adv Exp Med Biol., 2015, vol. 872, pp. 315-333.
Romero-Hernandez et al., "Diosgenin-based thio (seleno) ureas and triazolyl glycoconjugates as hybrid drugs. Antioxidant and antiproliferative profile", European Journal of Medicinal Chemistry, Editions Scientifique Elsevier, Paris, FR, May 14, 2015, vol. 99, pp. 67-81, XP029222662.
Samant et al., "Synthesis of 3-hydroxypyrid-2-ones from furfural for treatment against iron overload and iron deficiency", European Journal of Medicinal Chemistry, vol. 43, No. 9, Sep. 1, 2008, pp. 1978-1982.
Singh et al., "Polymer Drug Conjugates: Recent Advancements in Various Diseases", Current Pharmaceutical design, vol. 22, No. 19, May 10, 2016, pp. 2821-2843; XP055490895.
Tian et al., "Inhibition of influenza virus infection by multivalent pentacyclic triterpene-functionalized per-0-methylated cyclodextrin conjugates", European Journal of Medicinal Chemistry, Editions Scientifique Elsevier, Paris, FR, Apr. 2, 2017, vol. 134, pp. 133-139, XP029995979.
Tumey et al., "ADME Considerations for the Development of Biopharmaceutical Conjugates Using Cleavable Linkers", Current Topics in Medicinal Chemistry, vol. 17, No. 32, 2017, pp. 3444-3462.
Xiao et al., "Synthesis and biological evaluation of novel pentacyclic triterpene [alpha]—cyclodextrin conjugates as HCV entry inhibitors", European Journal of Medicinal Chemistry, Nov. 1, 2016, vol. 124, pp. 1-9, XP055490888.
Yano et al., "Preparation of prednisolone-appended [alpha]-, [beta]- and [gamma]-cyclodextrins: Substitution at secondary hydroxyl groups and in vitro hydrolysis behavior", Journal of Pharmaceutical Sciences, American Chemical Society and American Pharmaceutical Association, US, Apr. 1, 2001, vol. 90, No. 4, pp. 493-503, XP009506679.
Diamantis et al., "Antibody-drug conjugates an emerging class of cancer treatment", British Journal of Cancer, 2016, vol. 114, pp. 362-367; D01:10.1038/bjc.2015.435.
Friedman et al., "The Smart Targeting of Nanoparticles", Current Pharmaceutical Design, 2013, vol. 19, pp. 6315-6329.
Sagar S. et al., Bifidobacterium breve and Lactobacillus rhamnosus treatment is as effective as budesonide at reducing inflammation in a murine model for chronic asthma. Respiratory Research, Apr. 16, 2014, vol. 15, No. 1, article No. 46; Abstract.
Milles-Larsson et al., "Reversible Fatty Acid Conjugation of Budesonide—Novel Mechanism for Prolonged Retention of Topically Applied Steroid in Airway Tissue", Drug Metab. Dispos. 1998, vol. 26, pp. 623-630.
Tunek et al., "Reversible Formation of Fatty Acid Esters of Budesonide, an Antiasthma Glucocorticoid, in Human Lung and Liver Microsomes", Drug Metab. Dispos. 1997, vol. 25, No. 11, pp. 1311-1317.
Agard et al., "A Strain-Promoted [3+2] Azide-Alkyne Cycloaddition for Covalent Modification of Biomolecules in Living Systems", J. Am. Chem. Soc., Nov. 24, 2004, vol. 126, No. 46, pp. 15046-15047.

(56) References Cited

OTHER PUBLICATIONS

Agarwal et al., "Site-Specific Antibody—Drug Conjugates: The Nexus of Bioorthogonal Chemistry, Protein Engineering, and Drug Development", Bioconjugate Chem., 2015, 26, pp. 176-192.
Boersma et al., "DARPins and other repeat protein scaffolds: advances in engineering and applications", 2011, Current Opinion in Biotechnology, 2011, vol. 22, pp. 849-857.
Dennler et al., "Antibody Conjugates: From Heterogeneous Populations to Defined Reagents", Antibodies 2015, 4, pp. 197-224; doi:10.3390/antib4030197.
Huisgen, "1,3-Dipolar Cycloadditions", Proceedings of the Chemical Society, Oct. 1961, pp. 357-369.
Jain R. A., "The manufacturing techniques of various drug loaded biodegradable poly(lactide-co-glycolide) (PLGA) devices", Biomaterials 21(23), 2000, pp. 2475-2490.
Jain et al., "Current ADC Linker Chemistry", Pharm Res, 2015, vol. 32, pp. 3526-3540; DOI 10.1007/s11095-015-1657-7.
Lhospice et al., "Site-Specific Conjugation of Monomethyl Auristatin E to Anti-CD30 Antibodies Improves Their Pharmacokinetics and Therapeutic Index in Rodent Models", Mol. Pharmaceutics, 2015, vol. 12, pp. 1863-1871.
Tang et al., Org Biomol Chem 14:9501-9518, Oct. 28, 2016.
Uhrich et al., "Polymeric Systems for Controlled Drug Release", Chemical Reviews, 1999, vol. 11, pp. 3181-3198.
Vert et al., "Something new in the field of PLA/GA bioresorbable polymers?" Journal of Controlled Release 53, 1998, pp. 85-92.
Wang et al., "Bioconjugation by Copper(I)-Catalyzed Azide-Alkyne [3+2] Cycloaddition", J. Am. Chem. Soc. 2003, vol. 125, pp. 3192-3193.
Williams et al., Foye's Principles of Medicinal Chemistry, 5th Ed, pp. 59-63, 2002.
Gonzales et al., "Minimizing the Immunogenicity of Antibodies for Clinical Application", Tumor Biol. 2005; vol. 26, pp. 31-43; doi: 10.1159/000084184.
Kunik, Vered et al: "Structural consensus among antibodies defines the antigen binding site", PLoS Comput Biol 8(2): e1002388. https://doi.org/10.1371/journal.pcbi.1002388; Published Feb. 23, 2012.
Kussie et al., "A Single Engineered Amino Acid Substitution Changes Antibody Fine Specificity", Journal of Immunology, 1994, pp. 146-152.
Opalinski et al., "High Affinity Promotes Internalization of Engineered Antibodies Targeting FGFR1", International Journal of Molecular Sciences, 2018, vol. 19, 1435; Published online May 10, 2018. doi: 10.3390/ijms19051435.
Panka et al., "Variable region framework differences result in decreased or increased affinity of variant anti-digoxin antibodies", Proc. Natl. Acad. Sci. USA, vol. 85, May 1988, pp. 3080-30844, Immunology; doi: 10.1073/pnas.85.9.3080.
Rudikoff, Stuart el al., "Single amino acid substitution altering antigen-binding specificity", Proc. Nat. Acad. Sci., USA, vol. 79, Mar. 1982, pp. 1979-1983; DOI: 10.1073/pnas.79.6.1979.
Sela-Culang et al., "The Structural Basis of Antibody-Antigen Recognition", Frontiers in Immunology, vol. 4, article 302, Oct. 2013; doi: 10.3389/fimmu.2013.00302.
Wark et al., "Latest technologies for the enhancement of antibody affinity", Advanced Drug Delivery Reviews, 2006, vol. 58, pp. 657-670; doi:10.1016/j.addr.2006.01.025.
CAS Registry No. 803648-23-9; STN Entry Date Dec. 29, 2004; 21-(Diethylamino)-11,17-dihydroxy-(11β)-(9Cl)pregna-1,4-diene-3,20-dione [2] Category: X Claims: 1, 2, 4, 14; SciFinder"®.
Peng, J., et al. "Chemoselective reduction of 21-azidocorticosteroids to primary 21-primary aminocorticosteroids." Chemical Research in Chinese Universities (2004), 25(5), pp. 866-869.
Zoltan, T., et al, "Synthesis of biologically active amino and aza steroids and some of their new chemical reactions", Int. Conf. Chem. Biotechnol. Biol. Act. Nat. Prod., 1981, 2, pp. 135-149.
Mark Frigerio et al., "The Chemical Design and Synthesis of Linkers Used in Antibody Drug Conjugates", Current Topics in Medicinal Chemistry, 2017, 17(32), pp. 3393-3424.
Elgersma et al., "Design, Synthesis, and Evaluation of Linker-Duocarmycin Payloads: Toward Selection of HER2-Targeting Antibody-Drug Conjugate SYD985", Mol. Pharmaceutics 2015, 12, pp. 1813-1835; DOI: 10.1021/mp500781a.
Everts et al., "Selective Intracellular Delivery of Dexamethasone into Activated Endothelial Cells Using an E-Selectin-Directed Immunoconjugate", J Immunol (2002) 168 (2): 883-889; https://doi.org/10.4049/jimmunol.168.2.883.
Han et al., "Development of Novel Glucocorticoids for Use in Antibody-Drug Conjugates for the Treatment of Inflammatory Diseases", J. Med. Chem. 2021, 64, pp. 11958-11971.
Pang et al., "Synthesis of an enzyme-dependent prodrug and evaluation of its potential for colon targeting", World J Gastroenterol., Oct. 15, 2002; 8(5): 913-917; doi: 10.3748/wjg.v8.i5.913.
Varshosaz et al. "Synthesis and evaluation of dextran-budesonide conjugates as colon specific prodrugs for treatment of ulcerative colitis", International Journal of Pharmaceutics, Jan. 5, 2009;365(1-2):69-76; doi:10.1016/j.ijpharm.2008.08.034.
Makinen et al., "Silencing of either SR-A or CD36 reduces atherosclerosis in hyperlipidaemic mice and reveals reciprocal upregulation of these receptors", Cardiovascular Research, 2010, vol. 88, No. 3, pp. 530-538.
Ozment et al., "Blood Monocyte Scavenger Receptor A (Cd204) Expression Is Increased in Septic Patients", Shock, 2016, vol. 45, No. 6S, p. 129.

\* cited by examiner

Linker Payload Contribution in GR activation of steroid-ADC as tested in HEK293/PRLR/GRE-Luc cells where the y-axis is GRE-Luc (RLU)

Linker Payload Contribution in GR activation of steroid-ADC as tested in HEK 293/PRLR/GRE-Luc cells Table 8.

| Molecule | HEK293/PRLR/GRE-Luc cells | | |
|---|---|---|---|
| | $EC_{50}$ (24 hr) | $EC_{50}$ (48 hr) | $EC_{50}$ (72 hr) |
| Anti-PRLR Ab–2s | 0.9078 | 0.4239 | 0.4823 |
| Anti-PRLR Ab–2r | 34.98 | 18.33 | 13.35 |
| Anti-PRLR Ab–2b | 1.225 | 0.4674 | 0.4291 |
| Isotype Ab-2s | 1.461 | 0.6594 | 0.4904 |
| Isotype Ab-2r | 109.2 | 64.01 | 310.9 |
| Isotype Ab-2b | 15.04 | 8.201 | 5.243 |
| 1a | 0.5732 | 0.5679 | 1.043 |

Linker Payload Contribution in GR activation of steroid-ADC as tested in HEK293/PRLR/GRE-Luc cells Table 9.

| Steroid ADCs | HEK293/PRLR/GRE-Luc cells $EC_{50}$ (nM) at 72 hours |
|---|---|
| Anti-PRLR Ab–2b | 0.29 |
| Anti-PRLR Ab–2l | 8.98 |
| Anti-PRLR Ab–2g | 1.90 |
| Isotype Ab-2b | 4.16 |
| Isotype Ab-2l | NA |
| Isotype Ab-2g | 7.11 |
| Budesonide (1a) | 5.42 |
| Anti-PRLR Ab | NA |
| Isotype Ab | NA | where NA, means not active

Scheme 1. Synthesis of Spacer-Budesonide 1c-1e, 1g-1i, and 1j-1l

STEROIDS AND ANTIBODY-CONJUGATES THEREOF

CROSS-REFERENCE TO RELATED APPLICATIONS

This application claims priority to, and the benefit of, U.S. Provisional Patent Application No. 62/614,905, entitled Steroids and Antibody Conjugates Thereof, which was filed Jan. 8, 2018. The content of this provisional patent application is herein incorporated by reference in its entirety for all purposes.

SEQUENCE LISTING

The instant application contains a Sequence Listing which has been submitted in ASCII format via EFS-Web and is hereby incorporated by reference in its entirety. Said ASCII copy, created on Jan. 3, 2019, is named 114581_00229_ST25.txt and is 11,186 bytes in size.

FIELD

Provided herein are steroids, protein (e.g. antibody) conjugates thereof, and methods for treating diseases, disorders, and conditions comprising administering the steroids and conjugates.

BACKGROUND

Antibody-drug conjugates (ADCs) are antibodies that are covalently linked to biologically active small molecule drugs, thus combining the targeting specificity of antibodies with the mode-of-action and potency of small molecule drugs. The therapeutic utility of ADC(s) has been validated in cancer treatment and is a major ongoing focus of study. ADCETRIS® (bentruximab vedotin) and KADCYLA® (ado-trastuzumab emtansine) are ADCs approved for the treatment of certain cancer types, and several other ADCs are currently in clinical development.

Glucocorticoids (GCs) are small molecule steroids that bind to glucocorticoid receptors (GRs) and are utilized in anti-inflammatory and immunosuppressive therapies. However, due to the ubiquitous expression of glucocorticoid receptors in many cell types, glucocorticoid treatments are compromised by toxicities to most organ systems. Thus, there is need for both novel glucocorticoids as well as novel therapies that minimize the side effects arising from glucocorticoid administration, particularly those arising from activating glucocorticoid receptors in non-target cells. The instant disclosure provides solutions to the aforementioned needs as well as other unmet needs in the field to which the instant disclosure pertains. Included in the instant disclosure are antibody-drug conjugates comprising glucocorticoid payloads.

SUMMARY

Provided herein are compounds and methods useful for the treatment of various diseases, disorders, or conditions.

A first aspect is directed to a Compound of Formula (III):

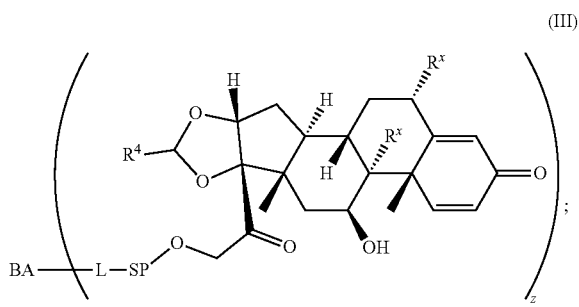

or a pharmaceutically acceptable salt, solvate, stereoisomer, or derivative thereof, wherein:

$R^4$ is alkyl, aryl, arylalkyl, or an N-containing heterocycloalkyl;

both $R^x$ are hydrogen; and SP is —C(O)—$C_1$-$C_{10}$-alkylene-C(O)—, —C(O)—N($C_{1-6}$alkyl)-$C_1$-$C_{10}$-alkylene-$X^1$- where $X^1$ is attached to L in Formula (III), —C(O)—N(H)—($C_1$-$C_{10}$-alkylene)-S— where S is attached to L in Formula (III), —C(O)—N($C_{1-6}$alkyl)-($C_1$-$C_{10}$-alkylene)-S— where S is attached to L in Formula (III),

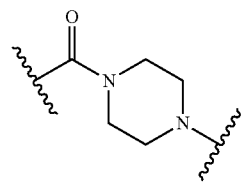 [SMILES: *C(=O)N1CCN(*)CC1]

where the point of attachment on the right hand side (i.e. at N) is to L in Formula (III), —$CH_2$—NH— where the N is attached to L in Formula (III),

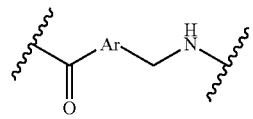

where the N is attached to L in Formula (III) and where Ar is optionally substituted arylene or optionally substituted heteroarylene, —($C_1$-$C_{10}$-alkylene)-$NR^{50}$C(O)—($C_1$-$C_{10}$-alkylene)-$NR^{50a}$- where $NR^{50a}$ is attached to L in Formula (III), —C(O)—($C_1$-$C_{10}$-alkylene)-$NR^{50}$C(O)—($C_1$-$C_{10}$-alkylene)-$NR^{50a}$- where $NR^{50a}$ is attached to L in Formula (III) and where each $C_1$-$C_{10}$-alkylene is independently optionally substituted with one or more hydroxy, —C(O)—N($R^5$)-$C_1$-$C_{10}$-alkylene-C(O)NH-$X^2$- where $X^2$ is attached to L in Formula (III), or

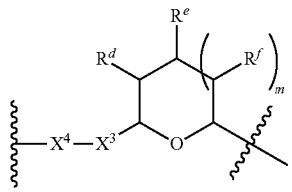

where $X^4$ is attached to L in Formula (III); or
both $R^x$ are fluoro; and SP is —C(O)—$C_1$-$C_{10}$-alkylene-C(O)—, —C(O)—N($C_{1-6}$alkyl)-$C_1$-$C_{10}$-alkylene-$X^{1b}$- where $X^{1b}$ is attached to L in Formula (III), —C(O)—N(H)—($C_1$-$C_{10}$-alkylene)-$X^{1b}$- where $X^{1b}$ is attached to L in Formula (III),

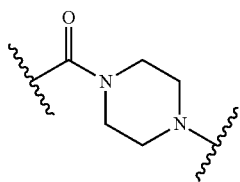 [SMILES: *C(=O)N1CCN(*)CC1]

where the point of attachment on the right hand side (i.e. at N) is to L in Formula (III), —$CH_2$—NH— where the N is attached to L in Formula (III),

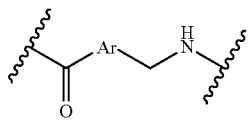

where the N is attached to L in Formula (III) and where Ar is optionally substituted arylene or optionally substituted heteroarylene, —($C_1$-$C_{10}$-alkylene)-$NR^{50}$C(O)—($C_1$-$C_{10}$-alkylene)-$NR^{50a}$- where $NR^{50a}$ is attached to L in Formula (III), —C(O)—($C_1$-$C_{10}$-alkylene)-$NR^{50}$C(O)—($C_1$-$C_{10}$-alkylene)-$NR^{50a}$- where $NR^{50a}$ is attached to L in Formula (III) and where each $C_1$-$C_{10}$-alkylene is independently optionally substituted with one or more hydroxy, —C(O)—N($R^5$)—($C_1$-$C_{10}$-alkylene)-C(O)NH-$X^2$- where $X^2$ is attached to L in Formula (III), or

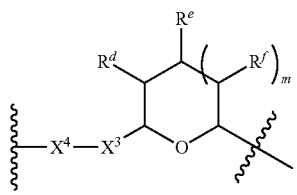

where $X^4$ is attached to L in Formula (III); and
$X^1$ is —N($C_{1-6}$alkyl)-;
$X^{1b}$ is —S—, —NH—, or —N($C_{1-6}$alkyl)-;
$X^2$ is —NH—;
$X^3$ is —$CH_2$—, $X^3$ is —$CH_2$—O—($C_1$-$C_{10}$-alkylene)-C(O)— where the C(O) is attached to $X^4$, or $X^3$ is —C(O)—;

$X^4$ is —O—;
$R^5$ is H, —OH, —$OCH_3$, or $C_{1-6}$alkyl;
$R^{50}$ and $R^{50a}$ are independently hydrogen or $C_1$-$C_6$-alkyl;
$R^d$, $R^e$, and $R^f$ are independently —H, —OH, hydroxyalkyl, alkoxycarbonyl, —C(O)OH, or —$CH_2OR^g$, where each $R^g$ is independently —$CH_2$C(O)OH or —$CH_2$C(O)O(alkyl); and m is 0 or 1;

z is an integer selected from 1-30, inclusive;

L is a linker; and

BA is a binding agent.

A second aspect is directed to a Compound according to Formula (I):

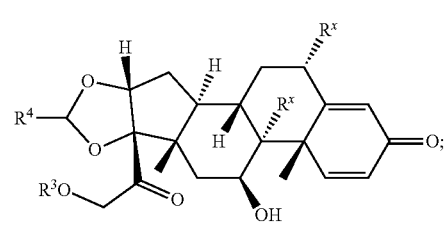

or a pharmaceutically acceptable salt, solvate, stereoisomer, or derivative thereof, wherein:

$R^4$ is alkyl, aryl, arylalkyl, or an N-containing heterocycloalkyl;

a) both $R^x$ are hydrogen; and
$R^3$ is —C(O)$R^Z$; —($C_1$-$C_{10}$-alkylene)-$NR^{50}$C(O)—($C_1$-$C_{10}$-alkylene)-$NR^{50a}R^{50b}$; —$CH_2NH_2$; or

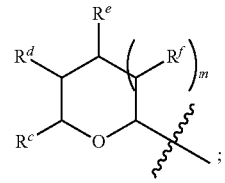

$R^Z$ is —$C_{4-10}$-alkylene-C(O)OH; —($C_1$-$C_{10}$-alkylene)-$NR^{50}$C(O)—($C_1$-$C_{10}$-alkylene)-$NR^{50a}R^{50b}$ where each $C_1$-$C_{10}$-alkylene is independently optionally substituted with one or more hydroxy;

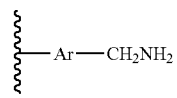

where Ar is optionally substituted aryl or heteroaryl; or $NR^{15}R^{15a}$;

$R^{15}$ is H or $C_1$-$C_6$alkyl and $R^{15a}$ is —($C_1$-$C_{10}$-alkylene)-SH or —($C_{1-6}$-alkylene)-C(O)$NHNH_2$;

b) both $R^x$ are fluoro; and
$R^3$ is —C(O)$R^Z$; —($C_1$-$C_{10}$-alkylene)-$NR^{50}$C(O)—($C_1$-$C_{10}$-alkylene)-$NR^{50a}R^{50b}$; —$CH_2NH_2$; or

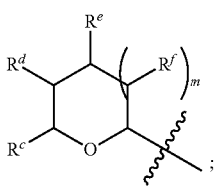

$R^Z$ is —$C_{4-10}$-alkylene-C(O)OH; —($C_1$-$C_{10}$-alkylene)-NR$^{50}$C(O)—($C_1$-$C_{10}$-alkylene)-NR$^{50a}$R$^{50b}$ where each $C_1$-$C_{10}$-alkylene is independently optionally substituted with one or more hydroxy;

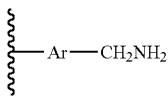

where Ar is optionally substituted aryl or heteroaryl; or NR$^{16}$R$^{16a}$;

$R^{16}$ is H or $C_1$-$C_6$alkyl and R$^{16a}$ is —($C_1$-$C_{10}$-alkylene)-SH, —($C_1$-$C_{10}$-alkylene)-NH$_2$, —($C_1$-$C_{10}$-alkylene)-NH($C_{1-6}$alkyl),

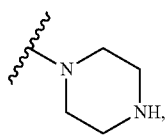

or —($C_{1-6}$-alkylene)-C(O)NHNH$_2$; and
each R$^{50}$, R$^{50a}$, and R$^{50b}$ are independently hydrogen or $C_1$-$C_6$-alkyl;
one of R$^c$, R$^d$, R$^e$, and R$^f$ is —CH$_2$OR$^g$ and the others are independently —H, —OH, hydroxyalkyl, —C(O)OH, or —CH$_2$OR$^g$, where each R$^g$ is independently —($C_{1-6}$-alkylene)-C(O)OH or —($C_{1-6}$-alkylene)-C(O)O(alkyl); or one of R$^c$, R$^d$, R$^e$, and R$^f$ is hydroxyalkyl and the others are —H; and
m is 0 or 1.

A third aspect is directed to a Compound of Formula (II):

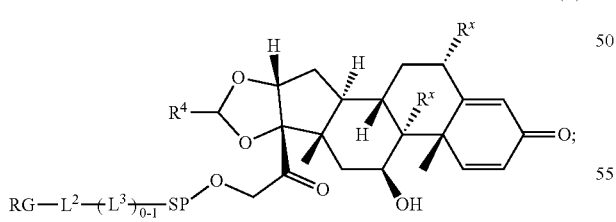

(II)

or a pharmaceutically acceptable salt, solvate, stereoisomer, or derivative thereof,
wherein:
$R^4$ is alkyl, aryl, arylalkyl, or an N-containing heterocycloalkyl;
both R$^x$ are hydrogen; SP is —C(O)—$C_1$-$C_{10}$-alkylene-C(O)—, —C(O)—N($C_{1-6}$alkyl)-$C_1$-$C_{10}$-alkylene-X$^1$- where X$^1$ is attached to (L$^3$)$_{0-1}$ in Formula (II), —C(O)—N(H)—($C_1$-$C_{10}$-alkylene)-S— where S is attached to (L$^3$)$_{0-1}$ in Formula (II), —C(O)—N($C_{1-6}$alkyl)-($C_1$-$C_{10}$-alkylene)-S— where S is attached to (L$^3$)$_{0-1}$ in Formula (II),

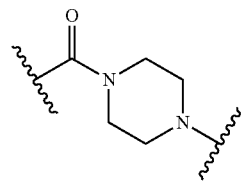 [SMILES: *C(=O)N1CCN(*)CC1]

where the point of attachment on the right hand side (i.e. at N) is to (L$^3$)$_{0-1}$ in Formula (II), —CH$_2$—NH— where the N is attached to (L$^3$)$_{0-1}$ in Formula (II),

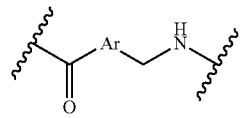

where the N is attached to (L$^3$)$_{0-1}$ in Formula (II) and where Ar is optionally substituted arylene or optionally substituted heteroarylene, —($C_1$-$C_{10}$-alkylene)-NR$^{50}$C(O)—($C_1$-$C_{10}$-alkylene)-NR$^{50a}$- where NR$^{50a}$ is attached to (L$^3$)$_{0-1}$ in Formula (II), —C(O)—($C_1$-$C_{10}$-alkylene)-NR$^{50}$C(O)—($C_1$-$C_{10}$-alkylene)-NR$^{50a}$- where NR$^{50a}$ is attached to (L$^3$)$_{0-1}$ in Formula (II) and where each $C_1$-$C_{10}$-alkylene is independently optionally substituted with one or more hydroxy, —C(O)—N(R$^5$)—$C_1$-$C_{10}$-alkylene-C(O)NH-X$^2$- where X$^2$ is attached to (L$^3$)$_{0-1}$ in Formula (II), or

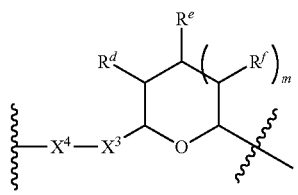

where X$^4$ is attached to L$^3$ in Formula (II); or
both R$^x$ are fluoro; SP is —C(O)—$C_1$-$C_{10}$-alkylene-C(O)—, —C(O)—N($C_{1-6}$alkyl)-$C_1$-$C_{10}$-alkylene-X$^{1b}$- where X$^{1b}$ is attached to (L$^3$)$_{0-1}$ in Formula (II), —C(O)—N(H)—($C_1$-$C_{10}$-alkylene)-X$^{1b}$- where X$^{1b}$ is attached to (L$^3$)$_{0-1}$ in Formula (II),

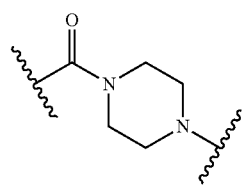 [SMILES: *C(=O)N1CCN(*)CC1]

where the point of attachment on the right hand side (i.e. at N) is to (L$^3$)$_{0-1}$ in Formula (II), —CH$_2$—NH— where the N is attached to (L$^3$)$_{0-1}$ in Formula (II),

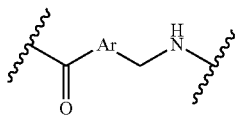

where the N is attached to $(L^3)_{0-1}$ in Formula (II) and where Ar is optionally substituted arylene or optionally substituted heteroarylene, —$(C_1$-$C_{10}$-alkylene)-$NR^{50}C(O)$—$(C_1$-$C_{10}$-alkylene)-$NR^{50a}$- where $NR^{50a}$ is attached to $(L^3)_{0-1}$ in Formula (II), —$C(O)$—$(C_1$-$C_{10}$-alkylene)-$NR^{50}C(O)$—$(C_1$-$C_{10}$-alkylene)-$NR^{50a}$- where $NR^{50a}$ is attached to $(L^3)_{0-1}$ in Formula (II) and where each $C_1$-$C_{10}$-alkylene is independently optionally substituted with one or more hydroxy, —$C(O)$—$N(R^5)$—$(C_1$-$C_{10}$-alkylene)-$C(O)NH$-$X^2$- where $X^2$ is attached to $(L^3)_{0-1}$ in Formula (II), or

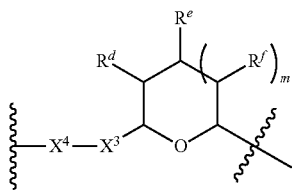

where $X^4$ is attached to $(L^3)_{0-1}$ in Formula (II); and
$X^1$ is —$N(C_{1-6}alkyl)$-;
$X^{1b}$ is —$S$—, —$NH$—, or —$N(C_{1-6}alkyl)$-;
$X^2$ is —$NH$—;
$X^3$ is —$CH_2$—, $X^3$ is —$CH_2$—$O$—$(C_1$-$C_{10}$-alkylene)-$C(O)$— where the $C(O)$ is attached to $X^4$, or $X^3$ is —$C(O)$—;
$X^4$ is —$O$—;
$R^5$ is H, —$OH$, —$OCH_3$, or $C_{1-6}alkyl$;
$R^{50}$ and $R^{50a}$ are independently hydrogen or $C_1$-$C_6$-alkyl;
$R^d$, $R^e$, and $R^f$ are independently —H, —OH, hydroxyalkyl, alkoxycarbonyl, —$C(O)OH$, or —$CH_2OR^g$, where each $R^g$ is independently —$CH_2C(O)OH$ or —$CH_2C(O)O(alkyl)$; and
m is 0 or 1;
RG is a reactive group;
$L^2$ is connecting linker; and
$L^3$, when present, is a self-immolative linker.

Another aspect is directed to pharmaceutical compositions comprising the Compound of Formula (I), Formula I-P, Formula I-P-1, Formula (III-P), Formula III-P-1, Formula (3000), or Formula (III) and a pharmaceutically acceptable carrier, diluent, and/or excipient.

Another aspect is directed to methods useful for the treatment of various diseases, disorders, or conditions comprising administering a Compound of Formula I, Formula I-P, Formula I-P-1, Formula (III-P), Formula III-P-1, Formula (3000), or Formula (III) or administering a pharmaceutical composition comprising a Compound of Formula I, Formula I-P, Formula I-P-1, Formula (III-P), Formula III-P-1, Formula (3000), or Formula (III) and a pharmaceutically acceptable carrier, diluent, and/or excipient.

BRIEF DESCRIPTIONS OF THE DRAWINGS

FIGS. 1A, 1B, and 1C, and 2 show GR activation of steroid-ADCs as tested in Example 7.

Figure 3:
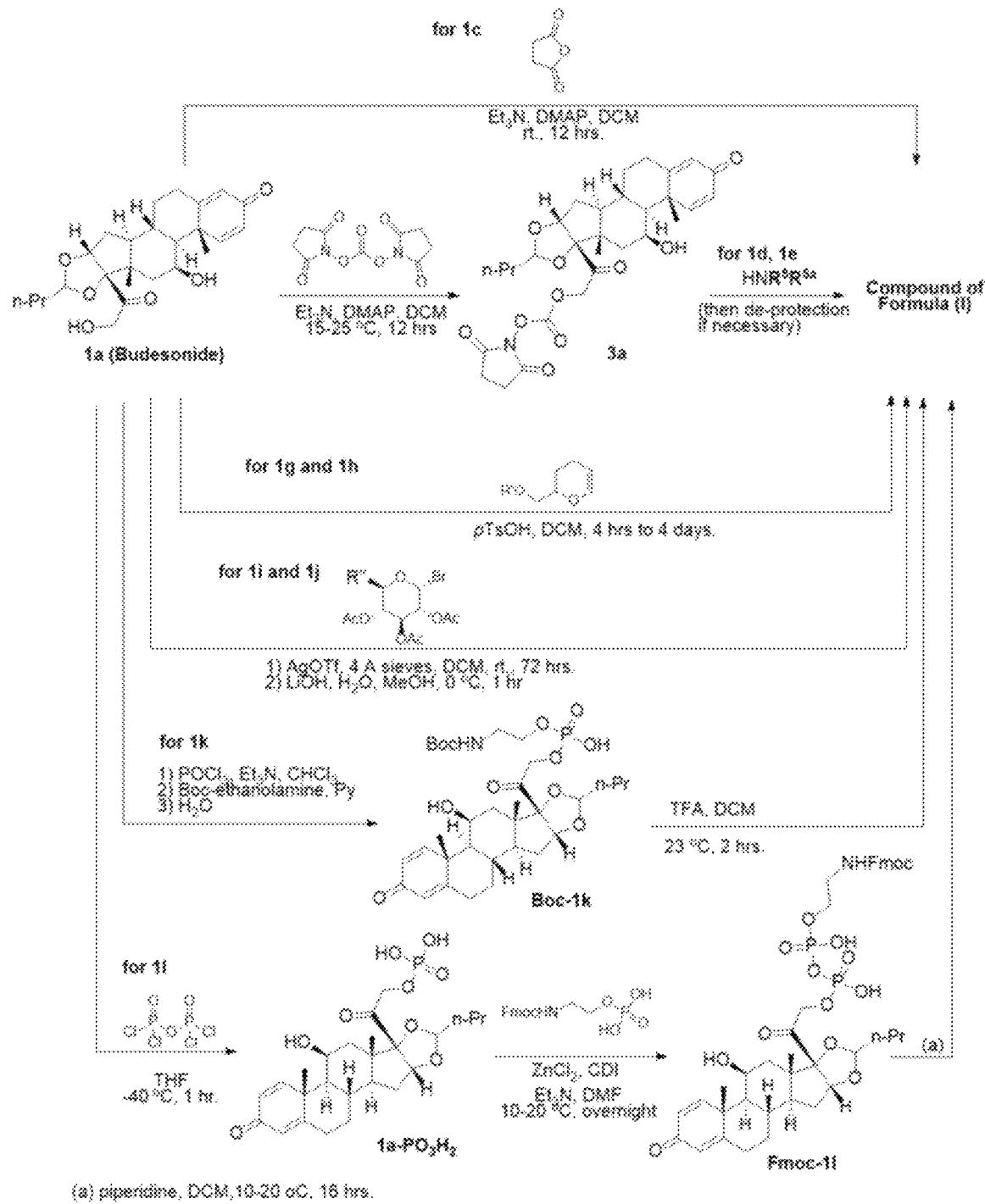

FIG. 3 shows Scheme 1. Synthesis of Spacer-Budesonide 1c-1e, 1g-1i, and 1j-1l.

DETAILED DESCRIPTION

A. Definitions

As used herein, "alkyl" refers to a monovalent and saturated hydrocarbon radical moiety. Unless specified otherwise, Alkyl is unsubstituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Cycloalkyl, which is a subset of alkyl includes, but is not limited to, groups having 3-20 carbon atoms, i.e., $C_{3-20}$ alkyl; 3-12 carbon atoms, i.e., $C_{3-12}$ alkyl; 3-10 carbon atoms, i.e., $C_{3-10}$ alkyl; 3-8 carbon atoms, i.e., $C_{3-8}$ alkyl; and 3-6 carbon atoms, i.e., $C_{3-6}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl.

"Alkylene" is divalent alkyl, as defined herein.

"Aminoalkyl," as used herein, means an alkyl group substituted with one or two —$NH_2$ groups.

As used herein, "alkenyl" refers to a monovalent hydrocarbon radical moiety containing at least two carbon atoms and one or more non-aromatic carbon-carbon double bonds. Alkenyl is unsubstituted, unless specified otherwise, and can be linear, branched, or cyclic. Alkenyl includes, but is not limited to, those having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Cycloalkenyl, which is a subset of alkenyl includes, but is not limited to, groups having 3-20 carbon atoms, i.e., $C_{3-20}$ alkenyl; 3-12 carbon atoms, i.e., $C_{3-12}$ alkenyl; 3-10 carbon atoms, i.e., $C_{3-10}$ alkenyl; 3-8 carbon atoms, i.e., $C_{3-8}$ alkenyl; and 3-6 carbon atoms, i.e., $C_{3-6}$ alkenyl. Examples of alkenyl moieties include, but are not limited to vinyl, propenyl, butenyl, and cyclohexenyl.

"Alkenylene" is divalent alkenyl, as defined herein.

As used herein, "alkynyl" refers to a monovalent hydrocarbon radical moiety containing at least two carbon atoms and one or more carbon-carbon triple bonds. Alkynyl is unsubstituted, unless specified otherwise, and can be linear, branched, or cyclic. Alkynyl includes, but is not limited to, those having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Cycloalkynyl, which is a subset of alkynyl includes, but is not limited to, groups having 3-20 carbon atoms, i.e., $C_{3-20}$ alkynyl; 3-12 carbon atoms, i.e., $C_{3-12}$ alkynyl; 3-10 carbon atoms, i.e., $C_{3-10}$ alkynyl; 3-8 carbon atoms, i.e., $C_{3-8}$ alkynyl; and 3-6 carbon atoms, i.e., $C_{3-6}$ alkynyl. Examples of alkynyl moieties include, but are not limited to ethynyl, propynyl, and butynyl.

"Alkynylene" is divalent alkynyl, as defined herein.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O for ethoxy. Alkoxy substituents bond to the compound which they substitute through this oxygen atom of the alkoxy substituent. Alkoxy is unsubstituted, unless specified otherwise, and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Cycloalkoxy, which is a subset of alkoxy includes, but is not limited to, groups having 3-20 carbon atoms, i.e., $C_{3-20}$ alkoxy; 3-12 carbon atoms, i.e., $C_{3-12}$ alkoxy; 3-10 carbon atoms, i.e., $C_{3-10}$ alkoxy; 3-8 carbon atoms, i.e., $C_{3-8}$ alkoxy; and 3-6 carbon atoms, i.e., $C_{3-6}$ alkoxy. Examples of alkoxy moieties include, but are not limited to methoxy, ethoxy, n-propoxy, i-propoxy, n-butoxy, s-butoxy, t-butoxy, i-butoxy, a pentyloxy moiety, a hexyloxy moiety, cyclopropyloxy, cyclobutyloxy, cyclopentyloxy, and cyclohexyloxy.

As used herein, "aryl" refers to a monovalent moiety that is a radical of a monocyclic or polycyclic ring system comprising at least one aromatic ring wherein the ring atoms are carbon atoms. Aryl is optionally substituted. When aryl is monocyclic, aryl is phenyl. When aryl is polycyclic, e.g., bicyclic or tricyclic, at least one of the rings is aromatic and the other rings may be aromatic or partially unsaturated. Examples of aryl moieties include, but are not limited to those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are limited to phenyl, naphthyl, tetrahydronaphthyl, fluorenyl, azulenyl, anthryl, phenanthryl, and pyrenyl.

As used herein, "arylene" refers to a divalent aryl group, as defined herein. In some embodiments the arylene is optionally substituted on one of the carbons which does not provide a point of attachment to the rest of the molecule. In some embodiments, the arylene is not optionally substituted. In some embodiments, the arylene is phenylene. In some embodiments, the arylene is

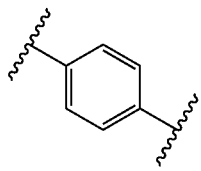 [SMILES: *c1ccc(*)cc1]

which is optionally substituted. In some embodiments, the arylene is

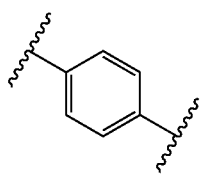 [SMILES: *c1ccc(*)cc1]

which is not optionally substituted. In some embodiments, the phenylene in

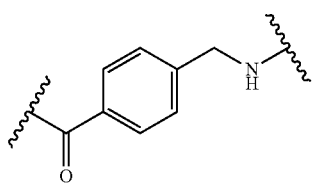 [SMILES: *NCc1ccc(C(*)=O)cc1]

is optionally substituted. In some embodiments, the phenylene in

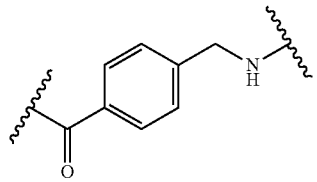 [SMILES: *NCc1ccc(C(*)=O)cc1]

is not optionally substituted.

As used herein, "arylalkyl" refers to an monovalent moiety that is a radical of an alkyl compound, wherein the alkyl compound is substituted with an aryl substituent, i.e., the aromatic compound includes a single bond to an alkyl group and wherein the radical is localized on the alkyl group. An arylalkyl group bonds to the illustrated chemical structure via the alkyl group. In some embodiments, arylalkyl includes benzyl, phenyleth-1-yl, and phenyleth-2-yl, and the like. Unless otherwise, arylalkyl is unsubstituted. However, when substituted, arylalkyl, i.e., the aryl group and/or the alkyl group, is substituted as disclosed herein. Examples of arylalkyl include, but are not limited to, benzyl.

As used herein, "haloalkyl" refers to alkyl, as defined herein, wherein the alkyl includes at least one substituent selected from a halogen, e.g., F, Cl, Br, or I. In some embodiments, the alkyl is substituted with 1, 2, 3, or 4 halo atoms which are independently selected.

As used herein, "haloalkoxy" refers to alkoxy, as defined above, wherein the alkoxy includes at least one substituent selected from a halogen, e.g., F, Cl, Br, or I.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms, which are independently selected. Heteroalkyl is unsubstituted, unless otherwise specified. Examples of heteroalkyl moieties include, but are not limited to, aminoalkyl, sulfonylalkyl, sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Heteroaryl includes monocyclic, fused bicyclic, or fused tricyclic radicals, wherein the ring comprising a monocyclic radical is aromatic and wherein at least one of the fused rings comprising a bicyclic or tricyclic radical is aromatic. Fused bicyclic radical includes bridged ring systems. Examples of heteroaryl moieties include, but are not limited to those having 5 to 20 ring atoms; 5 to 15 ring atoms; and 5 to 10 ring atoms. Heteroaryl is optionally substituted. In some embodiments, the heteroaryl ring comprises 1, 2, 3, or 4 (in some embodiments, 1, 2, or 3; in some embodiments 1 or 2; in some embodiments 1) oxygen, sulfur, nitrogen, and/or phosphorus atoms, which are independently selected. In some embodiments, heteroaryl is 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl As used herein, "heteroarylene" refers to a divalent heteroaryl, as defined herein. In some embodiments the heteroarylene is optionally substituted on one of the carbons or substitutable nitrogens which does not provide a point of attachment to the rest of the molecule. In some embodiments, the heteroarylene is not optionally substituted. In some embodiments, the heteroarylene is pyridin-diyl.

As used herein, "heterocycloalkyl" refers to a cycloalkyl, as defined above in "alkyl," in which one or more carbon atoms are replaced by heteroatoms, which are independently selected. Suitable heteroatoms include, but are not limited to, nitrogen, oxygen, and sulfur atoms. Unless specified otherwise heterocycloalkyl is unsubstituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "hydroxyalkylene" refers to alkylene, as defined herein, wherein the alkylene includes at least one hydroxy. In some embodiments, the alkylene is substituted with 1, 2, 3, or 4 hydroxy atoms.

As used herein, "N-containing heterocycloalkyl," refers to a cycloalkyl, as defined above in "alkyl," in which one or more carbon atoms are replaced by heteroatoms and wherein at least one heteroatom is a nitrogen atom. Suitable heteroatoms, which are independently selected, in addition to nitrogen, include, but are not limited to oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety (e.g., optionally substituted arylene, optionally substituted heteroarylene, optionally substituted aryl, optionally substituted heteroaryl, optionally substituted alkyl, and optionally substituted arylalkyl) means that such moiety is optionally bonded to one or more substituents on any substitutable atom in the moiety. Examples of such substituents include, but are not limited to halo, cyano, nitro, haloalkyl, azido, epoxy, optionally substituted heteroaryl, optionally substituted heterocycloalkyl,

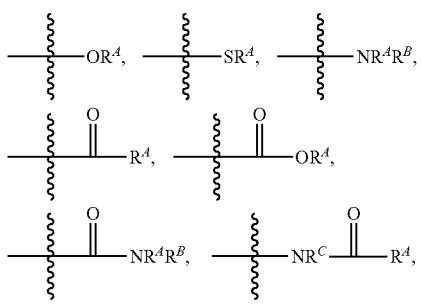

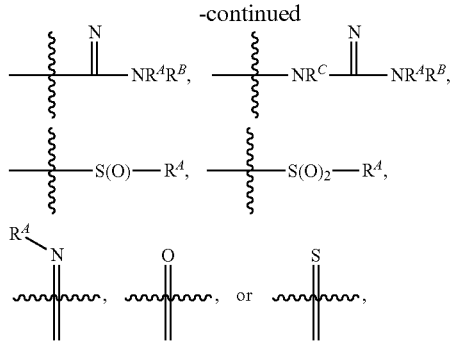

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$, together with the atoms to which they are bonded, form a saturated or unsaturated heterocyclic ring (i.e. heterocycloalkyl or heteroaryl), wherein the ring is optionally substituted and wherein, in addition to the nitrogen ring atom, one or more ring atoms is optionally a heteroatom independently selected from nitrogen, oxygen, sulfur, and phosphorous. In certain embodiments, when a radical moiety is optionally substituted with an optionally substituted heteroaryl, optionally substituted heterocycloalkyl, or optionally substituted saturated or unsaturated heterocyclic ring (i.e. heterocycloalkyl or heteroaryl), the substituents on the optionally substituted heteroaryl, optionally substituted heterocycloalkyl, or optionally substituted saturated or unsaturated heterocyclic ring (i.e. heterocycloalkyl or heteroaryl), if they are substituted, are not substituted with substituents which are further optionally substituted with additional substituents. In some embodiments, when a group described herein is optionally substituted, the substituent bonded to the group is unsubstituted unless otherwise specified, i.e. optionally substituted arylene as a substituent is not further substituted with a substituted arylene.

As used herein, "binding agent" refers to any protein-based or peptide-based molecule capable of binding with specificity to a given binding partner. In some embodiments, the binding agent is an antibody, or an antigen binding fragment thereof. In some embodiments, the binding agent is not albumin.

As used herein, "amide synthesis conditions" refers to reaction conditions suitable facilitate the formation of an amide, e.g., by the reaction of a carboxylic acid, activated carboxylic acid, or acyl halide with an amine. In some embodiments, "amide synthesis conditions" refers to reaction conditions suitable to facilitate the formation of an amide bond between a carboxylic acid and an amine. In some of these embodiments, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]1H-1,2,3-triazolo[4,5-b]pyridinium 3-oxid hexafluorophosphate (HATU), 2-Ethoxy-1-ethoxycarbonyl-1,2-dihydroquinoline (EEDQ), 1-Ethyl-3-(3-dimethylaminopropyl)carbodiimide (EDC), 2-Chloro-1,3-dimethylimidazolidinium hexafluorophosphate (CIP), 2-chloro-4,6-dimethoxy-1,3,5-triazine (CDMT), and carbonyldiimidazole (CDI). In some embodiments, a carboxylic acid is first converted to an activated carboxylic ester before reacting with an amine to form an amide bond. In certain embodiments, the carboxylic acid is reacted with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. For certain carboxylic acids, this activated ester is more susceptible subsequently to nucleophilic attack by an amine than the carboxylic acid is before it is converted. This results in amide bond formation. As such, the carboxylic acid is described as activated. Exemplary reagents include DCC and DIC.

As used herein, "therapeutically effective amount" refers to an amount (of a compound) that is sufficient to provide a therapeutic benefit to a patient in the treatment or management of a disease or disorder, or to delay or minimize one or more symptoms associated with the disease or disorder.

As used herein, "pharmaceutically acceptable salt" refers to any salt suitable for administration to a patient. Suitable salts include, but are not limited to, those disclosed in. Berge et al., "Pharmaceutical Salts", *J. Pharm. Sci.*, 1977, 66:1, incorporated herein by reference. Examples of salts include, but are not limited to, acid-derived, base-derived, organic, inorganic, amine, and alkali or alkaline earth metal salts, including but not limited to calcium salts, magnesium salts, potassium salts, sodium salts, salts of hydrochloric acid, hydrobromic acid, sulfuric acid, nitric acid, phosphoric acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid, and the like.

Certain groups, moieties, substituents, and atoms are depicted with a wavy line that intersects or caps a bond or bonds to indicate the atom through which the groups, moieties, substituents, atoms are bonded. For example, a phenyl group that is substituted with a propyl group depicted as:

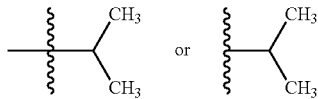

has the following structure:

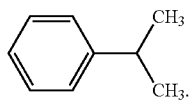

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

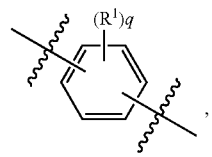

wherein subscript q is an integer selected from 0 to 4, inclusive and in which the positions of substituent $R^1$ are described generically, i.e., not directly attached to any vertex of the bond line structure, i.e., specific ring carbon atom, includes the following, non-limiting examples of, groups in which the substituent $R^1$ is bonded to a specific ring carbon atom:

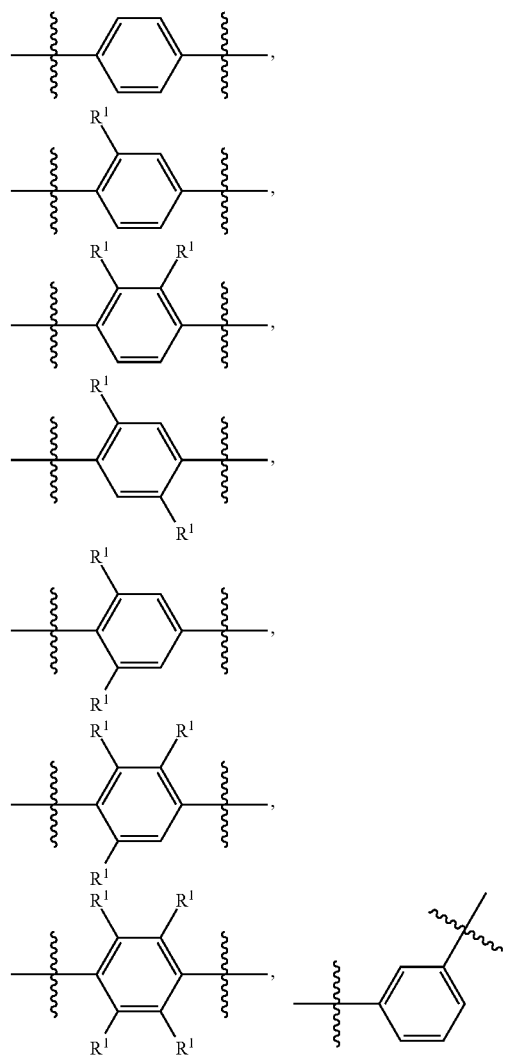

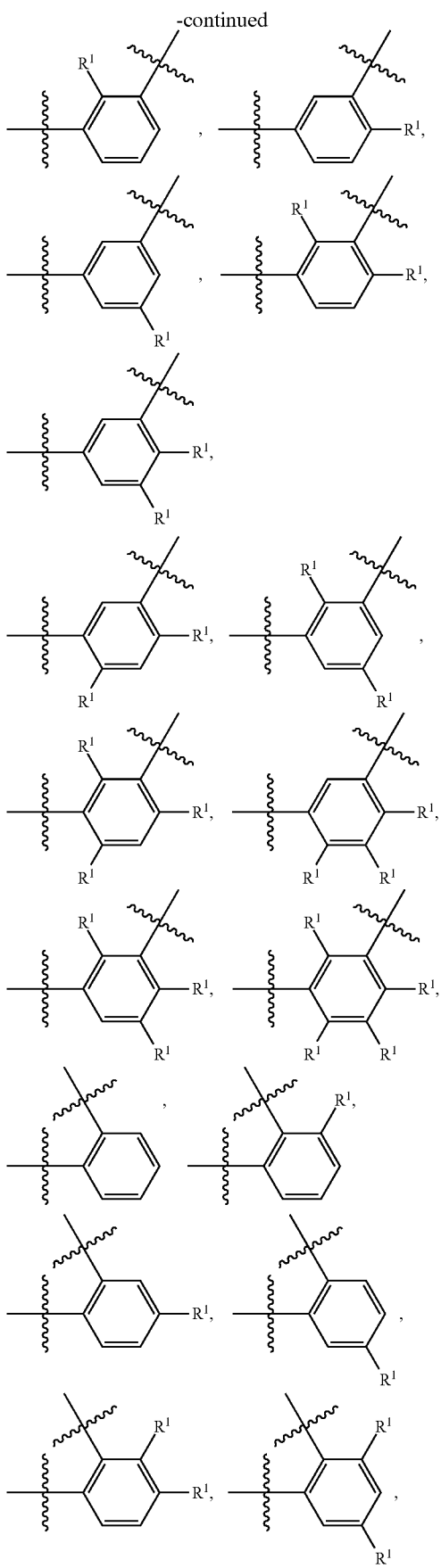

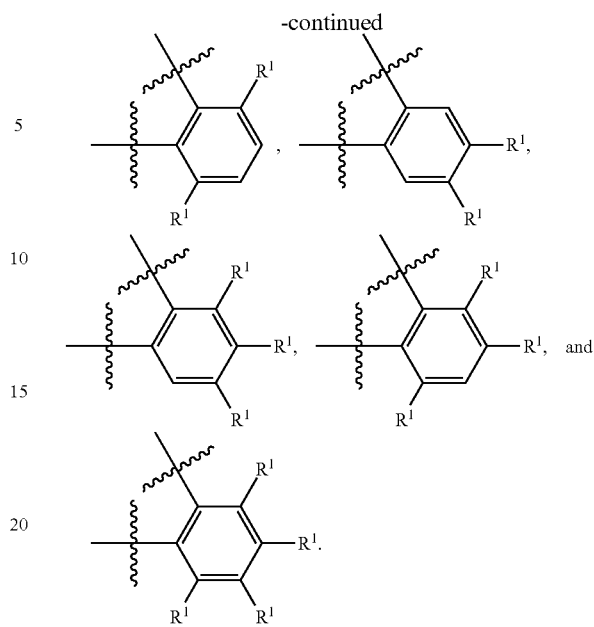

Where the compound name and structure conflict or are inconsistent, the structure controls, except where the context, e.g. as provided by NMR characterization data, may dictate otherwise.

As used herein, the phrase "reactive group" ("RG"), refers to a functional group or moiety that reacts with a reactive portion of an antibody, modified antibody, or antigen binding fragment thereof. In certain embodiments, the "reactive group" is a functional group or moiety (e.g., maleimide or NHS ester) that reacts with a cysteine or lysine residue of an antibody or antigen-binding fragment thereof. In certain embodiments, the "reactive group" is a functional group or moiety that is capable of undergoing a click chemistry reaction. In some embodiments of said click chemistry reaction, the reactive group comprises an alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable alkynes also include, but are not limited to, DIBAC (where the —C(O)CH$_2$CH$_2$C(O)— portion of DIBAC moiety is covered by L$^2$), DIBO (where the —O— portion of DIBO moiety is covered by L$^2$), BARAC (where the

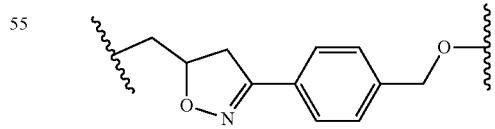

portion of BARAC moiety is covered by L$^2$), DIFO (where the —O— portion is covered by L$^2$), substituted alkynes, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue, e.g., heavy chain Q295 (EU numbering), with a compound according to the formula $H_2N$-LL-$N_3$, wherein LL is a divalent polyethylene glycol group, in the presence of the enzyme transglutaminase.

In some embodiments, the reactive group (RG) is an alkyne, e.g.,

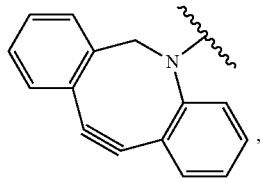 [SMILES: *N1Cc2ccccc2C#Cc2ccccc21]

which can react via click chemistry with an azide, e.g.,

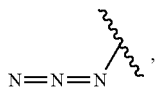

to form a click chemistry product, e.g.,

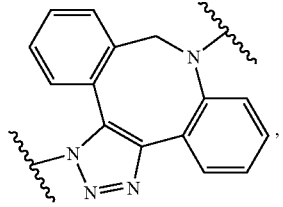 [SMILES: *N1Cc2ccccc2-c2c(nnn2*)-c2ccccc21]

its regioisomer, or mixture thereof. In some embodiments, the reactive group is an alkyne, e.g.,

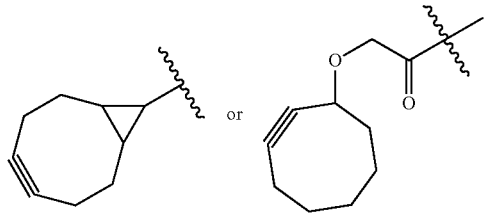 [SMILES: *C1C2CCC#CCCC12 ; *C(=O)COC1C#CCCCCC1]

or (where $L^2$ encompasses —OCH2C(O)—), which can react via click chemistry with an azide, e.g.,

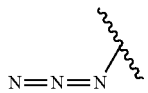

to form a click chemistry product, e.g.,

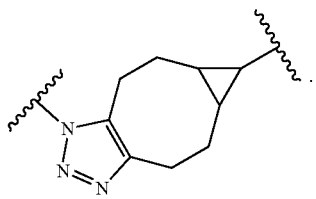 [SMILES: *C1C2CCc3nnn(*)c3CCC12]

In some embodiments, the reactive group is an alkyne, e.g.,

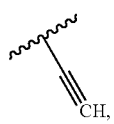

which can react via click chemistry with an azide, e.g.,

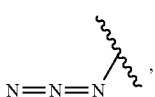

to form a click chemistry product, e.g.,

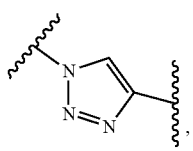 [SMILES: *c1cn(*)nn1]

its regioisomer, or mixture thereof. In some embodiments, the reactive group is a functional group, e.g.,

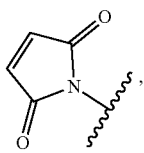 [SMILES: *N1C(=O)C=CC1=O]

which reacts with a cysteine residue on an antibody or antigen-binding fragment thereof, to form a bond thereto, e.g.,

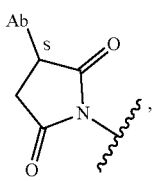

wherein Ab refers to an antibody or antigen-binding fragment thereof and S refers to the S atom on a cysteine residue through which the functional group bonds to the Ab. In some embodiments, the reactive group is a functional group, e.g.,

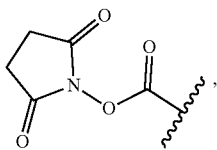 [SMILES: *C(=O)ON1C(=O)CCC1=O]

which reacts with a lysine residue on an antibody or antigen-binding fragment thereof, to form a bond thereto, e.g.,

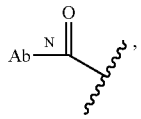

wherein Ab refers to an antibody or antigen-binding fragment thereof and N refers to the N atom on a lysine residue through which the functional group bonds to the Ab.

As used herein, the phrase "reactive group residue" (-$L^1$-) refers to a product of the reaction of a functional group in the linker moiety with the reactive portion of a binding agent (BA), including the product of click chemistry. The reactive group residue is formed by the reaction of a reactive group on an amino acid of the binding agent, and is attached to the binding agent (e.g. antibody) and to the connecting linker. In some embodiments, the reactive group residue is a group which comprises 1,2,3-tetrazole, i.e. is formed by the reaction of an alkyne with an azide. In some embodiments, the reactive group residue is (a)

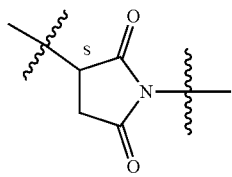

wherein S refers to the S atom on a cysteine residue through which (a) bonds to the Ab, and which is formed by the reaction of

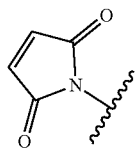 [SMILES: *N1C(=O)C=CC1=O]

with a cysteine residue on an antibody or antigen-binding fragment thereof. In some embodiments, the reactive group residue is

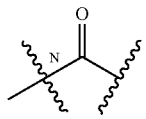

wherein N refers to the N atom on a lysine residue, and which is formed by the reaction of a functional group, e.g.,

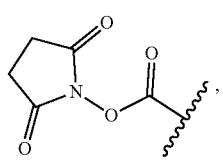 [SMILES: *C(=O)ON1C(=O)CCC1=O]

with a lysine residue on an antibody or antigen-binding fragment thereof.

In some embodiments, the linker -L- comprises and $L^1$ is the reactive group residue according to the following moiety:

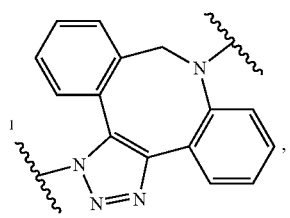 [SMILES: *N1Cc2ccccc2-c2c(nnn2*)-c2ccccc21]

its regioisomer, or mixture thereof, wherein $$\overset{1}{\xi}$$

is the bond to the binding agent. In some embodiments, the linker -L-comprises and $L^1$ is the reactive group residue according to the following moiety:

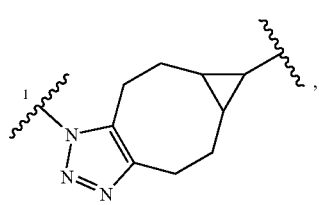 [SMILES: *C1C2CCc3nnn(*)c3CCC12]

its regioisomer, or mixture thereof, wherein $$\overset{1}{\xi}$$

is the bond to the binding agent. In some embodiments, the linker -L- comprises and $L^1$ is the reactive group residue according to the following moiety:

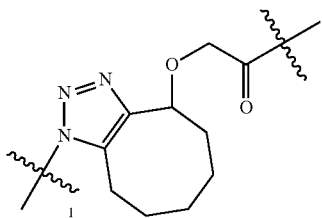 [SMILES: *C(=O)COC1CCCCCc2c1nnn2*]

where —OCH₂C(O)— is encompassed by $L^2$, its regioisomer, or mixture thereof, wherein

is the bond to the binding agent. In some embodiments, the linker -L- comprises and $L^1$ is the reactive group residue according to the following moiety:

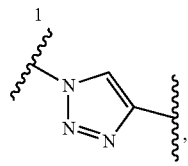 [SMILES: *c1cn(*)nn1]

its regioisomer, or mixture thereof, wherein

is the bond to the binding agent. In some embodiments, the linker -L- comprises and $L^1$ is the reactive group residue according to the following moiety:

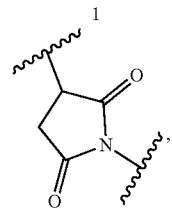 [SMILES: *C1CC(=O)N(*)C1=O]

wherein

is the bond to the cysteine of the antibody or antigen-binding fragment thereof. In some embodiments, the linker -L- comprises and $L^1$ is the reactive group residue according to the following moiety:

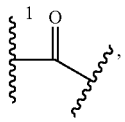

wherein

is the bond to the lysine of the antibody or antigen-binding fragment thereof. In these examples, the bond to the binding agent is direct or via a linker. In particular embodiments, the binding agent is modified with an azide to facilitate linkage to linker -L- or $L^1$ to form the reactive group residue.

As used herein. "connecting linker" ($L^2$) refers to divalent groups which are cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable connecting linkers include, but are not limited to, acid-labile linkers, hydrolysis-labile linkers, enzymatically cleavable linkers, reduction labile linkers, and non-cleavable linkers. Suitable linkers also include, but are not limited to, those that are or comprise glucuronides, succinimide-thioethers, polyethylene glycol (PEG) units, hydrazones, mal-caproyl units, disulfide units (e.g., —S—S—, —S—C($R^{1b}R^{2b}$)-, wherein $R^{1b}$ and $R^{2b}$ are independently hydrogen or hydrocarbyl), carbamate units, para-amino-benzyl units (PAB), phosphate units, e.g., mono-, bis-, or tris-phosphate units, and peptide units, e.g., peptide units containing two, three four, five, six, seven, eight, or more amino acid residues, including but not limited to valine-citrulline residue units. As used herein, "caproyl" means a —(CH₂)₅—C(O)— group. In some embodiments, $L^2$ comprises cyclodextrin (CD). In some embodiments, $L^2$ comprises —C(O)CH₂CH₂C(O)—, —C(O)CH₂CH₂CH₂C(O)—, —OCH₂C(O)—, —O—, or

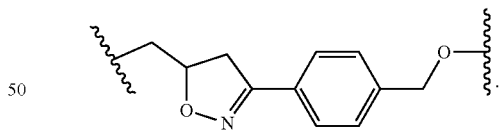

As used herein, "self-immolative linker" in ($L^3$) refers to any such group known to those of skill in the art. In particular embodiments, the self-immolative group is p-aminobenzyl (PAB), i.e.

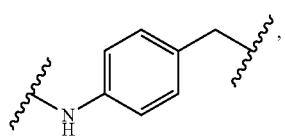 [SMILES: *Cc1ccc(N*)cc1]

or a derivative thereof. Useful derivatives include p-aminobenzoyloxy, i.e.

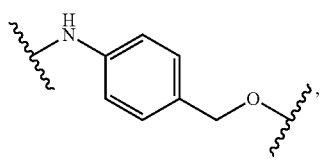 [SMILES: *Nc1ccc(CO*)cc1]

and p-aminobenzyloxycarbonyl (PABC), i.e.

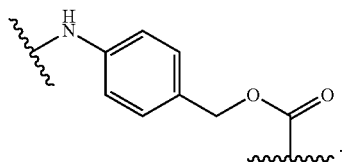 [SMILES: *Nc1ccc(COC(*)=O)cc1]

Those of skill will recognize that a self-immolative group is capable of carrying out a chemical reaction which releases the remaining atoms of a linker from a payload.

B. Steroid Payloads

Steroids suitable for the conjugates described herein include budesonide and prodrugs thereof, budesonide analogs or derivatives (including fluorinated analogs and derivatives) and prodrugs thereof, and steroids listed in Table A and prodrugs thereof. In some embodiments, the antibody-drug conjugates release budesonide, a prodrug of budesonide, a budesonide analog or derivative (including fluorinated analogs and derivatives), a prodrug of a budesonide analog or derivative (including fluorinated analogs and derivatives), a steroid in Table A, or a prodrug of a steroid in Table A, after binding the antibody's target antigen. In Table A, the following compounds are linked to BA of the Compound of Formula (III), Formula (III-P), Formula III-P-1, or (3000) through the hydroxy of the —C(O)CH$_2$OH group, i.e. by —C(O)CH$_2$—O—SP-L-, or through the hydroxy of Mapracorat, i.e. by -O-SP-L-; or are linked to RG of the Compound of Formula (II), Formula (II-P), Formula II-P-1, or (2000) through the hydroxy of the —C(O)CH$_2$OH group, i.e. by —C(O)CH$_2$—O-SP-(L$^3$)$_{0-1}$-L$^2$-, or through the hydroxy of Mapracorat, i.e. by -O-SP-(L$^3$)$_{0-1}$-L$^2$-.

TABLE A

| Trade name | Structure |
| --- | --- |
| Hydrocortisone butyrate<br>Locoid ® | 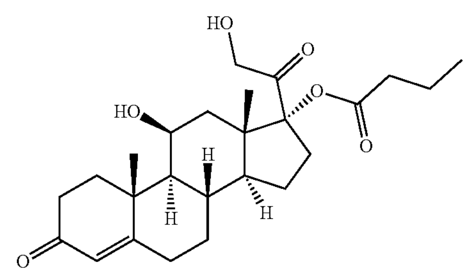 |
| Halometasone<br>Sicorten ®/<br>(C-48401-Ba) | 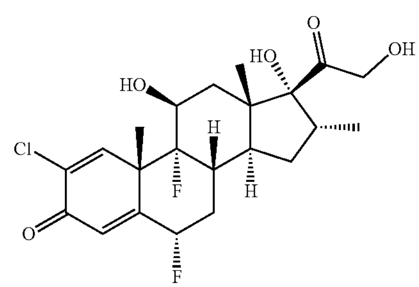 |
| Betamethasone<br>Celestone ®/Rinderon ®/Diprosone ®<br>(NSC-39470; Sch-4831) | 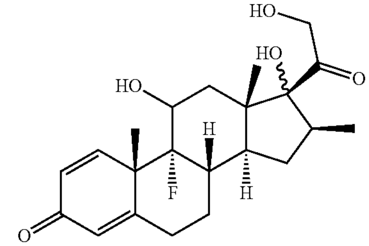 |

TABLE A-continued
| Trade name | Structure |
|---|---|
| Fluclorolone Acetonide<br>Cutanit ®/Topicon ®<br>(RS-2252) | 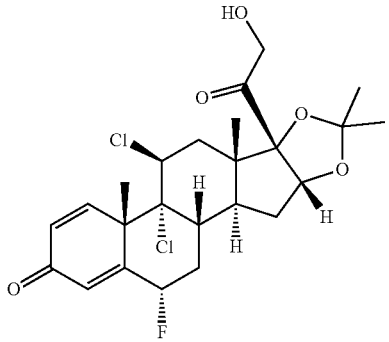 |
| Fluocinolone Acetonide<br>Flucort ®/Fluonid ®/Iluvien ®/Retisert ®/<br>Synalar ®/Synalar-HP ®/Synemol ®<br>(NSC-92339; DF-277) | 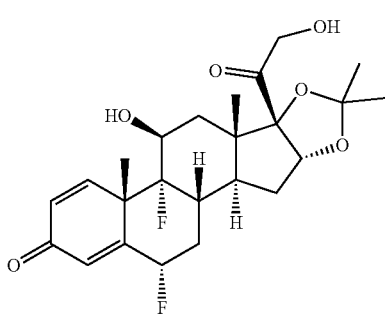 |
| Flunisolide<br>(RS-3999; RS-1320) | 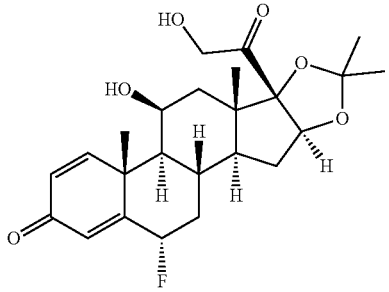 |
| Cloprednol<br>(RS-4691) | 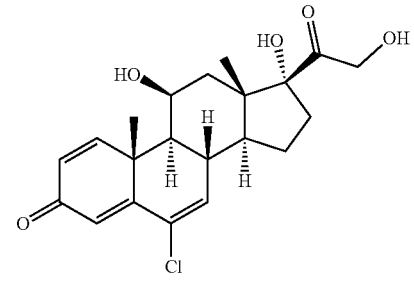 |
| Triamcinolone<br>Aristocort ®/Kenacort ® | 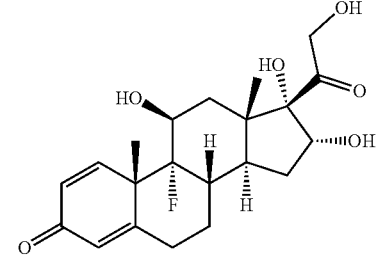 |

TABLE A-continued
| Trade name | Structure |
|---|---|
| Budesonide | 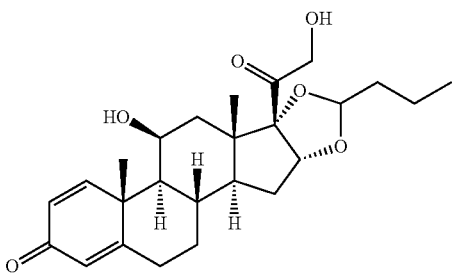 |
| Flurandrenolide<br>Cordran ® | 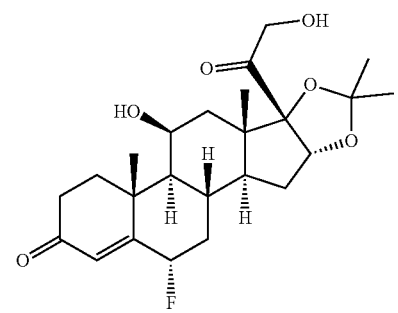 |
| Desoximetasone<br>Topicort ®<br>(DSXS) | 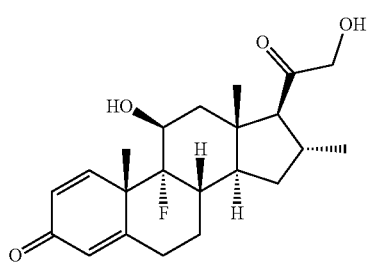 |
| Betamethasone benzoate<br>Uticort ®<br>(W-5975) | 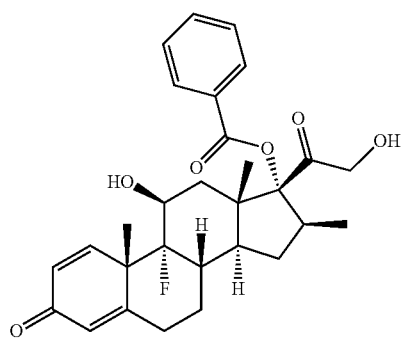 |
| Desonide<br>Desonate ®<br>(D-2083) | 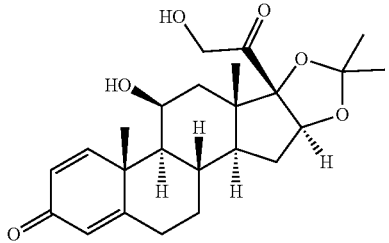 |

TABLE A-continued
| Trade name | Structure |
|---|---|
| Meprednisone (NSC-527579; Sch-4358) | 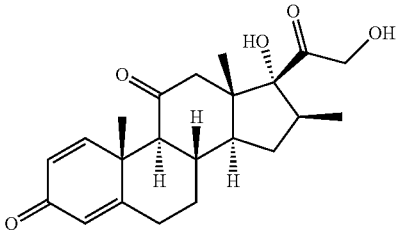 |
| Prednisolone Delta-Cortef ® (NCS-9120) | 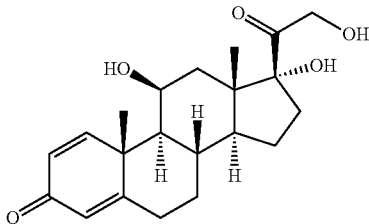 |
| Triamcinolone Acetonide | 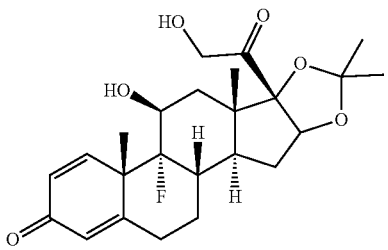 |
| Methylprednisolone Depo-Medrol; Medrol; Urbason ® (NSC-19987) | 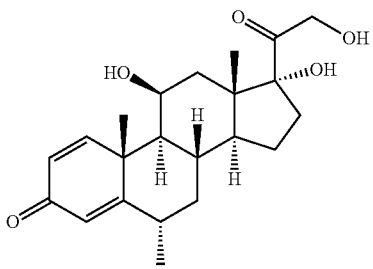 |
| Prednisone Decortin ®/Deltasone ®/Lodotra ®/ Meticorten ®/Rayos ® (NSC-10023) | 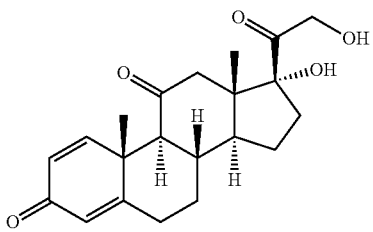 |
| Dexamethasone Decadron ® (FT-4145; ENV-1105; IBI-10090; ISV-305; OTO-104) | 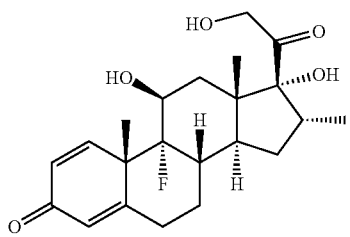 |

TABLE A-continued

| Trade name | Structure |
|---|---|
| Hydrocortisone valerate Westcort ® | 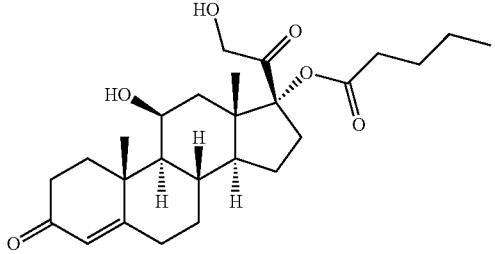 |
| Mapracorat (BOL-242X; BOL-303242-X; ZK-245186; BAY-865319; BOL-303242-X) | 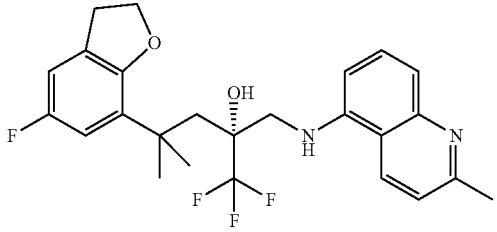 [SMILES: Cc1ccc2c(NC[C@](O)(CC(C)(C)c3cc(F)cc4c3OCC4)C(F)(F)F)cccc2n1] |
| Benzodrocortisone | 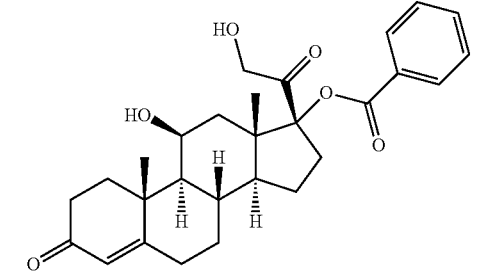 |

In some or any embodiments, the Compound of Formula (3000) or Formula (2000) comprises a prodrug of a steroid in Table A, where SP is —C(O)—$C_1$-$C_{10}$-alkylene-C(O)—, —CO—(O)—N($C_{1-6}$alkyl)-$C_1$-$C_{10}$-alkylene-$X^{1b}$- where $X^{1b}$ is attached to L in Formula (3000) or $(L^3)_{0-1}$ in Formula (2000), —C(O)—N(H)—($C_1$-$C_{10}$-alkylene)-$X^{1b}$- where $X^{1b}$ is attached to L in Formula (3000) or $(L^3)_{0-1}$ in Formula (2000),

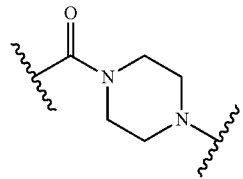 [SMILES: *C(=O)N1CCN(*)CC1]

where the point of attachment on the right hand side (i.e. at N) is to L in Formula (3000) or $(L^3)_{0-1}$ in Formula (2000), —$CH_2$—NH— where N is attached to L in Formula (3000) or $(L^3)_{0-1}$ in Formula (2000),

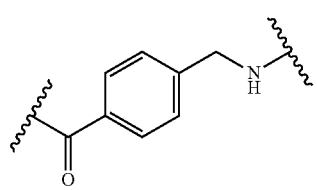

where N is attached to L in Formula (3000) or $(L^3)_{0-1}$ in Formula (2000), —($C_1$-$C_{10}$-alkylene)-$NR^{50}C(O)$—($C_1$-$C_{10}$-alkylene)-$NR^{50a}$- where $NR^{50a}$ is attached to L in Formula (3000) or $(L^3)_{0-1}$ in Formula (2000), —C(O)—($C_1$-$C_{10}$-alkylene)-$NR^{50}C(O)$—($C_1$-$C_{10}$-alkylene)-$NR^{50a}$- where $NR^{50a}$ is attached to L in Formula (3000) or $(L^3)_{0-1}$ in Formula (2000) and where each $C_1$-$C_{10}$-alkylene is independently optionally substituted with one or more hydroxy, —C(O)—N($R^5$)—($C_1$-$C_{10}$-alkylene)-C(O)NH-$X^2$- where $X^2$ is attached to L in Formula (3000) or $(L^3)_{0-1}$ in Formula (2000), or

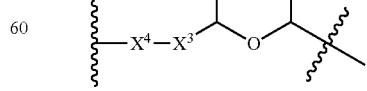

where $X^4$ is attached to L in Formula (3000) or $(L^3)_{0-1}$ in Formula (2000).

In some embodiments, a Compound according to Formula (I-P):

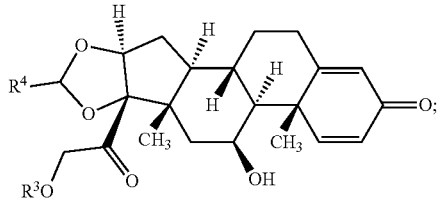
(I-P)

or a pharmaceutically acceptable salt, solvate, stereoisomer, or derivative thereof,
wherein:
R$^4$ is alkyl, aryl, arylalkyl, or an N-containing heterocycloalkyl;
R$^3$ is —C(O)R$^Z$ or

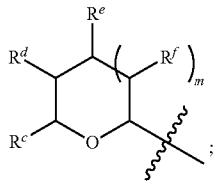
;

R$^Z$ is —C$_{4-10}$-alkylene-C(O)OH or NR$^{15}$R$^{15a}$;
R$^{15}$ is H or alkyl and R$^{15a}$ is —(C$_{1-6}$-alkylene)-C(O)NHNH$_2$;
one of R$^c$, R$^d$, R$^e$, and R$^f$ is —CH$_2$OR$^g$ and the others are independently —H, —OH, hydroxyalkyl, —C(O)OH, or —CH$_2$OR$^g$, where each R$^g$ is independently —(C$_{1-6}$-alkylene)-C(O)OH or —(C$_{1-6}$-alkylene)-C(O)O(alkyl); or one of R$^c$, R$^d$, R$^e$, and R$^f$ is hydroxyalkyl and the others are —H; and
m is 0 or 1.

In some embodiments, a Compound according to Formula (I-P-1):

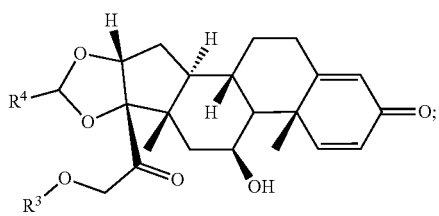
(I-P-1)

or a pharmaceutically acceptable salt, solvate, stereoisomer, or derivative thereof,
wherein:
R$^4$ is alkyl, aryl, arylalkyl, or an N-containing heterocycloalkyl;
R$^3$ is —C(O)R$^Z$ or

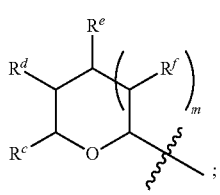
;

R$^Z$ is —C$_{4-10}$-alkylene-C(O)OH or NR$^5$R$^{5a}$;
R$^{15}$ is H or alkyl and R$^{15a}$ is —(C$_{1-6}$-alkylene)-C(O)NHNH$_2$;
one of R$^c$, R$^d$, R$^e$, and R$^f$ is —CH$_2$OR$^g$ and the others are independently —H, —OH, hydroxyalkyl, —C(O)OH, or —CH$_2$OR$^g$, where each R$^g$ is independently —(C$_{1-6}$-alkylene)-C(O)OH or —(C$_{1-6}$-alkylene)-C(O)O(alkyl); or one of R$^c$, R$^d$, R$^e$, and R$^f$ is hydroxyalkyl and the others are —H; and
m is 0 or 1.

In some embodiments, set forth herein is a compound of Formula (I), Formula (I-P), or Formula (I-P-1), where R$^4$ is alkyl. In some embodiments, R$^4$ is not cycloalkyl. In some of these embodiments, R$^4$ is linear or branched alkyl. In some of these embodiments, R$^4$ is aryl. In some of these embodiments, R$^4$ is arylalkyl. In some of these embodiments, R$^4$ is N-containing heterocycloalkyl. In some embodiments, R$^4$ is alkyl such as, but not limited to, methyl, ethyl, propyl, butyl, pentyl, hexyl, heptyl, octyl, or nonyl. In some embodiments, R$^4$ is methyl. In some embodiments, R$^4$ is ethyl. In some embodiments, R$^4$ is n-propyl. In some embodiments, R$^4$ is i-propyl. In some embodiments, R$^4$ is n-butyl. In some embodiments, R$^4$ is i-butyl. In some embodiments, R$^4$ is t-butyl. In some embodiments, R$^4$ is sec-butyl. In some embodiments, R$^4$ is pentyl. In some embodiments, R$^4$ is hexyl. In some embodiments, R$^4$ is heptyl. In some embodiments, R$^4$ is octyl, or nonyl. In some embodiments, R$^4$ is aryl such as but not limited to phenyl, phenol, or naphthyl. In some embodiments, R$^4$ is phenyl. In some embodiments, R$^4$ is naphthyl. In some embodiments, R$^4$ is heteroaryl—such as but not limited to thienyl. In some embodiments, R$^4$ is arylalkyl—such as but not limited to benzyl. In some embodiments, R$^4$ is N-containing heterocycloalkyl such as but not limited to piperidinyl. In some embodiments of Formula (I), both R$^x$ are hydrogen. In some embodiments of Formula (I), both R$^x$ are fluoro.

In some or any embodiments, set forth is a Compound of Formula (I), where both R$^x$ are fluoro and R$^3$ is —(C$_1$-C$_{10}$-alkylene)-NR$^{50}$C(O)—(C$_1$-C$_{10}$-alkylene)-NR$^{50a}$R$^{50b}$ or —C(O)R$^Z$ and R$^Z$ is NR$^{16}$R$^{16a}$ or —(C$_1$-C$_{10}$-alkylene)-NR$^{50}$C(O)—(C$_1$-C$_{10}$-alkylene)-NR$^{50a}$R$^{50b}$ where each C$_1$-C$_{10}$-alkylene is independently optionally substituted with one or more hydroxy.

In some embodiments of Formula (I), (I-P), or (I-P-1), both R$^x$ are hydrogen and R$^3$ is —C(O)R$^Z$. In some or any embodiments of Formula (I), (I-P), or (I-P-1), R$^Z$ is —C$_{4-10}$-alkylene-C(O)OH. In some or any embodiments of Formula (I), (I-P), or (I-P-1), R$^Z$ is —C$_{4-6}$-alkylene-C(O)OH. In some or any embodiments of Formula (I), (I-P), or (I-P-1), R$^Z$ is —C$_4$-alkylene-C(O)OH. In some or any embodiments of Formula (I), (I-P), or (I-P-1), R$^Z$ is —C$_5$-alkylene-C(O)OH. In some or any embodiments of Formula (I), (I-P), or (I-P-1), R$^Z$ is —C$_6$-alkylene-C(O)OH. In some or any embodiments of Formula (I), (I-P), or (I-P-1), R$^Z$ is NR$^{15}$R$^{15a}$. In some or any embodiments of Formula (I), (I-P), or (I-P-1), R$^{15}$ is H or C$_{1-3}$-alkyl and R$^{15a}$ is —(C$_{1-3}$-alkylene)-C(O)NHNH$_2$. In some or any embodiments of Formula (I), (I-P), or (I-P-1), R$^{15}$ is H or methyl and R$^{15a}$ is —(C$_{1-3}$-alkylene)-C(O)NHNH$_2$. In some or any embodiments of Formula (I), (I-P), or (I-P-1), R$^{15}$ is H and R$^{15a}$ is —(C$_{1-3}$-alkylene)-C(O)NHNH$_2$. In some or any embodiments of Formula (I), (I-P), or (I-P-1), R$^{15}$ is methyl and R$^{15a}$ is —(C$_{1-3}$-alkylene)-C(O)NHNH$_2$. In some or any embodiments of Formula (I), (I-P), or (I-P-1), R$^{15}$ is H and R$^{15a}$ is —(C$_1$-alkylene)-C(O)NHNH$_2$. In some or any embodiments of Formula (I), (I-P), or (I-P-1), R$^{15}$ is methyl and R$^{15a}$ is —(C$_1$-alkylene)-C(O)NHNH$_2$. In some or any embodiments of Formula (I), $R^{15}$ is H or $C_1$-$C_6$alkyl and $R^{15a}$ is —($C_1$-$C_{10}$-alkylene)-SH. In some or any embodiments of Formula (I), $R^{15}$ is H or $C_1$-$C_3$alkyl and $R^{15a}$ is —($C_1$-$C_{10}$-alkylene)-SH. In some or any embodiments of Formula (I), $R^{15}$ is H or $CH_3$ and $R^{15a}$ is —($C_1$-$C_{10}$-alkylene)-SH. In some or any embodiments of Formula (I), $R^Z$ is —($C_1$-$C_{10}$-alkylene)-$NR^{50}C(O)$—($C_1$-$C_{10}$-alkylene)-$NR^{50a}R^{50b}$ where each $C_1$-$C_{10}$-alkylene is independently optionally substituted with one or more hydroxy. In some or any embodiments of Formula (I), $R^Z$ is -(branched $C_1$-$C_6$-alkylene)-$NR^{50}C(O)$—($C_1$-$C_6$-hydroxy-alkylene)-$NR^{50a}R^{50b}$. In some or any embodiments of Formula (I), $R^Z$ is -(branched $C_1$-$C_6$-alkylene)-$NR^{50}C(O)$—($C_1$-$C_6$-alkylene)-$NR^{50a}R^{50b}$.

In some embodiments, provided is a Compound of Formula (I), where a) both $R^x$ are hydrogen; and
$R^3$ is —$C(O)R^Z$; —($C_1$-$C_{10}$-alkylene)-$NR^{50}C(O)$—($C_1$-$C_{10}$-alkylene)-$NR^{50a}R^{50b}$; or

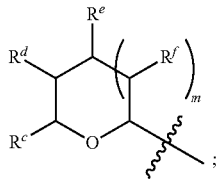
;

$R^Z$ is —$C_{4-10}$-alkylene-C(O)OH; —($C_1$-$C_{10}$-alkylene)-$NR^{50}C(O)$—($C_1$-$C_{10}$-alkylene)-$NR^{50a}R^{50b}$ where each $C_1$-$C_{10}$-alkylene is independently optionally substituted with one or more hydroxy; or $NR^{15}R^{15a}$;
$R^{15}$ is H or $C_1$-$C_6$alkyl and $R^{15a}$ is —($C_1$-$C_{10}$-alkylene)-SH or —($C_1$-$C_6$-alkylene)-C(O)NHNH$_2$; or b) both $R^x$ are fluoro; and
$R^3$ is —$C(O)R^Z$; —($C_1$-$C_{10}$-alkylene)-$NR^{50}C(O)$—($C_1$-$C_{10}$-alkylene)-$NR^{50a}R^{50b}$; or

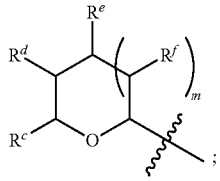
;

$R^Z$ is —$C_{4-10}$-alkylene-C(O)OH; —($C_1$-$C_{10}$-alkylene)-$NR^{50}C(O)$—($C_1$-$C_{10}$-alkylene)-$NR^{50a}R^{50b}$ where each $C_1$-$C_{10}$-alkylene is independently optionally substituted with one or more hydroxy; or $NR^{16}R^{16a}$;
$R^{16}$ is H or $C_1$-$C_6$alkyl and $R^{16a}$ is —($C_1$-$C_{10}$-alkylene)-SH, —($C_1$-$C_{10}$-alkylene)-NH$_2$, —($C_1$-$C_{10}$-alkylene)-NH($C_{1-6}$alkyl),

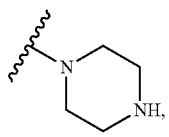

or —($C_{1-6}$-alkylene)-C(O)NHNH$_2$; and
each $R^{50}$, $R^{50a}$, and $R^{50b}$ are independently hydrogen or $C_1$-$C_6$-alkyl;

one of $R^c$, $R^d$, $R^e$, and $R^f$ is —$CH_2OR^g$ and the others are independently —H, —OH, hydroxyalkyl, —C(O)OH, or —$CH_2OR^g$, where each $R^g$ is independently —($C_{1-6}$-alkylene)-C(O)OH or —($C_{1-6}$-alkylene)-C(O)O(alkyl); or one of $R^c$, $R^d$, $R^e$, and $R^f$ is hydroxyalkyl and the others are —H; and
m is 0 or 1.

In some embodiments of Formula (I), both $R^x$ are fluoro and $R^3$ is —$C(O)R^Z$. In some or any embodiments, $R^Z$ is

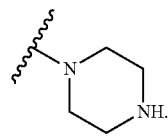

In some or any embodiments of Formula (I), $R^Z$ is —$C_{4-10}$-alkylene-C(O)OH. In some or any embodiments of Formula (I), $R^Z$ is —$C_{4-6}$-alkylene-C(O)OH. In some or any embodiments of Formula (I), $R^Z$ is —$C_4$-alkylene-C(O)OH. In some or any embodiments of Formula (I), $R^Z$ is —$C_5$-alkylene-C(O)OH. In some or any embodiments of Formula (I), $R^Z$ is —$C_6$-alkylene-C(O)OH. In some or any embodiments of Formula (I), $R^Z$ is $NR^{16}R^{16a}$. In some or any embodiments of Formula (I), $R^{16}$ is H or $C_{1-3}$-alkyl and $R^{16a}$ is —($C_{1-3}$-alkylene)-C(O)NHNH$_2$. In some or any embodiments of Formula (I), $R^{16}$ is H or methyl and $R^{16a}$ is —($C_{1-3}$-alkylene)-C(O)NHNH$_2$. In some or any embodiments of Formula (I), $R^{16}$ is H and $R^{16a}$ is —($C_{1-3}$-alkylene)-C(O)NHNH$_2$. In some or any embodiments of Formula (I), $R^{16}$ is methyl and $R^{16a}$ is —($C_{1-3}$-alkylene)-C(O)NHNH$_2$. In some or any embodiments of Formula (I), $R^{16}$ is H and $R^{16a}$ is —($C_1$alkylene)-C(O)NHNH$_2$. In some or any embodiments of Formula (I), $R^{16}$ is methyl and $R^{16a}$ is —($C_1$-alkylene)-C(O)NHNH$_2$. In some or any embodiments of Formula (I), $R^{16}$ is H or $C_1$-$C_6$alkyl and $R^{16a}$ is —($C_1$-$C_{10}$-alkylene)-SH. In some or any embodiments of Formula (I), $R^{16}$ is H or $C_1$-$C_3$alkyl and $R^{16a}$ is —($C_1$-$C_{10}$-alkylene)-SH. In some or any embodiments of Formula (I), $R^{16}$ is H or $CH_3$ and $R^{16a}$ is —($C_1$-$C_{10}$-alkylene)-SH. In some or any embodiments of Formula (I), $R^{16}$ is H or $C_1$-$C_6$alkyl and $R^{16a}$ is —($C_1$-$C_{10}$-alkylene)-NH$_2$. In some or any embodiments of Formula (I), $R^{16}$ is H or $C_1$-$C_3$alkyl and $R^{16a}$ is —($C_1$-$C_{10}$-alkylene)-NH$_2$. In some or any embodiments of Formula (I), $R^{16}$ is H or $CH_3$ and $R^{16a}$ is —($C_1$-$C_{10}$-alkylene)-NH$_2$. In some or any embodiments of Formula (I), $R^{16}$ is H or $C_1$-$C_6$alkyl and $R^{16a}$ is —($C_1$-$C_{10}$-alkylene)-NH($C_{1-6}$alkyl). In some or any embodiments of Formula (I), $R^{16}$ is H or $C_1$-$C_3$alkyl and $R^{16a}$ is —($C_1$-$C_{10}$-alkylene)-NH($C_{1-6}$alkyl). In some or any embodiments of Formula (I), $R^{16}$ is H or $CH_3$ and $R^{16a}$ is —($C_1$-$C_{10}$-alkylene)-NH($C_{1-6}$alkyl). In some or any embodiments of Formula (I), $R^Z$ is —($C_1$-$C_{10}$-alkylene)-$NR^{50}C(O)$—($C_1$-$C_{10}$-alkylene)-$NR^{50a}R^{50b}$ where each $C_1$-$C_{10}$-alkylene is independently optionally substituted with one or more hydroxy. In some or any embodiments of Formula (I), $R^Z$ is -(branched $C_1$-$C_6$-alkylene)-$NR^{50}C(O)$—($C_1$-$C_6$-hydroxy-alkylene)-$NR^{50a}R^{50b}$. In some or any embodiments of Formula (I), $R^Z$ is -(branched $C_1$-$C_6$-alkylene)-$NR^{50}C(O)$—($C_1$-$C_6$-alkylene)-$NR^{50a}R^{50b}$.

In some embodiments of Formula (I), (I-P), or (I-P-1), both $R^x$ are hydrogen and $R^3$ is —($C_1$-$C_{10}$-alkylene)-$NR^{50}C(O)$—($C_1$-$C_{10}$-alkylene)-$NR^{50a}R^{50b}$. In some or any embodiments of Formula (I), (I-P), or (I-P-1), $R^3$ is —($C_1$-$C_6$-alkylene)-$NR^{50}C(O)$—($C_1$-$C_6$-alkylene)-$NR^{50a}R^{50b}$. In some or any embodiments of Formula (I), (I-P), or (I-P-1), R³ is —(C₁-C₃-alkylene)-NR⁵⁰C(O)—(C₁-C₃-alkylene)-NR⁵⁰ᵃR⁵⁰ᵇ. In some or any embodiments of Formula (I), (I-P), or (I-P-1), R³ is -(linear C₁-C₃-alkylene)-NR⁵⁰C(O)-(linear C₁-C₃-alkylene)-NR⁵⁰ᵃR⁵⁰ᵇ.

In some embodiments of Formula (I), both Rˣ are fluoro and R³ is —(C₁-C₁₀-alkylene)-NR⁵⁰C(O)—(C₁-C₁₀-alkylene)-NR⁵⁰ᵃR⁵⁰ᵇ. In some or any embodiments of Formula (I), R³ is —(C₁-C₆-alkylene)-NR⁵⁰C(O)—(C₁-C₆-alkylene)-NR⁵⁰ᵃR⁵⁰ᵇ. In some or any embodiments of Formula (I), R³ is —(C₁-C₃-alkylene)-NR⁵⁰C(O)—(C₁-C₃-alkylene)-NR⁵⁰ᵃR⁵⁰ᵇ. In some or any embodiments of Formula (I), R³ is -(linear C₁-C₃-alkylene)-NR⁵⁰C(O)-(linear C₁-C₃-alkylene)-NR⁵⁰ᵃR⁵⁰ᵇ.

In some embodiments of Formula (I), (I-P), or (I-P-1), both Rˣ are hydrogen and R³ is

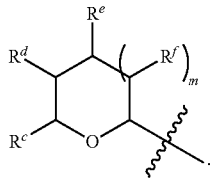

In some embodiments of Formula (I), (I-P), or (I-P-1), m is 0. In some embodiments of Formula (I), (I-P), or (I-P-1), m is 1. In some embodiments of Formula (I), (I-P), or (I-P-1), m is 1 and Rᶠ is —H or —OH. In some embodiments of Formula (I), (I-P), or (I-P-1), m is 1. In some embodiments of Formula (I), (I-P), or (I-P-1), m is 1 and one of Rᶜ, Rᵈ, Rᵉ, and Rᶠ is —CH₂ORᵍ and the others are independently —H, —OH, hydroxyalkyl, —C(O)OH, or —CH₂ORᵍ, where each Rᵍ is independently —(C₁₋₆-alkylene)-C(O)OH or —(C₁₋₆-alkylene)-C(O)O(alkyl). In some embodiments of Formula (I), (I-P), or (I-P-1), m is 1 and Rᶜ is —CH₂ORᵍ and the others are independently —H, —OH, or hydroxyalkyl. In some embodiments of Formula (I), (I-P), or (I-P-1), m is 1 and one of Rᶜ, Rᵈ, Rᵉ, and Rᶠ is hydroxyalkyl and the others are —H. In some embodiments of Formula (I), (I-P), or (I-P-1), m is 1 and Rᵉ is hydroxyalkyl, and Rᵈ, Rᵉ, and Rᶠ are —H.

In some embodiments of Formula (I), both Rˣ are fluoro and R³ is

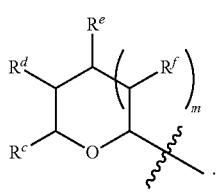

In some embodiments of Formula (I), m is 0. In some embodiments of Formula (I), m is 1. In some embodiments of Formula (I), m is 1 and Rᶠ is —H or —OH. In some embodiments of Formula (I), m is 1. In some embodiments of Formula (I), m is 1 and one of Rᶜ, Rᵈ, Rᵉ, and Rᶠ is —CH₂ORᵍ and the others are independently —H, —OH, hydroxyalkyl, —C(O)OH, or —CH₂ORᵍ, where each Rᵍ is independently —(C₁₋₆-alkylene)-C(O)OH or —(C₁₋₆-alkylene)-C(O)O(alkyl). In some embodiments of Formula (I), m is 1 and Rᶜ is —CH₂ORᵍ and the others are independently —H, —OH, or hydroxyalkyl. In some embodiments of Formula (I), m is 1 and one of Rᶜ, Rᵈ, Rᵉ, and Rᶠ is hydroxyalkyl and the others are —H. In some embodiments of Formula (I), m is 1 and Rᵉ is hydroxyalkyl, and Rᵈ, Rᵉ, and Rᶠ are —H.

In some embodiments of Formula (I), both Rˣ are fluoro and R³ is

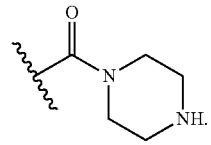 [SMILES: *C(=O)N1CCNCC1]

In some or any embodiments, the Compound according to Formula (Z):

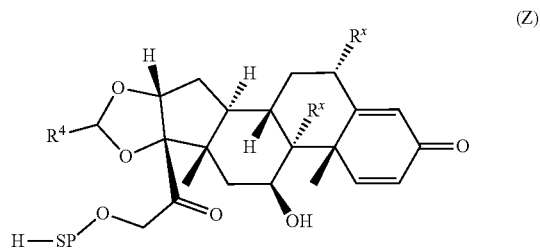

where
R⁴ is alkyl, aryl, arylalkyl, or an N-containing heterocycloalkyl;
both Rˣ are hydrogen or both Rˣ are fluoro; and
SP is —CH₂NH— where the NH is connected to H, or SP is

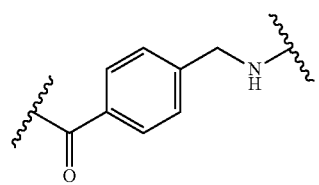 [SMILES: *NCc1ccc(C(*)=O)cc1]

where the NH of SP is connected to H in Formula (Z), or SP is

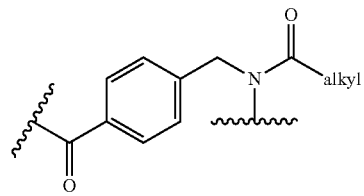

where the N of SP is connected to H in Formula (Z). In some or any embodiments, both Rˣ are hydrogen. In some or any embodiments, both Rˣ are fluoro. In some or any embodiments, R⁴ is alkyl. In some of these embodiments, R⁴ is linear alkyl. In some embodiments, R⁴ is alkyl such as, but not limited to, methyl, ethyl, propyl, butyl, pentyl, hexyl, heptyl, octyl, or nonyl. In some embodiments, R⁴ is methyl. In some embodiments, R⁴ is ethyl. In some embodiments, R⁴ is n-propyl. In some embodiments, R⁴ is i-propyl. In some embodiments, R⁴ is n-butyl. In some embodiments, R⁴ is i-butyl. In some embodiments, R⁴ is t-butyl. In some embodiments, R⁴ is sec-butyl. In some embodiments, R⁴ is pentyl. In some embodiments, R⁴ is hexyl. In some embodiments, R⁴ is heptyl. In some embodiments, R⁴ is octyl, or nonyl. In some or any embodiments, SP is —CH₂NH— where the NH is connected to H. In some or any embodiments, SP is

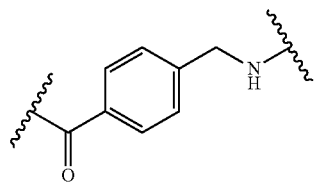 [SMILES: *NCc1ccc(C(*)=O)cc1]

where NH is connected to H in Formula (Z). In some or any embodiments, R⁴ is alkyl, both R$^x$ are fluoro, and SP is

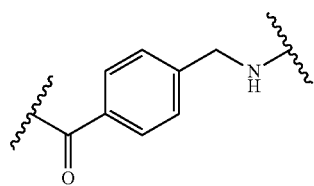 [SMILES: *NCc1ccc(C(*)=O)cc1]

where NH is connected to H in Formula (Z). In some embodiments, the Compound of Formula (Z) is

In some embodiments, the Compound of Formula (Z) is

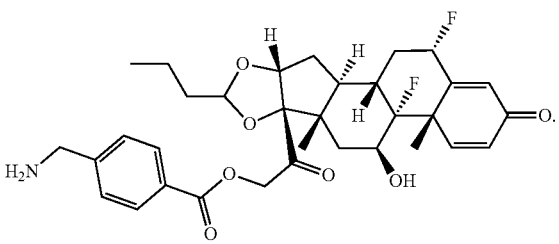

In some embodiments, the Compound of Formula (Z) is

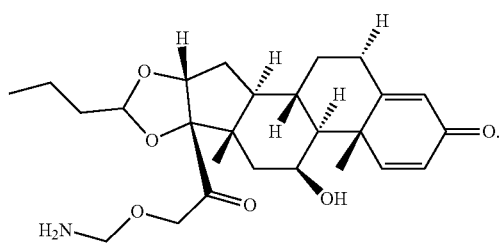

In some embodiments, the Compound of Formula (Z) is

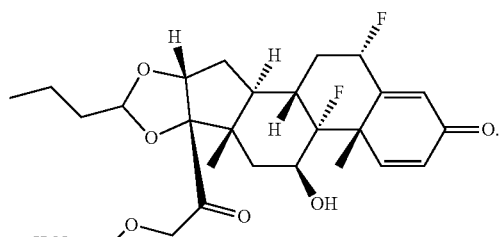

Suitable steroids for the conjugates described herein include those in the following table.

TABLE 1

| Budesonide-spacer (Budesonide-SP) | |
|---|---|
| Compound No. | Structure |
| 1a (Budesonide) | (structure) |

TABLE 1-continued

Budesonide-spacer (Budesonide-SP)

| Compound No. | Structure |
|---|---|
| 1c | 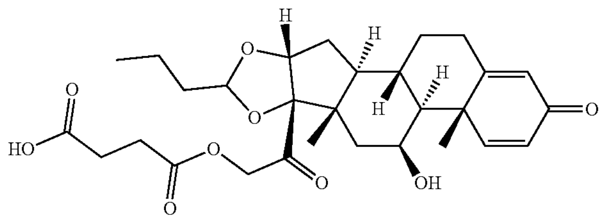 |
| 1d | 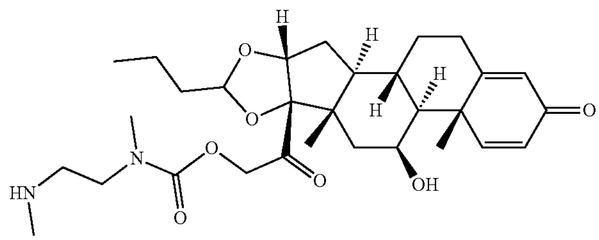 |
| 1e | 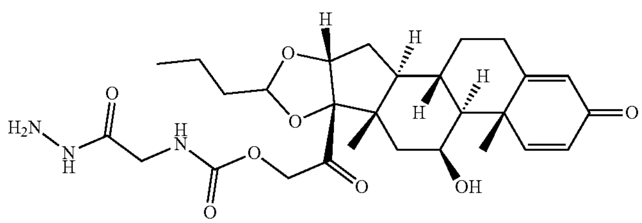 |
| 1g | 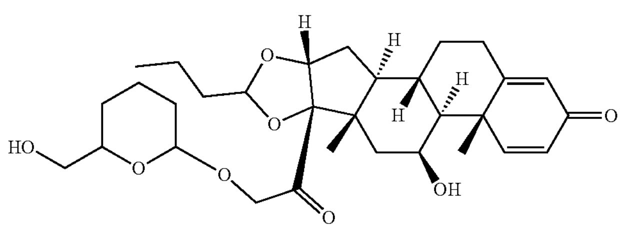 |
| 1h | 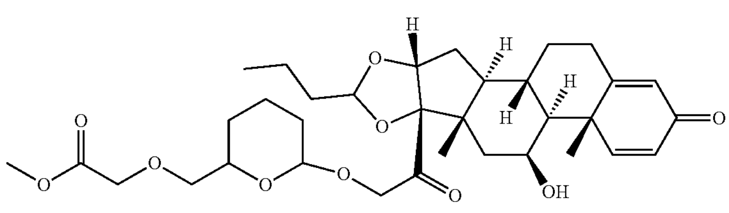 |
| 1i | 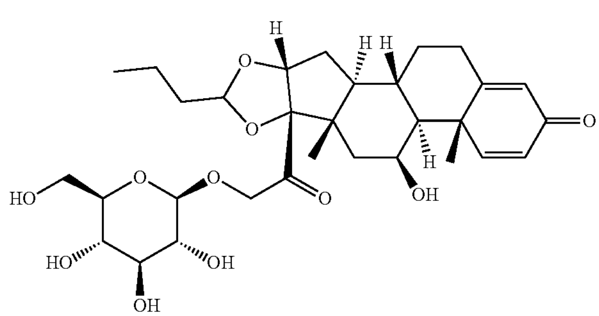 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](CO)[C@@H](O)[C@H](O)[C@H]2O)O1] |

TABLE 1-continued

Budesonide-spacer (Budesonide-SP)

| Compound No. | Structure |
|---|---|
| 1j | 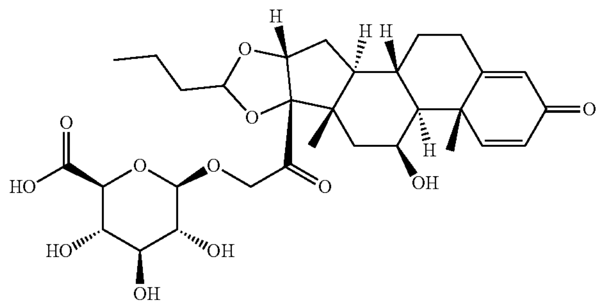 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](C(=O)O)[C@@H](O)[C@H](O)[C@H]2O)O1] |
| 1k | 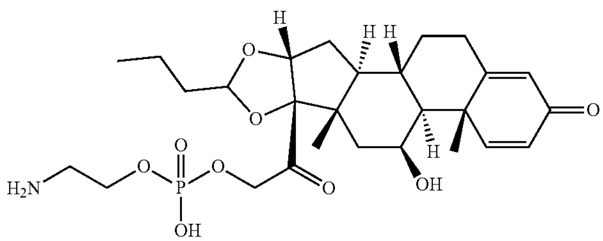 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OCCN)O1] |
| 1l | 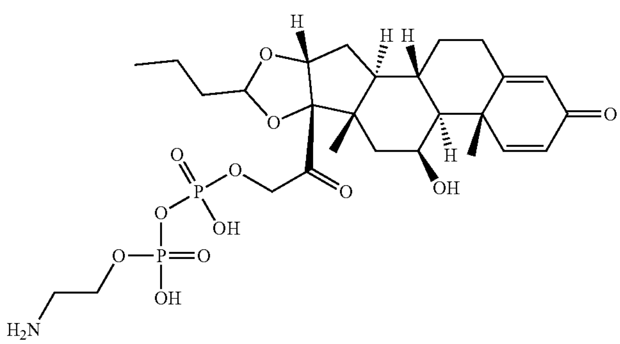 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OP(=O)(O)OCCN)O1] |
| 1m | 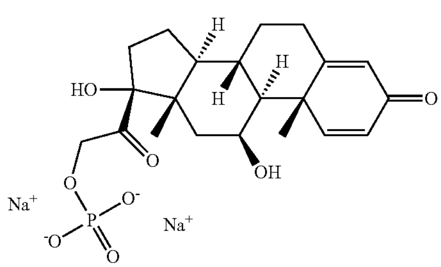 |
| 100 | 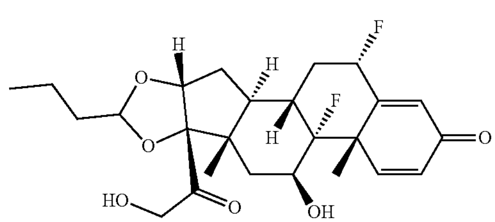 |

TABLE 1-continued
Budesonide-spacer (Budesonide-SP)
| Compound No. | Structure |
|---|---|
| 101a | 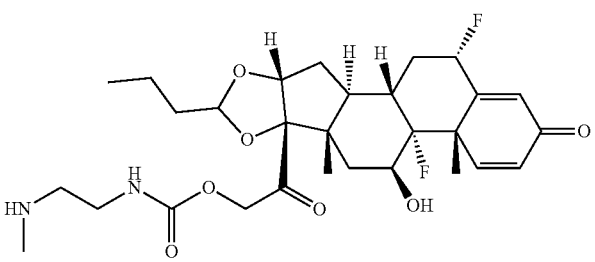 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCNC)O1] |
| 101b | 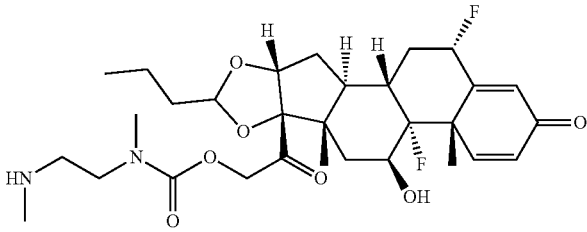 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCNC)O1] |
| 101c | 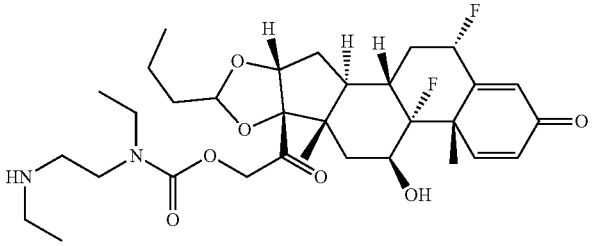 |
| 101d | 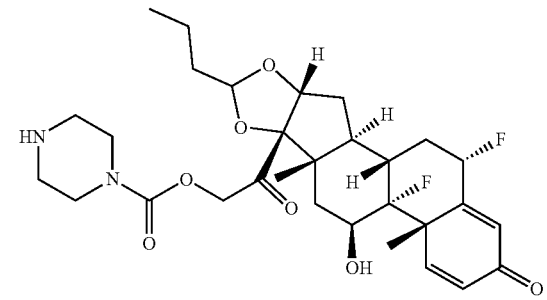 |
| 102c | 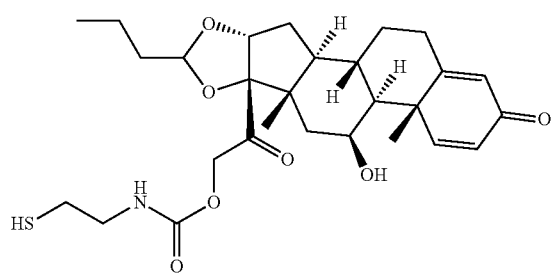 |

TABLE 1-continued

Budesonide-spacer (Budesonide-SP)

| Compound No. | Structure |
|---|---|
| 102d | 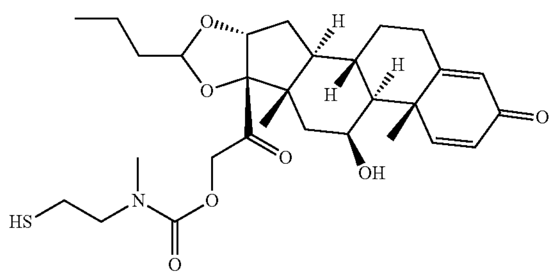 |
| 102e | 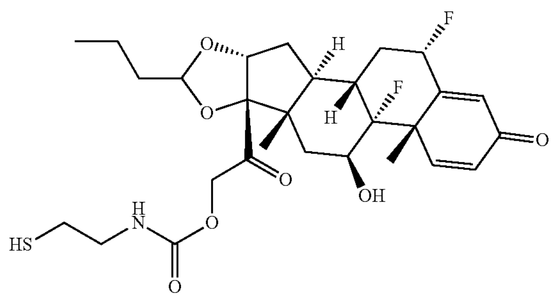 |
| 102f | 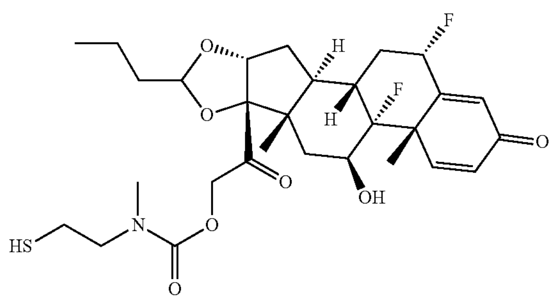 |
| 103a | 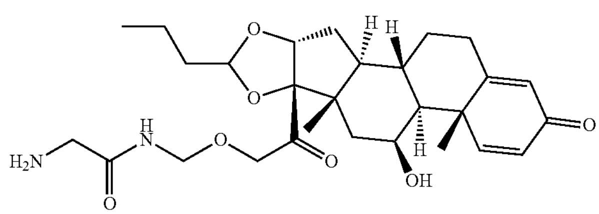 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COCNC(=O)CN)O1] |
| 103b | 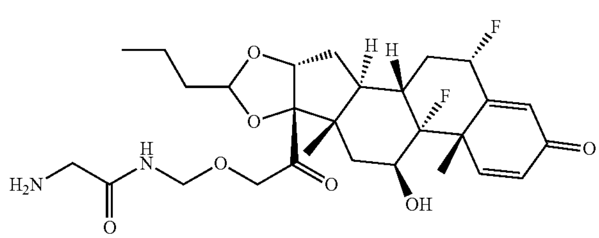 |

TABLE 1-continued

Budesonide-spacer (Budesonide-SP)

| Compound No. | Structure |
|---|---|
| 104a | 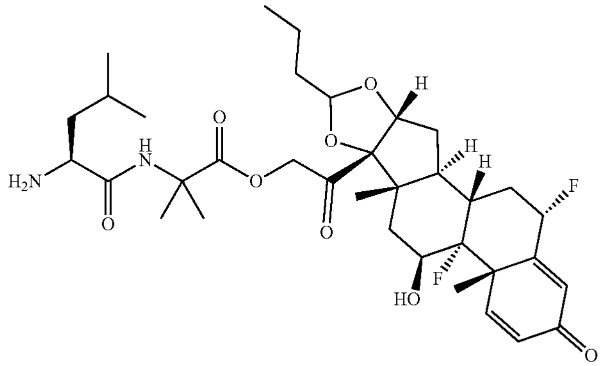 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@@H](N)CC(C)C)O1] |
| 104b | 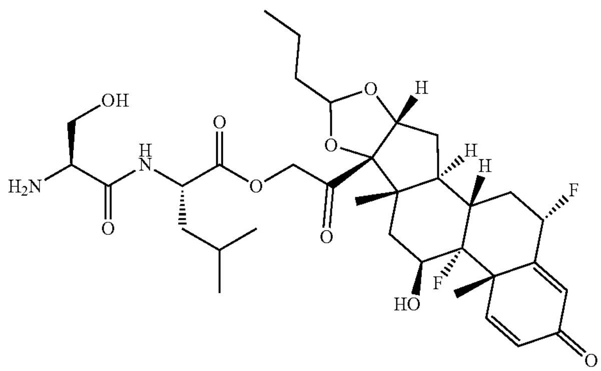 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@@H](N)CO)O1] |
| 105a | 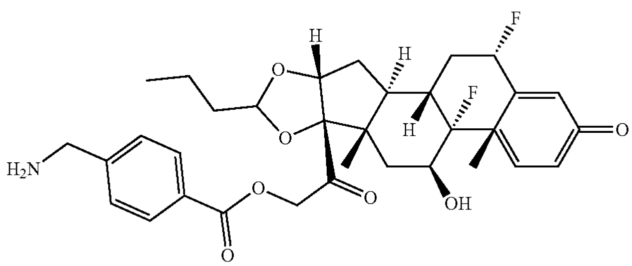 |
| 106a | 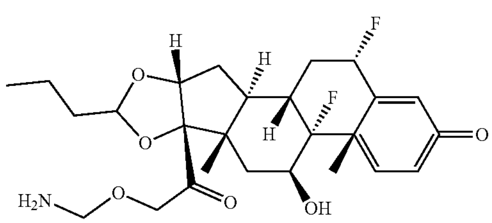 |
| 107a | | or a stereoisomer or mixture of stereoisomers thereof, and optionally a pharmaceutically acceptable salt, solvate, or stereoisomer thereof. In some instances, the n-propyl of

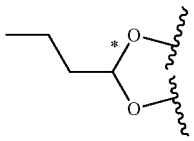 [SMILES: *OC(CCC)O*]

in each of the above structures is in the R-configuration, i.e. at the carbon indicated by the asterisk. In some instances, the n-propyl of

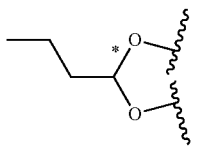 [SMILES: *OC(CCC)O*]

in each of the above structures is in the S-configuration, i.e. at the carbon indicated by the asterisk. In some instances, the n-propyl of

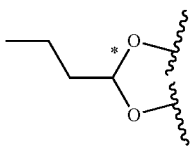 [SMILES: *OC(CCC)O*]

in each of the above structures is a mixture of the R- and S-configurations, i.e. at the carbon indicated by the asterisk. In some instances, the n-propyl of

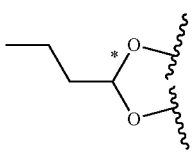 [SMILES: *OC(CCC)O*]

in each of the above structures is a mixture of the R- and S-configurations, i.e. at the carbon indicated by the asterisk, wherein the R:S mixture is about 1:1, about 2:1, about 3:1, about 4:1, about 5:1, about 6:1, about 7:1, about 8:1, about 9:1, or about 10:1.

In some embodiments of Formula (I), provided is a compound of formula 1d, 1e, 1g, 1h, 101a, 101b, 101c, 101d, 102c, 102d, 102e, 102f, 103a, 103b, 104a, or 104b, or a pharmaceutically acceptable salt, solvate, or stereoisomer thereof. In some embodiments of Formula (I), provided is a compound of formula 1d, 1e, 1g, or 1h, or a pharmaceutically acceptable salt, solvate, or stereoisomer thereof. In some embodiments, the n-propyl of the compounds of formula 1d, 1e, 1g, 1h, 101a, 101b, 101c, 101d, 102c, 102d, 102e, 102f, 103a, 103b, 104a, and 104b is in the R-configuration. In some embodiments, the n-propyl of the compounds of formula 1d, 1e, 1g, 1h, 101a, 101b, 101c, 101d, 102c, 102d, 102e, 102f, 103a, 103b, 104a, and 104b is in the S-configuration. In some embodiments, the n-propyl of the compounds of formula 1d, 1e, 1g, 1h, 101a, 101b, 101c, 101d, 102c, 102d, 102e, 102f, 103a, 103b, 104a, and 104b is a mixture of the R- and S-configurations. In some embodiments, the n-propyl of the compounds of formula 1d, 1e, 1g, 1h, 101a, 101b, 101c, 101d, 102c, 102d, 102e, 102f, 103a, 103b, 104a, and 104b is a mixture of the R- and S-configurations, wherein the R:S mixture is about 1:1, about 2:1, about 3:1, about 4:1, about 5:1, about 6:1, about 7:1, about 8:1, about 9:1, or about 10:1.

Included within the scope of this disclosure are pharmaceutically acceptable salts, solvates, crystalline forms, amorphous forms, polymorphic forms, regioisomers, stereoisomers, metabolites, and physiological adducts of the steroid payloads described herein.

C. Protein Steroid Conjugates

Provided herein are protein conjugates of the steroids described herein. Such conjugates include proteins, e.g., antibodies or antigen-binding fragments thereof, that are covalently linked, e.g., via the -L- and -$L^1$-$L^2$-($L^3$)$_{0-1}$-described herein, to the compounds described in Section B above.

In some or any embodiments, set forth is a Compound of Formula (3000):

or a pharmaceutically acceptable salt, solvate, stereoisomer, or derivative thereof,
wherein
D is selected from
a)

formula (a)

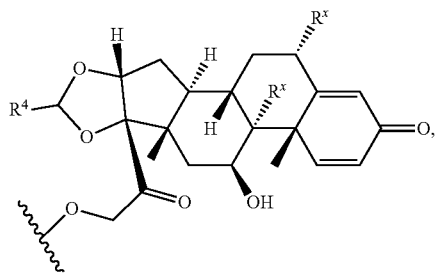

where both $R^x$ in formula (a) are hydrogen; $R^4$ is alkyl, aryl, arylalkyl, or an N-containing heterocycloalkyl; and SP is —C(O)—$C_1$-$C_{10}$-alkylene-C(O)—, —C(O)—N($C_{1-6}$alkyl)-$C_1$-$C_{10}$-alkylene-$X^1$- where $X^1$ is attached to L in Formula (3000), —C(O)—N(H)—($C_1$-$C_{10}$-alkylene)-S— where S is attached to L in Formula (3000), —C(O)—N($C_{1-6}$alkyl)-($C_1$-$C_{10}$-alkylene)-S— where S is attached to L in Formula (3000),

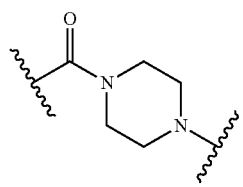 [SMILES: *C(=O)N1CCN(*)CC1]

where the point of attachment on the right hand side (i.e. at N) is to L in Formula (3000), —CH$_2$—NH— where the N is attached to L in Formula (3000),

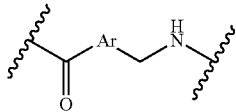

where the N is attached to L in Formula (3000) and where Ar is optionally substituted arylene (in some embodiments

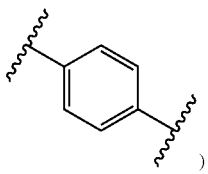 [SMILES: *c1ccc(*)cc1]

)

or optionally substituted heteroarylene, —(C$_1$-C$_{10}$-alkylene)-NR$^{50}$C(O)—(C$_1$-C$_{10}$-alkylene)-NR$^{50a}$- where NR$^{50a}$ is attached to L in Formula (3000), —C(O)—(C$_1$-C$_{10}$-alkylene)-NR$^{50}$C(O)—(C$_1$-C$_{10}$-alkylene)-NR$^{50a}$- where NR$^{50a}$ is attached to L in Formula (3000) and where each C$_1$-C$_{10}$-alkylene is independently optionally substituted with one or more hydroxy, —C(O)—N(R$^5$)—C$_1$-C$_{10}$-alkylene-C(O)NH-X$^2$- where X$^2$ is attached to L in Formula (3000), or

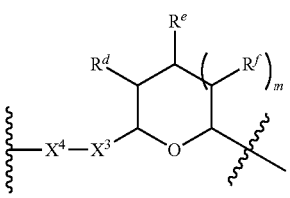

where X$^4$ is attached to L in Formula (3000); or where both R$^x$ in formula (a) are fluoro; R$^4$ is alkyl, aryl, arylalkyl, or an N-containing heterocycloalkyl; and SP is —C(O)—C$_1$-C$_{10}$-alkylene-C(O)—, —C(O)—N(C$_{1-6}$alkyl)-C$_1$-C$_{10}$-alkylene-X$^{1b}$- where X$^{1b}$ is attached to L in Formula (3000), —C(O)—N(H)—(C$_1$-C$_{10}$-alkylene)-X$^{1b}$- where X$^{1b}$ is attached to L in Formula (3000),

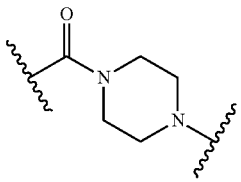 [SMILES: *C(=O)N1CCN(*)CC1]

(where the point of attachment on the right hand side (i.e. at N) is to L in Formula (3000), —CH$_2$—NH— where N is attached to L in Formula (3000),

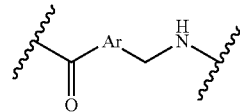

where the N is attached to L in Formula (3000) and where Ar is optionally substituted arylene (in some embodiments

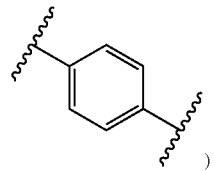 [SMILES: *c1ccc(*)cc1]

)

or optionally substituted heteroarylene, —(C$_1$-C$_{10}$-alkylene)-NR$^{50}$C(O)—(C$_1$-C$_{10}$-alkylene)-NR$^{50a}$- where NR$^{50a}$ is attached to L in Formula (3000), —C(O)—(C$_1$-C$_{10}$-alkylene)-NR$^{50}$C(O)—(C$_1$-C$_{10}$-alkylene)-NR$^{50a}$- where NR$^{50a}$ is attached to L in Formula (3000) and where each C$_1$-C$_{10}$-alkylene is independently optionally substituted with one or more hydroxy, —C(O)—N(R$^5$)—(C$_1$-C$_{10}$-alkylene)-C(O)NH-X$^2$- where X$^2$ is attached to L in Formula (3000), or

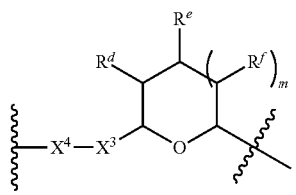

where X$^4$ is attached to L in Formula (3000); and
b) the compounds in Table A above, where the compounds in Table A are linked to BA of the Compound of Formula (3000) through the hydroxy of the —C(O)CH$_2$OH group, i.e. by —C(O)CH$_2$—O-SP-L-, or through the hydroxy of Mapracorat, i.e. by -O-SP-L-:

X$^1$ is —N(C$_{1-6}$alkyl)-;
X$^{1b}$ is —S—, —NH—, or —N(C$_{1-6}$alkyl)-;
X$^2$ is —NH—;
X$^3$ is —CH$_2$—, X$^3$ is —CH$_2$—O—(C$_1$-C$_{10}$-alkylene)-C(O)— where the C(O) is attached to X$^4$, or X$^3$ is —C(O)—;
X$^4$ is —O—;
R$^5$ is H, —OH, —OCH$_3$, or C$_{1-6}$alkyl;
R$^{50}$ and R$^{50a}$ are independently hydrogen or C$_1$-C$_6$-alkyl;
R$^d$, R$^e$, and R$^f$ are independently —H, —OH, hydroxyalkyl, alkoxycarbonyl, —C(O)OH, or —CH$_2$OR$^g$, where each R$^g$ is independently —CH$_2$C(O)OH or —CH$_2$C(O)O(alkyl); and
m is 0 or 1;
z is an integer selected from 1-30, inclusive;
L is a linker; and
BA is a binding agent.

In some or any embodiments, set forth is a Compound of Formula (III-P):

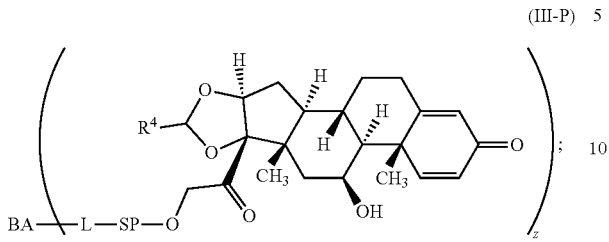

(III-P)

or a pharmaceutically acceptable salt, solvate, stereoisomer, or derivative thereof,
wherein:
R$^4$ is alkyl, aryl, arylalkyl, or an N-containing heterocycloalkyl;
SP is —C(O)—C$_1$-C$_{10}$-alkylene-C(O)—, —C(O)—N(C$_{1-3}$alkyl)-C$_1$-C$_{10}$-alkylene-X$^1$- where X$^1$ is attached to L in Formula (III), —C(O)—N(R$^5$)-C$_1$-C$_{10}$-alkylene-C(O)NH-X$^2$- where X$^2$ is attached to L in Formula (III), or

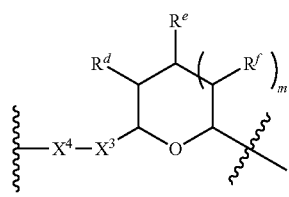

where X$^4$ is attached to L in Formula (III);
X$^1$ is —N(C$_{1-3}$alkyl)-;
X$^2$ is —NH—;
X$^3$ is —CH$_2$—, X$^3$ is —CH$_2$—O—(C$_1$-C$_{10}$-alkylene)-C(O)— where the C(O) is attached to X$^4$, or X$^3$ is —C(O)—;
X$^4$ is —O—;
R$^5$ is H, —OH, —OCH$_3$, or alkyl;
R$^d$, R$^e$, and R$^f$ are independently —H, —OH, hydroxyalkyl, alkoxycarbonyl, —C(O)OH, or —CH$_2$OR$^g$, where each R$^g$ is independently —CH$_2$C(O)OH or —CH$_2$C(O)O(alkyl); and
m is 0 or 1;
z is an integer selected from 1-30, inclusive;
L is a linker; and
BA is a binding agent.

In some or any embodiments, set forth is a Compound of Formula (III-P-1):

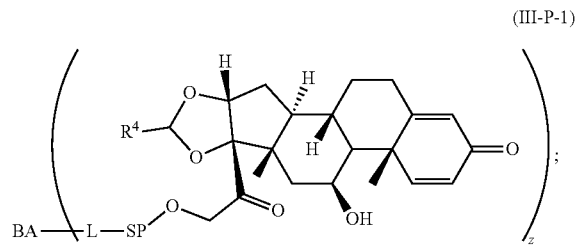

(III-P-1)

or a pharmaceutically acceptable salt, solvate, stereoisomer, or derivative thereof,
wherein:
R$^4$ is alkyl, aryl, arylalkyl, or an N-containing heterocycloalkyl;
SP is —C(O)—C$_1$-C$_{10}$-alkylene-C(O)—, —C(O)—N(C$_{1-3}$alkyl)-C$_1$-C$_{10}$-alkylene-X$^1$- where X$^1$ is attached to L in Formula (III), —C(O)—N(R$^5$)-C$_1$-C$_{10}$-alkylene-C(O)NH-X$^2$- where X$^2$ is attached to L in Formula (III), or

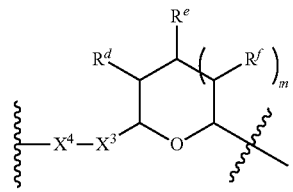

where X$^4$ is attached to L in Formula (III);
X$^1$ is —N(C$_{1-3}$alkyl)-;
X$^2$ is —NH—;
X$^3$ is —CH$_2$—, X$^3$ is —CH$_2$—O—(C$_1$-C$_{10}$-alkylene)-C(O)— where the C(O) is attached to X$^4$, or X$^3$ is —C(O)—;
X$^4$ is —O—;
R$^5$ is H, —OH, —OCH$_3$, or alkyl;
R$^d$, R$^e$, and R$^f$ are independently —H, —OH, hydroxyalkyl, alkoxycarbonyl, —C(O)OH, or —CH$_2$OR$^g$, where each R$^g$ is independently —CH$_2$C(O)OH or —CH$_2$C(O)O(alkyl); and
m is 0 or 1;
z is an integer selected from 1-30, inclusive;
L is a linker; and
BA is a binding agent.

In some embodiments, set forth herein is a compound of Formula (III), (III-P), or (III-P-1), where R$^4$ is alkyl. In some embodiments, R$^4$ is not cycloalkyl. In some of these embodiments, R$^4$ is linear or branched alkyl. In some of these embodiments, R$^4$ is aryl. In some of these embodiments, R$^4$ is arylalkyl. In some of these embodiments, R$^4$ is N-containing heterocycloalkyl. In some embodiments, R$^4$ is alkyl such as, but not limited to, methyl, ethyl, propyl, butyl, pentyl, hexyl, heptyl, octyl, or nonyl. In some embodiments, R$^4$ is methyl. In some embodiments, R$^4$ is ethyl. In some embodiments, R$^4$ is n-propyl. In some embodiments, R$^4$ is i-propyl. In some embodiments, R$^4$ is n-butyl. In some embodiments, R$^4$ is i-butyl. In some embodiments, R$^4$ is t-butyl. In some embodiments, R$^4$ is sec-butyl. In some embodiments, R$^4$ is pentyl. In some embodiments, R$^4$ is hexyl. In some embodiments, R$^4$ is heptyl. In some embodiments, R$^4$ is octyl, or nonyl. In some embodiments, R$^4$ is aryl such as but not limited to phenyl, phenol, or naphthyl. In some embodiments, R$^4$ is phenyl. In some embodiments, R$^4$ is naphthyl. In some embodiments, R$^4$ is heteroaryl—such as but not limited to thienyl. In some embodiments, R$^4$ is arylalkyl—such as but not limited to benzyl. In some embodiments, R$^4$ is N-containing heterocycloalkyl such as but not limited to piperidinyl. In some or any embodiments, both R$^x$ are hydrogen. In some or any embodiments, both R$^x$ are fluoro. In some embodiments, R$^4$ is in the R-configuration. In some embodiments, R$^4$ is in the S-configuration. In some embodiments, R$^4$ is a mixture of the R- and S-configurations. In some embodiments, R$^4$ is a mixture of the R- and S-configurations, wherein the R:S mixture is about 1:1, about 2:1, about 3:1, about 4:1, about 5:1, about 6:1, about 7:1, about 8:1, about 9:1, or about 10:1.

In some embodiments, provided is a Compound of Formula (III), where
  both $R^x$ are hydrogen; and SP is —C(O)—$C_1$-$C_{10}$-alkylene-C(O)—, —C(O)—N($C_{1-6}$alkyl)-$C_1$-$C_{10}$-alkylene-$X^1$- where $X^1$ is attached to L in Formula (III), (III-P), or (III-P-1); —C(O)—N(H)—($C_1$-$C_{10}$-alkylene)-S— where S is attached to L in Formula (III), (III-P), or (III-P-1); —C(O)—N($C_{1-6}$alkyl)-($C_1$-$C_{10}$-alkylene)-S— where S is attached to L in Formula (III), (III-P), or (III-P-1); —($C_1$-$C_{10}$-alkylene)-$NR^{50}$C(O)—($C_1$-$C_{10}$-alkylene)-$NR^{50a}$- where $NR^{50a}$ is attached to L in Formula (III), (III-P), or (III-P-1); —C(O)—($C_1$-$C_{10}$-alkylene)-$NR^{50}$C(O)—($C_1$-$C_{10}$-alkylene)-$NR^{50a}$- where $NR^{50a}$ is attached to L in Formula (III), (III-P), or (III-P-1), and where each $C_1$-$C_{10}$-alkylene is independently optionally substituted with one or more hydroxy; —C(O)—N($R^5$)—$C_1$-$C_{10}$-alkylene-C(O)NH-$X^2$- where $X^2$ is attached to L in Formula (III), (III-P), or (III-P-1); or

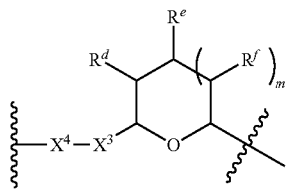

where $X^4$ is attached to L in Formula (III), (III-P), or (III-P-1); or
  both $R^x$ are fluoro; and SP is —C(O)—N($C_{1-6}$alkyl)-$C_1$-$C_{10}$-alkylene-$X^{1b}$- where $X^{1b}$ is attached to L in Formula (III), (III-P), or (III-P-1); —C(O)—N(H)—($C_1$-$C_{10}$-alkylene)-$X^{1b}$- where $X^{1b}$ is attached to L in Formula (III), (III-P), or (III-P-1);

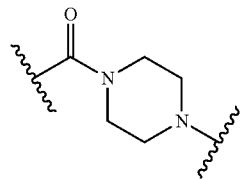 [SMILES: *C(=O)N1CCN(*)CC1]

where the point of attachment on the right hand side (i.e. at N) is to L in Formula (III); —($C_1$-$C_{10}$-alkylene)-$NR^{50}$C(O)—($C_1$-$C_{10}$-alkylene)-$NR^{50a}$- where $NR^{50a}$ is attached to L in Formula (III), (III-P), or (III-P-1); —C(O)—($C_1$-$C_{10}$-alkylene)-$NR^{50}$C(O)—($C_1$-$C_{10}$-alkylene)-$NR^{50a}$- where $NR^{50a}$ is attached to L in Formula (III), (III-P), or (III-P-1) and where each $C_1$-$C_{10}$-alkylene is independently optionally substituted with one or more hydroxy, or —C(O)—N($R^5$)—($C_1$-$C_{10}$-alkylene)-C(O)NH-$X^2$- where $X^2$ is attached to L in Formula (III), (III-P), or (III-P-1).

In some embodiments, set forth herein is a compound of Formula (III), (III-P), or (III-P-1), where both $R^x$ are hydrogen and SP is —C(O)—$C_1$-$C_{10}$-alkylene-C(O)—. In some embodiments, set forth herein is a compound of Formula (III), (III-P), or (III-P-1), where SP is —C(O)—$C_2$-$C_5$-alkylene-C(O)—. In some embodiments, set forth herein is a compound of Formula (III), (III-P), or (III-P-1), where SP is —C(O)—$CH_2CH_2$—C(O)—.

In some embodiments, set forth herein is a compound of Formula (III), where both $R^x$ are fluoro and SP is —C(O)—$C_1$-$C_{10}$-alkylene-C(O)—. In some embodiments, set forth herein is a compound of Formula (III), where SP is —C(O)—$C_2$-$C_5$-alkylene-C(O)—. In some embodiments, set forth herein is a compound of Formula (II), where SP is —C(O)—$CH_2CH_2$—C(O)—.

In some embodiments, set forth herein is a compound of Formula (III), (III-P), or (III-P-1), where both $R^x$ are hydrogen and SP is —C(O)—N($C_{1-6}$alkyl)-$C_1$-$C_{10}$-alkylene-$X^1$- where $X^1$ is attached to $L^3$ in Formula (III), (III-P), or (III-P-1). In some embodiments, set forth herein is a compound of Formula (III), (III-P), or (III-P-1), where SP is —C(O)—N($C_{1-3}$alkyl)-$C_1$-$C_{10}$-alkylene-$X^1$- where $X^1$ is attached to $L^3$ in Formula (III), (III-P), or (III-P-1). In some embodiments, set forth herein is a compound of Formula (III), (III-P), or (III-P-1), where $X^1$ is —N($C_{1-3}$alkyl)-. In some embodiments, set forth herein is a compound of Formula (III), (III-P), or (III-P-1), where SP is —C(O)—N($C_{1-3}$alkyl)-$C_2$-$C_5$-alkylene-$X^1$—. In some embodiments, set forth herein is a compound of Formula (III), (III-P), or (III-P-1), where SP is —C(O)—N($C_{1-3}$alkyl)-$CH_2CH_2$-$X^1$—. In some embodiments, set forth herein is a compound of Formula (III), (III-P), or (III-P-1), where SP is —C(O)—N($CH_3$)-$C_2$-$C_5$-alkylene-N($CH_3$)—. In some embodiments, set forth herein is a compound of Formula (III), (III-P), or (III-P-1), where SP is —C(O)—N($CH_3$)—$CH_2CH_2$—N($CH_3$)—.

In some embodiments, set forth herein is a compound of Formula (III), where both $R^x$ are fluoro and SP is —C(O)—N($C_{1-6}$alkyl)-$C_1$-$C_{10}$-alkylene-$X^{1b}$- where $X^{1b}$ is attached to $L^3$ in Formula (III) or —C(O)—N(H)—($C_1$-$C_{10}$-alkylene)-$X^{1b}$- where $X^{1b}$ is attached to L in Formula (III). In some embodiments, set forth herein is a compound of Formula (III), where SP is —C(O)—N(H)—$C_1$-$C_{10}$-alkylene-$X^{1b}$- where $X^{1b}$ is attached to $L^3$ in Formula (III). In some embodiments, set forth herein is a compound of Formula (III), where SP is —C(O)—N(H)—$C_1$-$C_6$-alkylene-$X^{1b}$- where $X^{1b}$ is attached to $L^3$ in Formula (III). In some embodiments, set forth herein is a compound of Formula (III), where SP is —C(O)—N(H)—$C_1$-$C_3$-alkylene-$X^{1b}$- where $X^{1b}$ is attached to $L^3$ in Formula (III). In some embodiments, set forth herein is a compound of Formula (III), where SP is —C(O)—N(H)—$CH_2CH_2$-$X^{1b}$—. In some embodiments, set forth herein is a compound of Formula (III), where SP is —C(O)—N(H)—$C_2$-$C_5$-alkylene-N($CH_3$)—. In some embodiments, set forth herein is a compound of Formula (III), where SP is —C(O)—N(H)—$C_2$-$C_5$-alkylene-N($CH_2CH_3$)—. In some embodiments, set forth herein is a compound of Formula (III), where SP is —C(O)—N(H)—$CH_2CH_2$—N($CH_3$)—.

In some embodiments, set forth herein is a compound of Formula (III), where both $R^x$ are fluoro and SP is —C(O)—N($C_{1-6}$alkyl)-$C_1$-$C_{10}$-alkylene-$X^{1b}$- where $X^{1b}$ is attached to $L^3$ in Formula (III). In some embodiments, set forth herein is a compound of Formula (III), where SP is —C(O)—N($C_{1-3}$alkyl)-$C_1$-$C_6$-alkylene-$X^{1b}$- where $X^{1b}$ is attached to $L^3$ in Formula (III). In some embodiments, set forth herein is a compound of Formula (III), where SP is —C(O)—N($C_{1-3}$alkyl)-$C_1$-$C_3$-alkylene-$X^{1b}$- where $X^{1b}$ is attached to $L^3$ in Formula (III). In some embodiments, set forth herein is a compound of Formula (III), where $X^{1b}$ is —N($C_{1-3}$alkyl)-. In some embodiments, set forth herein is a compound of Formula (III), where SP is —C(O)—N($C_{1-3}$alkyl)-$C_2$-$C_5$-alkylene-$X^{1b}$—. In some embodiments, set forth herein is a compound of Formula (III), where SP is —C(O)—N($C_{1-3}$alkyl)-$CH_2CH_2$-$X^{1b}$—. In some embodiments, set forth herein is a compound of Formula (III), where SP is —C(O)—N(CH$_3$)—C$_2$-C$_5$-alkylene-N(CH$_3$)—. In some embodiments, set forth herein is a compound of Formula (III), where SP is —C(O)—N(CH$_2$CH$_3$)—C$_2$-C$_5$-alkylene-N(CH$_2$CH$_3$)—. In some embodiments, set forth herein is a compound of Formula (III), where SP is —C(O)—N(CH$_3$)—CH$_2$CH$_2$—N(CH$_3$)—.

In some embodiments, set forth herein is a compound of Formula (III), where both R$^x$ are fluoro and SP is

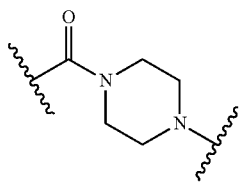 [SMILES: *C(=O)N1CCN(*)CC1]

where the point of attachment on the right hand side (i.e. at N) is to L in Formula (III).

In some embodiments, set forth herein is a compound of Formula (III), where both R$^x$ are hydrogen and SP is —C(O)—N(H)—(C$_1$-C$_{10}$-alkylene)-S— where S is attached to L in Formula (III), or —C(O)—N(C$_{1-6}$alkyl)-(C$_1$-C$_{10}$-alkylene)-S— where S is attached to L in Formula (III). In some embodiments, set forth herein is a compound of Formula (III), where SP is —C(O)—N(H)—(C$_1$-C$_6$-alkylene)-S— where S is attached to L in Formula (III), or —C(O)—N(C$_{1-3}$alkyl)-(C$_1$-C$_6$-alkylene)-S— where S is attached to L in Formula (III). In some embodiments, set forth herein is a compound of Formula (III), where SP is —C(O)—N(H)—(C$_1$-C$_{10}$-alkylene)-S— where S is attached to L in Formula (III). In some embodiments, set forth herein is a compound of Formula (III), where SP is —C(O)—N(H)—(C$_1$-C$_6$-alkylene)-S— where S is attached to L in Formula (III). In some embodiments, set forth herein is a compound of Formula (III), where SP is —C(O)—N(C$_{1-6}$alkyl)-(C$_1$-C$_{10}$-alkylene)-S— where S is attached to L in Formula (III). In some embodiments, set forth herein is a compound of Formula (III), where SP is —C(O)—N(C$_{1-3}$alkyl)-(C$_1$-C$_6$-alkylene)-S— where S is attached to L in Formula (III).

In some embodiments, set forth herein is a compound of Formula (III), where both R$^x$ are fluoro and SP is —C(O)—N(H)—(C$_1$-C$_{10}$-alkylene)-S— where S is attached to L in Formula (III), or —C(O)—N(C$_{1-6}$alkyl)-(C$_1$-C$_{10}$-alkylene)-S— where S is attached to L in Formula (III). In some embodiments, set forth herein is a compound of Formula (III), where SP is —C(O)—N(H)—(C$_1$-C$_6$-alkylene)-S— where S is attached to L in Formula (III), or —C(O)—N(C$_{1-3}$ alkyl)-(C$_1$-C$_6$-alkylene)-S— where S is attached to L in Formula (III). In some embodiments, set forth herein is a compound of Formula (III), where SP is —C(O)—N(H)—(C$_1$-C$_{10}$-alkylene)-S— where S is attached to L in Formula (III). In some embodiments, set forth herein is a compound of Formula (III), where SP is —C(O)—N(H)—(C$_1$-C$_6$-alkylene)-S— where S is attached to L in Formula (III). In some embodiments, set forth herein is a compound of Formula (III), where SP is —C(O)—N(C$_{1-6}$alkyl)-(C$_1$-C$_{10}$-alkylene)-S— where S is attached to L in Formula (III). In some embodiments, set forth herein is a compound of Formula (III), where SP is —C(O)—N(C$_{1-3}$alkyl)-(C$_1$-C$_6$-alkylene)-S— where S is attached to L in Formula (III).

In some embodiments, set forth herein is a compound of Formula (III), where both R$^x$ are hydrogen and SP is —(C$_1$-C$_{10}$-alkylene)-NR$^{50}$C(O)—(C$_1$-C$_{10}$-alkylene)-NR$^{50a}$ where NR$^{50a}$ is attached to L in Formula (III). In some or any embodiments of Formula (I), SP is —(C$_1$-C$_6$-alkylene)-NR$^{50}$C(O)—(C$_1$-C$_6$-alkylene)-NR$^{50a}$—. In some or any embodiments of Formula (III), SP is —(C$_1$-C$_3$-alkylene)-NR$^{50}$C(O)—(C$_1$-C$_3$-alkylene)-NR$^{50a}$-. In some or any embodiments of Formula (III), SP is -(linear C$_1$-C$_3$-alkylene)-NR$^{50}$C(O)-(linear C$_1$-C$_3$-alkylene)-NR$^{50a}$—.

In some embodiments, set forth herein is a compound of Formula (III), where both R$^x$ are fluoro and SP is —(C$_1$-C$_{10}$-alkylene)-NR$^{50}$C(O)—(C$_1$-C$_{10}$-alkylene)-NR$^{50a}$- where NR$^{50a}$ is attached to L in Formula (III). In some or any embodiments of Formula (I), SP is —(C$_1$-C$_6$-alkylene)-NR$^{50}$C(O)—(C$_1$-C$_6$-alkylene)-NR$^{50a}$—. In some or any embodiments of Formula (III), SP is —(C$_1$-C$_3$-alkylene)-NR$^{50}$C(O)—(C$_1$-C$_3$-alkylene)-NR$^{50a}$-. In some or any embodiments of Formula (III), SP is -(linear C$_1$-C$_3$-alkylene)-NR$^{50}$C(O)-(linear C$_1$-C$_3$-alkylene)-NR$^{50a}$—.

In some embodiments, set forth herein is a compound of Formula (III), where both R$^x$ are hydrogen and SP is —C(O)—(C$_1$-C$_{10}$-alkylene)-NR$^{50}$C(O)—(C$_1$-C$_{10}$-alkylene)-NR$^{50a}$- where NR$^{50a}$- is attached to L in Formula (III) and where each C$_1$-C$_{10}$-alkylene is independently optionally substituted with one or more hydroxy. In some or any embodiments of Formula (III), SP is -(branched C$_1$-C$_6$-alkylene)-NR$^{50}$C(O)—(C$_1$-C$_6$-hydroxy-alkylene)-NR$^{50a}$—. In some or any embodiments of Formula (III), SP is -(branched C$_1$-C$_6$-alkylene)-NR$^{50}$C(O)—(C$_1$-C$_6$-alkylene)-NR$^{50a}$—.

In some embodiments, set forth herein is a compound of Formula (III), where both R$^x$ are fluoro and SP is —C(O)—(C$_1$-C$_{10}$-alkylene)-NR$^{50}$C(O)—(C$_1$-C$_{10}$-alkylene)-NR$^{50a}$- where NR$^{50a}$- is attached to L in Formula (III) and where each C$_1$-C$_{10}$-alkylene is independently optionally substituted with one or more hydroxy. In some or any embodiments of Formula (III), SP is -(branched C$_1$-C$_6$-alkylene)-NR$^{50}$C(O)—(C$_1$-C$_6$-hydroxy-alkylene)-NR$^{50a}$—. In some or any embodiments of Formula (III), SP is -(branched C$_1$-C$_6$-alkylene)-NR$^{50}$C(O)—(C$_1$-C$_6$-alkylene)-NR$^{50a}$—.

In some embodiments, set forth herein is a compound of Formula (III), where both R$^x$ are hydrogen and SP is —C(O)—N(R$^5$)—C$_1$-C$_{10}$-alkylene-C(O)NH-X$^2$- where X$^2$ is attached to L$^3$ in Formula (III). In some embodiments, set forth herein is a compound of Formula (III), where SP is —C(O)—N(R$^5$)-C$_1$-C$_5$-alkylene-C(O)NH—NH—. In some embodiments, set forth herein is a compound of Formula (III), where SP is —C(O)—N(R$^5$)—CH$_2$—C(O)NH—NH—. In some embodiments, set forth herein is a compound of Formula (III), where R$^5$ is H or alkyl. In some embodiments, set forth herein is a compound of Formula (III), where R$^5$ is H or CH$_3$.

In some embodiments, set forth herein is a compound of Formula (III), where both R$^x$ are fluoro and SP is —C(O)—N(R$^5$)-C$_1$-C$_{10}$-alkylene-C(O)NH-X$^2$- where X$^2$ is attached to L$^3$ in Formula (III). In some embodiments, set forth herein is a compound of Formula (III), where SP is —C(O)—N(R$^5$)-C$_1$-C$_5$-alkylene-C(O)NH—NH—. In some embodiments, set forth herein is a compound of Formula (III), where SP is —C(O)—N(R$^5$)—CH$_2$—C(O)NH—NH—. In some embodiments, set forth herein is a compound of Formula (III), where R$^5$ is H or alkyl. In some embodiments, set forth herein is a compound of Formula (III), where R$^5$ is H or CH$_3$.

In some embodiments, set forth herein is a compound of Formula (III), (III-P), or (III-P-1), where both R$^x$ are hydrogen and SP is

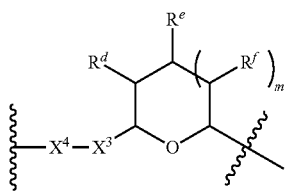

where $X^4$ is attached to $L^3$ in Formula (III), (III-P), or (III-P-1). In some embodiments, set forth herein is a compound of Formula (III), (III-P), or (III-P-1), where both $R^x$ are fluoro and SP is

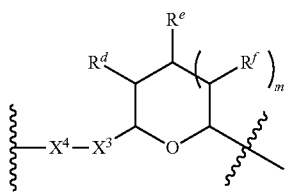

where $X^4$ is attached to $L^3$ in Formula (III), (III-P), or (III-P-1). In some embodiments, set forth herein is a compound of Formula (III), (III-P), or (III-P-1), where SP is

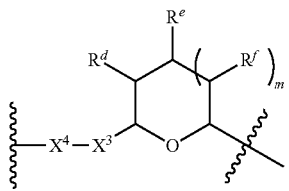

and $X^3$ is —CH$_2$—. In some embodiments, set forth herein is a compound of Formula (III), (III-P), or (III-P-1), where SP is

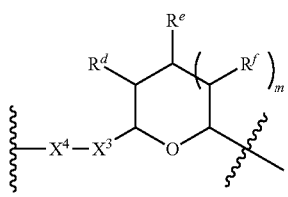

and $X^3$ is —CH$_2$—O—(C$_1$-C$_{10}$-alkylene)-C(O)— where the C(O) is attached to $X^4$. In some embodiments, set forth herein is a compound of Formula (III), (III-P), or (III-P-1), where SP is

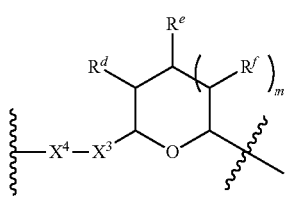

and $X^3$ is —C(O)—. In some embodiments, set forth herein is a compound of Formula (III), (III-P), or (III-P-1), where $R^d$, $R^e$, and $R^f$ are independently —H, —OH, hydroxyalkyl, alkoxycarbonyl, —C(O)OH, or —CH$_2$OR$^g$, where each $R^g$ is independently —CH$_2$C(O)OH or —CH$_2$C(O)O(alkyl). In some embodiments, set forth herein is a compound of Formula (III), (III-P), or (III-P-1), where $R^d$ and $R^e$ are independently —H or —OH. In some embodiments, set forth herein is a compound of Formula (III), (III-P), or (III-P-1), where m is 0. In some embodiments, set forth herein is a compound of Formula (III), (III-P), or (III-P-1), where m is 1. In some embodiments, set forth herein is a compound of Formula (III), (III-P), or (III-P-1), where m is 1 and $R^f$ is —H or —OH.

In some embodiments, provided is a Compound of Formula (III), (III-P), or (III-P-1), where both $R^x$ are hydrogen and SP is —C(O)—N(C$_{1-3}$alkyl)-C$_1$-C$_{10}$-alkylene-X$^1$- where $X^1$ is attached to $L^3$ in Formula (III), (III-P), or (III-P-1); SP is

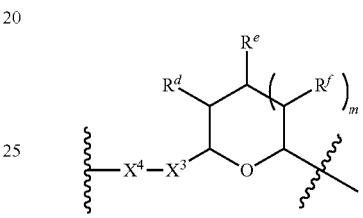

where $X^3$ is —CH$_2$—, m is 1, and $R^d$, $R^e$, and $R^f$ are —H; or SP is

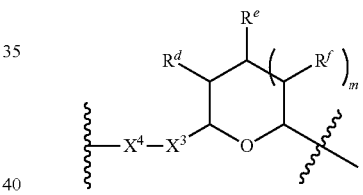

where $X^3$ is —CH$_2$—O—(C$_1$-C$_{10}$-alkylene)-C(O)— where the C(O) is attached to $X^4$, m is 1, and $R^d$, $R^e$, and $R^f$ are —H. In some embodiments, provided is a Compound of Formula (III), (III-P), or (III-P-1), where SP is —C(O)—N(CH$_3$)—CH$_2$CH$_2$—N(CH$_3$)—,

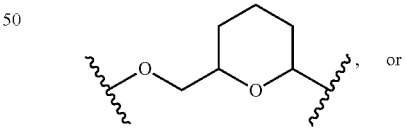

, or

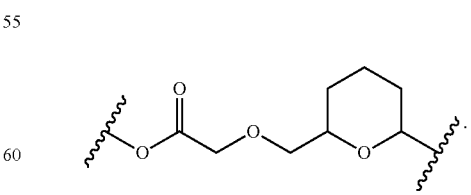

In some embodiments, provided is a Compound of Formula (III), (III-P), or (III-P-1), where both $R^x$ are fluoro and SP is —C(O)—N(C$_{1-3}$alkyl)-C$_1$-C$_{10}$-alkylene-X$^1$- where $X^1$ is attached to $L^3$ in Formula (III), (III-P), or (III-P-1); SP is

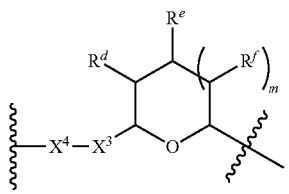

where $X^3$ is —CH$_2$—, m is 1, and $R^d$, $R^e$, and $R^f$ are —H; or SP is

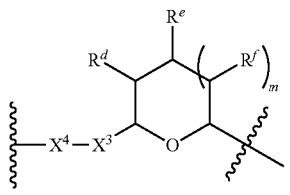

where $X^3$ is —CH$_2$—O—(C$_1$-C$_{10}$-alkylene)-C(O)— where the C(O) is attached to $X^4$, m is 1, and $R^d$, $R^e$, and $R^f$ are —H. In some embodiments, provided is a Compound of Formula (III), (III-P), or (III-P-1), where SP is —C(O)—N(CH$_3$)—CH$_2$CH$_2$—N(CH$_3$)—,

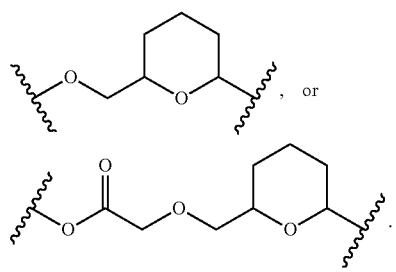

, or

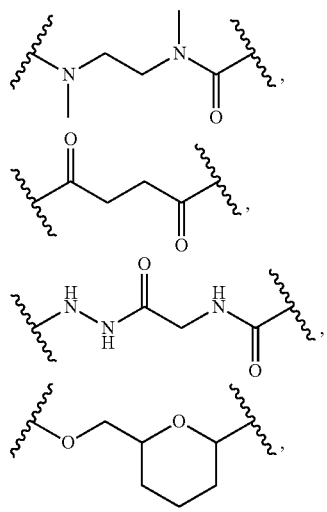

In some embodiments, provided is a Compound of Formula (III), where both $R^x$ are fluoro or both $R^x$ are hydrogen, or $R^x$ is as specified in this paragraph; SP is

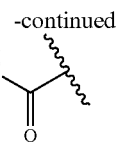

-continued (where both $R^x$ are fluoro),

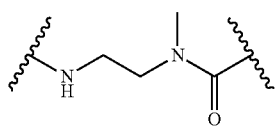 [SMILES: *NCCN(C)C(*)=O]

(where both $R^x$ are fluoro),

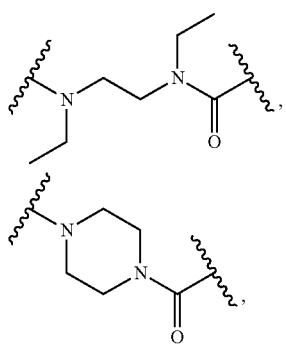

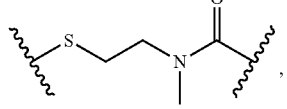

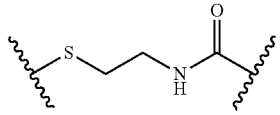

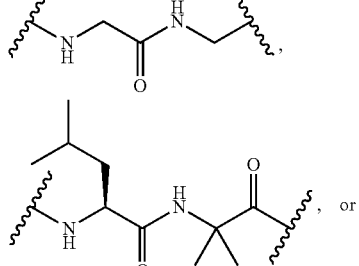

, or

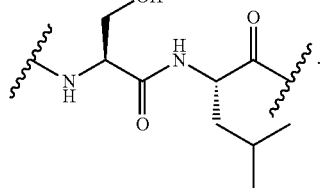

.

In some embodiments, provided is a Compound of Formula (III), (III-P), or (III-P-1), where z is 1. In certain embodiments, z is 2. In some other embodiments, z is 3. In certain embodiments, z is 4. In some embodiments, z is 5. In some other embodiments, z is 6. In certain embodiments, z is 7. In some other embodiments, z is 8. In certain embodiments, z is 9. In some embodiments, z is 10. In some other embodiments, z is 11. In some other embodiments, z is 12. In some other embodiments, z is 13. In some other embodiments, z is 14. In some other embodiments, z is 15. In some other embodiments, z is 15. In some other embodiments, z is 16. In some other embodiments, z is 17. In some other embodiments, z is 18. In certain embodiments, z is 19. In some other embodiments, z is 20. In some other embodiments, z is 21. In some other embodiments, z is 22. In some other embodiments, z is 23. In some other embodiments, z is 24. In some other embodiments, z is 25. In some other embodiments, z is 26. In some other embodiments, z is 27. In some other embodiments, z is 28. In some other embodiments, z is 29. In some other embodiments, z is 30. In some embodiments, z is an integer selected from 1-15, inclusive. In certain embodiments, z is selected from 1-10. In certain embodiments, z is selected from 1-5. In certain embodiments, z is selected from 2-5. In certain embodiments, z is selected from 2-4.

In some embodiments, -L- or $-L^1-L^2-(L^3)_{0-1}$- in Formula (III), (III-P), or (III-P-1), refers to any divalent group or moiety that links, connects, or bonds a binding agent (e.g., an antibody or an antigen-binding fragment thereof) with a payload compound set forth herein (e.g., steroid). Generally, suitable -L- and $-L^1-L^2-(L^3)_{0-1}$- for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise glucuronides, succinimide-thioethers, polyethylene glycol (PEG) units, carbamates, hydrazones, malcaproyl units, disulfide units (e.g., —S—S—, —S—S—C($R^{1b}$)($R^{2b}$)-, wherein $R^{1b}$ and $R^{2b}$ are independently hydrogen or hydrocarbyl), para-amino-benzyl (PAB) units, phosphate units, e.g., mono-, bis-, and tris-phosphate units, peptides, e.g., peptide units containing two, three, four, five, six, seven, eight, or more amino acid units, including but not limited to valine-citrulline units, valine-alanine units, valine-arginine units, valine-lysine units, -lysine-valine-citrulline units, and -lysine-valine-alanine units. In some embodiments, -L- and $-L^1-L^2-(L^3)_{0-1}$- are derived from the reaction of a "reactive group" (RG) of Formula (II) (and embodiments thereof) with a reactive portion of an antibody. The linking group is any divalent moiety that bridges BA to the payload. The linking group may also be any trivalent moiety that bridges BA, the payload, and a cyclodextrin moiety. In some embodiments, -L- and $-L^1-L^2-(L^3)_{0-1}$- are trivalent and includes a cyclodextrin moiety bonded to a trivalent group (e.g., a lysine residue) in the linking group. -L- and $-L^1-L^2-(L^3)_{0-1}$- contain a reactive group residue, which is a functional group or moiety that reacts with a reactive portion of an antibody, modified antibody, or antigen binding fragment thereof.

In some embodiments, provided is a Compound of Formula (III), (III-P), or (III-P-1), where L and $-L^1-L^2-(L^3)_{0-1}$- comprise

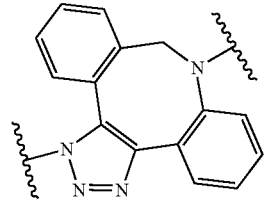 [SMILES: *N1Cc2ccccc2-c2c(nnn2*)-c2ccccc21]

or a regioisomer or mixture of isomers thereof;

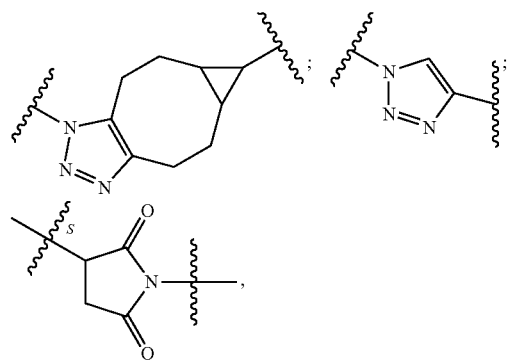

or a stereoisomer or mixture of stereoisomers thereof, where S refers to the S atom on a cysteine residue through which the reactive group residue is attached to BA; or

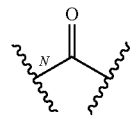

where N refers to the N atom on a lysine residue through which the reactive group residue is attached to BA.

In some embodiments, provided is a Compound of Formula (III), (III-P), or (III-P-1), where L and $-L^1-L^2-L^3$- comprise

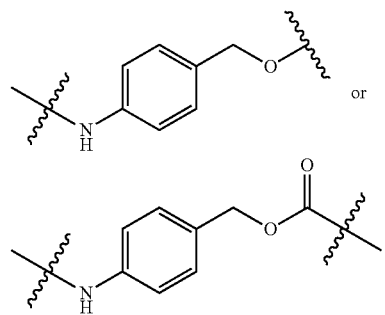

In some embodiments, provided is a Compound of Formula (III), (III-P), or (III-P-1), where L and -L¹-L²-(L³)₀₋₁- comprise

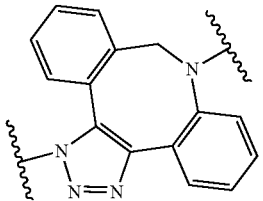 [SMILES: *N1Cc2ccccc2-c2c(nnn2*)-c2ccccc21]

or a regioisomer or mixture of isomers thereof;

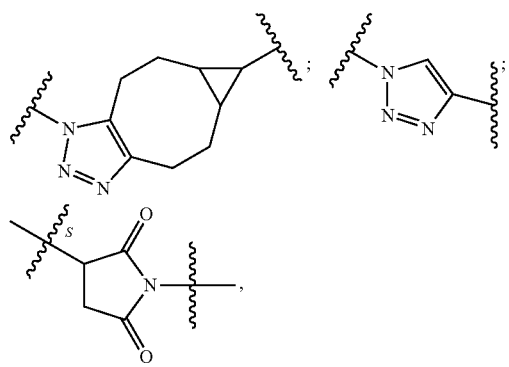

or a stereoisomer or mixture of stereoisomers thereof, where S refers to the S atom on a cysteine residue through which the reactive group residue is attached to BA; or

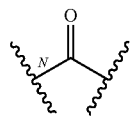

where N refers to the N atom on a lysine residue through which the reactive group residue is attached to BA; and L and -L¹-L²-(L³)₀₋₁-comprise

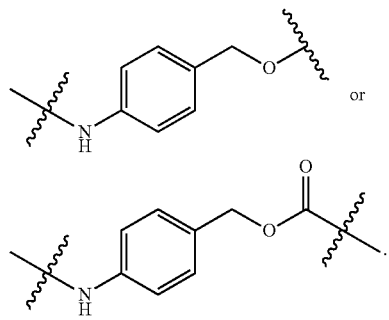

In some embodiments, provided is a Compound of Formula (III), (III-P), or (III-P-1), where L is -L¹-L²-(L³)₀₋₁-. In some embodiments, L³ is present. In some embodiments, L³ is not present.

In some embodiments, provided is a Compound of Formula (III), (III-P), or (III-P-1), where L is -L¹-L²-(L³)₀₋₁- and L¹ is selected from

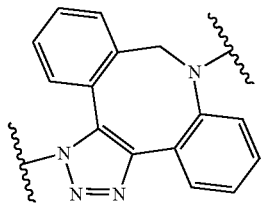 [SMILES: *N1Cc2ccccc2-c2c(nnn2*)-c2ccccc21]

or a regioisomer or mixture of isomers thereof;

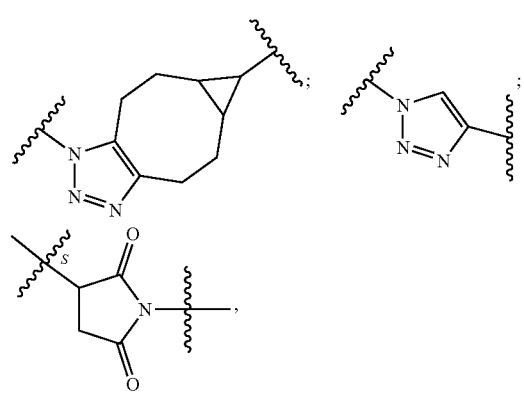

or a stereoisomer or mixture of stereoisomers thereof, where S refers to the S atom on a cysteine residue through which the reactive group residue is attached to BA; and

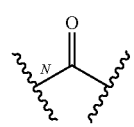

where N refers to the N atom on a lysine residue through which the reactive group residue is attached to BA. In some embodiments, provided is a Compound of Formula (III), (III-P), or (III-P-1), where L is -L¹-L²-(L³)₀₋₁- and L¹ is

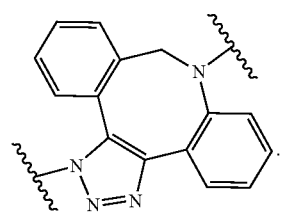 [SMILES: *N1Cc2ccccc2-c2c(nnn2*)-c2ccccc21]

In some embodiments, provided is a Compound of Formula (III), (III-P), or (III-P-1), where L is -L¹-L²-(L³)₀₋₁- and L is

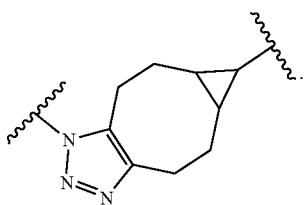 [SMILES: *C1C2CCc3nnn(*)c3CCC12]

In some embodiments, provided is a Compound of Formula (III), (III-P), or (III-P-1), where L is -L$^1$-L$^2$-(L$^3$)$_{0-1}$- and L$^1$ is

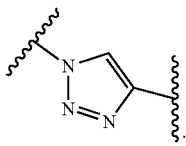 [SMILES: *c1cn(*)nn1]

In some embodiments, provided is a Compound of Formula (III), (III-P), or (III-P-1), where L is -L$^1$-L$^2$-(L$^3$)$_{0-1}$- and L$^1$ is

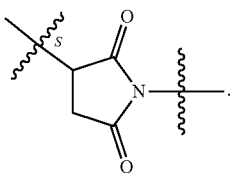

In some embodiments, provided is a Compound of Formula (III), (III-P), or (III-P-1), where L is -L$^1$-L$^2$-(L$^3$)$_{0-1}$- and L is

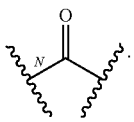

In some embodiments, provided is a Compound of Formula (III), (III-P), or (III-P-1), where L is -L$^1$-L$^2$-(L$^3$)$_{0-1}$- and L$^3$ is

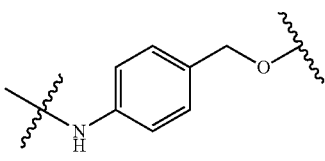 [SMILES: *Nc1ccc(CO*)cc1]

where the NH group is attached to L$^2$, when SP is —C(O)—C$_1$-C$_{10}$-alkylene-C(O)—; or L$^3$ is

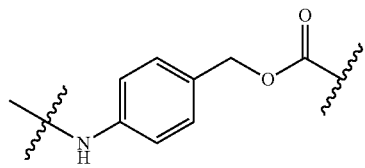 [SMILES: *Nc1ccc(COC(*)=O)cc1]

where the NH group is attached to L$^2$, when SP is —C(O)—N(C$_{1-3}$alkyl)-C$_1$-C$_{10}$-alkylene-X$^1$- or —C(O)—N(R$^5$)-C$_1$-C$_{10}$-alkylene-C(O)NH—X$^2$-; or L$^3$ is not present when SP is

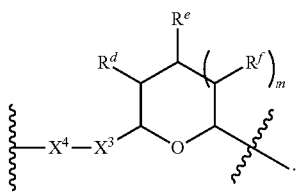

In some embodiments, provided is a Compound of Formula (III), (III-P), or (III-P-1), where L is -L$^1$-L$^2$-(L$^3$)- and L$^3$ is

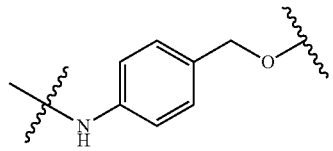 [SMILES: *Nc1ccc(CO*)cc1]

H where the NH group is attached to L$^2$, when SP is —C(O)—C$_1$-C$_{10}$-alkylene-C(O)—. In some embodiments, provided is a Compound of Formula (III), (III-P), or (III-P-1), where L is -L$^1$-L$^2$-(L$^3$)$_{0-1}$- and L$^3$ is

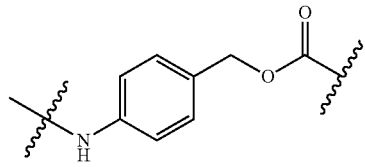 [SMILES: *Nc1ccc(COC(*)=O)cc1]

where the NH group is attached to L$^2$, when SP is —C(O)—N(C$_{1-3}$alkyl)-C$_1$-C$_{10}$-alkylene-X$^1$- or —C(O)—N(R$^5$)-C$_1$-C$_{10}$-alkylene-C(O)NH-X$^2$—. In some embodiments, provided is a Compound of Formula (III), (III-P), or (III-P-1), where L is -L$^1$-L$^2$-(L$^3$)$_{0-1}$- and L$^3$ is not present when SP is

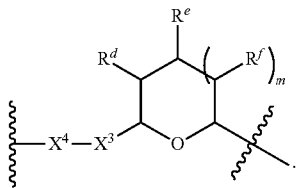

In some embodiments, provided is a Compound of Formula (III), (III-P), or (III-P-1), where L is -L$^1$-L$^2$-(L$^3$)$_{0-1}$- and L$^2$ comprises
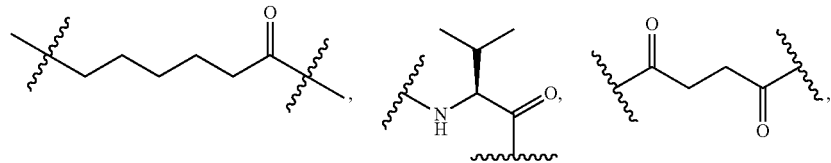
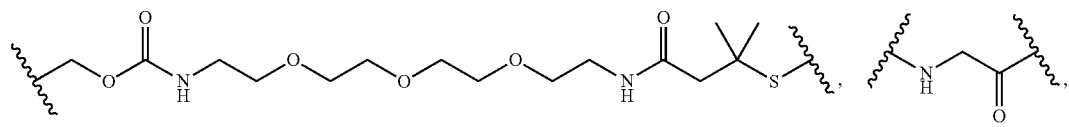
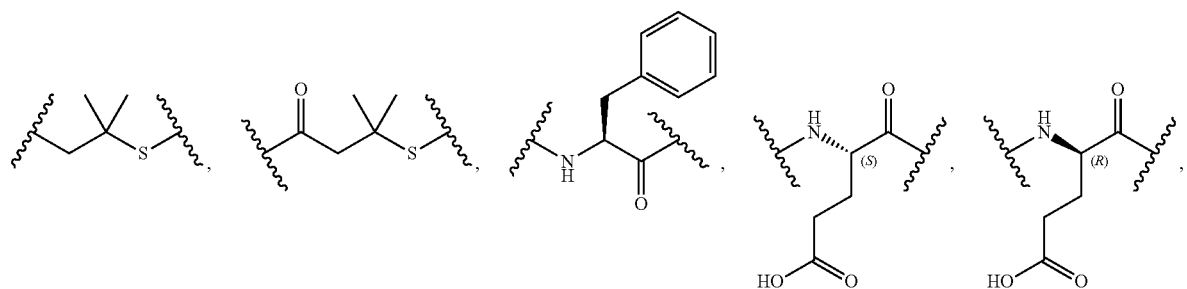
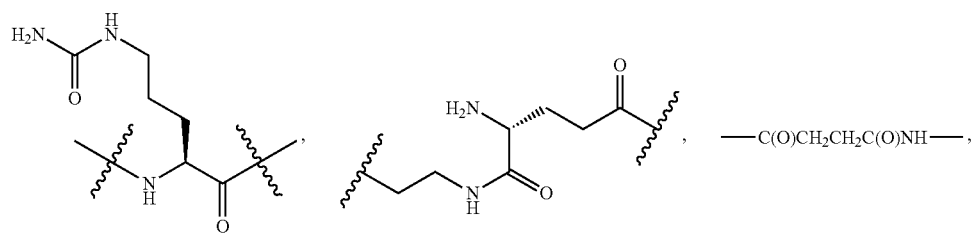
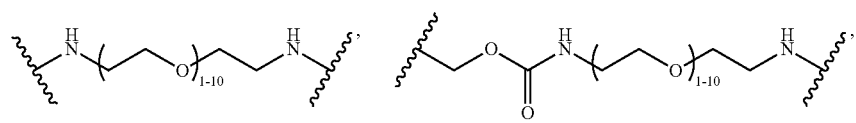
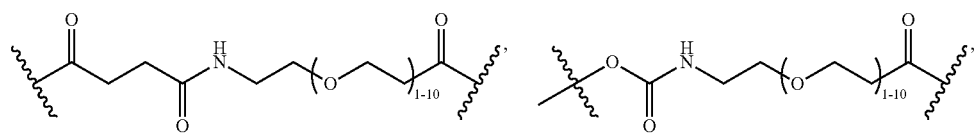

—OCH$_2$C(O)—, or cyclodextrin residue (CD); or combinations thereof. In some embodiments, provided is a Compound of Formula (III), (III-P), or (III-P-1), where L is
-L$^1$-L$^2$-(L$^3$)$_{0-1}$- and L$^2$ comprises

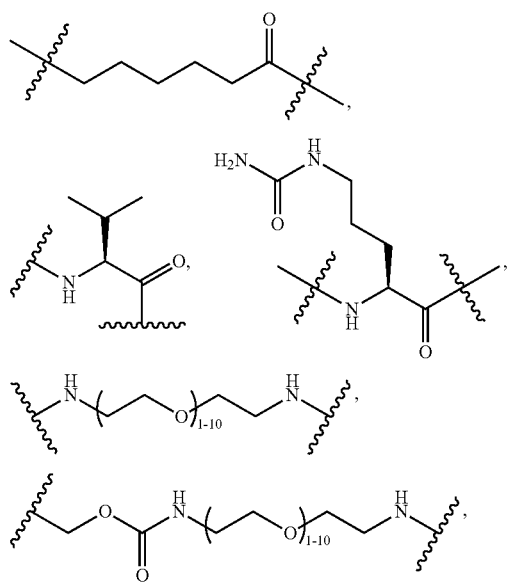

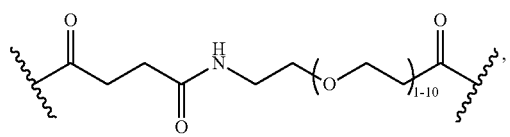

or CD, or combinations thereof. In some embodiments, provided is a Compound of Formula (III), (III-P), or (III-P-1), where L is -L$^1$-L$^2$-(L$^3$)$_{0-1}$- and L$^2$ comprises CD wherein CD is selected from the group consisting of

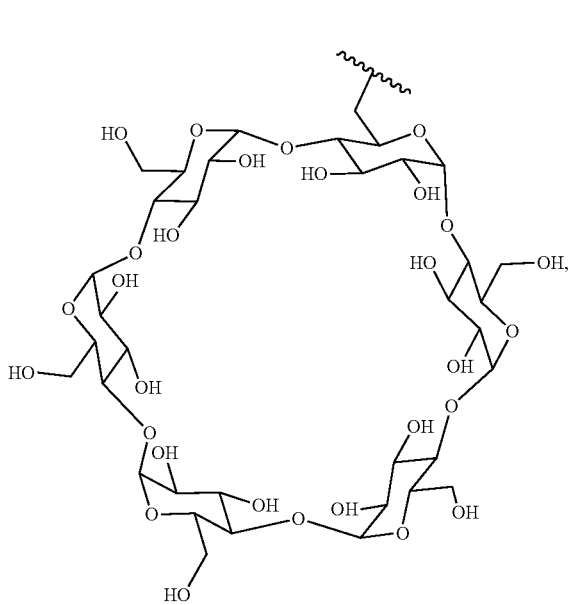

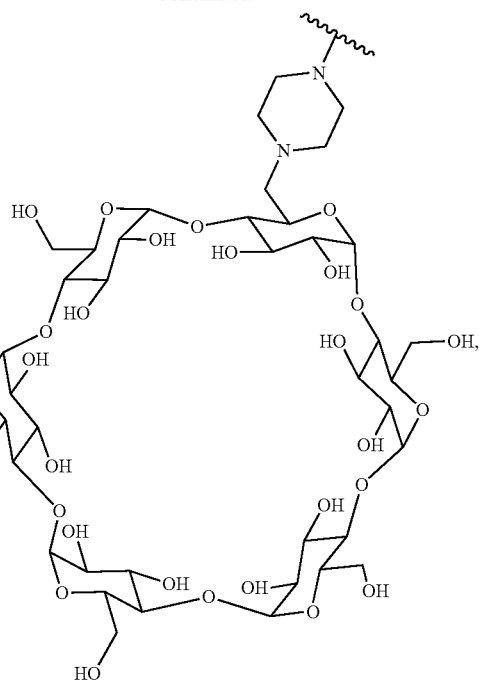

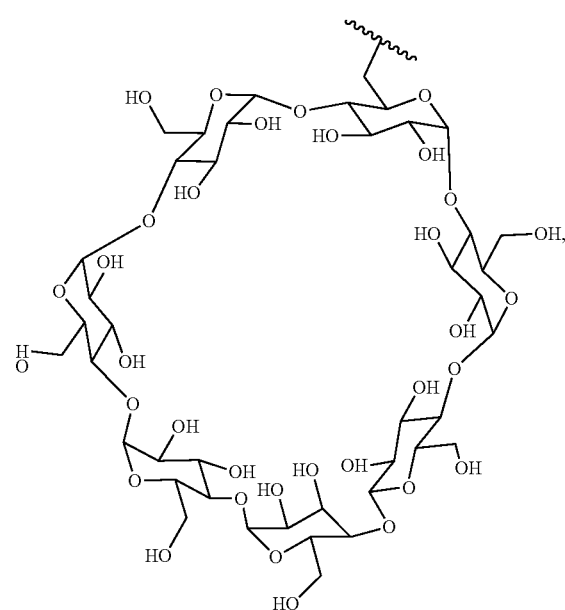

75
-continued
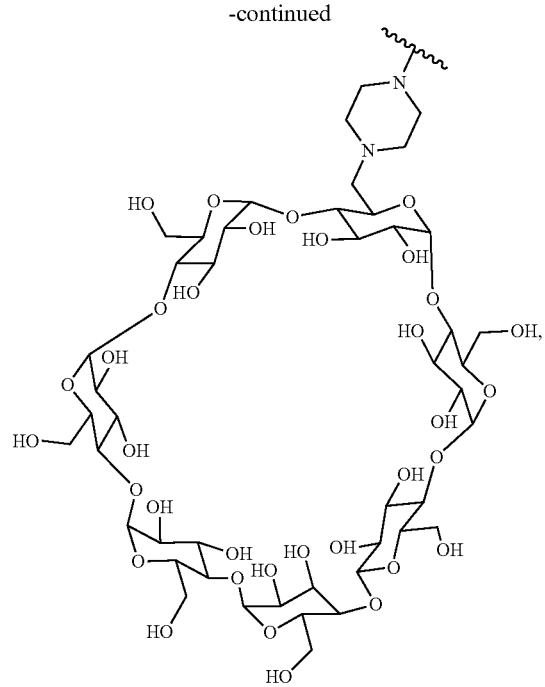
76
-continued
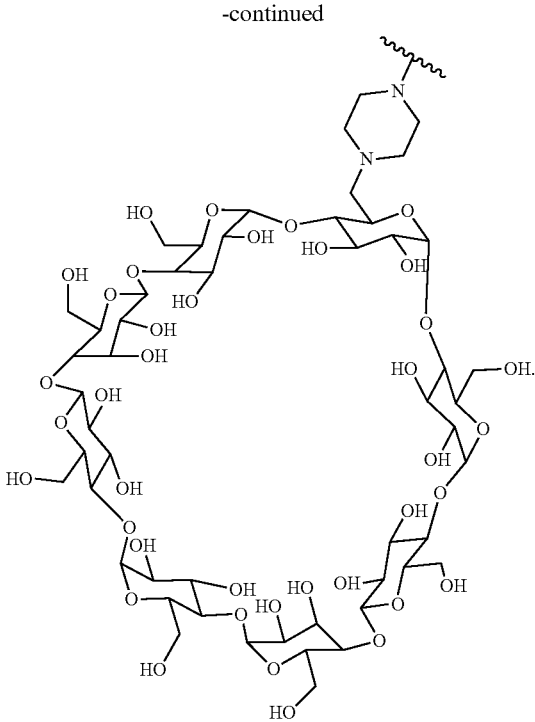
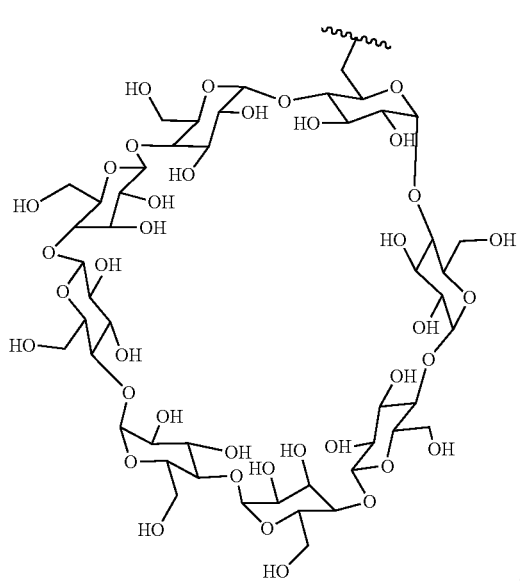, and
In some embodiments, provided is a Compound of Formula (III), (III-P), or (III-P-1), where L is
-$L^1$-$L^2$-($L^3$)$_{0-1}$- and -$L^2$-($L^3$)$_{0-1}$- comprise
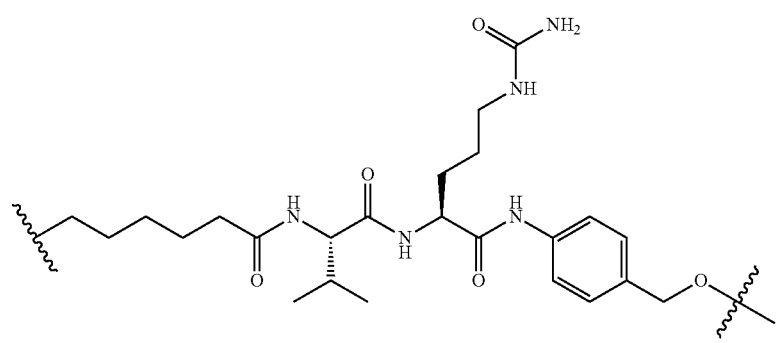

-continued
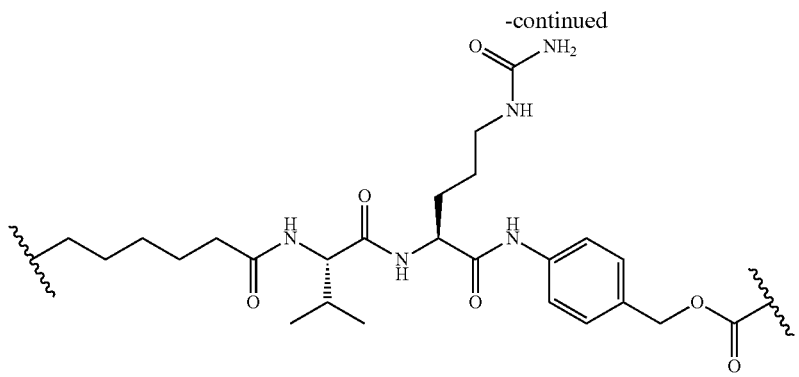
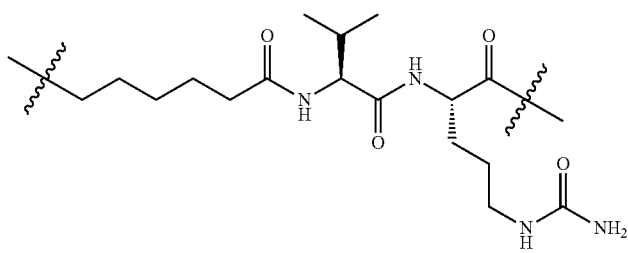
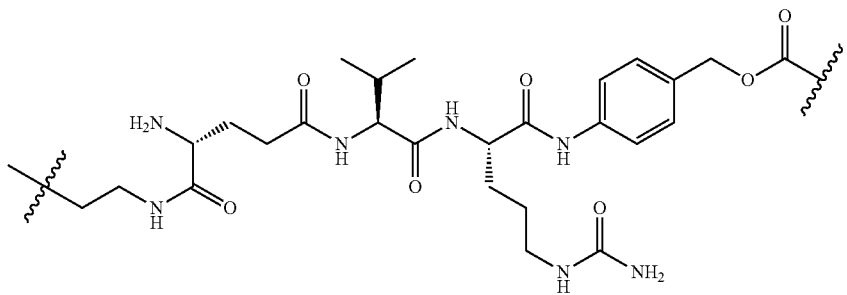

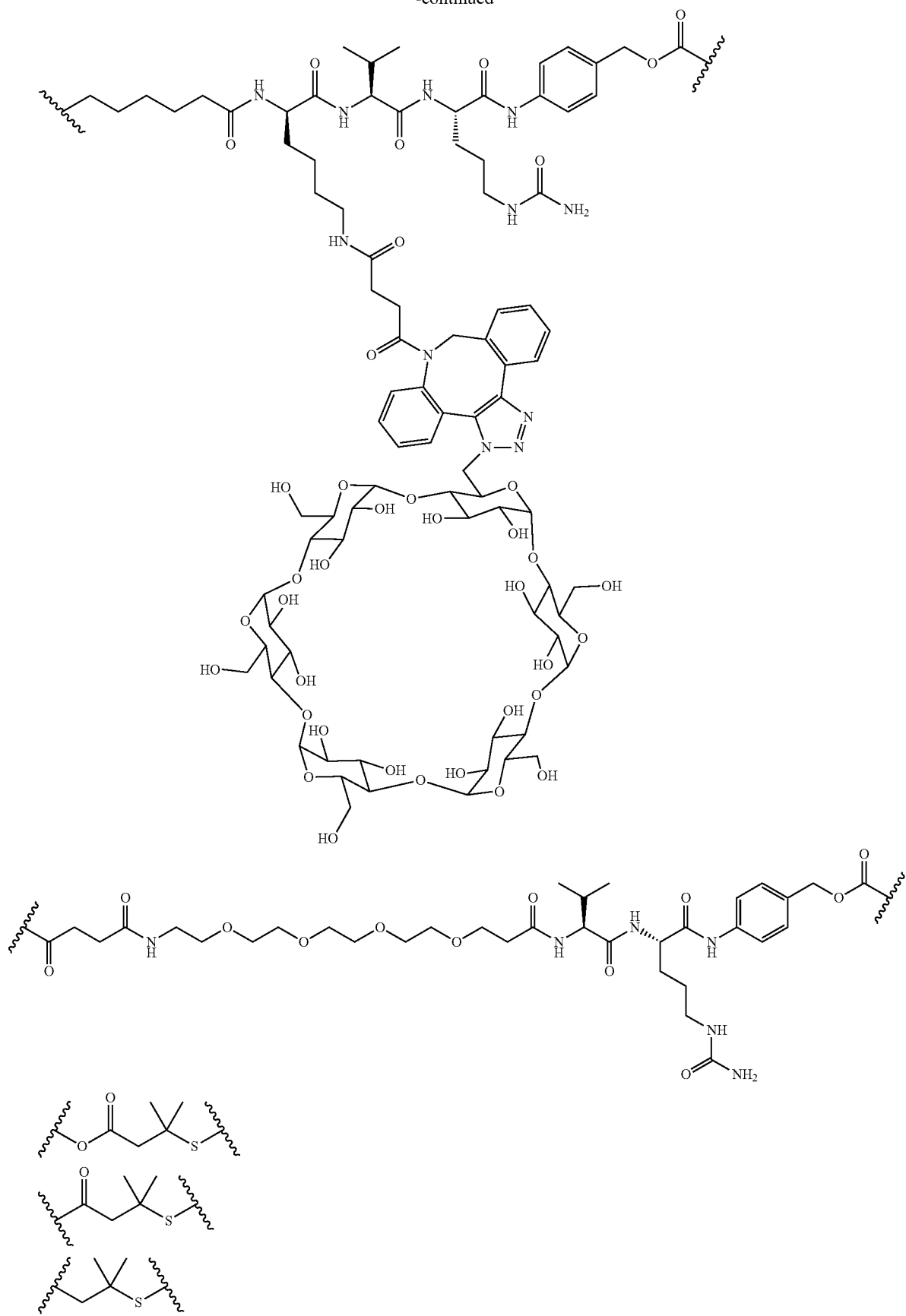

-continued
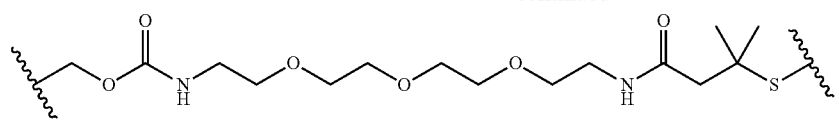
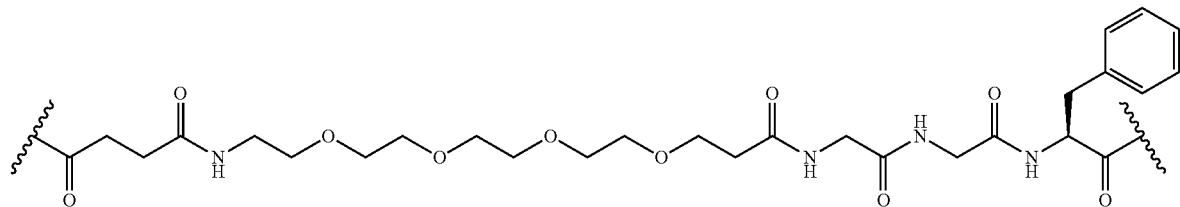
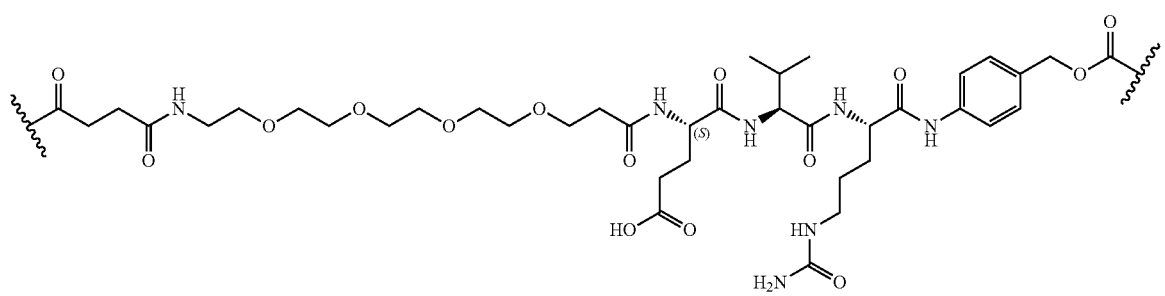
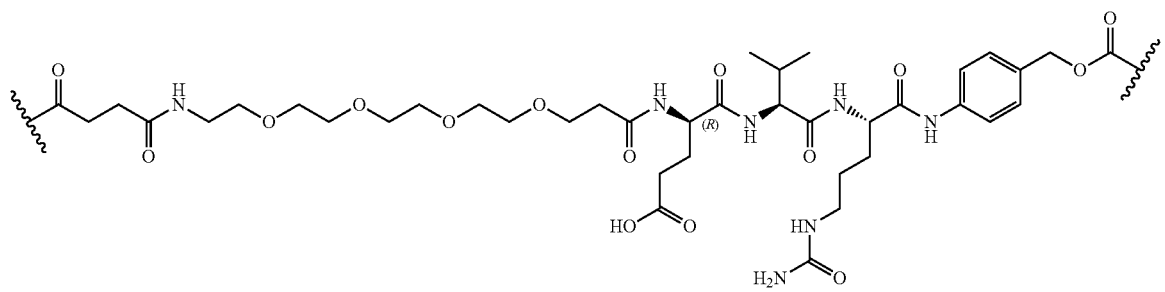
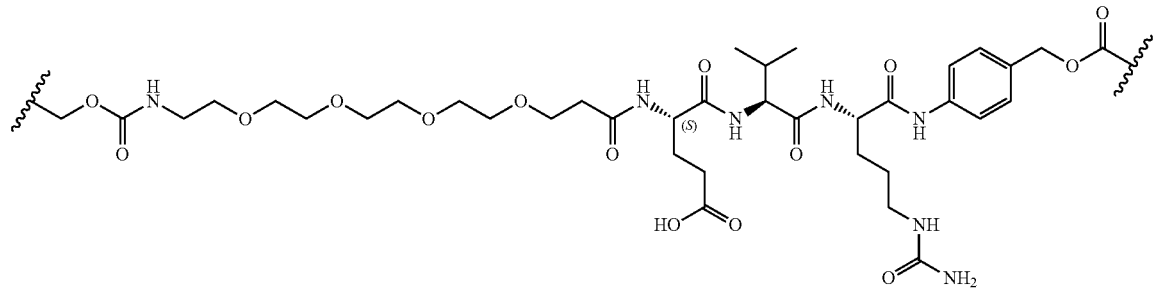
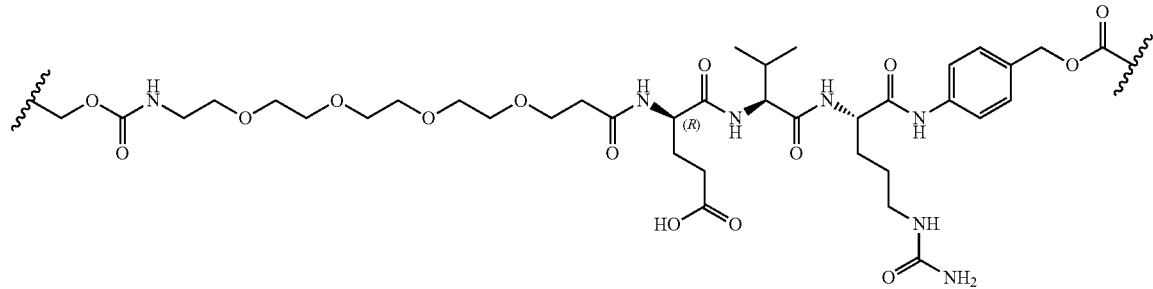

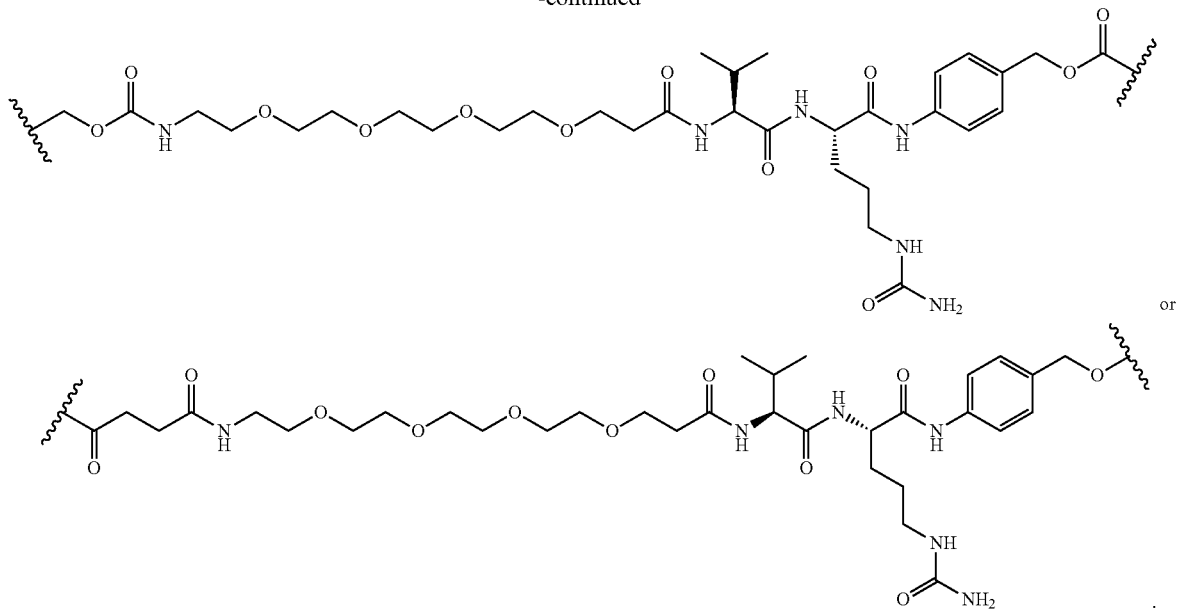

In some embodiments, provided is a Compound of Formula (III), (III-P), or (III-P-1), where $L^2$ comprises

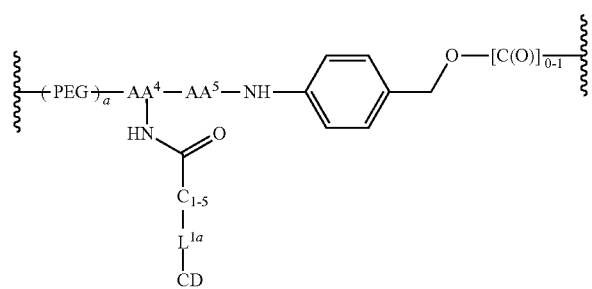

$L^{1a}$ is a reactive group residue;
CD is a cyclodextrin;
$AA^4$ is trivalent linker;
$AA^5$ is a peptide residue;
PEG is polyethylene glycol;
a is an integer selected from 0 to 5, inclusive.

In some embodiments, $AA^4$ is an amino acid residue; $AA^5$ is a di-peptide residue, a tri-peptide residue, tetra-peptide residue, or penta-peptide residue; PEG is a polyethylene glycol residue; wherein the

indicates the atom through which the indicated chemical group is bonded to the adjacent groups in the formula, CD is, independently in each instance, absent or a cyclodextrin residue, wherein at least one CD is present, subscript a is an integer selected from 0 to 5, inclusive; in these examples, subscript a is 0, 1, 2, 3, 4, or 5. In some embodiments, subscript a is 0. In some embodiments, subscript a is 1. In some embodiments, subscript a is 2. In some embodiments, subscript a is 3. In some embodiments, subscript a is 4. In some embodiments, subscript a is 5. In some embodiments, any one of $AA^4$ or $AA^5$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^4$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^4$ is lysine or a derivative of lysine. In certain embodiments, $AA^4$ is lysine. In certain embodiments, $AA^4$ is D-lysine. In certain embodiments, $AA^4$ is L-lysine. In certain embodiments, the $AA^5$ is a di-peptide residue. In certain embodiments, the $AA^5$ is valine-citrulline. In some embodiments, the $AA^5$ is citrulline-valine. In some embodiments, the $AA^5$ is valine-alanine. In some embodiments, the $AA^5$ is alanine-valine. In some embodiments, the $AA^5$ is valine-glycine. In some embodiments, the $AA^5$ is glycine-valine. In certain embodiments, the $AA^5$ is a tri-peptide residue. In some embodiments, the $AA^5$ is glutamate-valine-citrulline. In some embodiments, the $AA^5$ is glutamine-valine-citrulline. In some embodiments, the $AA^5$ is lysine-valine-alanine. In some embodiments, the $AA^5$ is lysine-valine-citrulline. In some embodiments, the $AA^5$ is glutamate-valine-citrulline. In some embodiments, the $AA^5$ is a tetra-peptide residue. In some embodiments, the $AA^5$ is glycine-glycine-phenylalanine-glycine. In some embodiments, the $AA^5$ is a tetra-peptide residue. In some embodiments, the $AA^5$ is glycine-glycine-glycine-glycine-glycine.

In certain embodiments, reactive group residue is derived from the reaction of RG with a cysteine or lysine residue of an antibody or antigen-binding fragment thereof. In certain embodiments, reactive group residue is derived from a click chemistry reaction. In some embodiments of said click chemistry reaction, $L^1$ is derived from a 1,3 cycloaddition reaction between an alkyne and an azide. Non-limiting examples of such reactive group residues include those derived from strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable Ls also include, but are not limited to moieties derived from DIBAC (where the —C(O)CH$_2$CH$_2$C(O)— portion of DIBAC moiety is covered by L$^2$), DIBO (where the —O— portion of DIBO moiety is covered by L$^2$), BARAC (where the

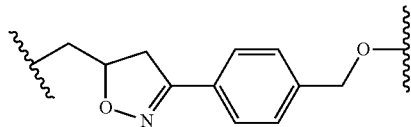 [SMILES: *CC1CC(c2ccc(CO*)cc2)=NO1]

portion of BARAC moiety is covered by L$^2$), substituted alkynes, e.g., fluorinated alkynes, aza-cycloalkynes, BCN, and derivatives thereof. Conjugates containing such reactive group residues can be derived from antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue with a compound according to the formula H$_2$N-LL-N$_3$, wherein LL is a divalent polyethylene glycol group, in the presence of the enzyme transglutaminase, e.g., microbial transglutaminase. Suitable glutamine residues of an antibody include Q295, or those derived by insertion or mutation, e.g., N297Q mutation.

In some embodiments, BA of the conjugates described herein is an antibody or an antigen-binding fragment thereof. In some embodiments, the conjugates described herein are derived from azido-functionalized antibodies. In certain embodiments, BA of the conjugates described herein is:

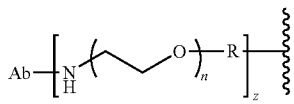

wherein Ab is an antibody or antigen-binding fragment thereof, n is an integer selected from 1 to 10, inclusive, z is the number of linker payload moieties, and

is a bond to L, or -L$^1$-L$^2$-(L$^3$)$_{0-1}$-, e.g., bond to a moiety derived from a 1,3-cycloaddition reaction between an alkyne and azide. In certain embodiments, z is 3. In certain embodiments, z is 2 or 4, i.e., the conjugate comprises 2 or 4 linker payload moieties.

In some embodiments, -L- and -L$^1$-L$^2$-L$^3$- are a divalent moiety of Formula (L$^A$);

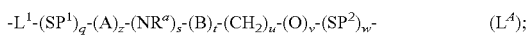      (L$^A$);

wherein L$^1$ is as defined herein;

A is an amino acid or a peptide;
R$^a$ is H or alkyl;
B is aryl, heteroaryl, or heterocycloalkyl, wherein aryl, heteroaryl, or
heterocycloalkyl is optionally substituted with alkyl, —OH, or —NR$^a$R$^b$;
SP$^1$ and SP$^2$ are, independently, a spacer groups; and q, z, s, t, u, v, and w are, independently in each instance, 0 or 1.

In some other embodiments, -L- and -L$^1$-L$^2$-(L$^3$)$_{0-1}$- are a trivalent moiety of Formula (L$^B$);

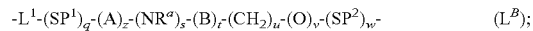      (L$^B$);

wherein L$^1$ is as defined herein;
A is a tripeptide or a tetrapeptide, wherein at least one of the amino acids in the tripeptide or tetrapeptide is bonded directly or indirectly to a cyclodextrin moiety;
R$^a$ is H or alkyl;
B is aryl, heteroaryl, or heterocycloalkyl, wherein aryl, heteroaryl, or
heterocycloalkyl is optionally substituted with alkyl, —OH, or —NR$^a$R$^b$;
SP$^1$ and SP$^2$ are, independently, a spacer groups; and q, z, s, t, u, v, and w are, independently in each instance, 0 or 1.

In some embodiments, the cyclodextrin (CD) is bonded directly to an amino acid residue, such as a lysine amino acid residue. This means that the CD is one bond position away from the lysine amino acid covalent linker. In some of these embodiments, the covalent linker is also bonded directly to a payload moiety. This means that the covalent linker is one bond position away from a payload such as, but not limited to a steroid payload set forth herein. In some of these embodiments, the covalent linker is also bonded directly to a CD moiety. This means that the covalent linker is one bond position away from a CD, such as the CD(s) set forth herein. In some of these embodiments, the covalent linker is a lysine amino acid or a derivative thereof.

In some embodiments, the CD is bonded indirectly to a covalent linker in a linking group (e.g., L, -L$^2$-(L$^3$)$_{0-1}$-, and -L$^1$-L$^2$-(L$^3$)$_{0-1}$). This means that the CD is more than one bond position away from the covalent linker. This also means that the CD is bonded through another moiety to the covalent linker. For example, the CD may be bonded to a maleimide group which is bonded to a polyethylene glycol group which is bonded to the covalent linker. In some of these embodiments, the covalent linker is also bonded indirectly to a payload moiety. This means that the covalent linker is more than one bond position away from a payload such as, but not limited to a steroid payload set forth herein. This also means that the covalent linker is bonded through another moiety to the payload. For example, the covalent linker may be bonded to a dipeptide, such as but not limited to Val-Ala or Val-Cit, which may be bonded to para-amino benzoyl which may be bonded to the payload. In some of these embodiments, the covalent linker is also bonded indirectly to a cyclodextrin moiety. This means that the covalent linker is more than one bond position away from a cyclodextrin, such as the cyclodextrins set forth herein. This also means that the covalent linker is bonded through another moiety to the cyclodextrin. For example, the covalent linker may be bonded to a polyethylene glycol group which may be bonded to reactive group which may be bonded to the cyclodextrin. In some of these embodiments, the covalent linker is a lysine amino acid or a derivative thereof.

In some embodiments, -L- and -L$^1$-L$^2$-(L$^3$)$_{0-1}$- are -L$^1$-(SP$^1$)$_q$-(A)$_z$-. In some embodiments, -L- and -L$^1$-L$^2$-(L$^3$)$_{0-1}$- are -L$^1$-(SP$^1$)$_q$-(A)$_2$-. In some embodiments, -L- and -L$^1$-L$^2$-(L$^3$)$_{0-1}$- are a moiety of Formula (L$^{A1}$)

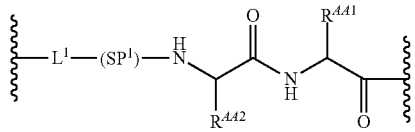
(L$^{A1}$)

wherein R$^{AA1}$ and R$^{AA2}$ are each, independently, amino acid side chains. In some embodiments of Formula L$^{A1}$, SP$^1$ is a divalent polyethylene glycol group and L$^1$ is a 1,3-cycloaddition reaction product of the reaction between an alkyne and an azide.

In some embodiments, -L- and -L$^1$-L$^2$-(L$^3$)$_{0-1}$- are -L$^1$-(SP$^1$)$_q$-(A)$_z$-. In some embodiments, -L- and -L$^1$-L$^2$-(L$^3$)$_{0-1}$- are -L$^1$-(SP$^1$)$_q$-(A)$_2$-. In some embodiments, -L- and -L$^1$-L$^2$-(L$^3$)$_{0-1}$- are a moiety of Formula (L$^{B1}$)

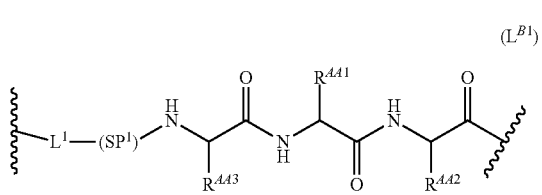
(L$^{B1}$)

wherein R$^{AA1}$ and R$^{AA2}$ are each, independently, amino acid side chains. R$^{AA3}$ is an amino acid side chain that is bonded directly or indirectly to a cyclodextrin moiety. In some embodiments of Formula L$^{B1}$, SP$^1$ is a divalent polyethylene glycol group and L$^1$ is a 1,3-cycloaddition reaction product of the reaction between an alkyne and an azide.

In some embodiments, -L- or -L$^1$-L$^2$-L$^3$- has the following structure:

-L$^1$-(SP$^1$)$_q$-Z$^1$-Z$^2$-Z$^3$$_{0-1}$- wherein:
L$^1$, SP$^1$, are as defined herein;
q is 0 or 1;
Z$^1$ is a polyethylene glycol or caproyl group;
Z$^2$ is a dipeptide, tripeptide, or tetrapeptide; and
Z$^3$ is a PAB group.

In certain embodiments, L$^1$ is derived from a click-chemistry reactive group and Z$^1$ is a polyethylene glycol group. In certain embodiments, L$^1$-(SP$^1$)q-Z$^1$- is:

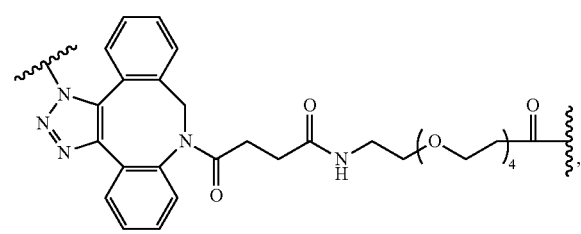

-continued

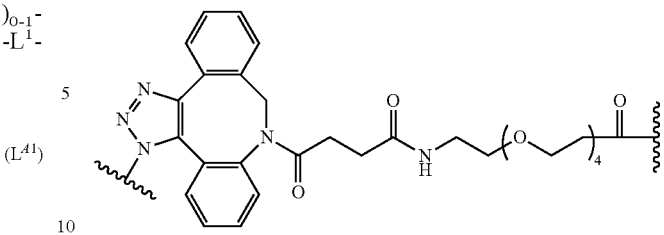

or mixture thereof; or

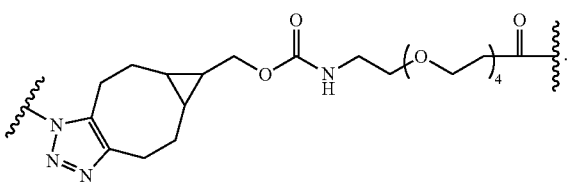

In some embodiments, the dipeptide is valine-citrulline or valine alanine. In some embodiments, the tripeptide is glutamate-valine-citrulline. In some embodiments, the tetrapeptide is glycine-glycine-phenylalanine-glycine.

In some embodiments, herein L$^1$ is derived from a click-chemistry reactive group. In some embodiments, L$^1$ is:

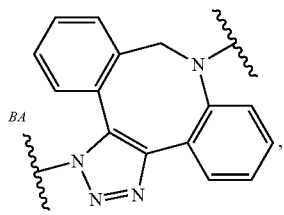

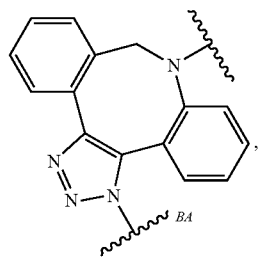

or mixture thereof;

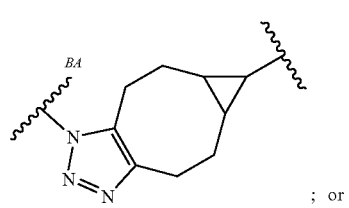

; or

-continued

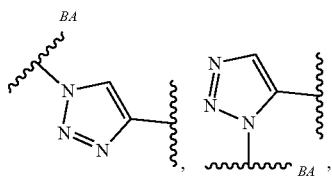

or mixture thereof; wherein

is a bond to a binding agent.

In some other examples, herein $L^1$ is selected from a group which reacts with a cysteine or lysine residue on an antibody or an antigen-binding fragment thereof. In some embodiments, $L^1$ is

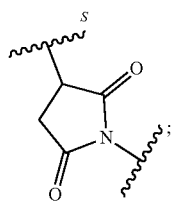

wherein

is a bond to cysteine of a binding agent, e.g., antibody. In some embodiments, $L^1$ is

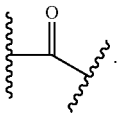

In some embodiments, $SP^1$ is selected from:

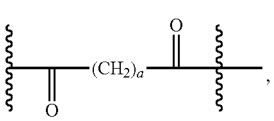

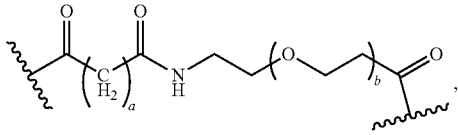

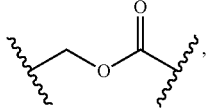

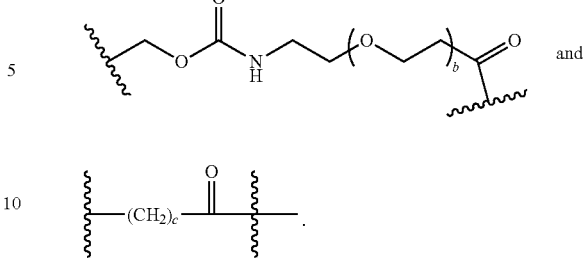 and

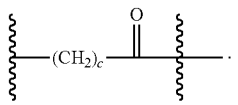

In some embodiments, $SP^1$ is

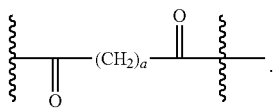

In some other examples, $SP^1$ is

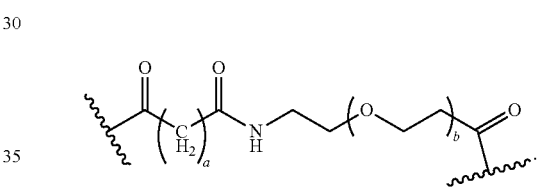

In other examples, $SP^1$ is

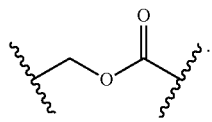 [SMILES: *COC(*)=O]

In still other examples, $SP^1$ is

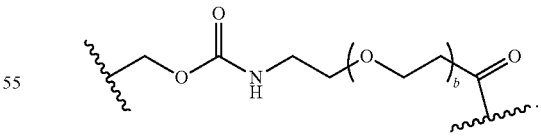

In some other examples, $SP^1$ is

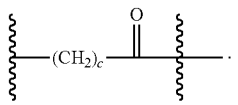

In any of the above examples, subscripts a, b, and c are independently, in each instance, an integer selected from 1 to 20, inclusive.
In some embodiments, $R^{AA3}$ is selected from
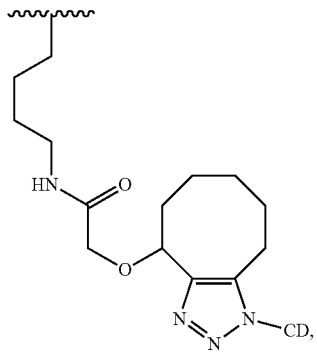
wherein CD is a cyclodextrin moiety. In some embodiments, $R^{AA3}$ is selected from
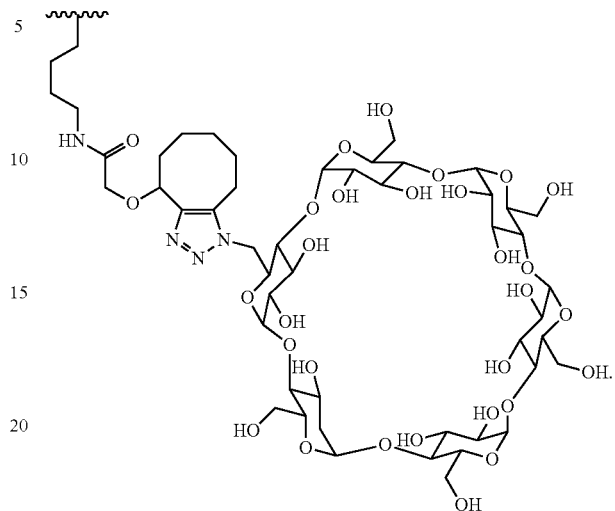
In some embodiments, $SP^1$ is selected from:
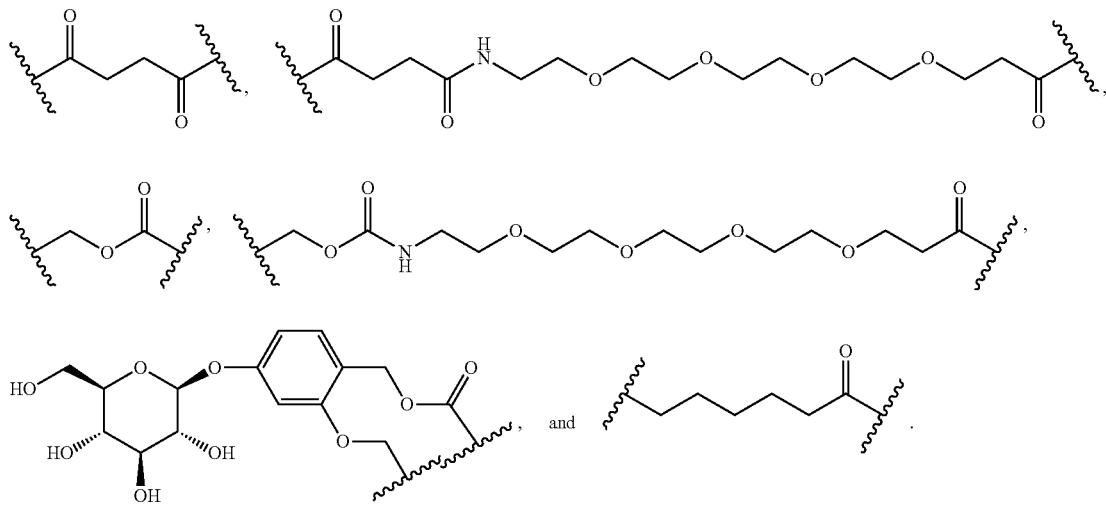
In some embodiments, $SP^1$ is
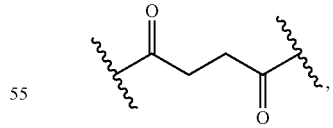
In some embodiments, $SP^1$ is
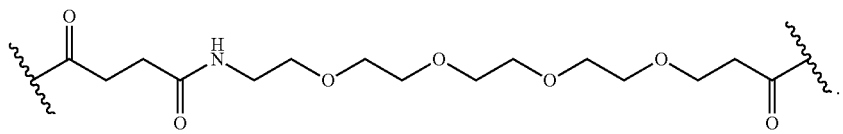 [SMILES: *C(=O)CCOCCOCCOCCOCCNC(=O)CCC(*)=O]

In some embodiments, SP¹ is
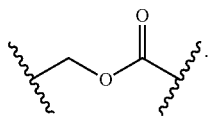 [SMILES: *COC(*)=O]
In some embodiments, SP¹ is
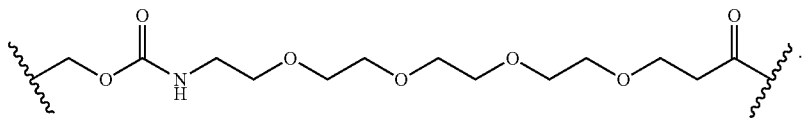 [SMILES: *COC(=O)NCCOCCOCCOCCOCCC(*)=O]
In some embodiments, SP¹ is
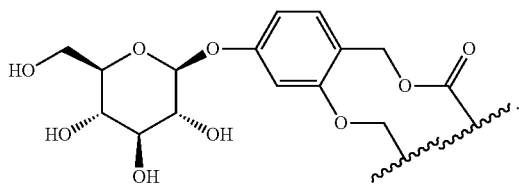 [SMILES: *COc1cc(O[C@@H]2O[C@H](CO)[C@@H](O)[C@H](O)[C@H]2O)ccc1COC(*)=O]
In some embodiments, SP¹ is
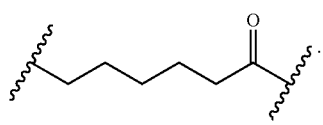 [SMILES: *CCCCCC(*)=O]
In some embodiments, SP¹ is
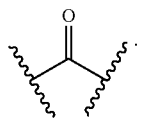
In some embodiments, SP¹ is
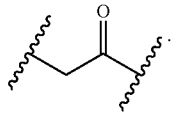 [SMILES: *CC(*)=O]
In some embodiments, SP¹ is
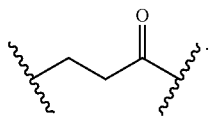 [SMILES: *CCC(*)=O]
In some embodiments, SP¹ is
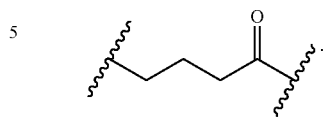
In some embodiments, SP¹ is
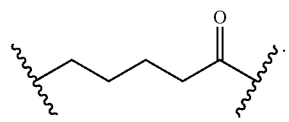 [SMILES: *CCCCC(*)=O]
In some embodiments, SP¹ is
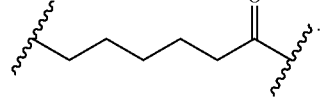
In some embodiments, -L¹-L²- comprise:
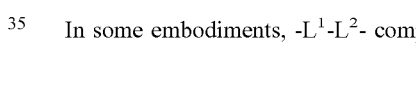
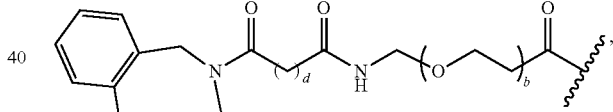
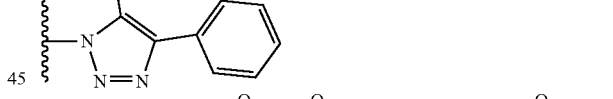
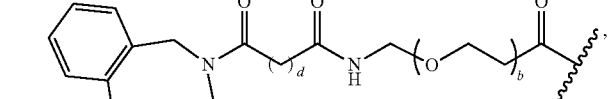
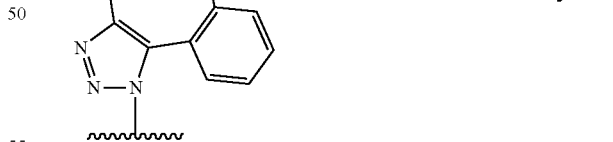
or mixture thereof;
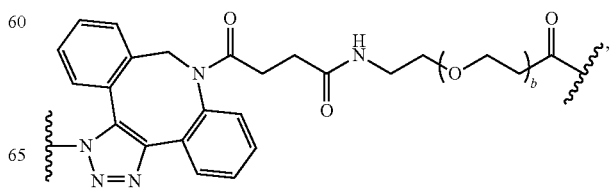

95
-continued
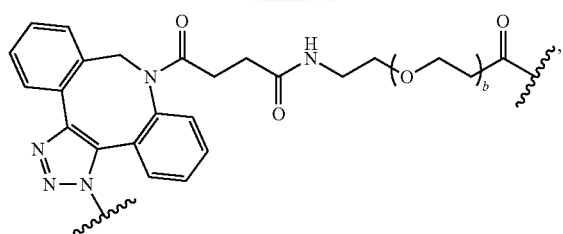
or mixture thereof;
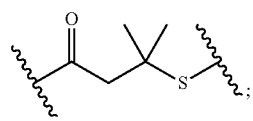
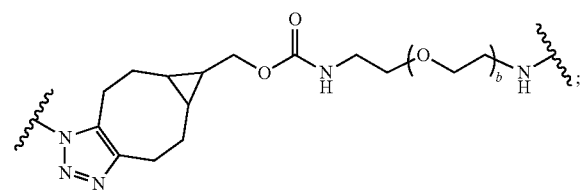
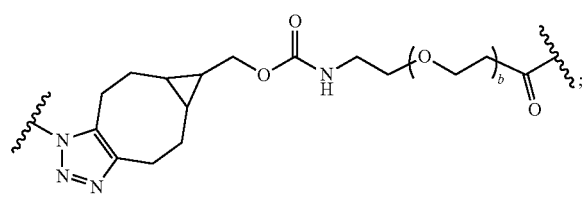
96
-continued
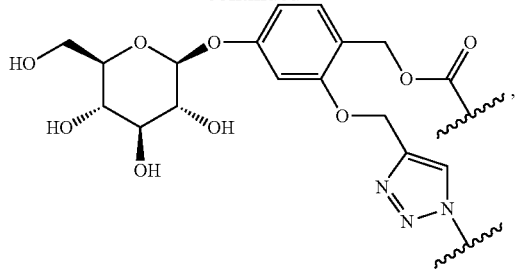
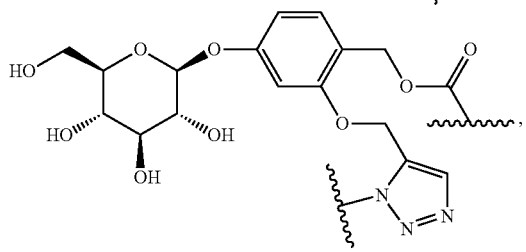
or mixture thereof;
or
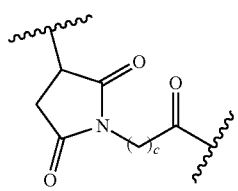
where b, c, and d are independently, in each instance, an integer selected from 1 to 20, inclusive. In some of these embodiments, subscripts b, c, and d are independently, in each instance, an integer selected from 1 to 6, inclusive.
In some embodiments, —SP$^1$ is selected from:
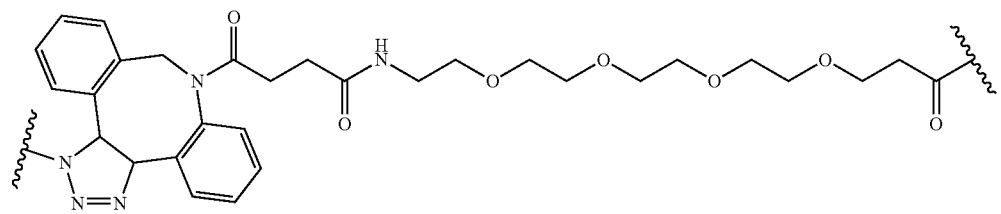
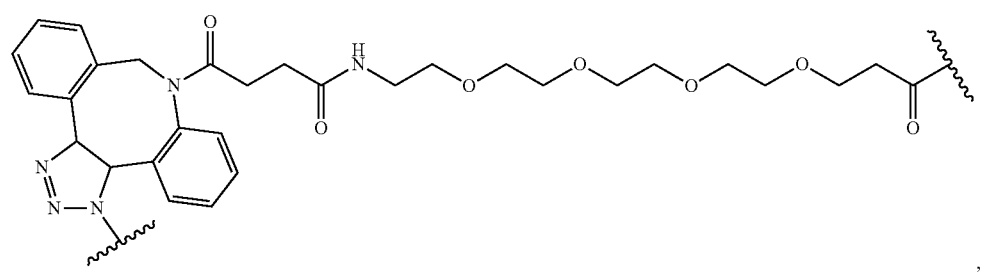
or mixture thereof;

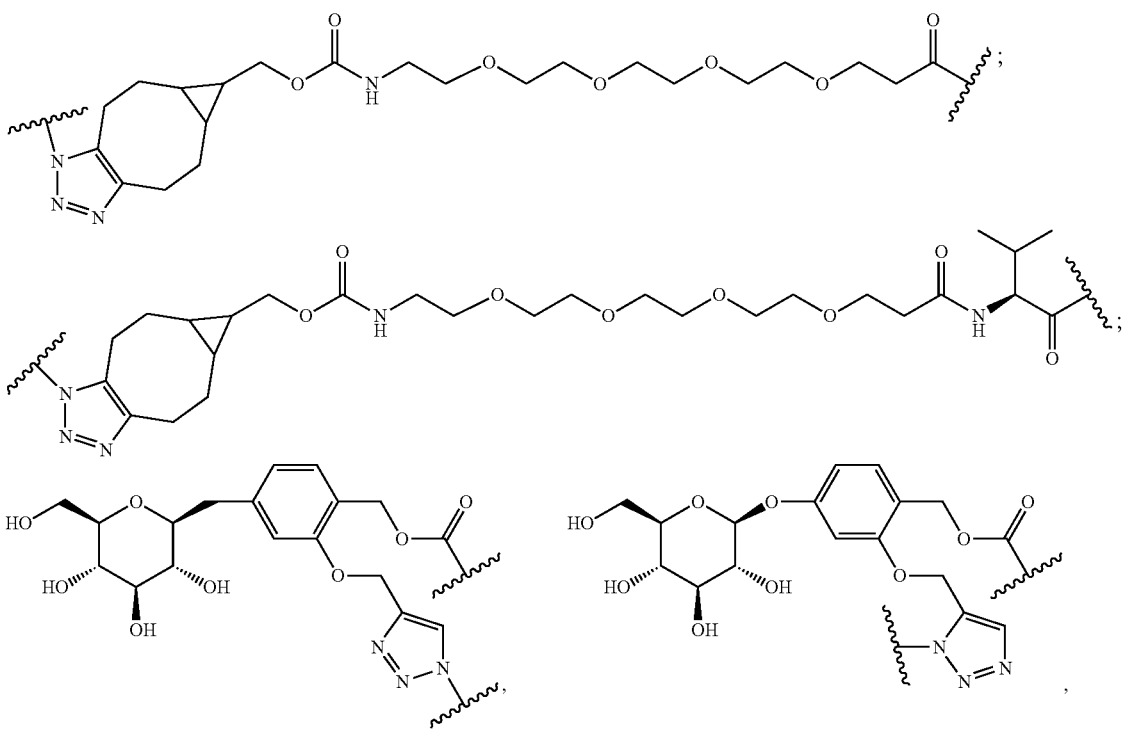

or mixture thereof;

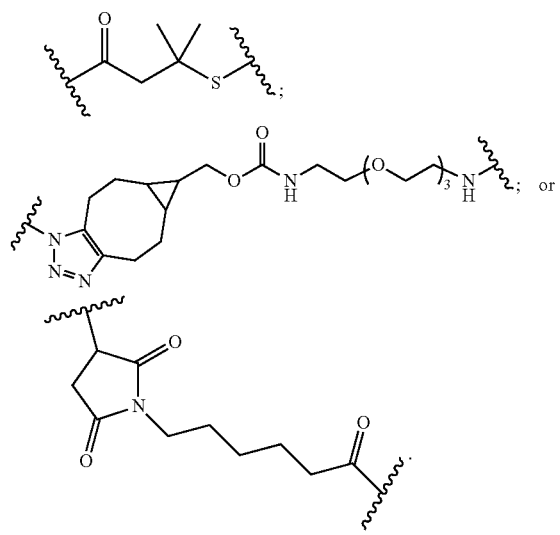

In some embodiments, A is a peptide selected from valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some embodiments, A is valine-citrulline or citrulline-valine.

In some embodiments, A is valine-alanine or alanine-valine.

In some embodiments, A is lysine-valine-alanine or alanine-valine-lysine.

In some embodiments, A is lysine-valine-citrulline or citrulline-valine-lysine.

In some embodiments, A is glutamate-valine-citrulline or citrulline-valine-glutamate.

In some embodiments, A is valine.

In some embodiments, A is alanine.

In some embodiments, A is citrulline.

In some embodiments, A is

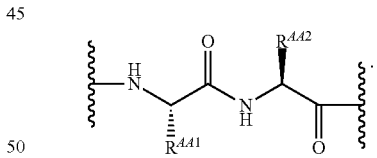

In some of these embodiments, $R^{AA1}$ is an amino acid side chain, and wherein $R^{AA2}$ is an amino acid side chain.

In some embodiments, A is

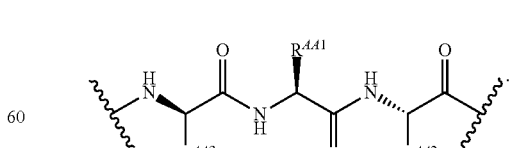

In some of these embodiments, $R^{AA1}$ is an amino acid side chain, $R^{AA2}$ is an amino acid side chain, and $R^{AA3}$ is an amino acid side chain that is bonded directly or indirectly to a cyclodextrin moiety.

In some embodiments, A is
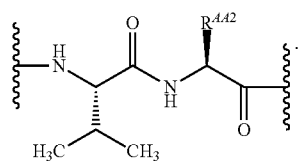
In some embodiments, A is
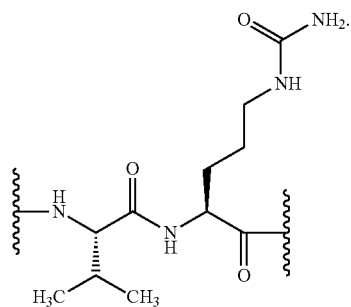 [SMILES: *N[C@H](C(=O)N[C@@H](CCCNC(N)=O)C(*)=O)C(C)C]
In some embodiments, A is
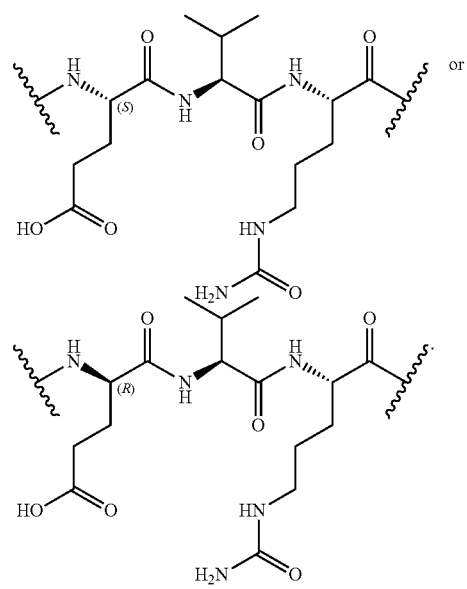
In some embodiments, A is
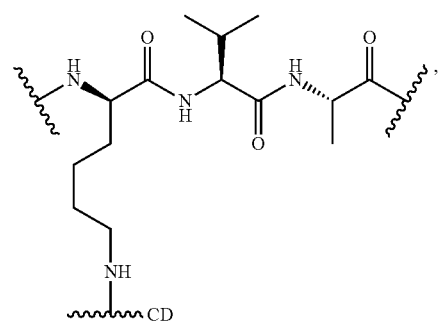
wherein
~~~CD
represents a direct or indirect bond to a cyclodextrin moiety.
In some embodiments, including any of the foregoing, CD is, independently in each instance, selected from
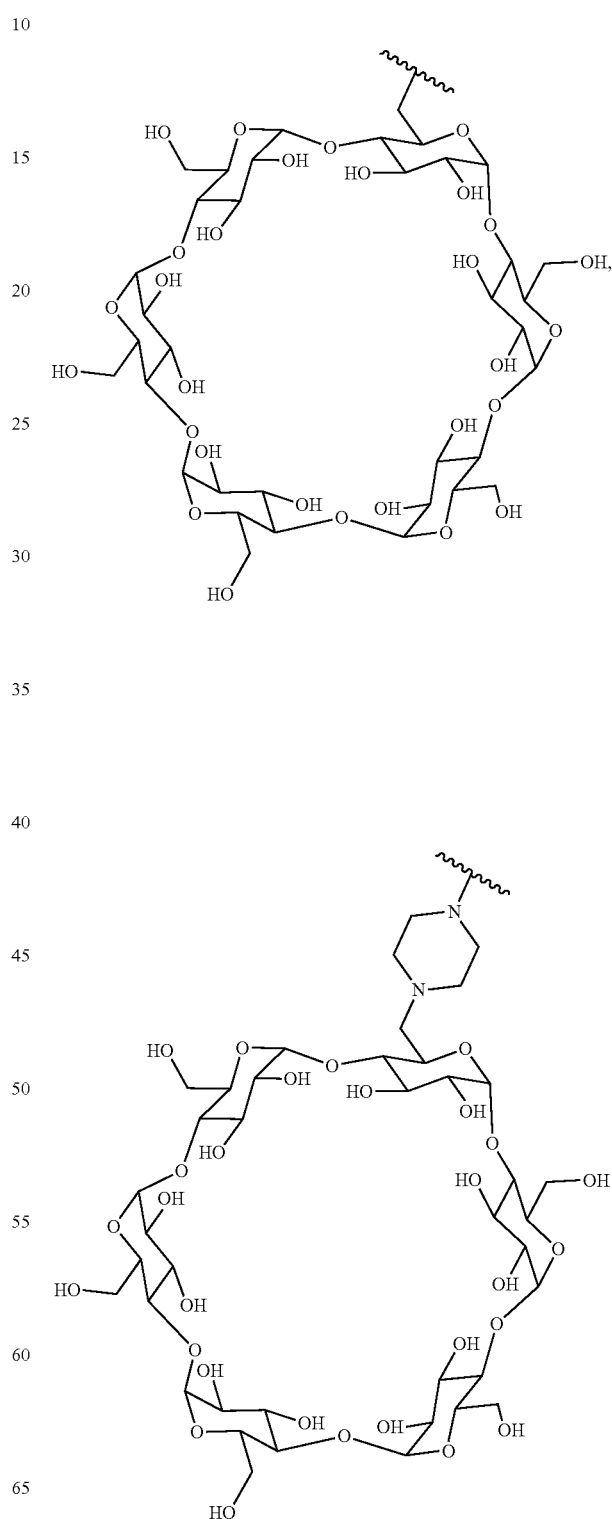

-continued
101
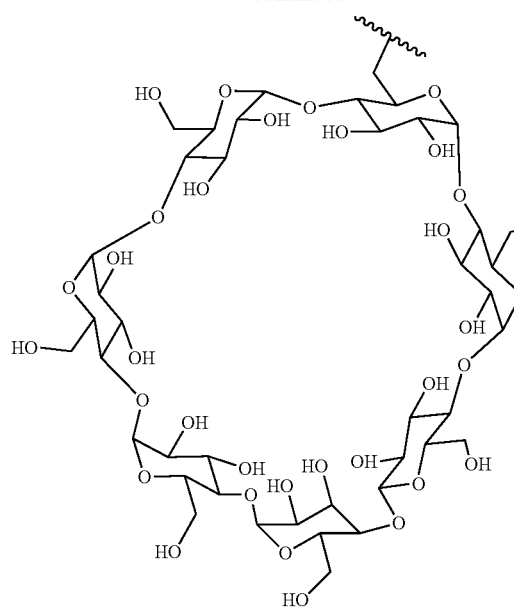
102
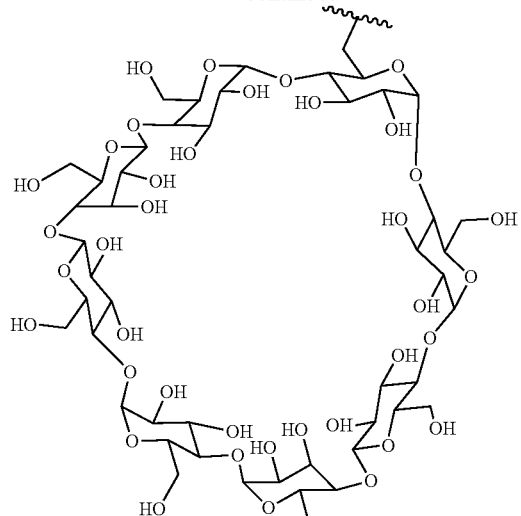
, and
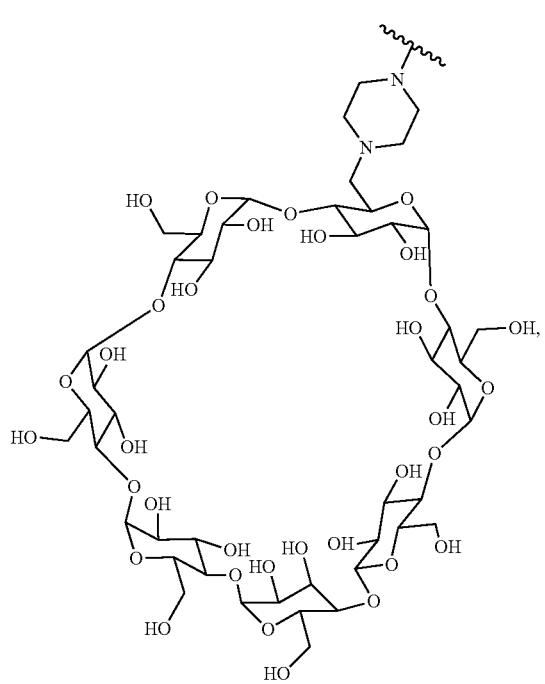
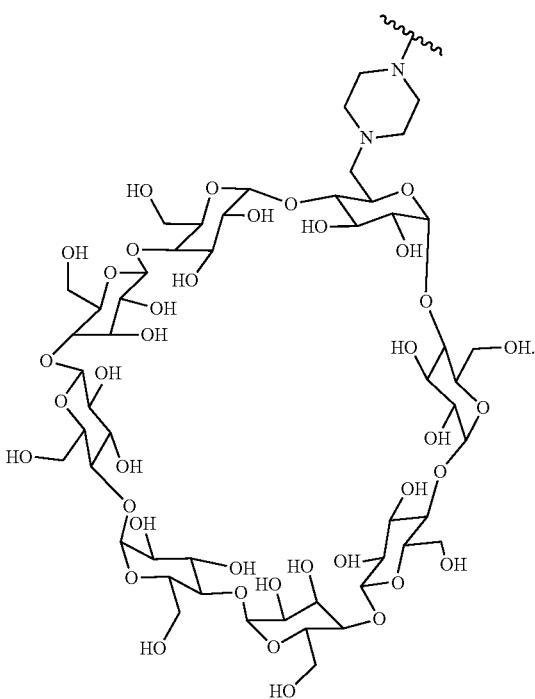 [SMILES: *N1CCN(CC2OC3OC4C(CO)OC(OC5C(CO)OC(OC6C(CO)OC(OC7C(CO)OC(OC8C(CO)OC(OC9C(CO)OC(OC%10C(CO)OC(OC2C(O)C3O)C(O)C%10O)C(O)C9O)C(O)C8O)C(O)C7O)C(O)C6O)C(O)C5O)C(O)C4O)CC1]

103
In some embodiments, the CD is
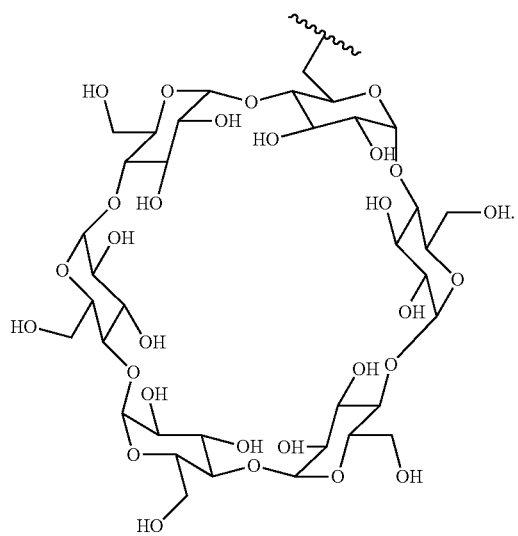 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]
In some embodiments, the CD is
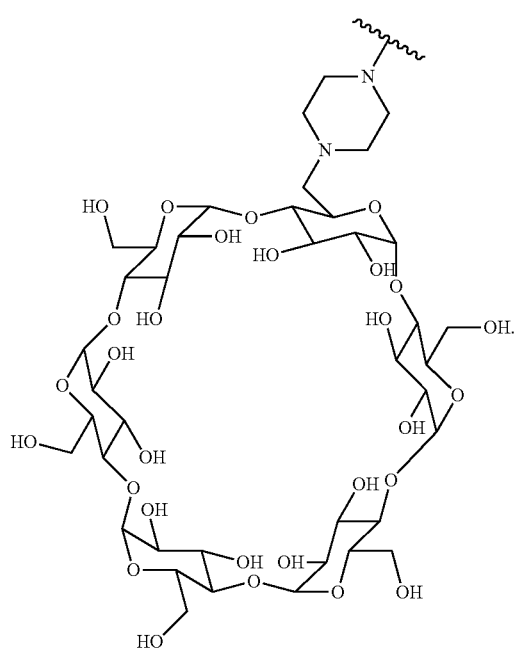 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]
104
In some embodiments, the CD is
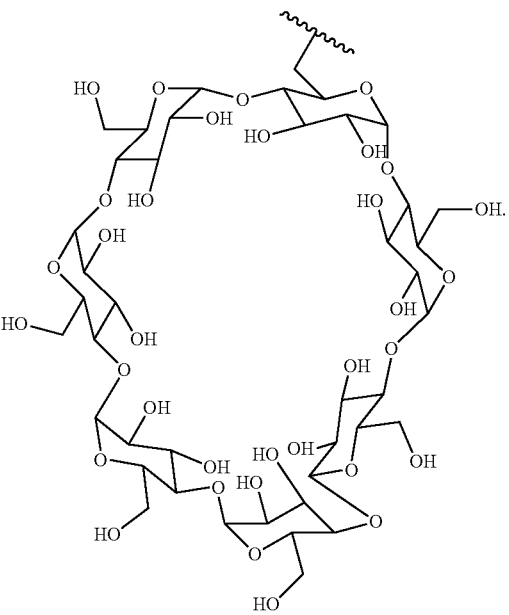 [SMILES: *CC1OC2OC3C(CO)OC(OC4C(CO)OC(OC5C(CO)OC(OC6C(CO)OC(OC7C(CO)OC(OC8C(CO)OC(OC1C(O)C2O)C(O)C8O)C(O)C7O)C(O)C6O)C(O)C5O)C(O)C4O)C(O)C3O]
In some embodiments, the CD is
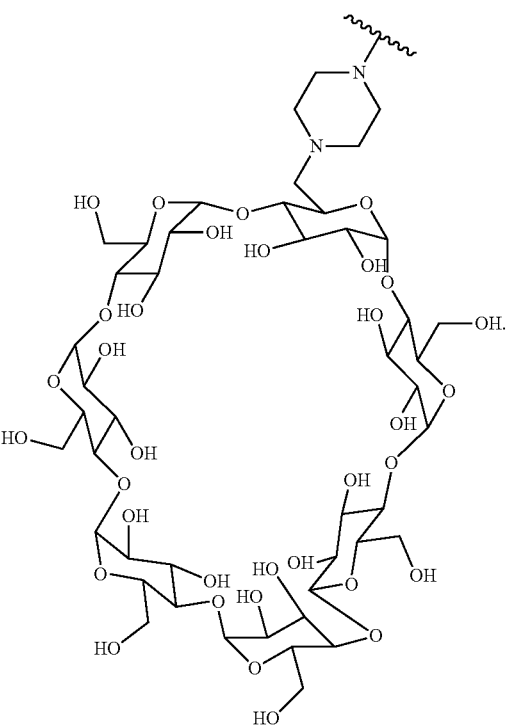 [SMILES: *N1CCN(CC2OC3OC4C(CO)OC(OC5C(CO)OC(OC6C(CO)OC(OC7C(CO)OC(OC8C(CO)OC(OC9C(CO)OC(OC2C(O)C3O)C(O)C9O)C(O)C8O)C(O)C7O)C(O)C6O)C(O)C5O)C(O)C4O)CC1]

105
In some embodiments, the CD is
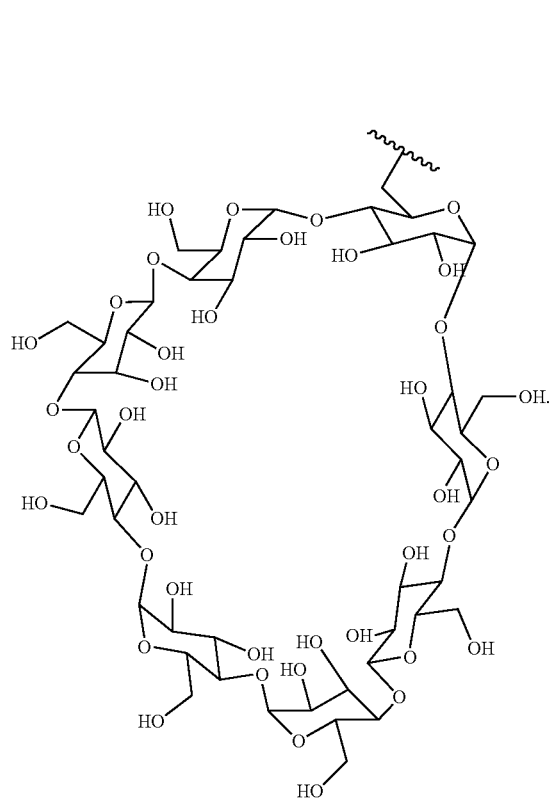 [SMILES: *CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]
106
In some embodiments, the CD is
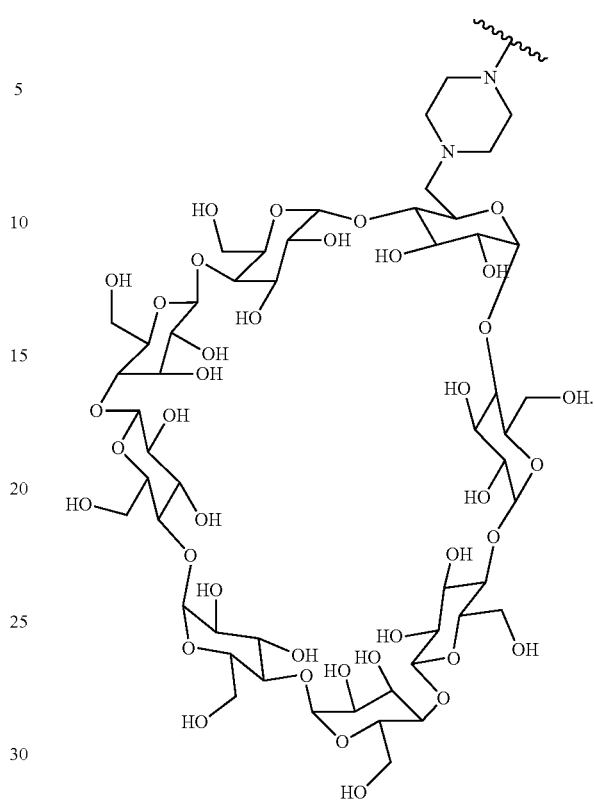
In some embodiments, A is
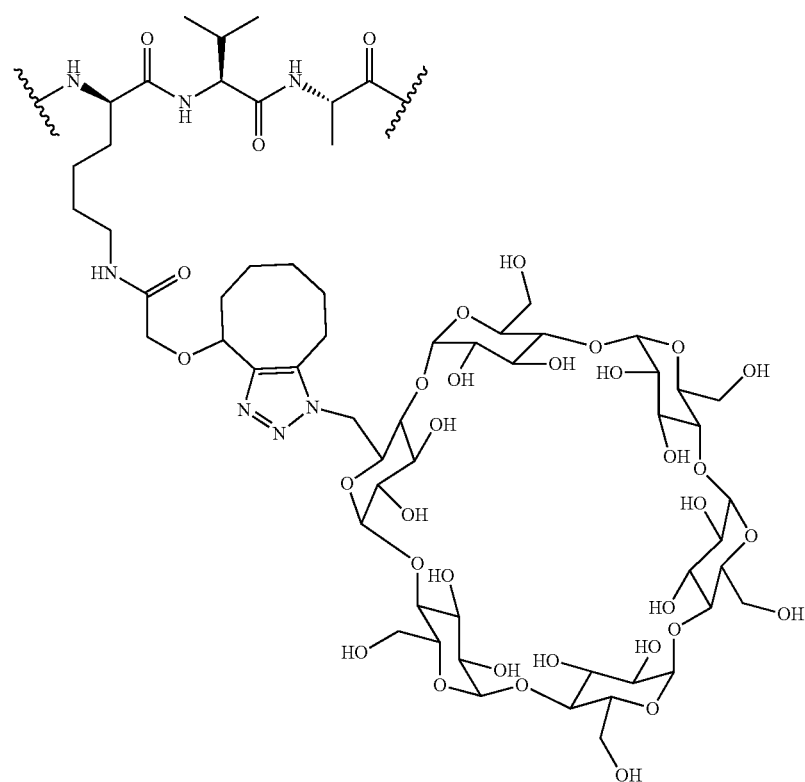 [SMILES: *N[C@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@H](C(=O)N[C@@H](C)C(*)=O)C(C)C]
or an isomer thereof.

In some embodiments, $R^a$ is H
In some embodiments, $R^a$ is alkyl
In some embodiments, $R^a$ is methyl, ethyl, n-propyl, i-propyl, n-butyl, t-butyl, i-butyl, or pentyl.
In some embodiments, B is aryl.
In some embodiments, B is phenyl.
In some embodiments, B is phenyl or pyridinyl.
In some embodiments herein, B is:

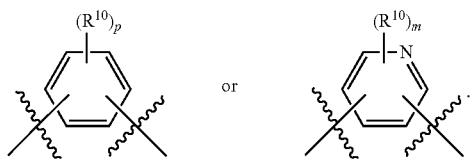

In these examples, $R^{10}$ is alkyl, alkenyl, alkynyl, alkoxy, aryl, alkylaryl, arylalkyl, halo, haloalkyl, haloalkoxy, heteroaryl, heterocycloalkyl, hydroxyl, cyano, nitro,

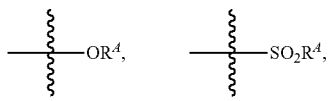

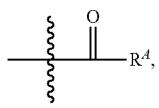

$NR^aR^b$, or azido. In these examples, subscripts p and m are independently, in each instance, selected from an integer selected from 0 to 4, inclusive.

In some embodiments herein, B is:

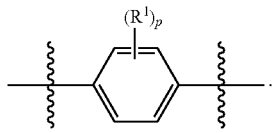

In these examples, p is 0, 1, 2, 3 or 4. In some of these embodiments, $R^1$ is, independently at each occurrence, alkyl, alkoxy, haloalkyl, or halo. In some embodiments, $R^1$ is alkyl. In some embodiments, $R^1$ is alkoxy. In some embodiments, $R^1$ is haloalkyl. In some embodiments, $R^1$ is halo.

In some embodiments of Formula ($L^A$), the $-(NR^a)_s$-$(B)_t$-$(CH_2)_u$-$(O)_v$-$(SP^2)_w$ is:

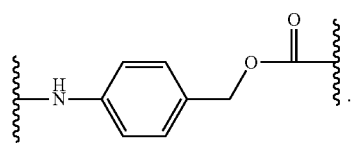 [SMILES: *Nc1ccc(COC(*)=O)cc1]

In any of the embodiments of L or $L^1$-$L^2$-$(L^3)_{0-1}$ described herein, one or more enhancement groups can be linked to the side chain of any amino acid in L or $L^1$-$L^2$-$(L^3)_{0-1}$. Useful amino acids for linking enhancement groups include lysine, asparagine, aspartate, glutamine, glutamate, and citrulline. The link to the enhancement group can be a direct bond to the amino acid side chain, or the link can be indirect via a spacer and/or reactive group. Useful spacers and reactive groups include any described herein. The enhancement group can be any group deemed useful by those of skill in the art. For example, the enhancement group can be any group that imparts a beneficial effect to the compound, payload, linker payload, or antibody conjugate including, but not limited to, biological, biochemical, synthetic, solubilizing, imaging, detecting, and reactivity effects, and the like. In certain embodiments, the enhancement group is a hydrophilic group. In certain embodiments, the enhancement group is a cyclodextrin. In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose. and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the enhancement group is capable of improving solubility of the remainder of the conjugate.

In certain embodiments, the enhancement group is an alkyl, heteroalkyl, alkylenyl, heteroalkylenyl sulfonic acid, heteroalkylenyl taurine, heteroalkylenyl phosphoric acid or phosphate, heteroalkylenyl amine (e.g., quaternary amine), or heteroalkylenyl sugar. In certain embodiments, sugars include, without limitation, monosaccharides, disaccharides, and polysaccharides. Exemplary monosaccharides include glucose, ribose, deoxyribose, xylose, arabinose, mannose, galactose, fructose. and the like. In certain embodiments, sugars include sugar acids such as glucuronic acid, further including conjugated forms such as glucuronides (i.e., via glucuronidation). Exemplary disaccharides include maltose, sucrose, lactose, lactulose, trehalose, and the like. Exemplary polysaccharides include amylose, amylopectin, glycogen, inulin, cellulose, and the like. The cyclodextrin can be any cyclodextrin known to those of skill. In certain embodiments, the cyclodextrin is alpha cyclodextrin, beta cyclodextrin, or gamma cyclodextrin, or mixtures thereof. In certain embodiments, the cyclodextrin is alpha cyclodextrin. In certain embodiments, the cyclodextrin is beta cyclodextrin. In certain embodiments, the cyclodextrin is gamma cyclodextrin. In certain embodiments, the enhancement group is capable of improving solubility of the remainder of the conjugate. In certain embodiments, the alkyl, heteroalkyl, alkylenyl, or heteroalkylenyl sulfonic acid is substituted or non-substituted. In certain embodiments, the alkyl, heteroalkyl, alkylenyl, or heteroalkylenyl sulfonic acid is $-(CH_2)_{1-5}SO_3H$, $-(CH_2)_n-NH-(CH_2)_{1-5}SO_3H$, $-(CH_2)_n-C(O)NH-(CH_2)_{1-5}SO_3H$, $-(CH_2CH_2O)_m-C$ (O)NH—(CH$_2$)$_{1-5}$SO$_3$H, —(CH$_2$)$_n$—N((CH$_2$)$_{1-5}$C(O)NH (CH$_2$)$_{1-5}$SO$_3$H)$_2$, —(CH$_2$)$_n$—C(O)N((CH$_2$)$_{1-5}$C(O)NH (CH$_2$)$_{1-5}$SO$_3$H)$_2$, or —(CH$_2$CH$_2$O)$_m$—C(O)N((CH$_2$)$_{1-5}$C (O)NH(CH$_2$)$_{1-5}$SO$_3$H)$_2$, wherein n is 1, 2, 3, 4, or 5, and m is 1, 2, 3, 4, or 5. In one embodiment, the alkyl or alkylenyl sulfonic acid is —(CH$_2$)$_{1-5}$SO$_3$H. In another embodiment, the heteroalkyl or heteroalkylenyl sulfonic acid is —(CH$_2$)$_n$—NH—(CH$_2$)$_{1-5}$SO$_3$H, wherein n is 1, 2, 3, 4, or 5. In another embodiment, the alkyl, heteroalkyl, alkylenyl, or heteroalkylenyl sulfonic acid is —(CH$_2$)$_n$—C(O)NH—(CH$_2$)$_{1-5}$SO$_3$H, wherein n is 1, 2, 3, 4, or 5. In another embodiment, the alkyl, heteroalkyl, alkylenyl, or heteroalkylenyl sulfonic acid is —(CH$_2$CH$_2$O)$_m$—C(O)NH—(CH$_2$)$_{1-5}$SO$_3$H, wherein m is 1, 2, 3, 4, or 5. In another embodiment, the alkyl, heteroalkyl, alkylenyl, or heteroalkylenyl sulfonic acid is —(CH$_2$)$_n$—N((CH$_2$)$_{1-5}$C(O)NH (CH$_2$)$_{1-5}$SO$_3$H)$_2$, wherein n is 1, 2, 3, 4, or 5. In another embodiment, the alkyl, heteroalkyl, alkylenyl, or heteroalkylenyl sulfonic acid is —(CH$_2$)$_n$—C(O)N((CH$_2$)$_{1-5}$C(O) NH(CH$_2$)$_{1-5}$SO$_3$H)$_2$, wherein n is 1, 2, 3, 4, or 5. In another embodiment, the alkyl, heteroalkyl, alkylenyl, or heteroalkylenyl sulfonic acid is —(CH$_2$CH$_2$O)$_m$—C(O)N((CH$_2$)$_{1-5}$ C(O)NH(CH$_2$)$_{1-5}$SO$_3$H)$_2$, wherein m is 1, 2, 3, 4, or 5.

Provided herein are antibody-drug conjugates comprising an antibody or an antigen-binding fragment thereof conjugated to a compound selected from Table 1. In some embodiments, the compound is according to formula 1d, 1e, 1g, or 1h.

Provided herein are also antibody-drug conjugates of formula Ab-L-SP-D or BA-L-SP-D, where D is a budesonide prodrug or a prodrug of a budesonide analog or derivative (including fluorinated analogs and derivatives), and where Ab, BA, L, and SP are as defined in any embodiment described herein. In some embodiments, D of Ab-L-SP-D and BA-L-SP-D and

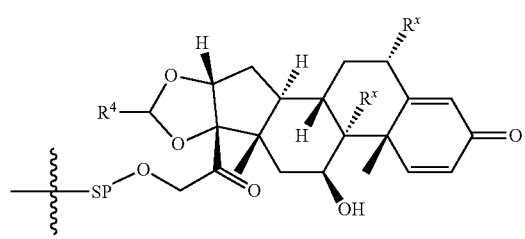

of Formula (II) and (III) is selected from:

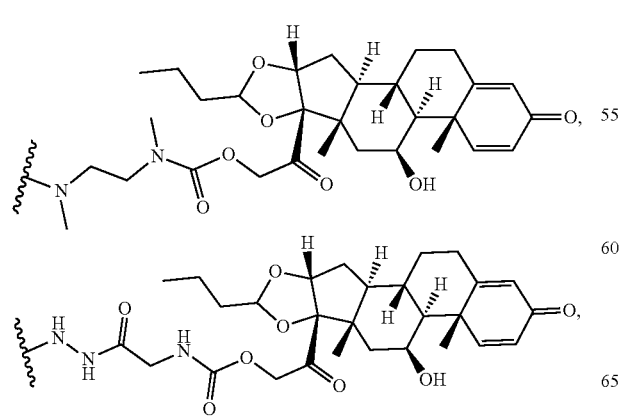

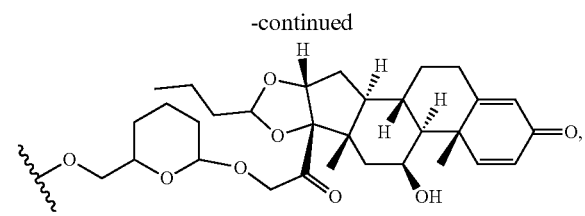

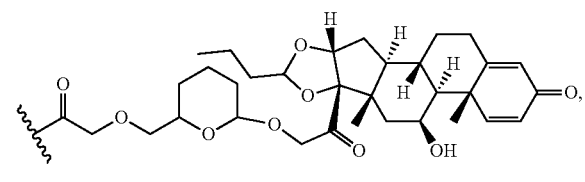

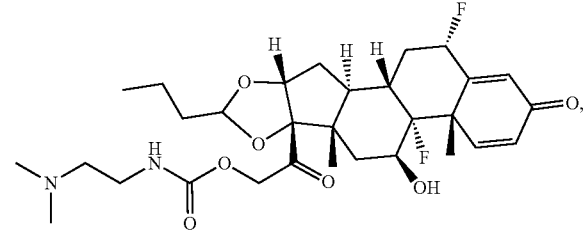

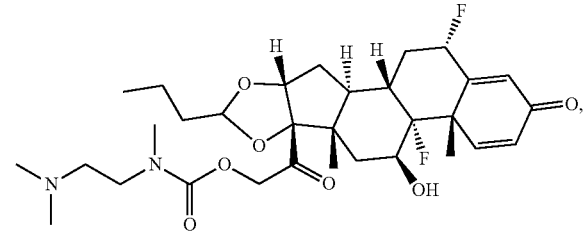

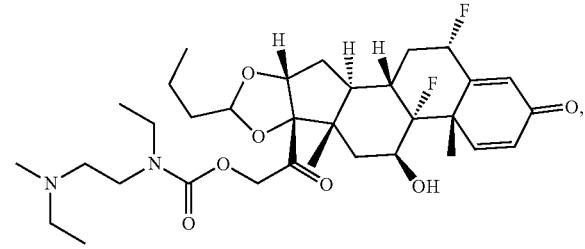

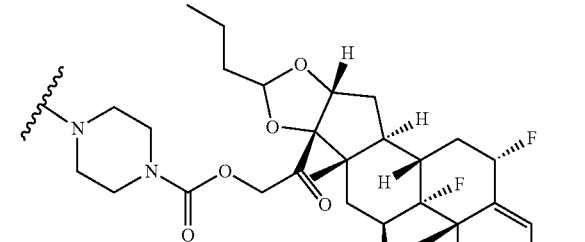

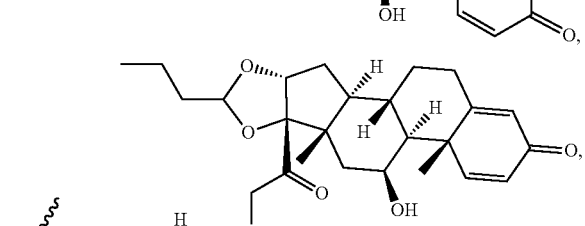

111
-continued
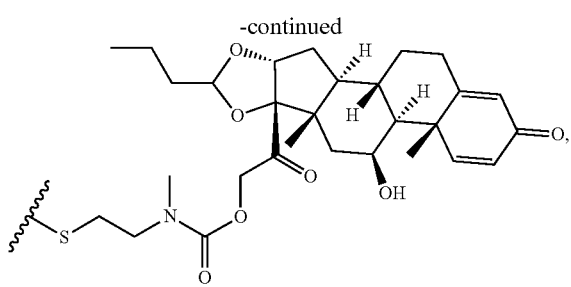
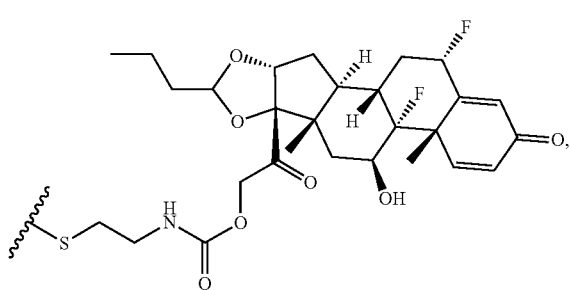
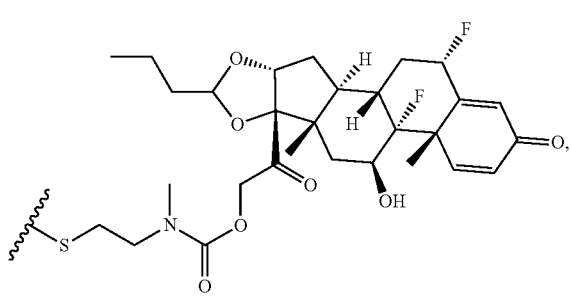
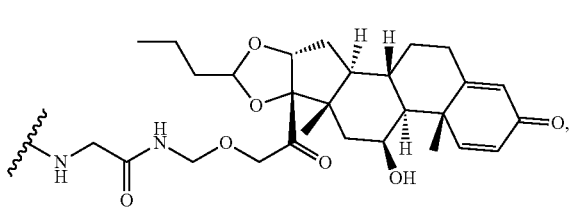
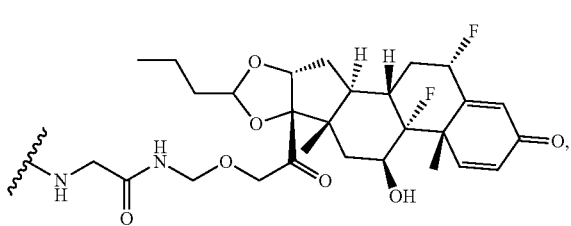
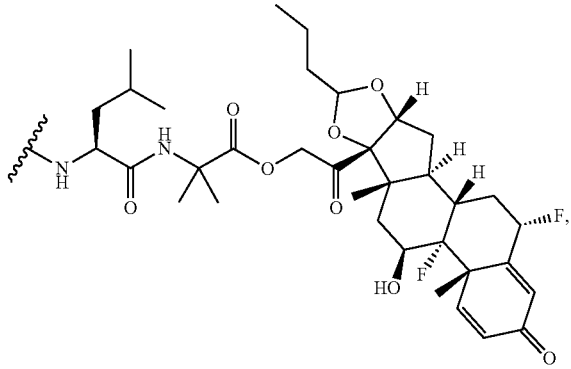
112
-continued
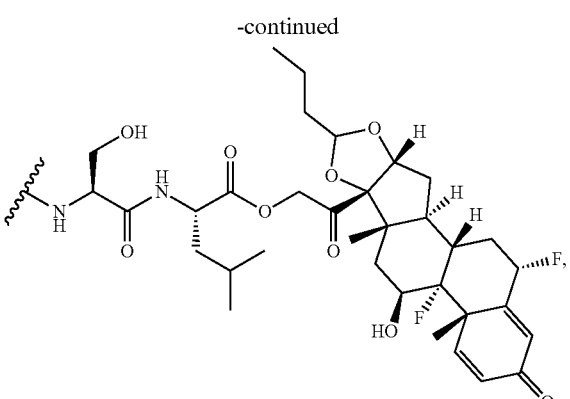
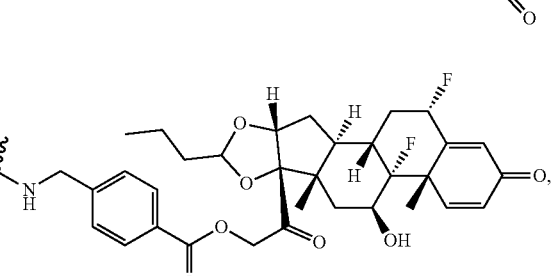
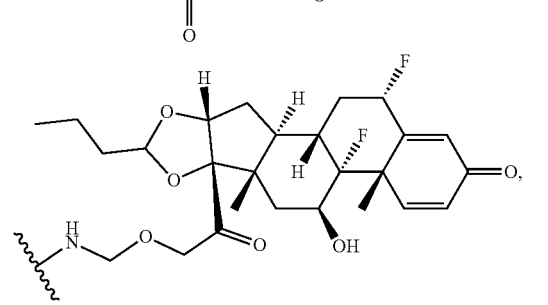
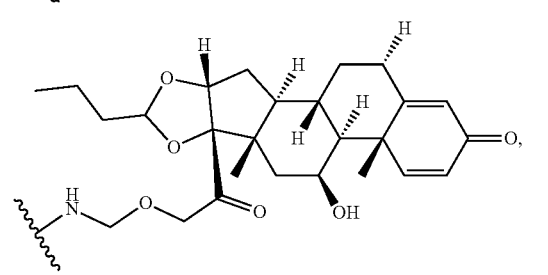
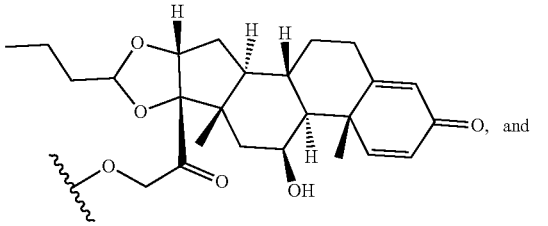, and
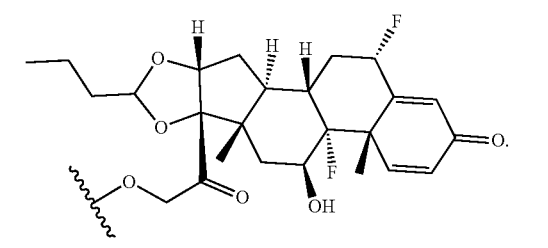 [SMILES: *OCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]
In some embodiments of Ab-L-SP-D, BA-L-SP-D, and Formula (III), SP is a moiety capable of releasing D or

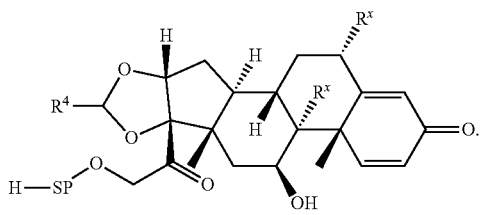

In some embodiments, under physiological conditions the bond between L and SP is cleaved to release a steroid prodrug, i.e. H-SP-D or

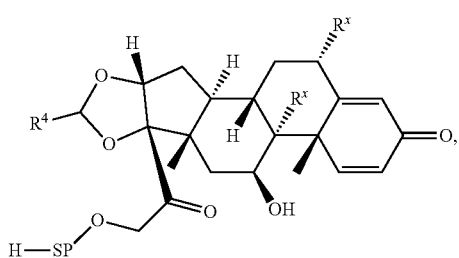

and the bond between SP and D or between SP and

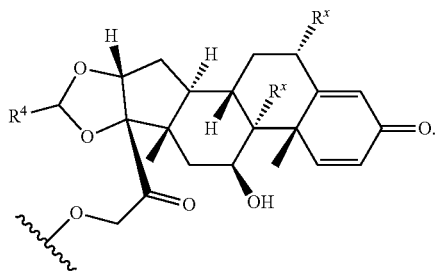

is subsequently cleaved to release a biologically active steroid. In some embodiments, the n-propyl of

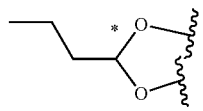

in each of the above structures is in the R-configuration, i.e. at the carbon indicated by the asterisk. In some embodiments, the n-propyl of

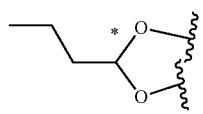 [SMILES: *OC(CCC)O*]

in each of the above structures is in the S-configuration, i.e. at the carbon indicated by the asterisk. In some embodiments, the n-propyl of

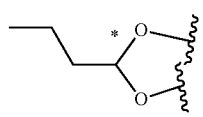

in each of the above structures is a mixture of the R- and S-configurations, i.e. at the carbon indicated by the asterisk. In some embodiments, the n-propyl of

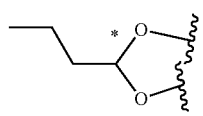 [SMILES: *OC(CCC)O*]

in each of the above structures is a mixture of the R- and S-configurations, i.e. at the carbon indicated by the asterisk, wherein the R:S mixture is about 1:1, about 2:1, about 3:1, about 4:1, about 5:1, about 6:1, about 7:1, about 8:1, about 9:1, or about 10:1.

Set forth herein are also antibody-steroid conjugates having the following formulas:

TABLE 3
Antibody-Drug Conjugates
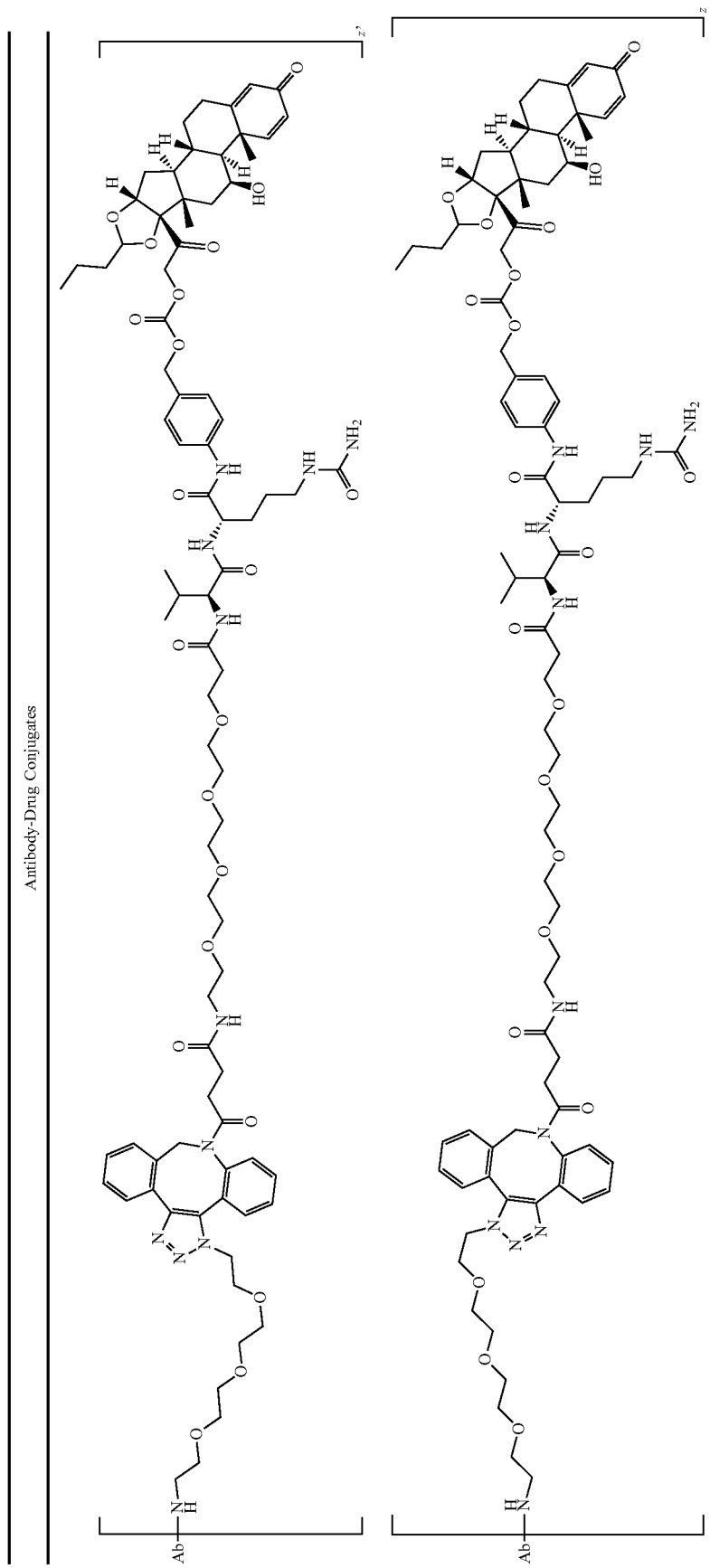
or a mixture thereof;

TABLE 3-continued
Antibody-Drug Conjugates
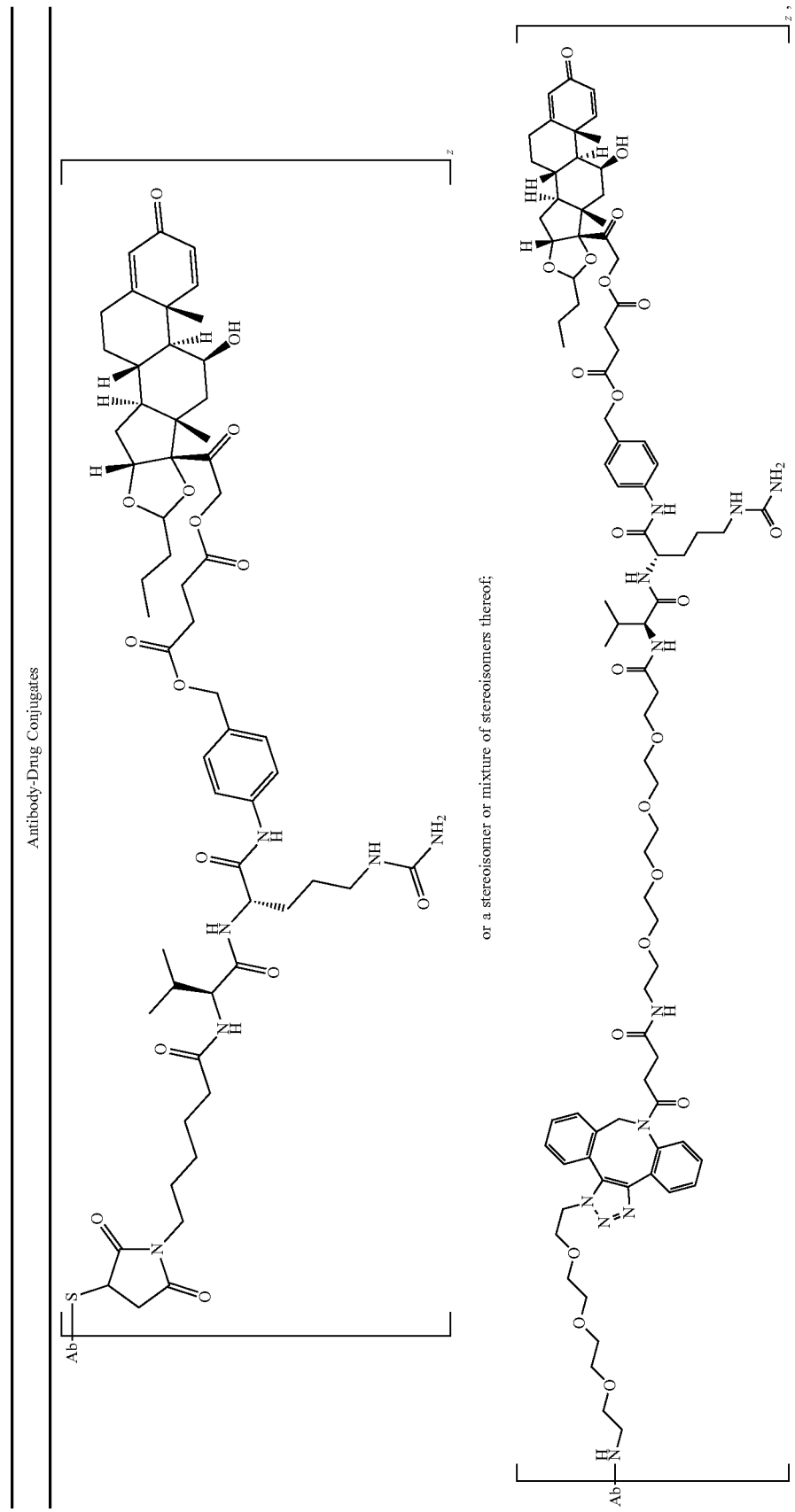
or a stereoisomer or mixture of stereoisomers thereof;

TABLE 3-continued
Antibody-Drug Conjugates
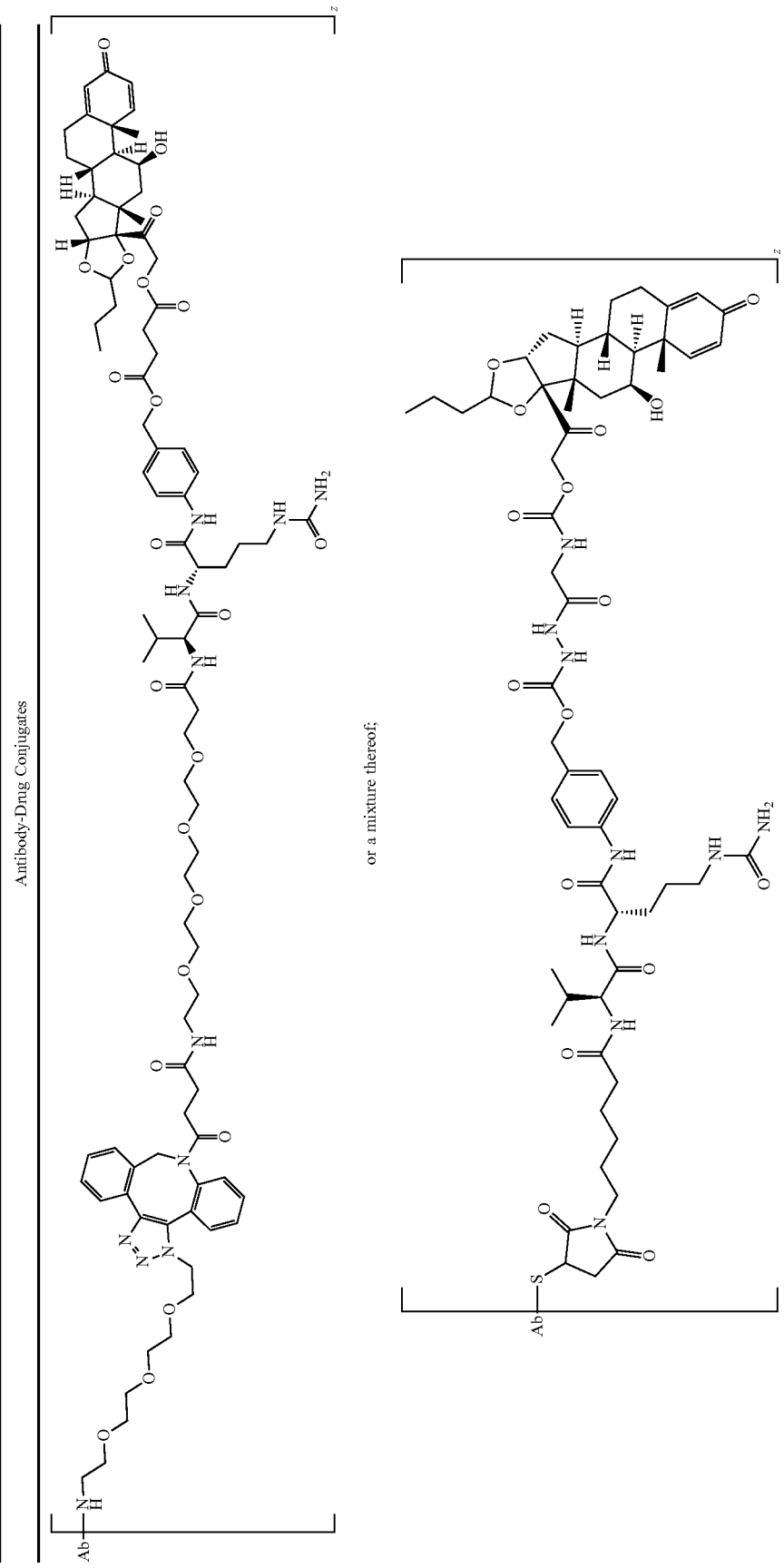
or a mixture thereof;
or a stereoisomer or mixture of stereoisomers thereof;

TABLE 3-continued
Antibody-Drug Conjugates
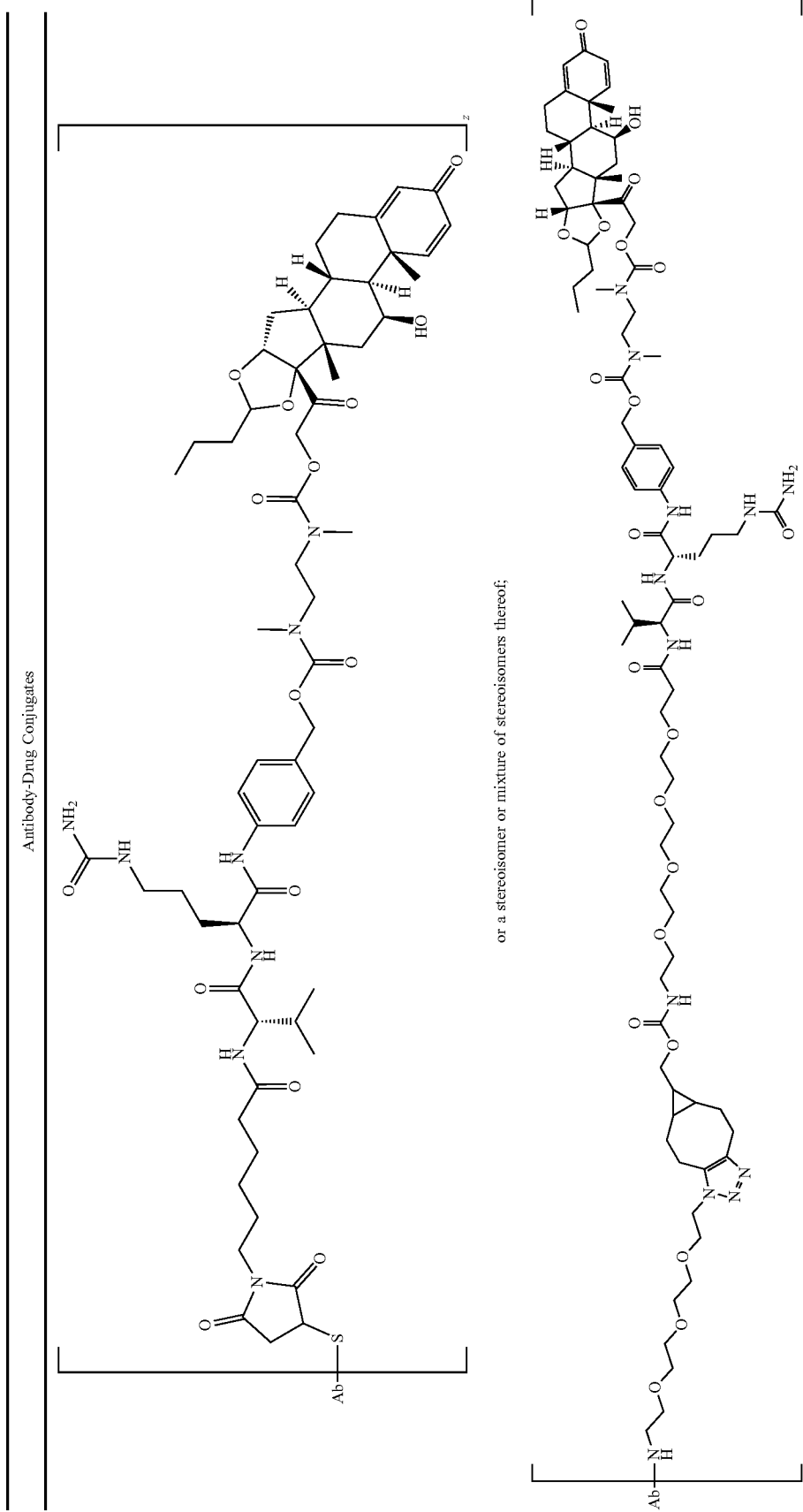
or a stereoisomer or mixture of stereoisomers thereof;

TABLE 3-continued
Antibody-Drug Conjugates
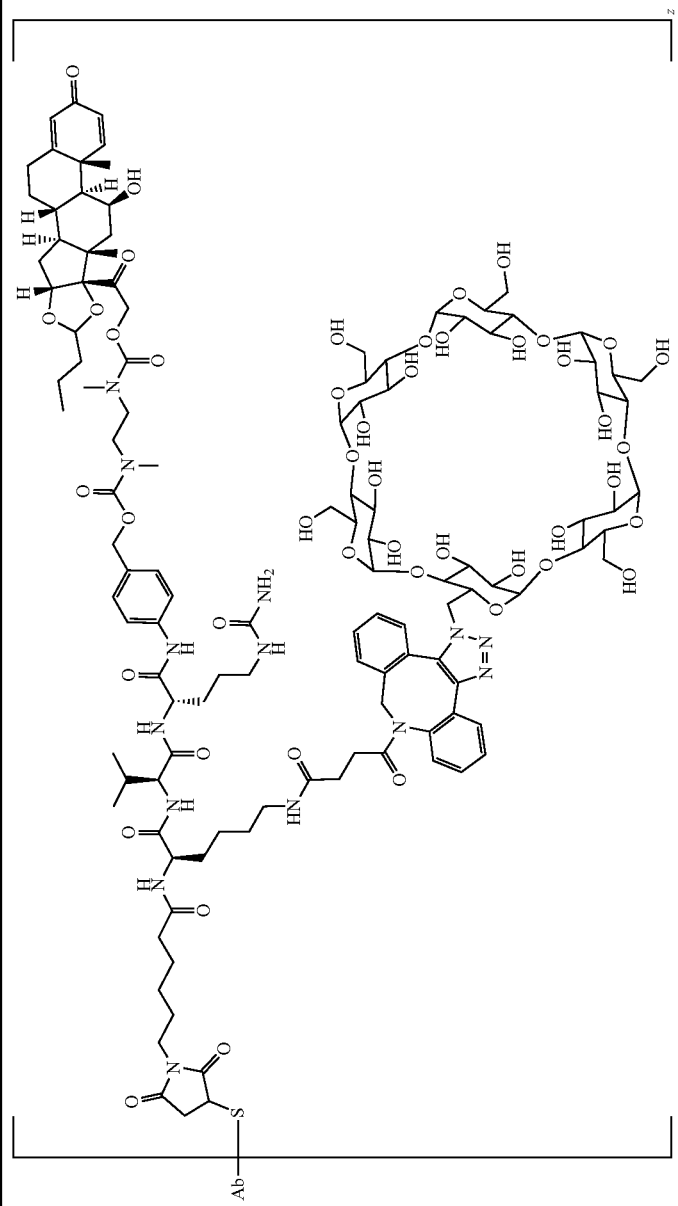

TABLE 3-continued
Antibody-Drug Conjugates
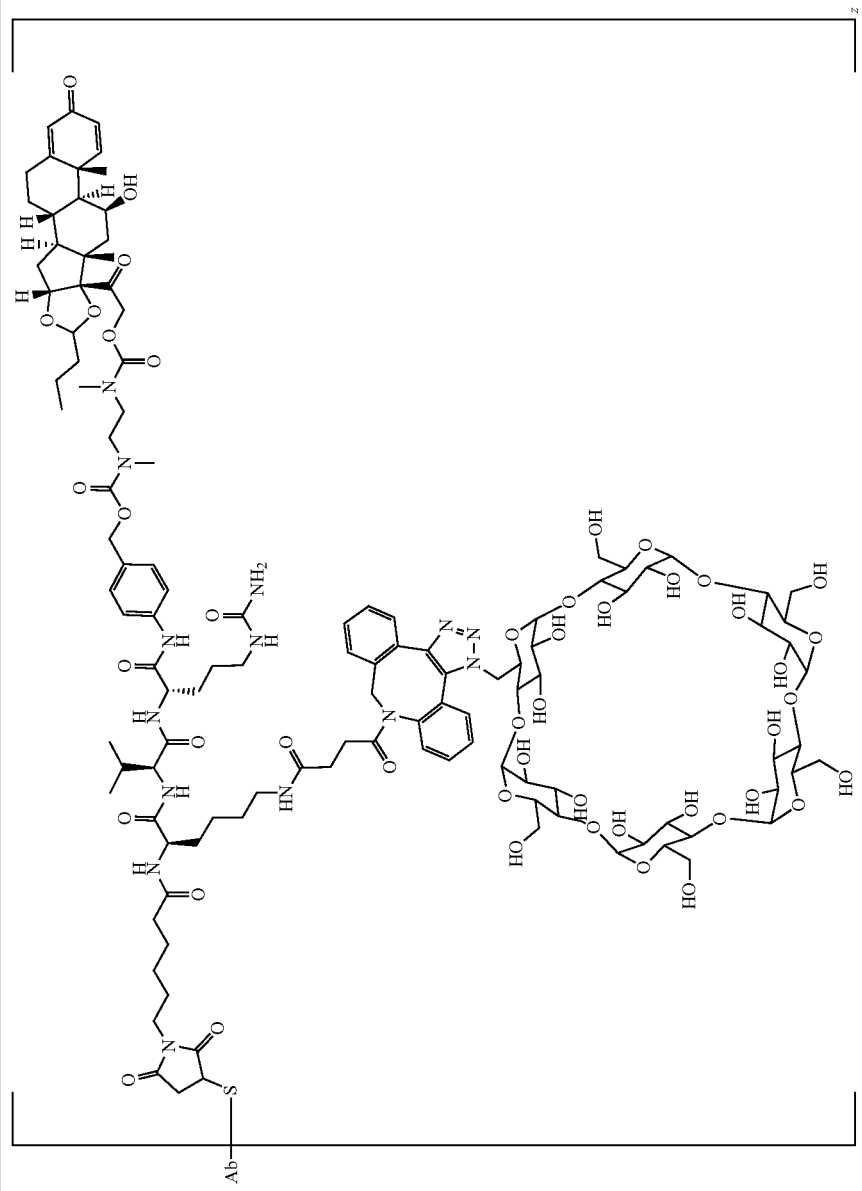
or a mixture thereof

TABLE 3-continued
Antibody-Drug Conjugates
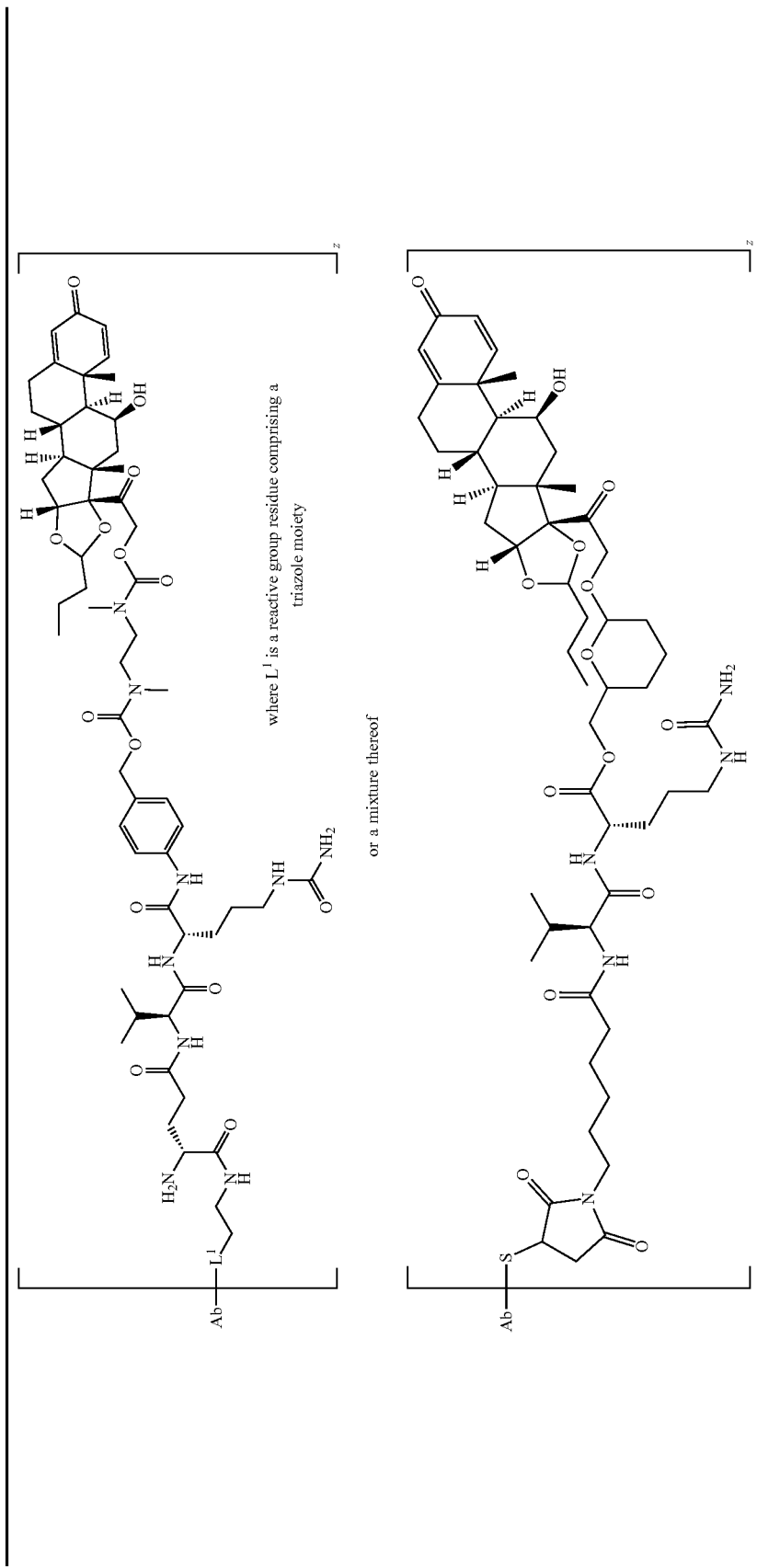

TABLE 3-continued
Antibody-Drug Conjugates
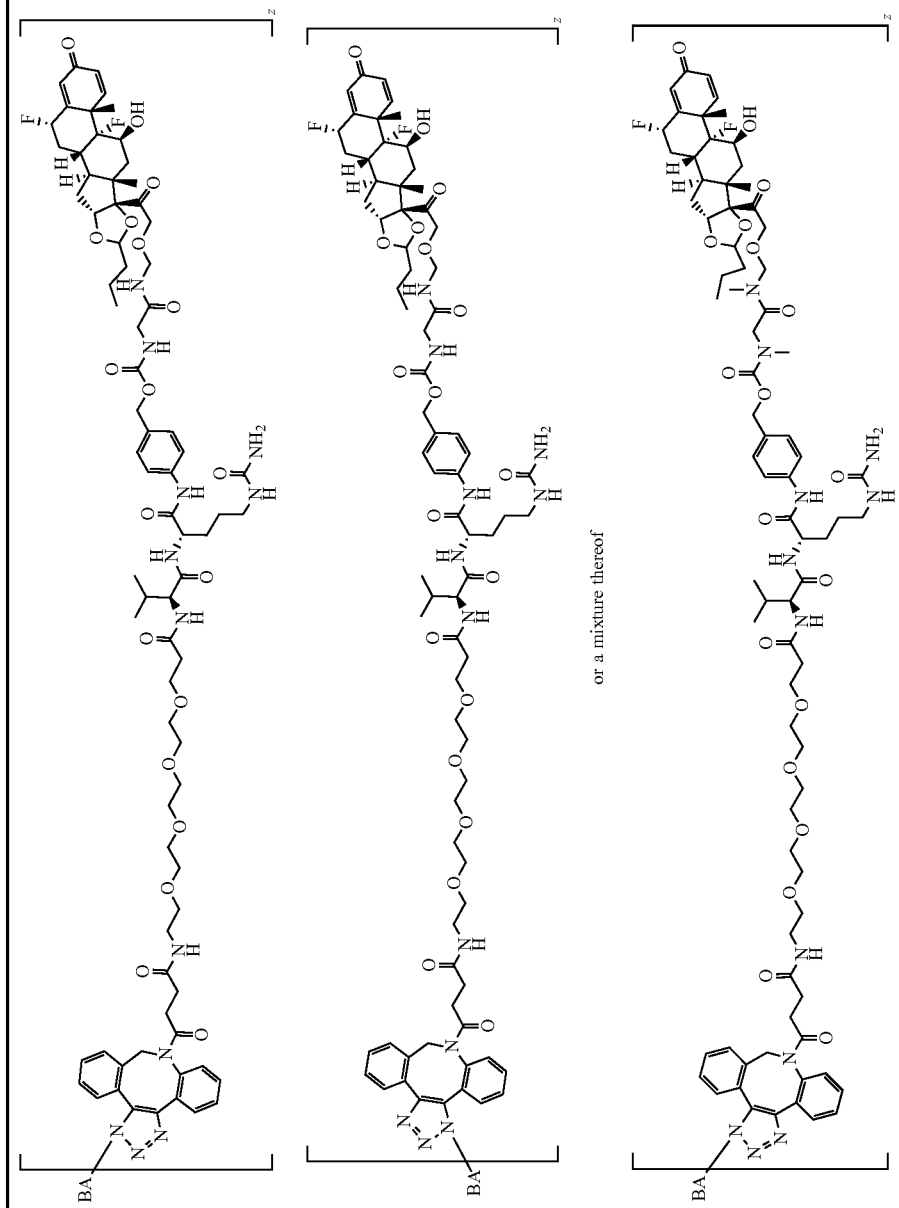
or a mixture thereof

TABLE 3-continued
Antibody-Drug Conjugates
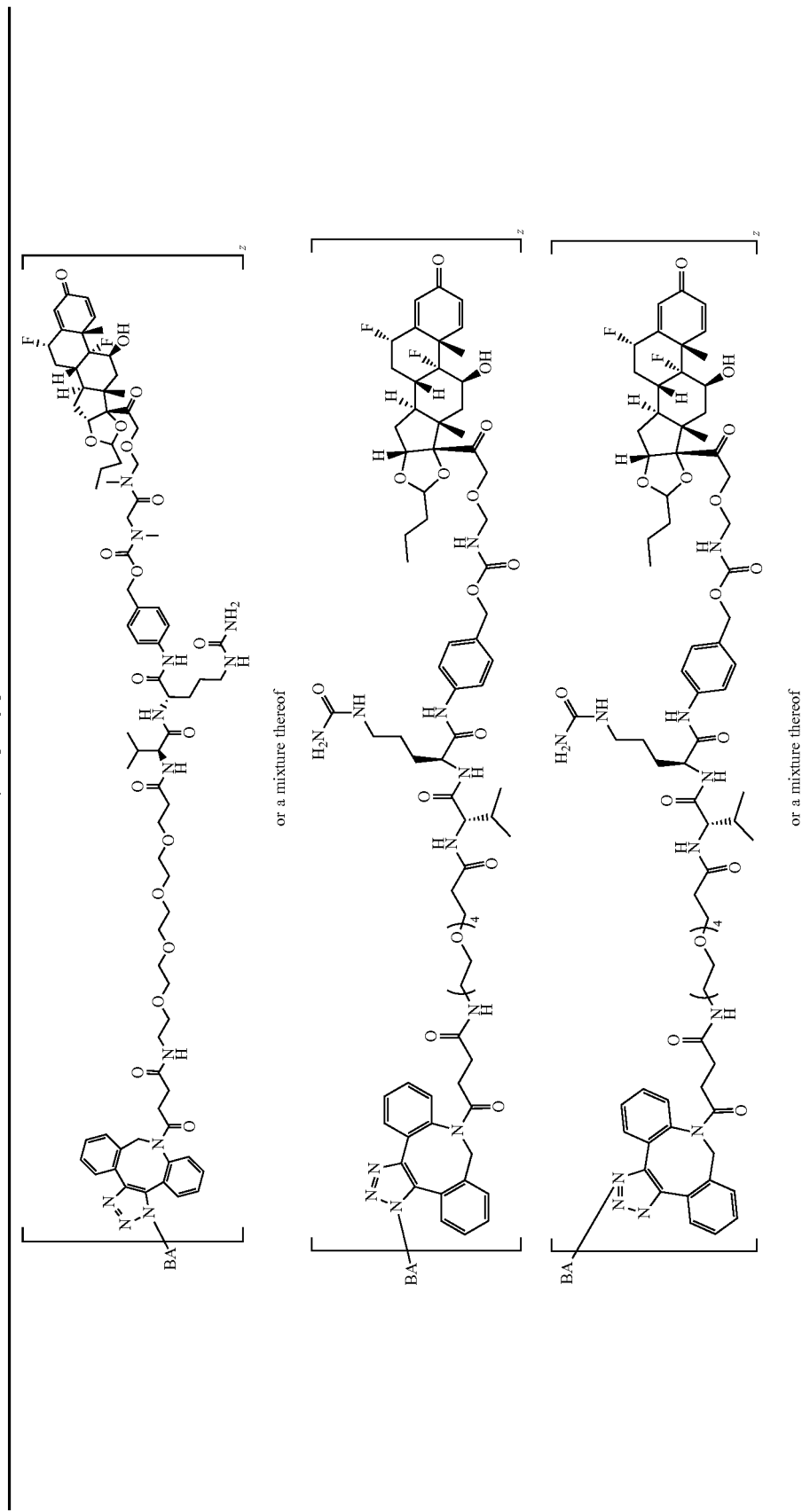
or a mixture thereof

TABLE 3-continued
Antibody-Drug Conjugates
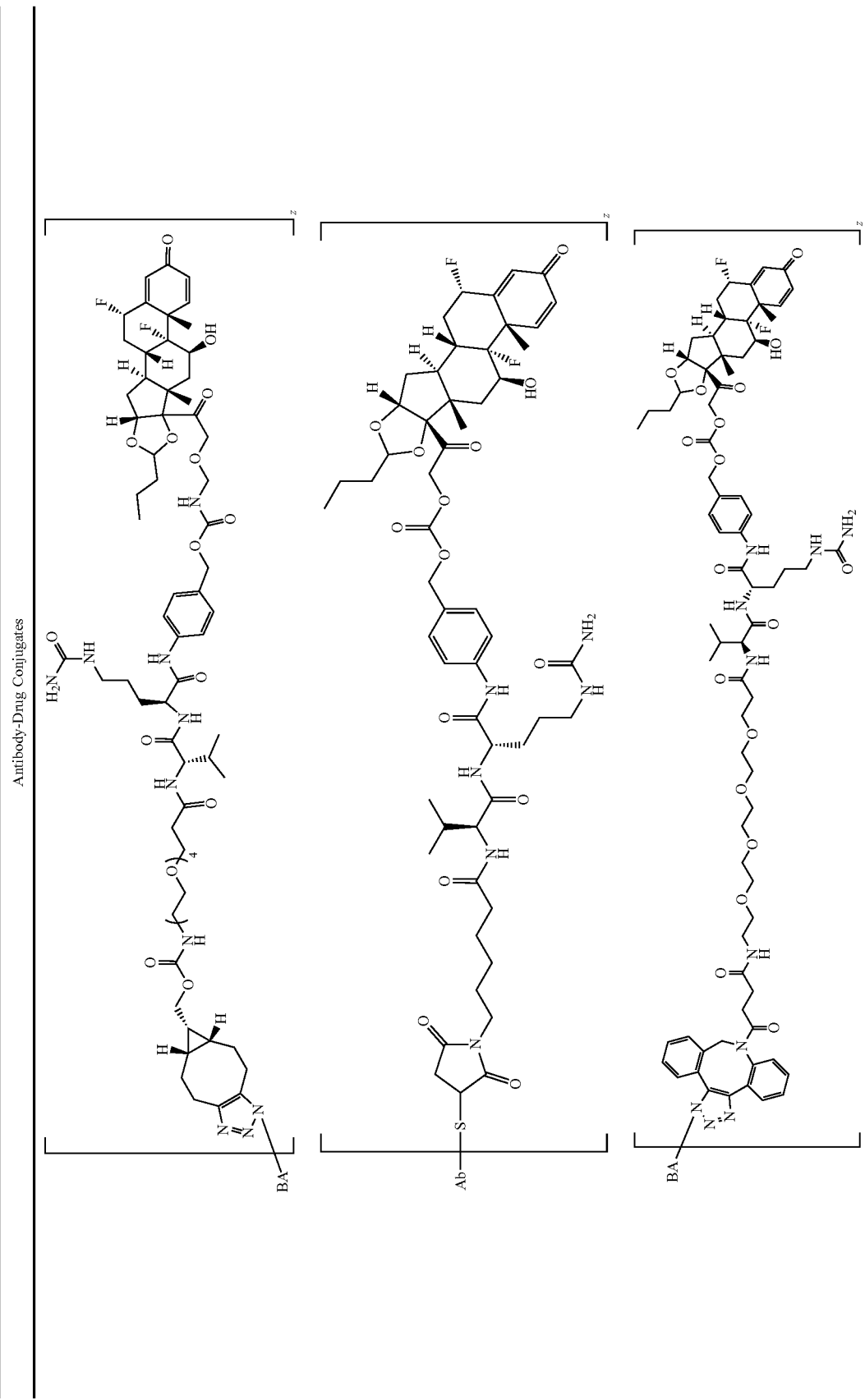

TABLE 3-continued
Antibody-Drug Conjugates
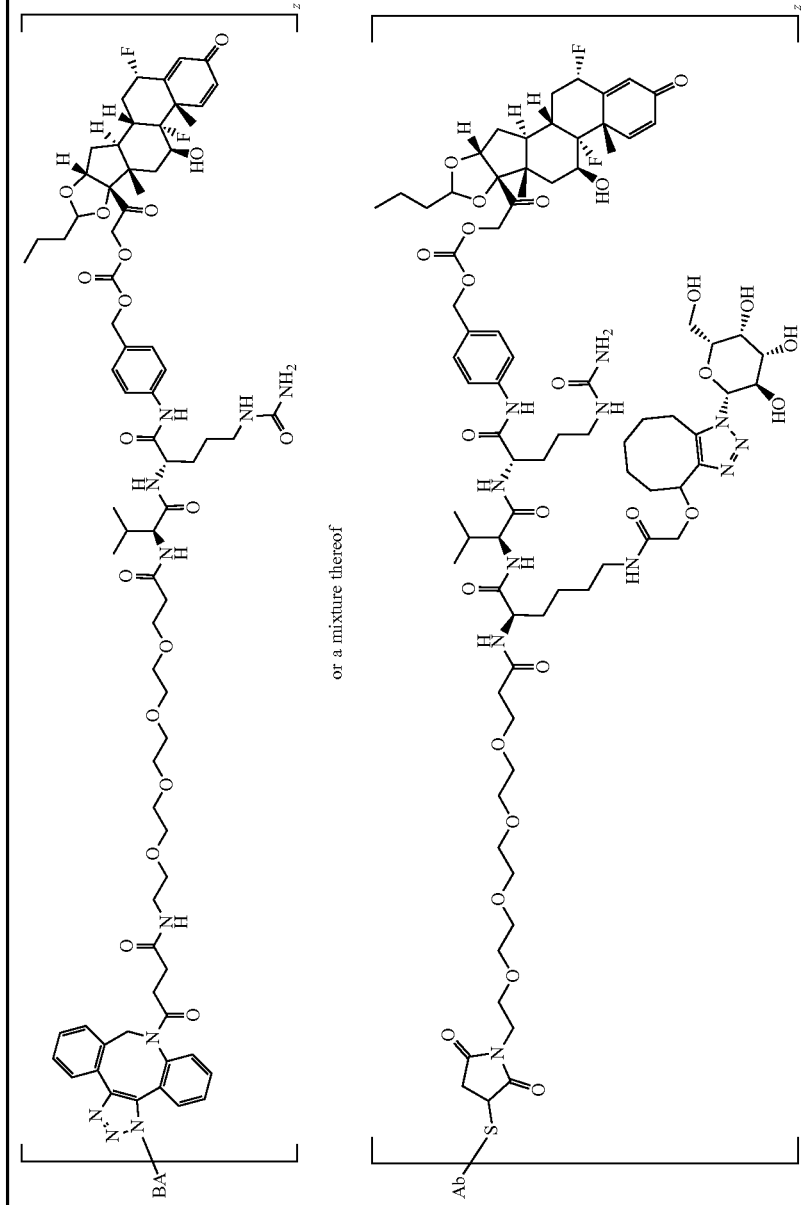
or a mixture thereof

TABLE 3-continued
Antibody-Drug Conjugates
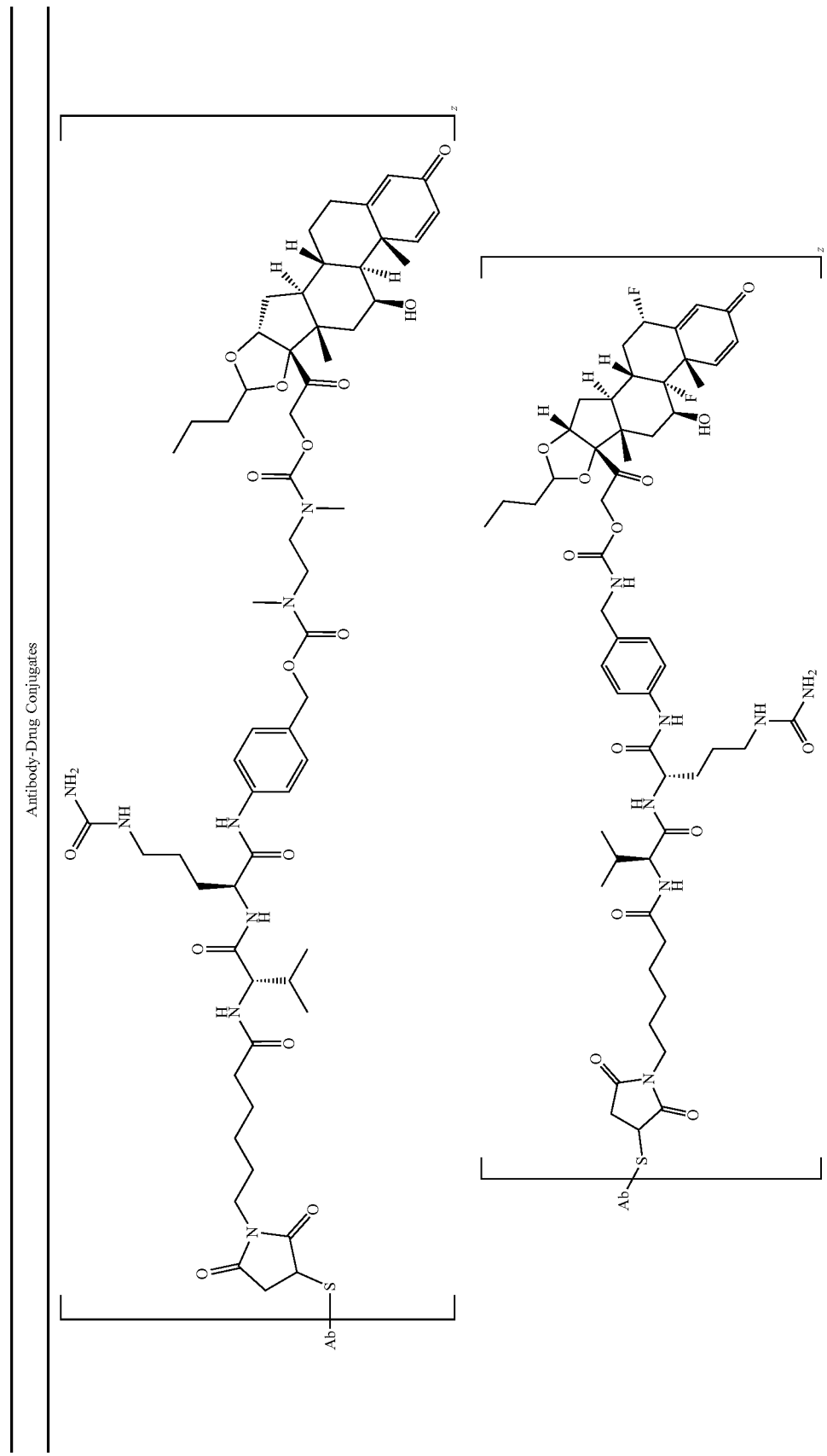

TABLE 3-continued
Antibody-Drug Conjugates
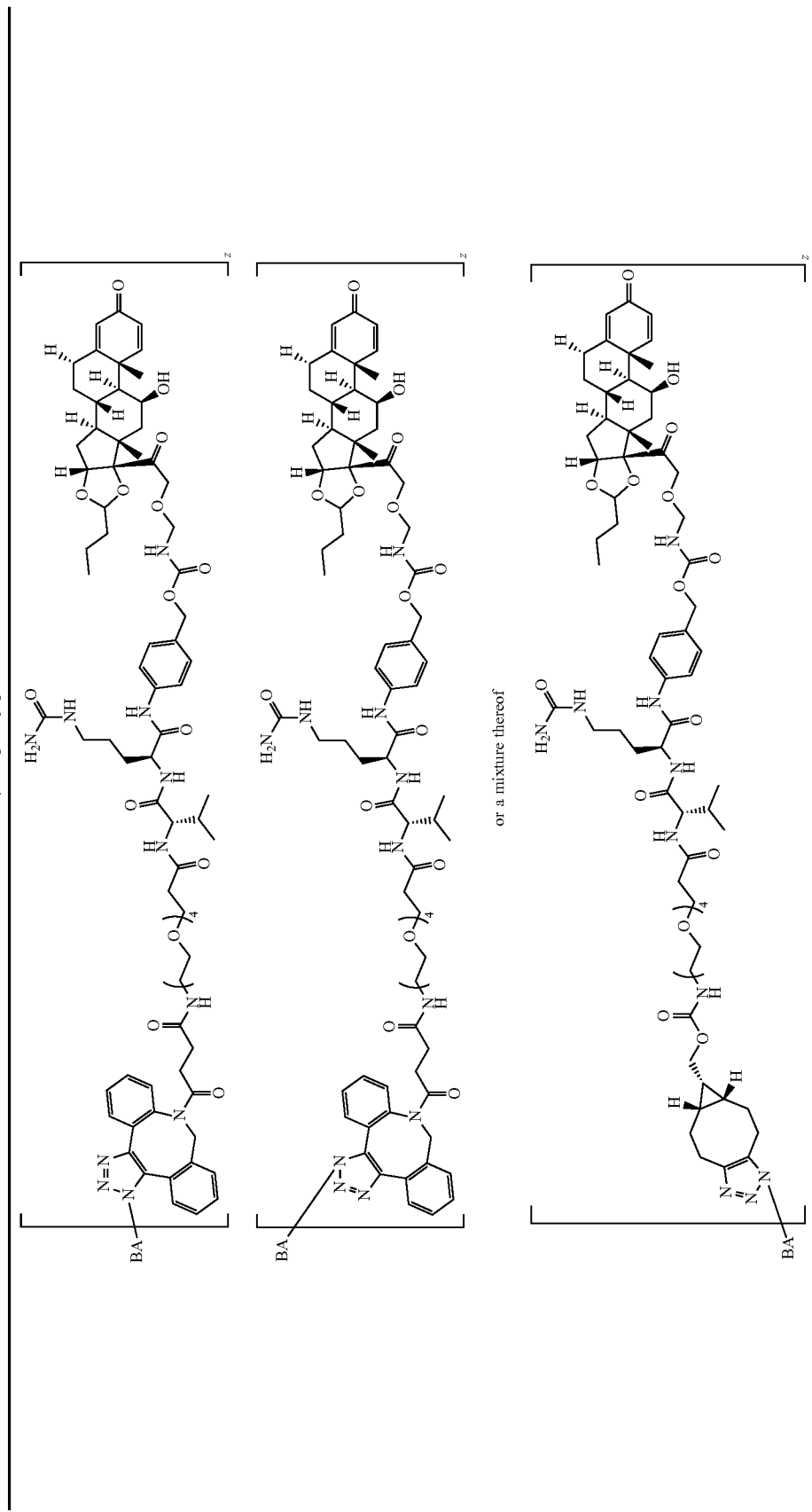
or a mixture thereof

TABLE 3-continued
Antibody-Drug Conjugates
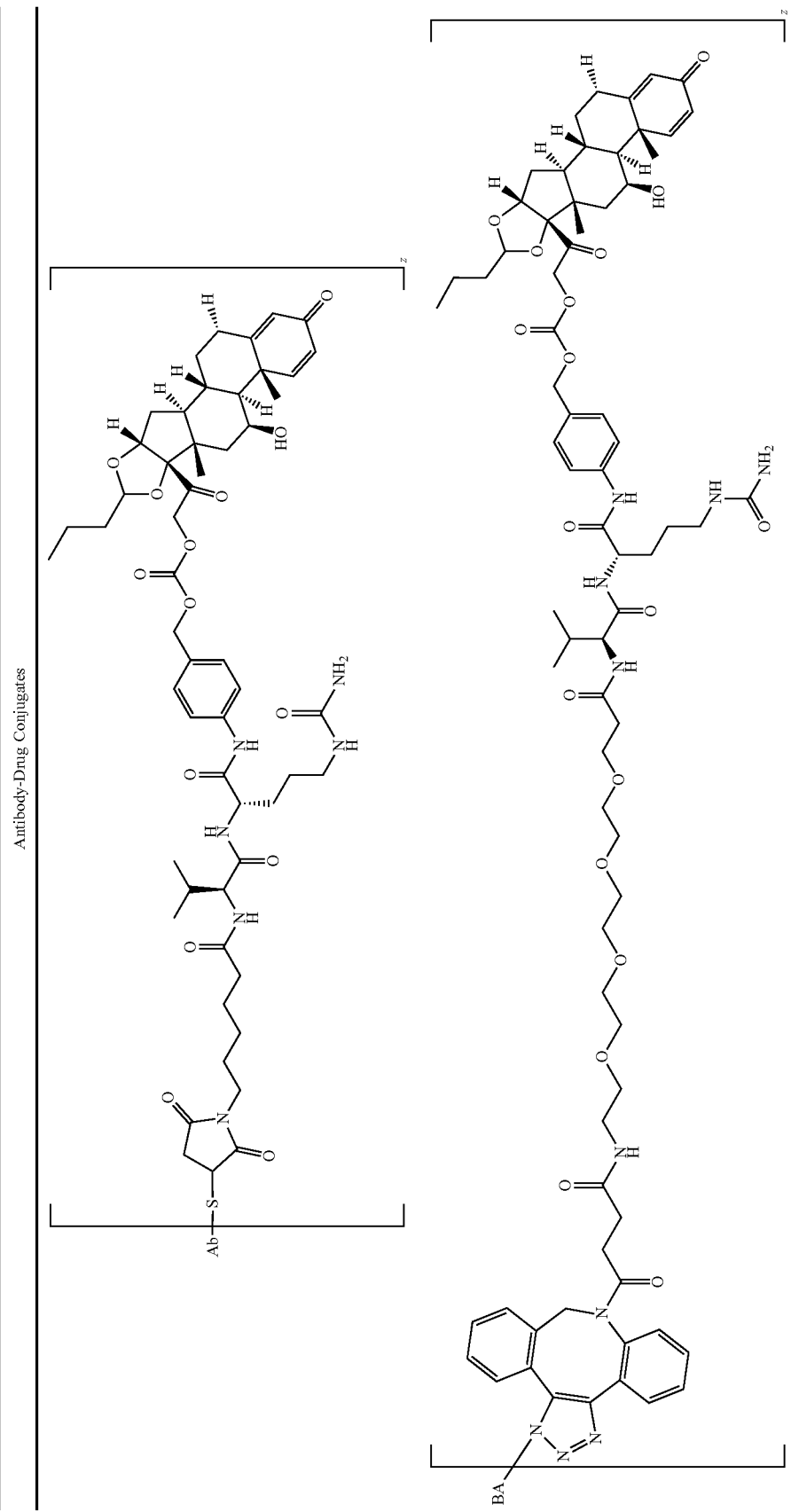

TABLE 3-continued
Antibody-Drug Conjugates
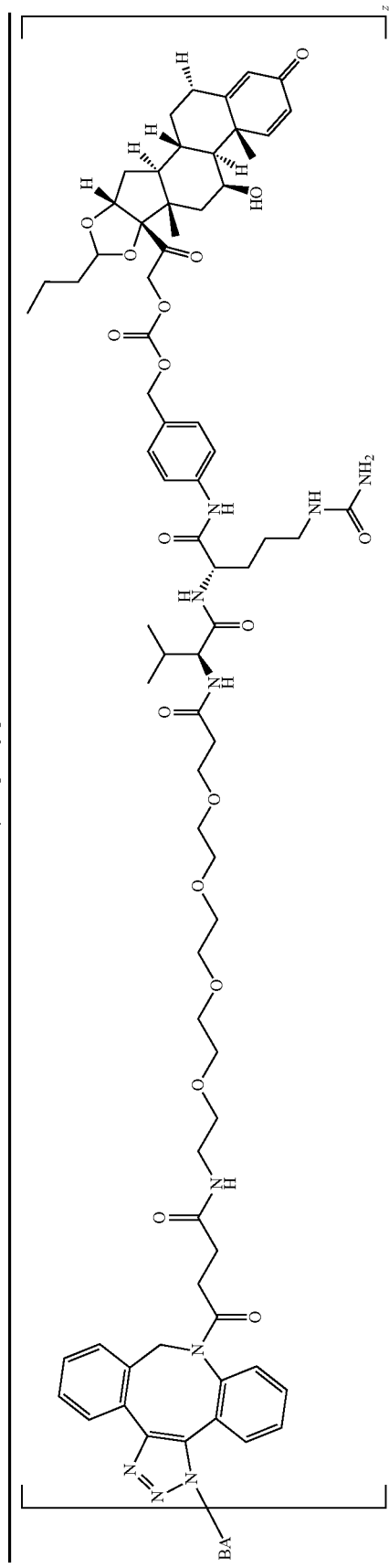
or a mixture thereof

TABLE 3-continued
Antibody-Drug Conjugates
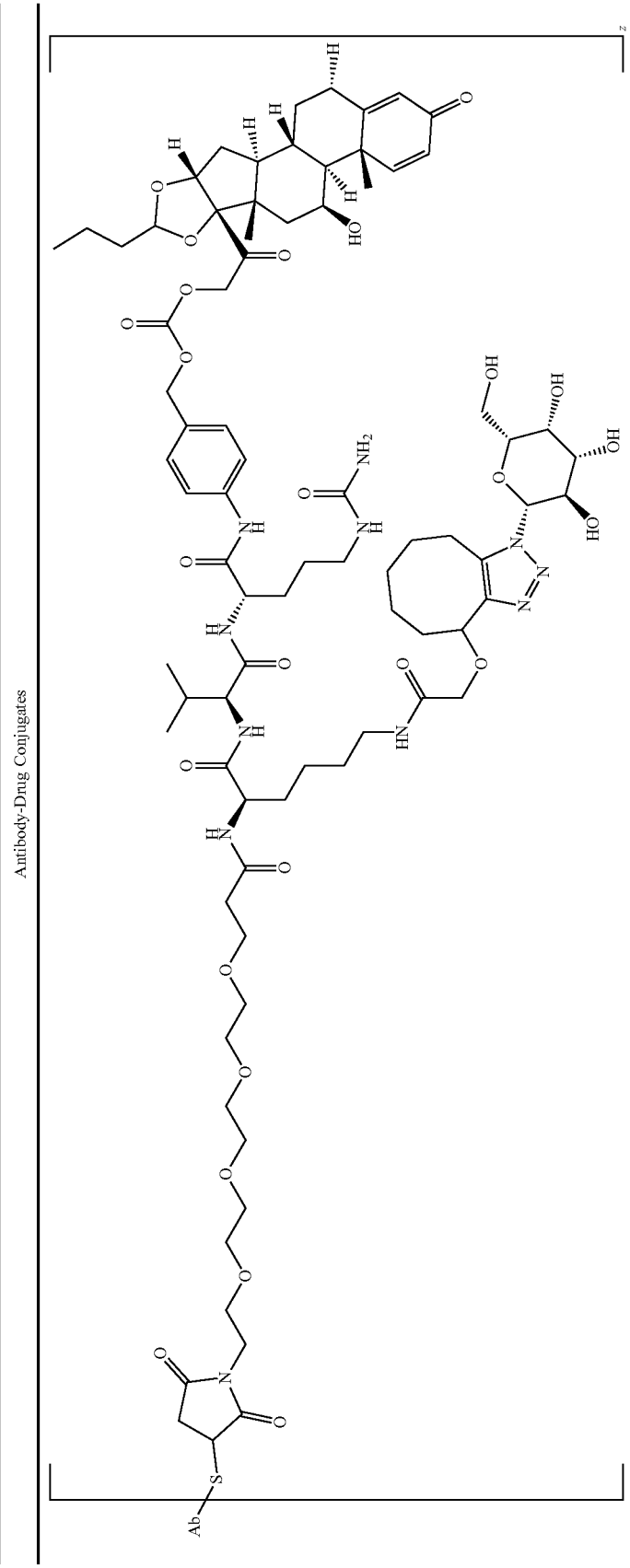

TABLE 3-continued
Antibody-Drug Conjugates
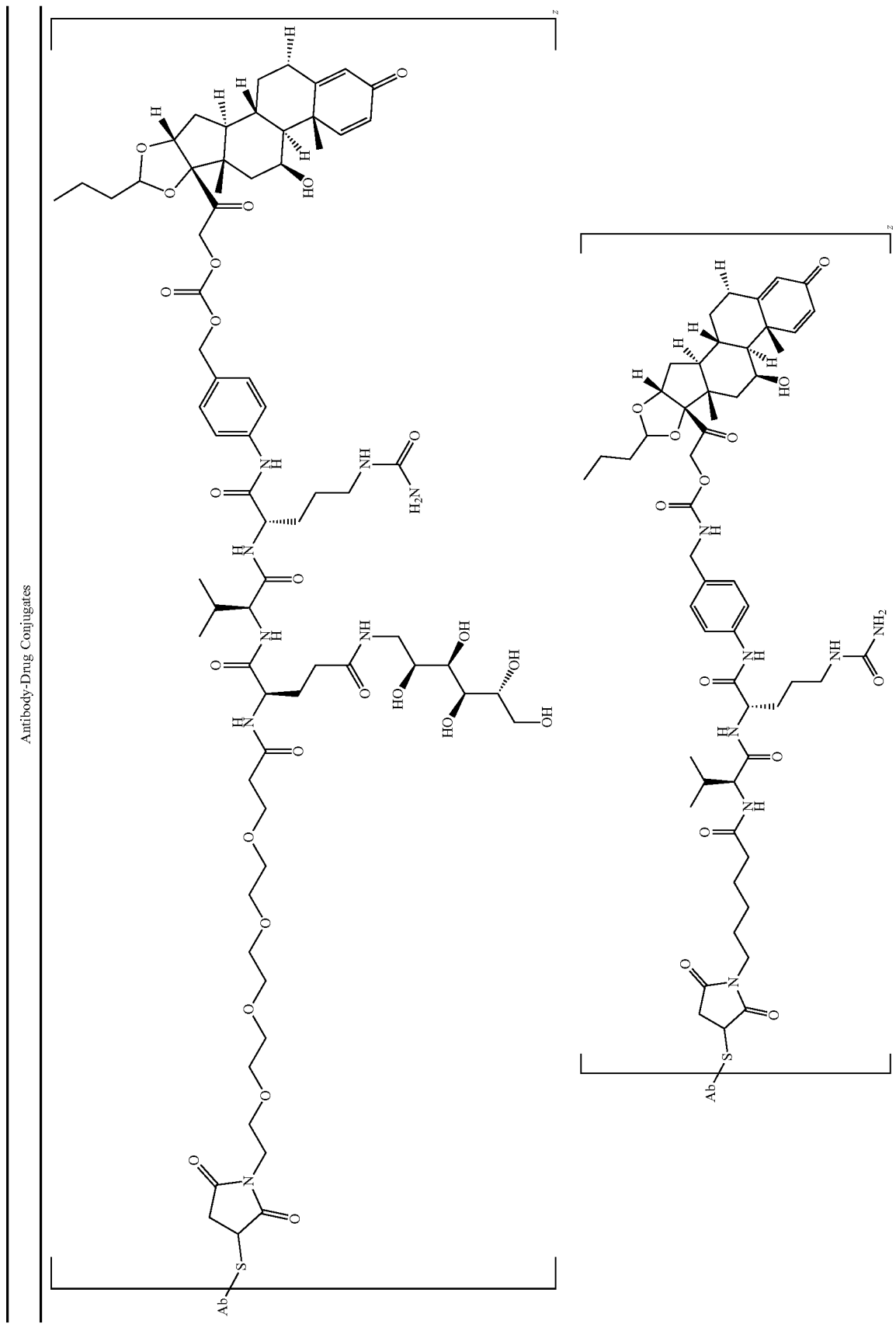

TABLE 3-continued
Antibody-Drug Conjugates
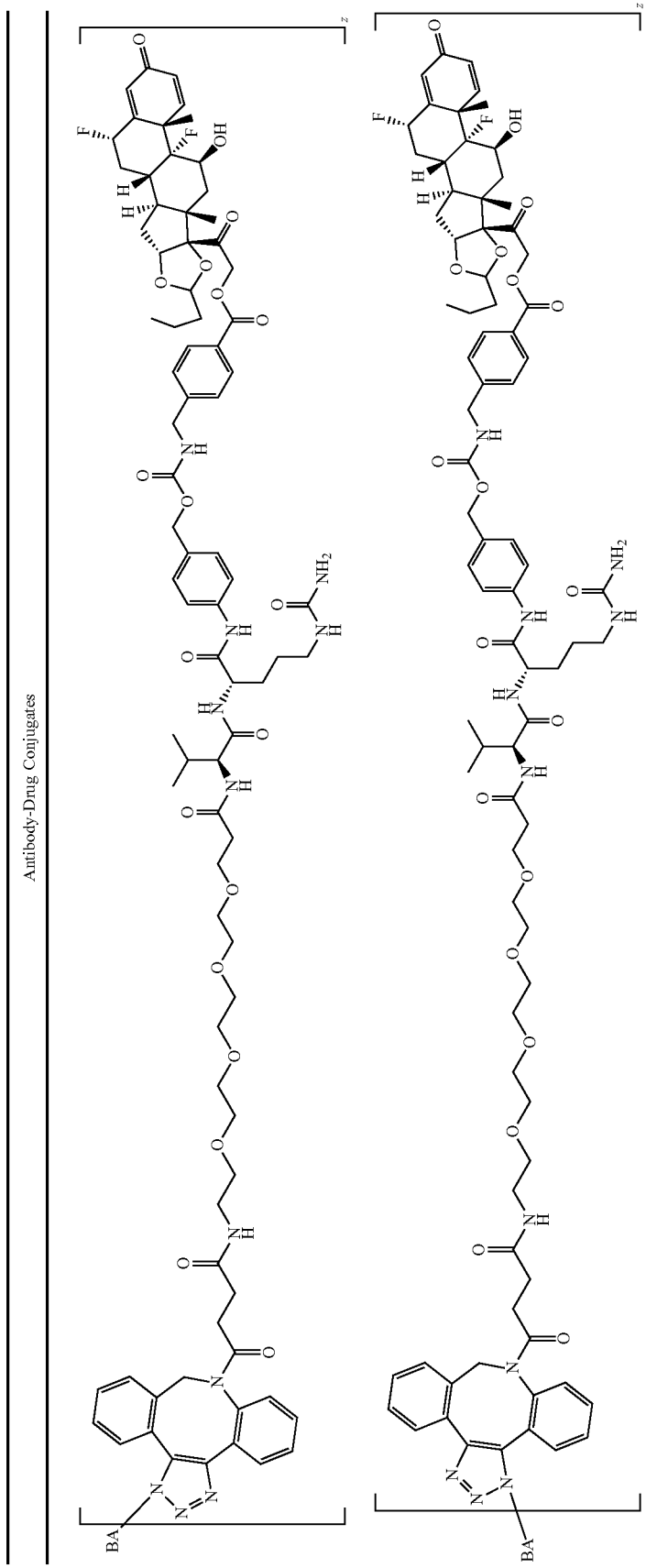

TABLE 3-continued
Antibody-Drug Conjugates
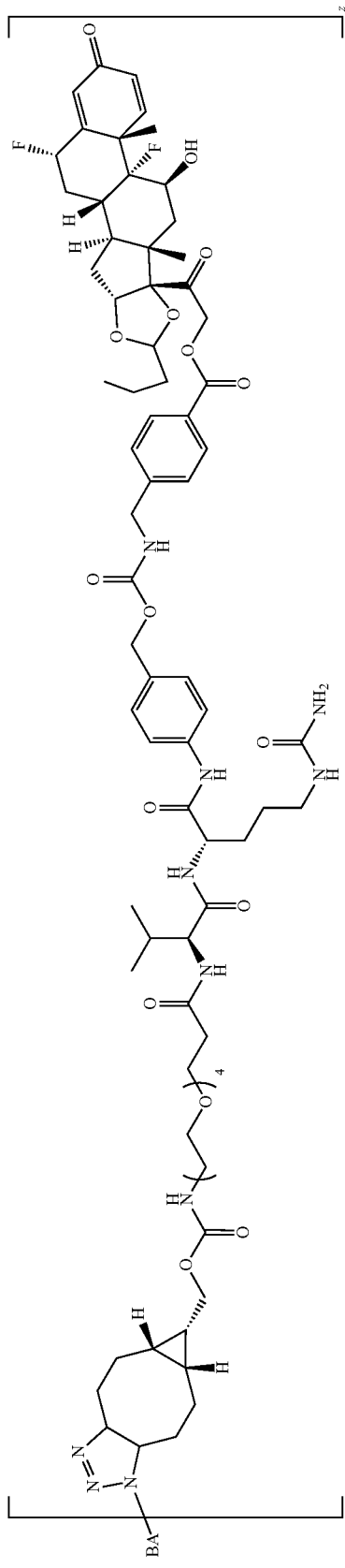
or a mixture thereof
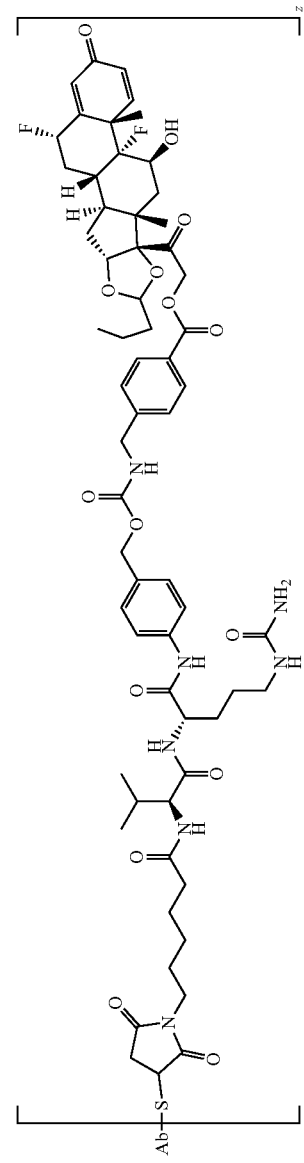

where BA comprises an antibody having the following structure

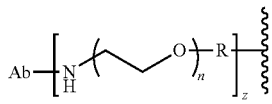

where Ab is a monoclonal antibody, polyclonal antibody, antibody fragment, or bispecific antibody; R is $C_{2-4}$-alkylene; and n is an integer selected from 2 to 4, inclusive. In some embodiments, the n-propyl of

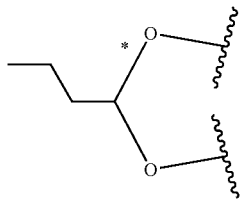 [SMILES: *OC(CCC)O*]

in each of the above structures is in the R-configuration, i.e. at the carbon indicated by the asterisk. In some embodiments, the n-propyl of

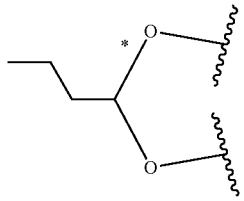 [SMILES: *OC(CCC)O*]

in each of the above structures is in the S-configuration, i.e. at the carbon indicated by the asterisk. In some embodiments, the n-propyl of

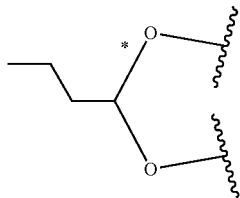 [SMILES: *OC(CCC)O*]

in each of the above structures is a mixture of the R- and S-configurations, i.e. at the carbon indicated by the asterisk. In some embodiments, the n-propyl of

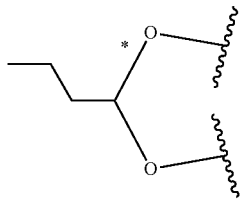 [SMILES: *OC(CCC)O*]

in each of the above structures is a mixture of the R- and S-configurations, i.e. at the carbon indicated by the asterisk, wherein the R:S mixture is about 1:1, about 2:1, about 3:1, about 4:1, about 5:1, about 6:1, about 7:1, about 8:1, about 9:1, or about 10:1.

In particular embodiments, BA is an antibody and z is an integer selected from 1-30, inclusive. In some embodiments, z is an integer selected from 1 to 4, inclusive. In some embodiments, z is 4. In some embodiments, z is 2.

Provided herein are also binding agent conjugates of budesonide, a prodrug of budesonide, a budesonide analog or derivative (including fluorinated analogs and derivatives), or a prodrug of a budesonide analog or derivative (including fluorinated analogs and derivatives).

Suitable binding agents for any of the conjugates provided in the instant disclosure include, but are not limited to, antibodies, lymphokines, hormones, growth factors, viral receptors, interleukins, or any other cell binding or peptide binding molecules or substances.

In some embodiments, the binding agent is an antibody. The term "antibody," as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

The amino acid sequence of an antibody can be numbered using any known numbering schemes, including those described by Kabat et al., ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Pluckthun, *J. Mol. Biol.*, 2001, 309:657-70 ("AHo" numbering scheme). Unless otherwise specified, the numbering scheme used herein is the Kabat numbering scheme. The "EU numbering scheme" is generally used when referring to a residue in an antibody heavy chain constant region (e.g., as reported in Kabat et al., supra). However, selection of a numbering scheme is not intended to imply differences in sequences where they do not exist, and one of skill in the art can readily confirm a sequence position by examining the amino acid sequence of one or more antibodies.

In some embodiments, the BA antibody is a functionalized antibody having the following structure:

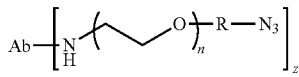

In some embodiments, R is alkylene, alkenylene, or alkynylene. In some embodiments, R is alkylene. In some embodiments, R is $C_{2-4}$-alkylene. In certain embodiments, R is ethylene. In certain embodiments, n is 3. In certain embodiments, z is 2 or 4.

In some embodiments, the BA antibody is not an anti-PSMA antibody or an anti-CD70 antibody.

Non-limiting examples of BA antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, camelid antibodies ($V_H$H fragments), domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the instant disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The antibodies useful for the compounds herein include human antibodies. The term "human antibody," as used herein, is intended to include antibodies having variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism.

The antibodies can, in some embodiments, be recombinant human antibodies. The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$ or $C_H3$ region which may be desirable, for example, in production, to improve the yield of the desired antibody form.

The antibodies useful for the compounds herein can be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the instant disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies useful for the compounds disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc.

In some embodiments, the antibody is a monoclonal antibody, polyclonal antibody, antibody fragment (Fab, Fab', and F(ab)2, minibody, diabody, tribody, and the like), or bispecific antibody. Antibodies herein can be humanized using methods described in U.S. Pat. No. 6,596,541 and US Publication No. 2012/0096572, each incorporated by reference in their entirety.

Where the binding agent is an antibody, it binds to an antigen binding partner that is a polypeptide and may be a transmembrane molecule (e.g., receptor) or a growth factor that might be glycosylated or phosphorylated.

Suitable targets to which the binding agent binds include any target/antigen to which selective delivery of a steroid is desirable. In some embodiments, the binding agent is an antibody, modified antibody, or antigen binding fragment there of that binds a target selected from: AXL, BAFFR, BCMA, BCR-list components, BDCA2, BDCA4, BTLA, BTNL2 BTNL3, BTNL8, BTNL9, C10orf54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD46, CD47, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, FCamR, FCMR, FcR's, Fire, GITR, HER2, HHLA2, HLA class II, HVEM, ICOSLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MMR, MSR1, NCR3LG1, NKG2D, NKp30, NKp46, PDCD1, PRLR, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TNF-α, TROY, TSLPR, TYRO, VLDLR, VSIG4, and VTCN1. In some embodiments, the binding agent is adalimumab or infliximab. In some embodiments, the binding agent is alemtuzumab, muromonab, rituximab, tositumomab, or agonistic antibodies (where immune stimulation might be part of the intended mechanism of action).

The expression prolactin receptor, "PRLR," and the like, as used herein, refers to the human prolactin receptor, comprising the amino acid sequence as set forth in SEQ ID NO:404 of WO2015026907, which is incorporated by reference herein in its entirety. The expression "PRLR" includes both monomeric and multimeric PRLR molecules. As used herein, the expression "monomeric human PRLR" means a PRLR protein or portion thereof that does not contain or possess any multimerizing domains and that exists under normal conditions as a single PRLR molecule without a direct physical connection to another PRLR molecule. An exemplary monomeric PRLR molecule is the molecule referred to herein as "hPRLR.mmh" comprising the amino acid sequence of SEQ ID NO:401 of WO2015026907 (see, e.g., Example 3 of WO2015026907). As used herein, the expression "dimeric human PRLR" means a construct comprising two PRLR molecules connected to one another through a linker, covalent bond, non-covalent bond, or through a multimerizing domain such as an antibody Fc domain. An exemplary dimeric PRLR molecule is the molecule referred to herein as "hPRLR.mFc" comprising the amino acid sequence of SEQ ID NO:402 of WO2015026907 (see, e.g., Example 3 of WO2015026907).

Exemplary anti-PRLR antibodies are listed in Table 1 of WO2015026907 sets forth the amino acid sequence identifiers—or a substantially similar sequence thereof having at least 90%, at least 95%, at least 98% or at least 99% sequence identity thereto—of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-PRLR antibodies. Table 2 of WO2015026907 sets forth the nucleic acid sequence identifiers—or a substantially similar sequence thereof having at least 90%, at least 95%, at least 98% or at least 99% sequence identity thereto—of the HCVRs, LCVRs, HCDR1, HCDR2 HCDR3, LCDR1, LCDR2, and LCDR3 of the exemplary anti-PRLR antibodies.

In some embodiments, the antibody, or antigen-binding fragment thereof, conjugated to the linker-payload or payload can be an antibody that targets human prolactin receptor (PRLR). Exemplary anti-PRLR antibodies can be found, for example, in WO 2015/026907. In some embodiments, an anti-PRLR antibody comprises a heavy chain complementarity determining region (HCDR)-1 comprising SEQ ID NO: 17; an HCDR2 comprising SEQ ID NO: 19; an HCDR3 comprising SEQ ID NO: 20; a light chain complementarity determining region (LCDR)-1 comprising SEQ ID NO: 22; an LCDR2 comprising SEQ ID NO: 23; and an LCDR3 comprising SEQ ID NO: 24. In some embodiments, an anti-PRLR antibody comprises a heavy chain variable region (HCVR) comprising SEQ ID NO: 17 and a light chain variable region (LCVR) comprising SEQ ID NO: 21. In any of the foregoing embodiments, the anti-PRLR antibody can be prepared by site-directed mutagenesis to insert a glutamine residue at a site without resulting in disabled antibody function or binding. For example, in any of the foregoing embodiments, the anti-PRLR antibody can comprise an Asn297Gln (N297Q) mutation. Such antibodies having an N297Q mutation can also contain one or more additional naturally occurring glutamine residues in their variable regions, which can be accessible to transglutaminase and therefore capable of conjugation to a payload or a linker-payload (Table B).

TABLE B

Sequences of Exemplary Antibody H1H6958N (anti-PRLR)

| SEQ ID NO: | Molecule/ AntibiDdy | Region | Sequence |
| --- | --- | --- | --- |
| 17 | H1H6958N | HCVR | QVQLVESGGGVVQPGRSLRLSCGASGFTFRNYGMQWVRQGP GKGLEWVTLISFDGNDKYYADSVKGRFTISRDNSKNTLFLQM NSLRTEDTAVYYCARGGDFDYWGQGTLVTVSS |
| 18 | H1H6958N | HCDR1 | GFTFRNYG |
| 19 | H1H6958N | HCDR2 | ISFDGNDK |
| 20 | H1H6958N | HCDR3 | ARGGDFDY |
| 21 | H1H6958N | LCVR | DIQMTQSPSSLSASVGDRVTITCRASQDIRKDLGWYQQKPGK APKRLIYAASSLHSGVPSRFSGSGSGTEFTLTISSLQPEDFATY YCLQHNSYPMYTFGQGTKLEIK |
| 22 | H1H6958N | LCDR1 | QDIRKD |

TABLE B-continued

Sequences of Exemplary Antibody H1H6958N (anti-PRLR)

| SEQ ID NO: | Molecule/ AntibiDdy | Region | Sequence |
|---|---|---|---|
| 23 | H1H6958N | LCDR2 | AAS |
| 24 | H1H6958N | LCDR3 | LQHNSYPMYT |
| 25 | hPRLR ecto-MMH | | MHRPRRRGTRPPPLALLAALLLAARGADAQLPPGKPEIFKCR SPNKETFTCWWRPGTDGGLPTNYSLTYHREGETLMHECPDYI TGGPNSCHFGKQYTSMWRTYIMMVNATNQMGSSFSDELYV DVTYIVQPDPPLELAVEVKQPEDRKPYLWIKWSPPTLIDLKTG WFTLLYEIRLKPEKAAEWEIHFAGQQTEFKILSLHPGQKYLVQ VRCKPDHGYWSAWSPATFIQIPSDFTMNDEQKLISEEDLGGE QKLISEEDLHHHHHH |

In any of the compound or conjugate embodiments provided, BA is an antibody, or antigen binding fragment thereof, that binds PRLR. In any of the compound or conjugate embodiments provided, BA is an antibody or antigen-binding fragment thereof, and conjugation is through at least one Q295 residue. In any of the compound or conjugate embodiments provided, BA is an antibody or antigen-binding fragment thereof, and conjugation is through two Q295 residues. In any of the compound or conjugate embodiments provided, BA is a N297Q antibody or antigen-binding fragment thereof. In any of the compound or conjugate embodiments provided, BA is a N297Q antibody or antigen-binding fragment thereof, and conjugation is through at least one Q295 and at least one Q297 residue. In any of the compound or conjugate embodiments provided, BA is a N297Q antibody or antigen-binding fragment thereof, and conjugation is through two Q295 residues and two Q297 residues. In particular embodiments, numbering is according to the EU numbering system.

In any of the embodiments above, BA is an anti-MSR1 antibody. In certain embodiments, BA is the anti-MSR1 antibody H1H21234N. In certain embodiments, BA is the anti-MSR1 antibody H1H21234N N297Q. In certain embodiments, BA is an anti-MSR1 antibody comprising an HCVR according to SEQ ID NO:2 and an LCVR according to SEQ ID NO:10. In certain embodiments, BA is an anti-MSRa antibody comprising one, two, three, four, five, or six of HCDR1, HCDR2, HCDR3, LCDR1, LCDR2, and LCDR3 according to SEQ ID NOS: 4, 6, 8, 12, 14, and 16, respectively. In certain embodiments, the HCVR is encoded by SEQ ID NO: 1. In certain embodiments, the LCVR is encoded by SEQ ID NO: 9. In certain embodiments, one, two, three, four, five, or six of HCDR1, HCDR2, HCDR3, LCDR1, LCDR2, and LCDR3 are encoded by the polynucleotide sequences SEQ ID NOS: 3, 5, 7, 11, 13, and 15, respectively. N297Q indicates that one or more residues 297 are mutated from asparagine (N) to glutamine (Q). Preferably, each residue 297 is mutated to Q. In preferred embodiments, numbering is according to the EU numbering system. In certain embodiments of this paragraph, z is from 1 to 4. In certain embodiments, z is 1, 2, 3, or 4. In certain embodiments, z is 2. In certain embodiments, z is 4.

| SEQ ID NO: | Molecule/ Antibody | Region | Sequence |
|---|---|---|---|
| 1 | | | caggtgcagc tgcaggagtc gggcccagga ctggtgaagc cttcggagac cctgtccctc acctgcactg tcactggtgg ctccatcagt aggaactact ggagttggat ccggcagccc ccagggaagg gactggaatg gattagatat atctattaca gtgggagtat cgactacaat ccctccctca agagtcgagt caccatatca gtagacacgt ccaagaacca gttctccctg aagctgagtt ctatgaccgc tgcggacacg gccgtatact actgtgcgag agatcggtgg aactggaaat acggtatgga cgtctgggc caagggacca cggtcatcgt ctcgtca |
| 2 | | | Gln Val Gln Leu Gln Glu Ser Gly Pro Gly Leu Val Lys Pro Ser Glu Thr Leu Ser Leu Thr Cys Thr Val Thr Gly Gly Ser Ile Ser Arg Asn Tyr Trp Ser Trp Ile Arg Gln Pro Pro Gly Lys Gly Leu Glu Trp Ile Gly Tyr Ile Tyr Tyr Ser Gly Ser Ile Asp Tyr Asn Pro Ser Leu Lys Ser Arg Val Thr Ile Ser Val Asp Thr Ser Lys Asn Gln Phe Ser Leu Lys Leu Ser Ser Met Thr Ala Ala Asp Thr Ala Val Tyr Tyr Cys Ala Arg Asp Arg Trp Asn Trp Lys Tyr Gly Met Asp Val Trp Gly Gln Gly Thr Thr Val Ile Val Ser Ser |
| 3 | | | ggtggctcca tcagtaggaa ctac |
| 4 | | | Gly Gly Ser Ile Ser Arg Asn Tyr |
| 5 | | | atctattaca gtgggagtat c |
| 6 | | | Ile Tyr Tyr Ser Gly Ser Ile |
| 7 | | | gcgagagatc ggtggaactg gaaatacggt atggacgtc |

-continued

| SEQ ID NO: | Molecule/ Antibody | Region | Sequence |
|---|---|---|---|
| 8 | | | Ala Arg Asp Arg Trp Asn Trp Lys Tyr Gly Met Asp Val |
| 9 | | | gaaattgtgt tgacgcagtc tccaggcacc ctgtctttgt ctccagggga aagagccacc ctctcctgca gggccagtca gactgttaga aacaactact tagcctggta ccaccagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttacagtgta ttactgtcac cagtatggta actcaccttg gacgttcggc caagggacca aaatggaaat caaacga |
| 10 | | | Glu Ile val Leu Thr Gln Ser Pro Gly Thr Leu Ser Leu Ser Pro Gly Glu Arg Ala Thr Leu Ser Cys Arg Ala Ser Gln Thr Val Arg Asn Asn Tyr Leu Ala Trp Tyr His Gln Lys Pro Gly Gln Ala Pro Arg Leu Leu Ile Tyr Gly Ala Ser Ser Arg Ala Thr Gly Ile Pro Asp Arg Phe Ser Gly Ser Gly Ser Gly Thr Asp Phe Thr Leu Thr Ile Ser Arg Leu Glu Pro Glu Asp Phe Thr Val Tyr Tyr Cys His Gln Tyr Gly Asn Ser Pro Trp Thr Phe Gly Gln Gly Thr Lys Met Glu Ile Lys Arg |
| 11 | | | cagactgtta gaaacaacta c |
| 12 | | | Gln Thr Val Arg Asn Asn Tyr |
| 13 | | | ggtgcatcc |
| 14 | | | Gly Ala Ser |
| 15 | | | caccagtatg gtaactcacc ttggacg |
| 16 | | | His Gln Tyr Gly Asn Ser Pro Trp Thr |

The binding agent, e.g., antibody or antigen-binding molecule, can comprise a linker bonded to the binding agent through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA*, 2008, 105: 12451-12456), formyl glycine (see, e.g., Carrico et al., *Nat. Chem. Biol.*, 2007, 3:321-322; Agarwal et al., *Proc. Natl. Acad. Sci., USA*, 2013, 110:46-51, and Rabuka et al., *Nat. Protocols*, 2012, 10:1052-1067), non-natural amino acids (see, e.g., WO 2013/068874, and WO 2012/166559), and acidic amino acids (see, e.g., WO 2012/05982). Linkers can be conjugated via glutamine via transglutaminase-based chemo-enzymatic conjugation (see, e.g., Dennler et al., *Bioconjugate Chem.* 2014, 25, 569-578). Linkers can also be conjugated to an antigen-binding protein via attachment to carbohydrates (see, e.g., US 2008/0305497, WO 2014/065661, and Ryan et al., *Food & Agriculture Immunol.*, 2001, 13:127-130) and disulfide linkers (see, e.g., WO 2013/085925, WO 2010/010324, WO 2011/018611, WO 2014/197854, and Shaunak et al., *Nat. Chem. Biol.*, 2006, 2:312-313). In some embodiments, the binding agent is an antibody, and the antibody is bonded to the linker through a lysine residue. In some embodiments, the antibody is bonded to the linker through a cysteine residue.

In any of the embodiments above, BA is an anti-PRLR antibody. In certain embodiments, BA is the anti-PRLR antibody H1H6958N. In certain embodiments, BA is the anti-PRLR antibody H1H6958N N297Q. In certain embodiments, BA is an anti-PRLR antibody comprising an HCVR according to SEQ ID NO:17 and an LCVR according to SEQ ID NO:21. In certain embodiments, BA is an anti-PRLR antibody comprising one, two, three, four, five, or six of HCDR1, HCDR2, HCDR3, LCDR1, LCDR2, and LCDR3 according to SEQ ID NOS:18, 19, 20, 22, 23, and 24, respectively. N297Q indicates that one or more residues 297 are mutated from asparagine (N) to glutamine (Q). Preferably, each residue 297 is mutated to Q. In preferred embodiments, numbering is according to the EU numbering system. In certain embodiments of this paragraph, k is from 1 to 4. In certain embodiments, k is 1, 2, 3, or 4. In certain embodiments, k is 4.

D. Methods of Preparing Compounds

The conjugates described herein can be synthesized by coupling the linker-payloads described herein with a binding agent, e.g., antibody under standard conjugation conditions (see, e.g., *Drug Deliv.* 2016 June; 23(5):1662-6; *AAPS Journal*, Vol. 17, No. 2, March 2015; and *Int. J. Mol. Sci.* 2016, 17, 561, the entireties of which are incorporated herein by reference). Linker-payloads are synthetic intermediates comprising the payload of interest and linking moiety that ultimately serves as the moiety (or portion thereof) that connects the binding agent with the payload. Linker-payloads comprise a reactive group that reacts with the binding agent to form the conjugates described herein. When the binding agent is an antibody, the antibody can be coupled to a linker-payload via one or more cysteine, lysine, or other residue of the antibody. Linker payloads can be coupled to cysteine residues, for example, by subjecting the antibody to a reducing agent, e.g., dithiotheritol, to cleave the disulfide bonds of the antibody, optionally purifying the reduced antibody, e.g., by gel filtration, and subsequently reacting the antibody with a linker-payload containing a reactive moiety, e.g., a maleimido group. Suitable solvents include, but are not limited to water, DMA, DMF, and DMSO. Linker-payloads containing a reactive group, e.g., activated ester or acid halide group, can be coupled to lysine residues. Suitable solvents include, but are not limited to water, DMA, DMF, and DMSO. Conjugates can be purified using known protein techniques, including, for example, size exclusion chromatography, dialysis, and ultrafiltration/diafiltration.

Linker-Steroid Intermediates

Provided herein are linker-steroids according to Formula (2000),

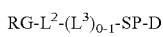

or a pharmaceutically acceptable salt, solvate, stereoisomer, or derivative thereof,
which are useful in the preparation of antibody-drug conjugates,
wherein
D is selected from
a)

formula (a)

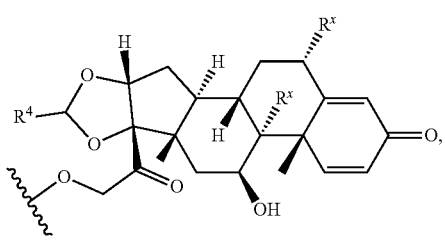

where both $R^x$ in formula (a) are hydrogen; $R^4$ is alkyl, aryl, arylalkyl, or an N-containing heterocycloalkyl; and SP is —C(O)—$C_1$-$C_{10}$-alkylene-C(O)—, —C(O)—N($C_{1-6}$alkyl)-$C_1$-$C_{10}$-alkylene-$X^1$- where $X^1$ is attached to $(L^3)_{0-1}$ in Formula (2000), —C(O)—N(H)—($C_1$-$C_{10}$-alkylene)-S— where S is attached to $(L^3)_{0-1}$ in Formula (2000), —C(O)—N($C_{1-6}$alkyl)-($C_1$-$C_{10}$-alkylene)-S— where S is attached to $(L^3)_{0-1}$ in Formula (2000),

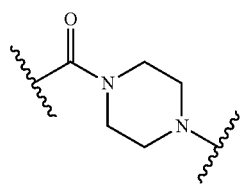 [SMILES: *C(=O)N1CCN(*)CC1]

where the point of attachment on the right hand side (i.e. at N) is to $(L^3)_{0-1}$ in Formula (2000), —$CH_2$—NH— where N is attached to $(L^3)_{0-1}$ in Formula (2000),

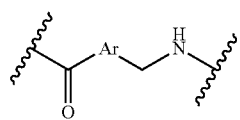

where the N is attached to $(L^3)_{0-1}$ in Formula (2000) and where Ar is optionally substituted arylene (in some embodiments,

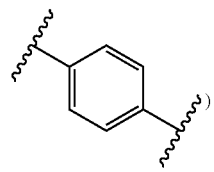 [SMILES: *c1ccc(*)cc1]

or optionally substituted heteroarylene, —($C_1$-$C_{10}$-alkylene)-$NR^{50}C(O)$—($C_1$-$C_{10}$-alkylene)-$NR^{50a}$- where $NR^{50a}$ is attached to $(L^3)_{0-1}$ in Formula (2000), —C(O)—($C_1$-$C_{10}$-alkylene)-$NR^{50}C(O)$—($C_1$-$C_{10}$-alkylene)-$NR^{50a}$- where $NR^{50a}$- is attached to $(L^3)_{0-1}$ in Formula (2000) and where each $C_1$-$C_{10}$-alkylene is independently optionally substituted with one or more hydroxy, —C(O)—N($R^5$)-$C_1$-$C_{10}$-alkylene-C(O)NH-$X^2$- where $X^2$ is attached to $(L^3)_{0-1}$ in Formula (2000), or

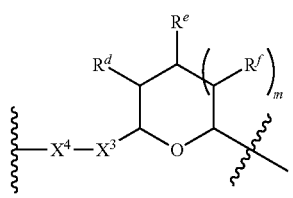

where $X^4$ is attached to $(L^3)_{0-1}$ in Formula (2000); or
where both $R^x$ in formula (a) are fluoro; $R^4$ is alkyl, aryl, arylalkyl, or an N-containing heterocycloalkyl; and SP is —C(O)—$C_1$-$C_{10}$-alkylene-C(O)—, —C(O)—N ($C_{1-6}$ alkyl)-$C_1$-$C_{10}$-alkylene-$X^{1b}$- where $X^{1b}$ is attached to $(L^3)_{0-1}$ in Formula (2000), —C(O)—N (H)—($C_1$-$C_{10}$-alkylene)-$X^{1b}$- where $X^{1b}$ is attached to $(L^3)_{0-1}$ in Formula (2000),

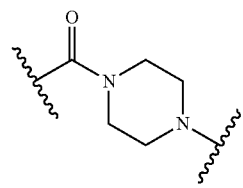 [SMILES: *C(=O)N1CCN(*)CC1]

where the point of attachment on the right hand side (i.e. at N) is to $(L^3)_{0-1}$ in Formula (2000), —$CH_2$—NH— where N is attached to $(L^3)_{0-1}$ in Formula (2000),

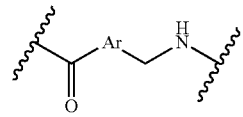

where the N is attached to $(L^3)_{0-1}$ in Formula (2000) and where Ar is optionally substituted arylene (in some embodiments,

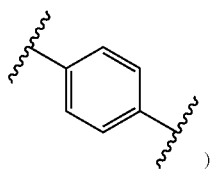 [SMILES: *c1ccc(*)cc1]

or optionally substituted heteroarylene, —(C$_1$-C$_{10}$-alkylene)-NR$^{50}$C(O)—(C$_1$-C$_{10}$-alkylene)-NR$^{50a}$- where NR$^{50a}$ is attached to (L$^3$)$_{0-1}$ in Formula (2000), —C(O)—(C$_1$-C$_{10}$-alkylene)-NR$^{50}$C(O)—(C$_1$-C$_{10}$-alkylene)-NR$^{50a}$- where NR$^{50a}$ is attached to (L$^3$)$_{0-1}$ in Formula (2000) and where each C$_1$-C$_{10}$-alkylene is independently optionally substituted with one or more hydroxy, —C(O)—N(R$^5$)—(C$_1$-C$_{10}$-alkylene)-C(O)NH-X$^2$- where X$^2$ is attached to (L$^3$)$_{0-1}$ in Formula (2000), or

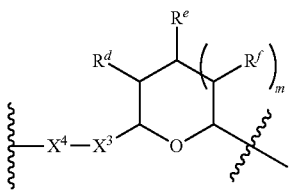

where X$^4$ is attached to (L$^3$)$_{0-1}$$^3$ in Formula (2000); and
b) the compounds in Table A above, where the compounds in Table A are linked to RG of the Compound of Formula (2000) through the hydroxy of the —C(O)CH$_2$OH group, i.e. by —C(O)CH$_2$—O-SP-(L$^3$)$_{0-1}$-, or through the hydroxy of Mapracorat, i.e. by -O-SP-(L$^3$)$_{0-1}$-.

X$^1$ is —N(C$_{1-6}$alkyl)-;
X$^{1b}$ is —S—, —NH—, or —N(C$_{1-6}$alkyl)-;
X$^2$ is —NH—;
X$^3$ is —CH$_2$—, X$^3$ is —CH$_2$—O—(C$_1$-C$_{10}$-alkylene)-C(O)— where the C(O) is attached to X$^4$, or X$^3$ is —C(O)—;
X$^4$ is —O—;
R$^5$ is H, —OH, —OCH$_3$, or C$_{1-6}$alkyl;
R$^{50}$ and R$^{50a}$ are independently hydrogen or C$_1$-C$_6$-alkyl;
R$^d$, R$^e$, and R$^f$ are independently —H, —OH, hydroxyalkyl, alkoxycarbonyl, —C(O)OH, or —CH$_2$OR$^g$, where each R$^g$ is independently —CH$_2$C(O)OH or —CH$_2$C(O)O(alkyl); and
m is 0 or 1;
RG is a reactive group;
L$^2$ is connecting linker; and
L$^3$, when present, is a self-immolative linker.

Provided herein are linker-steroids according to Formula (II), (II)

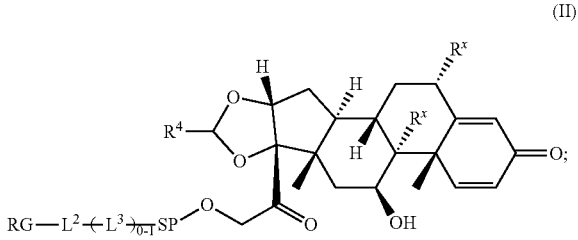

which are useful in the preparation of antibody-drug conjugates; wherein RG, L$^2$, L$^3$, SP, R$^4$, and R$^x$ are as defined herein.

In some or any embodiments, the compound of Formula (II-P) is set forth below:

(II-P)

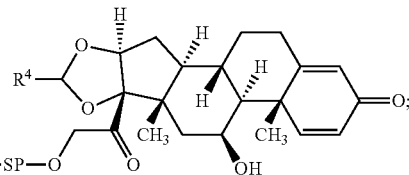

or a pharmaceutically acceptable salt, solvate, stereoisomer, or derivative thereof, wherein:
R$^4$ is alkyl, aryl, arylalkyl, or an N-containing heterocycloalkyl;
SP is —C(O)—C$_1$-C$_{10}$-alkylene-C(O)—, —C(O)—N(C$_{1-3}$alkyl)-C$_1$-C$_{10}$-alkylene-X$^1$- where X$^1$ is attached to L$^3$ in Formula (II), —C(O)—N(R$^5$)-C$_1$-C$_{10}$-alkylene-C(O)NH-X$^2$- where X$^2$ is attached to L$^3$ in Formula (II), or

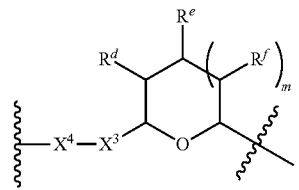

where X$^4$ is attached to L$^3$ in Formula (II);
X$^1$ is —N(C$_{1-3}$alkyl)-;
X$^2$ is —NH—;
X$^3$ is —CH$_2$—, X$^3$ is —CH$_2$—O—(C$_1$-C$_{10}$-alkylene)-C(O)— where the C(O) is attached to X$^4$, or X$^3$ is —C(O)—;
X$^4$ is —O—;
R$^5$ is H, —OH, —OCH$_3$, or alkyl;
R$^d$, R$^e$, and R$^f$ are independently —H, —OH, hydroxyalkyl, alkoxycarbonyl, —C(O)OH, or —CH$_2$OR$^g$, where each R$^g$ is independently —CH$_2$C(O)OH or —CH$_2$C(O)O(alkyl); and
m is 0 or 1;
RG is a reactive group;
L$^2$ is connecting linker; and
L$^3$, when present, is a self-immolative linker.

In some or any embodiments, the compound of Formula (II-P-1) is set forth below:

(II-P-1)

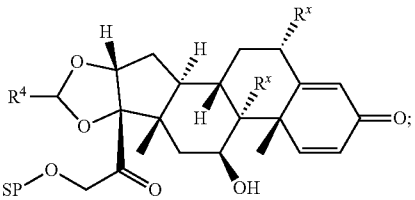

or a pharmaceutically acceptable salt, solvate, stereoisomer, or derivative thereof,
wherein:
R$^4$ is alkyl, aryl, arylalkyl, or an N-containing heterocycloalkyl;
SP is —C(O)—C$_1$-C$_{10}$-alkylene-C(O)—, —C(O)—N(C$_{1-3}$alkyl)-C$_1$-C$_{10}$-alkylene-X$^1$- where X$^1$ is attached to L$^3$ in Formula (II), —C(O)—N(R$^5$)-C$_1$-C$_{10}$-alkylene-C(O)NH-X$^2$- where X$^2$ is attached to L$^3$ in Formula (II), or

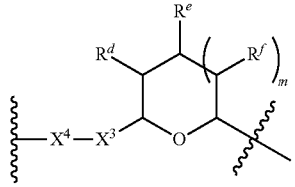

where X$^4$ is attached to L$^3$ in Formula (II);
X$^1$ is —N(C$_{1-3}$alkyl)-;
X$^2$ is —NH—;
X$^3$ is —CH$_2$—, X$^3$ is —CH$_2$—O—(C$_1$-C$_{10}$-alkylene)-C(O)— where the C(O) is attached to X$^4$, or X$^3$ is —C(O)—;
X$^4$ is —O—;
R$^5$ is H, —OH, —OCH$_3$, or alkyl;
R$^d$, R$^e$, and R$^f$ are independently —H, —OH, hydroxyalkyl, alkoxycarbonyl, —C(O)OH, or —CH$_2$OR$^g$, where each R$^g$ is independently —CH$_2$C(O)OH or —CH$_2$C(O)O(alkyl); and
m is 0 or 1;
RG is a reactive group;
L$^2$ is connecting linker; and
L$^3$, when present, is a self-immolative linker.

In some embodiments, set forth herein is a compound of Formula (II), where both R$^x$ are hydrogen. In some or any embodiments, both R$^x$ are fluoro.

In some embodiments, set forth herein is a compound of Formula (II), (II-P), and (II-P-1), where R$^4$ is alkyl. In some embodiments, R$^4$ is not cycloalkyl. In some of these embodiments, R$^4$ is linear or branched alkyl. In some of these embodiments, R$^4$ is aryl. In some of these embodiments, R$^4$ is arylalkyl. In some of these embodiments, R$^4$ is N-containing heterocycloalkyl. In some embodiments, R$^4$ is alkyl such as, but not limited to, methyl, ethyl, propyl, butyl, pentyl, hexyl, heptyl, octyl, or nonyl. In some embodiments, R$^4$ is methyl. In some embodiments, R$^4$ is ethyl. In some embodiments, R$^4$ is n-propyl. In some embodiments, R$^4$ is i-propyl. In some embodiments, R$^4$ is n-butyl. In some embodiments, R$^4$ is i-butyl. In some embodiments, R$^4$ is t-butyl. In some embodiments, R$^4$ is sec-butyl. In some embodiments, R$^4$ is pentyl. In some embodiments, R$^4$ is hexyl. In some embodiments, R$^4$ is heptyl. In some embodiments, R$^4$ is octyl, or nonyl. In some embodiments, R$^4$ is aryl such as but not limited to phenyl, phenol, or naphthyl. In some embodiments, R$^4$ is phenyl. In some embodiments, R$^4$ is naphthyl. In some embodiments, R$^4$ is heteroaryl—such as but not limited to thienyl. In some embodiments, R$^4$ is arylalkyl—such as but not limited to benzyl. In some embodiments, R$^4$ is N-containing heterocycloalkyl such as but not limited to piperidinyl. In some embodiments, set forth herein is a compound of Formula (II), where both R$^x$ are hydrogen. In some or any embodiments, both R$^x$ are fluoro. In some embodiments, R$^4$ is in the R-configuration.

In some embodiments, R$^4$ is in the S-configuration. In some embodiments, R$^4$ is a mixture of the R- and S-configurations. In some embodiments, R$^4$ is a mixture of the R- and S-configurations, wherein the R:S mixture is about 1:1, about 2:1, about 3:1, about 4:1, about 5:1, about 6:1, about 7:1, about 8:1, about 9:1, or about 10:1.

In some embodiments, provided is a Compound of Formula (II) where
both R$^x$ are hydrogen; and SP is —C(O)—C$_1$-C$_{10}$-alkylene-C(O)—, —C(O)—N(C$_{1-6}$alkyl)-C$_1$-C$_{10}$-alkylene-X$^1$- where X$^1$ is attached to L in Formula (II), —C(O)—N(H)—(C$_1$-C$_{10}$-alkylene)-S— where S is attached to L in Formula (II), —C(O)—N(C$_{1-6}$alkyl)-(C$_1$-C$_{10}$-alkylene)-S— where S is attached to L in Formula (II), —(C$_1$-C$_{10}$-alkylene)-NR$^{50}$C(O)—(C$_1$-C$_{10}$-alkylene)-NR$^{50a}$- where NR$^{50a}$ is attached to L in Formula (II), —C(O)—(C$_1$-C$_{10}$-alkylene)-NR$^{50}$C(O)—(C$_1$-C$_{10}$-alkylene)-NR$^{50a}$- where NR$^{50a}$ is attached to L in Formula (II) and where each C$_1$-C$_{10}$-alkylene is independently optionally substituted with one or more hydroxy, —C(O)—N(R$^5$)—C$_1$-C$_{10}$-alkylene-C(O)NH-X$^2$- where X$^2$ is attached to L in Formula (II), or

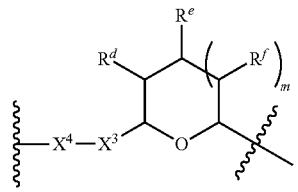

where X$^4$ is attached to L in Formula (II); or
both R$^x$ are fluoro; and SP is —C(O)—N(C$_{1-6}$alkyl)-C$_1$-C$_{10}$-alkylene-X$^{1b}$- where X$^{1b}$ is attached to L in Formula (II), —C(O)—N(H)—(C$_1$-C$_{10}$-alkylene)-X$^{1b}$- where X$^{1b}$ is attached to L in Formula (II),

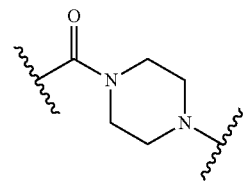 [SMILES: *C(=O)N1CCN(*)CC1]

where the point of attachment on the right hand side (i.e. at N) is to L in Formula (II), —(C$_1$-C$_{10}$-alkylene)-NR$^{50}$C(O)—(C$_1$-C$_{10}$-alkylene)-NR$^{50a}$- where NR$^{50a}$ is attached to L in Formula (II), —C(O)—(C$_1$-C$_{10}$-alkylene)-NR$^{50}$C(O)—(C$_1$-C$_{10}$-alkylene)-NR$^{50a}$- where NR$^{50a}$ is attached to L in Formula (III) and where each C$_1$-C$_{10}$-alkylene is independently optionally substituted with one or more hydroxy, or —C(O)—N(R$^5$)—(C$_1$-C$_{10}$-alkylene)-C(O)NH-X$^2$- where X$^2$ is attached to L in Formula (II).

In some embodiments, set forth herein is a compound of Formula (II), (II-P), or (II-P-1), where both R$^x$ are hydrogen and SP is —C(O)—C$_1$-C$_{10}$-alkylene-C(O)—. In some embodiments, set forth herein is a compound of Formula (II), (II-P), or (II-P-1), where SP is —C(O)—C$_2$-C$_5$-alkylene-C(O)—. In some embodiments, set forth herein is a compound of Formula (II), (II-P), or (II-P-1), where SP is —C(O)—CH$_2$CH$_2$—C(O)—.

In some embodiments, set forth herein is a compound of Formula (II), (II-P), or (II-P-1), where both $R^x$ are fluoro and SP is —C(O)—$C_1$-$C_{10}$-alkylene-C(O)—. In some embodiments, set forth herein is a compound of Formula (II), (II-P), or (II-P-1), where SP is —C(O)—$C_2$-$C_5$-alkylene-C(O)—. In some embodiments, set forth herein is a compound of Formula (II), (II-P), or (II-P-1), where SP is —C(O)—$CH_2CH_2$—C(O)—.

In some embodiments, set forth herein is a compound of Formula (II), (II-P), or (II-P-1), where both $R^x$ are hydrogen and SP is —C(O)—N($C_{1-6}$alkyl)-$C_1$-$C_{10}$-alkylene-$X^1$- where $X^1$ is attached to $L^3$ in Formula (II), (II-P), or (II-P-1). In some embodiments, set forth herein is a compound of Formula (II), (II-P), or (II-P-1), where SP is —C(O)—N($C_{1-3}$alkyl)-$C_1$-$C_{10}$-alkylene-$X^1$- where $X^1$ is attached to $L^3$ in Formula (II), (II-P), or (II-P-1). In some embodiments, set forth herein is a compound of Formula (II), (II-P), or (II-P-1), where $X^1$ is —N($C_{1-3}$alkyl)-. In some embodiments, set forth herein is a compound of Formula (II), (II-P), or (II-P-1), where SP is —C(O)—N($C_{1-3}$alkyl)-$C_2$-$C_5$-alkylene-$X^1$—. In some embodiments, set forth herein is a compound of Formula (II), (II-P), or (II-P-1), where SP is —C(O)—N($C_{1-3}$alkyl)-$CH_2CH_2$-$X^1$—. In some embodiments, set forth herein is a compound of Formula (II), (II-P), or (II-P-1), where SP is —C(O)—N($CH_3$)—$C_2$-$C_5$-alkylene-N($CH_3$)—. In some embodiments, set forth herein is a compound of Formula (II), (II-P), or (II-P-1), where SP is —C(O)—N($CH_3$)—$CH_2CH_2$—N($CH_3$)—.

In some embodiments, set forth herein is a compound of Formula (II), where both $R^x$ are fluoro and SP is —C(O)—N($C_{1-6}$alkyl)-$C_1$-$C_{10}$-alkylene-$X^{1b}$- where $X^{1b}$ is attached to $L^3$ in Formula (II) or —C(O)—N(H)—($C_1$-$C_{10}$-alkylene)-$X^{1b}$- where $X^{1b}$ is attached to $L^3$ in Formula (II) in Formula (II). In some embodiments, set forth herein is a compound of Formula (II), where SP is —C(O)—N(H)—$C_1$-$C_{10}$-alkylene-$X^{1b}$- where $X^{1b}$ is attached to $L^3$ in Formula (II). In some embodiments, set forth herein is a compound of Formula (II), where SP is —C(O)—N(H)—$C_1$-$C_6$-alkylene-$X^{1b}$- where $X^{1b}$ is attached to $L^3$ in Formula (II). In some embodiments, set forth herein is a compound of Formula (II), where SP is —C(O)—N(H)—$C_1$-$C_3$-alkylene-$X^{1b}$- where $X^{1b}$ is attached to $L^3$ in Formula (II). In some embodiments, set forth herein is a compound of Formula (II), where SP is —C(O)—N(H)—$CH_2CH_2$-$X^{1b}$—. In some embodiments, set forth herein is a compound of Formula (II), where SP is —C(O)—N(H)—$C_2$-$C_5$-alkylene-N($CH_3$)—. In some embodiments, set forth herein is a compound of Formula (II), where SP is —C(O)—N(H)—$C_2$-$C_5$-alkylene-N($CH_2CH_3$)—. In some embodiments, set forth herein is a compound of Formula (II), where SP is —C(O)—N(H)—$CH_2CH_2$—N($CH_3$)—.

In some embodiments, set forth herein is a compound of Formula (II), where both $R^x$ are fluoro and SP is —C(O)—N($C_{1-6}$alkyl)-$C_1$-$C_{10}$-alkylene-$X^{1b}$- where $X^{1b}$ is attached to $L^3$ in Formula (II). In some embodiments, set forth herein is a compound of Formula (II), where SP is —C(O)—N($C_{1-3}$alkyl)-$C_1$-$C_6$-alkylene-$X^{1b}$- where $X^{1b}$ is attached to $L^3$ in Formula (II). In some embodiments, set forth herein is a compound of Formula (II), where SP is —C(O)—N($C_{1-3}$alkyl)-$C_1$-$C_3$-alkylene-$X^{1b}$- where $X^{1b}$ is attached to $L^3$ in Formula (II). In some embodiments, set forth herein is a compound of Formula (II), where $X^{1b}$ is —N($C_{1-3}$alkyl)-. In some embodiments, set forth herein is a compound of Formula (II), where SP is —C(O)—N($C_{1-3}$alkyl)-$C_2$-$C_5$-alkylene-$X^{1b}$—. In some embodiments, set forth herein is a compound of Formula (II), where SP is —C(O)—N($C_{1-3}$alkyl)-$CH_2CH_2$-$X^{1b}$—. In some embodiments, set forth herein is a compound of Formula (II), where SP is —C(O)—N($CH_3$)—$C_2$-$C_5$-alkylene-N($CH_3$)—. In some embodiments, set forth herein is a compound of Formula (II), where SP is —C(O)—N($CH_2CH_3$)-$C_2$-$C_5$-alkylene-N($CH_2CH_3$)—. In some embodiments, set forth herein is a compound of Formula (II), where SP is —C(O)—N($CH_3$)—$CH_2CH_2$—N($CH_3$)—.

In some embodiments, set forth herein is a compound of Formula (II), where both $R^x$ are fluoro and SP is where the point of attachment on the right hand side (i.e. at N) is to L in Formula (II).

In some embodiments, set forth herein is a compound of Formula (II), where both $R^x$ are hydrogen and SP is —C(O)—N(H)—($C_1$-$C_{10}$-alkylene)-S— where S is attached to $L^3$ in Formula (II) in Formula (II), or —C(O)—N($C_{1-6}$alkyl)-($C_1$-$C_{10}$-alkylene)-S— where S is attached to $L^3$ in Formula (II). In some embodiments, set forth herein is a compound of Formula (II), where SP is —C(O)—N(H)—($C_1$-$C_6$-alkylene)-S— where S is attached to $L^3$ in Formula (II), or —C(O)—N($C_{1-3}$alkyl)-($C_1$-$C_6$-alkylene)-S— where S is attached to $L^3$ in Formula (II). In some embodiments, set forth herein is a compound of Formula (II), where SP is —C(O)—N(H)—($C_1$-$C_{10}$-alkylene)-S— where S is attached to $L^3$ in Formula (II). In some embodiments, set forth herein is a compound of Formula (II), where SP is —C(O)—N(H)—($C_1$-$C_6$-alkylene)-S— where S is attached to $L^3$ in Formula (II). In some embodiments, set forth herein is a compound of Formula (II), where SP is —C(O)—N($C_{1-6}$alkyl)-($C_1$-$C_{10}$-alkylene)-S— where S is attached to $L^3$ in Formula (II). In some embodiments, set forth herein is a compound of Formula (II), where SP is —C(O)—N($C_{1-3}$alkyl)-($C_1$-$C_6$-alkylene)-S— where S is attached to $L^3$ in Formula (II).

In some embodiments, set forth herein is a compound of Formula (II), where both $R^x$ are fluoro and SP is —C(O)—N(H)—($C_1$-$C_{10}$-alkylene)-S— where S is attached to $L^3$ in Formula (II), or —C(O)—N($C_{1-6}$alkyl)-($C_1$-$C_{10}$-alkylene)-S— where S is attached to $L^3$ in Formula (II) in Formula (II). In some embodiments, set forth herein is a compound of Formula (II), where SP is —C(O)—N(H)—($C_1$-$C_6$-alkylene)-S— where S is attached to $L^3$ in Formula (II), or —C(O)—N($C_{1-3}$alkyl)-($C_1$-$C_6$-alkylene)-S— where S is attached to $L^3$ in Formula (II). In some embodiments, set forth herein is a compound of Formula (II), where SP is —C(O)—N(H)—($C_1$-$C_{10}$-alkylene)-S— where S is attached to $L^3$ in Formula (II). In some embodiments, set forth herein is a compound of Formula (II), where SP is —C(O)—N(H)—($C_1$-$C_6$-alkylene)-S— where S is attached to $L^3$ in Formula (II). In some embodiments, set forth herein is a compound of Formula (II), where SP is —C(O)—N($C_{1-6}$alkyl)-($C_1$-$C_{10}$-alkylene)-S— where S is attached to $L^3$ in Formula (II). In some embodiments, set forth herein is a compound of Formula (II), where SP is —C(O)—N($C_{1-3}$alkyl)-($C_1$-$C_6$-alkylene)-S— where S is attached to $L^3$ in Formula (II).

In some embodiments, set forth herein is a compound of Formula (II), where both $R^x$ are hydrogen and SP is —($C_1$-$C_{10}$-alkylene)-$NR^{50}C(O)$—($C_1$-$C_{10}$-alkylene)-$NR^{50a}$- where $NR^{50a}$ is attached to $L^3$ in Formula (II). In some or any embodiments of Formula (I), SP is —($C_1$-$C_6$-alkylene)-$NR^{50}C(O)$—($C_1$-$C_6$-alkylene)-$NR^{50a}$—. In some or any embodiments of Formula (II), SP is —($C_1$-$C_3$-alkylene)-$NR^{50}C(O)$—($C_1$-$C_3$-alkylene)-$NR^{50a}$-. In some or any embodiments of Formula (II), SP is -(linear $C_1$-$C_3$-alkylene)-$NR^{50}C(O)$-(linear $C_1$-$C_3$-alkylene)-$NR^{50a}$—.

In some embodiments, set forth herein is a compound of Formula (II), where both $R^x$ are fluoro and SP is —($C_1$-$C_{10}$-alkylene)-$NR^{50}C(O)$—($C_1$-$C_{10}$-alkylene)-$NR^{50a}$- where $NR^{50a}$ is attached to $L^3$ in Formula (II). In some or any embodiments of Formula (I), SP is —($C_1$-$C_6$-alkylene)-$NR^{50}C(O)$—($C_1$-$C_6$-alkylene)-$NR^{50a}$-. In some or any embodiments of Formula (II), SP is —($C_1$-$C_3$-alkylene)-$NR^{50}C(O)$—($C_1$-$C_3$-alkylene)-$NR^{50a}$-. In some or any embodiments of Formula (II), SP is -(linear $C_1$-$C_3$-alkylene)-$NR^{50}C(O)$-(linear $C_1$-$C_3$-alkylene)-$NR^{50a}$—.

In some embodiments, set forth herein is a compound of Formula (II), where both $R^x$ are hydrogen and SP is —C(O)—($C_1$-$C_{10}$-alkylene)-$NR^{50}C(O)$—($C_1$-$C_{10}$-alkylene)-$NR^{50a}$- where $NR^{50a}$- is attached to $L^3$ in Formula (II) and where each $C_1$-$C_{10}$-alkylene is independently optionally substituted with one or more hydroxy. In some or any embodiments of Formula (II), SP is -(branched $C_1$-$C_6$-alkylene)-$NR^{50}C(O)$—($C_1$-$C_6$-hydroxy-alkylene)-$NR^{50a}$—. In some or any embodiments of Formula (II), SP is -(branched $C_1$-$C_6$-alkylene)-$NR^{50}C(O)$—($C_1$-$C_6$-alkylene)-$NR^{50a}$—.

In some embodiments, set forth herein is a compound of Formula (II), where both $R^x$ are fluoro and SP is —C(O)—($C_1$-$C_{10}$-alkylene)-$NR^{50}C(O)$—($C_1$-$C_{10}$-alkylene)-$NR^{50a}$- where $NR^{50a}$- is attached to $L^3$ in Formula (II) and where each $C_1$-$C_{10}$-alkylene is independently optionally substituted with one or more hydroxy. In some or any embodiments of Formula (II), SP is -(branched $C_1$-$C_6$-alkylene)-$NR^{50}C(O)$—($C_1$-$C_6$-hydroxy-alkylene)-$NR^{50a}$—. In some or any embodiments of Formula (II), SP is -(branched $C_1$-$C_6$-alkylene)-$NR^{50}C(O)$—($C_1$-$C_6$-alkylene)-$NR^{50a}$—.

In some embodiments, set forth herein is a compound of Formula (II), (II-P), or (II-P-1), where both $R^x$ are hydrogen and SP is —C(O)—N($R^5$)—$C_1$-$C_{10}$-alkylene-C(O)NH-$X^2$- where $X^2$ is attached to $L^3$ in Formula (II), (II-P), or (II-P-1). In some embodiments, set forth herein is a compound of Formula (II), (II-P), or (II-P-1), where SP is —C(O)—N($R^5$)-$C_1$-$C_5$-alkylene-C(O)NH—NH—. In some embodiments, set forth herein is a compound of Formula (II), (II-P), or (II-P-1), where SP is —C(O)—N($R^5$)-$CH_2$—C(O)NH—NH—. In some embodiments, set forth herein is a compound of Formula (II), (II-P), or (II-P-1), where $R^5$ is H or alkyl. In some embodiments, set forth herein is a compound of Formula (II), (II-P), or (II-P-1), where $R^5$ is H or $CH_3$.

In some embodiments, set forth herein is a compound of Formula (II), (II-P), or (II-P-1), where both $R^x$ are fluoro and SP is —C(O)—N($R^5$)—$C_1$-$C_{10}$-alkylene-C(O)NH-$X^2$- where $X^2$ is attached to $L^3$ in Formula (II). In some embodiments, set forth herein is a compound of Formula (II), (II-P), or (II-P-1), where SP is —C(O)—N($R^5$)—$C_1$-$C_5$-alkylene-C(O)NH—NH—. In some embodiments, set forth herein is a compound of Formula (II), (II-P), or (II-P-1), where SP is —C(O)—N($R^5$)—$CH_2$—C(O)NH—NH—. In some embodiments, set forth herein is a compound of Formula (II), (II-P), or (II-P-1), where $R^5$ is H or alkyl. In some embodiments, set forth herein is a compound of Formula (II), (II-P), or (II-P-1), where $R^5$ is H or $CH_3$.

In some embodiments, set forth herein is a compound of Formula (II), (II-P), or (II-P-1), where both $R^x$ are hydrogen and SP is

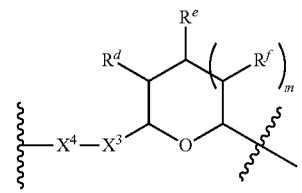

where $X^4$ is attached to $L^3$ in Formula (II), (II-P), or (II-P-1). In some embodiments, set forth herein is a compound of Formula (II), (II-P), or (II-P-1), where both $R^x$ are fluoro and SP is

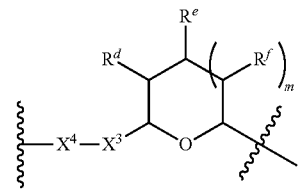

where $X^4$ is attached to $L^3$ in Formula (II), (II-P), or (II-P-1). In some embodiments, set forth herein is a compound of Formula (II), (II-P), or (II-P-1), where SP is

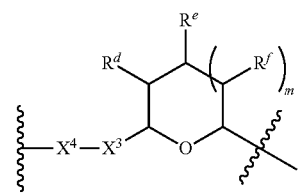

and $X^3$ is —$CH_2$—. In some embodiments, set forth herein is a compound of Formula (II), (II-P), or (II-P-1), where SP is

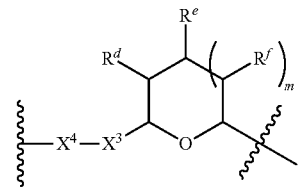

and $X^3$ is —$CH_2$—O—($C_1$-$C_{10}$-alkylene)-C(O)— where the C(O) is attached to $X^4$. In some embodiments, set forth herein is a compound of Formula (II), (II-P), or (II-P-1), where SP is

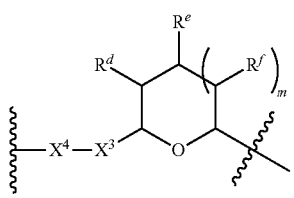

and $X^3$ is —C(O)—. In some embodiments, set forth herein is a compound of Formula (II), (II-P), or (II-P-1), where $R^d$, $R^e$, and $R^f$ are independently —H, —OH, hydroxyalkyl, alkoxycarbonyl, —C(O)OH, or —CH$_2$OR$^g$, where each $R^g$ is independently —CH$_2$C(O)OH or —CH$_2$C(O)O(alkyl). In some embodiments, set forth herein is a compound of Formula (II), (II-P), or (II-P-1), where $R^d$ and $R^e$ are independently —H or —OH. In some embodiments, set forth herein is a compound of Formula (II), (II-P), or (II-P-1), where m is 0. In some embodiments, set forth herein is a compound of Formula (II), (II-P), or (II-P-1), where m is 1. In some embodiments, set forth herein is a compound of Formula (II), (II-P), or (II-P-1), where m is 1 and $R^f$ is —H or —OH.

In some embodiments, provided is a Compound of Formula (II), (II-P), or (II-P-1), where both $R^x$ are hydrogen and SP is —C(O)—N(C$_{1-3}$alkyl)-C$_1$-C$_{10}$-alkylene-X$^1$- where X$^1$ is attached to L$^3$ in Formula (II), (II-P), or (II-P-1); SP is

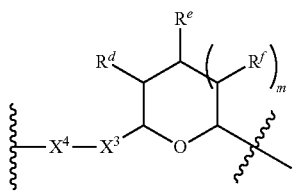

where $X^3$ is —CH$_2$—, m is 1, and $R^d$, $R^e$, and $R^f$ are —H; or SP is

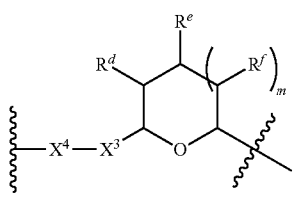

where $X^3$ is —CH$_2$—O—(C$_1$-C$_{10}$-alkylene)-C(O)— where the C(O) is attached to X$^4$, m is 1, and $R^d$, $R^e$, and $R^f$ are —H. In some embodiments, provided is a Compound of Formula (II), (II-P), or (II-P-1), where SP is —C(O)—N(CH$_3$)—CH$_2$CH$_2$—N(CH$_3$)—,

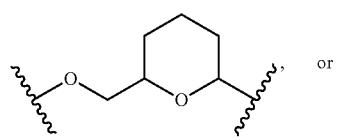

or

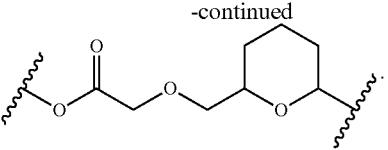

In some embodiments, provided is a Compound of Formula (II), (II-P), or (II-P-1), where both $R^x$ are fluoro and SP is —C(O)—N(C$_{1-3}$alkyl)-C$_1$-C$_{10}$-alkylene-X$^1$- where X$^1$ is attached to L$^3$ in Formula (II), (II-P), or (II-P-1); SP is

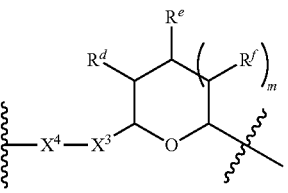

where $X^3$ is —CH$_2$—, m is 1, and $R^d$, $R^e$, and $R^f$ are —H; or SP is

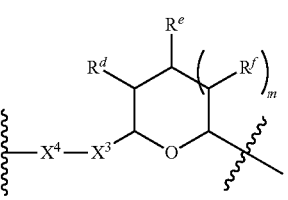

where $X^3$ is —CH$_2$—O—(C$_1$-C$_{10}$-alkylene)-C(O)— where the C(O) is attached to X$^4$, m is 1, and $R^d$, $R^e$, and $R^f$ are —H. In some embodiments, provided is a Compound of Formula (II), (II-P), or (II-P-1), where SP is —C(O)—N(CH$_3$)—CH$_2$CH$_2$—N(CH$_3$)—,

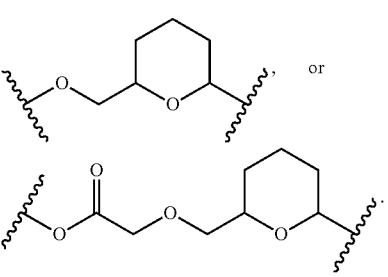

In some embodiments, provided is a Compound of Formula (II), where both $R^x$ are fluoro or both $R^x$ are hydrogen, or $R^x$ is as specified in this paragraph; SP is

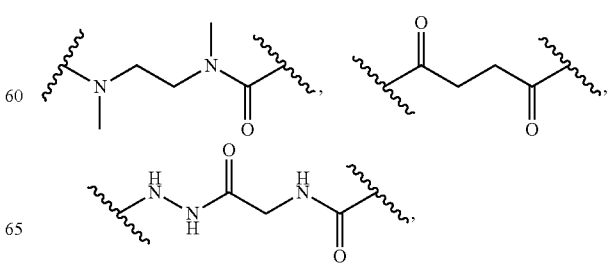

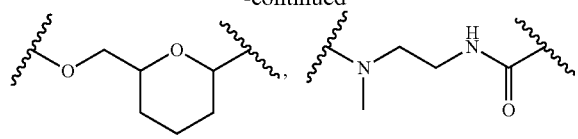

(where both R$^x$ are fluoro),

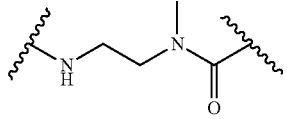 [SMILES: *NCCN(C)C(*)=O]

(where both R$^x$ are fluoro),

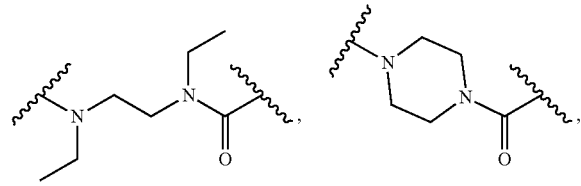

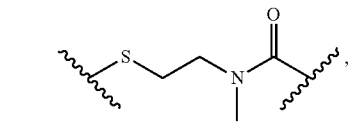

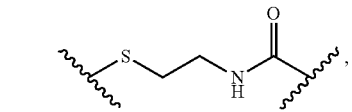

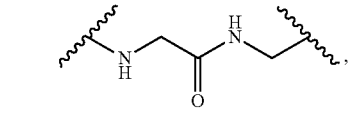

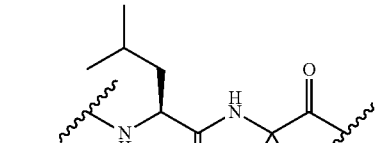, or

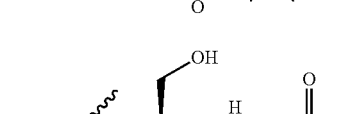

In some embodiments, set forth herein is a compound of Formula (II), (II-P), or (II-P-1), where RG is a reactive group selected from

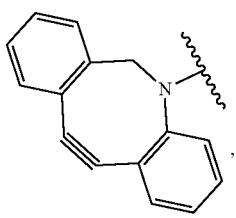 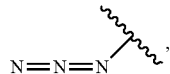,

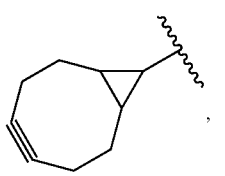, 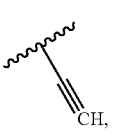,

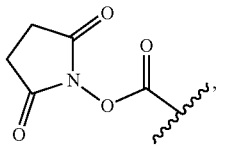 and 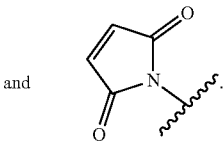.

In some embodiments, set forth herein is a compound of Formula (II), (II-P), or (II-P-1), where RG is

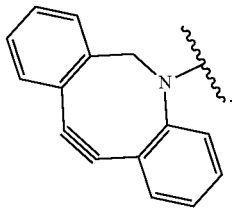 [SMILES: *N1Cc2ccccc2C#Cc2ccccc21]

In some embodiments, set forth herein is a compound of Formula (II), (II-P), or (II-P-1), where RG is

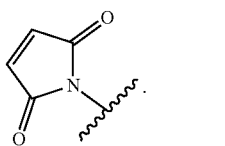 [SMILES: *N1C(=O)C=CC1=O]

In some embodiments, set forth herein is a compound of Formula (II), (II-P), or (II-P-1), where RG is

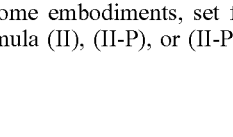

In some embodiments, set forth herein is a compound of Formula (II), (II-P), or (II-P-1), where RG is

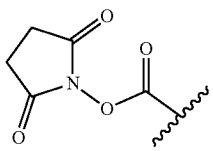 [SMILES: *C(=O)ON1C(=O)CCC1=O]

In some embodiments, -L$^2$-(L$^3$)$_{0-1}$- in Formula (II), (II-P), or (II-P-1) refers to any divalent group or moiety that links, connects, or bonds a reactive group (RG in Formula (II), (II-P), or (II-P-1) with a payload compound set forth herein (e.g., steroid). Generally, suitable -L$^2$-(L$^3$)$_{0-1}$- are those that are sufficiently stable to exploit the circulating half-life of the antibody and, at the same time, capable of releasing its payload after antigen-mediated internalization of the conjugate. -L$^2$-(L$^3$)$_{0-1}$ can be cleavable or non-cleavable linkers. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise glucuronides, succinimide-thioethers, polyethylene glycol (PEG) units, carbamates, hydrazones, mal-caproyl units, disulfide units (e.g., —S—S—, —S—S—C(R$^{1b}$)(R$^{2b}$)-, wherein R$^{1b}$ and R$^{2b}$ are independently hydrogen or hydrocarbyl), para-amino-benzyl (PAB) units, phosphate units, e.g., mono-, bis-, and tris-phosphate units, peptides, e.g., peptide units containing two, three, four, five, six, seven, eight, or more amino acid units, including but not limited to valine-citrulline units, valine-alanine units, valine-arginine units, valine-lysine units, -lysine-valine-citrulline units, and -lysine-valine-alanine units. In some embodiments, -L$^2$-(L$^3$)$_{0-1}$- is trivalent and includes a cyclodextrin moiety bonded to a trivalent group (e.g., a lysine residue) in -L$^2$-(L$^3$)$_{0-1}$-. In some embodiments, L$^3$ is present. In some embodiments, L$^3$ is not present.

In some embodiments, provided is a Compound of Formula (II), (II-P), or (II-P-1), where L$^2$ comprises

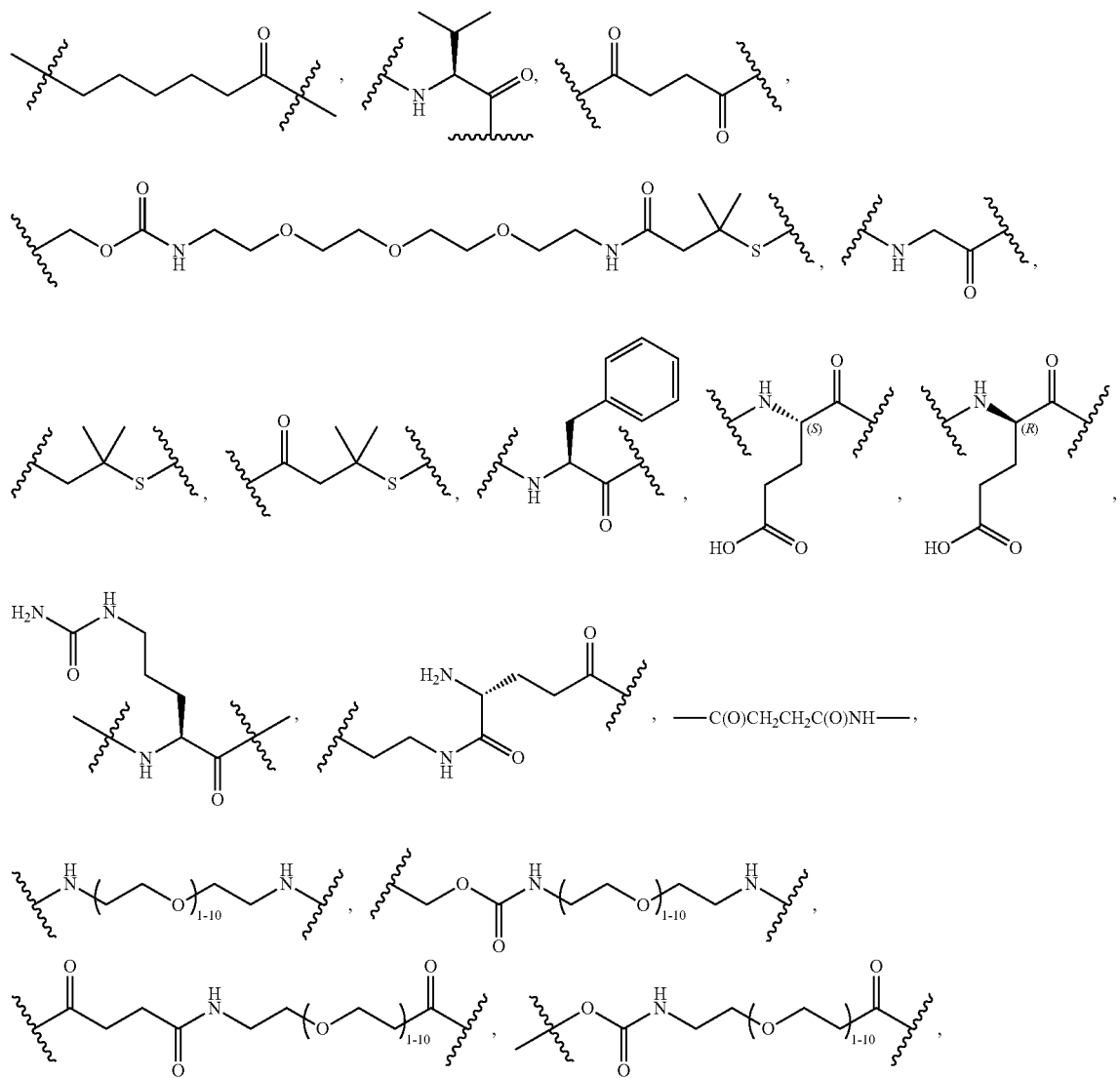

or cyclodextrin residue (CD); or combinations thereof. In some embodiments, provided is a Compound of Formula (II), (II-P), or (II-P-1), where L² comprises
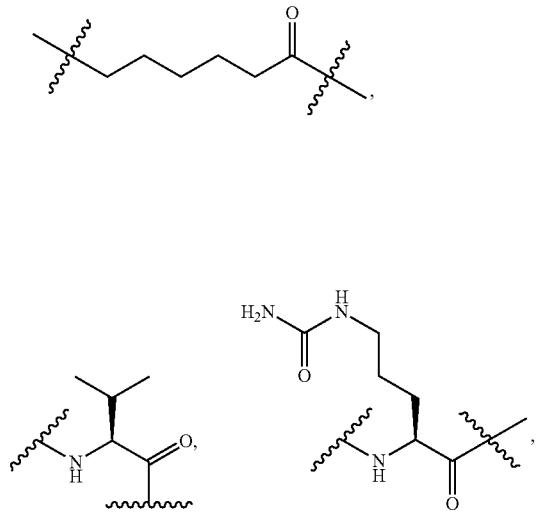
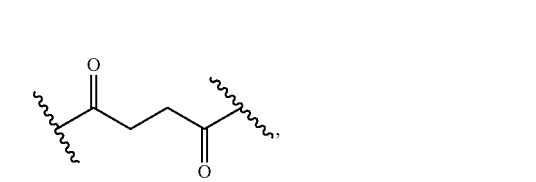
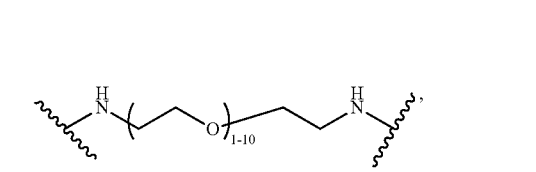
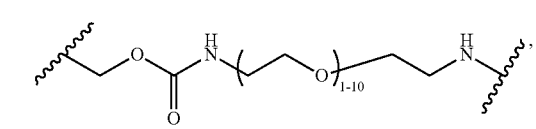
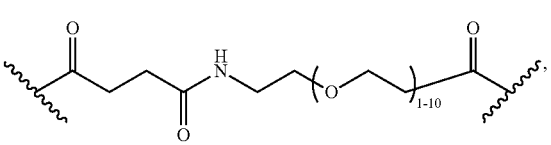
or CD, or combinations thereof. In some embodiments, provided is a Compound of Formula (II), (II-P), or (II-P-1), where L² comprises CD wherein CD is selected from the group consisting of
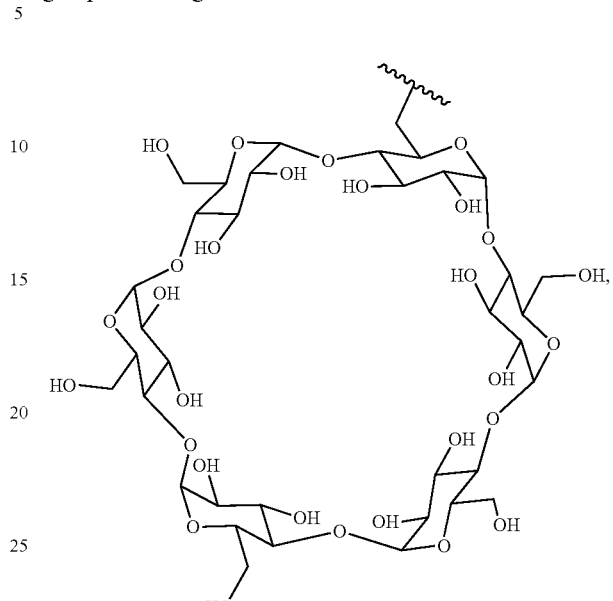
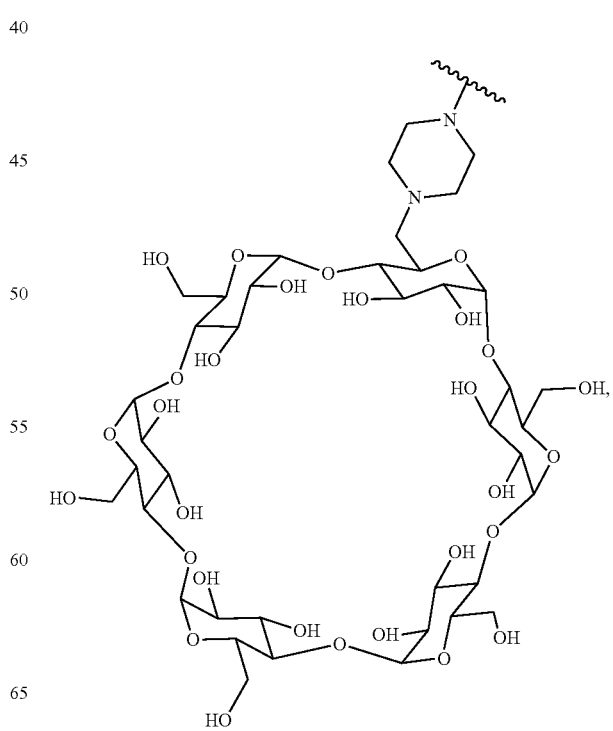

183
-continued
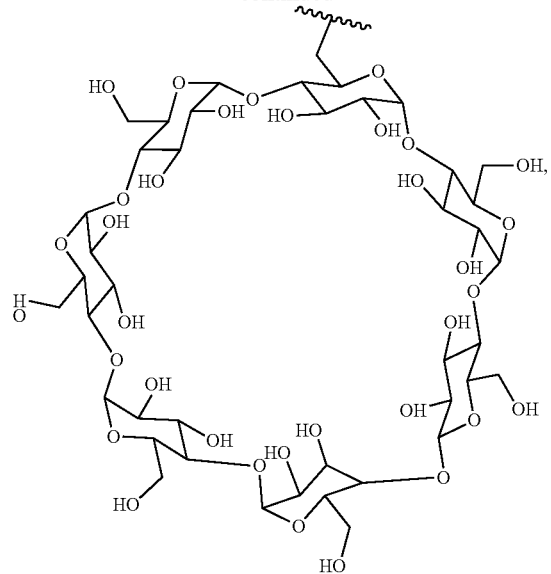
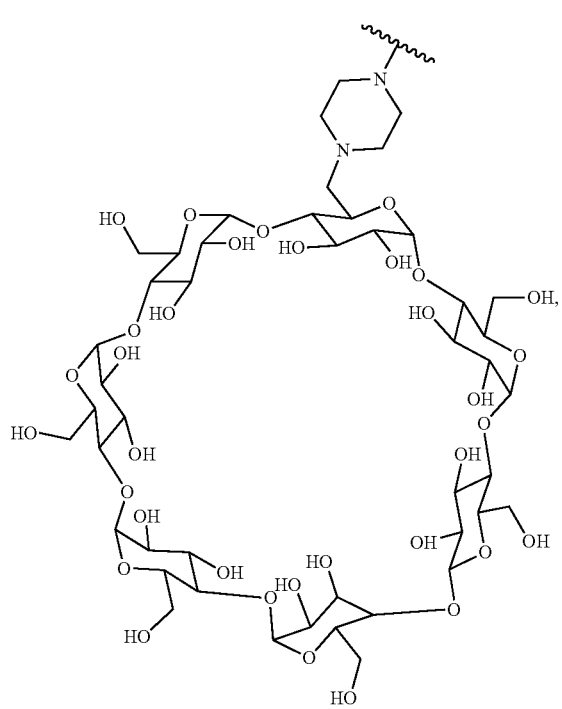
184
-continued
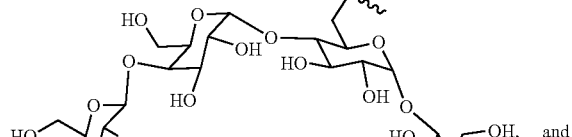
and
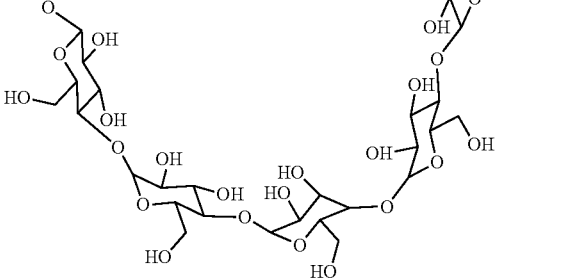
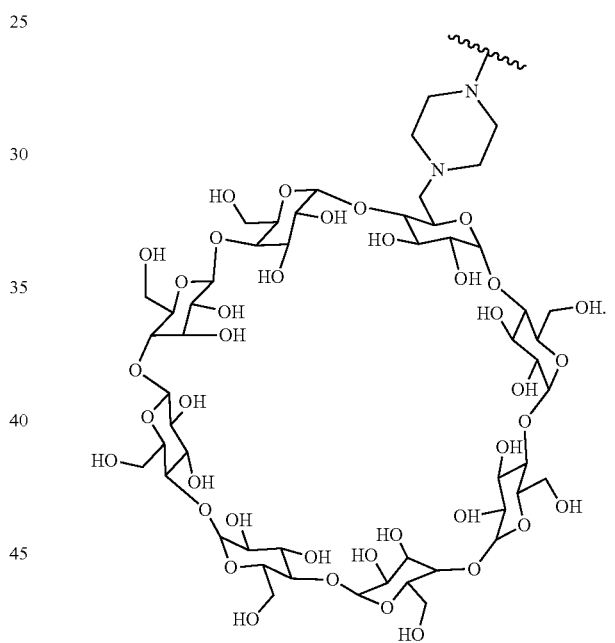
In some embodiments, provided is a Compound of Formula (II), (II-P), or (II-P-1), where -L$^2$-(L$^3$)$_{0-1}$- comprise
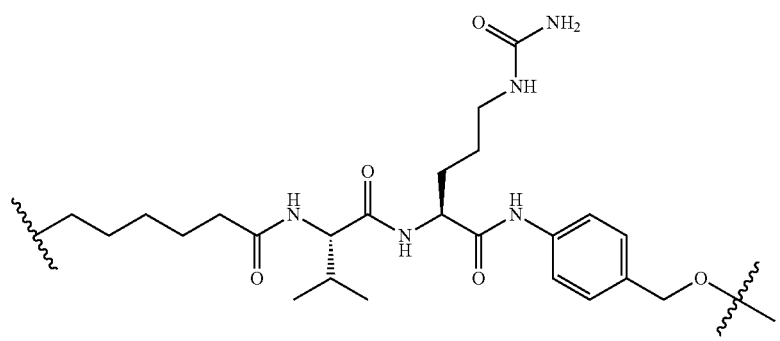

-continued
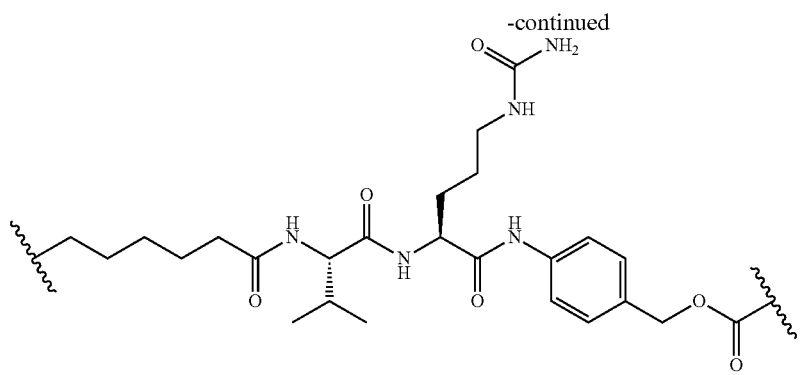
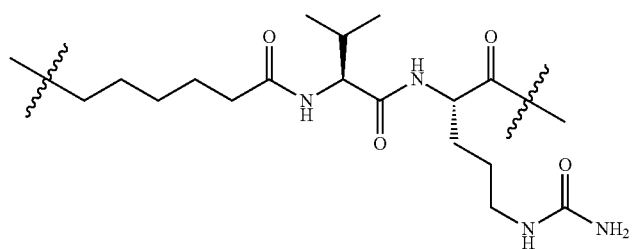
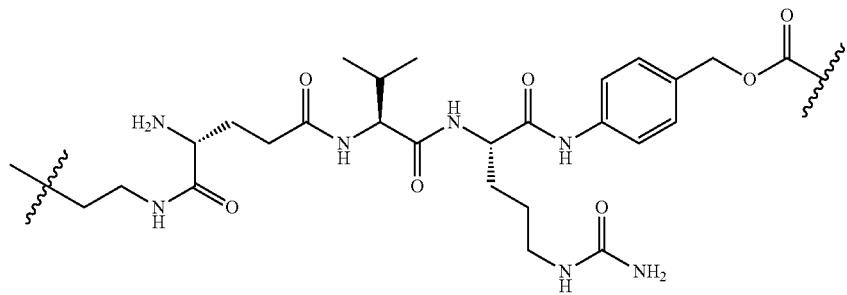

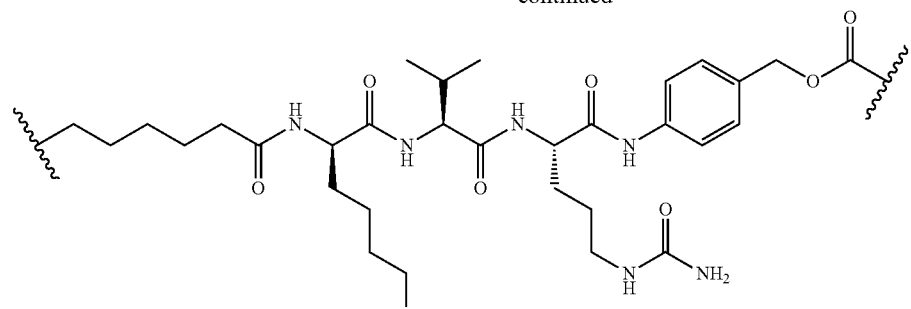
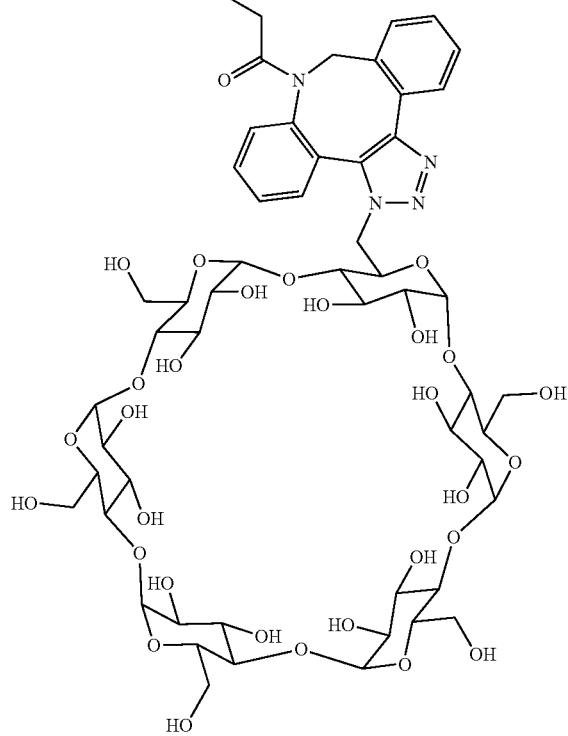
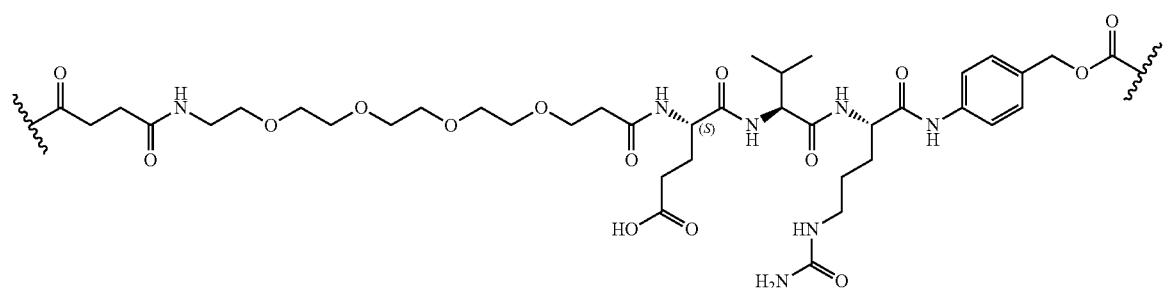
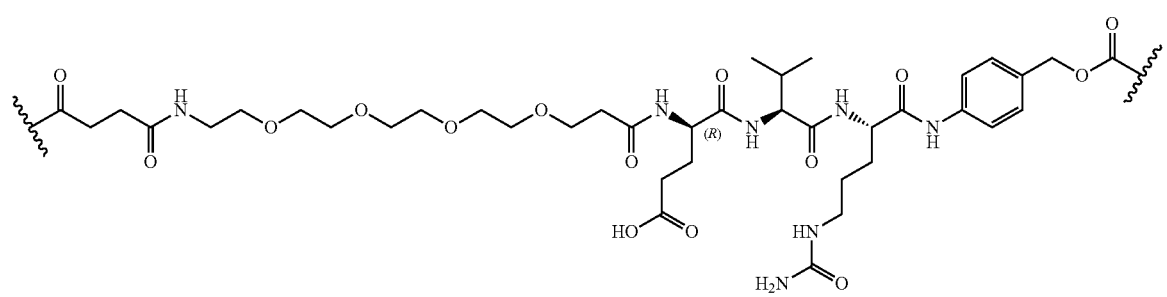

-continued

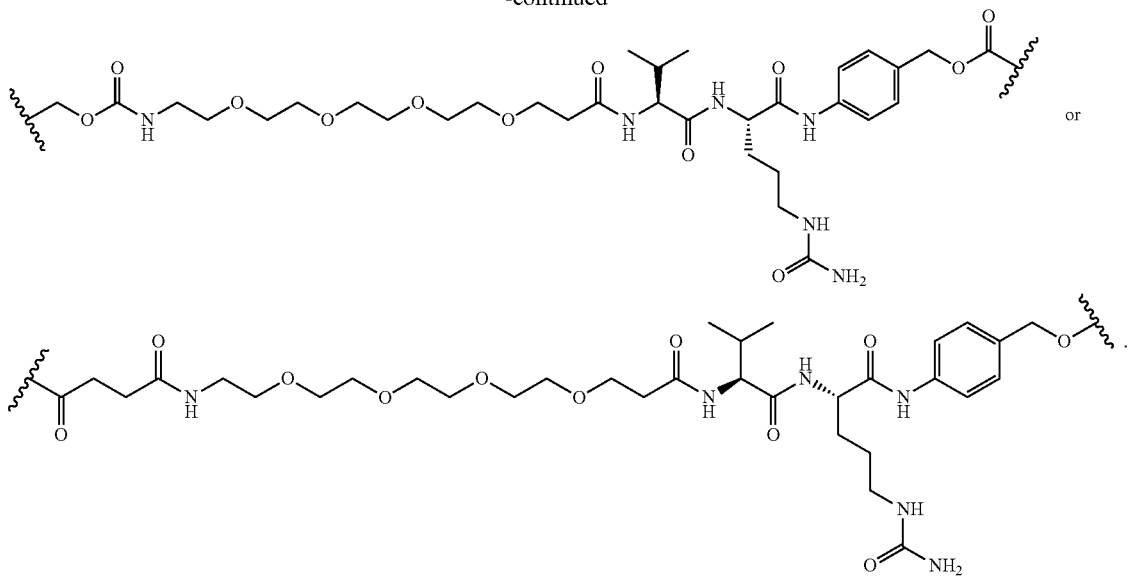

or

In some embodiments, provided is a Compound of Formula (II), (II-P), or (II-P-1), where $L^3$ is

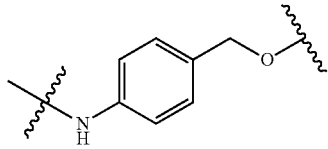 [SMILES: *Nc1ccc(CO*)cc1]

where the NH group is attached to $L^2$, when SP is —C(O)—$C_1$-$C_{10}$-alkylene-C(O)—; or $L^3$ is

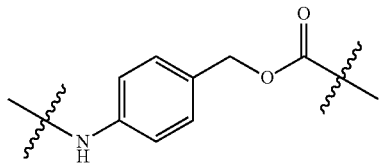 [SMILES: *Nc1ccc(COC(*)=O)cc1]

where the NH group is attached to $L^2$, when SP is —C(O)—N($C_{1-3}$alkyl)-$C_1$-$C_{10}$-alkylene-$X^1$- or —C(O)—N($R^5$)-$C_1$-$C_{10}$-alkylene-C(O)NH-$X^2$-; or $L^3$ is not present when SP is

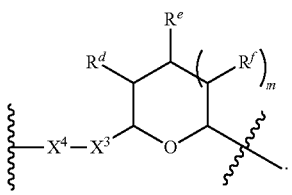

In some embodiments, provided is a Compound of Formula (II), (II-P), or (II-P-1), where $L^3$ is

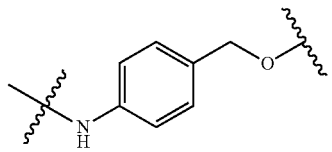 [SMILES: *Nc1ccc(CO*)cc1]

where the NH group is attached to $L^2$, when SP is —C(O)—$C_1$-$C_{10}$-alkylene-C(O)—. In some embodiments, provided is a Compound of Formula (II), (II-P), or (II-P-1), where $L^3$ is

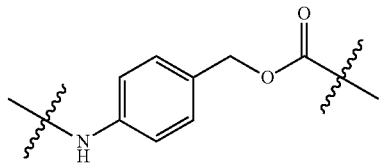 [SMILES: *Nc1ccc(COC(*)=O)cc1]

where the NH group is attached to $L^2$, when SP is —C(O)—N($C_{1-3}$alkyl)-$C_1$-$C_{10}$-alkylene-$X^1$- or —C(O)—N($R^5$)-$C_1$-$C_{10}$-alkylene-C(O)NH-$X^2$—. In some embodiments, provided is a Compound of Formula (II), (II-P), or (II-P-1), where $L^3$ is not present when SP is

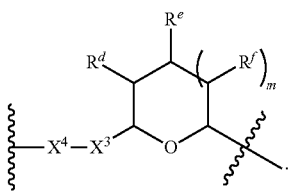

Set forth herein are also compounds having the following structures:

TABLE 2
Budesonide-spacer-linker-reactive group
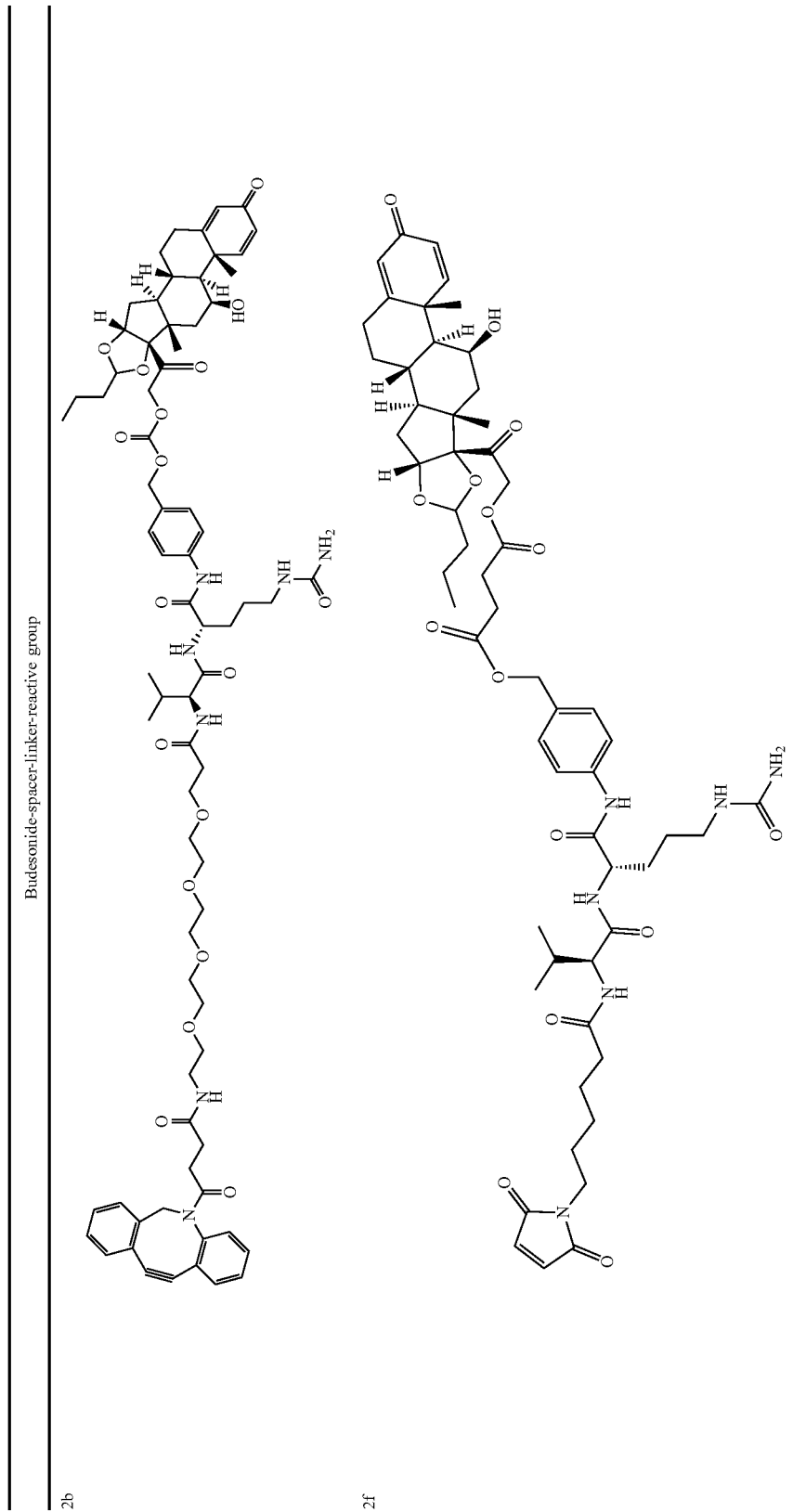
2b
2f

TABLE 2-continued
Budesonide-spacer-linker-reactive group
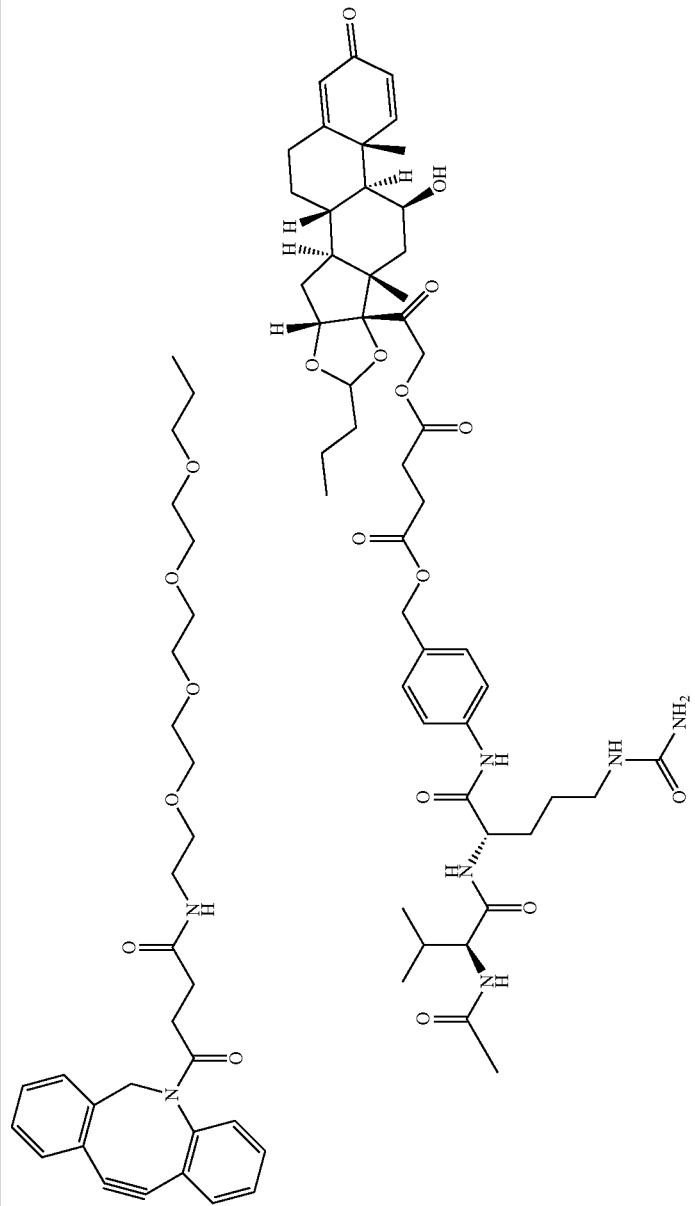
2g

TABLE 2-continued
Budesonide-spacer-linker-reactive group
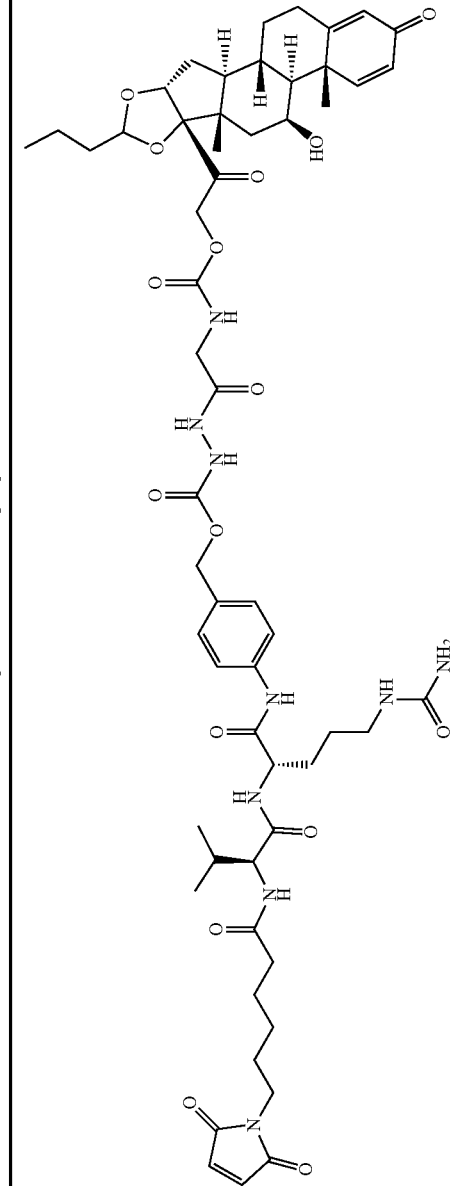
2j
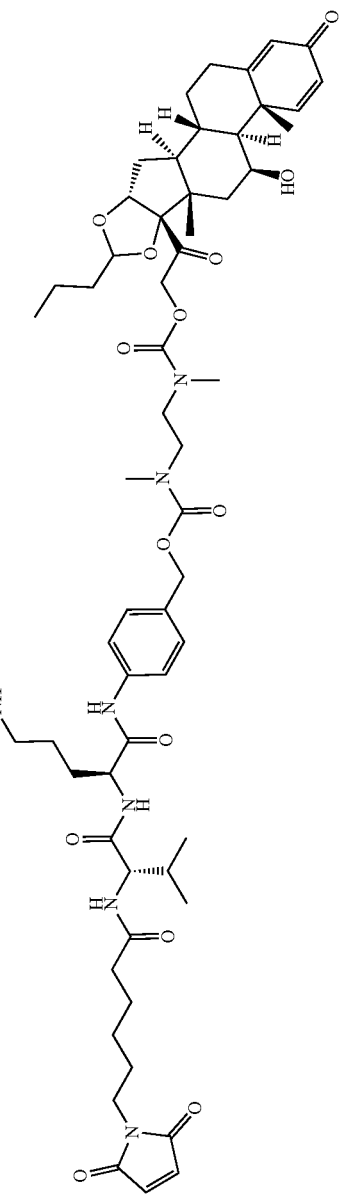
2k TABLE 2-continued
Budesonide-spacer-linker-reactive group
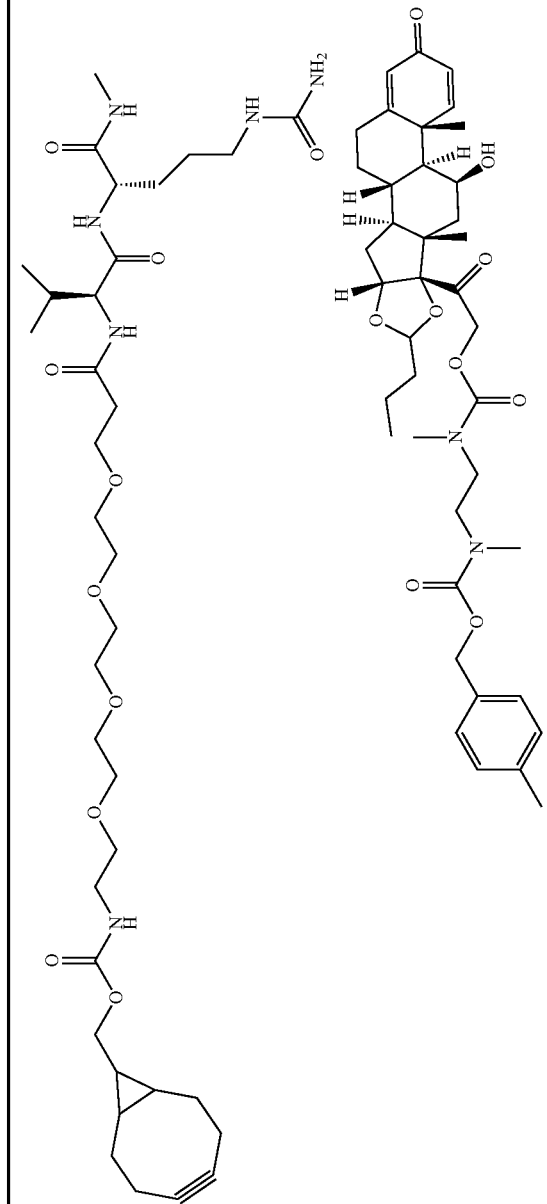
21

TABLE 2-continued
Budesonide-spacer-linker-reactive group
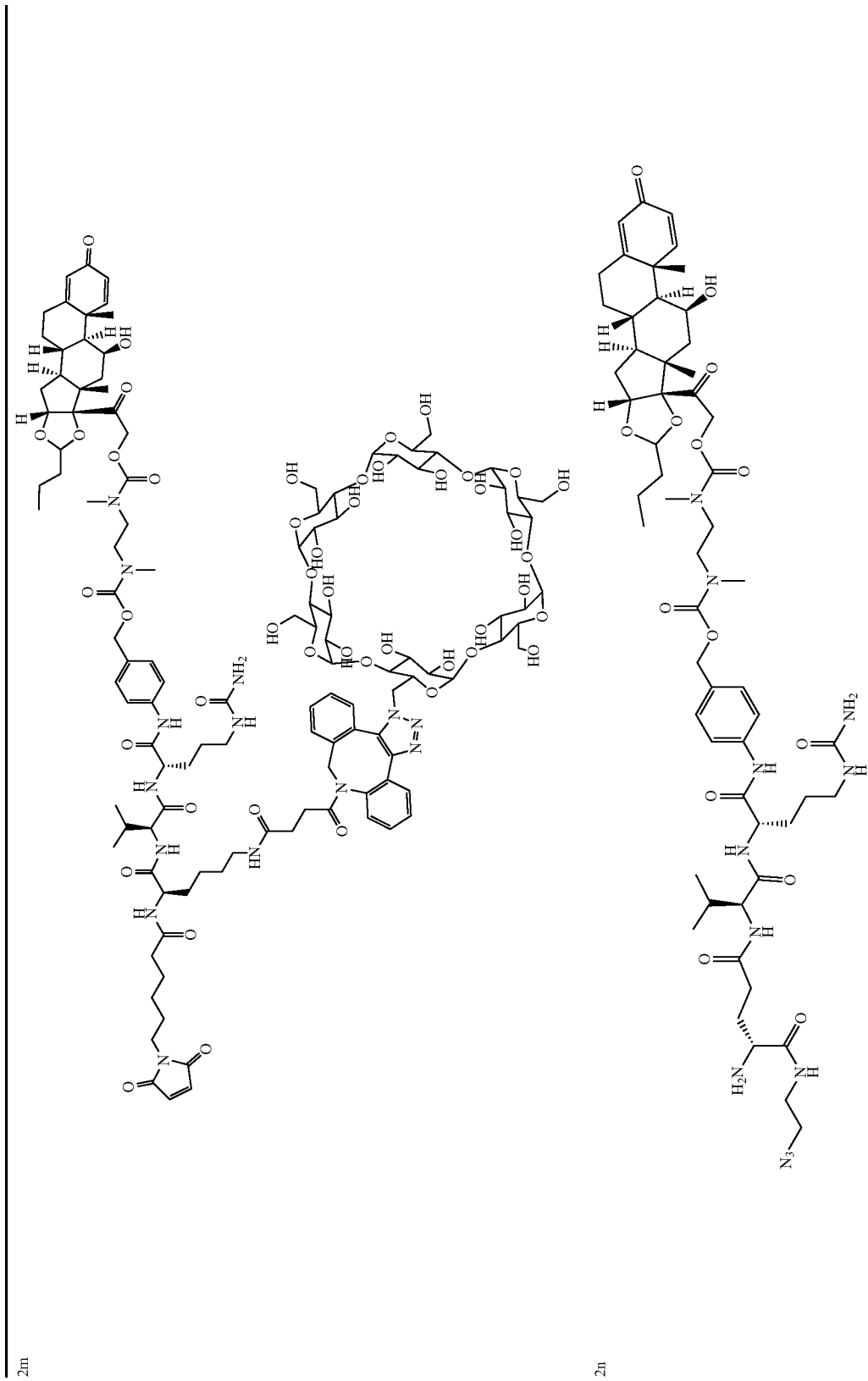
2m
2n

TABLE 2-continued
Budesonide-spacer-linker-reactive group
| 2q | LP1 |
|---|---|
| 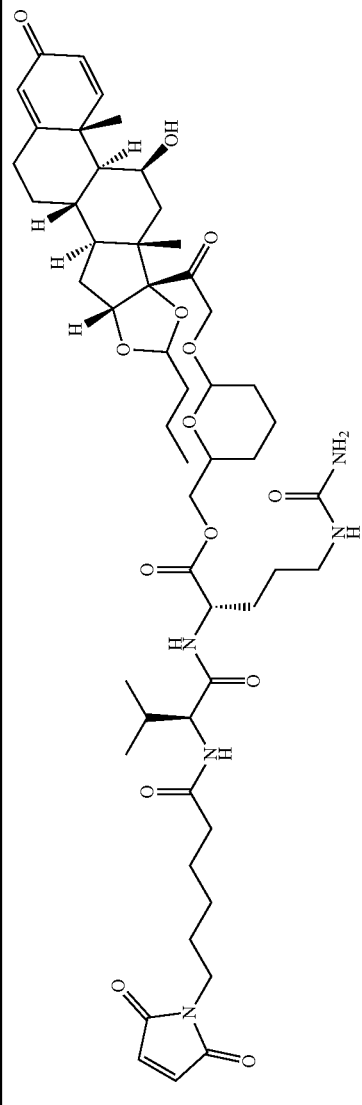 | 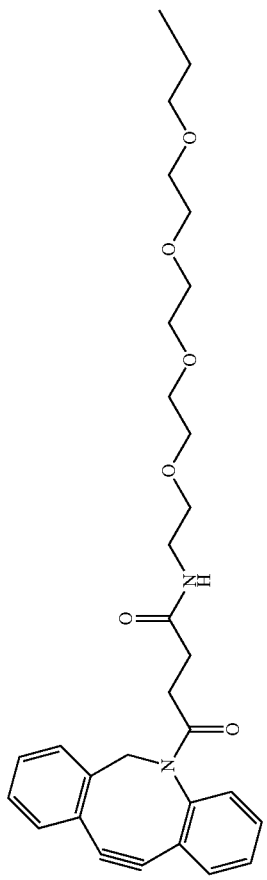 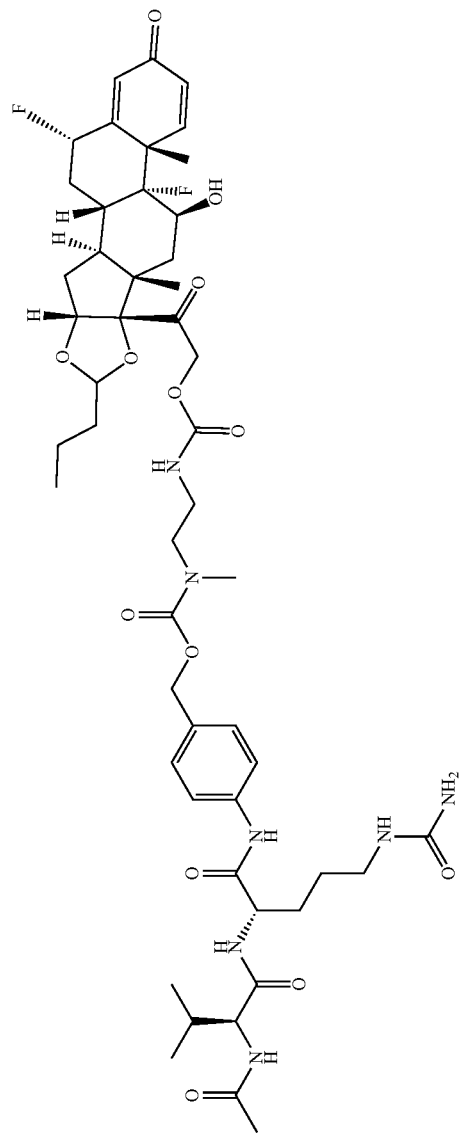 |

TABLE 2-continued
Budesonide-spacer-linker-reactive group
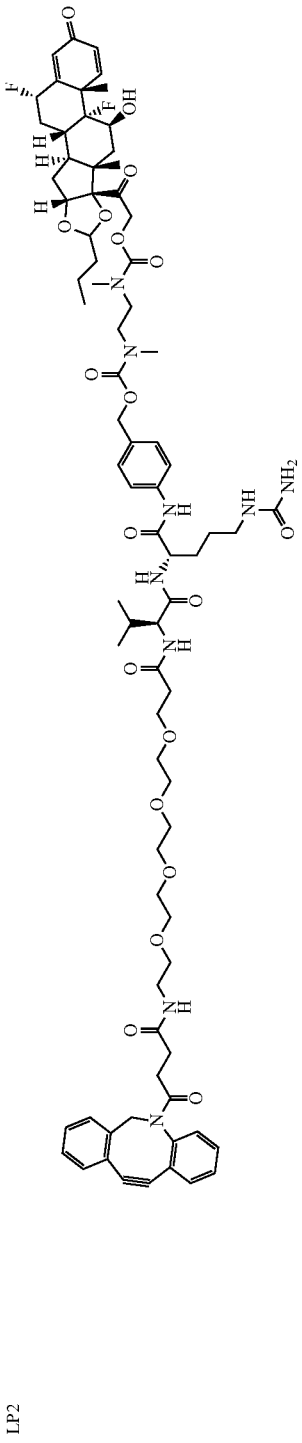
LP2
LP3
LP4

TABLE 2-continued
Budesonide-spacer-linker-reactive group
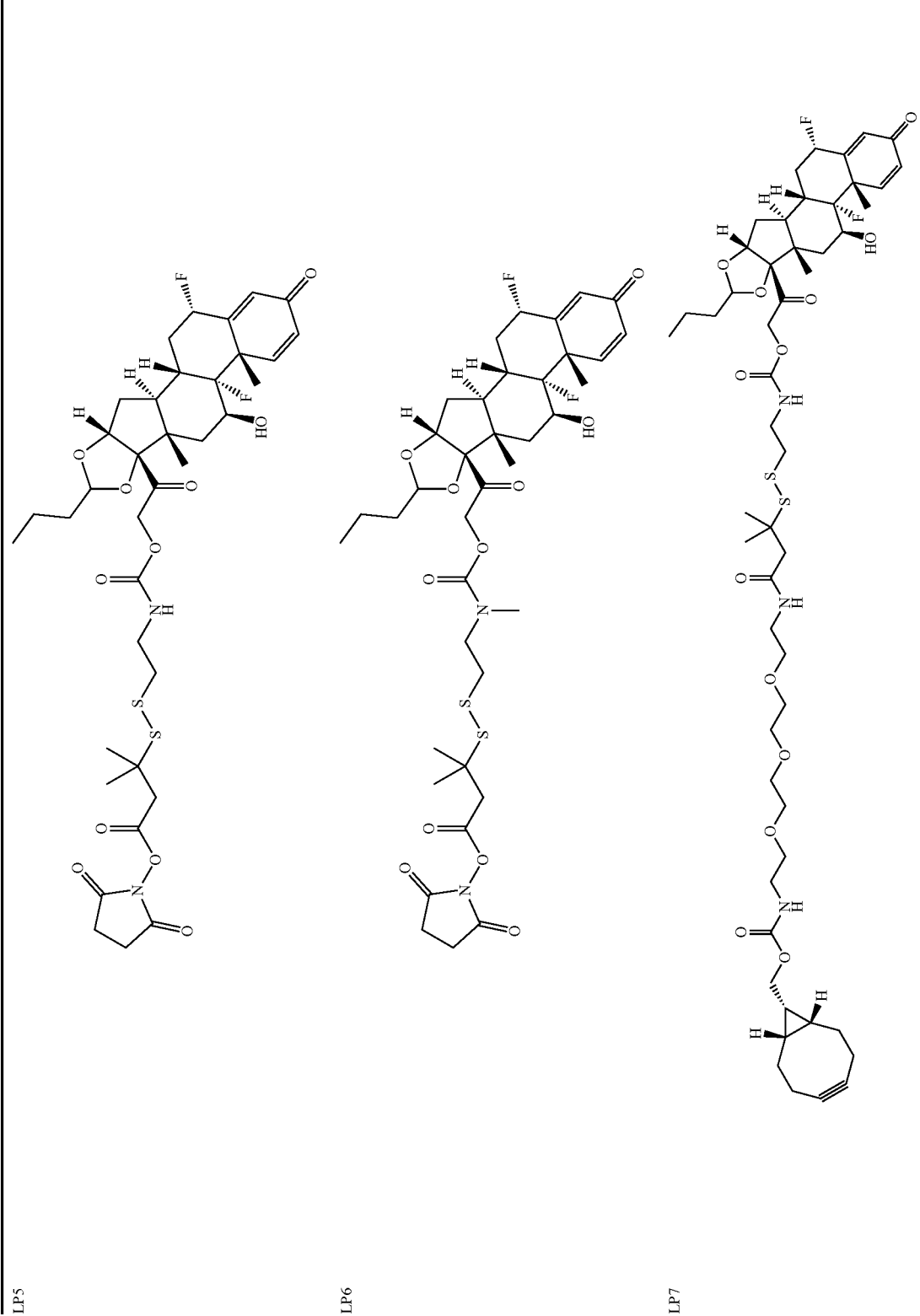
LP5
LP6
LP7

TABLE 2-continued
Budesonide-spacer-linker-reactive group
| | |
|---|---|
| LP8 | 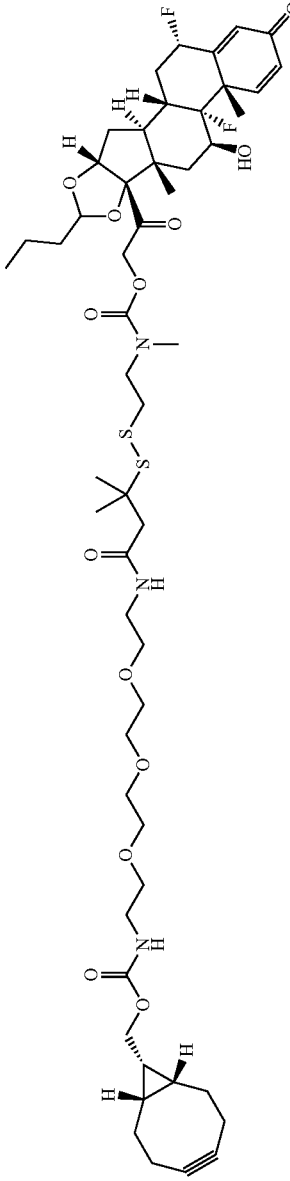 |
| LP9 | 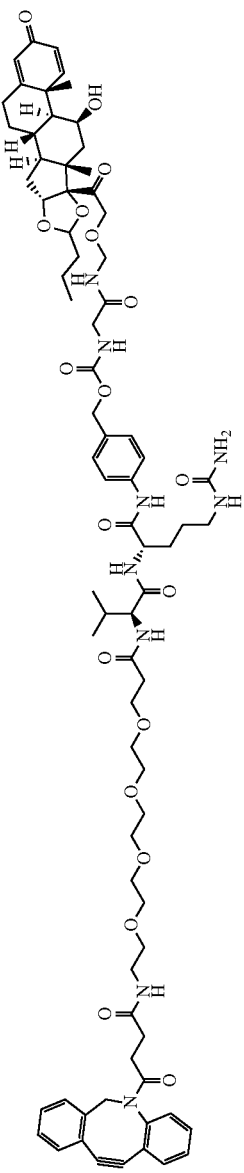 |
| LP10 | 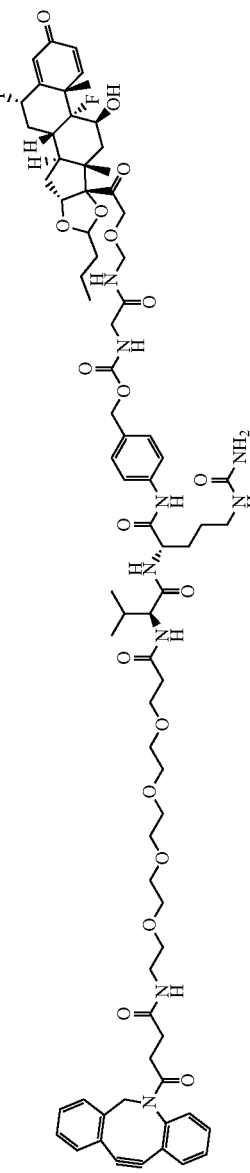 |

TABLE 2-continued

Budesonide-spacer-linker-reactive group

LP11

LP12

LP13

TABLE 2-continued
Budesonide-spacer-linker-reactive group
| LP18 | 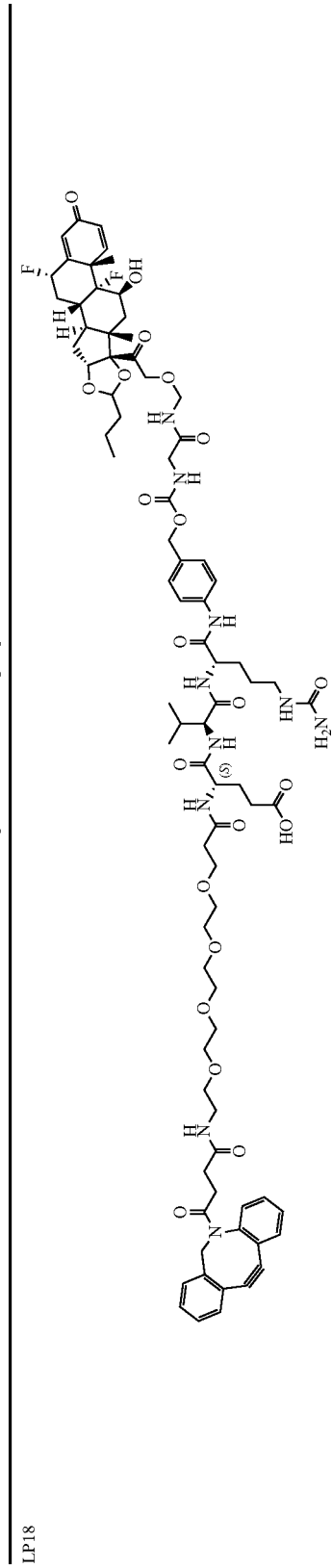 |
| LP19 | 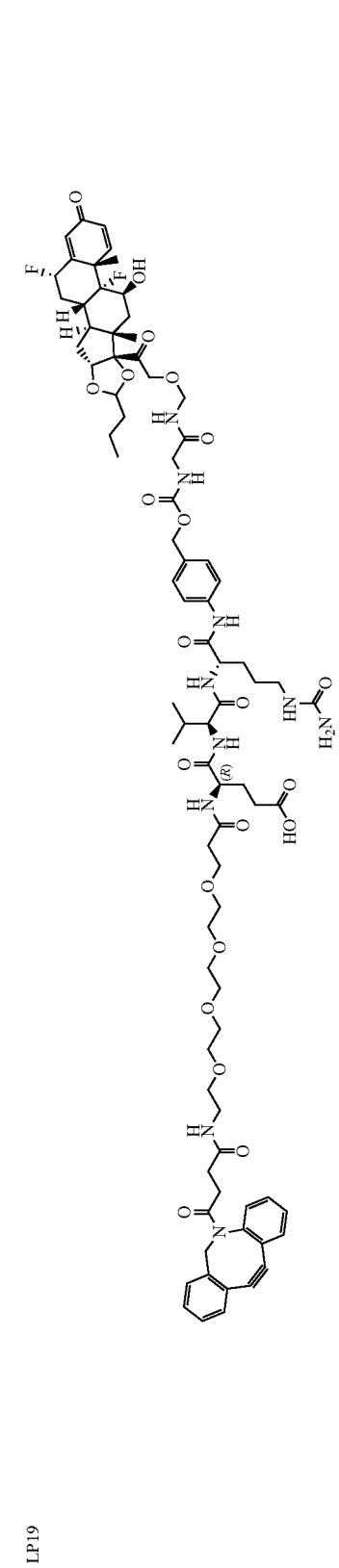 |
| LP20 | 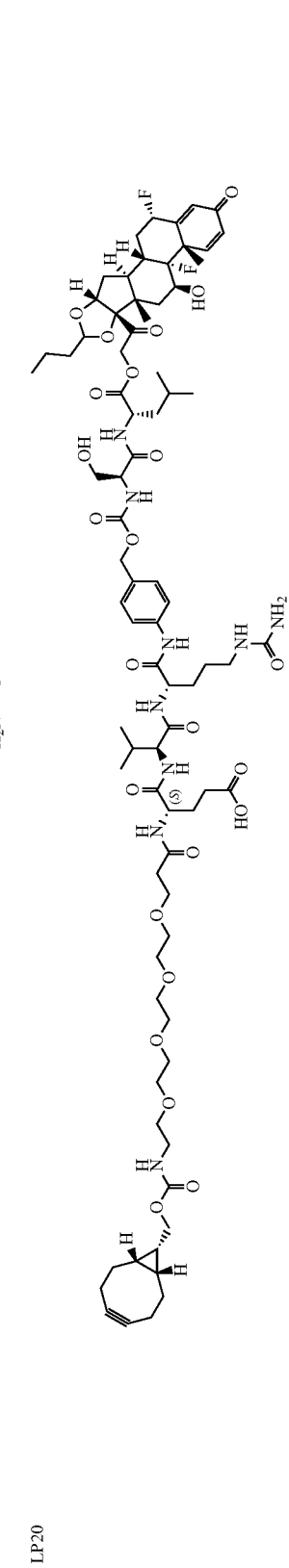 |

TABLE 2-continued
Budesonide-spacer-linker-reactive group
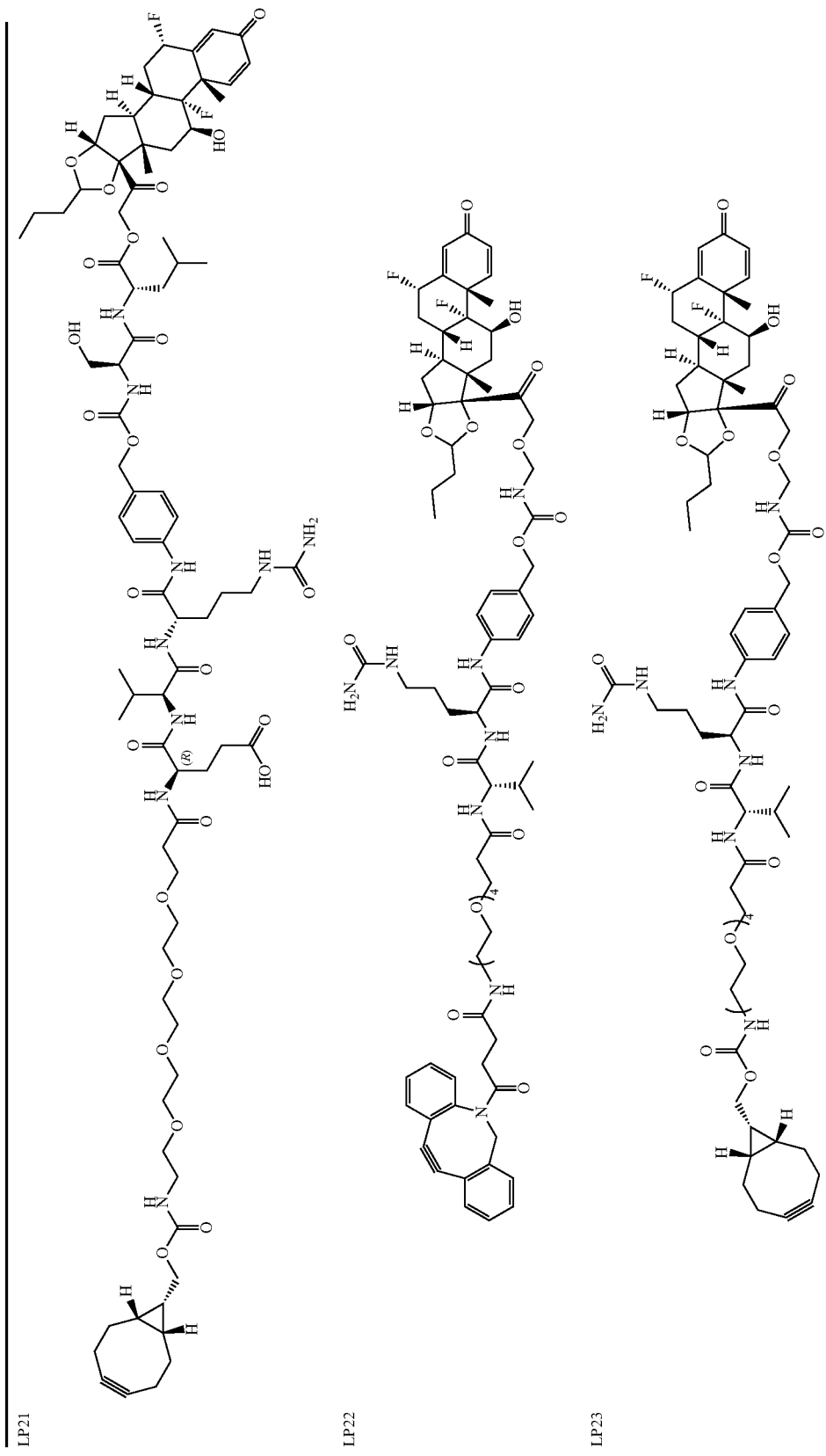
LP21
LP22
LP23

TABLE 2-continued
Budesonide-spacer-linker-reactive group
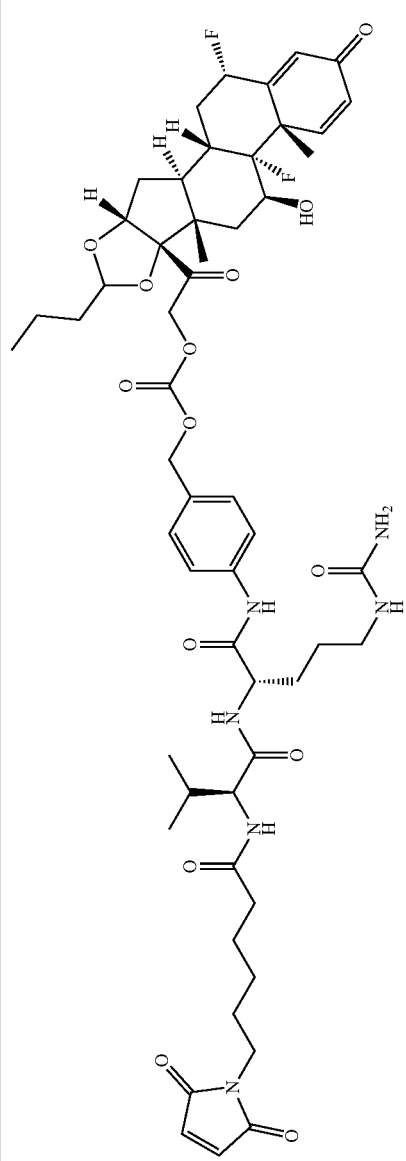
LP24
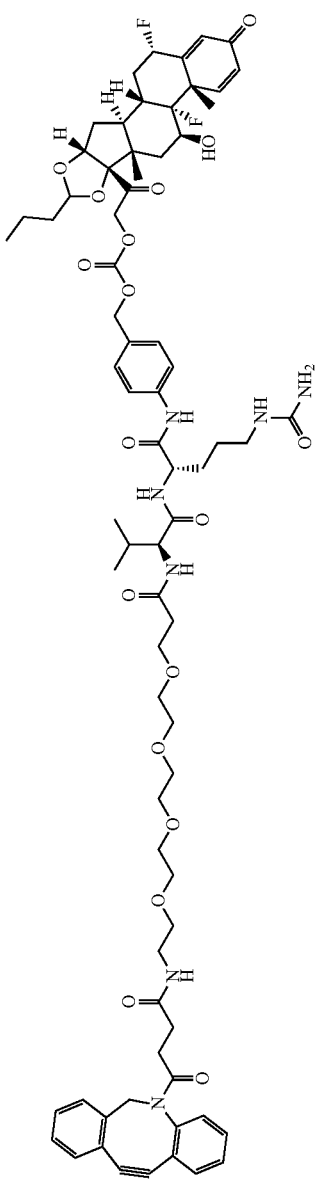
LP25

TABLE 2-continued
Budesonide-spacer-linker-reactive group
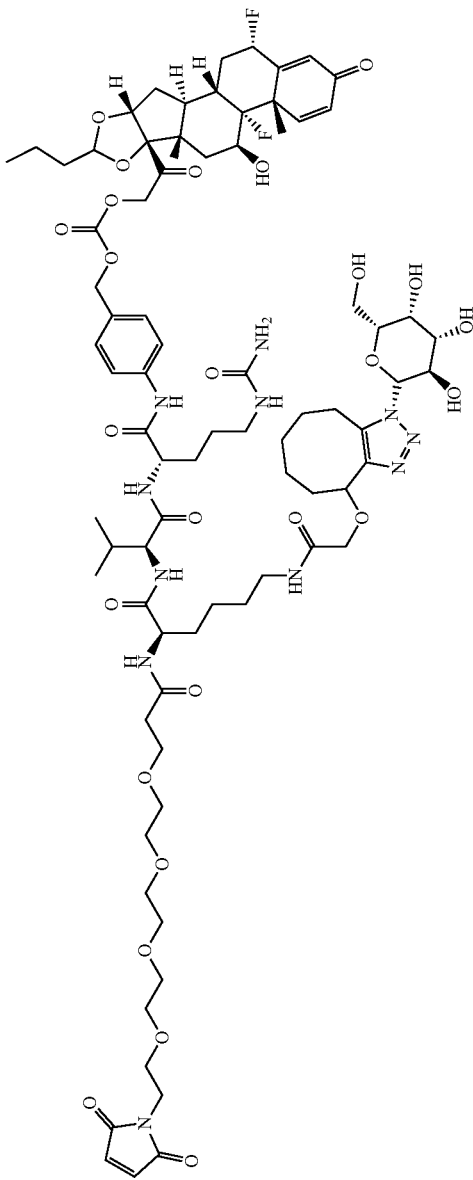
LP26
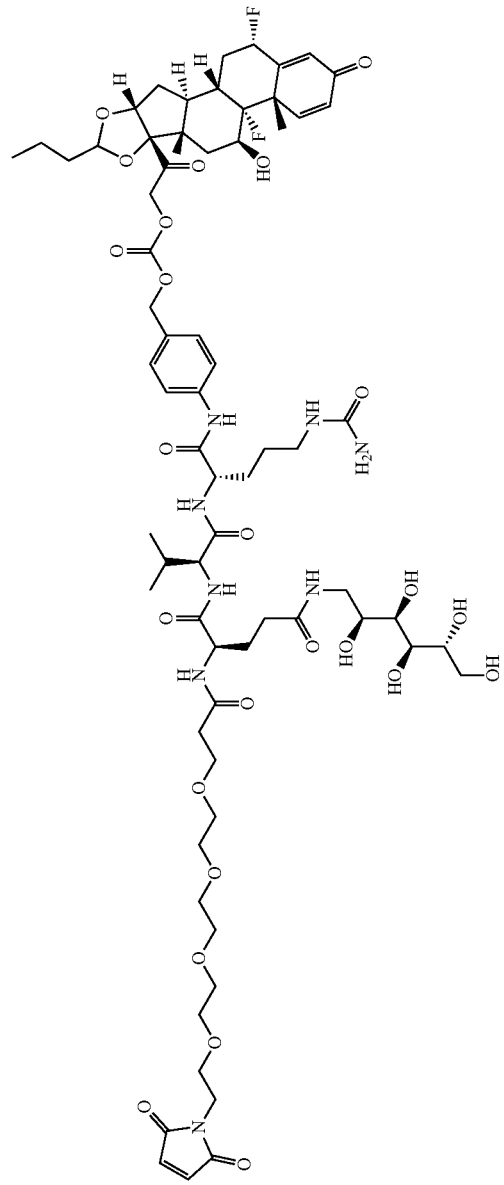
LP27

TABLE 2-continued
Budesonide-spacer-linker-reactive group
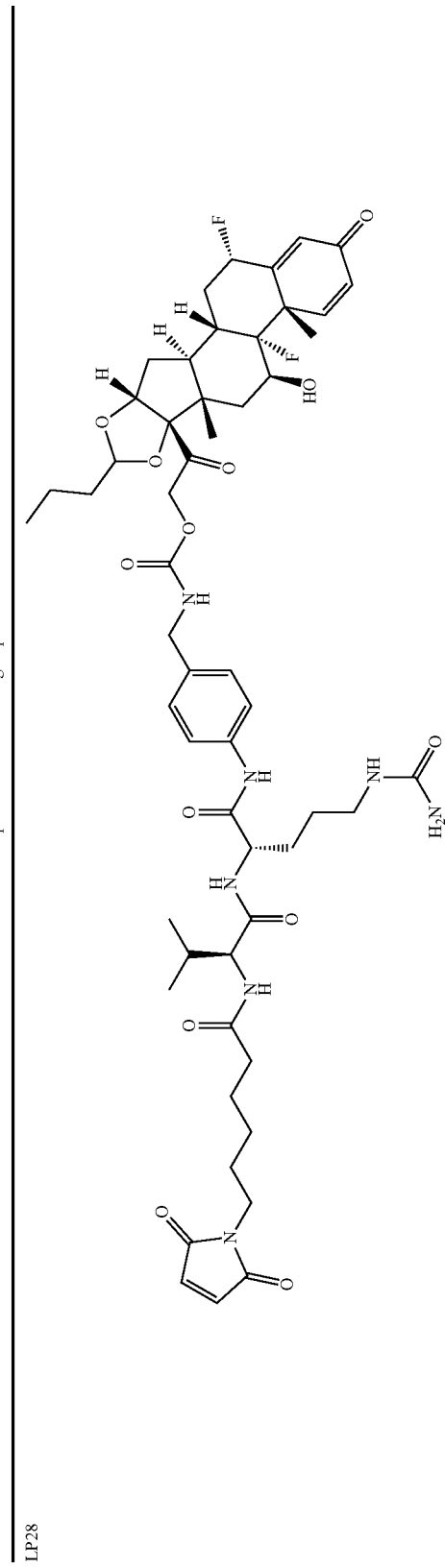
LP28
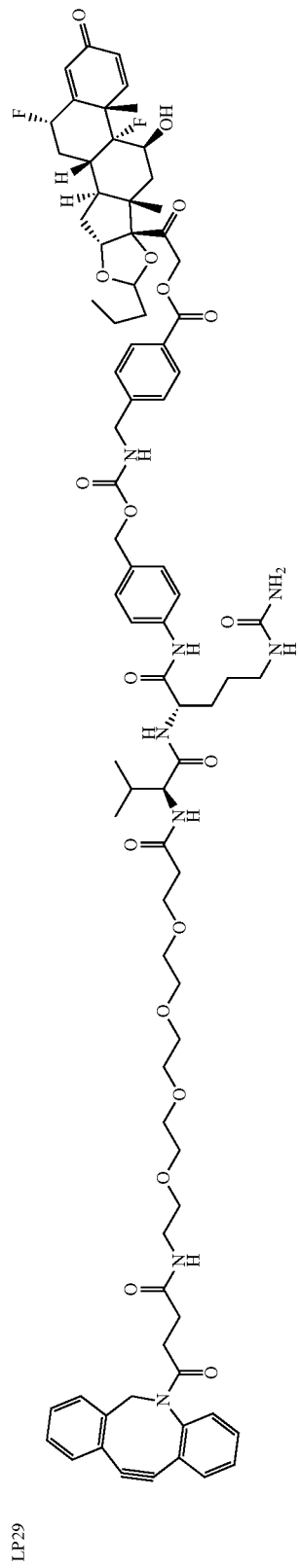
LP29

TABLE 2-continued
Budesonide-spacer-linker-reactive group
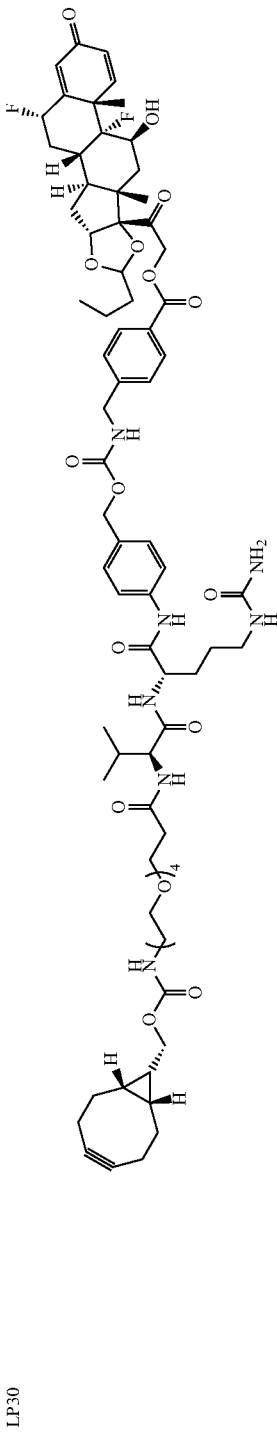
LP30
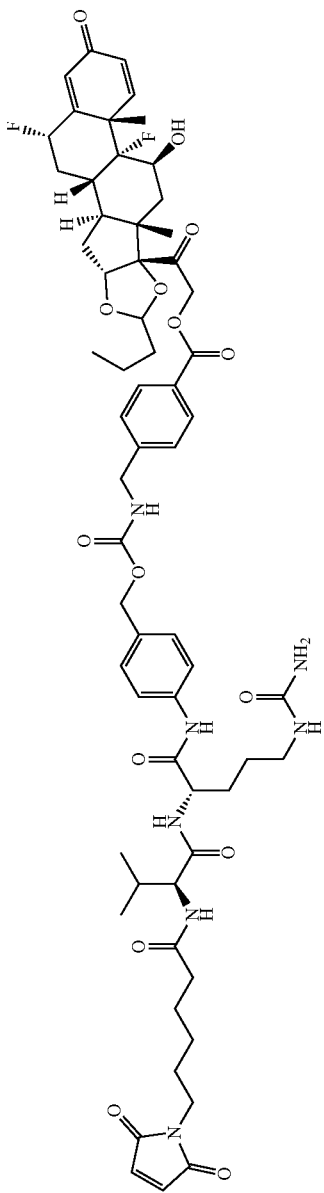
LP31

Binding agents, e.g., antibodies, can also be conjugated via click chemistry reaction. In some embodiments of said click chemistry reaction, the linker-payload comprises a reactive group, e.g., alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable alkynes also include, but are not limited to, DIBAC, DIBO, BARAC, DIFO, substituted alkynes, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue, e.g., heavy chain Q295, with a compound according to the formula $H_2N-LL-N_3$, wherein LL is a divalent polyethylene glycol group, in the presence of the enzyme transglutaminase. For convenience, in certain Formulas herein, the antibody Ab is a modified antibody with one or more covalently linked $-LL-N_3$ groups, or residues thereof. Preferably, each $-LL-N_3$ is covalently bonded to an amino acid side chain of a glutamine residue of the antibody. Also preferably, the $-LL-N_3$ is or can be reacted with a reactive group RG to form a covalent bond to a linker-payload. Again for convenience, in certain Formulas herein, the $-LL-N_3$ groups are expressly drawn.

Set forth here are methods of synthesizing the conjugates described herein comprising contacting a binding agent, e.g., antibody, with a linker-payload described herein. In certain embodiments, the linker-payload includes a cyclodextrin moiety.

Compounds of Formula (II), (II-P), or (II-P-1) are linker-payloads that are useful as synthetic intermediates in the synthesis of the conjugates described herein. These linker-payloads comprise a reactive group that can react with an antibody to form the conjugates described herein.

In some embodiments of Formula (II), (II-P), or (II-P-1), $R^4$ is alkyl. In some embodiments of Formula (II), (II-P), or (II-P-1), $R^4$ is methyl, ethyl, n-propyl, i-propyl, n-butyl, s-butyl, t-butyl, i-butyl, a pentyl moiety, a hexyl moiety, cyclopropyl, cyclobutyl, cyclopentyl, or cyclohexyl. In some embodiments of Formula (II), (II-P), or (II-P-1), R4 is alkyl. In some embodiments of Formula (II), (II-P), or (II-P-1), R4 is methyl, ethyl, n-propyl, i-propyl, n-butyl, s-butyl, t-butyl, i-butyl, a pentyl moiety, or a hexyl moiety. In some embodiments of Formula (II), (II-P), or (II-P-1), $R^4$ is n-propyl.

In certain embodiments, $RG-L^2-(L^3)_{0-1}-$ is

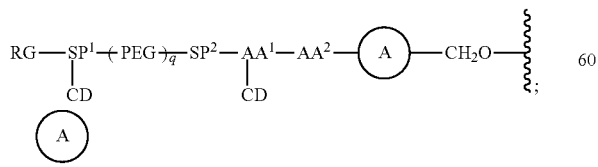

is aryl or heteroaryl; RG is a reactive group, defined below; $SP^1$ and $SP^2$ are each, independently in each instance, absent or a spacer group residue, and wherein $SP^1$ comprises a trivalent linker; $AA^1$ is a trivalent linker comprising an amino acid residue; $AA^2$ is a peptide residue; PEG is a polyethylene glycol residue; wherein the

indicates the atom through which the indicated chemical group is bonded to the adjacent groups in the formula, CD is, independently in each instance, absent or a cyclodextrin residue, wherein at least one CD is present, subscript q is an integer selected from 0 to 5, inclusive. In these examples, subscript q is 0, 1, 2, 3, 4, or 5. In some embodiments, subscript q is 0. In some embodiments, subscript q is 1. In some embodiments, subscript q is 2. In some embodiments, subscript q is 3. In some embodiments, subscript q is 4. In some embodiments, subscript q is 5. In some embodiments, any one of $AA^1$ or $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is lysine or a derivative of lysine. In certain embodiments, $AA^1$ is lysine. In certain embodiments, $AA^1$ is D-lysine. In certain embodiments, $AA^1$ is L-lysine. In certain embodiments, $AA^2$ is a di-peptide residue, a tri-peptide residue, tetra-peptide residue, or penta-peptide residue. In certain embodiments, the $AA^2$ is a di-peptide residue. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In certain embodiments, the $AA^2$ is a tri-peptide residue. In some embodiments, the $AA^2$ glutamate-valine-citrulline. In some embodiments, the $AA^2$ is glutamine-valine-citrulline. In some embodiments, the $AA^2$ is lysine-valine-alanine. In some embodiments, the $AA^2$ is lysine-valine-citrulline. In some embodiments, the $AA^2$ is glutamate-valine-citrulline. In some embodiments, the $AA^2$ is a tetra-peptide residue. In some embodiments, the $AA^2$ is glycine-glycine-phenylalanine-glycine. In some embodiments, the $AA^2$ is a penta-peptide residue. In some embodiments, the $AA^2$ is glycine-glycine-glycine-glycine-glycine. In some embodiments, $SP^1$ is independently in each instance, selected from the group consisting of $C_{1-6}$ alkylene, $-NH-$, $-C(O)-$, $(-CH_2-CH_2-O)_e$, $-NH-CH_2-CH_2-(-O-CH_2-CH_2)_e-C(O)-$, $-C(O)-(CH_2)_u-C(O)-$, $-C(O)-NH-(CH_2)_v-$, and combinations thereof, wherein subscript e is an integer selected from 0 to 4, inclusive, subscript u is an integer selected from 1 to 8, inclusive, and subscript v is an integer selected from 1 to 8, inclusive. In some embodiments, SP² is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, and combinations thereof, wherein subscript e is an integer selected from 0 to 4, inclusive, subscript u is an integer selected from 1 to 8, inclusive, and subscript v is an integer selected from 1 to 8, inclusive.

In certain embodiments, set forth herein is a compound having the structure of Formula (IIIc-R):

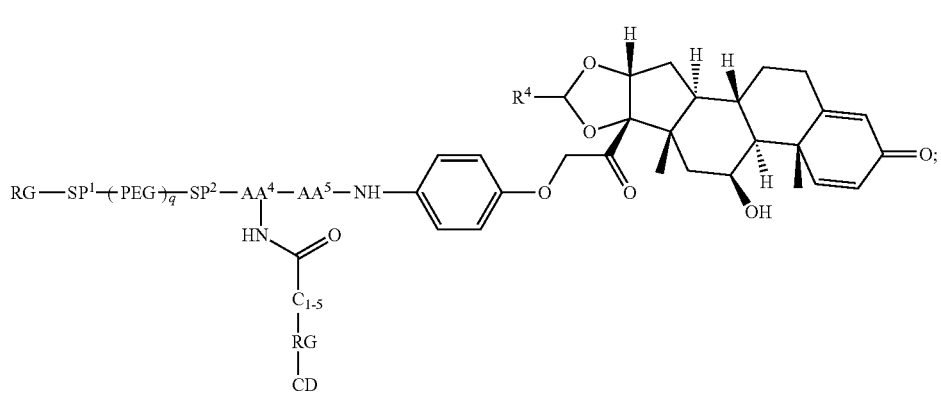

Formula (IIIc-R)

RG is a reactive group;
CD is a cyclodextrin;
SP¹ is a spacer group;
AA⁴ is an amino acid residue;
AA⁵ is a dipeptide residue;
PEG is polyethylene glycol;
q is an integer selected from 0 to 5, inclusive;
x is an integer selected from 0 to 30, inclusive;
R⁴ is as defined herein;
SP¹ and SP² are each, independently in each instance, absent or a spacer group residue, and wherein SP¹ comprises a trivalent linker; AA⁴ is a trivalent linker comprising an amino acid residue; AA⁵ is a di-peptide residue; PEG is a polyethylene glycol residue; wherein the

indicates the atom through which the indicated chemical group is bonded to the adjacent groups in the formula, CD is, independently in each instance, absent or a cyclodextrin residue, wherein at least one CD is present, subscript q is an integer selected from 0 to 5, inclusive; In these examples, subscript q is 0, 1, 2, 3, 4, or 5. In some embodiments, subscript q is 0. In some embodiments, subscript q is 1. In some embodiments, subscript q is 2. In some embodiments, subscript q is 3. In some embodiments, subscript q is 4. In some embodiments, subscript q is 5. In some embodiments, any one of AA⁴ or AA⁵ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, AA⁴ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, AA⁴ is lysine. In certain embodiments, AA⁴ is lysine or a derivative of lysine. In certain embodiments, the AA⁵ is valine-citrulline. In some embodiments, the AA⁵ is citrulline-valine. In some embodiments, the AA⁵ is valine-alanine. In some embodiments, the AA⁵ is alanine-valine. In some embodiments, the AA⁵ is valine-glycine. In some embodiments, the AA⁵ is glycine-valine. In some embodiments, the AA⁵ glutamate-valine-citrulline. In some embodiments, the AA⁵ is glutamine-valine-citrulline. In some embodiments, the AA⁵ is lysine-valine-alanine. In some embodiments, the AA⁵ is lysine-valine-citrulline. In some embodiments, the AA⁵ is glutamate-valine-citrulline. In some embodiments, SP¹ is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, and combinations thereof, wherein subscript e is an integer selected from 0 to 4, inclusive, subscript u is an integer selected from 1 to 8, inclusive, and subscript v is an integer selected from 1 to 8, inclusive. In some embodiments, SP² is independently in each instance, selected from the group consisting of $C_{1-6}$ alkylene, —NH—, —C(O)—, (—CH$_2$—CH$_2$—O)$_e$, —NH—CH$_2$—CH$_2$—(—O—CH$_2$—CH$_2$)$_e$—C(O)—, —C(O)—(CH$_2$)$_u$—C(O)—, —C(O)—NH—(CH$_2$)$_v$—, and combinations thereof, wherein subscript e is an integer selected from 0 to 4, inclusive, subscript u is an integer selected from 1 to 8, inclusive, and subscript v is an integer selected from 1 to 8, inclusive. The reactive group (RG) is a functional group or moiety that reacts with a reactive portion of an antibody, modified antibody, or antigen binding fragment thereof. In certain embodiments, the "reactive group" is a functional group or moiety (e.g., maleimide or NHS ester) that reacts with a cysteine or lysine residue of an antibody or antigen-binding fragment thereof. In certain embodiments, the "reactive group" is a functional group or moiety that is capable of undergoing a click chemistry reaction. In some embodiments of said click chemistry reaction, the reactive group is an alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with alkynes in the absence of copper catalysts. Suitable alkynes also include, but are not limited to, DIBAC, DIBO, BARAC, substituted alkynes, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue, e.g., heavy chain Q295, with a compound according to the formula $H_2N$-LL-$N_3$, wherein LL is, for example, a divalent polyethylene glycol group, or wherein LL is a trivalent group which includes polyethylene glycol and a cyclodextrin moiety, in the presence of the enzyme transglutaminase. In some embodiments, the reactive group is an alkyne, e.g.,

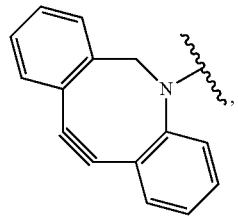 [SMILES: *N1Cc2ccccc2C#Cc2ccccc21]

which can react via click chemistry with an azide, e.g.,

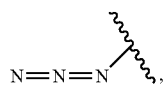

to form a click chemistry product, e.g.,

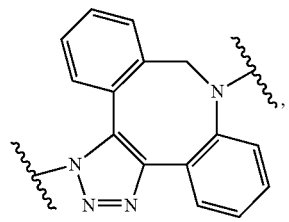 [SMILES: *N1Cc2ccccc2-c2c(nnn2*)-c2ccccc21]

its regioisomer, or a mixture thereof. In some embodiments, the reactive group is an alkyne, e.g.,

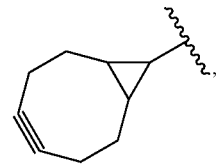 [SMILES: *C1C2CCC#CCCC12]

which can react via click chemistry with an azide, e.g.,

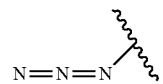

to form a click chemistry product, e.g.,

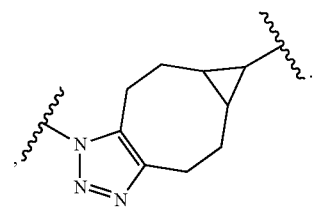 [SMILES: *C1C2CCc3nnn(*)c3CCC12]

In some embodiments, the reactive group is an alkyne, e.g.,

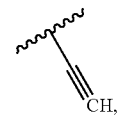

which can react via click chemistry with an azide, e.g.,

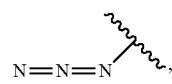

to form a click chemistry product, e.g.,

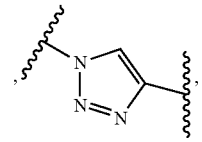 [SMILES: *c1cn(*)nn1]

its regioisomer, or a mixture thereof. In some embodiments, the reactive group is a functional group, e.g.,

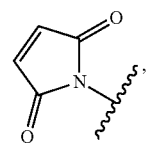

which reacts with a cysteine residue on an antibody or antigen-binding fragment thereof, to form a bond thereto, e.g.,

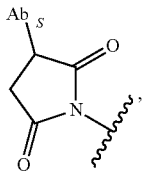

wherein Ab refers to an antibody or antigen-binding fragment thereof and S refers to the S atom on a cysteine residue through which the functional group bonds to the Ab. In some embodiments, the reactive group is a functional group, e.g.,

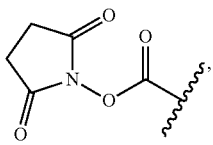 [SMILES: *C(=O)ON1C(=O)CCC1=O]

which reacts with a lysine residue on an antibody or antigen-binding fragment thereof, to form a bond thereto, e.g.,

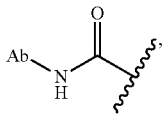

wherein Ab refers to an antibody or antigen-binding fragment thereof and —NH— refers to the end of the lysine residue through which the functional group bonds to the Ab. In some embodiments, this N atom on a lysine residue through which the functional group bonds is indicated herein as the letter N above a bond, e.g.,

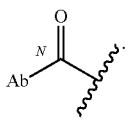

In some embodiments, $RG-L^2-(L^3)_{0-1}-$ is a monovalent moiety of Formula ($L^A$);

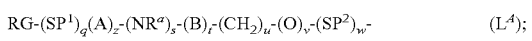

wherein RG is a reactive group;
A is an amino acid or a peptide;
$R^a$ is H or alkyl;
B is aryl, heteroaryl, or heterocycloalkyl, wherein aryl, heteroaryl, or
heterocycloalkyl is optionally substituted with alkyl, —OH, or —N—$R^aR^b$;
$SP^1$ and $SP^2$ are, independently, a spacer groups; and q, z, s, t, u, v, and w are, independently in each instance, 0 or 1.

In some embodiments, $RG-L^2-(L^3)_{0-1}-$ is $RG-(SP^1)_q-(A)_z-$. In some embodiments, $RG-L^2-(L^3)_{0-1}-$ is $RG-(SP^1)_q-(A)_2-$. In some embodiments, $RG-L^2-(L^3)_{0-1}-$ is a moiety of Formula ($L^{A1}$)

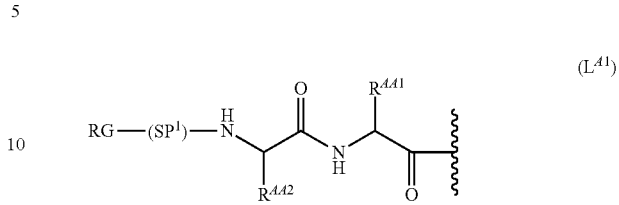

wherein $R^{AA1}$ and $R^{AA2}$ are each, independently, amino acid side chains. In some embodiments of Formula $L^{A1}$, $SP^1$ is a divalent polyethylene glycol group and RG is a group comprising an alkyne that is capable of undergoing a 1,3-cycloaddition reaction with an azide.

In some embodiments, $RG-L^2-(L^3)_{0-1}-$ has the following structure:

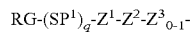

wherein:
RG, $SP^1$, and q are as defined herein;
$Z^1$ is a polyethylene glycol or caproyl group;
$Z^2$ is a dipeptide; and
$Z^3$ is a PAB group.

In some other embodiments, $-L^1-L^2-(L^3)_{0-1}-$ is a trivalent moiety of Formula ($L^B$);

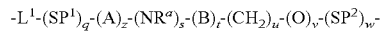

wherein $L^1$ is as defined herein;
A is tripeptide or tetrapeptide, wherein at least one of the amino acids in the tripeptide or tetrapeptide is bonded directly or indirectly to a cyclodextrin moiety;
$R^a$ is H or alkyl;
B is aryl, heteroaryl, or heterocycloalkyl, wherein aryl, heteroaryl, or heterocycloalkyl is optionally substituted with alkyl, —OH, or —$NR^aR^b$;
$SP^1$ and $SP^2$ are, independently, a spacer groups; and in formula $L^B$, q, z, s, t, u, v, and w are, independently in each instance, 0 or 1.

In some embodiments, the cyclodextrin (CD) is bonded directly to an amino acid residue, such as a lysine amino acid residue. This means that the CD is one bond position away from the lysine amino acid covalent linker. In some of these embodiments, the covalent linker is also bonded directly to a payload moiety. This means that the covalent linker is one bond position away from a payload such as, but not limited to a steroid payload set forth herein. In some of these embodiments, the covalent linker is also bonded directly to a CD moiety. This means that the covalent linker is one bond position away from a CD, such as the CD(s) set forth herein. In some of these embodiments, the covalent linker is a lysine amino acid or a derivative thereof.

In some embodiments, the CD is bonded indirectly to a covalent linker in a linking group (e.g., L, $-L^2-(L^3)_{0-1}-$, and $-L^1-L^2-(L^3)_{0-1}$). This means that the CD is more than one bond position away from the covalent linker. This also means that the CD is bonded through another moiety to the covalent linker. For example, the CD may be bonded to a maleimide group which is bonded to a polyethylene glycol group which is bonded to the covalent linker. In some of these embodiments, the covalent linker is also bonded indirectly to a payload moiety. This means that the covalent linker is more than one bond position away from a payload such as, but not limited to a steroid payload set forth herein.

This also means that the covalent linker is bonded through another moiety to the payload. For example, the covalent linker may be bonded to a dipeptide, such as but not limited to Val-Ala or Val-Cit, which may be bonded to para-amino benzoyl which may be bonded to the payload. In some of these embodiments, the covalent linker is also bonded indirectly to a cyclodextrin moiety. This means that the covalent linker is more than one bond position away from a cyclodextrin, such as the cyclodextrins set forth herein. This also means that the covalent linker is bonded through another moiety to the cyclodextrin. For example, the covalent linker may be bonded to a polyethylene glycol group which may be bonded to reactive group which may be bonded to the cyclodextrin. In some of these embodiments, the covalent linker is a lysine amino acid or a derivative thereof.

In some embodiments, $-L^1-L^2-(L^3)_{0-1}-$ is $-L^1-(SP^1)_q-(A)_z-$. In some embodiments, $-L^1-L^2-(L^3)_{0-1}-$ is $-L^1-(SP^1)_q-(A)_2-$. In some embodiments, $-L^1-L^2-(L^3)_{0-1}-$ is a moiety of Formula ($L^{B1}$)

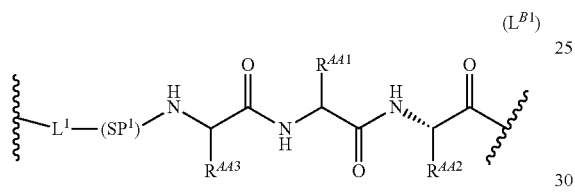

($L^{B1}$)

wherein $R^{AA1}$ and $R^{AA2}$ are each, independently, amino acid side chains. $R^{AA3}$ is an amino acid side chain that is bonded directly or indirectly to a cyclodextrin moiety. In some embodiments of Formula $L^{B1}$, $SP^1$ is a divalent polyethylene glycol group and $L^1$ is a 1,3-cycloaddition reaction product of the reaction between an alkyne and an azide.

In some embodiments, A is

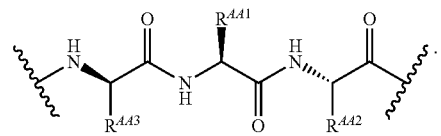

In some of these embodiments, $R^{AA1}$ is an amino acid side chain, $R^{AA2}$ is an amino acid side chain, and $R^{AA3}$ is an amino acid side chain that is bonded directly or indirectly to a cyclodextrin moiety.

In some embodiments, A is

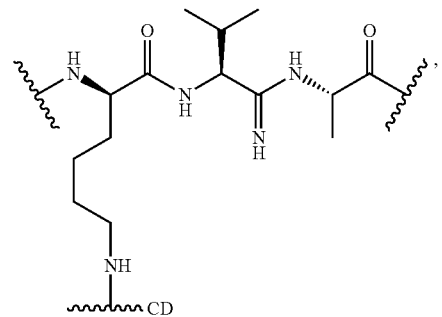

wherein ⌇CD represents a direct or indirect bond to a cyclodextrin moiety.

In some embodiments, including any of the foregoing, CD is, independently in each instance, selected from

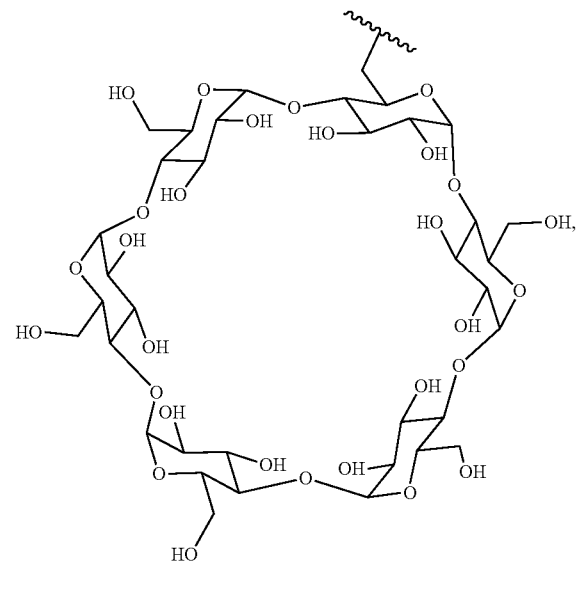

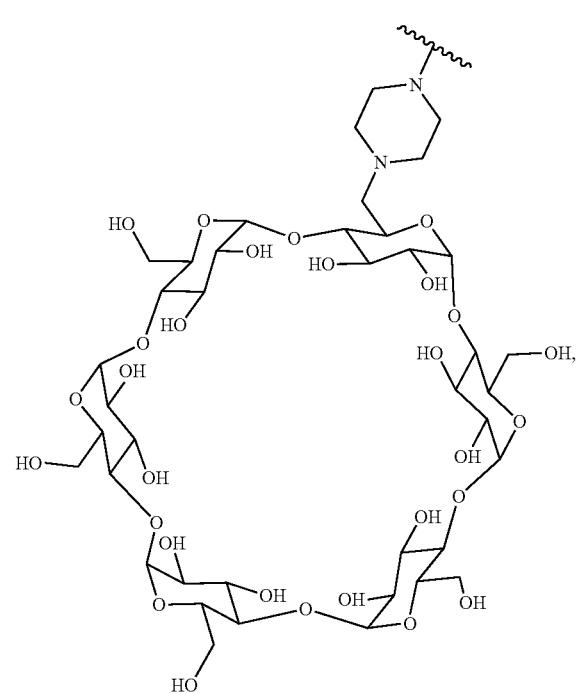

233
-continued
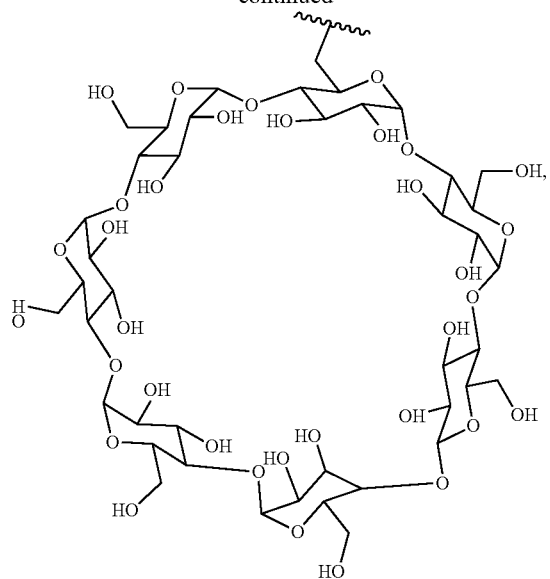
,
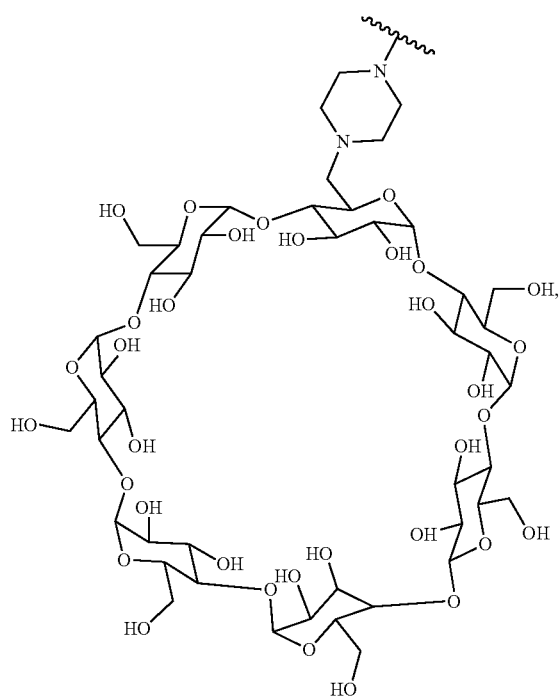
,
234
-continued
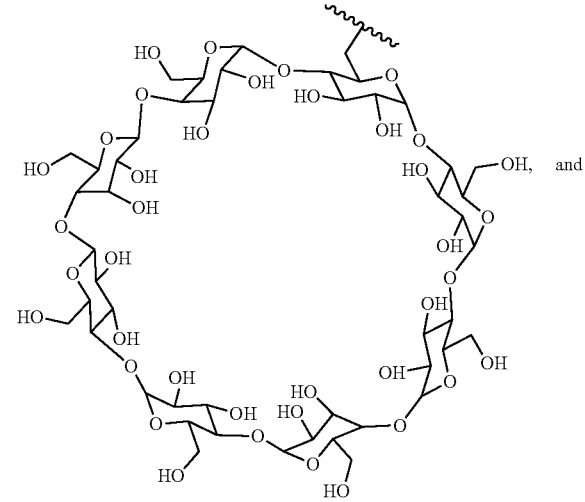
, and
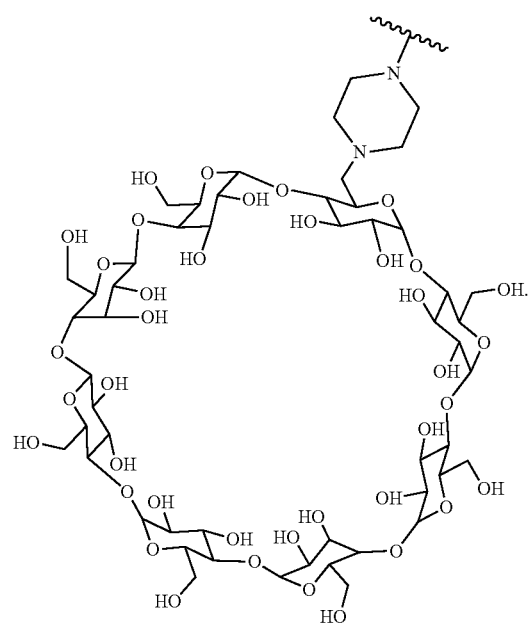
.

In some embodiments, the CD is
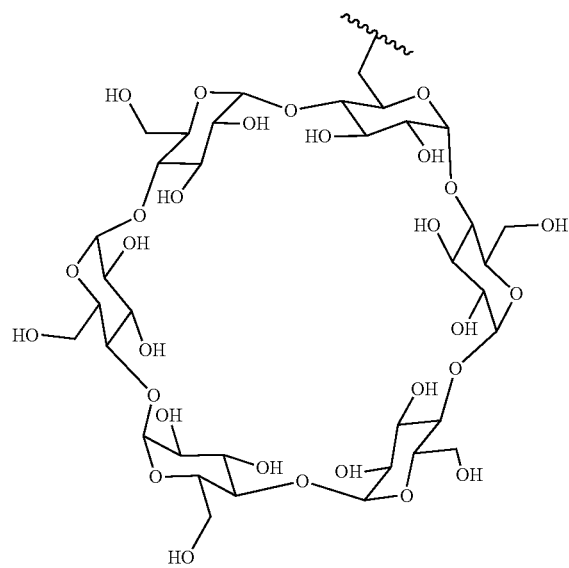 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]
In some embodiments, the CD is
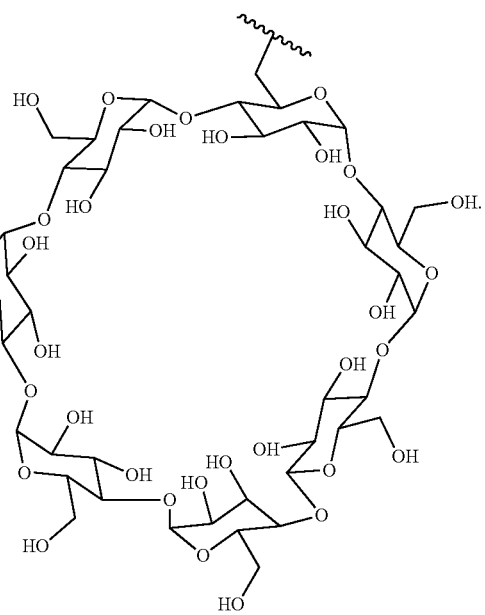
In some embodiments, the CD is
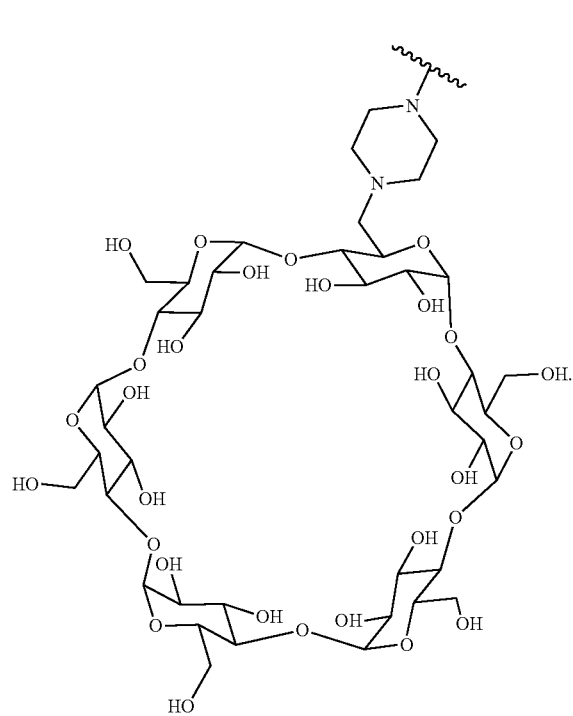 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]
In some embodiments, the CD is
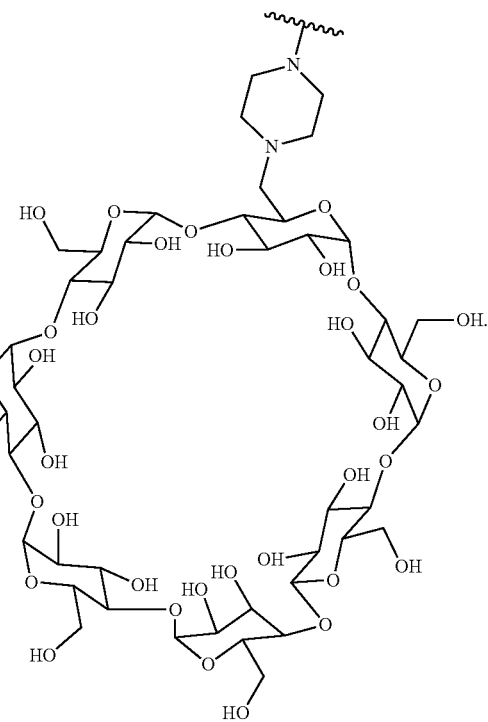

In some embodiments, the CD is

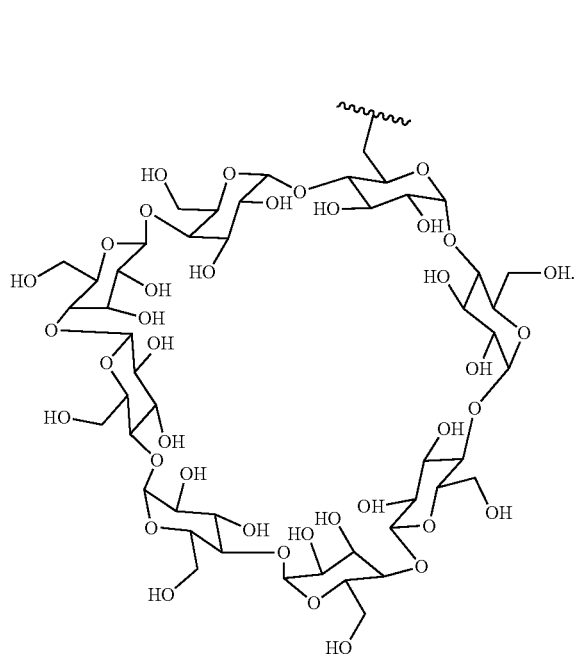 [SMILES: *CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

In some embodiments, the CD is

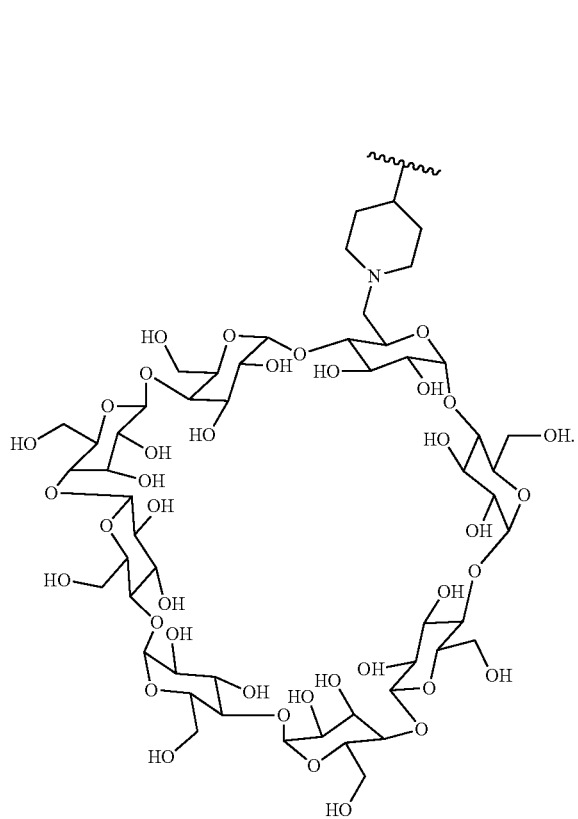 [SMILES: *C1CCN(CC2OC3OC4C(CO)OC(OC5C(CO)OC(OC6C(CO)OC(OC7C(CO)OC(OC8C(CO)OC(OC9C(CO)OC(OC%10C(CO)OC(OC2C(O)C3O)C(O)C%10O)C(O)C9O)C(O)C8O)C(O)C7O)C(O)C6O)C(O)C5O)C(O)C4O)CC1]

In some embodiments, A is

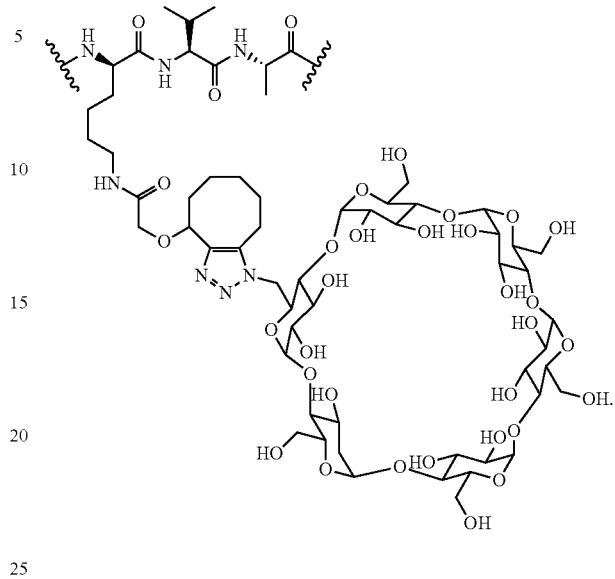

In some embodiments, herein RG is selected from a click-chemistry reactive group.

In some other examples, herein RG is selected from a group which reacts with a cysteine or lysine residue on an antibody or an antigen-binding fragment thereof.

In some embodiments, RG is

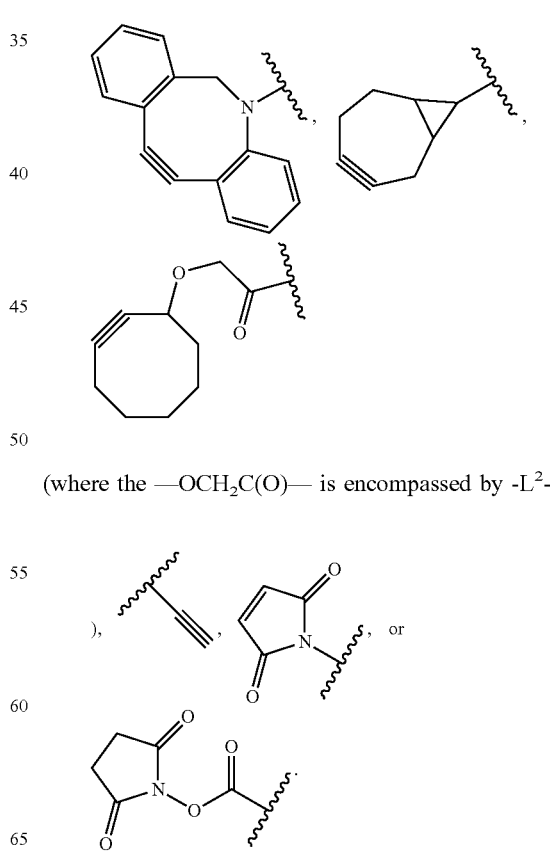

(where the —OCH$_2$C(O)— is encompassed by -L$^2$-

In some embodiments, RG is

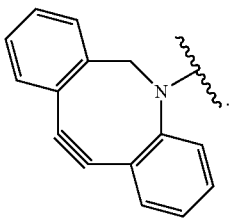 [SMILES: *N1Cc2ccccc2C#Cc2ccccc21]

In other examples, RG is

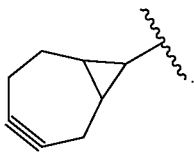 [SMILES: *C1C2CC#CCCC12]

In some other examples, RG is

In some embodiments, RG is

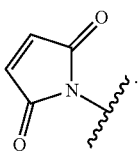 [SMILES: *N1C(=O)C=CC1=O]

In other examples, RG is

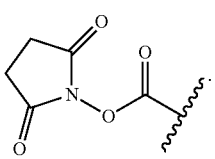 [SMILES: *C(=O)ON1C(=O)CCC1=O]

In other examples, RG is

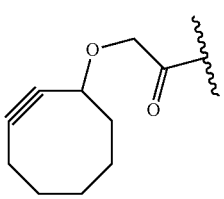 [SMILES: *C(=O)COC1C#CCCCCC1]

where the —OCH$_2$C(O)— is encompassed by -L$^2$-.

In some embodiments, SP$^1$ is encompassed by -L$^2$-. In some embodiments, SP$^1$ may be selected from:

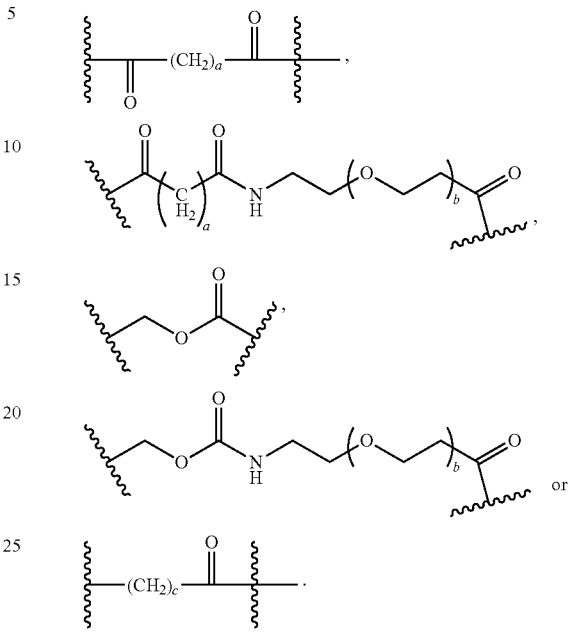

In some embodiments SP$^1$ is

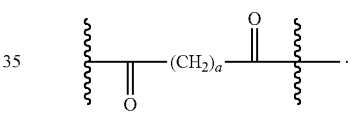

In some other examples, SP$^1$ is

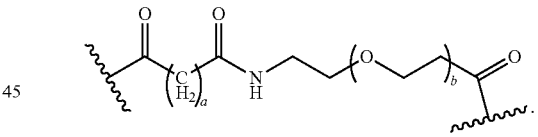

In other examples, SP$^1$ is

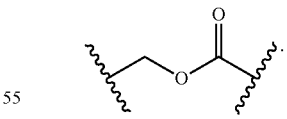

In still other examples, SP$^1$ is

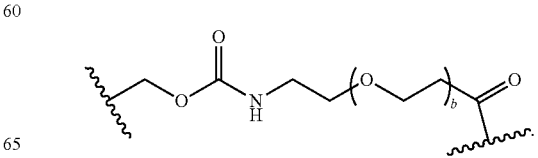

In some other examples, SP¹ is

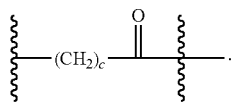

In any of the above examples, subscripts a, b, and c are independently, in each instance, an integer selected from 1 to 20, inclusive.

In some embodiments, SP¹ is encompassed by -L²-. In any of the compounds, SP¹ is:

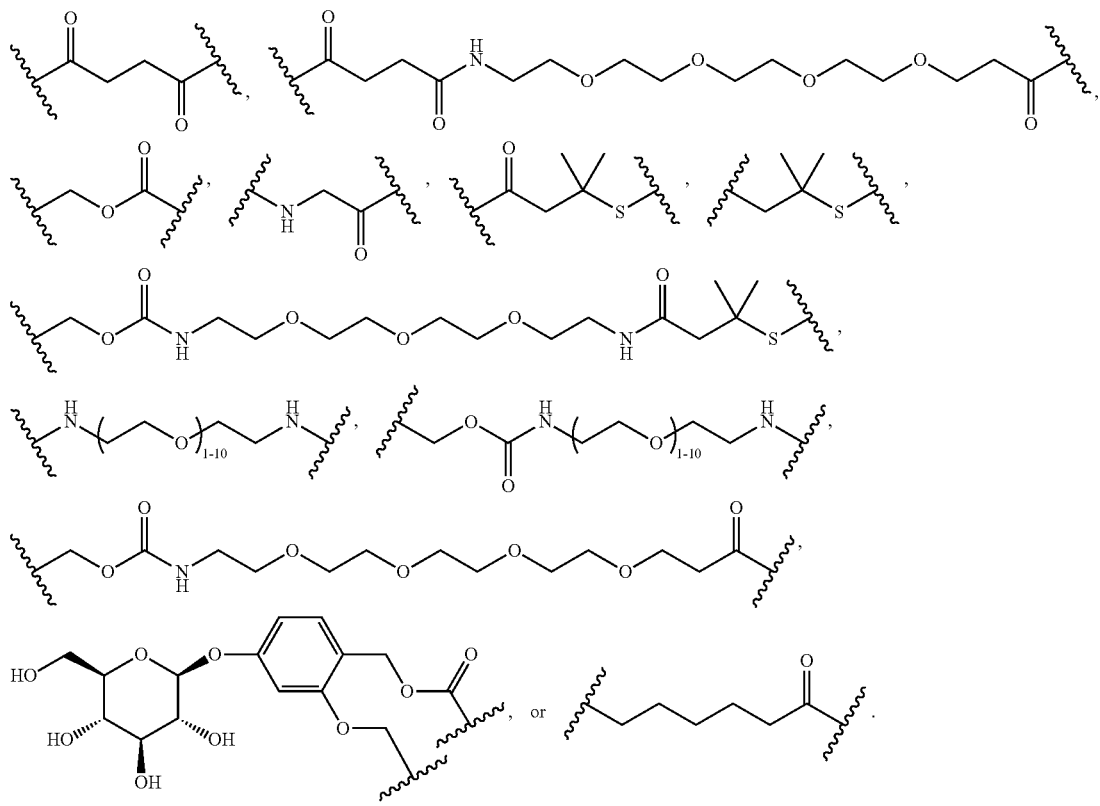

In some embodiments, SP¹ is encompassed by -L²-. In some embodiments, SP¹ is

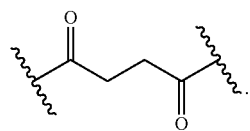 [SMILES: *C(=O)CCC(*)=O]

In some embodiments, SP¹ is

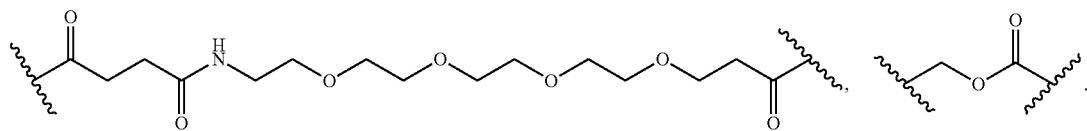 [SMILES: *C(=O)CCOCCOCCOCCOCCNC(=O)CCC(*)=O ; *COC(*)=O]

In some embodiments, SP¹ is

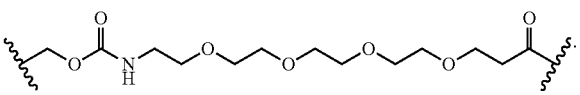 [SMILES: *COC(=O)NCCOCCOCCOCCOCCC(*)=O]

In some embodiments, SP¹ is

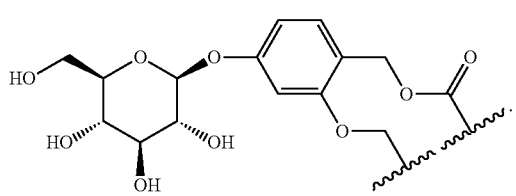 [SMILES: *COc1cc(O[C@@H]2O[C@H](CO)[C@@H](O)[C@H](O)[C@H]2O)ccc1COC(*)=O]

In some embodiments, SP¹ is

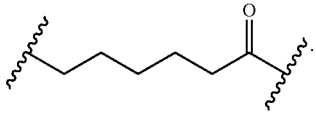 [SMILES: *CCCCCC(*)=O]

In some embodiments, SP¹ is

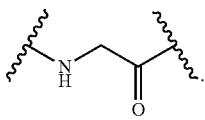 [SMILES: *NCC(*)=O]

In some embodiments, SP¹ is

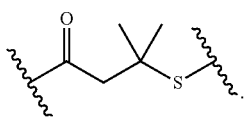 [SMILES: *SC(C)(C)CC(*)=O]

In some embodiments, SP¹ is

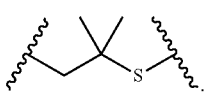 [SMILES: *CC(C)(C)S*]

In some embodiments, SP¹ is

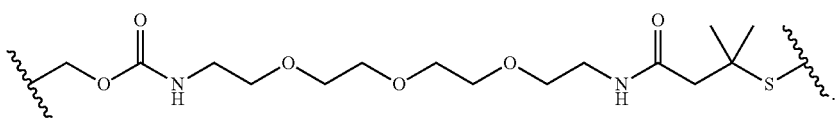 [SMILES: *COC(=O)NCCOCCOCCOCCNC(=O)CC(C)(C)S*]

In some embodiments, SP¹ is

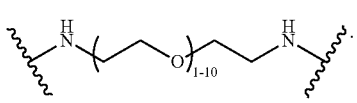

In some embodiments, SP¹ is

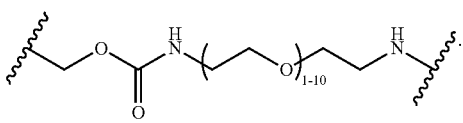

In some embodiments, SP¹ is encompassed by -L²-. In some embodiments, SP¹ is

In some embodiments, SP¹ is

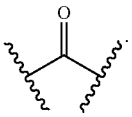

In some embodiments, SP¹ is

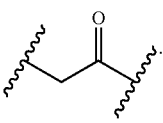 [SMILES: *CC(*)=O]

In some embodiments, SP¹ is

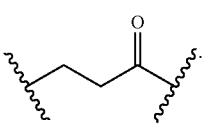 [SMILES: *CCC(*)=O]

In some embodiments, SP¹ is

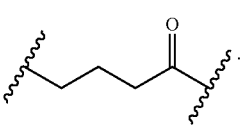

In some embodiments, SP¹ is

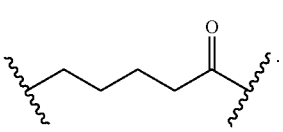 [SMILES: *CCCCC(*)=O]

In some embodiments, SP¹ is

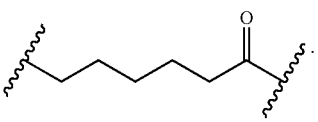 [SMILES: *CCCCCC(*)=O]

In some embodiments, RG-SP¹ (where SP¹ is encompassed by -L²-) may be selected from the group consisting of:

245

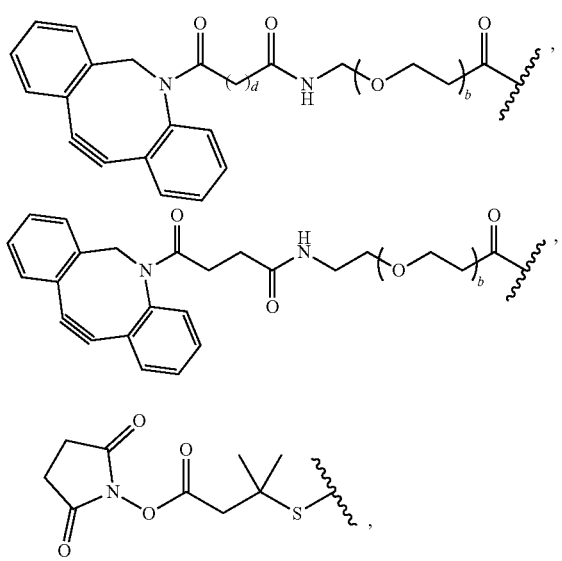

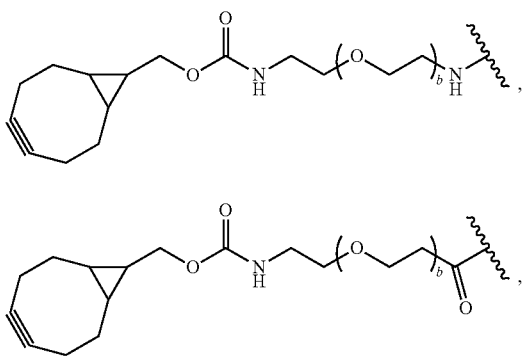

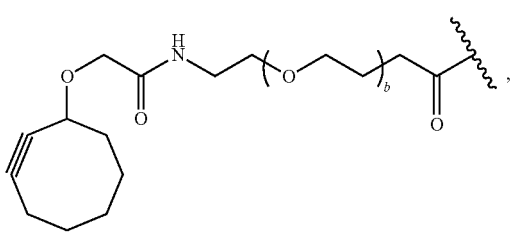

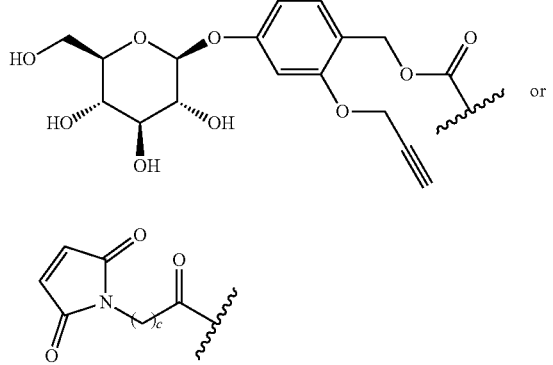

where b, c, and d are independently, in each instance, an integer selected from 1 to 20, inclusive. In some of these embodiments, subscripts b, c, and d are independently, in each instance, an integer selected from 1 to 6, inclusive.

246

In some embodiments RG-SP$^1$- is

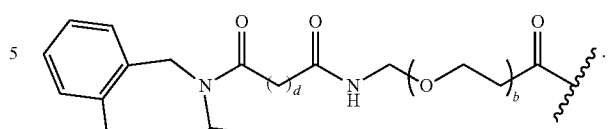

In some embodiments RG-SP$^1$ is

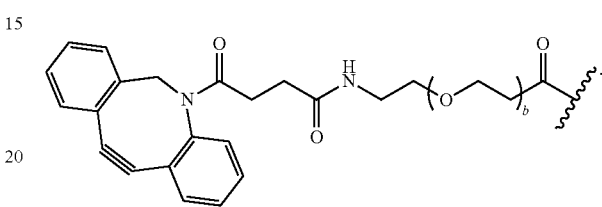

In some embodiments RG-SP$^1$ is

In some embodiments RG-SP$^1$ is

In some embodiments RG-SP$^1$ is

In some embodiments RG-SP$^1$ is

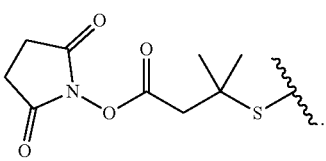 [SMILES: *SC(C)(C)CC(=O)ON1C(=O)CCC1=O]

247
In some embodiments RG-SP¹ is
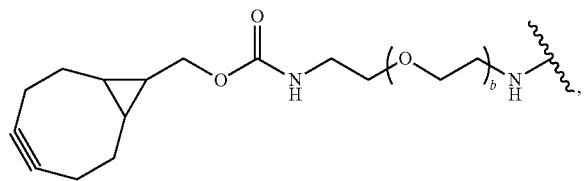
248
In some embodiments RG-SP¹ is
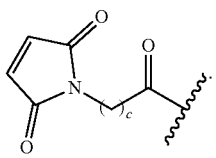
In any of the compounds, RG-SP¹ is:
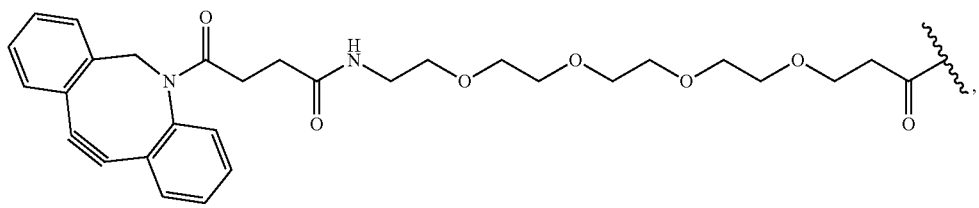
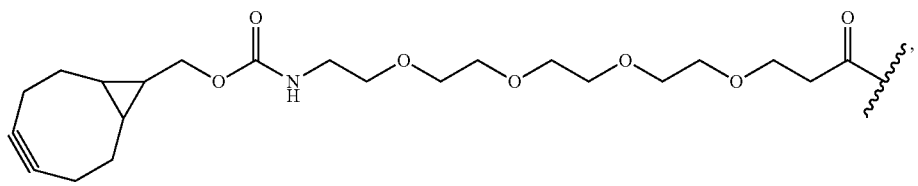
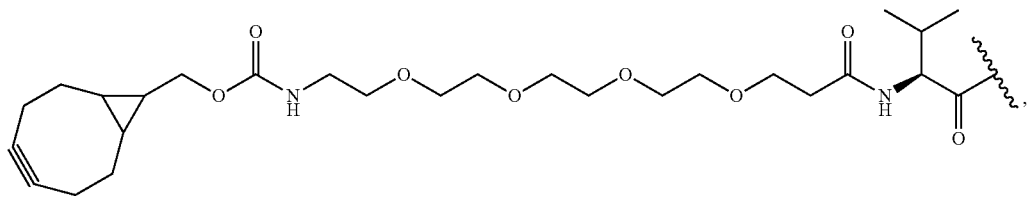
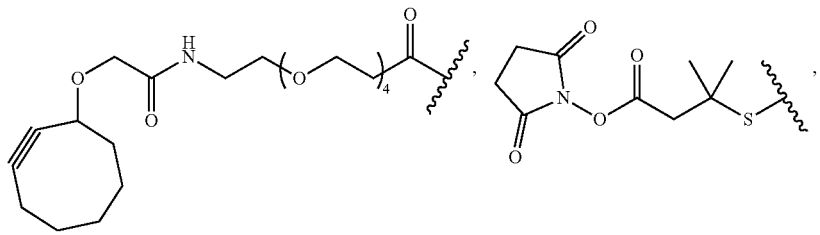
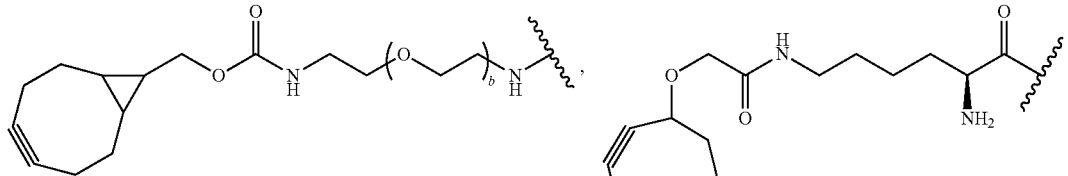
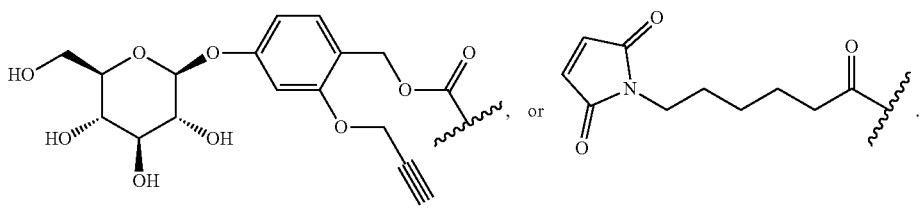

In some embodiments, A is a peptide selected from valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some embodiments, A is valine-citrulline or citrulline-valine.

In some embodiments, A is valine-alanine or alanine-valine.

In some embodiments, A is glutamate-valine-citrulline or citrulline-valine-glutamate.

In some embodiments, A is valine.

In some embodiments, A is alanine.

In some embodiments, A is citrulline.

In some embodiments, A is

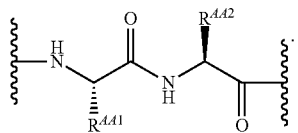

In some of these embodiments, $R^{AA1}$ is an amino acid side chain, and wherein $R^{AA2}$ is an amino acid side chain.

In some embodiments, A is

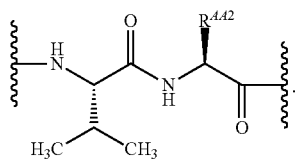

In some embodiments, A is

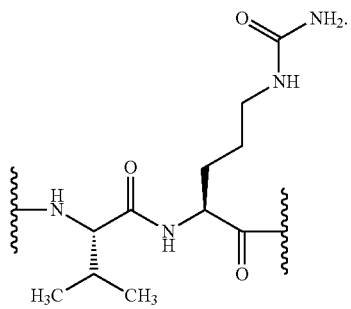 [SMILES: *N[C@H](C(=O)N[C@@H](CCCNC(N)=O)C(*)=O)C(C)C]

In some embodiments, $R^a$ is H.

In some embodiments, $R^a$ is alkyl.

In some embodiments, $R^a$ is methyl, ethyl, n-propyl, i-propyl, n-butyl, t-butyl, i-butyl, or pentyl.

In some embodiments, B is aryl.

In some embodiments, B is phenyl.

In some embodiments, B is phenyl or pyridinyl.

In some embodiments herein, B is:

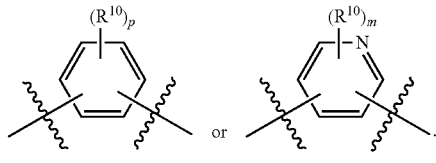

In these examples, $R^{10}$ is alkyl, alkenyl, alkynyl, alkoxy, aryl, alkylaryl, arylalkyl, halo, haloalkyl, haloalkoxy, heteroaryl, heterocycloalkyl, hydroxyl, cyano, nitro,

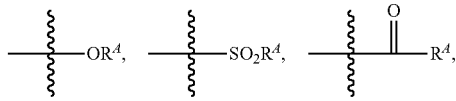

$NR^a R^b$, or azido. In these examples, subscripts p and m are independently, in each instance, selected from an integer selected from 0 to 4, inclusive. In some embodiments herein, B is:

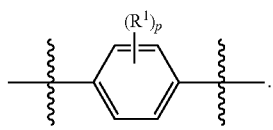

In these examples, p is 0, 1, 2, 3 or 4. In some of these embodiments, $R^1$ is, independently at each occurrence, alkyl, alkoxy, haloalkyl, or halo. In some embodiments, $R^1$ is alkyl. In some embodiments, $R^1$ is alkoxy. In some embodiments, $R^1$ is haloalkyl. In some embodiments, $R^1$ is halo.

In some embodiments of Formula ($L^A$), the $-(NR^a)_s$-(B)$_t$-(CH$_2$)$_u$-(O)$_v$-(SP$^2$)$_w$ is:

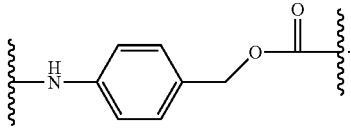 [SMILES: *Nc1ccc(COC(*)=O)cc1]

Provided herein are also linker-payloads of budesonide, a prodrug of budesonide, a budesonide analog or derivative (including fluorinated analogs and derivatives), or a prodrug of a budesonide analog or derivative (including fluorinated analogs and derivatives). In some embodiments, provided herein is a linker-payload having the following structure:

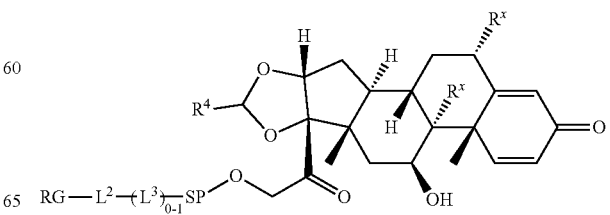

wherein RG, $R^4$, $L^2$, $L^3$, and SP are as defined herein.

E. Pharmaceutical Compositions and Methods of Treatment

The present disclosure includes methods of treating diseases, conditions, or disorders e.g., inflammatory diseases and autoimmune disorders, or managing symptoms thereof, comprising administering a therapeutically effective amount of one or more of the compounds disclosed herein. Included are any diseases, disorders, or conditions associated with the glucocorticoid receptor, glucocorticoid binding, and/or glucocorticoid receptor signaling. Such methods comprise administering a steroid payload or protein conjugate thereof described herein to a patient. Thus, included in this disclosure are methods of treating a disease, disorder, or condition associated with the glucocorticoid receptor comprising administering a compound of Formula (I), Formula I-P, Formula I-P-1, Formula (III-P), Formula III-P-1, Formula (3000), or (III), to a patient having said disease, disorder, or condition.

The present disclosure includes methods of preventing certain disorders or conditions comprising administering a therapeutically effective amount of one or more of the compounds disclosed herein (i.e., prophylactic uses). Examples include, but are not limited to preventing cytokine release syndrome for CD3 bispecifics, and adoptive cellular therapies such as CAR T cells, systemic IL-2 administration, graft-versus-host disease, and post-operative nausea and vomiting. Examples also include, but are not limited to therapeutic antibodies such as alemtuzumab, muromonab, rituximab, tosituzumab, and agonistic Ab's where immune stimulation might be part of the intended mechanism of action.

In some embodiments, the disease, disorder, or condition is allergic state, including but not limited to asthma, atopic dermatitis, contact dermatitis, allergic dermatitis, drug hypersensitivity reactions, anaphylactic rhinitis, perennial or seasonal allergic rhinitis, and serum sickness; dermatologic diseases and conditions, including but not limited to skin itching, seborrheic dermatitis, neurodermatitis, eczema, bullous dermatitis herpetiformis, exfoliative erythroderma, mycosis fungoides, pemphigus, and severe erythema multiforme (Stevens-Johnson syndrome); endocrine disorders, including but not limited to primary or secondary adrenocortical insufficiency, congenital adrenal hyperplasia, hypercalcemia associated with cancer, and nonsuppurative thyroiditis; gastrointestinal diseases; hematologic disorders, including but not limited to acquired (autoimmune) hemolytic anemia, congenital (erythroid) hypoplastic anemia (Diamond-Blackfan anemia), idiopathic thrombocytopenic purpura in adults, pure red cell aplasia, and secondary thrombocytopenia; trichinosis; tuberculous meningitis with subarachnoid block or impending block; neoplastic diseases, including but not limited to leukemias and lymphomas; nervous system disorders, including but not limited to acute exacerbations of multiple sclerosis, cerebral edema associated with primary or metastatic brain tumor, craniotomy, or head injury; ophthalmic diseases, including but not limited to sympathetic ophthalmia, temporal arteritis, uveitis, xerophthahnia, and ocular inflammatory conditions unresponsive to topical corticosteroids; renal diseases, including but not limited to for inducing a diuresis or remission of proteinuria in idiopathic nephrotic syndrome or that due to lupus erythematosus; respiratory diseases, including but not limited to berylliosis, fulminating or disseminated pulmonary tuberculosis when used concurrently with appropriate antituberculous chemotherapy, idiopathic eosinophilic pneumonias, symptomatic sarcoidosis; and Rheumatic disorders, including but not limited to use as adjunctive therapy for short-term administration (to tide the patient over an acute episode or exacerbation) in acute gouty arthritis, acute rheumatic carditis, ankylosing spondylitis, psoriaticarthritis, rheumatoid arthritis, including juvenile rheumatoid arthritis, and for use in dermatomyositis, polymyositis, stomatitis, and systemic lupus erythematosus.

In some embodiments, set forth herein is a method for treating a disease, disorder, or condition selected from an autoimmune disease, an allergy, arthritis, asthma, a breathing disorder, a blood disorder, a cancer, a collagen disease, a connective tissue disorders, a dermatological disease, an eye disease, an endocrine problem, an immunological disease, an inflammatory disease, an intestinal disorders, a gastrointestinal disease, a neurological disorder, an organ transplant condition, a rheumatoid disorder, a skin disorder, a swelling condition, a wound healing condition, and a combination thereof comprising administering a steroid payload or conjugate thereof described herein.

In some embodiments, the autoimmune disorder is selected from multiple sclerosis, autoimmune hepatitis, shingles, systemic lupus erythematosus (i.e., lupus), myasthenia gravis, Duchenne muscular dystrophy, and sarcoidosis. In some embodiments, the breathing disorder is selected from asthma, chronic respiratory disease, chronic obstructive pulmonary disease, bronchial inflammation, and acute bronchitis. In some embodiments, the cancer is selected from leukemia, lymphoblastic leukemia, acute lymphoblastic leukemia, chronic lymphoblastic leukemia, Hodgkin's lymphoma, Non-Hodgkin's lymphoma (NHL), and multiple myeloma. In some embodiments, the collagen disease is systemic lupus erythematosus. In some embodiments, the eye disease is keratitis. In some embodiments, the endocrine problem is selected from Addison's Disease, adrenal insufficiency, adrenal cortical dysfunction, adrenocortical, and congenital adrenal hyperplasia. In some embodiments, the inflammatory disease is selected from inflammation after cataract surgery, joint inflammation, immune inflammation, tendon inflammation, bursitis, epicondylitis, Crohn's disease, inflammatory bowels disease, lipid pneumonitis thyroiditis, urticaria (hives), pericarditis, nephrotic syndrome, and uveitis. In some embodiments, the intestinal disorder is selected from collagenous colitis, ulcerative colitis, Crohn's disease, and inflammatory bowels disease. In some embodiments, the rheumatoid disorder is selected from rheumatoid arthritis, polymyalgia rheumatic, psoriatic arthritis, ankylosing spondylitis, and systemic lupus erythematosus. In some embodiments, the skin disorder is selected from psoriasis, eczema, and poison ivy. In some embodiments, the neurological disorder is chronic inflammatory demyelinating polyradiculoneuropathy.

In some embodiments, the compounds described herein are administered to a patient to treat an acute inflammatory event, including but not limited to shock, brain edema, and graft-vs-host disease. In some embodiments, the compounds described herein are administered to treat lympholytic effects, including but not limited to those associated with hematological malignancies, e.g., leukemias, lymphomas, and myelomas.

In some embodiments, set forth herein is a method for reducing inflammation in a subject in need thereof, comprising administering to a subject in need thereof a therapeutically effective amount of a steroid or conjugate thereof described herein. In some embodiments, set forth herein is a method for modulating the immune system in a subject in need thereof, comprising administering to a subject in need thereof a therapeutically effective amount of a steroid or conjugate thereof described herein. In some embodiments, set forth herein is a method for modulating cortisol levels in a subject in need thereof, comprising administering to a subject in need thereof a therapeutically effective amount of a steroid or conjugate thereof described herein. In some embodiments, set forth herein is a method of reducing lymphocyte migration in a subject in need thereof, comprising administering to a subject in need thereof a therapeutically effective amount of a steroid or conjugate thereof described herein. In some embodiments, set forth herein is a method of treating hypercalcemia due to cancer, Meniere's disease, a migraine headache, a cluster headache, a severe aphthous ulcer, laryngitis, severe tuberculosis, a Herxheimer reaction to syphilis, a decompensated heart failure, allergic rhinitis or nasal polyps, comprising administering to a subject in need thereof a steroid payload or conjugate thereof described herein. In some embodiments, the compounds disclosed herein can be used for treating inflammatory bowel disease, Crohn's disease, or ulcerative colitis. In some embodiments, the disease, disorder, or condition is a chronic inflammatory condition, including but not limited to asthma, skin infections, and ocular infections. In some embodiments, compounds described herein are used for immunosuppression in patients undergoing organ transplantation.

In some embodiments, the steroid payloads and conjugates thereof described herein are administered to a patient to treat a nervous disorder associated with GR signaling, including but not limited to psychiatric disorders such as schizophrenia, drug addiction, post-traumatic stress disorder (PTSD), and mood disorders, substance abuse, stress, and anxiety.

In some embodiments, the steroid payloads and conjugates thereof described herein are administered to a patient to treat a visual system disorder, including but not limited to ocular inflammation (e.g., conjunctivitis, keratitis, uveitis), macular edema, and macular degeneration. In some embodiments, the steroid payloads and conjugates thereof described herein are administered to a patient to treat a cardiovascular disorder. In some embodiments, the steroid payloads and conjugates thereof described herein are administered to a patient to treat a glucose and/or liver metabolism disorder. In some embodiments, the steroid payloads and conjugates thereof described herein are administered to a patient to treat a musculoskeletal system disorder. In some embodiments, the steroid payloads and conjugates thereof described herein are administered to a patient to treat a cutaneous inflammatory condition, such as eczema and psoriasis.

The protein conjugates described herein provide a means for targeted delivery of its steroid payload to particular cells or organ systems, thereby reducing or preventing side effects that result from administration of the free unconjugated steroid payload. Examples of such potential side effects to be reduced or prevented include those listed in the approved drug label for Decadron® (dexamethasome), which is incorporated herein by reference in its entirety. In some embodiments, the side effect to be reduced or prevented is selected from elevation of blood pressure; sodium retention; water/fluid retention (edema, angioedema, pulmonary edema); increased excretion of potassium; reversible hypothalamic-pituitary adrenal (HPA) axis suppression; potential corticosteroid insufficiency after withdrawal of treatment; susceptibility to infections; exacerbation of systemic fungal infections; worsening of severity of chickenpox in pediatric and adult patients; worsening of severity of measles in pediatric and adult patients; posterior subcapsular cataracts; glaucoma with possible damage to the optic nerves; enhancement of the establishment of secondary ocular infections due to bacteria, fungi, or viruses; increase in new episodes of optic neuritis; Kaposi's sarcoma; drug-induced secondary adrenocortical insufficiency; increased risk of a perforation when active or latent peptic ulcers, diverticulitis, fresh intestinal anastomoses, and nonspecific ulcerative colitis, are present; peritoneal irritation following gastrointestinal perforation; decreased bone formation; increased bone resorption; inhibition of osteoblast function; inhibition of bone growth in pediatric patients; development of osteoporosis at any age; acute myopathy (possibly involving ocular and respiratory muscles, and potentially resulting in quadriparesis); elevation of creatinine kinase; psychic derangements, ranging from euphoria, insomnia, mood swings, personality changes, and severe depression, to frank psychotic manifestations; aggravation of existing emotional instability or psychotic tendencies; elevated intraocular pressure; bradycardia; cardiac arrest; cardiac arrhythmias; cardiac enlargement; circulatory collapse; congestive heart failure; fat embolism; hypertension; hypertrophic cardiomyopathy in premature infants; myocardial rupture following recent myocardial infarction; syncope; tachycardia; thromboembolism; thrombophlebitis; vasculitis; acne; allergic dermatitis; dry scaly skin; ecchymoses and petechiae; erythema; impaired wound healing; increased sweating; rash; striae; suppression of reactions to skin tests; thin fragile skin; thinning scalp hair; urticarial; decreased carbohydrate and glucose tolerance; development of cushingoid state; hyperglycemia; glycosuria; hirsutism; hypertrichosis; increased requirements for insulin or oral hypoglycemic agents in diabetes (insulin resistance); manifestations of latent diabetes mellitus; menstrual irregularities; secondary adrenocortical and pituitary unresponsiveness (particularly in times of stress; as in trauma; surgery; or illness); suppression of growth in pediatric patients; congestive heart failure in susceptible patients; fluid retention; hypokalemic alkalosis; potassium loss; sodium retention; abdominal distention; elevation in serum liver enzyme levels (usually reversible upon discontinuation); hepatomegaly; increased appetite; nausea; pancreatitis; peptic ulcer with possible perforation and hemorrhage; perforation of the small and large intestine (particularly in patients with inflammatory bowel disease); ulcerative esophagitis; negative nitrogen balance due to protein catabolism; aseptic necrosis of femoral and humeral heads; loss of muscle mass; muscle weakness; osteoporosis; pathologic fracture of long bones; steroid myopathy; tendon rupture; vertebral compression fractures; convulsions; depression; emotional instability; euphoria; headache; increased intracranial pressure with papilledema (pseudotumor cerebri) usually following discontinuation of treatment; insomnia; mood swings; neuritis; neuropathy; paresthesia; personality changes; psychic disorders; vertigo; exophthalmos; glaucoma; increased intraocular pressure; posterior subcapsular cataracts; abnormal fat deposits; decreased resistance to infection; hiccups; increased or decreased motility and number of spermatozoa; malaise; moon face; and weight gain; and those side effects associated with drug-drug interactions. In some embodiments, the side effect to be reduced or prevented are those associated with drug-drug interactions. In some embodiments, the side effect to be reduced or prevented is associated with drug-drug interactions from the use of a corticosteroid with aminoglutethimide including diminishment of adrenal suppression by corticosteroids; amphotericin B injection and potassium-depleting agents, including development of hypokalemia, cardiac enlargement, and congestive heart failure; antibiotics including a significant decrease in corticosteroid clearance; anticholinesterases including producing severe weakness in patients with myasthenia gravis; oral anticoagulants including inhibition of response to warfarin; antidiabetics including increased blood glucose concentrations; antitubercular drugs including decreased serum concentrations of isoniazid; cholestyramine including increased clearance of corticosteroids; cyclosporine including increased activity of both cyclosporine and corticosteroids, and incidence of convulsions; dexamethasone suppression test (DST) interference including false-negative results in patients being treated with indomethacin; digitalis glycosides including increased risk of arrhythmias due to hypokalemia; ephedrine including enhancement of the metabolic clearance of corticosteroids, resulting in decreased blood levels and lessened physiologic activity; estrogens, including oral contraceptives, including decreased hepatic metabolism of certain corticosteroids and associated increase in their effect; hepatic enzyme inducers, inhibitors and substrates (drugs which induce cytochrome P450 3A4 (CYP 3A4) enzyme activity e.g., barbiturates, phenytoin, carbamazepine, rifampin), including enhancing of metabolism of corticosteroids; drugs which inhibit CYP 3A4 (e.g., ketoconazole, macrolide antibiotics such as erythromycin), including the potential for increased plasma concentrations of corticosteroids; drugs that are metabolized by CYP 3A4 (e.g., indinavir, erythromycin), including increase in their clearance, resulting in decreased plasma concentration; ketoconazole including decreased metabolism of certain corticosteroids by up to 60%, leading to increased risk of corticosteroid side effects, and inhibition of adrenal corticosteroid synthesis potentially causing adrenal insufficiency during corticosteroid withdrawal; nonsteroidal anti-inflammatory agents (NSAIDS), including increased risk of gastrointestinal side effects and increased clearance of salicylates; phenytoin, including increases or decreases in phenytoin level, altered seizure control; skin tests, including suppression of reactions to skin tests; thalidomide including toxic epidermal necrolysis; and vaccines including a diminished response to toxoids and live or inactivated vaccines due to inhibition of antibody response or potentiation of the replication of some organisms contained in live attenuated vaccines).

Thus, provided herein are methods for treating a disease, disorder, or condition associated with the glucocorticoid receptor comprising administering a conjugate of Formula (III), to a patient having said disease, disorder, or condition, wherein the side effects associated with administration of the free steroid payload of said conjugate is reduced. Furthermore, provided herein are methods of delivering a compound of Formula (III-P), Formula III-P-1, Formula (3000), or Formula (III) to a cell comprising contacting said cell with a protein conjugate the compound of Formula (III-P), Formula III-P-1, Formula (3000), or Formula (III), wherein the protein conjugate comprises an antibody or antigen binding fragment thereof that binds a surface antigen of said cell.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second glucocorticoid, an autoimmune therapeutic agent, a hormone, a biologic, or a monoclonal antibody. Suitable therapeutic agents also include, but are not limited to any pharmaceutically acceptable salts, acids or derivatives of a compound set forth herein.

The compounds described herein can also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

In some embodiments of the methods described herein, multiple doses of a compound described herein (or a pharmaceutical composition comprising a combination of an compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all contain the same amount the compound described herein, but generally can differ from one another in terms of frequency of administration. In certain embodiments, the amount of the compound contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula (I), Formula I-P, Formula I-P-1, Formula (III-P), Formula III-P-1, Formula (3000), and Formula (III), e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to: buffers for maintenance of proper composition pH (e.g., citrate buffers, succinate buffers, acetate buffers, phosphate buffers, lactate buffers, oxalate buffers and the like), carrier proteins (e.g., human serum albumin), nanoparticles, saline, polyols (e.g., trehalose, sucrose, xylitol, sorbitol, and the like), surfactants (e.g., polysorbate 20, polysorbate 80, polyoxolate, and the like), antimicrobials, and antioxidants.

In some embodiments, set forth herein is a method of treating a disease, disorder or condition including administering to a patient having said disorder a therapeutically effective amount of a compound of Formula (I), Formula I-P, Formula I-P-1, Formula (III-P), Formula III-P-1, Formula (3000), or Formula (III), or a pharmaceutical composition thereof.

In some embodiments, set forth herein is a method of treating a disease, disorder or condition including administering to a patient having said disorder a therapeutically effective amount of a compound set forth herein, or a pharmaceutical composition thereof.

In some embodiments, set forth herein is a method of treating a disease, disorder or condition selected from the group consisting of an immunological disease, autoimmune disease, inflammation, asthma, or an inflammatory bowel disorder, Crohn's disease, ulcerative colitis.

In some embodiments, set forth herein is a method of treating a disease, disorder or condition by targeting an antigen, e.g., cell-surface expressing antigen, to which steroid delivery can achieve a therapeutic benefit comprising administering the conjugates described herein. In some embodiments, the antigen is AXL, BAFFR, BCMA, BCR-list components, BDCA2, BDCA4, BTLA, BTNL2 BTNL3, BTNL8, BTNL9, C10orf54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD47, CD46, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, FCamR, FCMR, FcR's, Fire, GITR, HHLA2, HLA class II, HVEM, ICO-SLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MMR, MSR1, NCR3LG1, NKG2D, NKp30, NKp46, PDCD1, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, or VTCN1. In some embodiments, the antigen is IL2R-γ.

In some embodiments, set forth herein is a method for treating a disease, disorder, or condition selected from an immunological disease, an autoimmune disease, an inflammatory disease, a dermatological disease, or a gastrointestinal disease.

In some embodiments, the disease is Crohn's disease, ulcerative colitis, Cushing's syndrome, adrenal insufficiency, or congenital adrenal hyperplasia.

In some embodiments, the disease is inflammation, asthma, or an inflammatory bowel disorder.

In some embodiments, the disease is an autoimmune diseases selected from multiple sclerosis, rheumatoid arthritis, inflammatory bowel disease, ulcerative colitis, psoriasis, or eczema.

In some embodiments, set forth herein is a method for reducing or ameliorating the side effects of chemotherapy, wherein the method includes administering to a patient having said disorder a therapeutically effective amount of a compound or a composition described herein.

In some embodiments, set forth herein is a method for reducing or ameliorating the side effects of immunosuppressive therapy, wherein the method includes administering to a patient having said disorder a therapeutically effective amount of a compound or a composition described herein.

In some embodiments, set forth herein is a method for treating cancer, wherein the method includes administering to a patient having said disorder a therapeutically effective amount of a compound or a composition described herein. In some embodiments, the cancer is selected from acute lymphoblastic leukemia, chronic lymphoblastic leukemia, Hodgkin's lymphoma, Non-Hodgkin's lymphoma (NHL), or multiple myeloma, as well as others.

F. EXAMPLES

Certain embodiments are illustrated by the following non-limiting examples.

Reagents and solvents were obtained from commercial sources such as Sinopharm Chemical Reagent Co. (SCRC), Sigma-Aldrich, Alfa, or other vendors, unless explicitly stated otherwise.

$^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethyl silane.

HPLC-MS measurements were run on an Agilent 1200 HPLC/6100 SQ System using the follow conditions:

Method A for HPLC-MS measurement included, as the Mobile Phase: A: Water (0.01% trifluoroacetic acid TFA) and B: acetonitrile (0.01% TFA). The Gradient Phase was 5% of B that was increased to 95% of B over a time period of 15 minutes (min) and at a flow rate of 1.0 mL/min. The column used was a SunFire C18, 4.6×50 mm, 3.5 µm. The column temperature was 50° C. The detectors included an Analog to Digital Converter ELSD (Evaporative Light-scattering Detector, hereinafter "ADC ELSD"), DAD (Diode array detector, 214 nm and 254 nm), and Electrospray Ionization-Atmospheric Pressure Ionization (ES-API).

Method B for HPLC-MS measurements included, as the Mobile Phase: A: Water (10 mM $NH_4HCO_3$) and B: acetonitrile. The Gradient Phase was 5% of B that was increased to 95% of B over a time period of 15 min and a flow rate of 1.0 mL/min. The column used was a XBridge C18, 4.6×50 mm, 3.5 µm. The column temperature was 50° C. The detectors included an ADC ELSD, DAD (214 nm and 254 nm), and a mass-selective detector (MSD ES-API).

LC-MS measurement was run on an Agilent 1200 HPLC/6100 SQ System using the follow conditions:

Method A for LC-MS measurement was performed on a WATERS 2767 instrument. The column was a Shimadzu Shim-Pack, PRC-ODS, 20×250 mm, 15 µm, two connected in series. The Mobile Phase was A: Water (0.01% TFA) and B: acetonitrile (0.01% TFA). The Gradient Phase was 5% of B that was increased to 95% of B over a time period of 3 min and at a flow rate of 1.8-2.3 m/min. The column used was a SunFire C18, 4.6×50 mm, 3.5 µm. The column temperature was 50° C. The detectors included an Analog to Digital Converter ELSD (Evaporative-Light Scattering Detector), DAD (Diode Array Detector) (214 nm and 254 nm), and ES-API.

Method B for LC-MS measurement was performed on a Gilson GX-281 instrument. The column was an Xbridge Prep C18 10 µm OBD, 19×250 mm. The Mobile Phase was A: Water (10 mM $NH_4HCO_3$) and B: Acetonitrile. The Gradient Phase was 5% of B that was increased to 95% of B over a time period of 3 min and at a flow rate of 1.8-2.3 mL/min. The column used was an XBridge C18, 4.6×50 mm, 3.5 µm. The column temperature was 50° C. The detectors included ADC ELSD, DAD (214 nm and 254 nm), and Mass Selective Detector (MSD) (ES-API).

Preparative high-pressure liquid chromatography (Prep-HPLC) was performed on a Gilson GX-281 instrument. Two solvent systems were used, one acidic and one basic. The acidic solvent system included a Waters SunFire 10 µm C18 column (100 Å, 250×19 mm). Solvent A for prep-HPLC was 0.05% TFA in water and solvent B was acetonitrile. The elution condition was a linear gradient that increased solvent B from 5% to 100% over a time period of 20 minutes and at a flow rate of 30 mL/min. The basic solvent system included a Waters Xbridge 10 µm C18 column (100 Å, 250×19 mm). Solvent A for prep-HPLC was 10 mM ammonium bicarbonate ($NH_4HCO_3$) in water and solvent B was acetonitrile. The elution condition was a linear gradient that increased solvent B from 5% to 100% over a time period of 20 minutes and at a flow rate of 30 mL/min.

Flash chromatography was performed on a Biotage instrument, with Agela Flash Column silica-CS. Reversed phase flash chromatography was performed on Biotage instrument, with Boston ODS or Agela C18, unless explicitly indicated otherwise.

The following abbreviations are used in the Examples and throughout the specification:

| Abbreviation | Term |
|---|---|
| ADC | Antibody-drug conjugate |
| Aglycosylated antibody | Antibody does not have any glycan |
| aq | Aqueous |
| BARAC | Biarylazacyclooctynone |
| BCN | (1R,8S,9s)-Bicyclo[6.1.0]non-4-yn-9-yl |
| Boc | N-tert-butoxycarbonyl |
| BupH ™ | Thermo Scientific Prod # 28372, containing 100 mM sodium phosphate and 150 mM sodium chloride, potassium free, pH was adjusted from 7.2 to 7.6-7.8 MQ, unless otherwise noted. |
| CD | Cyclodexnin |
| COT | Cyclooctynol |
| Da | Dalton |
| DAR | Drug to antibody ratio. |
| DCM | Dichloromethane |
| DIBAC | Dibenz[b, f]azocine, 11,12-didehydro-5,6-dihydro-; dibenzocyclooctyne; or Dibenz[b, f]azocine-5(6H)-butanoic acid, 11,12-didehydro |
| DIBAC-Suc | Dibenz[b, f]azocine-5(6H)-butanoic acid, 11,12-didehydro |
| DIBACT | 3H-Benzo[c]-1,2,3-triazolo[4,5-e][1]benzazocine, 8,9-dihydro- |
| DIBO | Dibenzocyclooctyne |
| DIFO | Difluorinated cyclooctyne |
| DIPEA | Diisopropylethylamine |
| DMA | N,N-dimethylacetamide |
| DMAP | 4-Di-methylaminopyridine |
| DMF | N,N-dimethylformamide |
| DMSO | Dimethylsulfoxide |
| ESI | Electrospray ionization |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr or hrs | Hours |
| LC | Light chain of immunoglobulin |
| LC | Liquid chromatography |
| MC | Maleimidocaproyl |
| mg | milligrams |
| min | minutes |
| mL | milliliters |
| mM | millimolar |
| MMAE | Monomethyl auristatin E |
| MS | Mass spectrometry |
| MsCl | Methanesulfonyl chloride |
| MSD | Mass-selective detector |
| MTG | Microbial transglutaminase |
| MW | Molecular weight |
| ncADC | Non-Cytotoxic antibody drug conjugate |
| NHS | N-hydroxy succinimide |
| nM | nanomolar |
| NMR | Nuclear magnetic resonance |
| NOESY | Nuclear Overhauser effect spectroscopy |
| PAB | Para-aminobezyloxy(carbonyl) |
| PBS | 10 mM sodium phosphate buffer and 150 mM sodium chloride |

261

-continued

| Abbreviation | Term |
|---|---|
| PBSg | 10 mM phosphate, 150 mM sodium chloride, 5% glycerol |
| PEG | Polyethyleneglycol |
| PNP | p-Nitrophenol |
| ppm | Parts per million (chemical shift) |
| RP | Reversed phase |
| RT | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VA | Valine-Aniline |
| VC | Valine-citrulline |
| µL | microliters |
| µM | micromolar |

PREPARATION METHODS

Example 1

Scheme 1 in FIG. 3 shows the synthesis of Budesonide-spacers containing the reactive groups, suc-acid (compound 1c), carbamate analogues (1d, 1e), THP-analogues (1g and 1h), glucose analogues (1i and 1j), phosphate analogues (1k and 1l), and a commercial phosphate analogue (1m).

Intermediate 3a

1-[({2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethoxy}carbonyl)oxy]pyrrolidine-2,5-dione (3a)

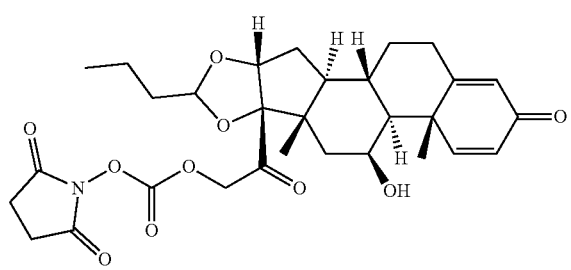 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)ON2C(=O)CCC2=O)O1]

To a solution of budesonide 1a (0.10 g, 0.26 mmol) in DCM (1 mL) were added bis(2,5-dioxopyrrolidin-1-yl) carbonate (71 mg, 0.30 mmol), triethylamine (47 mg, 0.52 mmol) and DMAP (3.0 mg, cat.). The reaction mixture was stirred at 15-25° C. for 12 hours until budesonide was consumed, which was monitored by LCMS. The reaction mixture was then diluted with DCM and washed by water. The organic solution was dried over sodium sulfate. After filtered, the solution was concentrated in vacuo and the residue (crude 3a) was used for the next step directly without purification. (93 mg, yield 71%). ESI m/z: 572.2 (M+H)$^+$.

262

Example 1c

4-{2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethoxy}-4-oxobutanoic acid (1c)

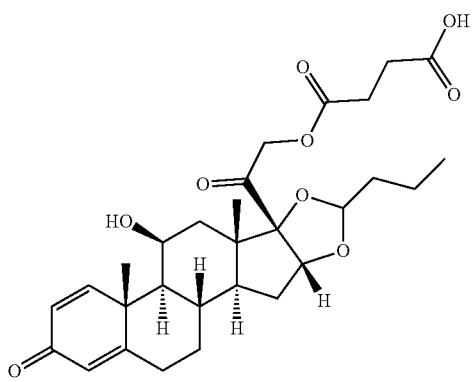

See WO2015005459; WO2013074988; *Research in Pharmaceutical Science*, 2011, 6(2), 107-116; and *International Journal of Pharmaceutics*, 2009, 365(1-2), 69-76.

To a solution of budesonide (1a, 0.10 g, 0.26 mmol) in DCM (1 mL) were added succinic anhydride (30 mg, 0.30 mmol), triethylamine (47 mg, 0.52 mmol) and DMAP (3 mg, catalyst, 0.02 mmol). The mixture was stirred at RT for 12 hours until budesonide was consumed, which was monitored by TLC and LCMS. The reaction mixture was then diluted with DCM and washed with water. The organic solution was dried over sodium sulfate. After filtered, the solution was concentrated in vacuo and the residue was purified by prep-HPLC to give title compound 1c (22 mg, yield 18%) as a white solid. ESI m/z: 531.3 (M+H)$^+$. $^1$H NMR (500 MHz, CDCl$_3$) δ 7.48 (d, J=10 Hz, 1H), 6.28-6.26 (m, 1H), 6.04-6.02 (m, 1H), 5.23-5.11 (m, 1H), 5.06-4.99 (m, 1H), 4.83-4.68 (m, 1H), 4.45-4.43 (m, 1H), 2.76-2.63 (m, 5H), 2.41-2.39 (m, 1H), 2.26-2.12 (m, 2H), 1.99-1.66 (m, 6H), 1.57-1.38 (m, 6H), 1.32 (s, 1H), 1.16-0.94 (m, 8H) ppm.

Example 1d

2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethyl N-methyl-N-[2-(methylamino)ethyl]carbamate (1d)

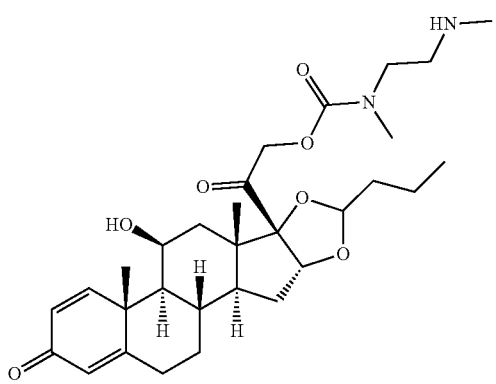

To a solution of crude intermediate 3a (63 mg, 0.11 mmol) in DCM (5 mL) were added N,N'-dimethylethane-1,2-diamine (28 mg, 0.32 mmol) and triethylamine (38 mg, 0.38 mmol) at RT. The resulting mixture was stirred at RT for 2 hours until most of 3a was consumed, which was monitored by LCMS. The volatiles were removed in vacuo and the residue was purified by prep-HPLC (method B) to give 1d (4 mg, yield 4.5%) as a white solid. ESI m/z: 545.3 (M+H)$^+$. $^1$H NMR (500 MHz, CDCl$_3$), 7.32-7.30 (m, 1H), 6.28-6.25 (m, 1H), 6.02-6.01 (m, 1H), 4.42 (br s, 1H), 3.50-3.23 (m, 3H), 3.10-3.02 (m, 3H), 2.82-2.71 (m, 3H), 2.57-2.55 (m, 1H), 2.35-2.33 (m, 1H), 2.15-2.06 (m, 2H), 1.96-1.79 (m, 12H), 1.60-1.56 (m, 3H), 1.46 (m, 3H), 1.37-1.33 (m, 2H), 1.23-1.04 (m, 4H), 0.92-0.86 (m, 3H) ppm.

Example 1e

2-[(1S,2S,4R,8S,9S,11S,13R)-11-Hydroxy-9,13-dimethyl-16-oxo-6-propyl-5,7-dioxapenta cyclo[10.8.0.0$^{2,9}$.0$^{4,8}$.0$^{13,18}$]icosa-14,17-dien-8-yl]-2-oxo-ethyl N-[(hydrazinecarbonyl)methyl]carbamate (1e)

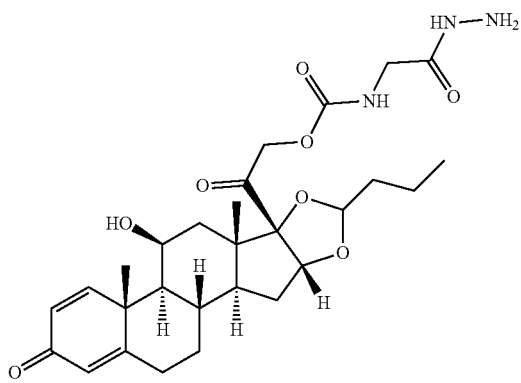

To a mixture of crude 3a (0.16 g, 0.28 mmol) in DMF (3 mL) were added Boc-2-(2-aminoacetyl)hydrazine (80 mg, 0.42 mmol) and triethylamine (85 mg, 0.84 mmol). The reaction mixture was stirred at 25° C. for 16 hours and intermediate 3a was consumed, which was monitored by LCMS. The mixture was then quenched with water and extracted with ethyl acetate. The combined organic solution was dried over anhydrous sodium sulfate. After filtered, the solution was concentrated in vacuo. The residue was purified by silica gel column chromatography (30-50% ethyl acetate in petroleum ether) to give Boc-1e (70 mg) as a white solid (ESI m/z: 646 (M+H)$^+$), which was dissolved in DCM (2 mL). To the solution was added dropwise TFA (1 mL) at 0° C. The mixture was stirred at 25° C. for 2 hours until Boc-1e was consumed, which was monitored by LCMS. The volatiles were removed in vacuo and the residue was purified by prep-HPLC to give title compound 1e (7 mg, yield 12%) as a white solid. ESI m/z: 546 (M+H)$^+$.

Example 1g (1S,2S,4R,8S,9S,11S,12S,13R)-11-Hydroxy-8-(2-{[6-(hydroxymethyl)oxan-2-yl]oxy}acetyl)-9,13-dimethyl-6-propyl-5,7-dioxapentacyclo[10.8.0.0$^{2,9}$.0$^{4,8}$.0$^{13,18}$]icosa-14,17-dien-16-one (1g)

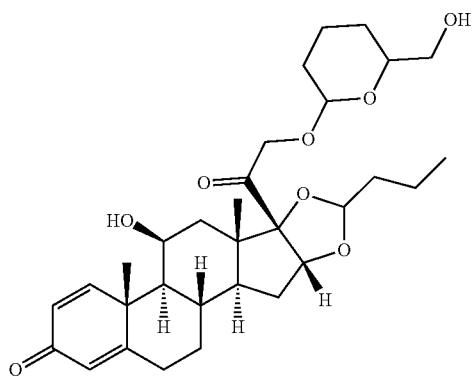

To a solution of budesonide (1a, 50 mg, 0.12 mmol) in anhydrous DCM (4 mL) were added (3,4-dihydro-2H-pyran-2-yl)methanol (0.11 g, 0.93 mmol) and p-toluenesulfonic acid (31 mg, 0.18 mmol) at 0° C. The reaction mixture was stirred at RT for 4 days, which was monitored by LCMS. The volatiles were removed in vacuo and the residue was dissolved in DMF and separated by prep-HPLC (method B) to give title compound 1g (13 mg, yield 20%) as a white solid. ESI m/z: 545 (M+H)$^+$.

Example 1h

Methyl 2-[(6-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}oxan-2-yl)methoxy]acetate (1h)

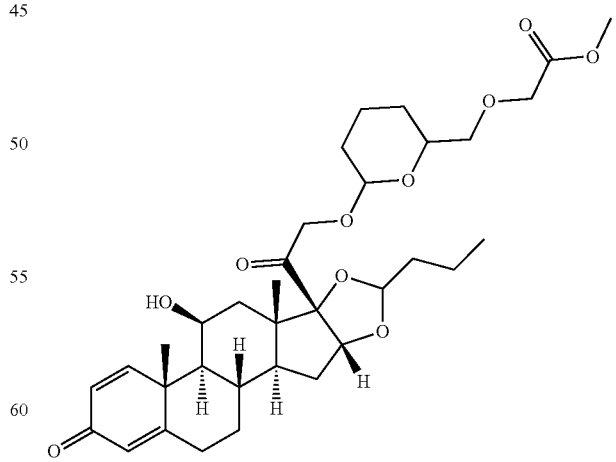

To a solution of (3,4-dihydro-2H-pyran-2-yl)methanol (2.0 g, 18 mmol) in THF (30 mL) was added sodium hydride (60% in mineral oil, 0.88 g, 22 mmol) portion wise at 0° C. under nitrogen protection. The suspension was stirred at 0°

C. until the end of hydrogen evolution. To the resulting mixture was then added a solution of ethyl 2-bromoacetate (4.0 g, 26 mmol) in THF (18 mL). The mixture was stirred at RT overnight until the starting material was mostly consumed according to LCMS. After cooled to 0° C., the reaction was quenched with water under nitrogen protection and extracted with ethyl acetate. The combined organic solution was washed with water and brine, dried over sodium sulfate and concentrated in vacuo. The residue was purified by flash chromatography (0-8% ethyl acetate in petroleum ether) to give ethyl 2-((3,4-dihydro-2H-pyran-2-yl)methoxy)acetate (0.70 g, 21% yield) as colorless oil. ($^1$H NMR (500 MHz, DMSO$_{d6}$) δ 6.36 (d, J=6.0 Hz, 1H), 4.67 (m, 1H), 4.16 (s, 2H), 3.92 (m, 1H), 3.65 (s, 3H), 3.57 (d, J=5.5 Hz, 2H), 2.50-1.99 (m, 1H), 1.93-1.82 (m, 1H), 1.80 (m, 1H), 1.60 (m, 1H) ppm.)

To a solution of budesonide (1a, 0.11 g, 0.25 mmol) in anhydrous DCM (8 mL) were added ethyl 2-((3,4-dihydro-2H-pyran-2-yl)methoxy)acetate (0.35 g, 1.9 mmol) obtained above and p-toluenesulfonic acid (66 mg, 0.35 mmol) at 0° C. The reaction mixture was stirred at RT for 4 hours, which was monitored by LCMS. The volatiles were removed in vacuo and the residue was dissolved in DMF and separated by prep-HPLC (method A) to give title compound 1h (46 mg, yield 29%) as a white solid. ESI m/z: 617 (M+H)$^+$.

Example 1i (1S,2S,4R,8S,9S,11S,12S,13R)-11-Hydroxy-9,13-dimethyl-6-propyl-8-(2-{[(2R,3R,4S,5S,6R)-3,4,5-trihydroxy-6-(hydroxymethyl)oxan-2-yl]oxy}acetyl)-5,7-dioxapentacyclo[10.8.00$^{2,9}$.0$^{4,8}$.0$^{13,18}$]icosa-14,17-dien-16-one (1i, with epimers)

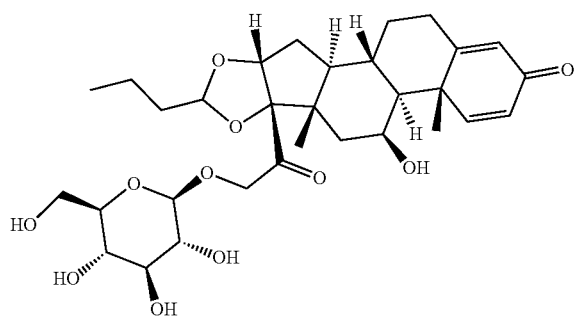 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](CO)[C@@H](O)[C@H](O)[C@H]2O)O1]

To a mixture of budesonide (1a, 0.22 g, 0.50 mmol) and acetobromo-α-D-Glucose (0.33 g, 0.80 mmol) in DCM (15 mL) was added 4 Å molecular sieves (1.0 g), and the mixture was stirred at RT for half an hour followed by the addition of silver trifluoromethanesulfonate (0.19 g, 0.75 mmol) at 0° C. The suspension was stirred in dark at RT over weekend (72 hours) under nitrogen protection. The mixture was filtered through Celite and the filtrate was concentrated in vacuo. The residue was purified by prep-HPLC (method B) to give Ac-1i (25 mg, yield 9.2%) as a white solid. ESI m/z: 761 (M+H)$^+$. $^1$H NMR (DMSO$_{d6}$, 400 MHz) (with epimers) δ 7.34-7.30 (m, 1H), 6.19-6.14 (m, 1H), 5.91 (s, 1H), 5.29 (t, J=9.2 Hz, 1H), 5.17-5.15 (m, 0.5H), 5.03-5.01 (m, 0.5H), 4.96-4.90 (m, 1H), 4.85-4.74 (m, 3H), 4.70-4.67 (m, 1H), 4.64-4.63 (m, 0.5H), 4.59-4.56 (m, 0.5H), 4.39-4.28 (m, 2H), 4.20-4.16 (m, 1H), 4.05-3.99 (m, 2H), 2.56-2.40 (m, 1H), 2.32-2.26 (m, 1H), 2.13-1.89 (m, 14H), 1.83-1.63 (m, 3H), 1.59-1.48 (m, 3H), 1.44-1.21 (m, 6H), 1.15-0.91 (m, 2H), 0.86-0.81 (m, 6H) ppm.

To a solution of the compound Ac-1i (30 mg, 39 μmol) obtained above in water (1 mL) and methanol (3 mL) was added lithium hydroxide monohydrate (17 mg, 0.40 mmol) at 0° C. After stirred at 0° C. for an hour, the mixture was directly purified by prep-HPLC (method B) to give 1i (24 mg, 98% yield) as a white solid. ESI m/z: 593 (M+H)$^+$. $^1$H NMR (MeOD$_{d4}$, 400 MHz) (with epimers) δ 7.46 (t, J=10.4 Hz, 1H), 6.26 (dt, J=10.0 and 2.0 Hz, 1H), 6.02 (s, 1H), 5.21 and 4.64 (t, J=4.8 Hz, 1H), 5.16 (t, J=7.2 Hz, 0.5H), 4.94-4.80 (m, 2.5H), 4.57-4.47 (m, 1H), 4.44-4.41 (m, 1H), 4.34-4.31 (m, 1H), 3.90-3.87 (m, 1H), 3.70-3.64 (m, 1H), 3.39-3.24 (m, 4H), 2.70-2.62 (m, 1H), 2.41-2.36 (m, 1H), 2.27-2.08 (m, 2H), 2.00-1.93 (m, 1H), 1.88-1.81 (m, 1H), 1.74-1.32 (m, 9H), 1.22-0.90 (m, 8H) ppm.

Example 1j (2S,3S,4S,5R,6R)-3,4,5-Trihydroxy-6-{2-[(1S,2S,4R,8S,9S,11S,12S,13R)-11-hydroxy-9,13-dimethyl-16-oxo-6-propyl-5,7-dioxapentacyclo[10.8.00$^{2,9}$.0$^{4,8}$.0$^{13,18}$]icosa-14,17-dien-8-yl]-2-oxoethoxy}oxane-2-carboxylic acid (1j, with epimers)

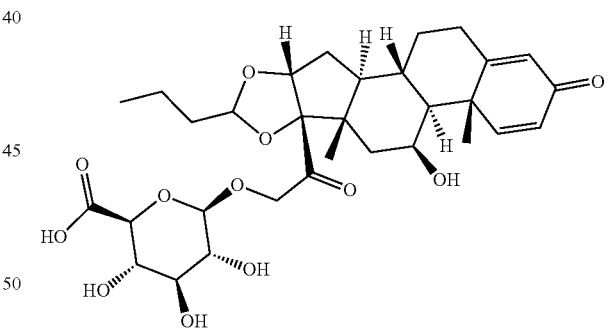

Following the similar procedures as 1i except substituting acetobromo-α-D-Glucuronic acid methyl ester for acetobromo-α-D-Glucose, the compound 1j (24 mg, 9.2% yield in 2 steps) as a white solid was obtained. ESI m/z: 607 (M+H)$^+$. $^1$H NMR (MeOD$_{d4}$, 400 MHz) δ 7.48 (t, J=10.0 Hz, 1H), 6.28-6.24 (m, 1H), 6.02 (s, 1H), 5.22-5.15 (m, 1H), 4.98-4.81 (m, 2.5H), 4.65-4.56 (m, 1.5H), 4.45-4.39 (m, 2H), 3.62-3.59 (m, 1H), 3.52-3.46 (m, 1H), 3.41 (t, J=8.8 Hz, 1H), 3.30-3.28 (m, 1H), 2.70-2.62 (m, 1H), 2.40-2.36 (m, 1H), 2.27-2.10 (m, 2H), 1.95-1.92 (m, 2H), 1.75-1.54 (m, 3H), 1.50 (s, 3H), 1.51-1.32 (m, 3H), 1.12-0.90 (m, 8H) ppm.

Example 1k (2, 2113ethoxy)({2 1H)S,2S,4R,8S,9S,11S,12S, 13R)13oxy)({2 1H), 3.30-3.28 (m, 1H), 2.70-2.62 (m, 1H), 2.40-2.36 (m, 1H)$^{2,9}$.0$^{4,8}$.0$^{13,18}$]icosa)({2 1H), 3.30-3.28 oxoethoxy})phosphinic acid (1k)

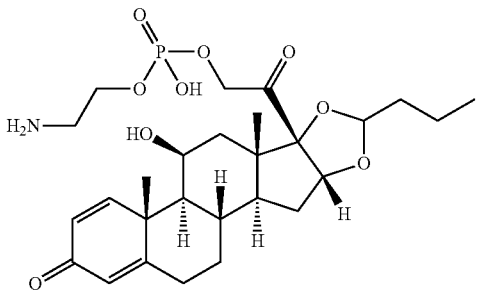

To a solution of triethylamine (0.67 g, 6.6 mmol) in chloroform (4 mL) was added phosphorus oxychloride (0.51 mg, 3.3 mmol) at 0° C., followed by the addition of a solution of budesonide (1a, 1.3 g, 3.0 mmol) in chloroform (4 mL). After stirred at 20° C. for 2 hours, the mixture was cooled to 0° C. and was added a solution of Boc-ethanolamine (0.41 mg, 2.6 mmol) in chloroform (4 mL) and pyridine (3 mL). After stirred at 20° C. for an hour until the reaction was completed according to LCMS, the reaction mixture was quenched by the addition of water (2 mL) at 0° C. The mixture was stirred at 20° C. overnight. The volatiles were removed in vacuo and the residue was purified by prep-HPLC (method B) to afford crude Boc-1k (330 mg, 17%) as yellow film. ESI m/z: 676 (M+Na)$^+$.

To a solution of Boc-1k (0.18 g, 0.28 mmol) in DCM (5 mL) was added trifluoroacetic acid (0.5 mL) at 0° C. The resulting mixture was stirred at 23° C. for 2 hours until Boc was totally removed according to LCMS. The volatiles were removed in vacuo. The residue was purified by prep-HPLC (method B) to afford 1k as a white solid (90 mg, 59% yield). ESI m/z: 554 (M+H)$^+$. $^1$H NMR (500 MHz, MeOD$_{d4}$) δ 7.49 (d, J=10.1 Hz, 1H), 6.28 (d, J=10.1 Hz, 1H), 6.03 (s, 1H), 5.24-5.15 (m, 1H), 4.87-4.62 (m, 3H), 4.45 (d, J=6.1 Hz, 1H), 4.18-4.15 (m, 2H), 3.22-3.20 (m, 2H), 2.71-2.64 (m, 1H), 2.40 (d, J=13.4 Hz, 1H), 2.29-1.71 (m, 6H), 1.65-1.32 (m, 9H), 1.22-0.91 (m, 7H) ppm. Anal. HPLC: >99.9%, Retention time: 3.90 min (method B).

Example 1l (2-{[(9H-Fluoren-9-ylmethoxy)carbonyl]amino}ethoxy)phosphonic acid See J. Am. Chem. Soc., 2016, 138(4), 1430-1445; WO2015153401; and Phosphorus, Sulfur and Silicon and the Related Elements, 2000, 165, 83-90.

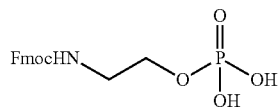

To a mixture of Fmoc-ethanolamine (1.1 g, 3.9 mmol) in THF (16 mL) was added diphosphoryl chloride (2.2 g, 8.8 mmol) by syringe at −40° C. After stirred at −40° C. for an hour until the starting material was totally consumed, which was monitored by LCMS, the reaction mixture was quenched with water (1 mL) at −40° C., treated with saturated aqueous sodium bicarbonate solution (200 mL) and kept at 10-20° C. overnight. The resulting mixture was acidified with conc. HCl to pH 2 and was then extracted with ethyl acetate. The combined organic solution was dried over sodium sulfate and concentrated to afford the crude title compound (1.6 g, crude) as a white solid, which was used for the next step without purification. ESI m/z: 364 (M+H)$^+$.

(2-{[(9H-Fluoren-9-ylmethoxy)carbonyl]amino}ethoxy)({[hydroxy({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy})phosphoryl]oxy})phosphinic acid (Fmoc-1l)

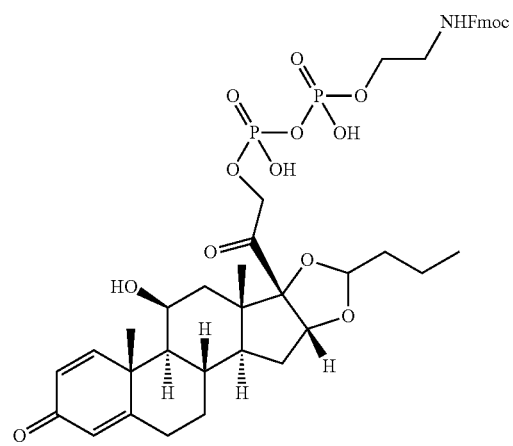

Following the above procedure except substituting budesonide (1a, 0.86 g, 20 mmol) for Fmoc-ethanolamine, the phosphonic budesonide intermediate 1a-PO$_3$H$_2$ (1.1 g, crude) as a white solid (ESI m/z: 551 (M+H)$^+$) was obtained.

To a solution of crude (2-{[(9H-Fluoren-9-ylmethoxy)carbonyl]amino}ethoxy)phosphonic acid (0.29 g, 0.80 mmol) in DMF (5 mL) were added triethylamine (81 mg, 0.80 mmol) and 1,1'-carbonyldiimidazole (CDI, 0.32 g, 2.0 mmol) at 10° C. The mixture was stirred at 10-20° C. for 30 minutes before the phosphonic budesonide intermediate 1a-PO$_3$H$_2$ obtained above (0.41 g, 0.80 mmol) and zinc chloride (0.87 g, 6.4 mmol) were added into the reaction mixture. The resulting mixture was stirred at 10-20° C. overnight and starting material was totally consumed according to LCMS. The reaction was then quenched with diluted aq. HCl (1 N, 50 mL) and extracted with ethyl acetate. The combined organic solution was concentrated and the residue was purified by prep-HPLC (method B) to afford Fmoc-1l (0.32 g, yield 47%) as a white solid. ESI m/z: 856 (M+H)$^+$.

(2-Aminoethoxy)({[hydroxy({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy})phosphoryl]oxy})phosphinic acid (11)

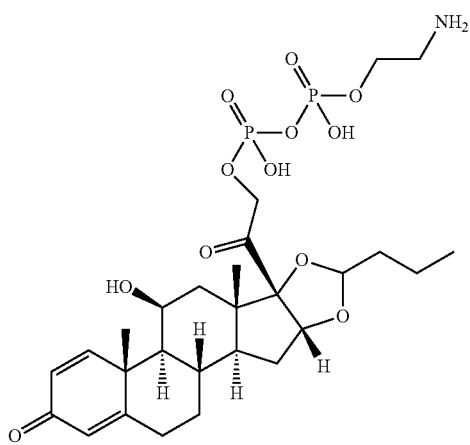

See WO2015153401.

To a solution of Fmoc-11 (0.10 g, 0.12 mmol) in DCM (2 mL) was added piperidine (67 mg, 0.79 mmol) at 10 TC. The reaction mixture was stirred at 10-20° C. for 16 hours. Compound Fmoc-11 was totally consumed according to LCMS. The volatiles were removed in vacuo and the residue was purified by prep-HPLC (method B) to afford 11 (50 mg, yield 68%) as a white solid. ESI m/z: 634 (M+H)$^+$. $^1$H NMR (500 MHz, MeOD$_{d4}$) δ 7.50 (d, J=10.0 Hz, 1H), 6.28 (d, J=9.9 Hz, 1H), 6.03 (s, 1H), 5.23-5.16 (m, 1H), 5.02-4.97 (m, 1H), 4.88-4.67 (m, 1H), 4.45 (d, J=3.4 Hz, 1H), 4.23 (s, 2H), 3.24 (s, 2H), 2.67 (dd, J=13.5, 8.3 Hz, 1H), 2.40 (d, J=11.3 Hz, 1H), 2.28-1.32 (m, 15H), 1.23-0.92 (m, 8H) ppm. Anal. HPLC: >99.9%, Retention time: 2.74 min (method B).

Table 1a below presents steroids made using the methods described herein.

TABLE 1a

| # | Structure | HPLC purity | cLog P | MF | MW (Cal.) | MS (M + H) |
|---|---|---|---|---|---|---|
| 1a | 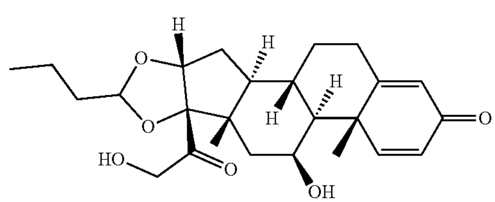 | 95 | 2.73 | C$_{25}$H$_{34}$O$_6$ | 430.55 | 431.3 |
| 1c | 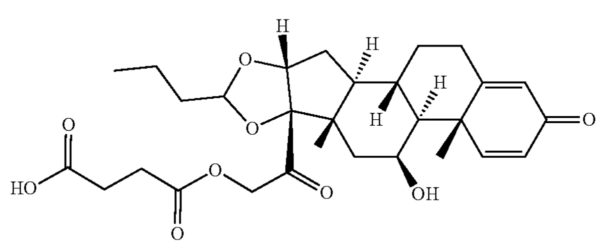 | 98 | 3.00 | C$_{29}$H$_{38}$O$_9$ | 530.25 | 531.2 |
| 1d | 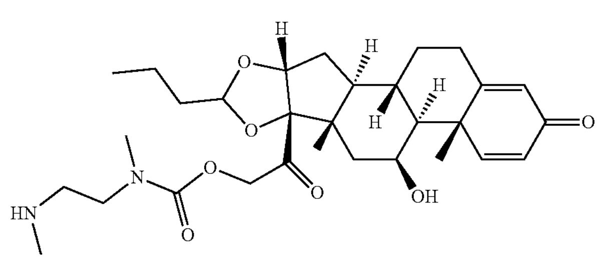 | 93 | 2.92 | C$_{30}$H$_{44}$N$_2$O$_7$ | 544.69 | 545.3 |

TABLE 1a-continued

Structure and Chemical-Physical Properties of Compounds

| # | Structure | HPLC purity | cLog P | MF | MW (Cal.) | MS (M + H) |
|---|---|---|---|---|---|---|
| 1e | 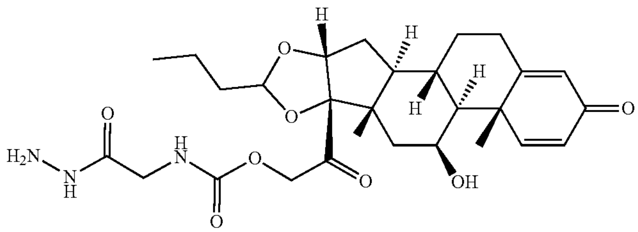 | 100 | 1.44 | $C_{28}H_{39}N_3O_8$ | 545.62 | 546.2 |
| 1g | 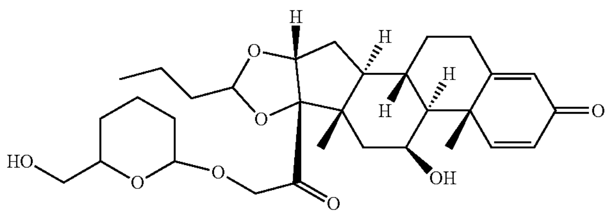 | 92 | 3.65 | $C_{31}H_{44}O_8$ | 544.68 | 545.3 |
| 1h | 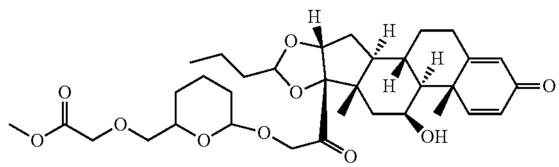 | 98 | 3.19 | $C_{34}H_{48}O_{10}$ | 616.32 | 616.32 |
| 1i | 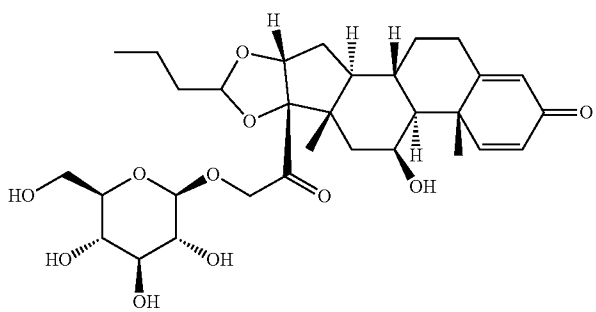 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](CO)[C@@H](O)[C@H](O)[C@H]2O)O1] | 100 | 0.96 | $C_{31}H_{44}O_{11}$ | 592.67 | 593.4 |
| 1j | 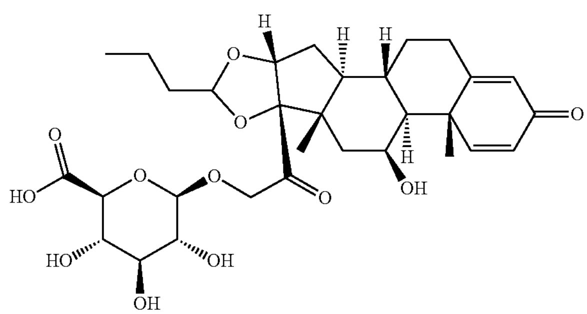 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](C(=O)O)[C@@H](O)[C@H](O)[C@H]2O)O1] | 98 | 1.28 | $C_{31}H_{42}O_{12}$ | 606.66 | 607.3 |
| 1k | 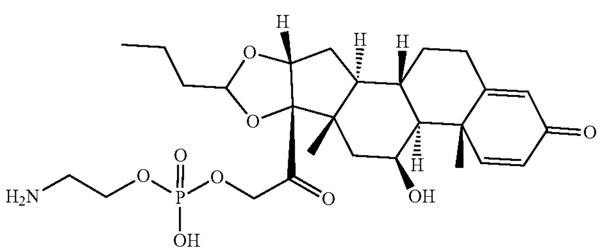 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OCCN)O1] | 100 | 1.18 | $C_{27}H_{40}NO_9P$ | 553.58 | 554.1 |

TABLE 1a-continued

Structure and Chemical-Physical Properties of Compounds

| # | Structure | HPLC purity P | cLog P | MF | MW (Cal.) | MS (M + H) |
|---|---|---|---|---|---|---|
| 1l | 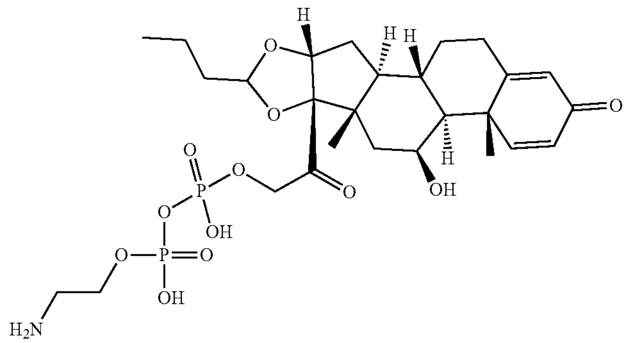 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OP(=O)(O)OCCN)O1] | 100 | 0.55 | $C_{27}H_{41}NO_{12}P_2$ | 633.56 | 634.0 |
| 1m | 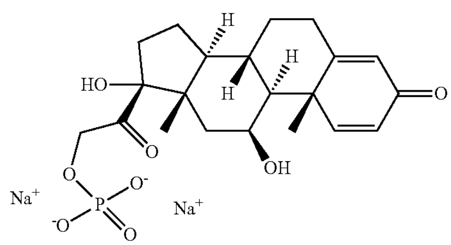 | 100 | 1.15 | $C_{21}H_{27}Na_2O_8P$ | 484.39 | 590.3 |
| 100 | 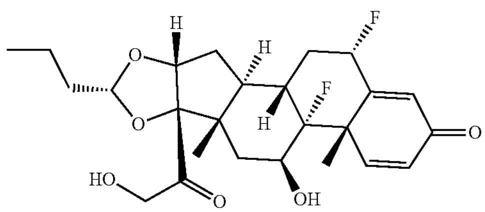 | 100 | 2.44 | $C_{25}H_{32}F_2O_6$ | 466.51 | 467 |
| 101a | 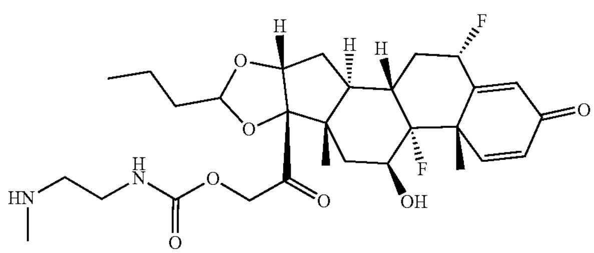 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCNC)O1] | >95 | 2.40 | $C_{29}H_{40}F_2N_2O_7 \cdot C_2HF_3O_2$ | 663.66 | 567 |
| 101b | 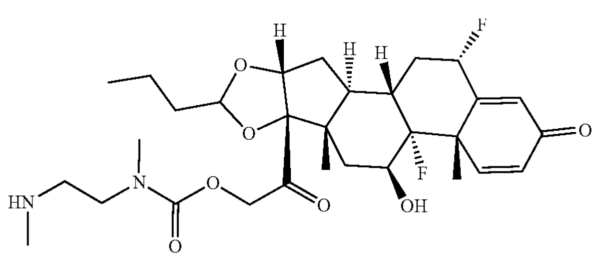 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCNC)O1] | >95 | 2.63 | $C_{30}H_{42}F_2N_2O_7 \cdot C_2HF_3O_2$ | 678.69 | 581 |

TABLE 1a-continued

Structure and Chemical-Physical Properties of Compounds

| # | Structure | HPLC purity | cLog P | MF | MW (Cal.) | MS (M + H) |
|---|---|---|---|---|---|---|
| 101c | 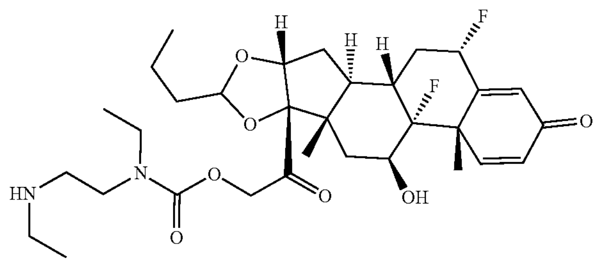 | 100 | 3.34 | C₃₂H₄₆F₂N₂O₇•C₂HF₃O₂ | 722.74 | 609 |
| 101d | 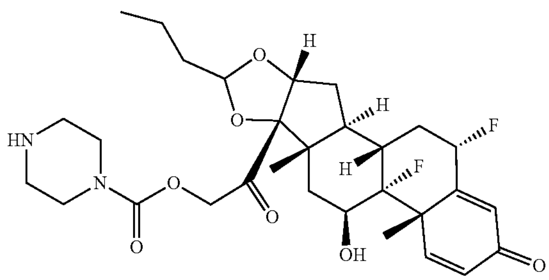 | 100 | 2.46 | C₃₀H₄₀F₂N₂O₇ | 578.64 | 579 |
| 102c | 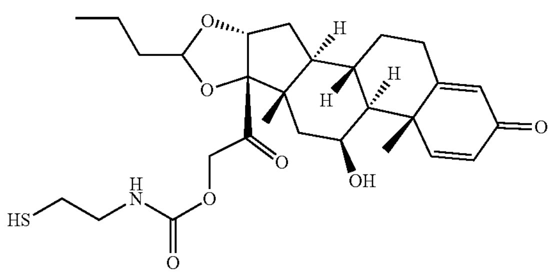 | >95 | 3.47 | C₂₈H₃₉NO₇S | 533.68 | 531 |
| 102d | 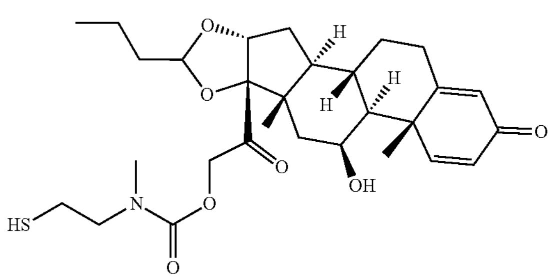 | >95 | 3.69 | C₂₉H₄₁NO₇S | 547.71 | 548 |
| 102e | 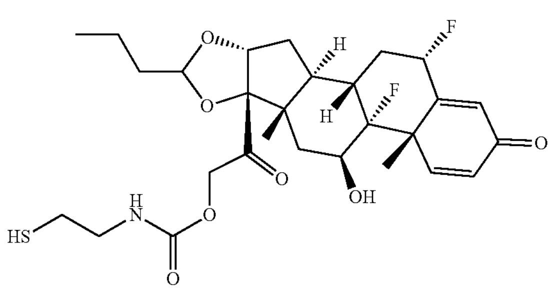 | >95 | 3.17 | C₂₈H₃₇F₂NO₇S | 569.66 | 570 |

TABLE 1a-continued

Structure and Chemical-Physical Properties of Compounds

| # | Structure | HPLC purity | cLog P | MF | MW (Cal.) | MS (M + H) |
|---|---|---|---|---|---|---|
| 102f | 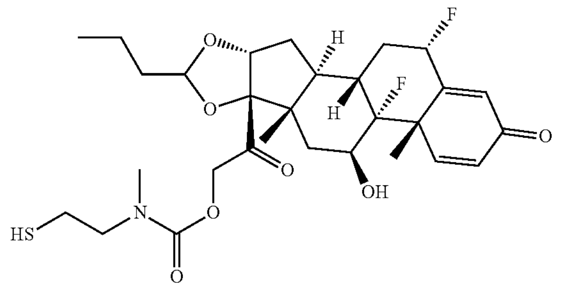 | >95 | 3.40 | $C_{29}H_{39}F_2NO_7S$ | 583.69 | 584 |
| 103a | 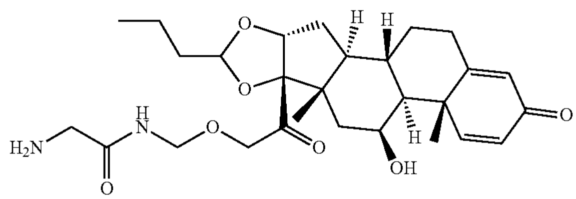 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COCNC(=O)CN)O1] | 98 | 1.58 | $C_{28}H_{40}N_2O_7$ | 516.64 | 517 |
| 103b | 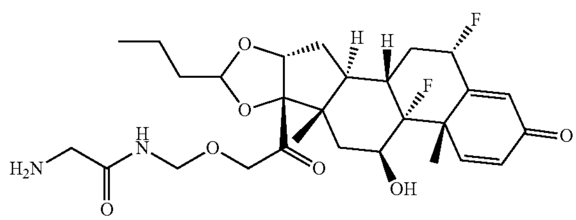 | 98 | 1.29 | $C_{28}H_{38}F_2N_2O_7$ | 552.62 | 553 |
| 104a | 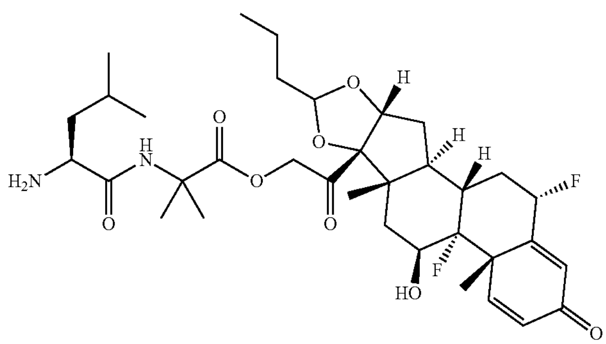 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@@H](N)CC(C)C)O1] | >90 | 3.67 | $C_{35}H_{50}F_2N_2O_8$ | 664.7 | 665 |
| 104b | 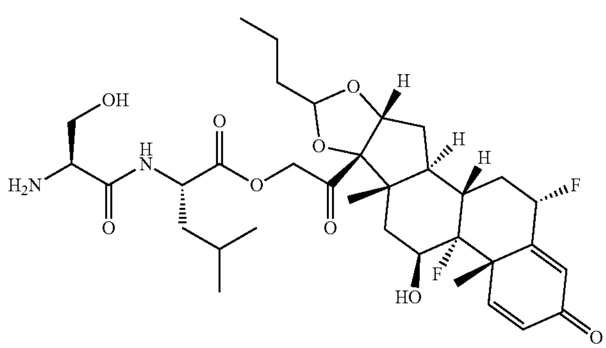 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@@H](N)CO)O1] | >95 | 2.19 | $C_{34}H_{48}F_2N_2O_9$ | 666.76 | 667 |

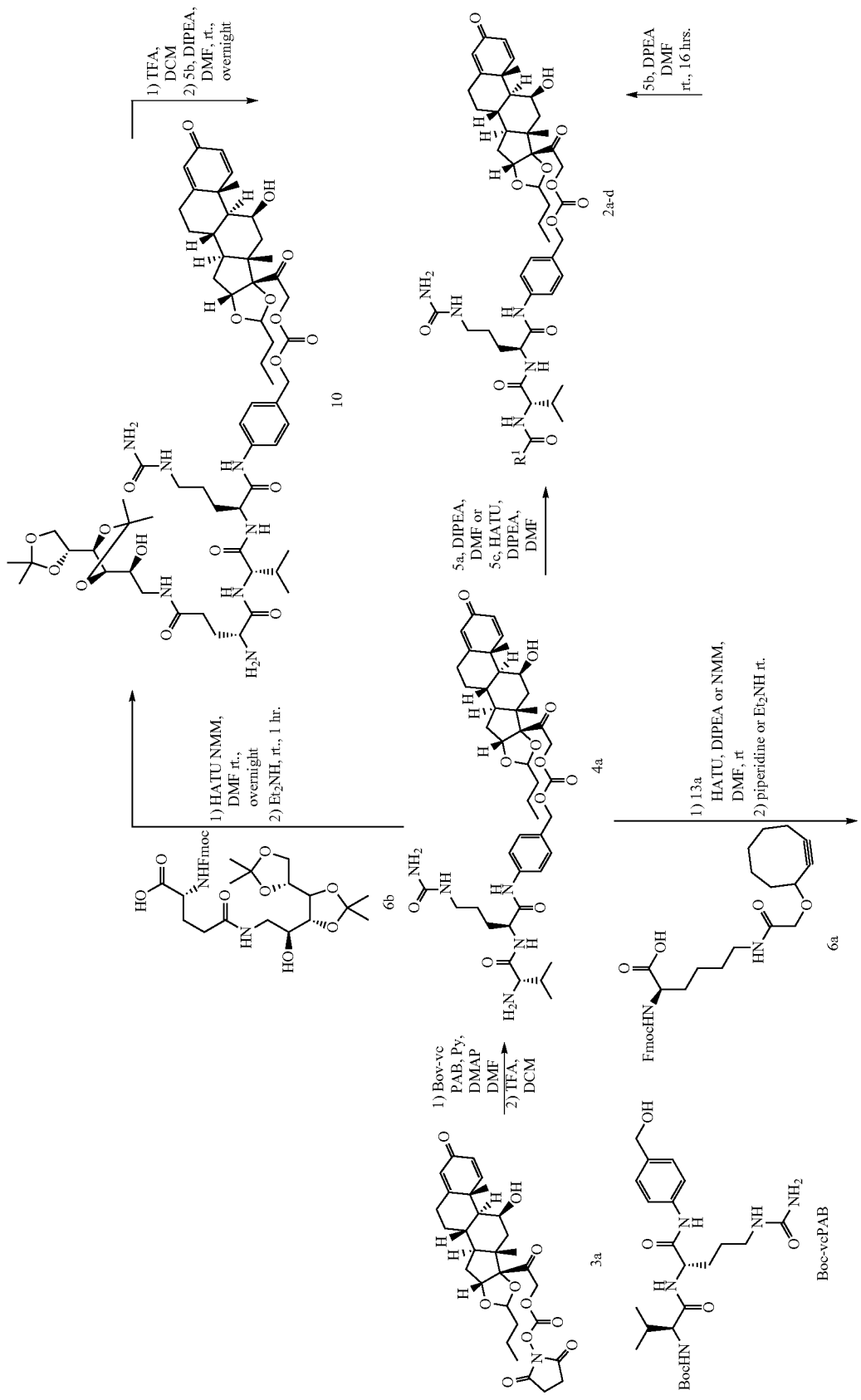

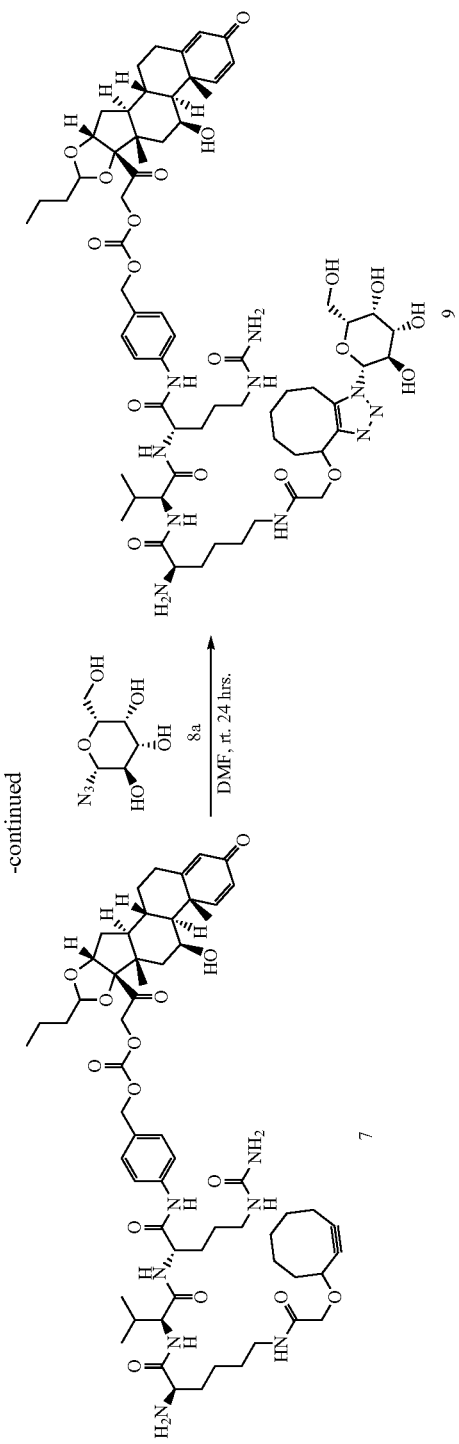

General Procedure A for Synthesis of
MC-Spacer-Budesonide (2a & 2c)

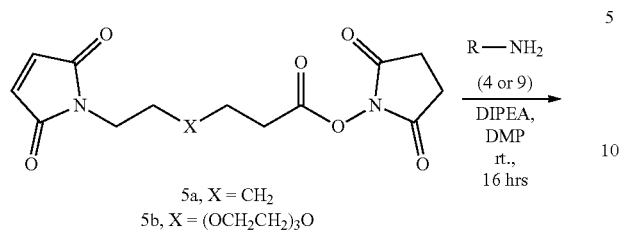

5a, X = CH$_2$
5b, X = (OCH$_2$CH$_2$)$_3$O 2a, c

To a solution of vcPAB-Budesonide (4a A=CO, 1.0 equiv.) or amine 9 (1.0 equiv.) in Scheme 2 in DMF (ca. 1 mL per 10 mg amine) were added activated NHS ester 5 (1.5-3.0 equiv.) in the table below and DIPEA (2.0 equiv.) at RT. The reaction mixture was stirred at RT overnight when NHS ester and most of amine were consumed according to LCMS spectra. After filtration, the reaction solution was directly purified by prep-HPLC or reversed phase flash chromatography to give the desired amide 2 (ca. 17% yield) as a white solid.

| Amines | Activated ester 5 | Base/reagents | Solvent | Time (hr) | Purification | Product 2 |
|---|---|---|---|---|---|---|
| 4a$^c$ 50 mg, 56 μmol | 5a 28 mg, 91 μmol | DIPEA (23 mg, 0.18 mmol) | DMF (3 mL) | 16 | Prep-HPLC (method A) | 2a (10 mg, 17%) |
| rxn solution of 9 | 5b 8.8 mg, 20 μmol | DIPEA (4.0 mg, 31 μmol) | DMF 1 mL) | 16 | Prep-HPLC (method A) | 2c (3.5 mg, 4%) | c. TFA Salt

General Procedure B for Synthesis of Amides 2b, 2l, 2m-Precursor from Acid

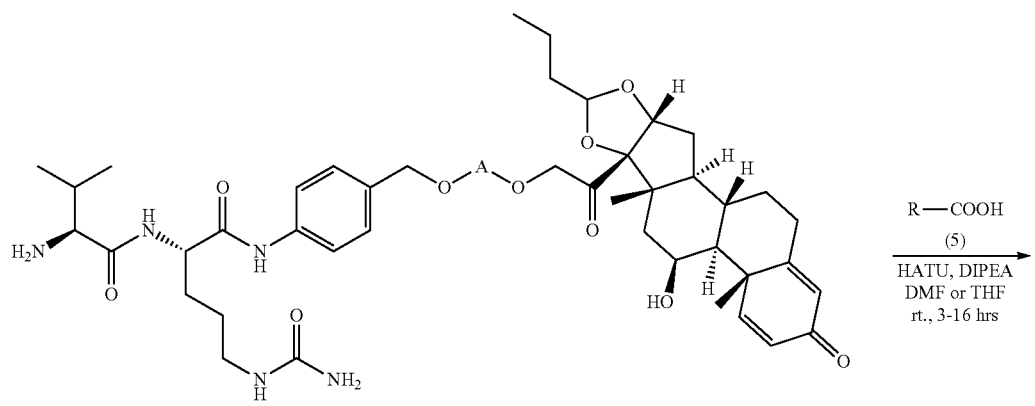

4a-c

-continued
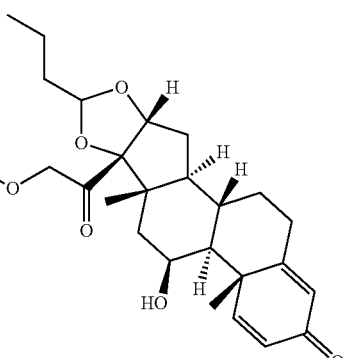
2b, 2l, 2m-precursor
| Products | Amines | Acids | A | R |
|---|---|---|---|---|
| 2b | 4a | 5c | 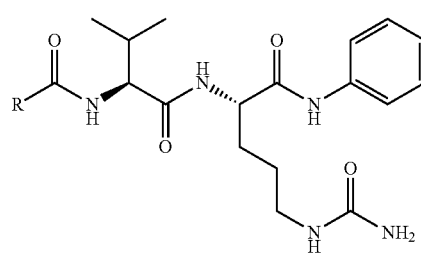 | |
| 2l | 4c | 5d | | |
| 2m-precursor | 4c | 5e | | |

To a solution of acid 5 (1.0-1.5 equiv.) in DMF or DCM or THF (1 m per 5 mg 5) were added DIPEA (2.0-5.0 equiv.) and HATU (1.4-2.2 equiv.) at RT. The resulting mixture was stirred at this temperature for 0.5-1 hour before the vcPAB-Budesonide (4, 1.0 equiv.) was added. The reaction mixture 5 was stirred at RT for 3-16 hours until the amine was totally consumed, which was monitored by LCMS. The reaction mixture was filtered through membrane and the filtration was then separated by prep-HPLC or reversed phase flash chromatography to give the amide 2 (21-54% yield) as a white solid. In the table below are additional details.

| Amines | acid | Base/reagents | Solvent | Time (hr) | Purification | Product 2 |
|---|---|---|---|---|---|---|
| 4b 10 mg, 11 μmol | 5c 10 mg, 18 μmol | DIPEA (6.2 mg, 48 μmol) HATU (9.0 mg, 24 μmol) | DMF (1 mL) | 16 | Prep-HPLC (method B) | 2b (3.0 mg, 21%) |
| 4c 58 mg, 61 μmol | 5c 37 mg, 67 μmol | DIPEA (15 mg, 0.12 mmol) HATU (34 mg, 89 μmol) | DMF (5 mL) | 3 | Prep-HPLC (method B) | 2i (21 mg, 24%) |
| 4c 8.9 mg, 9.4 μmol | 5d 6.3 mg, 14 μmol | DIPEA (3.6 mg, 27 μmol) HATU (8.0 mg, 20 μmol) | DMF (1 mL) | 16 | Prep-HPLC (method B) | 2l (7 mg, 54%) |
| 4c 20 mg, 21 μmol | 5e 13 mg, 21 μmol | DIPEA (8.0 mg, 62 μmol) HATU (12 mg, 31 μmol) | THF (5 mL) | 16 | Prep-HPLC (method A) | 2m-precursor (5 mg) |

General Procedure C for Synthesis of Intermediate 7 and 10

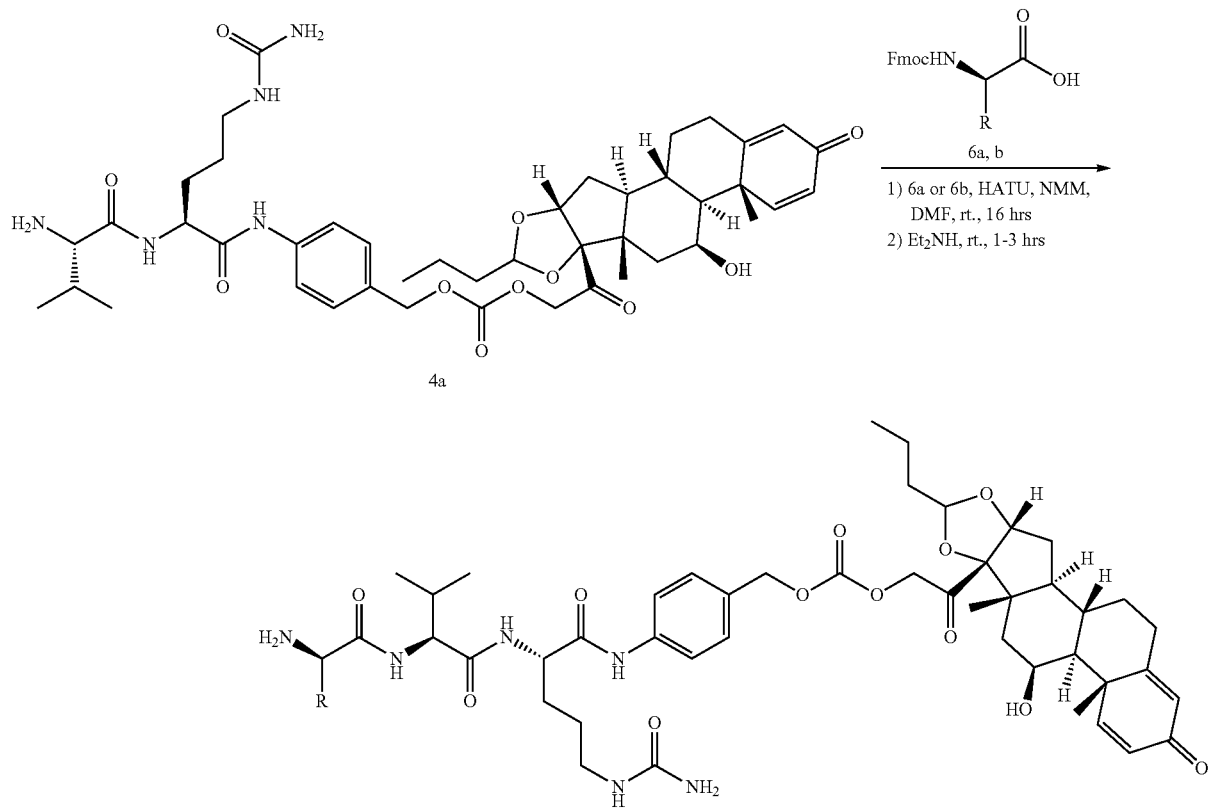

| Fmoc-Aminoacid 6 | Product | R |
|---|---|---|
| 6a | 7 | |
| 6b | 10 | |

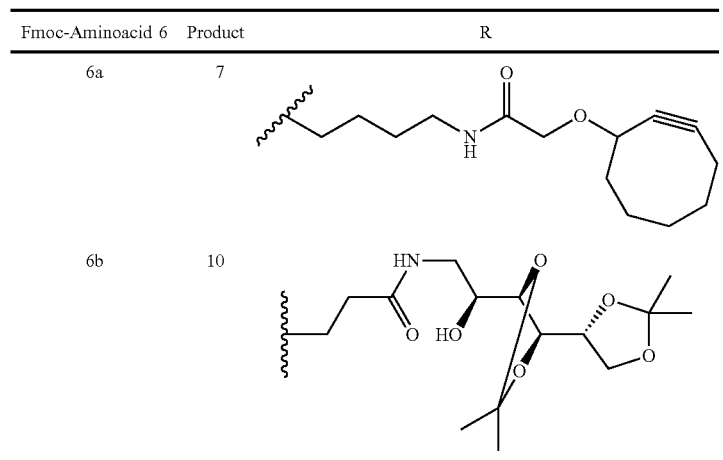

To a solution of intermediate 6 (1.2-1.4 equiv.) in DMF was added HATU (1.5-1.7 equiv.) at RT. The solution obtained was stirred at RT for an hour. To this suspension were added a solution of vcPAB-budesonide (4a, 1.0 equiv.) in DMF (0.10 mL per mg of 4a) and subsequently NMM (2.3-3.0 equiv.). The reaction mixture was stirred at RT for 16 hours and turned clear. The reaction was monitored by LCMS until compound 4a was totally consumed. To the reaction mixture was then added diethylamine (excess), and the resulting mixture was then stirred at RT for 1-3 hours until Fmoc was removed according to LCMS. The volatiles were removed in vacuo and the residue was purified by prep-HPLC (method A) to give compound 7 (18% yield from compound 4a) or purified by prep-HPLC (method B) to give compound 10 (5-% yield) as a white solid. In the table below are additional details.

| Amines | | Intermediate 6 | | Base/reagents | Solvent | Time | Purification | Product |
|---|---|---|---|---|---|---|---|---|
| 4a | 60 mg, 64 μmol | 6a | 46 mg, 86 μmol | NMM (15 mg, 0.15 mmol) HATU (41 mg, 0.11 mmol) then Et$_2$NH (0.5 mL) | DMF (3 mL) | 16 hrs then 3 hrs | Prep-HPLC (method A) | 7 (13 mg, 18%) |
| 4a | 0.19 g, 0.20 mmol | 6b | 0.15 g, 0.24 mmol | NMM (61 mg, 0.60 mmol) HATU (0.11 g, 0.29 mmol) then Et$_2$NH (1 mL) | DMF (5 mL) | 16 hrs then 1 hr | Prep-HPLC (method B) | 10 (13 mg, 5%) |

General Procedure D for Synthesis of Carbamates 2j, 2k, 2r, and 2s

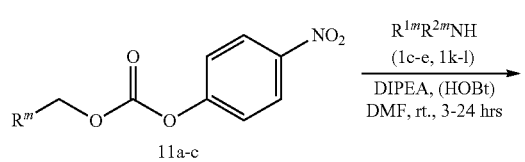

11a-c $R^{1m}R^{2m}NH$
(1c-e, 1k-l)
———————→
DIPEA, (HOBt)
DMF, rt., 3-24 hrs

-continued

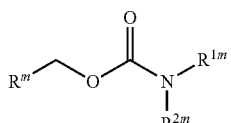

2j, 2k, 2r, 2s

The mixture was stirred at RT for 3-24 hours until PNP activated ester was totally consumed, which was monitored by LCMS. The reaction mixture was filtered through membrane and the filtrate was separated directly by prep-HPLC to give compound 2 (with or without diastereoisomers, 11-63% yield) as a white solid(s). In the table below are additional details.

| Spacer-budesonide 21 | | Activated ester 23 | | Base/reagents | Solvent | Time (hr) | Purification | Product 2 |
|---|---|---|---|---|---|---|---|---|
| 1e | 15 mg, 28 μmol | 11a | 15 mg, 20 μmol | DIPEA (12 mg, 93 μmol) HOBt (4.0 mg, 30 μmol) | DMF (1 mL) | 12 | Prep-HPLC (method A) | 2j (3.0 mg, 13%) |
| 1d | 20 mg, 37 μmol | 11a | 22 mg, 30 μmol | DIPEA (12 mg, 93 μmol) HOBt (6.0 mg, 44 μmol) | DMF (1 mL) | 12 | Prep-HPLC (method A) | 2k-A (3.3 mg, 10%) 2k-B (4.1 mg, 12%) |
| 1k | 50 mg, 90 μmol | 11c | 30 mg, 95 μmol | DIPEA (50 mg, 0.39 μmol) | DMF (1 mL) | 3 | Prep-HPLC (method B) | 2r (40 mg, yield 61%) |

Synthesis of 2a-d

Budesonide-Linkers 2a-d were prepared from three approaches according to Scheme 2. The first approach was directly amide coupling reactions from vcPAB-Budesonide (4a), which was obtained from the activated ester of budesonide 3a with linkers 5. The second approach was via initial amide coupling reactions from vcPAB-Budesonide (4a) with intermediate 6a to generate Budesonide-Linkers 7, followed by 3+2 cyclization with galactose-azide (8a) to generate intermediates 9, and finally by secondary amide coupling reactions with 5. The third approach was via first amide coupling reactions of 4 with intermediate 6b, followed by amide formation with 5b and sequentially deprotection of acetone to give 2d.

Intermediate 4a

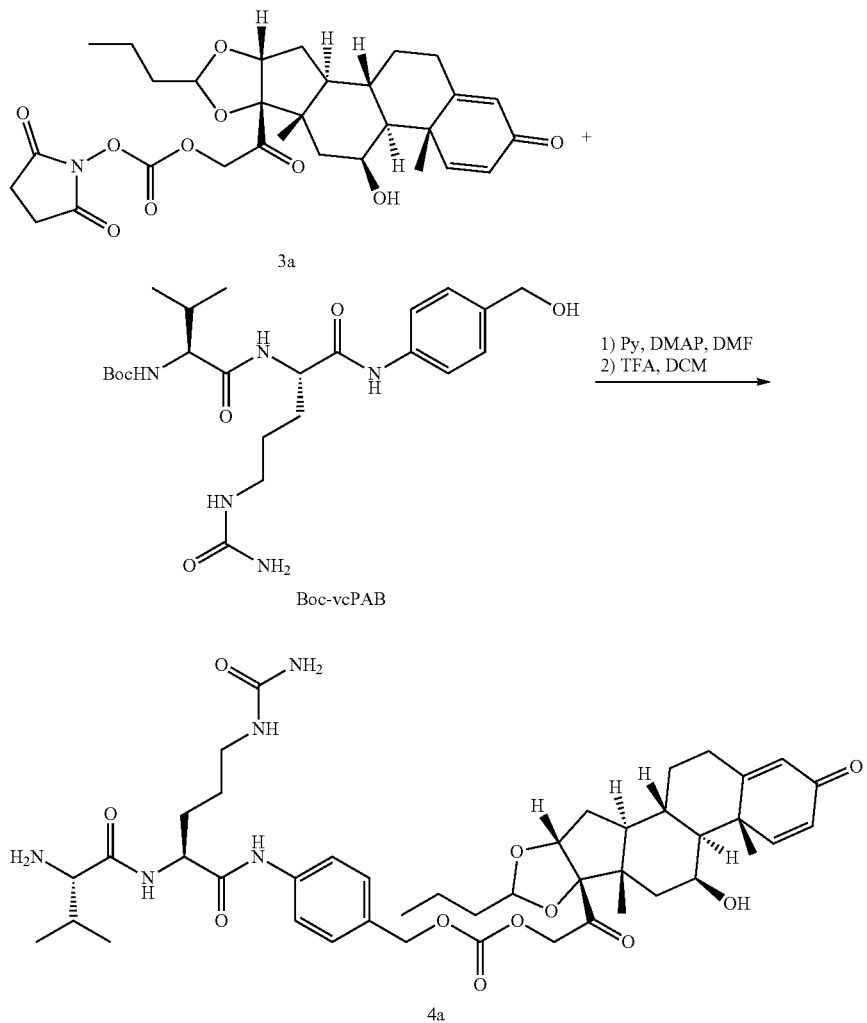

1.4 mmol) in dry DMF (10 mL) were added Boc-vc-PAB (12a) [WO2008/34124 A2] (0.59 g, 1.2 mmol), DMAP (0.30 g, 2.4 mmol) and pyridine (0.29 g, 3.7 mmol). The mixture was stirred at RT for 16 hours until 3a was totally consumed according to LCMS. The reaction mixture was directly purified by reversed phase flash chromatography (50-80% acetonitrile in water) to give intermediate Boc-4a (0.74 g, yield 38%, ESI m/z: 936 (M+H)$^+$) as a white solid, which was dissolved in DCM (40 mL). To 5 mL of the DCM solution (containing 94 mg Boc-4a) was added TFA (0.5 mL) dropwise at 0° C. After stirred at RT for 1.5 hours until the Boc-4a was consumed, which was monitored by LCMS, the resulting mixture was concentrated in vacuo to give crude title product 4a (83 mg, yield 34% from budesonide) as its TFA salt as colorless oil, which can be used without purification for next step synthesis. 20 mg of the crude 4a was purified by prep-HPLC (method B) to give pure 4a (8 mg) as free base for plasma stability test. ESI m/z: 836 (M+H)$^+$. $^1$H NMR (400 MHz, DMSO$_{d6}$) δ 10.17 (s, 1H), 8.12 (br s, 1H), 7.62 (d, J=8.5 Hz, 2H), 7.31 (d, J=10.2 Hz, 3H), 6.17 (d, J=10.1 Hz, 1H), 5.97 (t, J=5.7 Hz, 1H), 5.92 (s, 1H), 5.40 (s, 2H), 5.22-5.01 (m, 4H), 4.89-4.62 (m, 3H), 4.53-4.40 (m, 1H), 4.30 (s, 1H), 3.09-2.87 (m, 3H), 2.36-2.22 (m, 1H), 2.14-1.87 (m, 4H), 1.81 (d, J=5.6 Hz, 2H), 1.75 (s, 2H), 1.62-1.52 (m, 4H), 1.51-1.41 (m, 2H), 1.40-1.19 (m, 8H), 1.18-0.92 (m, 2H), 0.92-0.82 (m, 9H), 0.78 (d, J=6.8 Hz, 3H) ppm.

Example 2a

N-[(1S)-1-{[(1S)-4-(Carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-6-(2,5-dioxo-2,5-dihydro-1H-pyrrol-1-yl)hexanamide (2a)

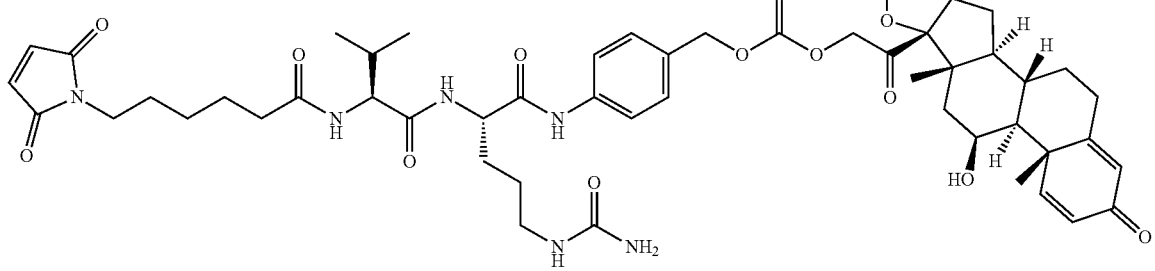

Following the general procedure A, the title compound 2a (10 mg, 17% yield) was obtained as a white solid. ESI m/z: 1029 (M+H)$^+$. Anal. HPLC: 92.5%, Retention time: 7.66 min (method A).

Example 2b 1-(4-{2-Azatricyclo[10.4.0.0$^{4,9}$]hexadeca-1(12),4(9),5,7,13,15-hexaen-10-yn-2-yl}-4-oxobutanam-[(1S,2S,4R,8S,9S,11S,12S,13R)-11-hydroxy-9,13-dimethyl-16-oxo-6-propyl-5,7-ido)-N-[(1S)-1-{[(1S)-4-(carbamoylamino)-1-[(4-{[({2dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-3,6,9,12-tetraoxapentadecan-15-amide (2b)

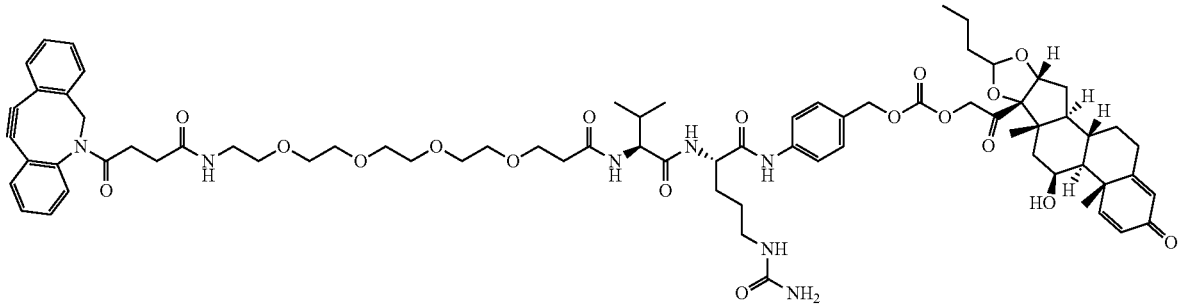 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

Following the general procedure B, the title compound 2b (3.0 mg, 21% yield) was obtained as a white solid. ESI m/z: 686 (M/2+H)$^+$. $^1$H NMR (400 MHz, DMSO$_{d6}$) δ 10.05 (s, 1H), 8.15 (d, J=7.5 Hz, 1H), 7.88 (d, J=8.8 Hz, 1H), 7.77 (t, J=5.7 Hz, 1H), 7.71-7.66 (m, 1H), 7.66-7.59 (m, 3H), 7.52-7.27 (m, 9H), 6.17 (d, J=10.0 Hz, 1H), 6.03-5.95 (m, 1H), 5.92 (s, 1H), 5.79-5.74 (m, 1H), 5.43 (s, 2H), 5.22-4.99 (m, 6H), 4.88-4.84 (m, 1H), 4.84-4.60 (m, 2H), 4.42-4.34 (m, 1H), 4.33-4.26 (m, 1H), 4.26-4.20 (m, 1H), 3.65-3.55 (m, 3H), 3.48-3.44 (m, 12H), 3.32-3.26 (m, 2H), 3.12-2.91 (m, 4H), 2.63-2.54 (m, 1H), 2.41-2.19 (m, 3H), 2.03-1.94 (m, 4H), 1.84-1.78 (m, 2H), 1.63-1.22 (m, 14H), 1.03-0.82 (m, 15H) ppm. Anal. HPLC: 96.9%, Retention time: 8.10 min (method B).

Example 2c (2R)-2-Amino-N-[(1S)-1-{[(1S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-6-[2-(cyclooct-2-yn-1-yloxy)acetamido]hexanamide (7)

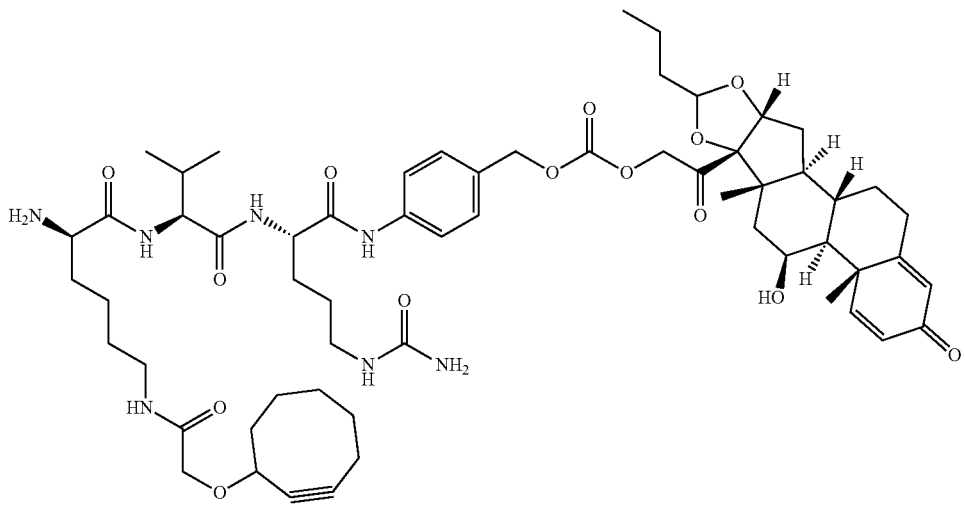 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@H](N)CCCCNC(=O)COC3C#CCCCCC3)C(C)C)cc2)O1]

ESI m/z: 565 (M/2+H)$^+$. $^1$H NMR (500 MHz, DMSO$_{d6}$) δ 10.17-10.00 (m, 1H), 8.47-7.73 (m, 2H), 7.69-7.57 (m, 3H), 7.38-7.26 (m, 3H), 6.17 (d, J=10.0 Hz, 1H), 5.99 (s, 1H), 5.92 (s, 1H), 5.76 (s, 1H), 5.42 (s, 2H), 5.23-5.01 (m, 4H), 4.88-4.61 (m, 3.4H), 4.43-4.16 (m, 4.6H), 3.85 (d, J=14.7 Hz, 1H), 3.73 (d, J=14.5 Hz, 1H), 3.23-3.18 (m, 1H), 3.09-2.90 (m, 4H), 2.33-2.18 (m, 3H), 2.18-2.04 (m, 3H), 2.03-1.66 (m, 10H), 1.64-1.50 (m, 7H), 1.49-1.22 (m, 13H), 1.17-0.90 (m, 4H), 0.90-0.79 (m, 12H) ppm.

(2R)-2-Amino-N-[(1S)-1-{[(1S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}carbonyl)oxy]methyl}phenyl)carbamoyl]butyl]carbamoyl}-2-methylpropyl]-6-[2-({1-[(2R,3R,4S,5R,6R)-3,4,5-trihydroxy-6-(hydroxymethyl)oxan-2-yl]-1H,4H,5H,6H,7H,8H,9H-cycloocta[d][1,2,3]triazol-4-yl}oxy)acetamido]hexanamide (9)

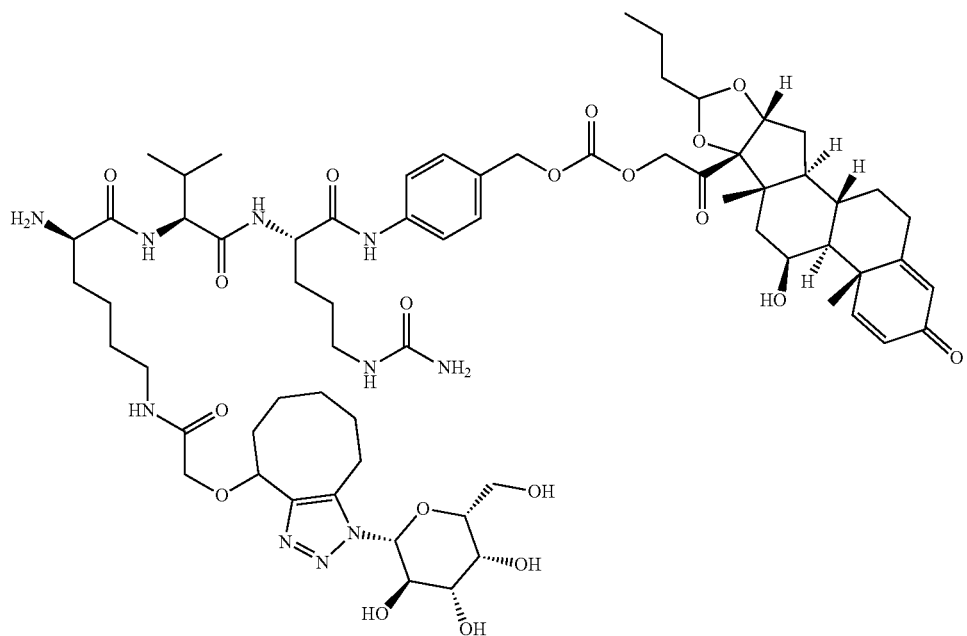 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@H](N)CCCCNC(=O)COC3CCCCCc4c3nnn4[C@@H]3O[C@H](CO)[C@H](O)[C@H](O)[C@H]3O)C(C)C)cc2)O1]

After filtered, the resulting solution of 9 was directly used directly for the next step. ESI m/z: 667 (M/2+H)⁺

N-[(1R)-1-{[(1S)-1-{[(1S)-4-(Carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}carbonyl)oxy]methyl}phenyl)carbamoyl]butyl]carbamoyl}-2-methylpropyl]carbamoyl}-5-[2-({1-[(2R,3R,4S,5R,6R)-3,4,5-trihydroxy-6-(hydroxymethyl)oxan-2-yl]-4H,5H,6H,7H,8H,9H-cycloocta[d][1,2,3]triazol-4-yl}oxy)acetamido]pentyl]-1-(2,5-dioxopyrrol-1-yl)-3,6,9,12-tetraoxapentadecan-15-amide (Mc-PEG₄-N(sugar-COT)Lys-vc-PAB-Budesonide) (2c)

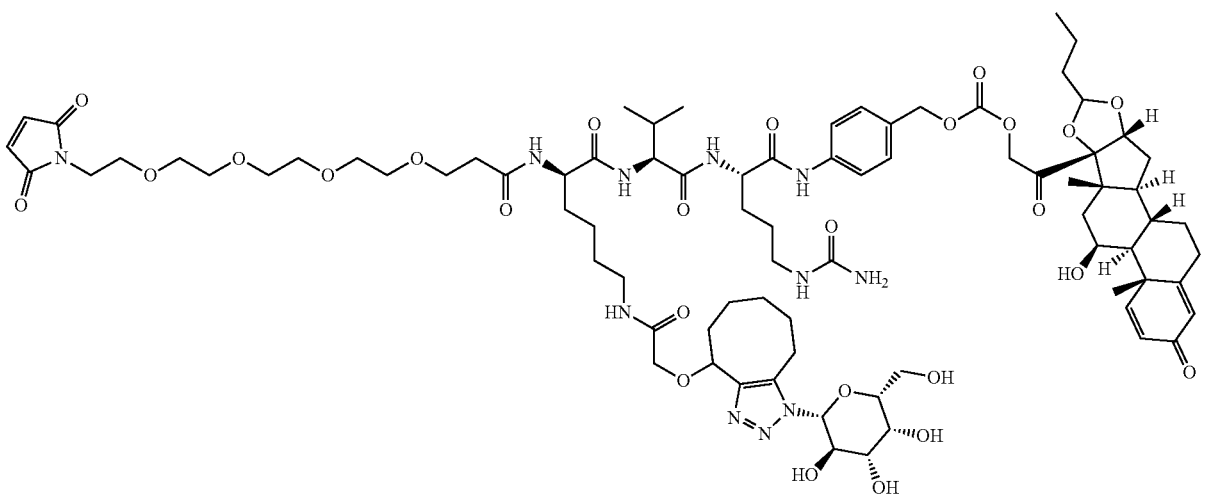 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@@H](CCCCNC(=O)COC3CCCCCc4c3nnn4[C@@H]3O[C@H](CO)[C@H](O)[C@H](O)[C@H]3O)NC(=O)CCOCCOCCOCCOCCN3C(=O)C=CC3=O)C(C)C)cc2)O1]

ESI m/z: 831 (M/2+H)⁺. ¹H NMR (400 MHz, DMSO$_{d6}$) δ 9.73 (s, 1H), 8.21-8.07 (m, 3H), 7.94-7.82 (m, 1H), 7.71-7.59 (m, 3H), 7.39-7.26 (m, 4H), 7.02 (s, 1H), 6.17 (d, J=10.0 Hz, 1H), 6.09-5.98 (m, 1H), 5.92 (s, 1H), 5.56-5.28 (m, 4H), 5.25-5.01 (m, 4H), 4.90-4.62 (m, 5H), 4.39-4.13 (m, 5H), 3.84-3.69 (m, 4H), 3.59-3.40 (m, 16H), 3.17-2.79 (m, 9H), 2.43-1.71 (m, 13H), 1.71-1.42 (m, 15H), 1.40-1.19 (m, 11H), 1.04-0.77 (m, 15H) ppm. Anal. HPLC: 97.6%, Retention time: 7.63 min (method A).

Example 2d (2R)-2-Amino-N-[(1S)-1-{[(1S)-4-(carbamoyl-amino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}carbonyl)oxy]methyl}phenyl)carbamoyl]butyl]carbamoyl}-2-methylpropyl]-N'-[(2S)-2-[(4R,5R)-5-[(4R)-2,2-dimethyl-1,3-dioxolan-4-yl]-2,2-dimethyl-1,3-dioxolan-4-yl]-2-hydroxyethyl]pentanediamide (10)

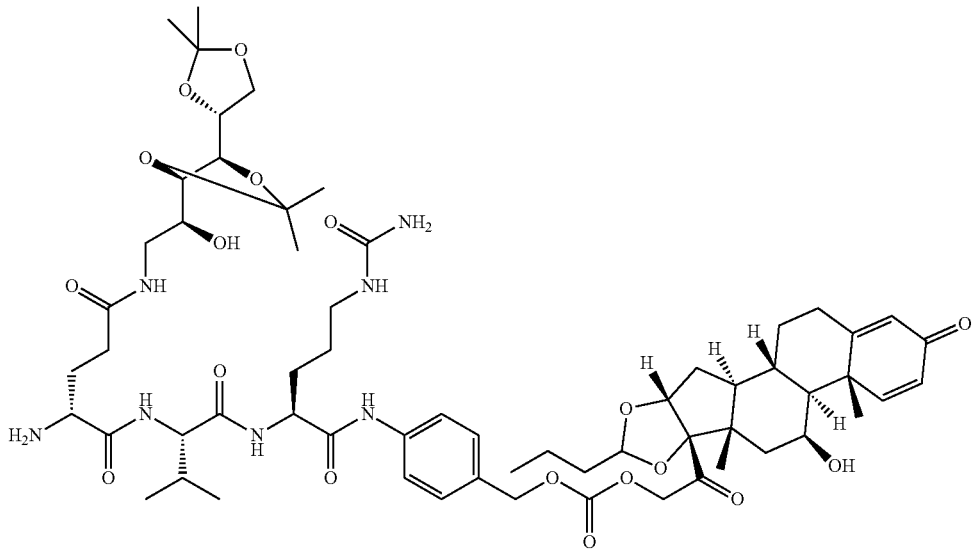

Following the general procedure C, compound 10 (13 mg, 5% yield) was obtained as a white solid. ESI m/z: 605 (M/2+H)⁺. ¹H NMR (500 MHz, DMSO$_{d6}$) δ 10.08 (s, 1H), 8.34-8.17 (m, 1H), 7.98 (s, 1H), 7.93-7.81 (m, 1H), 7.62 (d, J=8.4 Hz, 2H), 7.42-7.26 (m, 3H), 6.17 (d, J=10.1 Hz, 1H), 5.99 (s, 1H), 5.92 (s, 1H), 5.76 (s, 1H), 5.42 (s, 2H), 5.23-5.01 (m, 4H), 4.91-4.61 (m, 4H), 4.43-4.20 (m, 3H), 4.10-3.72 (m, 6H), 3.60-3.54 (m, 1H), 3.24-3.09 (m, 2H), 3.07-2.91 (m, 2H), 2.32-2.25 (m, 1H), 2.22-2.10 (m, 2H), 2.04-1.93 (m, 2H), 1.88-1.67 (m, 5H), 1.64-1.22 (m, 27H), 1.17-0.93 (m, 3H), 0.91-0.81 (m, 12H) ppm.

(2R)-2-Amino-N-[(1S)-1-{[(1S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}carbonyl)oxy]methyl}phenyl)carbamoyl]butyl]carbamoyl}-2-methylpropyl]-N-[(2S,3R,4R,5R)-2,3,4,5,6-pentahydroxyhexyl]pentanediamide (10A)

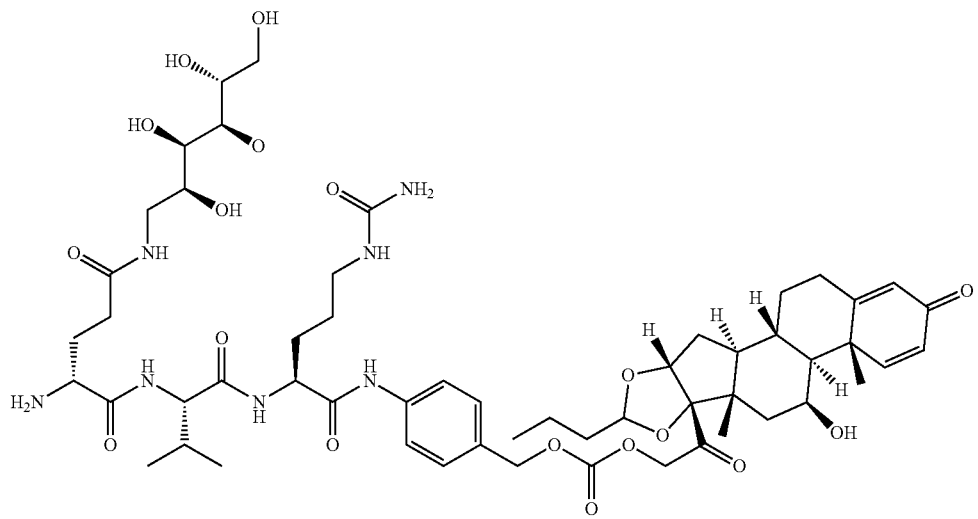 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@H](N)CCC(=O)NC[C@H](O)[C@@H](O)[C@H](O)[C@H](O)CO)C(C)C)cc2)O1]

To a mixture of compound 10 (13 mg, 11 μmol) in DCM (1 mL) was added TFA (1 mL) dropwise. The mixture was stirred at RT for an hour which was monitored by LCMS. The volatiles were removed in vacuo to give crude deprotection product 10A (13 mg) as a light yellow oil, which was used for the next step without further purification. ESI m/z: 565 (M/2+H)⁺.

(2R)-N-[(1S)-1-{[(1S)-4-(Carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}carbonyl)oxy]methyl}phenyl)carbamoyl]butyl]carbamoyl}-2-methylpropyl]-2-[1-(2,5-dioxopyrrol-1-yl)-3,6,9,12-tetraoxapentadecan-15-amido]-N'-[(2S,3R,4R,5R)-2,3,4,5,6-pentahydroxyhexyl]pentanediamide (2d)

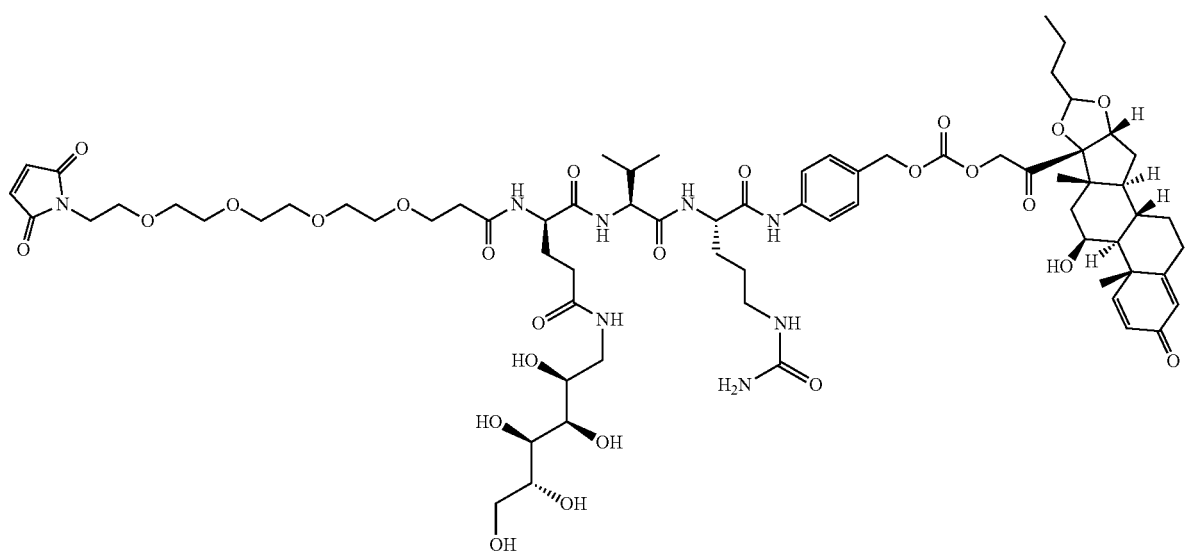 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCN3C(=O)C=CC3=O)C(C)C)cc2)O1]

Following the general procedure A, the title compound 2d (3.5 mg, 1% total yield from 4a) was obtained as a white solid. ESI m/z: 829.7 (M/2+H)⁺. ¹H NMR (400 MHz, DMSO$_{d6}$) δ 10.10 (s, 0.25H), 9.79 (s, 0.75H), 8.22 (d, J=7.1 Hz, 1H), 8.12 (d, J=7.5 Hz, 1H), 8.07 (d, J=7.8 Hz, 1H), 7.79-7.71 (m, 1H), 7.69-7.60 (m, 2H), 7.38-7.27 (m, 4H), 7.02 (d, J=1.4 Hz, 2H), 6.17 (dt, J=7.6, 1.6 Hz, 1H), 6.03-5.97 (m, 1H), 5.92 (s, 1H), 5.46-5.40 (m, 2H), 5.35-5.02 (m, 4H), 4.89-4.61 (m, 4H), 4.50-4.45 (m, 1H), 4.40-4.16 (m, 7H), 3.65-3.37 (m, 21H), 3.07-2.90 (m, 3H), 2.44-2.23 (m, 4H), 2.17-1.93 (m, 6H), 1.90-1.71 (m, 4H), 1.62-1.20 (m, 15H), 1.06-0.76 (m, 15H) ppm. Anal. HPLC: >99%, Retention time: 6.40 min (method A).
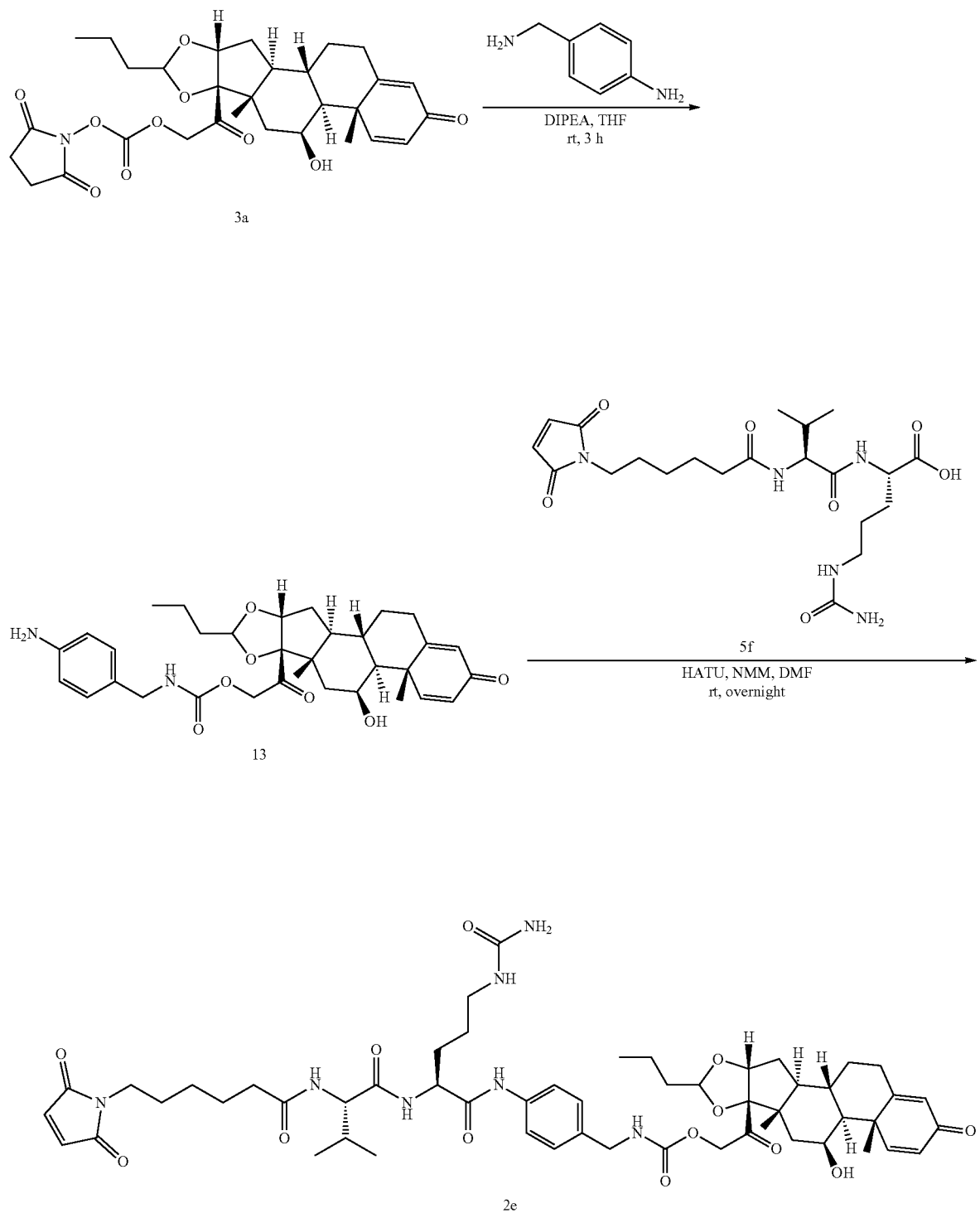

Example 2e

2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-[(4-aminophenyl)methyl]carbamate (13)

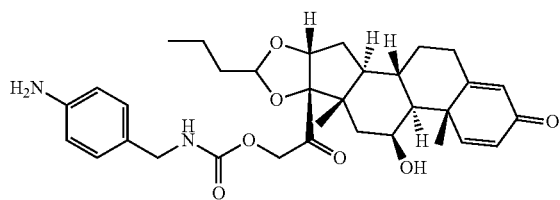 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)NCc2ccc(N)cc2)O1]

To a solution of 4-aminobenzylamine (9.7 mg, 79 μmol) and DIPEA (12 mg, 93 μmol) in THF (10 mL) was added a solution of 3a (24 mg, 44 μmol) in THF (5.0 mL) dropwise at RT. The mixture was stirred at RT for 3 hours until 3a was totally consumed, which was monitored by LCMS. The volatiles were removed in vacuo and residue was purified via prep-HPLC (method B) to give compound 13 (5.6 mg, yield 22%) as a white solid. ESI m/z: 579.2 (M+H)$^+$. $^1$H NMR (400 MHz, MeOD$_{d4}$) δ 7.48-7.45 (m, 3H), 7.31-7.28 (m, 2H), 6.27-6.24 (m, 1H), 6.02 (s, 1H), 5.22 (m, 1H), 5.12-5.11 (m, 1H), 4.96 (m, 1H), 4.86-4.81 (m, 2H), 4.66 (m, 1H), 4.44-4.35 (m, 3H), 2.66-2.65 (m, 1H), 2.40-2.36 (m, 1H), 2.15-2.10 (m, 2H), 1.97-1.60 (m, 6H), 1.53-1.36 (m, 6H), 1.09-0.92 (m, 7H) ppm.

2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-({4-[(2S)-5-(carbamoylamino)-2-[(2S)-2-[6-(2,5-dioxo-2,5-dihydro-1H-pyrrol-1-yl)hexanamido]-3-methylbutanamido]pentanamido]phenyl}methyl)carbamate (2e)

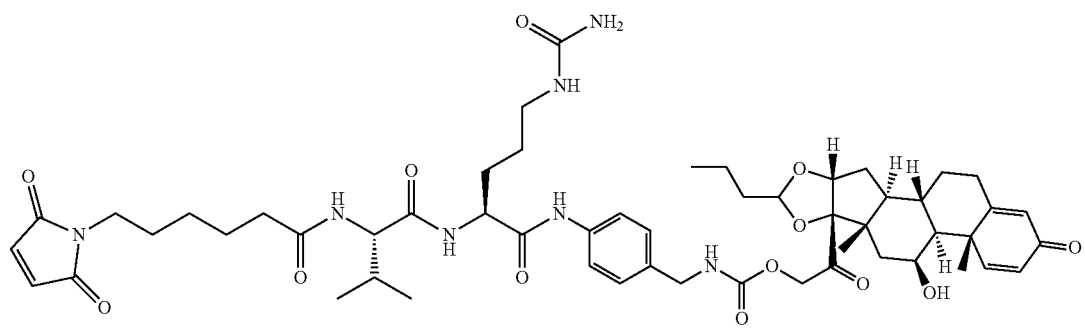 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)NCc2ccc(NC(=O)[C@H](CCCNC(N)=O)NC(=O)[C@@H](NC(=O)CCCCCN3C(=O)C=CC3=O)C(C)C)cc2)O1]

To a mixture of MC-VC-OH 5f (WO2014/191578 A1) (5.7 mg, 12 μmol) in dry DMF (1.5 mL) were added HATU (4.6 mg, 12 μmol) and NMM (4.0 mg, 40 μmol) at RT. The mixture was stirred at RT for 10 minutes before compound 13 (4.7 mg, 8.1 μmol) was added into the reaction mixture. The resulting mixture was stirred at RT overnight. Compound 13 was totally consumed and desired product was detected as major product according to LCMS. The mixture was directly purified by prep-HPLC to give title compound 2e (2.9 mg, yield 35%) as a white solid. ES m/z: 1029.1 (M+H)$^+$, 514.7 (M/2+H)$^+$. Anal. HPLC: >99%, Retention time: 7.54 min (method A).

Scheme 4. Synthesis of linker-spacer-budesonide (via ester) 2f & 2g

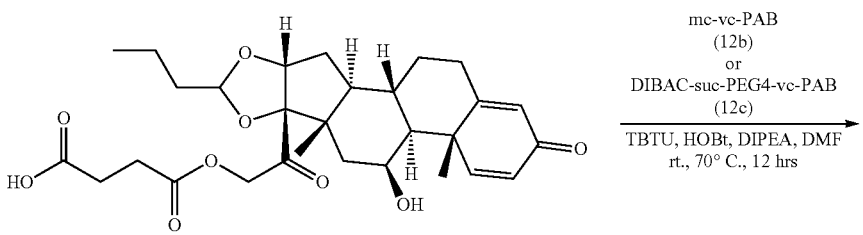

Scheme 4. Synthesis of linker-spacer-budesonide (via ester) 2f & 2g

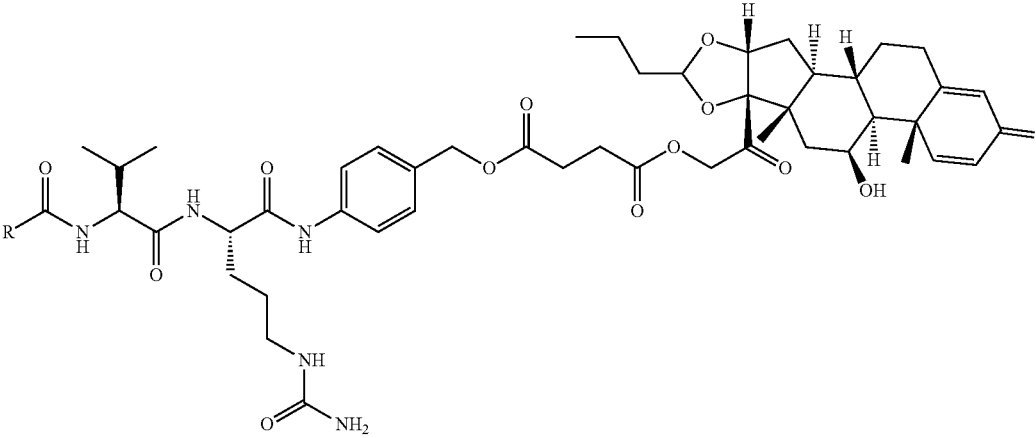

2f, 2g

| Compd # | R |
|---|---|
| 2f | MC |
| 2g | DIBAC-suc-PEG4 |

Example 2f

1-{4-[(2S)-5-(Carbamoylamino)-2-[(2S)-2-[6-(2,5-dioxo-2,5-dihydro-1H-pyrrol-1-yl)hexanamido]-3-methylbutanamido]pentanamido]phenyl}methyl 4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxo-ethyl} butanedioate (2f)

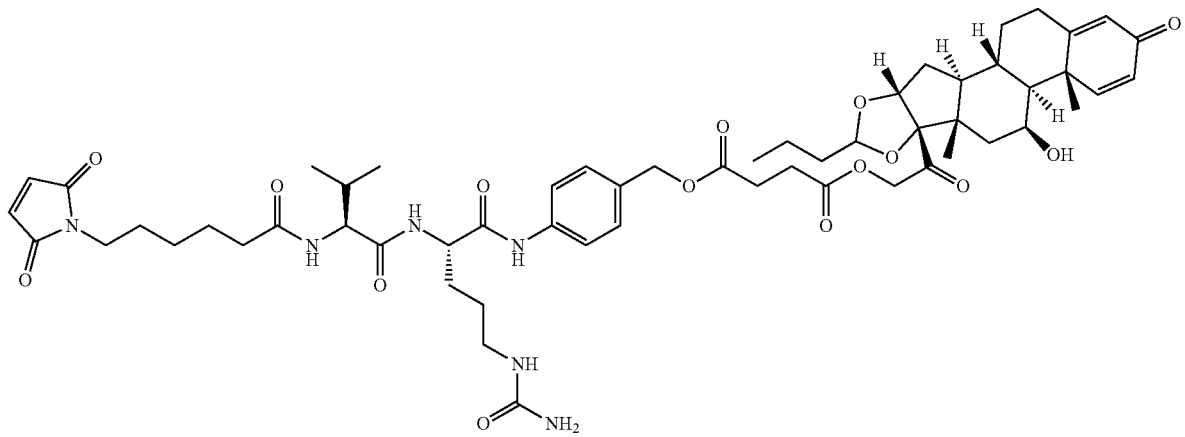 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(NC(=O)[C@H](CCCNC(N)=O)NC(=O)[C@@H](NC(=O)CCCCCN3C(=O)C=CC3=O)C(C)C)cc2)O1]

To a solution of 1c (20 mg, 38 μmol) in DMF (2 mL) were added MC-VCPAB (12b, 0.11 g, 0.19 mmol), TBTU (63 mg, 0.19 mmol), HOBt (26 mg, 0.19 mmol) and DIPEA (41 mg, 0.19 mmol) at RT. The resulting mixture was stirred at 70° C. for 12 hours. No more product 2f was formed, which was monitored by LCMS. The reaction mixture was directly purified by prep-HPLC (method A) to give title compound 2f (2.6 mg, yield 6%) as a white solid. ESI m/z: 1085.3 (M+H)$^+$. $^1$H NMR (400 MHz, CDCl$_3$) δ 7.55-7.52 (m, 1H), 7.34-7.30 (m, 1H), 6.67 (br s, 1H), 6.30-6.27 (m, 1H), 6.03 (br s, 1H), 5.16-5.11 (m, 2H), 5.09-4.87 (m, 2H), 4.80-4.61 (m, 1H), 4.60-4.30 (m, 2H), 3.47-3.44 (m, 1H), 3.21-3.10 (m, 1H), 3.03-2.96 (m, 2H), 2.79-2.55 (m, 4H), 2.35-1.73 (m, 28H), 1.71-1.32 (m, 15H), 1.29-1.07 (m, 4H), 0.99-0.85 (m, 9H) ppm.

Example 2g

1-{4-[(2S)-2-[(2S)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-{2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl} butanedioate (2g)

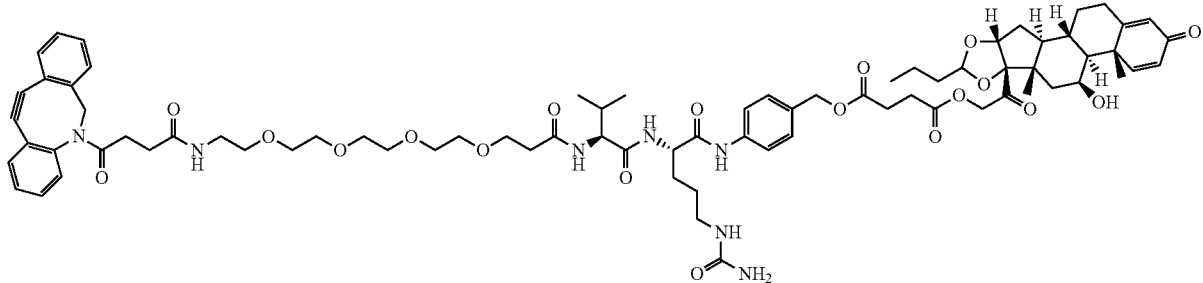 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

Following the procedures of example 2f except substituting DIBAC-suc-PEG4-ve-PAB (12c) for 12b, the title compound 2g (15 mg, yield 19%) as a white solid. ESI m/z: 714 (M/2+H)⁺. ¹H NMR (500 MHz, MeOD$_{d4}$) δ 7.67-7.60 (m, 4H), 7.48-7.46 (m, 4H), 7.38-7.32 (m, 4H), 7.26 (d, J=6.8 Hz, 1H), 6.27 (d, J=10.0 Hz, 1H), 6.03 (s, 1H), 5.24-5.10 (m, 4H), 5.02-4.97 (m, 1H), 4.85-4.66 (m, 2H), 4.61 (s, 1H), 4.53 (dd, J=9.1, 4.9 Hz, 1H), 4.45-4.43 (m, 1H), 4.22 (dd, J=6.7, 4.7 Hz, 1H), 3.78-3.69 (m, 3H), 3.60-3.55 (m, 11H), 3.47-3.40 (m, 2H), 3.26-3.10 (m, 4H), 2.78-2.54 (m, 8H), 2.41-2.35 (m, 2H), 2.25-2.11 (m, 4H), 2.02-1.31 (m, 17H), 1.21-0.92 (m, 14H) ppm. Anal. HPLC: 99.5%, Retention time: 7.86 min (method B).

Scheme 5. Synthesis of linker-spacer-budesonide 2j-2n (via amide or carbamate)

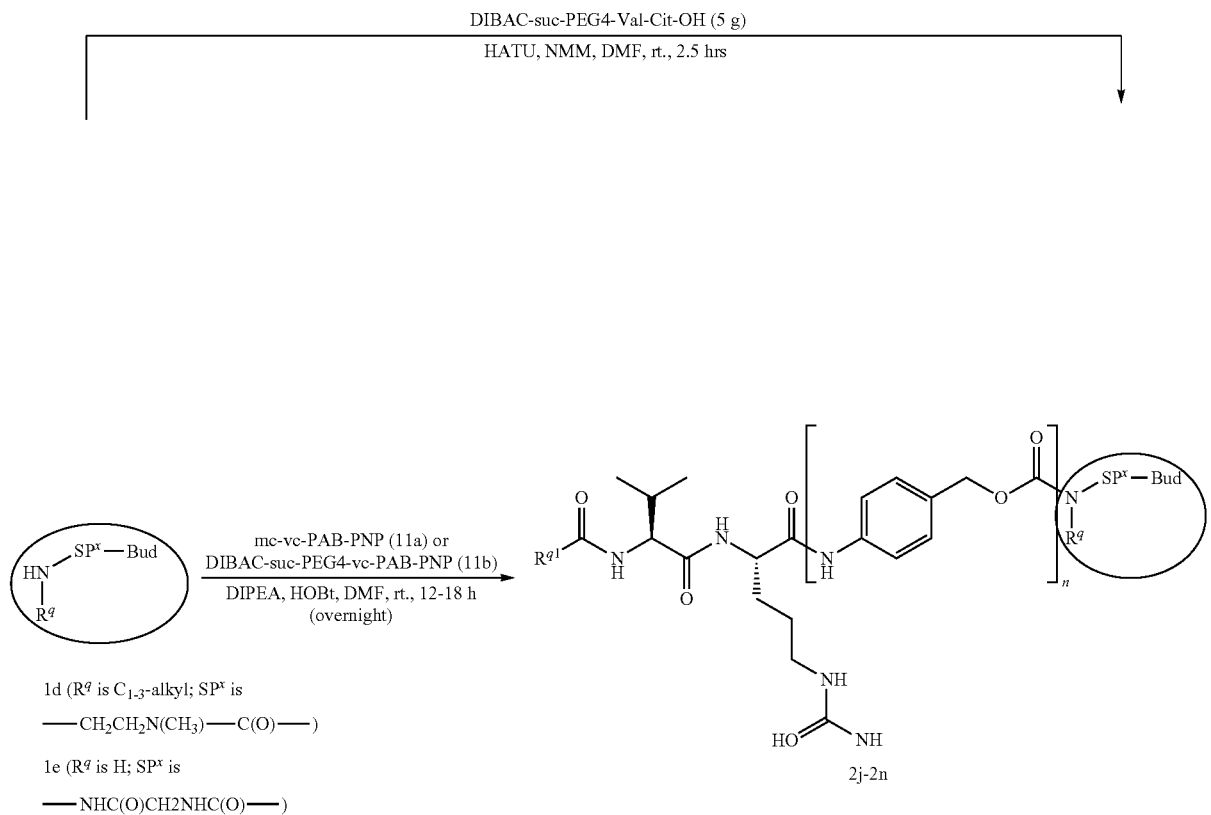

-continued

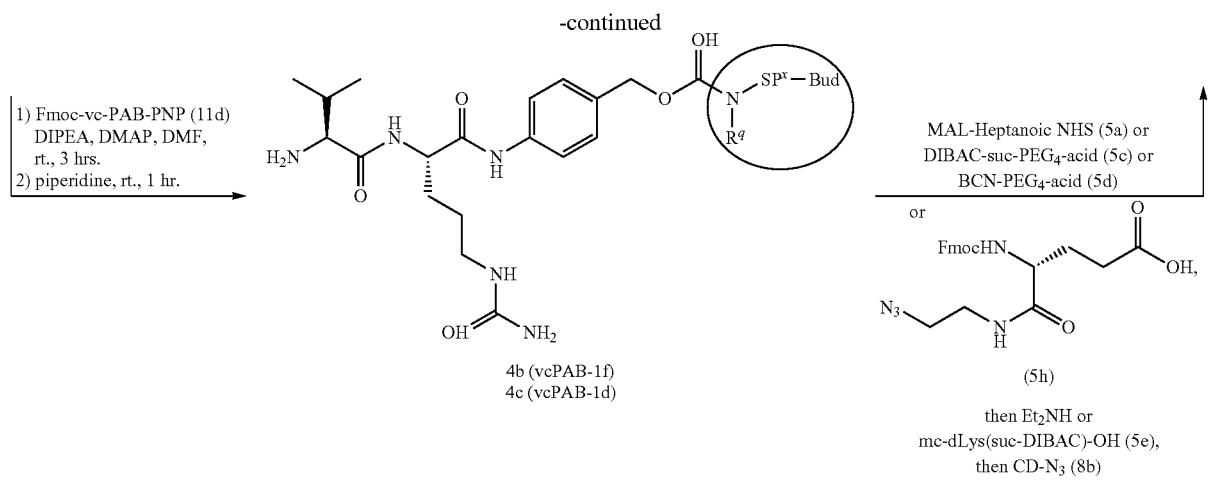

4b (vcPAB-1f)
4c (vcPAB-1d)

then Et₂NH or
mc-dLys(suc-DIBAC)-OH (5e),
then CD-N₃ (8b)

In Scheme 5, Bud refers to budesonide.

Most Budesonide-Linkers (2) having VC-PAB moiety were synthesized from three approaches via amide or carbamate (Scheme 5). The compounds 1d, 1e were separately conjugated with linkers by amide coupling to give amide or carbamate (Scheme 5). In the table below are additional details.

| Compd No | $R^{q1}$ in 2j, 2k, 2l, 2m, 2n | n in 2j-n | $R^q$-NH-Spacer-Budesonide |
|---|---|---|---|
| 2j | (maleimide-hexyl) | 1 | 1e |
| 2k | (maleimide-hexyl) | 1 | 1d |
| 2l | (BCN-carbamate-PEG4) | 1 | 1d |

-continued
| Compd No | R$^{q1}$ in 2j, 2k, 2l, 2m, 2n | n in 2j-n | R$^q$-NH-Spacer-Budesonide |
|---|---|---|---|
| 2m | 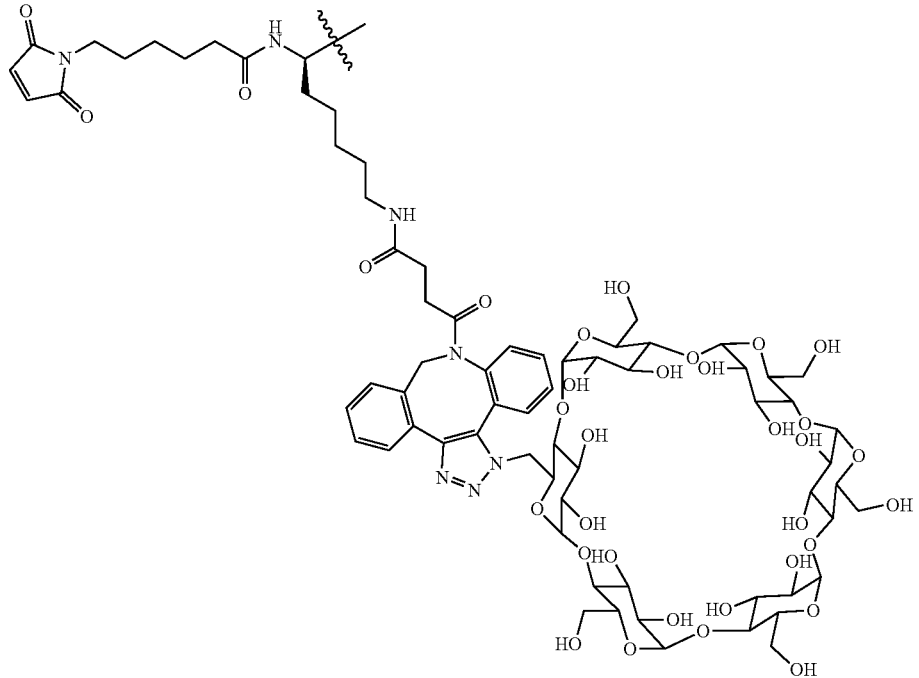 [SMILES: *[C@@H](CCCCCNC(=O)CCC(=O)N1Cc2ccccc2-c2nnn(CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)c2-c2ccccc21)NC(=O)CCCCCN1C(=O)C=CC1=O] | 1 | 1d |
| 2n | 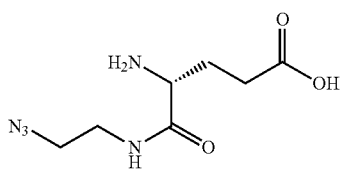 [SMILES: [N-]=[N+]=NCCNC(=O)[C@H](N)CCC(=O)O] | 1 | 1d |

Intermediate 4c

2-[(1S,2S,4R,8S,9S,11S,12S,13R)-11-Hydroxy-9,13-dimethyl-16-oxo-6-propyl-5,7-dioxapentacyclo[1.8.0.0²,⁹.0⁴,⁸.0¹³,¹⁸]icosa-14,17-dien-8-yl]-2-oxo-ethyl N-(2-{[({4-[(2S)-2-[(2S)-2-amino-3-methylbutanamido]-5-(carbamoylamino)pentanamido]phenyl}methoxy)carbonyl](methyl)amino}ethyl)-N-methylcarbamate (4c)

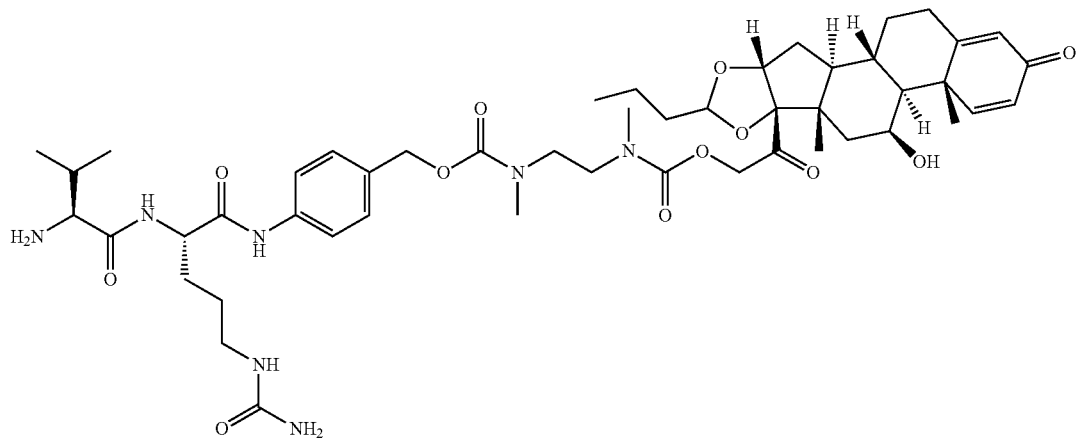 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](N)C(C)C)cc2)O1]

To a solution of compound 1d (40 mg, 73 μmol) in DMF (3 mL) were added Fmoc-vcPAB-PNP (11d, 60 mg, 78 μmol), DMAP (9.0 mg, 74 μmol) and DIPEA (20 mg, 0.16 mmol) at room temperature. The mixture was stirred at room temperature for 3 hours until most of starting materials were consumed, which was monitored by LCMS. To the reaction mixture was then added piperidine (1 mL). After stirred at room temperature for an hour until the de-Fmoc reaction was completed, which was monitored by LCMS, the reaction mixture was directly purified by prep-HPLC (method B) to give compound 4c (9.0 mg, yield 13%, the 2$^{nd}$ peak in LC) as a white solid. ESI m/z: 951 (M+H)⁺, 973 (M+Na)⁺.

Example 2j

2-[(1S,2S,4R,8S,9S,11S,12S,13R)-11-Hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxo-ethyl N-({N'-[({4-[(2S)-5-(carbamoylamino)-2-[(2S)-2-[6-(2,5-dioxo-2,5-dihydro-1H-pyrrol-1-yl)hexanamido]-3-methylbutanamido]pentanamido]phenyl}methoxy)carbonyl]hydrazinecarbonyl}methyl)carbamate (2j)

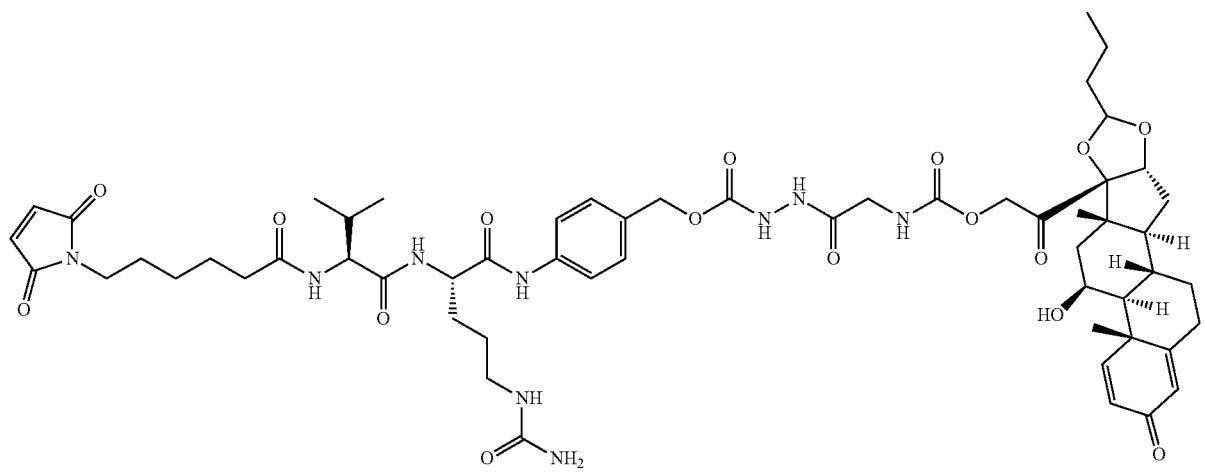

ESI m/z: 1144.3 (M+H)⁺. ¹H NMR (400 MHz, CDCl₃) δ 10.02 (s, 1H), 9.77 (s, 1H), 9.18 (s, 1H), 8.12 (d, J=7.2 Hz, 1H), 7.83 (d, J=8.4 Hz, 1H), 7.73-7.70 (m, 1H), 7.61-7.59 (m, 2H), 7.32-7.29 (m, 3H), 7.01 (s, 2H), 6.19-6.16 (m, 1H), 6.00-5.92 (m, 2H), 5.05-5.00 (m, 2H), 4.95-4.85 (m, 2H), 4.71-4.62 (m, 2H), 4.40-4.17 (m, 3H), 3.71-3.58 (m, 2H), 3.45-3.39 (m, 2H), 3.06-2.89 (m, 3H), 2.33-2.28 (m, 2H), 2.20-2.07 (m, 3H), 2.02-1.91 (m, 3H), 1.81-1.75 (m, 2H), 1.75-1.62 (m, 2H), 1.60-1.44 (m, 11H), 1.42-1.20 (m, 6H), 1.19-1.12 (m, 4H), 1.00-0.92 (m, 2H), 0.88-0.81 (m, 10H) ppm.

Example 2k

2-[(1S,2S,4R,8S,9S,11S,12S,13R)-11-Hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl N-(2-{[({4-[(2S)-5-(carbamoylamino)-2-[(2S)-2-[6-(2,5-dioxo-2,5-dihydro-1H-pyrrol-1-yl)hexanamido]-3-methylbutanamido]pentanamido]phenyl}methoxy)carbonyl](methyl)amino}ethyl)-N-methylcarbamate (2k-A and 2k-B)

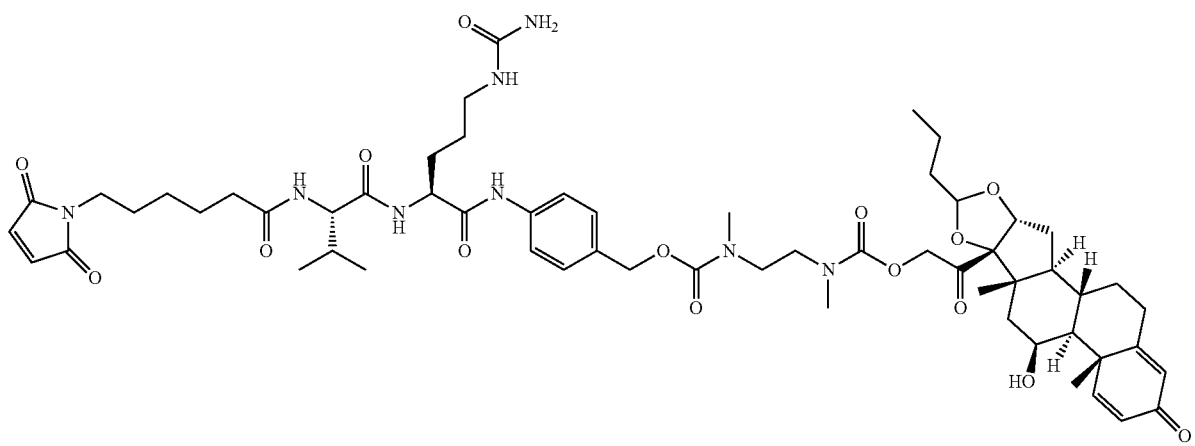 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCCCCN3C(=O)C=CC3=O)C(C)C)cc2)O1]

Following the general procedure D, the title compounds 2k-A (3.3 mg, yield 10%, the second peak in LC) and 2k-B (4.1 mg, yield 12%, the first peak in LC) as diastereoisomers were obtained as white solids. 2k-A: ESI m/z: 1143.4 (M+H)⁺, Retention time: 1.70 min (method A). 2k-B: ESI m/z: 1143.4 (M+H)⁺, Retention time: 1.65 min (method A).

Example 2l

Bicyclo[6.1.0]non-4-yn-9-ylmethyl N-(14-{[(1S)-1-{[(1S)-4-(carbamoylamino)-1-[(4-{[({2-[({2-[(1S,2S,4R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}carbonyl)(methyl)amino]ethyl}(methyl)carbamoyl)oxy]methyl}phenyl)carbamoyl]butyl]carbamoyl}-2-methylpropyl]carbamoyl}-3,6,9,12-tetraoxatetradecan-1-yl)carbamate (2l)

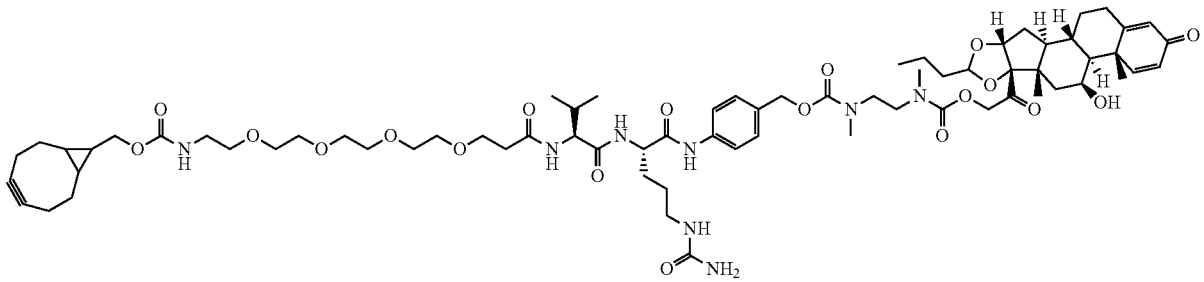 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)OCC3C4CCC#CCCC43)C(C)C)cc2)O1]

ESI m/z: 687.5 (M/2+H)⁺, 1396.8 (M+Na)⁺ (50%), H NMR (500 MHz, MeOD$_{d4}$) δ 7.66 (d, J=7.5 Hz, 2H), 7.50 (d, J=10.0 Hz, 1H), 7.36 (d, J=7.0 Hz, 2H), 6.28 (d, J=10.0 Hz, 1H), 6.04 (s, 1H), 5.15-5.05 (m, 2H), 4.87-4.62 (m, 4H), 4.53 (s, 1H), 4.46 (s, 1H), 4.21 (d, J=6.5 Hz, 1H), 4.16 (d, J=8.0 Hz, 2H), 3.83-3.72 (m, 2H), 3.66-3.60 (m, 12H), 3.56-3.52 (m, 3H), 3.49-3.42 (m, 1H), 3.30 (s, 3H), 3.25-3.09 (m, 3H), 3.02-2.96 (m, 4H), 2.87 (dd, J=16.6, 4.8 Hz, 2H), 2.72-2.64 (m, 1H), 2.58 (t, J=6.0 Hz, 2H), 2.40 (d, J=13.1 Hz, 1H), 2.31-2.10 (m, 9H), 2.01-1.91 (m, 3H), 1.81-1.70 (m, 2H), 1.63 (s, 7H), 1.51 (s, 3H), 1.48-1.30 (m, 4H), 1.11 (s, 1H), 1.02-0.91 (m, 15H) ppm. Anal. HPLC: >99.9%, Retention time: 9.40 min (method A).

Example 2m

2-[(1S,2S,4R,8S,9S,11S,12S,13R)-11-Hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxo-ethyl N-(2-{[({4-[(2S)-2-[(2S)-2-[(2R)-6-(4-{2-azatricyclo[10.4.0.0⁴,⁹]hexadeca-1(12),4(9),5,7,13,15-hexaen-10-yn-2-yl}-4-oxobutanamido)-2-[6-(2,5-dioxo-2,5-dihydro-1H-pyrrol-1-yl)hexanamido]hexanamido]-3-methylbutanamido]-5-(carbamoylamino)pentanamido]phenyl}methoxy)carbonyl](methyl) amino}ethyl)-N-methylcarbamate (2m-precursor)

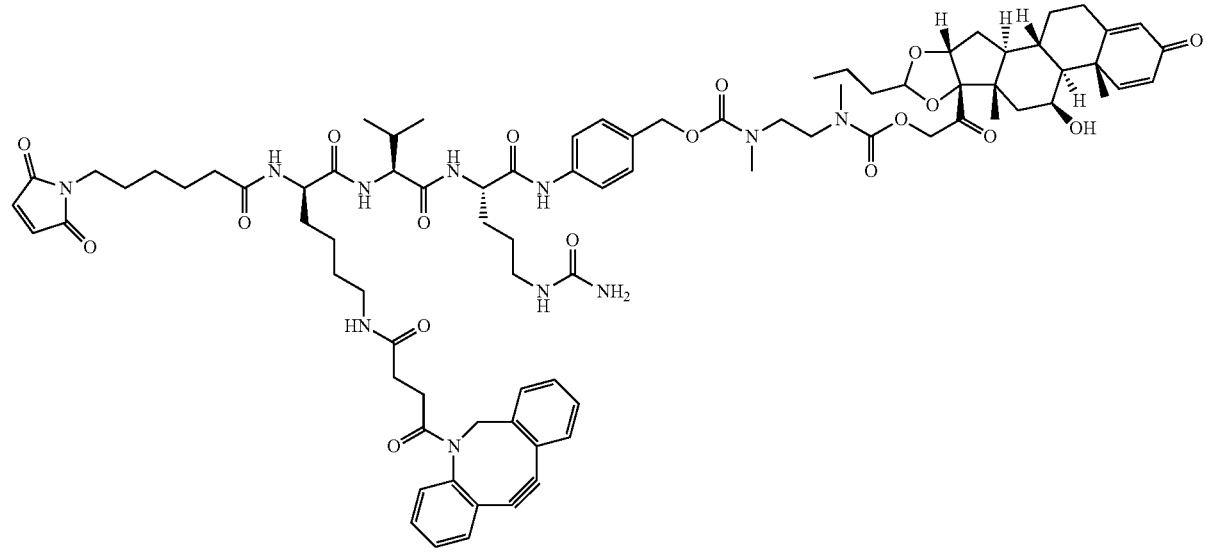 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)[C@@H](CCCCNC(=O)CCC(=O)N3Cc4ccccc4C#Cc4ccccc43)NC(=O)CCCCCN3C(=O)C=CC3=O)C(C)C)cc2)O1]

Following the general procedure B, the crude compound 2m-precursor (the precursor of 2m) (5 mg) was obtained as light yellow oil, which was used directly for the next step. ESI m/z: 780 (M/2+H)⁺

2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxo-ethyl N-(2-{[({4-[(2S)-5-(carbamoylamino)-2-[(2S)-2-[(2R)-2-[6-(2,5-dioxo-2,5-dihydro-1H-pyrrol-1-yl)hexanamido]-6-[4-(3-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-3,4,5,13-tetraaza-tetracyclo[13.4.0.0$^{2,6}$.0$^{7,12}$]nonadeca-1(15),2(6),4,7(12),8,10,16,18-octaen-13-yl)-4-oxobutanamido]hexanamido]-3-methylbutanamido]pentanamido]phenyl}methoxy) carbonyl](methyl)amino}ethyl)-N-methylcarbamate (2m)

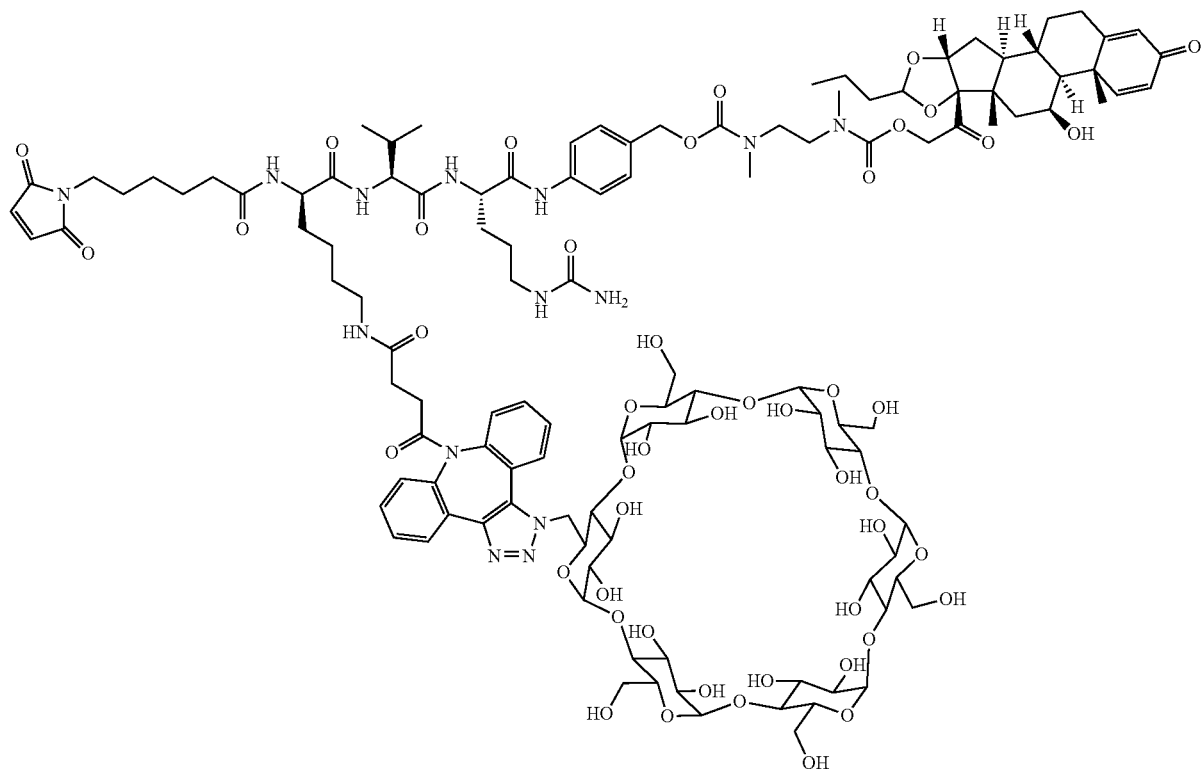 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)[C@@H](CCCCNC(=O)CCC(=O)N3c4ccccc4-c4nnn(CC5OC6OC7C(CO)OC(OC8C(CO)OC(OC9C(CO)OC(OC%10C(CO)OC(OC%11C(CO)OC(OC5C(O)C6O)C(O)C%11O)C(O)C%10O)C(O)C9O)C(O)C8O)C(O)C7O)c4-c4ccccc43)NC(=O)CCCCCN3C(=O)C=CC3=O)C(C)C)cc2)O1]

To a solution of crude 2m (5 mg) in DMF (1 mL) was added CD-N$_3$ (8b, 63 mg, 63 μmol). The resulting mixture was stirred at RT for 72 hours, which was monitored by LCMS. The resulting mixture was directly purified by prep-HPLC (method A) to give compound 2m (2 mg, 4% yield from 4c) as a white solid. ESI m/z: 1278.8 (M/2+H)$^+$. Anal. HPLC: 97.9%, Retention time: 6.49 min (method A).

Example 2n

2-[(1S,2S,4R,8S,9S,11S,12S,13R)-11-Hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl N-(2-{[({4-[(2S)-2-[(2S)-2-[(4R)-4-amino-4-[(2-azidoethyl)carbamoyl]butanamido]-3-methylbutanamido]-5-(carbamoylamino)pentanamido]phenyl}methoxy)carbonyl](methyl)amino}ethyl)-N-methylcarbamate (2n)

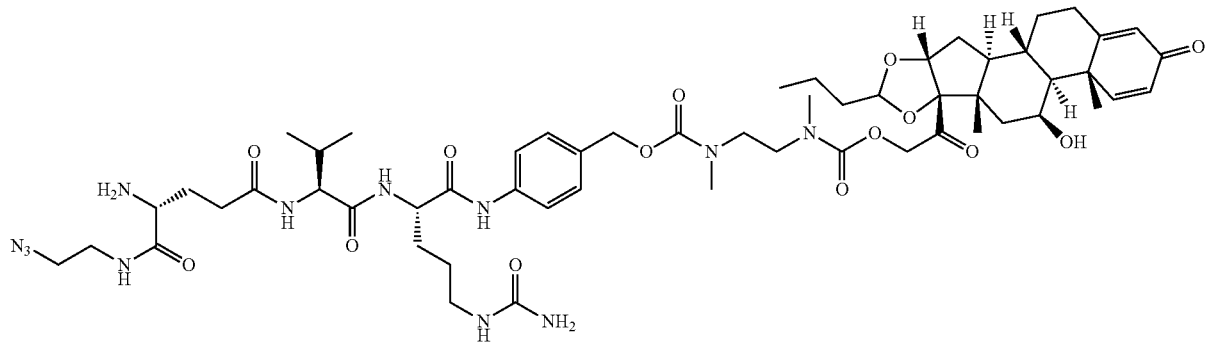 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CC[C@@H](N)C(=O)NCCN=[N+]=[N-])C(C)C)cc2)O1]

The reaction mixture was then stirred at RT overnight. Compound 4c was totally consumed according to LCMS. The mixture was separated by prep-HPLC (method A) and after lyophilization, Fmoc-2n was obtained (20 mg), which was dissolved in DMF (2 mL). To the DMF solution was added diethylamine (4 drops, c.a. 0.08 mL). The reaction mixture was stirred at RT for 2 hours until de-Fmoc reaction was completed, which was monitored by LCMS. The mixture was filtered through filter membrane and the solution was purified by prep-HPLC (method A) to give the title compound 2n (10 mg, yield 8.4%) as a white solid. ESI m/z: 1147 (M+H)⁺. Anal. HPLC: 99.6%, Retention time: 5.67 min (method A); 7.72 min (method B).

Scheme 6. Synthesis of Linker-Budesonide 2q (THP analog)

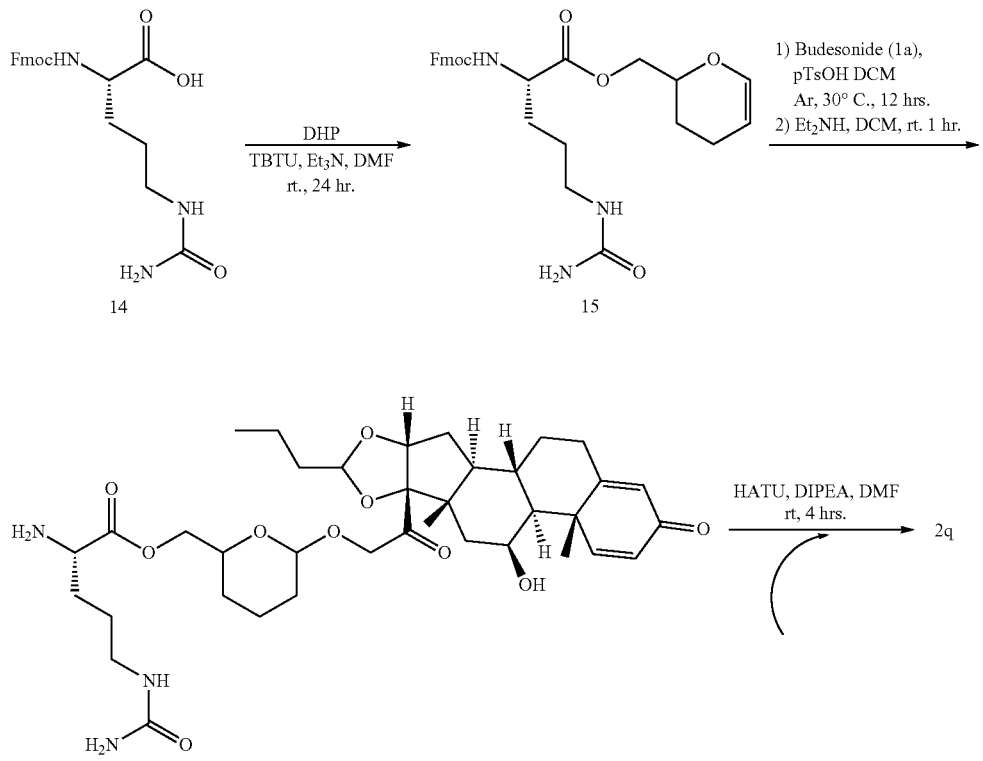

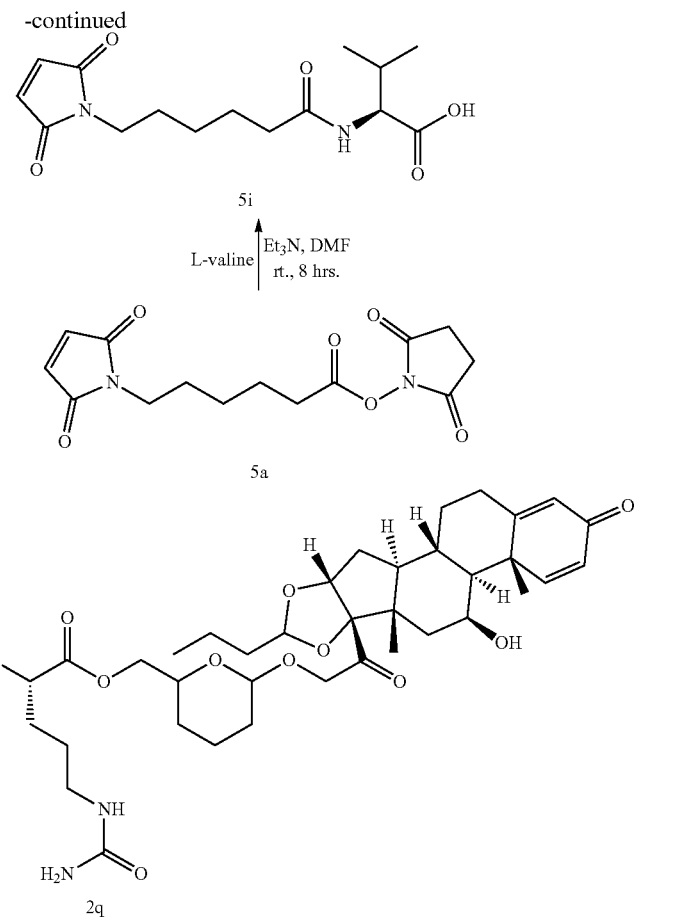

Example 2q (2S)-(3,4-Dihydro-2H-pyran-2-yl)methyl 2-(((9H-fluoren-9-yl)methoxy)carbonylamino)-5-ureidopentanoate (15)

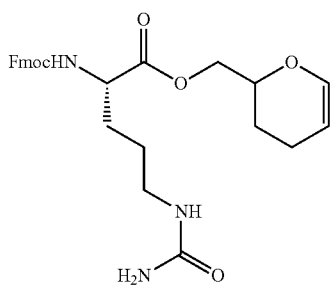

To a mixture of Fmoc-Cit-OH (14, 0.29 g, 0.73 mmol) in DMF (5 mL) were added DHP (0.10 mg, 0.88 mmol), TBTU (0.70 g, 2.2 mmol) and triethylamine (0.37 g, 3.7 mmol) at RT. The resulting mixture was stirred at RT for 24 hours. 15% of desired mass was detected by LCMS. The reaction was quenched with water (30 mL) and extracted with ethyl acetate (10 mL×3). The combined organic solution was washed with water and brine, dried over sodium sulfate and concentrated in vacuo. The crude product was purified by reversed phase flash chromatography (0-100% acetonitrile in water) to give title compound 15 (110 mg, yield 30%) as colorless oil. ESI m/z: 494 (M+H)$^+$.

(6-{2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}oxan-2-yl)methyl (2S)-2-amino-5-(carbamoylamino)pentanoate (16)

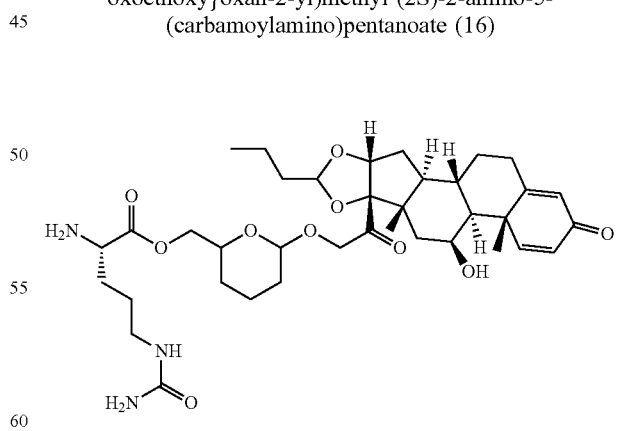

To a solution of compound 15 (80 mg, 0.16 mmol) in anhydrous DCM (3 mL) was added a solution of budesonide (1a, 70 mg, 0.16 mmol) and p-toluenesulfonic acid (42 mg, 0.24 mmol) in anhydrous DCM (2 mL) by syringe under protection of argon balloon at RT. The reaction mixture was stirred at 30° C. under argon balloon for 12 hours. Most of compound 15 was consumed according to LCMS. The reaction mixture was cooled to RT, and to the reaction mixture was added diethylamine (1 mL). The reaction mixture was stirred at RT for 1 hours until de-Fmoc reaction was completed, which was monitored by LCMS. The volatiles were removed in vacuo and the residue was purified by prep-HPLC (method B) to give the title compound 16 (17 mg, yield 31%) as a white solid. ESI m/z: 702 (M+H)$^+$.

(S)-2-(6-(2,5-Dioxo-2,5-dihydro-1H-pyrrol-1-yl) hexanamido)-3-methylbutanoic acid (5i)

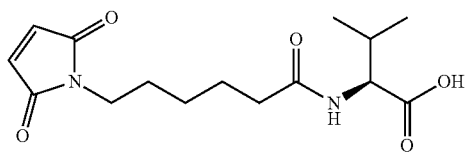 [SMILES: CC(C)[C@H](NC(=O)CCCCCN1C(=O)C=CC1=O)C(=O)O]

To a solution of L-valine (0.12 g, 1.0 mmol) in anhydrous DMF (2 mL) were added compound 5a (0.31 g, 1.0 mmol) and triethylamine (0.51 g, 5.0 mmol) at RT. The reaction mixture was stirred at RT for 8 hours until compound 5a was totally consumed, which was monitored by LCMS. The reaction mixture was filtered through filtering membrane and the filtrate was directly purified by prep-HPLC (method A) to give the title compound 5i (0.14 g, yield 46%) as colorless oil. ESI m/z: 311 (M+H)$^+$.

6-{2-[(1S,2S,4R,8S,9S,11S,12S,13R)-11-Hydroxy-9, 13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethoxy}oxan-2-yl)methyl (2S)-5-(carbamoylamino)-2-[(2S)-2-[6-(2,5-dioxo-2,5-dihydro-1H-pyrrol-1-yl)hexanamido]-3-methylbutanamido]pentanoate (2q)

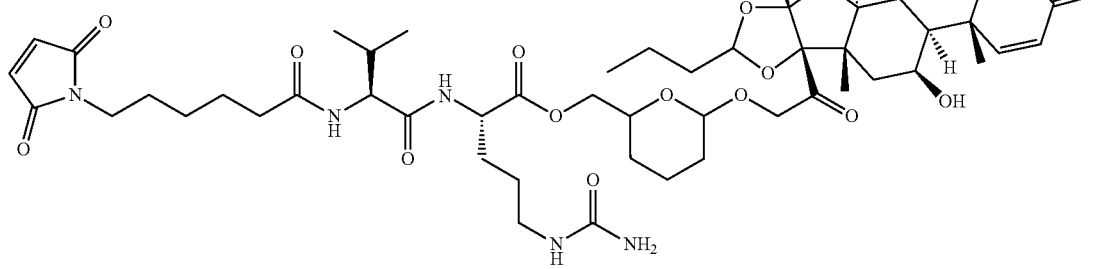

To a solution of compound 5i (5.8 mg, 19 μmol) in DMF (1 mL) were added HATU (10 mg, 26 μmol) and DIPEA (6.6 mg, 51 μmol) at RT. The mixture was stirred at RT for 15 minutes, and to the solution was then added compound 16 (12 mg, 17 μmol) at RT. The resulting mixture was stirred at RT for 4 hours until compound 5i was totally consumed, which was monitored by LCMS. The reaction mixture was then filtered though filtering membrane and the filtrate was directly purified by prep-HPLC (method A) twice to give the title compound 2q (2 mg, yield 12%) as a white solid. ESI m/z: 995.3 (M+H)$^+$. Anal. HPLC: 83.5%, Retention time: 10.36 min (method B).

Scheme 7. Synthesis of linker-phosphate-budesonide 2r and 2s

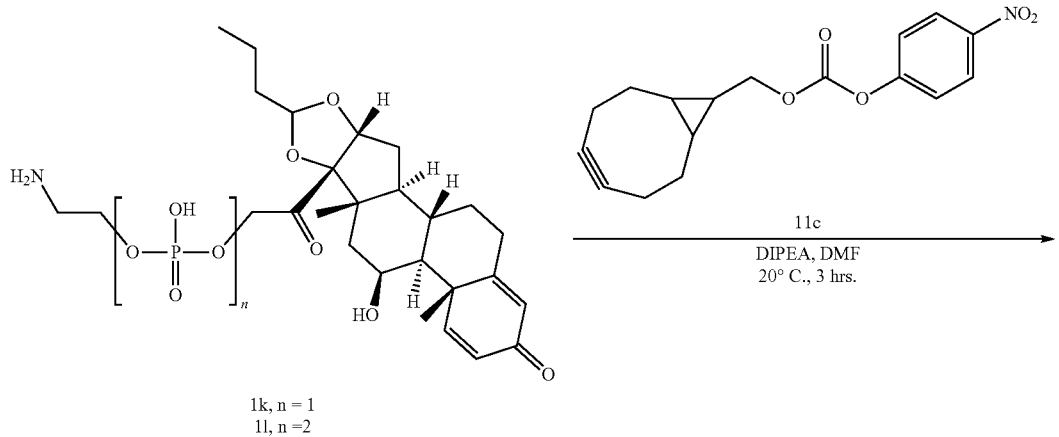

-continued

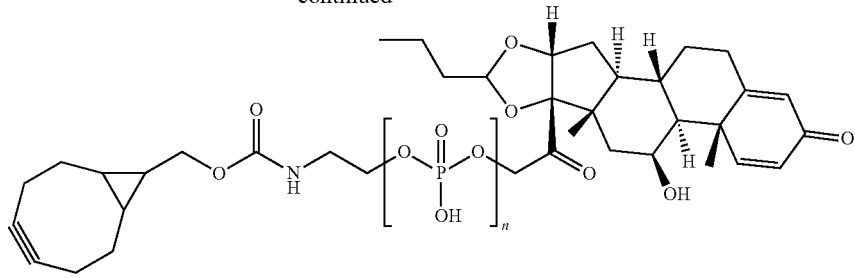

2r, n = 1
2s, n = 2

Phosphate-budesonides were coupled with BCN-PNP (tic) to give BCN-phosphate-Budesonides (compound 2r and 2s) (scheme 7).

Example 2r

{2-[({Bicyclo[6.1.0]non-4-yn-9-ylmethoxy}carbonyl)amino]ethoxy}({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}) phosphinic acid (2r)

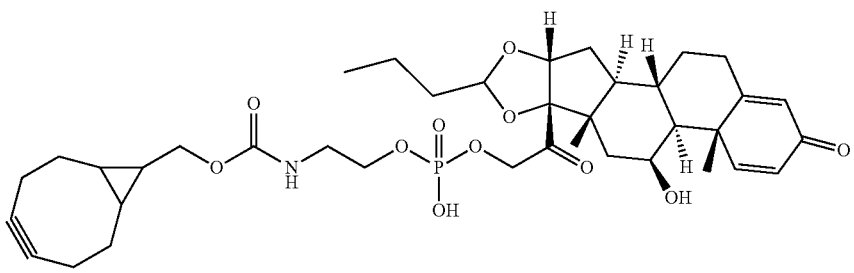 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OCCNC(=O)OCC2C3CCC#CCCC32)O1]

Following the general procedure D, compound 2r (40 mg, 61% yield) was obtained as a white solid. ESI m/z: 730 (M+H)$^+$. $^1$H NMR (500 MHz, MeOD$_{d4}$) δ 7.49 (d, J=10.1 Hz, 1H), 6.29-6.26 (m, 1H), 6.03 (s, 1H), 5.23-5.16 (m, 1H), 4.88-4.64 (m, 3H), 4.45 (dd, J=8.0, 3.1 Hz, 1H), 4.23-4.13 (m, 2H), 3.97 (dd, J=11.9, 5.7 Hz, 2H), 3.36 (t, J=4.7 Hz, 2H), 2.67 (td, J=13.4, 5.3 Hz, 1H), 2.40 (d, J=9.6 Hz, 1H), 2.30-1.34 (m, 23H), 1.21-0.92 (m, 10H) ppm. Anal. HP-LC: >99.9%, Retention time: 5.26 min (method B).

Example 2s

{2-[({Bicyclo[6.1.0]non-4-yn-9-ylmethoxy}carbonyl)amino]ethoxy}({[hydroxy({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy})phosphoryl]oxy})phosphinic acid (2s)

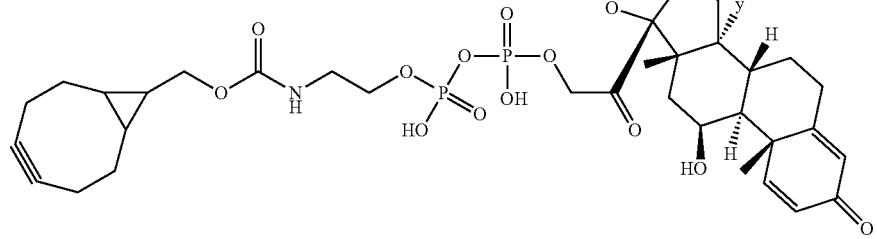

ESI m/z: 810 (M+H)+. $^1$H NMR (500 MHz, MeOD$_{d4}$) δ 7.51 (d, J=10.1 Hz, 1H), 6.28 (d, J=10.0 Hz, 1H), 6.03 (s, 1H), 5.22-5.16 (m, 1H), 4.98-4.66 (m, 3H), 4.46 (s, 1H), 4.12 (dt, J=45.0, 13.0 Hz, 4H), 3.39 (t, J=11.9 Hz, 2H), 2.67 (dd, J=13.3, 8.0 Hz, 1H), 2.40 (d, J=11.2 Hz, 1H), 2.30-1.32 (m, 23H), 1.22-0.92 (m, 10H) ppm. Anal. HPLC: >99.9%, Retention time: 4.03 min (method B).

Experimental Procedures for Intermediates

TABLE 4

Key intermediates and starting materials

| Structures | Intermediate No. | References or synthesis |
|---|---|---|
| [budesonide structure] | 1a (budesonide) | Commercially available (51333-22-3) |
| [vcPAB-budesonide structure] | 4a (vcPAB-budesonide) | See scheme 2 |

TABLE 4-continued

Key intermediates and starting materials

| Structures | Intermediate No. | References or synthesis |
|---|---|---|
| [structure] | 4c (vcPAB-1d) | See scheme 5 |
| [structure] | 5a (mc-NHS) | Commercially available (55750-63-5) |
| [structure] | 5b (MAL-PEG4-NHS) | Commercially available (1325208-25-0) |

TABLE 4-continued
Key intermediates and starting materials
| Structures | Intermediate No. | References or synthesis |
|---|---|---|
| 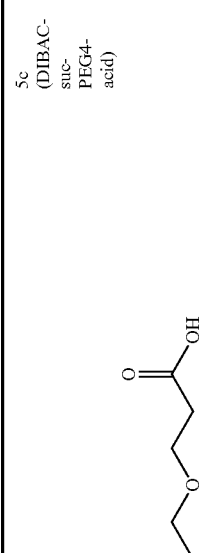 | 5c (DIBAC-suc-PEG4-acid) | Commercially available (1537170-85-6) |
| 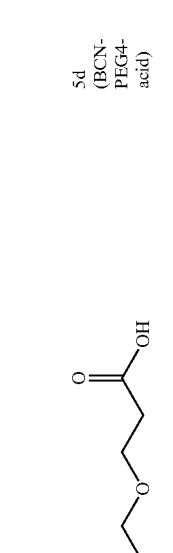 | 5d (BCN-PEG4-acid) | Commercially available (1421932-54-8) |

TABLE 4-continued
Key intermediates and starting materials
| Structures | Intermediate No. | References or synthesis |
|---|---|---|
| 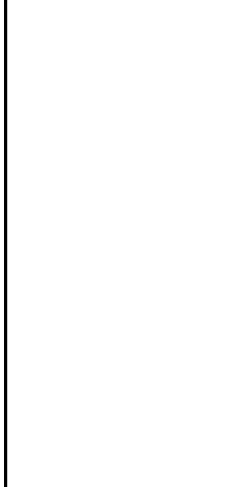 | 5e | Scheme 8 |
| 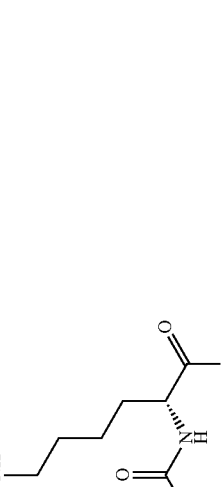 | 5f (mc-Val-Cit-OH) | WO2014/191578 A1 |

TABLE 4-continued

Key intermediates and starting materials

| Structures | Intermediate No. | References or synthesis |
|---|---|---|
| (structure shown) | 5g (DIBAC-suc-PEG4-Val-Cit-OH) | Scheme 9 |
| (structure shown) | 5h | Scheme 10 |
| (structure shown) | 5i | See scheme 6 |

TABLE 4-continued

Key intermediates and starting materials

| Structures | Intermediate No. | References or synthesis |
|---|---|---|
| (structure) | 6a | Scheme 11 |
| (structure) | 6b | *J. Org. Chem.* 2010, 75, 3685-3691 |
| (structure) | 8a | Commercially available (35899-89-9) |

TABLE 4-continued
Key intermediates and starting materials
| Structures | Intermediate No. | References or synthesis |
|---|---|---|
| 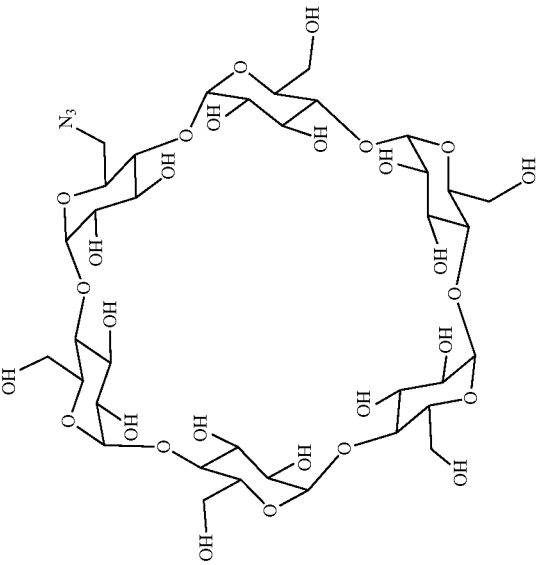 | 8b | Synth. Commun., 2002, 32(21), 3367-3372 J. Am. Chem. Soc., 2012, 134(46), 19108-19117 J. Med. Chem., 1997, 40(17), 2755-2761 J. Am. Chem. Soc., 1993, 115(12), 5035-5040 |
| 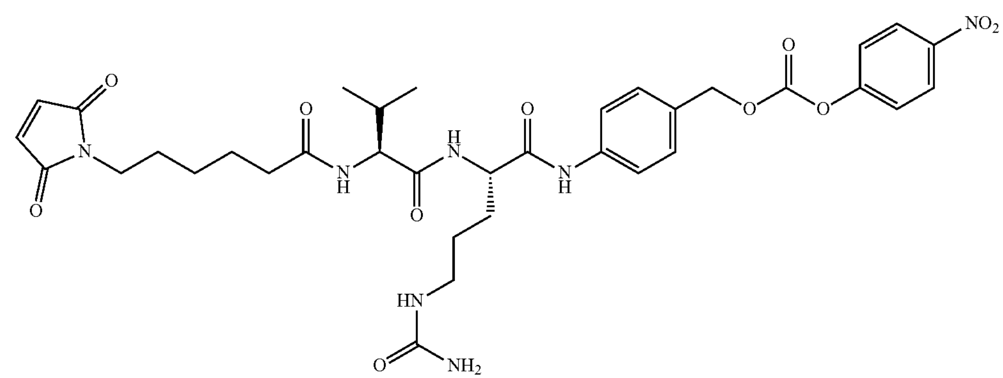 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1] | 11a (MC-VC-PAB-PNP) | Commercially available (159857-81-5) WO2014/191578 A1 |

TABLE 4-continued

Key intermediates and starting materials

| Structures | Intermediate No. | References or synthesis |
|---|---|---|
| 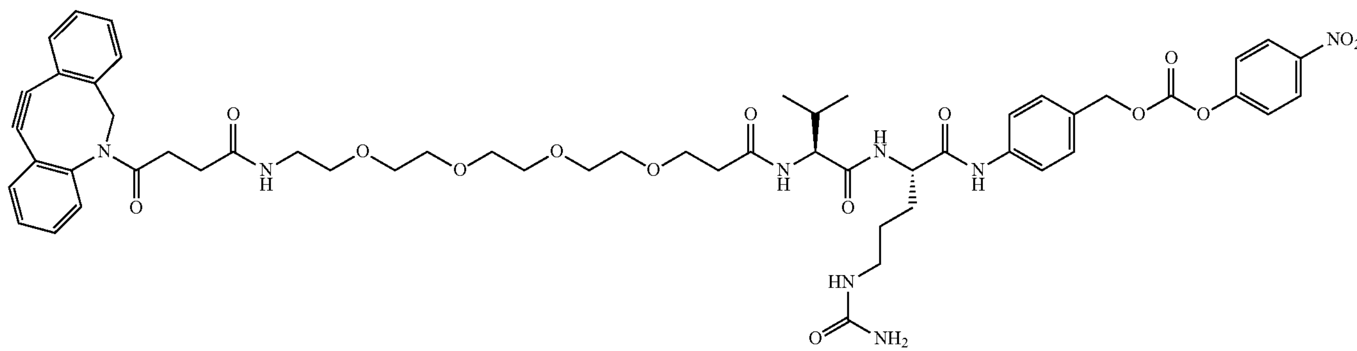 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)Oc2ccc([N+](=O)[O-])cc2)cc1] | 11b (DIBAC-suc-PEG4-vc-PAB-PNP) | Scheme 12 |
| 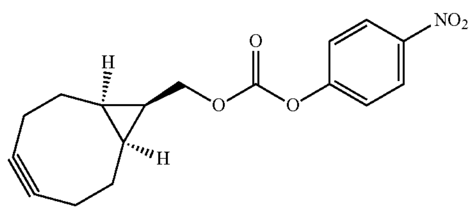 [SMILES: O=C(OC[C@@H]1[C@@H]2CCC#CCC[C@@H]21)Oc1ccc([N+](=O)[O-])cc1] | 11c (BCN-PNP) | WO2013/181697 A1 *Angew. Chem. Int. Ed.*, 2010, 49 (49), 9422-9425 |
| 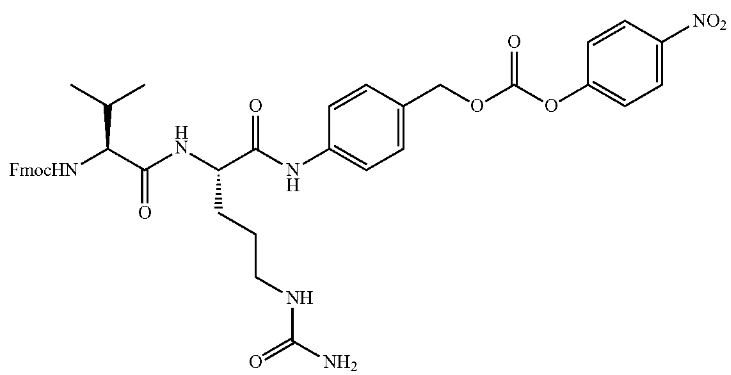 | 11d (Fmoc-vc-PAB-PNP) | Commercially available 863971-53-3 |

TABLE 4-continued

Key intermediates and starting materials

| Structures | Intermediate No. | References or synthesis |
|---|---|---|
| (structure of Boc-vc-PAB) | 12a (Boc-vc-PAB) | Commercially available (870487-09-5) WO2008/34124 A2 |
| (structure of MC-VC-PAB) | 12b (MC-VC-PAB) | Commercially available 159857-80-4 |

TABLE 4-continued
Key intermediates and starting materials
| Structures | Intermediate No. | References or synthesis |
|---|---|---|
| 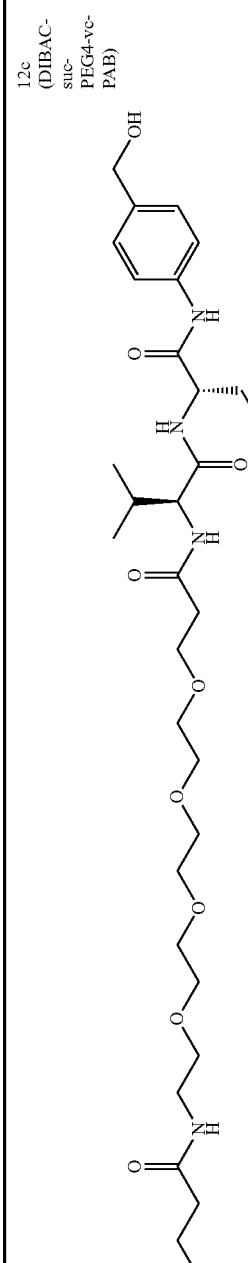 | 12c (DIBAC-suc-PEG4-vc-PAB) | Scheme 12 |

Scheme 8. Synthesis of 5e
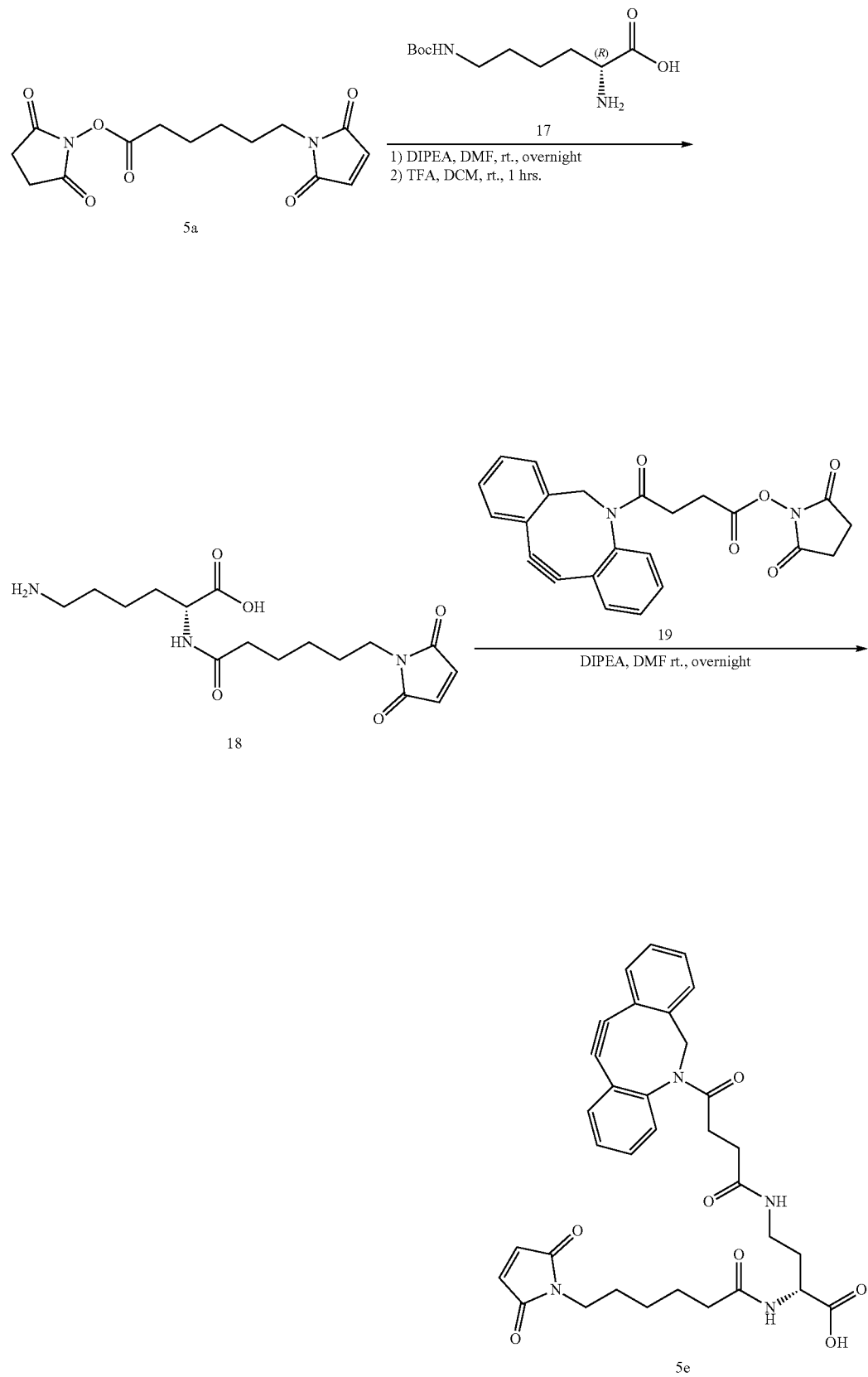

357

(2R)-6-(4-{2-Azatricyclo[10.4.0.0⁴,⁹]hexadeca-1(12),4,6,8,13,15-hexaen-10-yn-2-yl}-4-oxobutanamido)-2-[6-(2,5-dioxo-2,5-dihydro-1H-pyrrol-1-yl)hexanamido]hexanoic acid (5e)

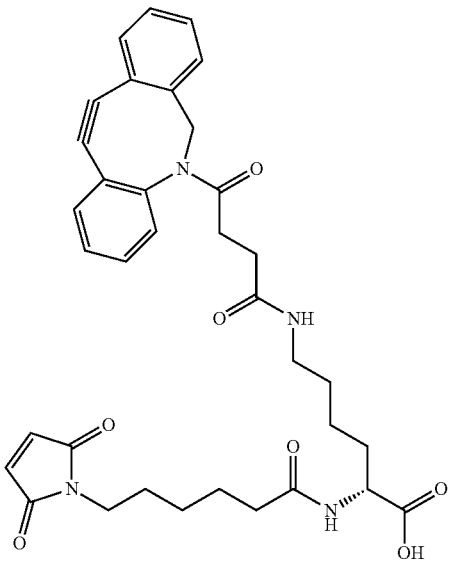 [SMILES: O=C(CCC(=O)N1Cc2ccccc2C#Cc2ccccc21)NCCCC[C@@H](NC(=O)CCCCCN1C(=O)C=CC1=O)C(=O)O]

To a mixture of H-D-Lys(Boc)-OH (17, 0.25 g, 1.0 mmol) in DMF (10 mL) were added 6-Maleimidocarproic acid-NHS (5a, 0.31 g, 1.0 mmol) and diisopropylethylamine (DIPEA, 0.26 g, 2.0 mmol) at RT. After the reaction was stirred at RT overnight, compound 5a was totally consumed. The mixture was directly separated by reversed phase flash chromatography (0-100% acetonitrile in water (0.05% TFA)) to give intermediate Boc-18 (ESI m/z: 440 (M+H)⁺) as colorless oil, which was dissolved in DCM (5 mL). To the solution was added TFA (0.5 mL) dropwise at 0° C., and the mixture was stirred at RT for an hour. The reaction was monitored by LCMS and intermediate Boc-18 was totally consumed. The volatiles were removed in vacuo to give crude 18 (ESI m/z: 340 (M/2+H)⁺), which was used for the next step without further purification. To the mixture of crude compound 18 (0.21 g, 0.62 mmol) in DMF (5 mL) was added activated ester 19 (0.20 g, 0.50 mmol) and DIPEA (50 mg, 0.39 mmol) at RT. After the reaction mixture was stirred at RT overnight, compound 19 was totally consumed, which was monitored by LCMS. The reaction mixture was then directly separated by reversed phase flash chromatography (0-100% acetonitrile in water) to give title compound 5e (0.10 g, 20% yield in 3 steps from 5a) as a white solid. ESI m/z: 627 (M+H)⁺. ¹H NMR (DMSO$_{d6}$, 400 MHz): δ 7.89 (d, J=13.2 Hz, 1H), 7.69-7.62 (m, 3H), 7.48-7.47 (m, 3H), 7.36-7.28 (m, 3H), 6.99 (s, 2H), 5.03 (d, J=13.6 Hz, 1H), 4.09-4.04 (m, 1H), 3.60 (d, J=13.6 Hz, 1H), 3.38-3.34 (m, 1H), 2.90-2.87 (m, 2H), 2.61-2.55 (m, 1H), 2.25-2.17 (m, 1H), 2.08-1.51 (m, 5H), 1.46-1.15 (m, 12H) ppm.

Scheme 9. Synthesis of 5g

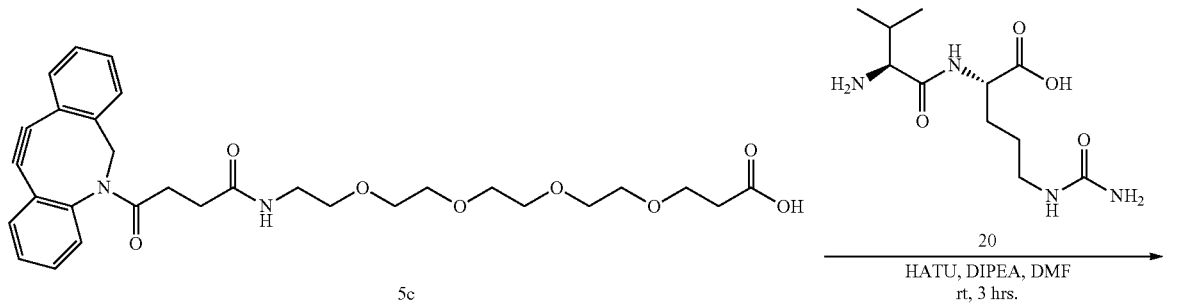

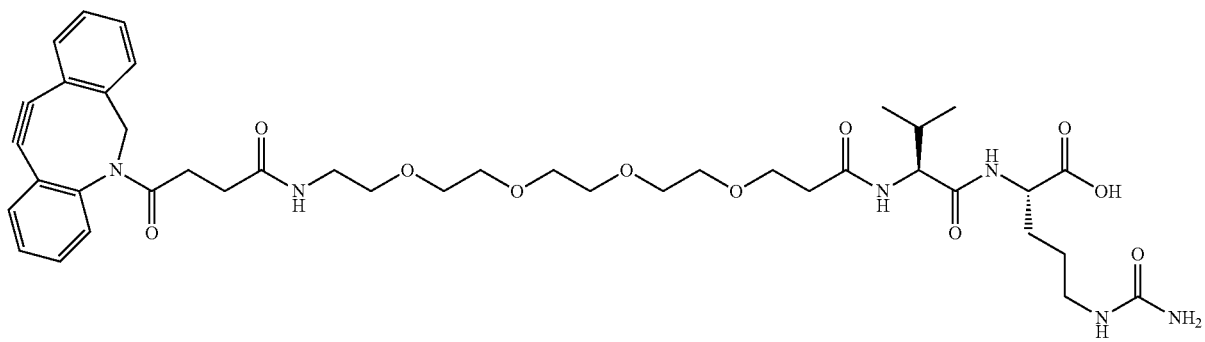 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)O]

(2S)-2-[(2S)-2-[1-(4-{2-Azatricyclo[10.4.0.0⁴,⁹]
hexadeca-1(12),4(9),5,7,13,15-hexaen-10-yn-2-yl}-
4-oxobutanamido)-3,6,9,12-tetraoxapentadecan-15-
amido]-3-methylbutanamido]-5-(carbamoylamino)
pentanoic acid (5g)

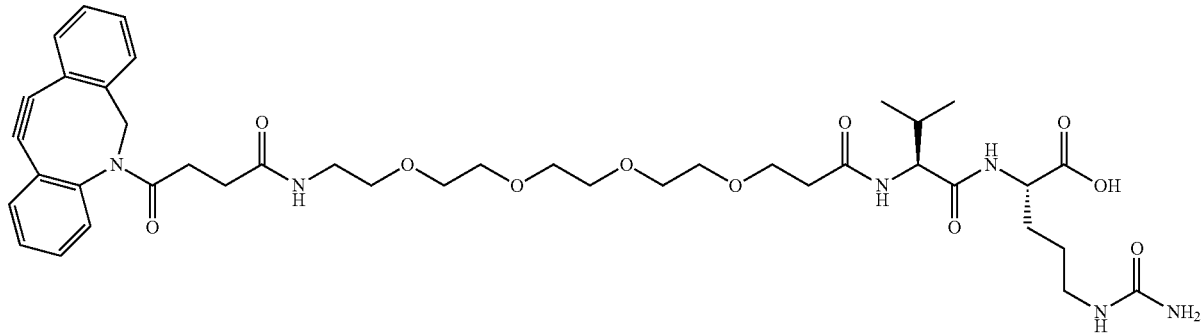

To a solution of compound 5c (0.30 g, 0.54 mmol) in DMF (10 mL) were added HATU (0.31 g, 0.81 mmol) and DIPEA (0.14 g, 1.1 mmol) at RT. The mixture was stirred at RT for 15 minutes. To the reaction solution was added Val-Cit-OH (20 (CAS #159858-33-0), 0.21 g, 0.76 mmol) at RT, and the resulting mixture was stirred at RT for 3 hours until most materials were consumed, which was monitored by LCMS. The reaction mixture was filtered through filtering membrane and the filtrate was directly purified by reversed flash chromatography (0-100% acetonitrile in water (with 10 mmol/L ammonium bicarbonate)) to give title intermediate 5g (0.25 g, yield 57%) as a white solid. ESI m/z: 809.5 (M+H)⁺.

Scheme 10. Synthesis of intermediates 5h

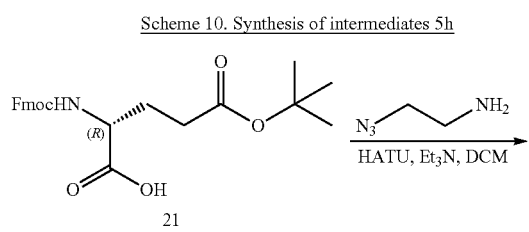

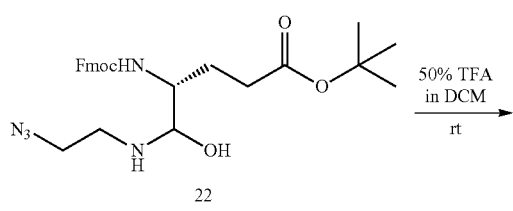

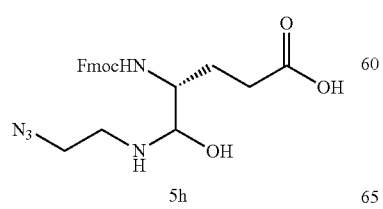

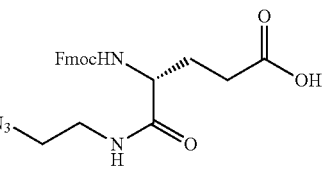

tert-Butyl (4R)-4-[(2-azidoethyl)carbamoyl]-4-{
[(9H-fluoren-9-ylmethoxy)carbonyl]
amino}butanoate (22)

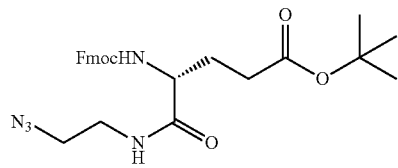

To a mixture of Fmoc-D-Glu(OTBU)-OH (21, (104091-08-9), 0.30 g, 0.71 mmol) and 2-azidoethanamine (87156-40-9, 73 mg, 0.85 mmol) in DCM (50 mL) were added HATU (0.41 g, 1.1 mmol) and triethylamine (0.3 mL) at RT. The reaction mixture was stirred at RT overnight. Most of compound 21 was then consumed according to TLC and LCMS. After the reaction mixture was quenched with water (50 mL) at RT, the organic solution was washed with water and brine, dried over sodium sulfate and concentrated in vacuo. The residue was purified by prep-TLC (silica gel, eluting with petroleum ether/ethyl acetate (v/v=1)) to give the title compound 22 (0.30 g, yield 76%) as yellow viscous oil. ESI m/z: 494 (M+H)⁺. ¹H NMR (400 MHz, DMSO$_{d6}$): δ 8.09 (m, 1H), 7.84-7.90 (m, 4H), 7.33-7.44 (m, 4H), 6.28 (s, 2H), 3.35 (m, 6H), 3.26 (m, 1H), 2.50 (m, 2H), 2.25 (m, 1H), 1.80 (m, 1H), 1.39 (s, 9H) ppm.

(4R)-4-[(2-Azidoethyl)carbamoyl]-4-{[(9H-fluoren-
9-ylmethoxy)carbonyl]amino}butanoic acid (5h)

The resulting mixture was stirred at RT for 2 hours until compound 22 was totally consumed, which was monitored by TLC and LCMS. The volatiles were removed in vacuo to give crude compound 5h (17 mg, yield 96%) as yellow oil, which was used for the next step without further purification. ESI m/z: 438 (M+H)⁺.

(2R)-6-[2-(Cyclooct-2-yn-1-yloxy)acetamido]-2-{[(9H-fluoren-9-ylmethoxy)carbonyl]amino}hexanoic acid (6a)

Scheme 11. Synthesis of Intermediates 6a

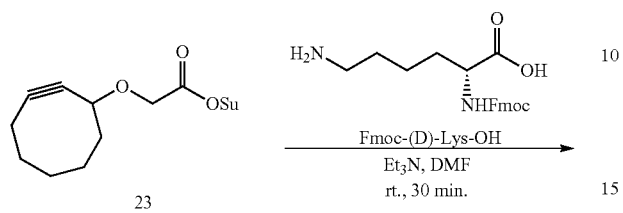

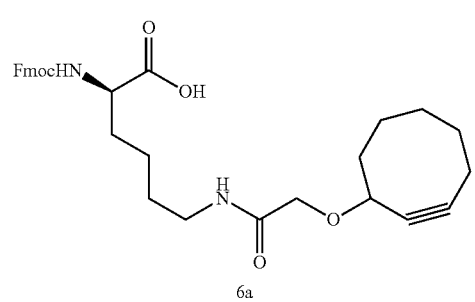

To a mixture of commercial compound 23 (65 mg, 0.23 mmol, CAS: 1425803-45-7) in DMF (2 mL) were added Fmoc-D-Lys-OH (85 mg, 0.23 mmol) and triethylamine (52 mg, 0.51 mmol). The reaction mixture was stirred at RT for 30 minutes. The mixture was directly separated by reversed phase flash chromatography (0-100% acetonitrile in water (0.05% TFA)) to give intermediate 6a (85 mg, yield 70%) as a white solid. ESI m/z: 533 (M+H)⁺. ¹H NMR (MeOD$_{d4}$, 500 MHz): δ 7.70 (d, J=7.5 Hz, 2H), 7.59 (t, J=8.0 Hz, 2H), 7.30 (t, J=7.5 Hz, 2H), 7.22 (t, J=7.4 Hz, 2H), 4.35-4.22 (m, 2H), 4.22-4.09 (m, 2H), 4.09-3.99 (m, 1H), 3.94-3.81 (m, 1H), 3.79-3.67 (m, 1H), 3.15 (t, J=6.9 Hz, 2H), 2.17-1.96 (m, 3H), 1.96-1.86 (m, 1H), 1.85-1.66 (m, 4H), 1.66-1.41 (m, 5H), 1.41-1.25 (m, 3H) ppm.

Scheme 12. Synthesis of Intermediates 11b and 12c

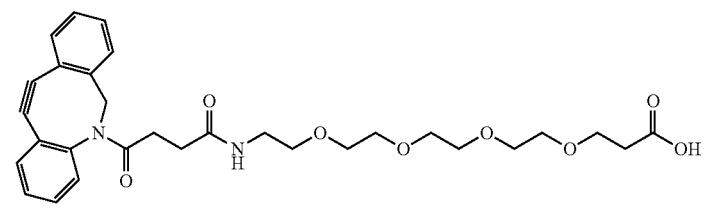

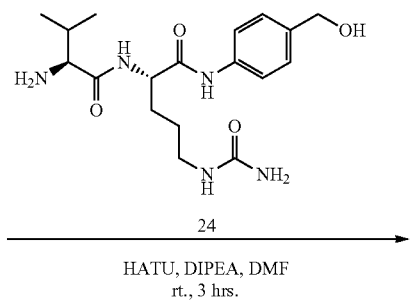

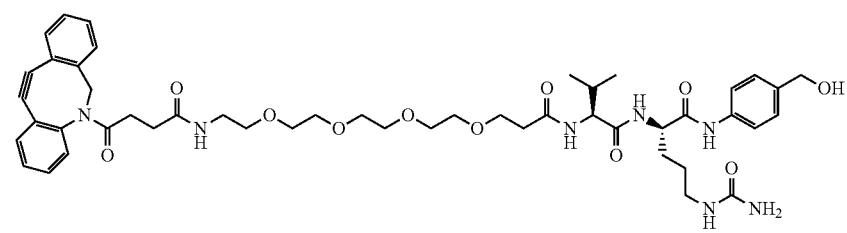

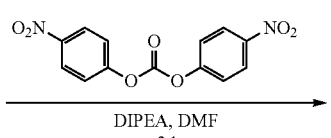

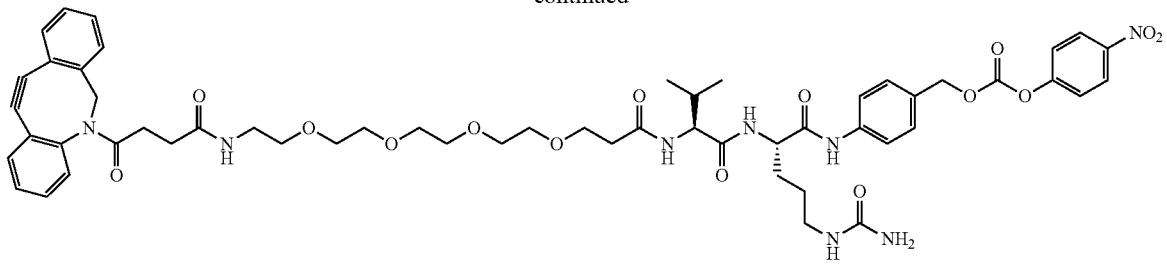

11b

15

1-(4-{2-Azatricyclo[10.4.0.0^{4,9}]hexadeca-1(12),4(9),5,7,13,15-hexaen-10-yn-2-yl}-4-oxobutanamido)-N-[(1S)-1-{[(1S)-4-(carbamoylamino)-1-{[4-(hydroxymethyl)phenyl]carbamoyl}butyl]carbamoyl}-2-methylpropyl]-3,6,9,12-tetraoxapentadecan-15-amide (12c)

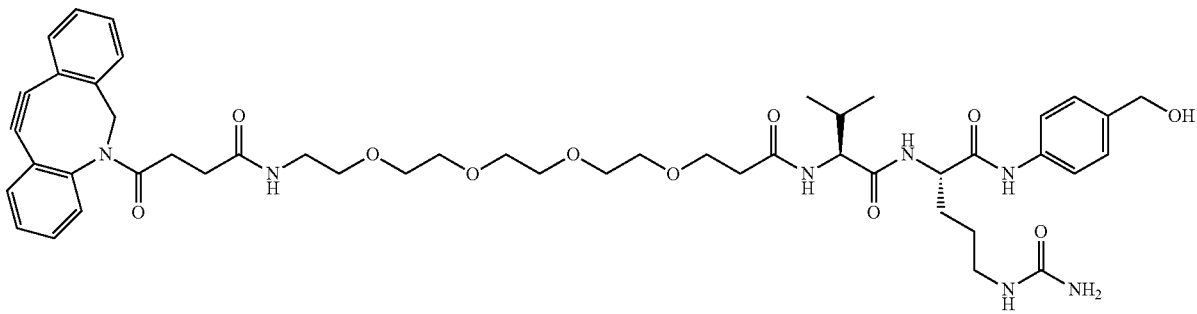 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(CO)cc1]

The mixture was stirred at RT for 15 minutes. To the reaction solution was added vc-PAB (24 (159857-79-1), 0.21 g, 0.54 mmol) at RT, and the resulting mixture was stirred at RT for 3 hours until most materials were consumed, which was monitored by LCMS. The reaction mixture was filtered through filtering membrane and the filtrate was directly purified by reversed flash chromatography (0-100% acetonitrile in water (with 10 mmol/L ammonium bicarbonate)) to give title intermediate 12c (0.30 g, yield 60%) as a white solid. ESI m/z: 617 (M+H)$^+$.

{4-[(2S)-2-[(2S)-2-[1-(4-{2-Azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate (11b)

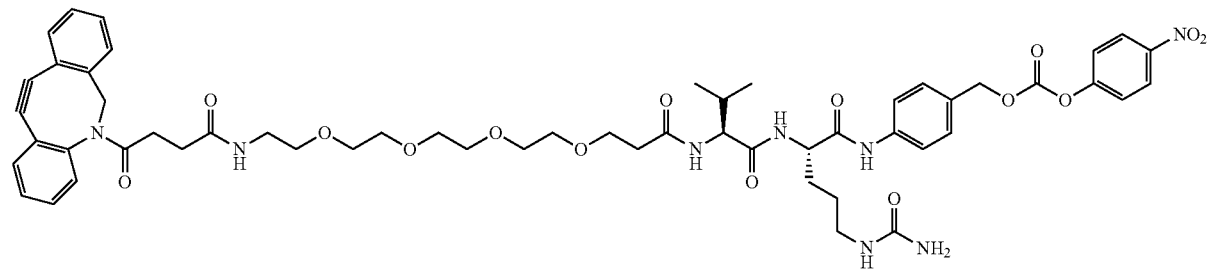 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)Oc2ccc([N+](=O)[O-])cc2)cc1]

To a solution of compound 12c (0.15 g, 0.16 mmol) in DMF (10 mL) were added bis(4-nitrophenyl) carbonate (0.15 g, 0.49 mmol) and DIPEA (63 mg, 0.49 mmol) at 0° C. The mixture was then stirred at RT for 3 hours until 12c was mostly consumed, which was monitored by LCMS. The reaction mixture was filtered through filtering membrane and the filtrate was directly purified by reversed flash chromatography (0-100% acetonitrile in water (with 10 mmol/L ammonium bicarbonate)) to give title intermediate 11b (50 mg, yield 28%) as a white solid. ESI m/z: 1079 $(M+H)^+$.

Table 5 below presents linker payloads made using the methods described herein.

TABLE 5
Examples of Linker-Payloads
| LP | Payload | Linker name | Structures |
|---|---|---|---|
| 2a | 1a | MC-VC-PAB | 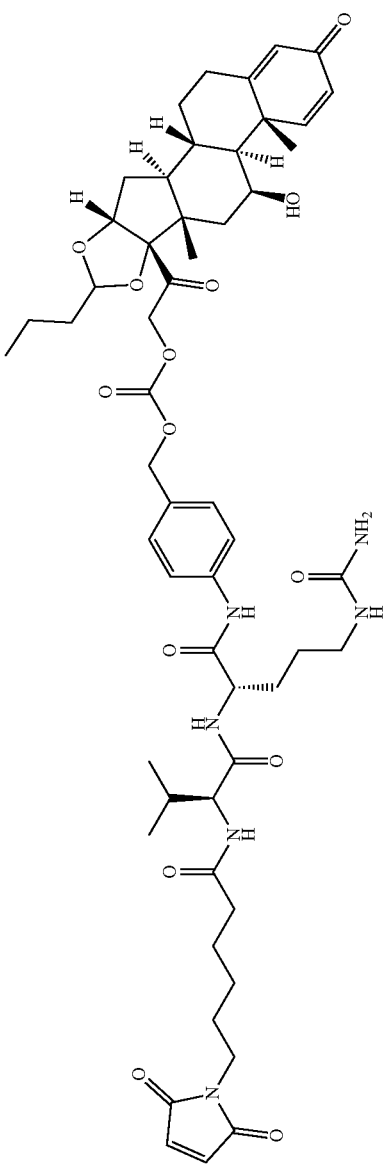 |
| 2b | 1a | DIBAC-suc-vc-PAB | 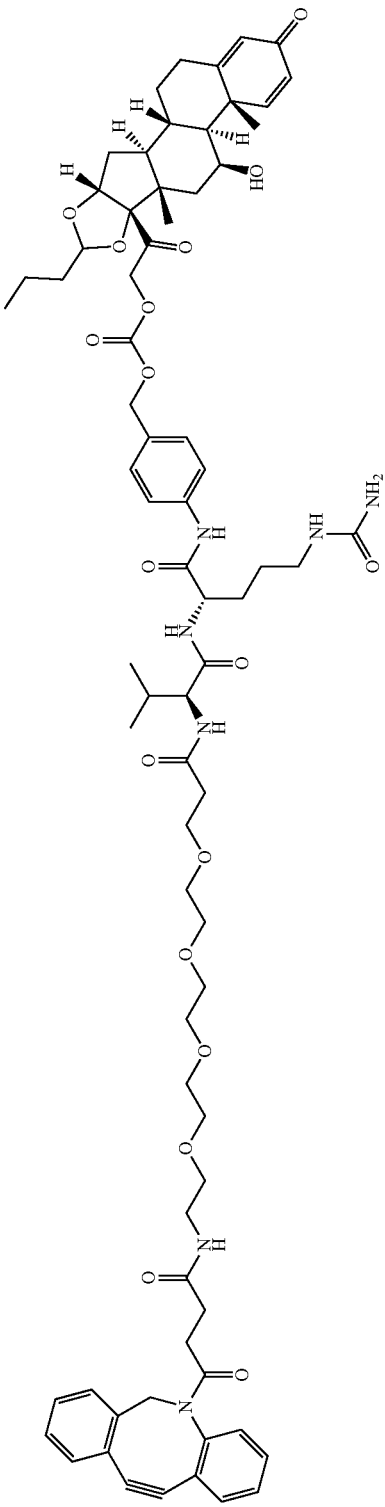 |

TABLE 5-continued

Examples of Linker-Payloads

| LP | Payload | Linker name | Structures |
|---|---|---|---|
| 2c | 1a | mc-PEG4-(sugar-COT)dLys-vc-PAB | 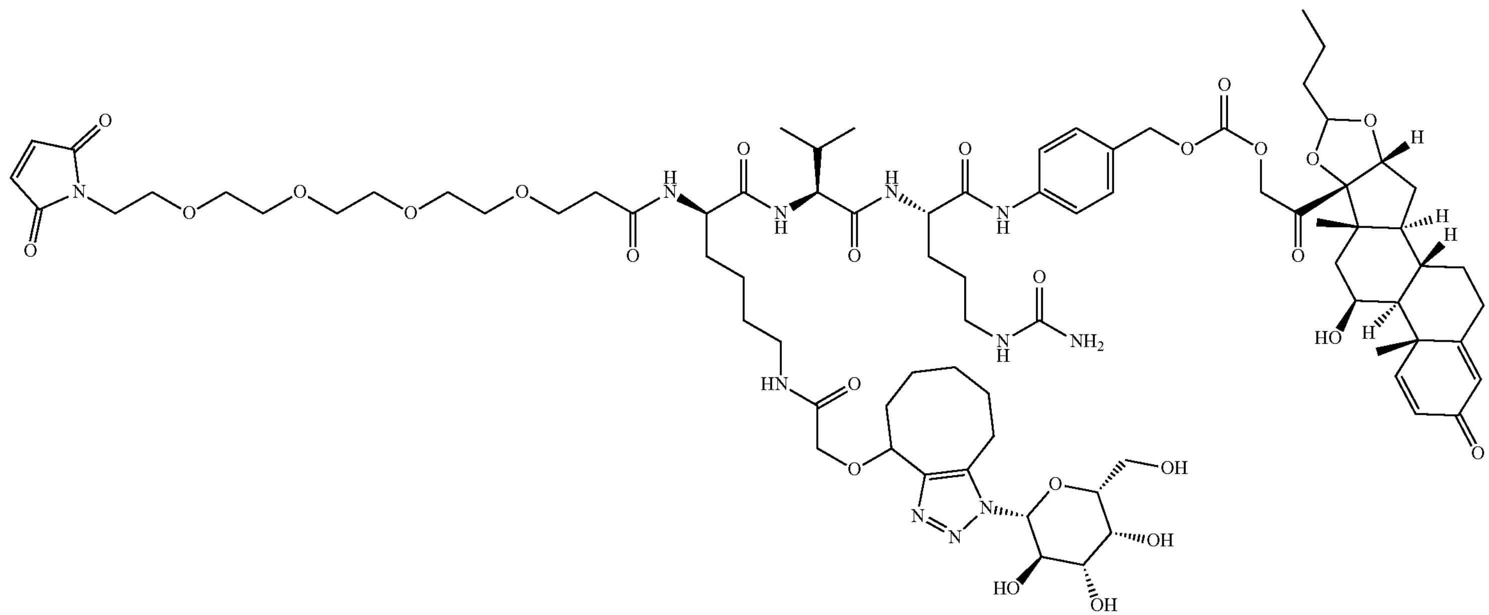 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@@H](CCCCNC(=O)COC3CCCCCc4c3nnn4[C@@H]3O[C@H](CO)[C@H](O)[C@H](O)[C@H]3O)NC(=O)CCOCCOCCOCCOCCN3C(=O)C=CC3=O)C(C)C)cc2)O1] |

TABLE 5-continued
Examples of Linker-Payloads
| LP | Payload | Linker name | Structures |
|---|---|---|---|
| 2d | 1a | mc-PEG4-(sugar2)dGlu-vc-PAB | 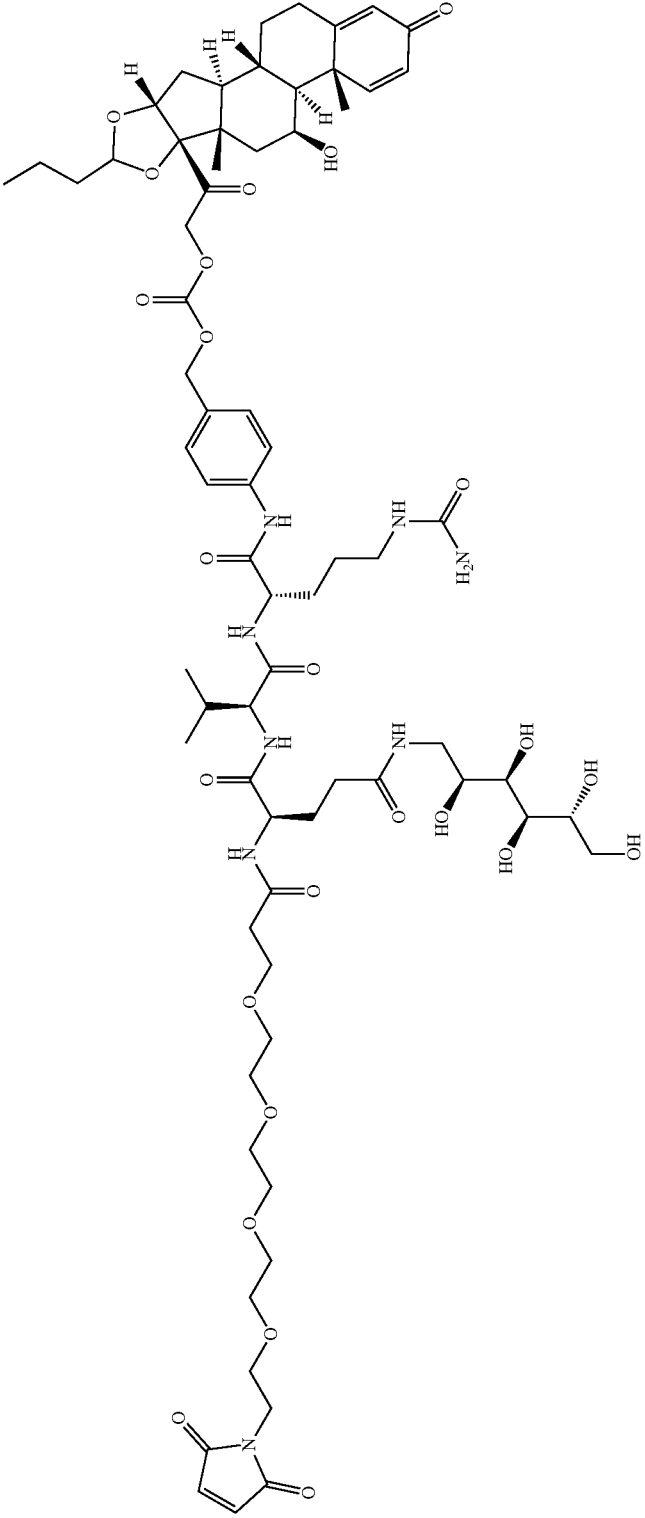 |

TABLE 5-continued
Examples of Linker-Payloads
| LP | Payload | Linker name | Structures |
|---|---|---|---|
| 2e | 1a | MC-VC-PABA | 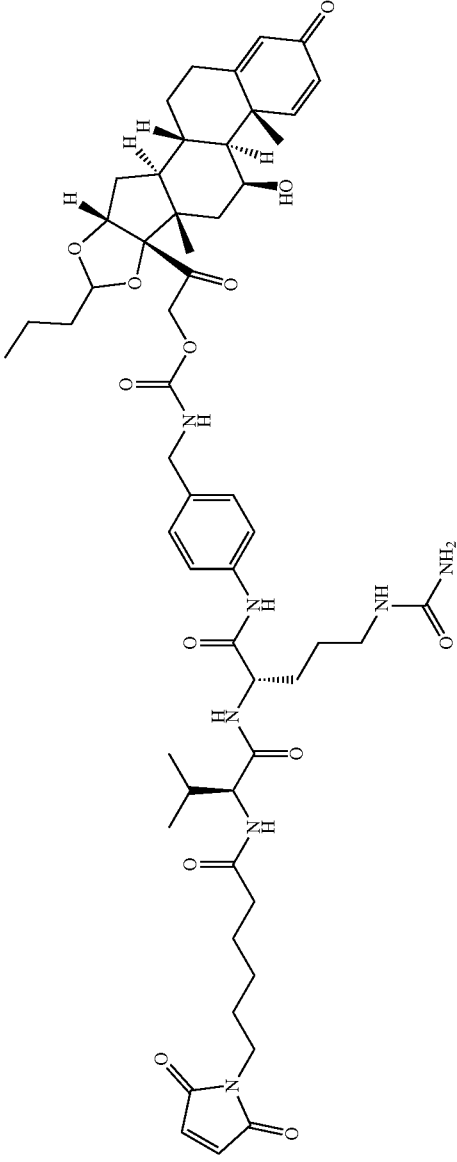 |
| 2f | 1c | MC-VC-PAB | 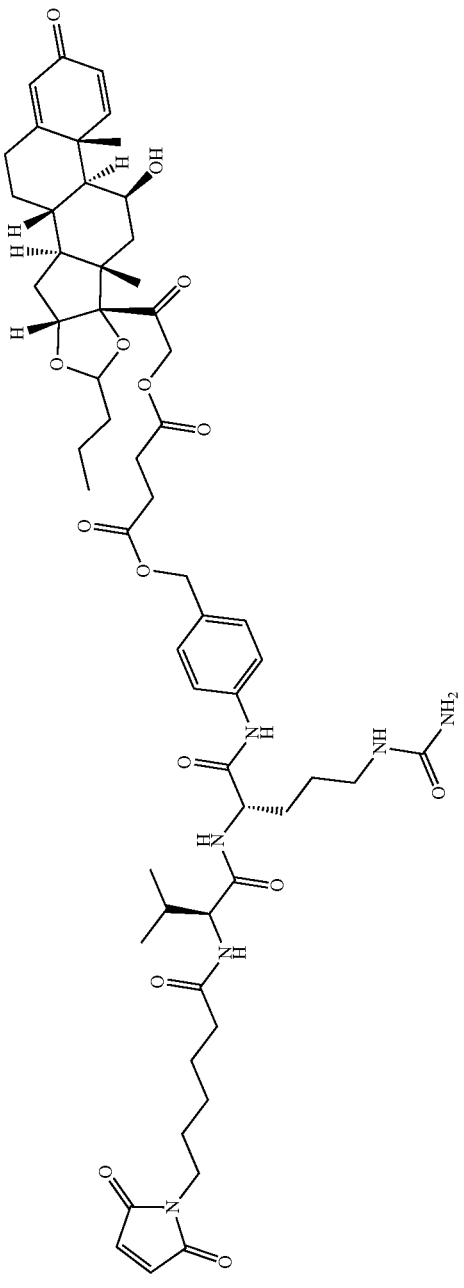 |

TABLE 5-continued
Examples of Linker-Payloads
| LP | Payload | Linker name | Structures |
|---|---|---|---|
| 2g | 1c | DIBAC-suc-vc-PAB | 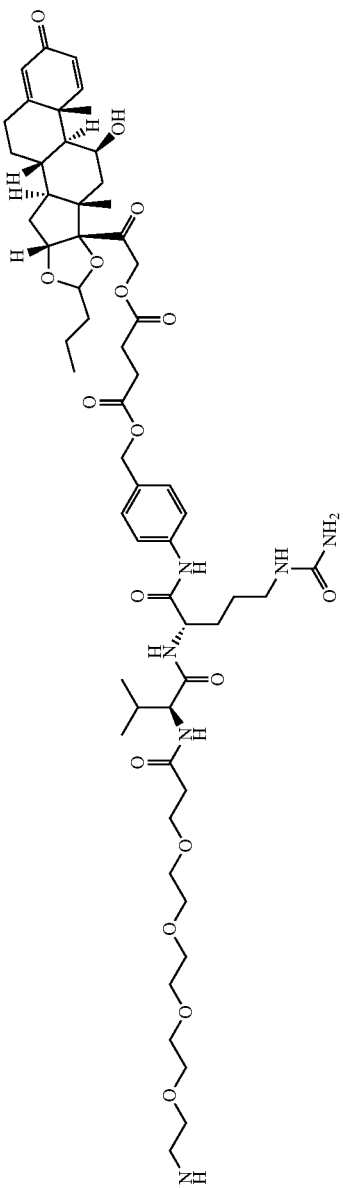 |
| 2j | 1e | MC-VC-PAB | 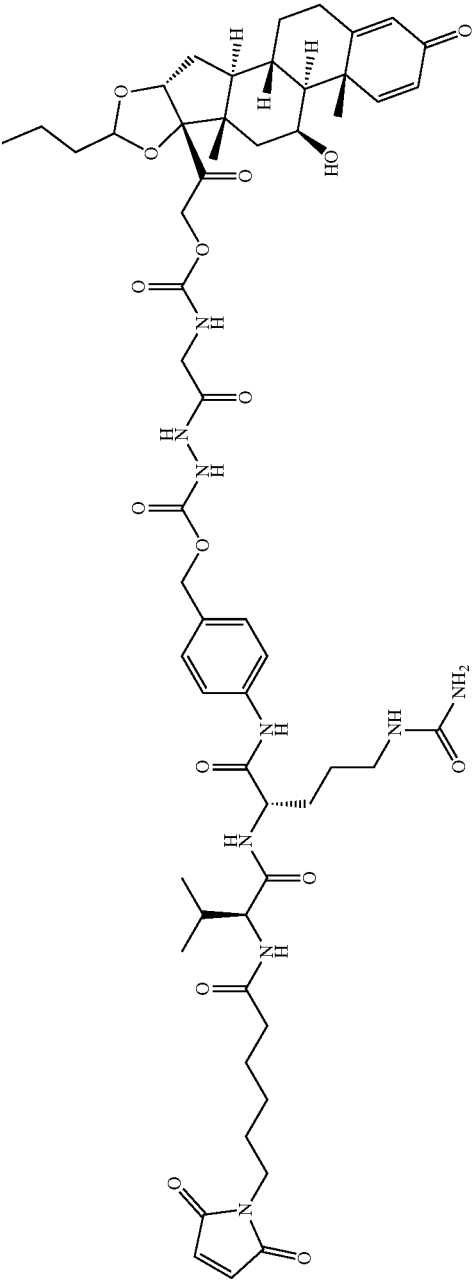 |

TABLE 5-continued

Examples of Linker-Payloads

| LP | Payload | Linker name | Structures |
|---|---|---|---|
| 2k | 1d | MC-VC-PAB | 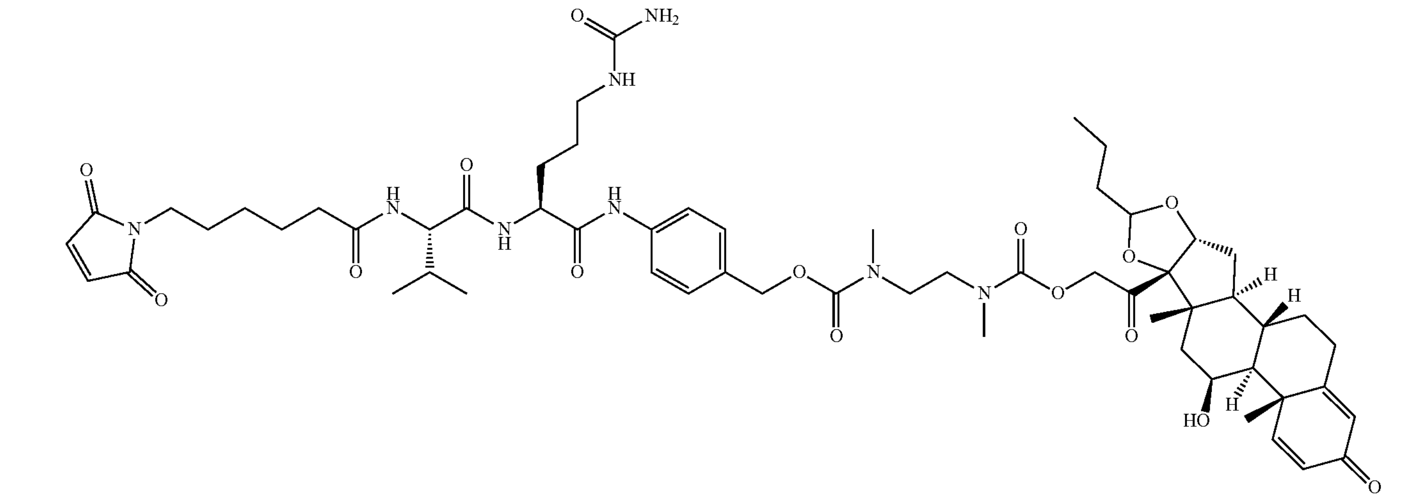 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCCCCN3C(=O)C=CC3=O)C(C)C)cc2)O1] |
| 2l | 1d | BCN-PEG4-vc-PAB | 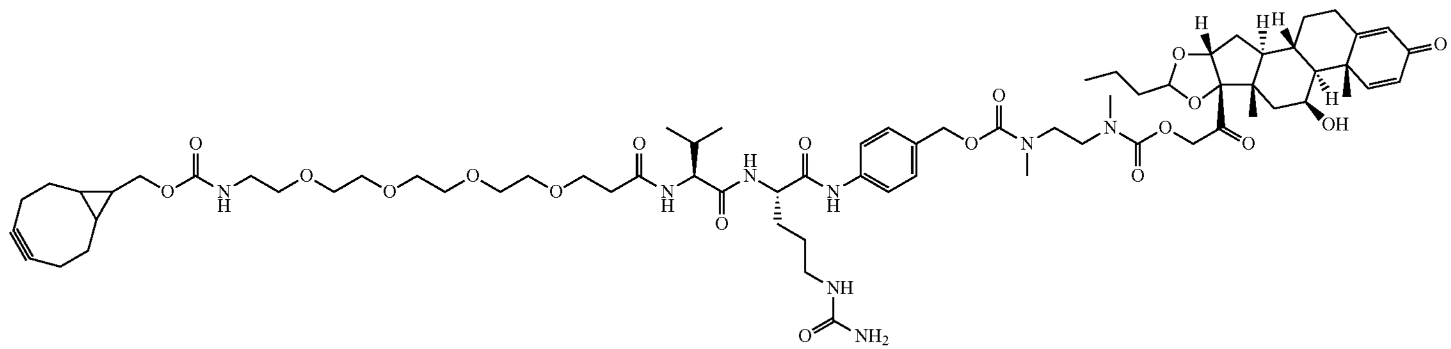 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)OCC3C4CCC#CCCC43)C(C)C)cc2)O1] |

TABLE 5-continued
Examples of Linker-Payloads
| LP | Payload | Linker name | Structures |
|---|---|---|---|
| 2m | 1d | mc-N5(CD-DIBAC-suc)Lys-vc-PAB | 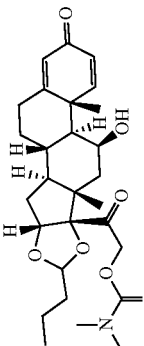 |

TABLE 5-continued

Examples of Linker-Payloads

| LP | Payload | Linker name | Structures |
|---|---|---|---|
| 2n | 1d | azidoethyl-GLu-vc-PAB | 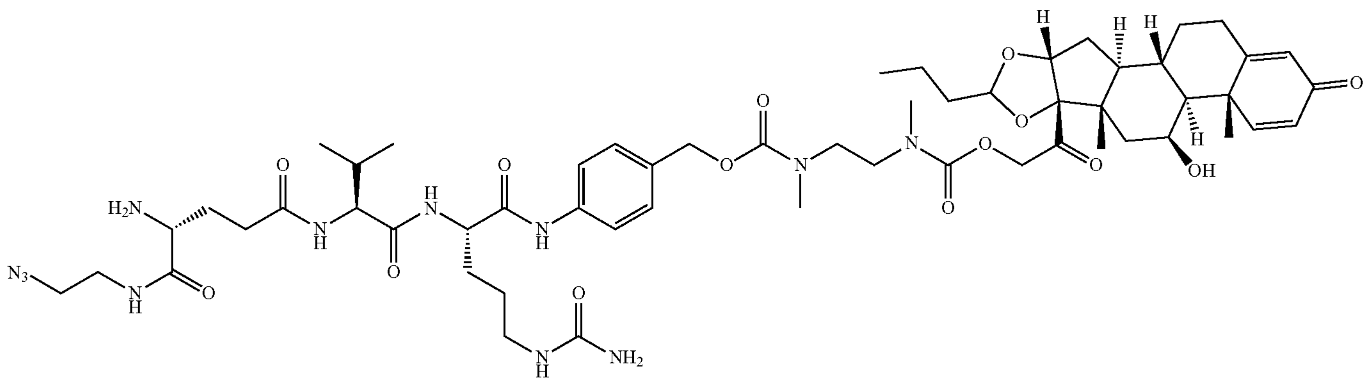 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CC[C@@H](N)C(=O)NCCN=[N+]=[N-])C(C)C)cc2)O1] |
| 2q | 1g | MC-VC | 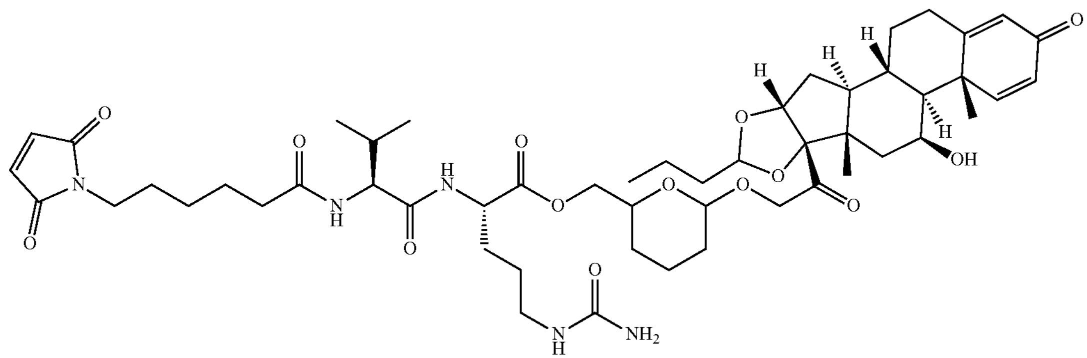 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC2CCCC(COC(=O)[C@H](CCCNC(N)=O)NC(=O)[C@@H](NC(=O)CCCCCN3C(=O)C=CC3=O)C(C)C)O2)O1] |

TABLE 5-continued
Examples of Linker-Payloads
| LP | Payload | Linker name | Structures |
|---|---|---|---|
| 2r | 1k | BCN | 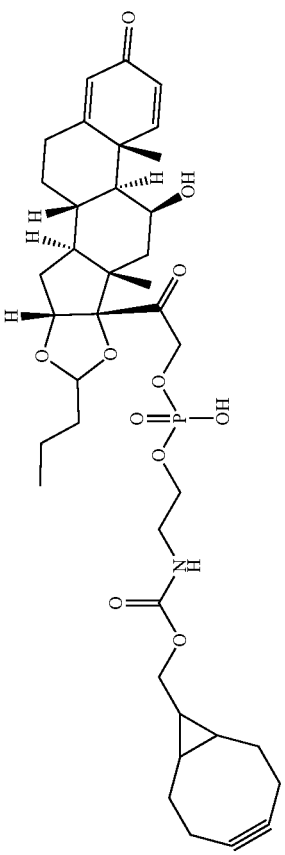 |
| 2s | 1l | BCN | 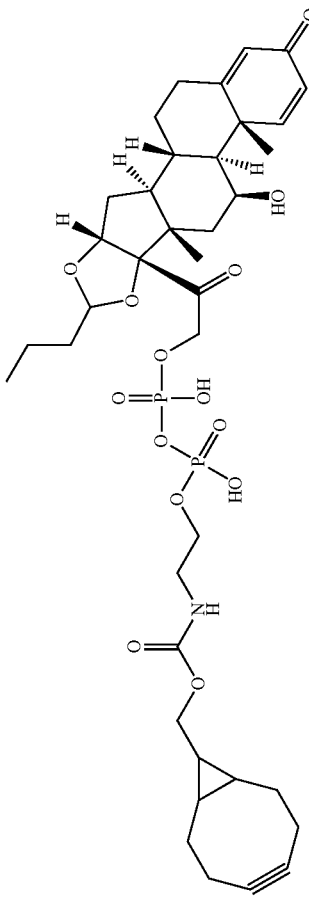 |

TABLE 6

Characterization Data for Linker-Payloads

| LP | cLogP | MF | MW | HPLC purity (%) | HPLC RT (min) | MS (m/z) 100% | Highest m/z peak |
|---|---|---|---|---|---|---|---|
| 2a | 4.18 | $C_{54}H_{72}N_6O_{14}$ | 1029.2 | 92 | 7.6 (A) | 1029 (M + H) | 1029 (M + H) |
| 2b | 5.42 | $C_{74}H_{95}N_7O_{18}$ | 1370.6 | 97 | 8.1 (B) | 685.8 (M/2 + H) | 685.8 (M/2 + H) |
| 2c | 1.03 | $C_{81}H_{117}N_{11}O_{26}$ | 1660.9 | 97 | 7.0 (A) | 830.8 (M/2 + H) | 830.8 (M/2 + H) |
| 2d | −1.87 | $C_{70}H_{102}N_8O_{25}$ | 1455.6 | 100 | 6.48 (A) | 728 (M/2 + H) | 1456 (M + H) (10%) |
| 2e | 3.45 | $C_{54}H_{73}N_7O_{13}$ | 1028.2 | 100 | 7.54 (A) | 1028.3 (M + H) | 1028.3 (M + H) |
| 2f | 3.54 | $C_{57}H_{76}N_6O_{15}$ | 1085.2 | 98 | 1.71 (LCMS) | 1085.3 (M + H) | 1085.3 (M + H) |
| 2g | 4.77 | $C_{77}H_{99}N_7O_{19}$ | 1426.7 | >99 | 7.86 (B) | 714.0 (M/2 + H) | 1427 (M + H) (15%) |
| 2j | 2.16 | $C_{57}H_{77}N_9O_{16}$ | 1144.3 | 98 | 1.57 (LCMS) | 1144.3 (M + H) | 1144.3 (M + H) |
| 2k | 3.54 | $C_{59}H_{82}N_8O_{15}$ | 1143.4 | 98 | 1.70 (LCMS) | 1143.4 (M + H) | 1143.3 (M + H) |
| 2l | 4.66 | $C_{71}H_{104}N_8O_{19}$ | 1373.6 | 100 | 9.40 (A) | 687.5 (M/2 + H) | 1396.8 (M + Na) (50%) |
| 2m | −4.89 | $C_{120}H_{166}N_{14}O_{47}$ | 2556.7 | 100 | 6.49 (A) | 1278.8 (M/2 + H) | 1278.8 (M/2 + H) |
| 2n | 1.68 | $C_{56}H_{82}N_{12}O_{14}$ | 1147.3 | 100 | 7.72 (B) | 1147.5 (M + H) | 1147.5 (M + H) |
| 2q | 3.52 | $C_{52}H_{75}N_5O_{14}$ | 994.2 | 79 | 10.36 (B) | 995.3 (M + H) | 995.3 (M + H) |
| 2r | 4.88 | $C_{38}H_{52}NO_{11}P$ | 729.8 | 100 | 5.26 (B) | 686.2 (weak mass) | 1459.1 (2M + H) |
| 2s | 0.55 | $C_{38}H_{53}NO_{14}P_2$ | 809.8 | 100 | 4.03 (B) | 766.1 (M-44) | 810.1 (M + H) (70%) |

Synthesis of Linker-Payloads LP1-4

Scheme 101. Synthesis of Payload 100, its spacer-payload 101a-d and linker-payloads LP1-4

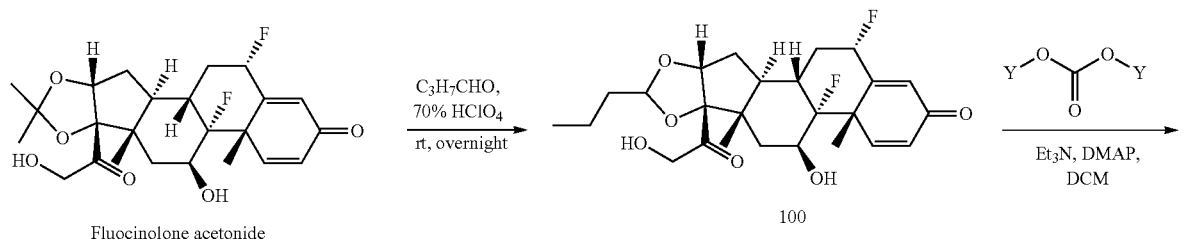

387
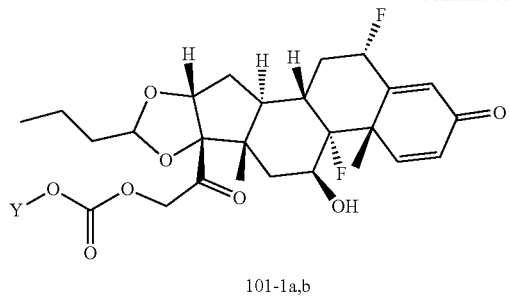
101-1a,b
a, Y = 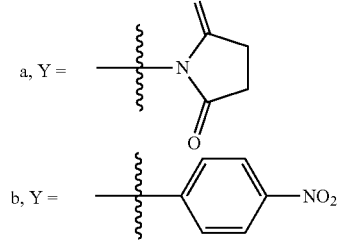
b, Y = (p-nitrophenyl)
388
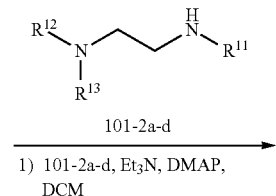
101-2a-d
1) 101-2a-d, Et$_3$N, DMAP, DCM
2) TFA
101-2a, R$^{11}$ = H, R$_{12}$ = Me, R$_{13}$ = Boc
101-2b, R$^{11}$ = R$_{12}$ = Me, R$_{13}$ = H
101-2c, R$^{11}$ = R$_{12}$ = Et, R$_{13}$ = Boc
101-2d, Boc-Piperazine
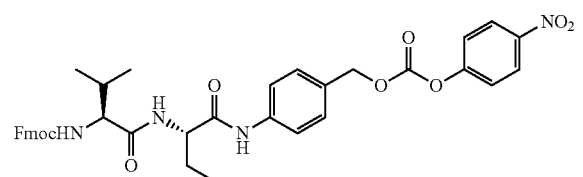
11d
1) 11d, HOBt, DIPEA, DMF, rt.
2) piperidine, rt.
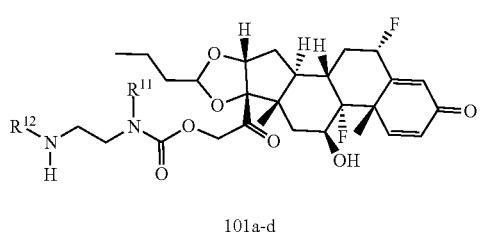
101a-d
101a, R$^{11}$ = H, R$_{12}$ = Me
101b, R$^{11}$ = R$_{12}$ = Me
101c, R$^{11}$ = R$_{12}$ = Et
101d, R$^{11}$, R$^{12}$ together = -CH$_2$CH$_2$- (forming piperazine)

389
390
-continued
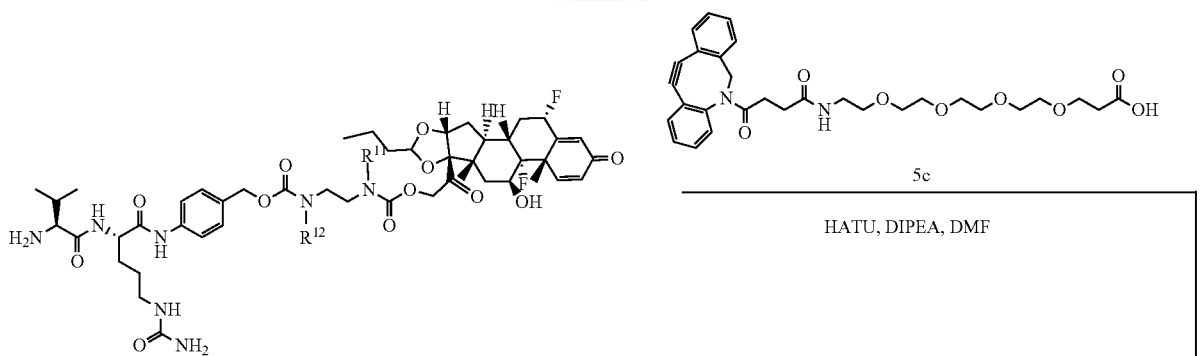
101-3a,b,d
a, R[11] = H, R[12] = Me
b, R[11] = R[12] = Me
d, R[11], R[12] together = -CH$_2$CH$_2$-
(forming piperazine)
5c
HATU, DIPEA, DMF
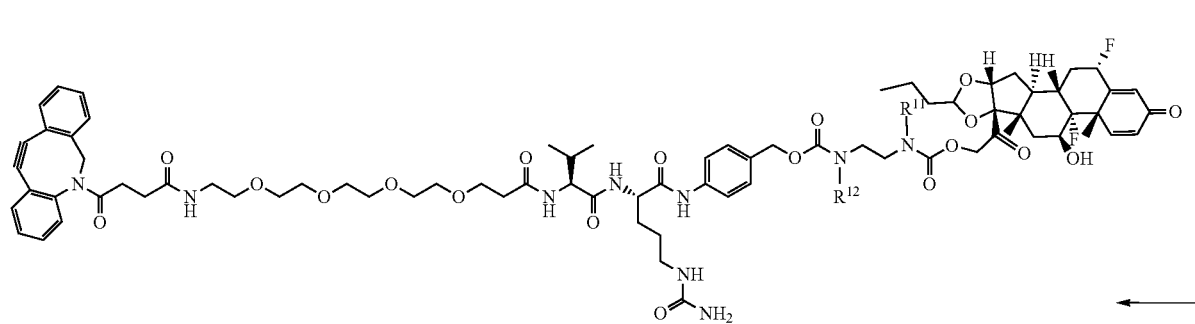
LP1-4
LP1, R[11] = H, R[12] = Me
LP2, R[11] = R[12] = Me
LP3, R[11] = R[12] = Et
LP4, R[11], R[12] together = -CH$_2$CH$_2$-
(forming piperazine)
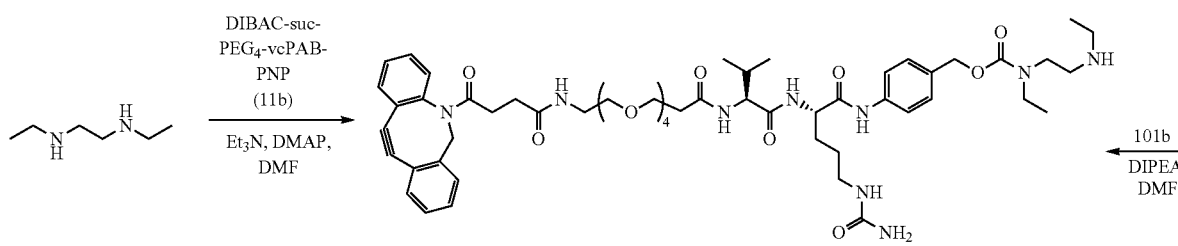
DIBAC-suc-PEG$_4$-vcPAB-PNP (11b)
Et$_3$N, DMAP, DMF
101b
DIPEA, DMF
101-4

(1S,2S,4R,8S,9S,11S,12R,13S,19S)-12,19-Difluoro-
11-hydroxy-8-(2-hydroxyacetyl)-9,13-dimethyl-6-
propyl-5,7-dioxapentacyclo[10.8.0.0$^{2,9}$.0$^{4,8}$.0$^{13,18}$]
icosa-14,17-dien-16-one (100)

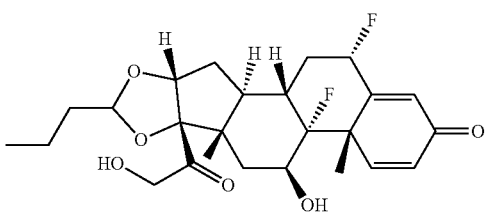

To a mixture of fluocinolone acetonide (10 g, 22 mmol) and silica gel (100 g) in heptanes (900 mL) was added butyraldehyde (3.0 mL, 33 mmol) below 10° C. and the suspension was stirred at 10-20° C. for 30 minutes. To the mixture was added perchloric acid (70%, 7.6 mL, 91 mmol) dropwise at 0° C. The reaction mixture was then stirred at RT overnight. Most of fluocinolone acetonide was consumed according to TLC and LCMS. The reaction mixture was diluted with petroleum ether and quenched with sat. aq. sodium carbonate. The suspension was filtered and the solid was washed with DCM/methanol (v/v=1:1). The combined filtrate was concentrated in vacuo. The residue was purified by flash chromatography (0-1.5% methanol in DCM) to give compound 100 (8.0 g, yield: 78%) as a white solid. ESI m/z: 467.1 (M+H)$^+$.

1-[({2-[(1S,2S,4R,8S,9S,11S,12R,13S,19S)-12,19-
Difluoro-11-hydroxy-9,13-dimethyl-16-oxo-6-pro-
pyl-5,7-dioxapentacyclo[10.8.0.0$^{2,9}$.0$^{4,8}$.0$^{13,18}$]icosa-
14,17-dien-8-yl]-2-oxoethoxy}carbonyl)oxy]
pyrrolidine-2,5-dione (101-1a)

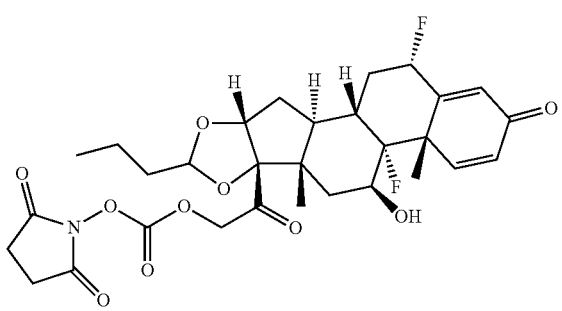 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)ON2C(=O)CCC2=O)O1]

To a solution of compound 100 (0.47 g, 1.0 mmol) in DCM (20 mL) were added bis(2,5-dioxopyrrolidin-1-yl) carbonate (0.28 g, 1.1 mmol), triethylamine (0.40 g, 4.0 mmol) and DMAP (3.0 mg, cat.). The reaction mixture was stirred at RT for 4 hours until compound 100 was consumed, which was monitored by LCMS. The reaction mixture was then diluted with DCM and washed by water. The organic solution was dried over sodium sulfate. After filtered, the solution was concentrated in vacuo and the residue (crude 101-1a) was used for the next step directly without purification. ESI m/z: 608.2 (M+H)$^+$.

(1S,2S,4R,8S,9S,11S,12R,13S,19S)-12,19-Difluoro-
11-hydroxy-9,13-dimethyl-8-{2-[(4-nitrophenoxy-
carbonyl)oxy]acetyl}-6-propyl-5,7-dioxapentacyclo
[10.8.0.0$^{2,9}$.0$^{4,8}$.0$^{13,18}$]icosa-14,17-dien-16-one
(101-1b)

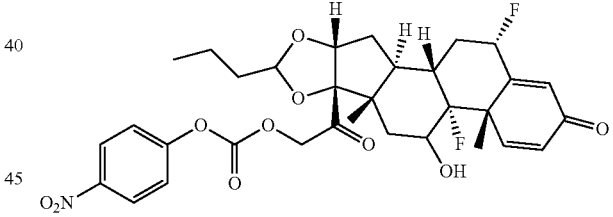

A mixture of compound 100 (0.80 g, 1.7 mmol), bis(4-nitrophenyl) carbonate (1.6 g, 5.2 mmol) and DIPEA (1.1 g, 8.6 mmol) in THF (20 mL) was stirred at RT for 4 hours, which was monitored by LCMS. The mixture was concentrated in vacuo. The crude product was purified by silica gel column chromatography (50% ethyl acetate in petroleum ether) to give compound 101-1b (0.75 g, 69% yield) as colorless oil. ESI m/z: 632 (M+H)$^+$.

General Procedure for Compound 101
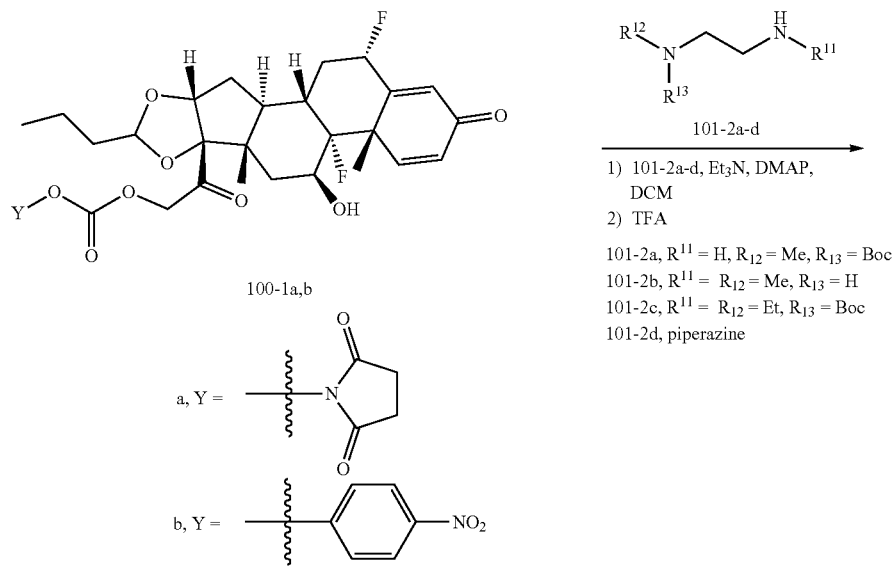
1) 101-2a-d, Et₃N, DMAP, DCM
2) TFA
101-2a, $R^{11}$ = H, $R_{12}$ = Me, $R_{13}$ = Boc
101-2b, $R^{11}$ = $R_{12}$ = Me, $R_{13}$ = H
101-2c, $R^{11}$ = $R_{12}$ = Et, $R_{13}$ = Boc
101-2d, piperazine
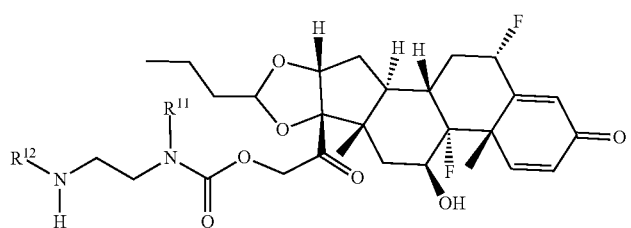
101a-d
101a, $R^{11}$ = H, $R_{12}$ = Me
101b, $R^{11}$ = $R_{12}$ = Me
101c, $R^{11}$ = $R_{12}$ = Et
101d, $R^{11}$, $R_{12}$ together = -CH₂CH₂- (forming piperazine)

To a solution of compound 101-1a or 101-1b (crude, calculated as 1.0 mmol) in DCM (20 mL) were added diamine 101-2(a, b, c, or d) (1.1 mmol) and DMAP (0.1 mmol). The reaction mixture was stirred at RT for 4 hours before TFA (1 mL) was added into. The mixture was stirred at RT for half an hour (for $R^{13}$=Boc, the reaction was stirred until Boc was totally removed, which monitored by LCMS). The resulting mixture was concentrated in vacuo and the residue was purified by reversed phase flash chromatography (50-80% acetonitrile in aq. TFA (0.5%)) to give compound 101(a, b, c, or d) as colorless oil.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-[2-(methylamino)ethyl]carbamate (101a)

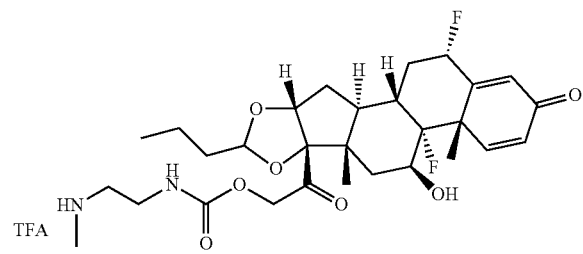 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCNC)O1]

Following the general procedure and using compound 101-1a with Boc-diamine 101-2a, compound 101a (0.38 g, 57% in 2 steps, TFA salt) was obtained as colorless oil. ESI m/z: 567 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-[2-(methylamino)ethyl]carbamate (101b)

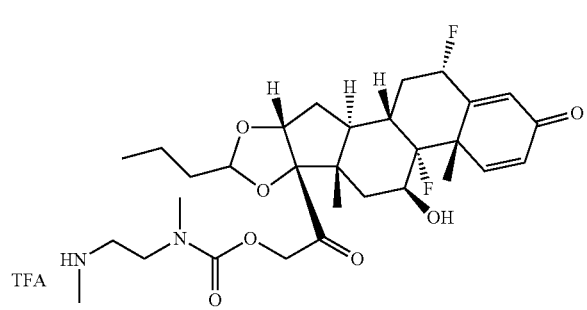 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCNC)O1]

Following the general procedure and using compound 101-1a with diamine 101-2b, compound 101b (0.45 g, 66% yield in 2 steps, TFA salt) was obtained as colorless oil. ESI m/z: 581 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-ethyl-N-[2-(ethylamino)ethyl]carbamate (101c)

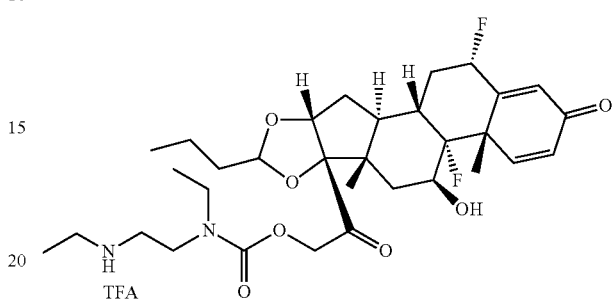

Following the general procedure and using compound 101-1b with diamine 101-2c, compound 101c (24 mg, 18% yield in 2 steps, TFA salt) was obtained as colorless oil. ESI m/z: 609 (M+H)$^+$. $^1$H NMR (500 MHz, DMSO$_{d6}$) δ 8.38 (s, 2H), 7.30 (d, J=10.5 Hz, 1H), 6.24 (dd, J=10.5 Hz, 2.0 Hz, 1H), 6.11 (s, 1H), 5.70-5.54 (m, 2H), 5.10-4.91 (m, 1H), 4.85-4.65 (m, 3H), 4.25-4.16 (m, 1H), 3.60-3.40 (m, 2H), 3.33-3.20 (m, 4H), 3.20-2.90 (m, 4H), 2.67-2.53 (m, 1H), 2.30-2.20 (m, 1H), 2.10-2.00 (m, 2H), 1.80-1.70 (m, 1H), 1.64-1.51 (m, 4H), 1.49 (s, 3H), 1.40-1.30 (m, 2H), 1.20-1.10 (m, 4H), 1.10-1.00 (m, 1H), 0.90-0.80 (m, 6H) ppm.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl piperazine-1-carboxylate (101d)

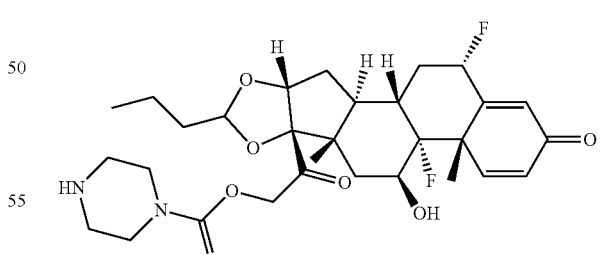

Following the general procedure and using compound 101-1b with piperazine (101-2d) without treatment with TFA and purified by silica gel column chromatography (0-10% methanol in DCM), compound 101d (0.21 g, 49% yield in 2 steps, free base) was obtained as colorless oil. ESI m/z: 579 (M+H)$^+$.

General Procedure for Compound 101-3

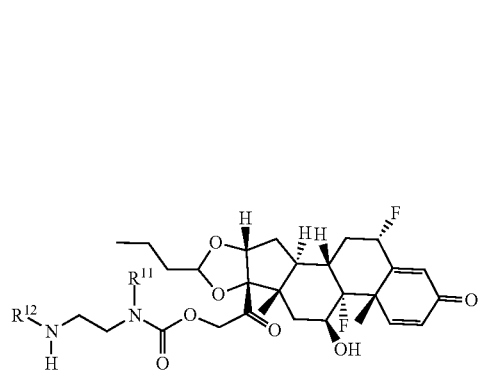

101a,b,d
101a, $R^{11}$ = H, $R_{12}$ = Me
101b, $R^{11}$ = $R_{12}$ = Me
101d, $R^{11}$, $R^{12}$ = -CH$_2$CH$_2$-
(piperazine)

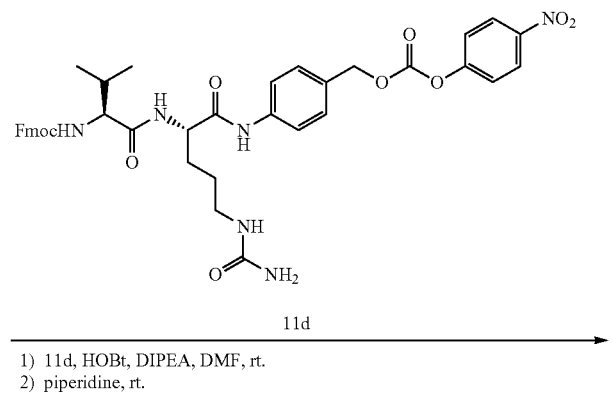

11d 1) 11d, HOBt, DIPEA, DMF, rt.
2) piperidine, rt.

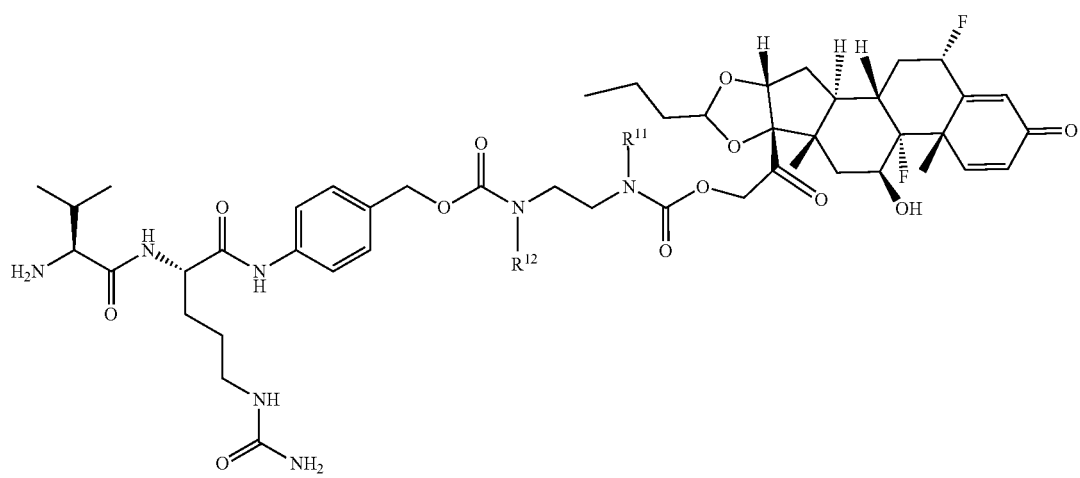

101-3a,b,d
a, $R^{11}$ = H, $R_{12}$ = Me
b, $R^{11}$ = $R_{12}$ = Me
d, $R^{11}$, $R^{12}$
together = -CH$_2$CH$_2$-
(forming piperazine)

To a solution of compound 101a, b or d (0.20 mmol) in DMF (3 mL) were added Fmoc-VC-PAB-PNP 11d (0.17 g, 0.22 mmol), HOBT (41 mg, 0.30 mmol) and DIPEA (77 mg, 0.60 mmol). The mixture was stirred at RT for 3 hours, which was monitored by LCMS. To the mixture was then added piperidine (0.3 mL). The reaction mixture was stirred at RT for an hour until Fmoc was totally removed according to LCMS. The resulting mixture was directly purified by reversed phase flash chromatography (50-80% acetonitrile in aq. NH$_4$HCO$_3$ (10 mM)) to give compound 101-3a, b or d as a white solid.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl N-(2-{[({4-[(2S)-2-[(2S)-2-amino-3-methylbutanamido]-5-(carbamoylamino)pentanamido]phenyl}methoxy)carbonyl](methyl)amino}ethyl)carbamate (101-3a)

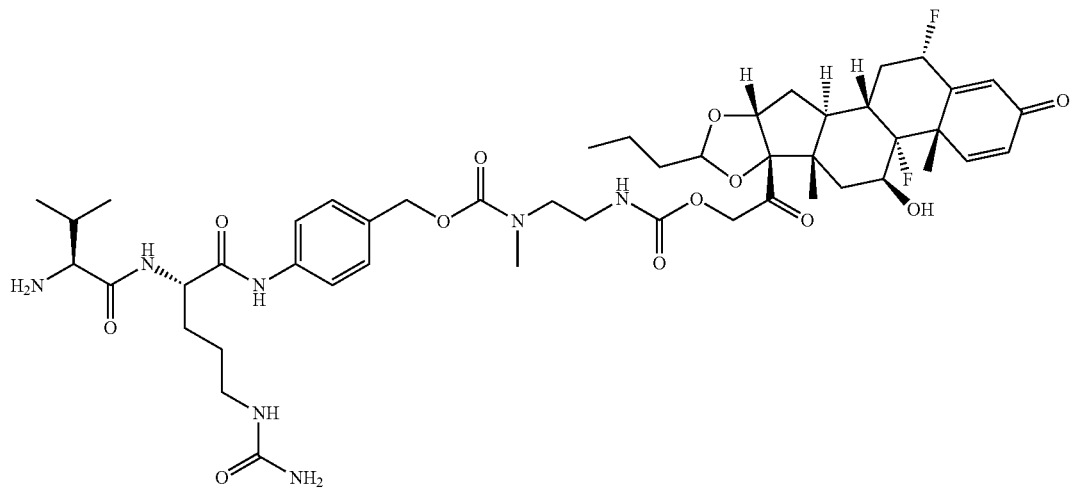 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCN(C)C(=O)OCc2ccc(NC(=O)[C@H](CCCNC(N)=O)NC(=O)[C@@H](N)C(C)C)cc2)O1]

Following the general procedure and using compound 101a, compound 101-3a (0.11 g, 57% yield) was obtained as a white solid. ESI m/z: 972 (M+H)⁺.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl N-methyl-N-[2-(methylamino)ethyl]carbamate (101-3b)

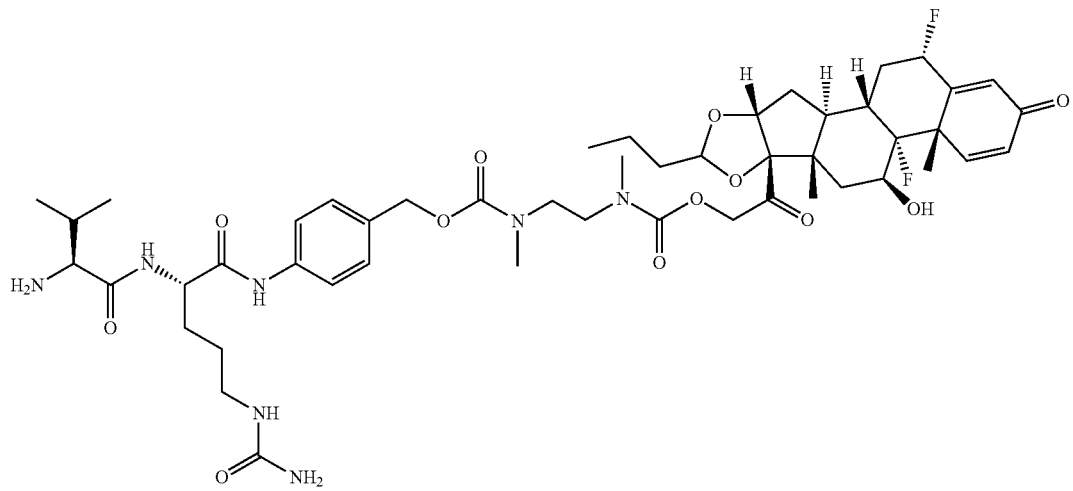 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](N)C(C)C)cc2)O1]

Following the general procedure and using compound 101b, compound 101-3b (0.13 g, 65% yield) was obtained as a white solid. ESI m/z: 986 (M+H)⁺.

1-{4-[(2S)-2-[(2S)-2-Amino-3-methylbutanamido]-5-(carbamoylamino)pentanamido]phenyl}methyl 4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl} piperazine-1,4-dicarboxylate (101-3d)

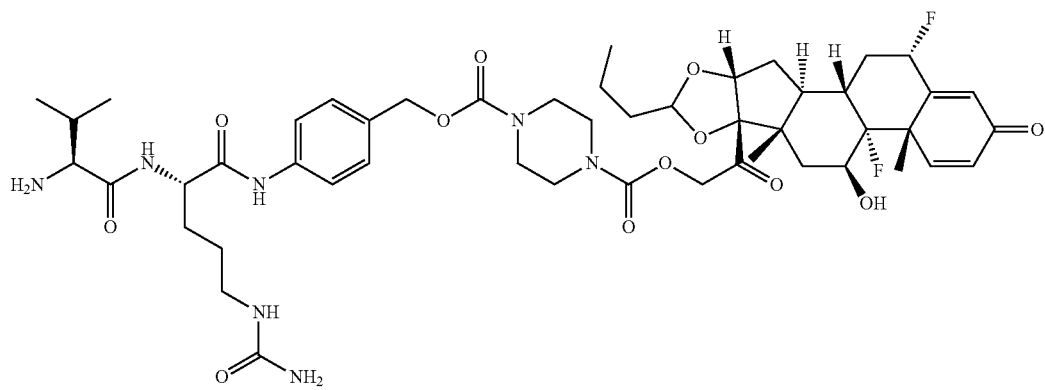 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N2CCN(C(=O)OCc3ccc(NC(=O)[C@H](CCCNC(N)=O)NC(=O)[C@@H](N)C(C)C)cc3)CC2)O1]

Following the general procedure and using compound 101d (58 mg, 0.10 mmol), compound 101-3d (52 mg, 53% yield) was obtained as a white solid. ESI m/z: 984 (M+H)$^+$. $^1$H NMR (500 MHz, DMSO$_{d6}$) δ 10.0 (s, 1H), 8.14 (d, J=7.5 Hz, 1H), 7.60 (d, J=8.5 Hz, 2H), 7.31 (d, J=8.5 Hz, 2H), 7.26 (d, J=8.5 Hz, 1H), 6.30 (dd, J=1.5 Hz, 10.5 Hz, 1H), 6.11 (s, 1H), 6.02-5.88 (m, 1H), 5.70-5.50 (m, 2H), 5.42 (s, 2H), 5.20-4.92 (m, 3H), 4.80-4.62 (m, 3H), 4.50-4.45 (m, 1H), 4.25-4.15 (m, 1H), 3.50-3.35 (m, 8H), 3.05-2.90 (m, 3H), 2.70-2.54 (m, 2H), 2.32-2.20 (m, 1H), 2.10-1.50 (m, 10H), 1.46 (s, 3H), 1.45-1.30 (m, 5H), 0.95 (d, J=7.5 Hz, 1H), 0.90-0.80 (m, 9H), 0.77 (d, J=7.0 Hz, 3H) ppm.

General Procedure for Compounds LP1, LP2 and LP4

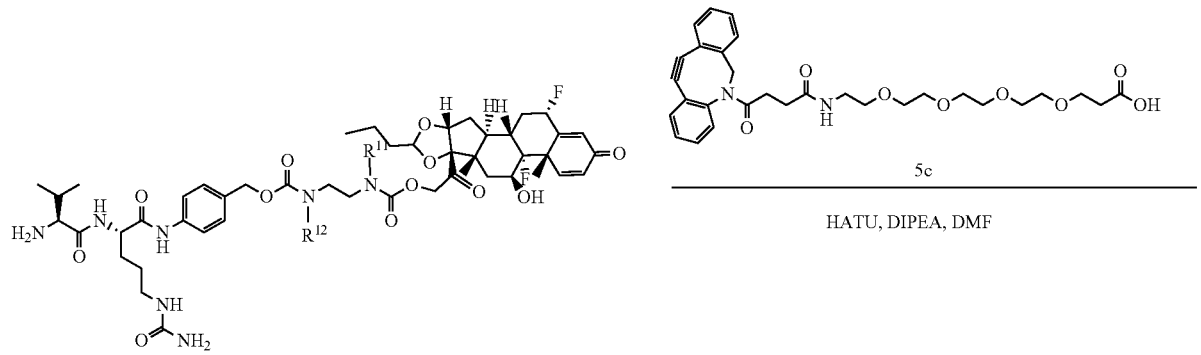

101-3a,b,d
a, R$^{11}$ = H, R$_{12}$ = Me
b, R$^{11}$ = R$_{12}$ = Me
d, R$^{11}$, R$^{12}$ = -CH$_2$CH$_2$-
(piperazine)

-continued

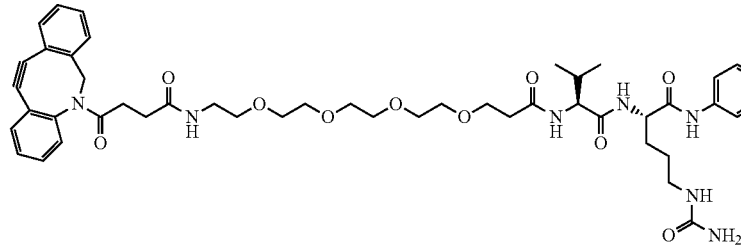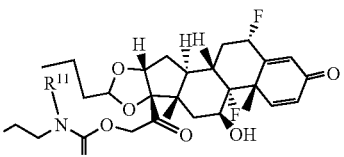

LP1,2,4
LP1, $R^{11}$ = H, $R_{12}$ = Me
LP2, $R^{11}$ = $R_{12}$ = Me
LP4, $R^{11}$, $R^{12}$
together = -CH$_2$CH$_2$-
(forming piperazine)

To a solution of compound 5c (34 mg, 60 μmol) in DMF (1 mL) were added HATU (27 mg, 71 μmol) and DIPEA (20 mg, 0.15 mmol). The mixture was stirred at RT for 5 minutes before compound 101-3a, b, or d (50 μmol) was added into the mixture. The mixture was stirred at RT for 2 hours, which was monitored by LCMS. The resulting mixture was directly purified by prep-HPLC (method B) to give compound LP1, 2 or 4 as a white solid.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](methyl)amino}ethyl)carbamate (LP1)

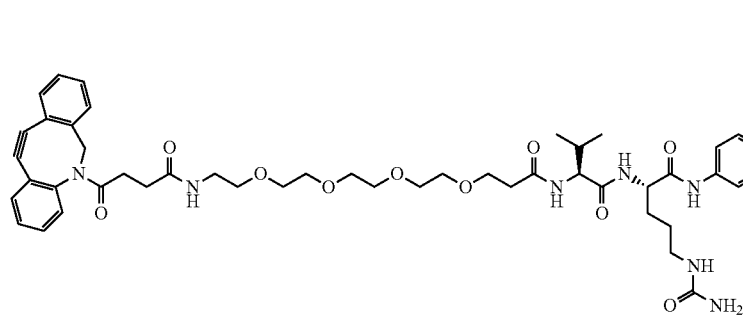

Following the general procedure and using compound 101-3a, linker-payload LP1 (20 mg, 26% yield) was obtained as a white solid. ESI m/z: 754 (M/2+H)$^+$.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl N-(2-{[({4-[(2S)-2-[(2S)-2-[1-(4-{2-azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](methyl)amino}ethyl)-N-methylcarbamate (LP2)

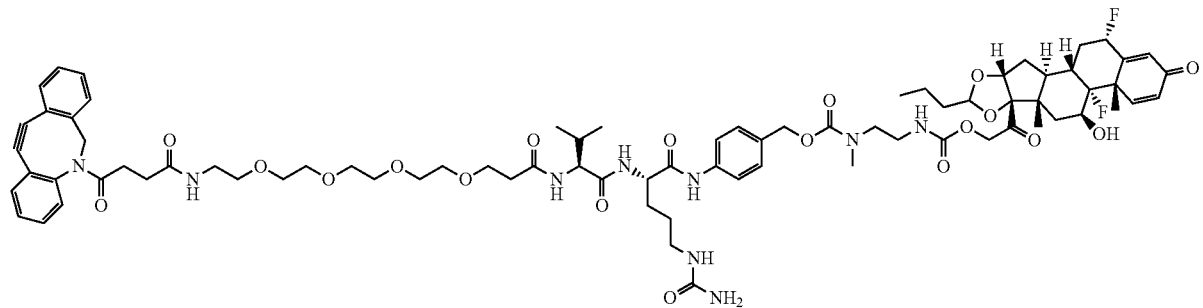 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCN(C)C(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

Following the general procedure and using compound 101-3b, linker-payload LP2 (20 mg, 26% yield) was obtained as a white solid. ESI m/z: 761 (M/2+H)⁺. ¹H NMR (500 MHz, DMSO$_{d6}$) δ 9.98 (s, 1H), 8.12 (d, J=7.4 Hz, 1H), 7.87 (d, J=8.6 Hz, 1H), 7.76 (t, J=5.4 Hz, 1H), 7.69-7.66 (m, 1H), 7.64-7.57 (m, 3H), 7.51-7.44 (m, 3H), 7.40-7.33 (m, 2H), 7.32-7.25 (m, 4H), 6.33-6.27 (m, 1H), 6.11 (s, 1H), 5.98 (t, J=5.5 Hz, 1H), 5.70-5.55 (m, 2H), 5.41 (s, 2H), 5.08-4.91 (m, 4H), 4.79-4.66 (m, 2H), 4.41-4.35 m, 1H), 4.25-4.17 (m, 2H), 3.64-3.56 (m, 3H), 3.49-3.41 (m, 15H), 3.30-3.27 (m, 2H), 3.13-3.00 (m, 3H), 2.98-2.75 (m, 8H), 2.65-2.54 (m, 2H), 2.48-2.43 (m, 1H), 2.41-2.34 (m, 1H), 2.28-2.19 (m, 2H), 2.07-1.94 (m, 4H), 1.81-1.67 (m, 3H), 1.63-1.53 (m, 5H), 1.48 (s, 3H), 1.45-1.31 (m, 5H), 0.88-0.82 (m, 13H) ppm.

1-{4-[(2S)-2-[(2S)-2-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl}piperazine-1,4-dicarboxylate (LP4)

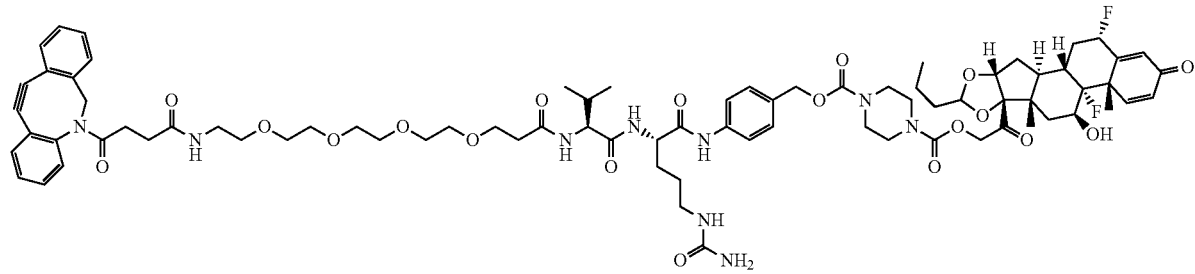 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N2CCN(C(=O)OCc3ccc(NC(=O)[C@H](CCCNC(N)=O)NC(=O)[C@@H](NC(=O)CCOCCOCCOCCOCCNC(=O)CCC(=O)N4Cc5ccccc5C#Cc5ccccc54)C(C)C)cc3)CC2)O1]

Following the general procedure and using compound 101-3d, linker-payload LP4 (35 mg, 44% yield) was obtained as a white solid. ESI m/z: 760 (M/2+H)⁺. ¹H NMR (500 MHz, DMSO$_{d6}$) δ 10.0 (s, 1H), 8.14 (d, J=7.5 Hz, 1H), 7.88 (d, J=8.5 Hz, 1H), 7.77 (t, J=5.0 Hz, 1H), 7.70-7.66 (m, 1H), 7.63-7.55 (m, 3H), 7.52-7.43 (m, 3H), 7.40-7.27 (m, 6H), 6.30 (d, J=10.5 Hz, 1H), 6.11 (s, 1H), 6.02-5.88 (m, 1H), 5.70-5.50 (m, 2H), 5.42 (s, 2H), 5.20-4.92 (m, 4H), 4.80-4.62 (m, 3H), 4.40-4.35 (m, 1H), 4.26-4.20 (m, 2H), 3.64-3.55 (m, 3H), 3.50-3.35 (m, 17H), 3.30-3.25 (m, 3H), 3.15-2.90 (m, 4H), 2.64-2.54 (m, 2H), 2.50-2.45 (m, 1H), 2.41-2.34 (m, 1H), 2.32-2.20 (m, 2H), 2.10-1.92 (m, 4H), 1.80-1.68 (m, 3H), 1.62-1.50 (m, 5H), 1.46 (s, 3H), 1.45-1.40 (m, 2H), 1.40-1.30 (m, 3H), 1.22-1.20 (m, 1H), 0.90-0.80 (m, 13H) ppm.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-ethyl-N-[2-(ethylamino)ethyl]carbamate (101-4)

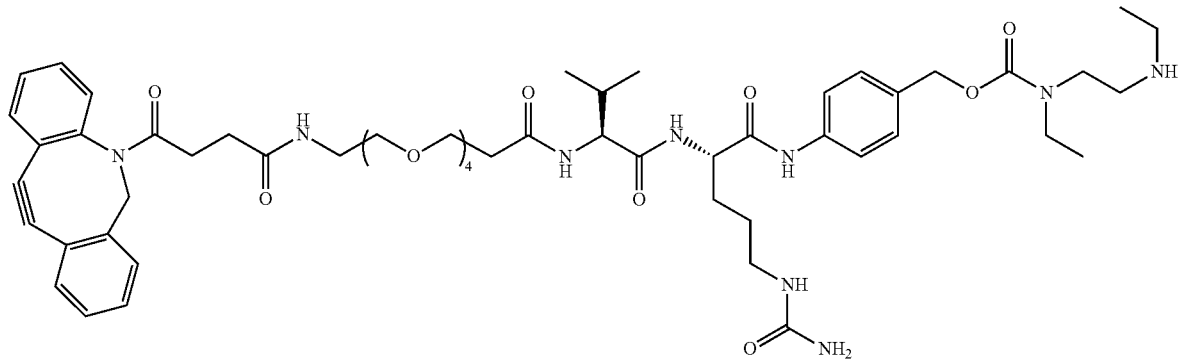

To a solution of DIBAC-suc-PEG$_4$-vcPAB-PNP 11b (0.11 g, 0.10 mmol) in DMF (5 mL) were added N,N'-diethylethylenediamine (58 mg, 0.50 mmol) and DMAP (1 mg, 0.01 mmol). The reaction mixture was stirred at RT for 4 hours, which was monitored by LCMS. The resulting mixture was directly purified by prep-HPLC (method B) to give compound 101-4 as colorless oil. ESI m/z: 1056.6 (M+H)⁺, 529 (M/2+H)⁺.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](ethyl)amino}ethyl)-N-ethylcarbamate (LP3)

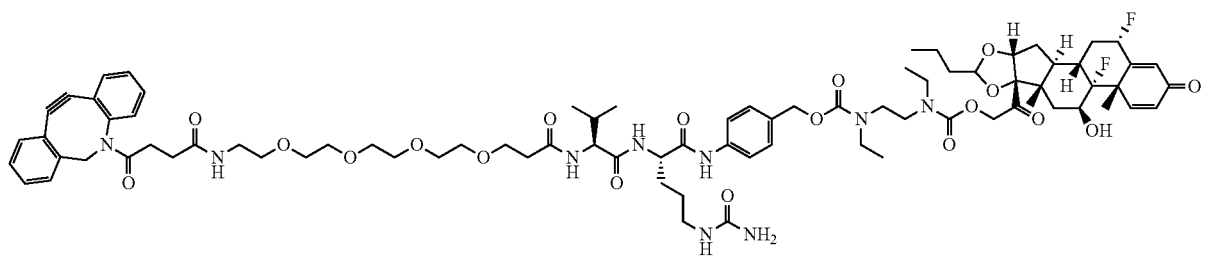

A mixture of compound 101-4 (16 mg, 15 μmol), 101-1b (11 mg, 17 μmol) and DIPEA (4.0 mg, 31 μmol) in DMF (5 mL) was stirred at RT for 4 hours, which was monitored by LCMS. The reaction mixture was directly purified by prep-HPLC (method B) to give linker-payload LP3 (3 mg, 13% yield) as a white solid. ESI m/z: 775 (M/2+H)$^+$. $^1$H NMR (500 MHz, DMSO$_{d6}$) δ 10.0 (s, 1H), 8.14 (d, J=7.5 Hz, 1H), 7.88 (d, J=8.5 Hz, 1H), 7.77 (t, J=5.0 Hz, 1H), 7.70-7.66 (m, 1H), 7.63-7.55 (m, 3H), 7.52-7.43 (m, 3H), 7.40-7.27 (m, 7H), 6.30 (d, J=10.5 Hz, 1H), 6.11 (s, 1H), 6.02-5.88 (m, 1H), 5.70-5.50 (m, 2H), 5.42 (s, 2H), 5.20-4.92 (m, 4H), 4.80-4.62 (m, 3H), 4.40-4.35 (m, 1H), 4.26-4.20 (m, 2H), 3.64-3.55 (m, 4H), 3.50-3.35 (m, 18H), 3.12-2.90 (m, 7H), 2.64-2.54 (m, 3H), 2.41-2.34 (m, 2H), 2.32-2.20 (m, 3H), 2.10-1.92 (m, 5H), 1.88-1.68 (m, 3H), 1.62-1.50 (m, 6H), 1.50-1.40 (m, 6H), 1.40-1.30 (m, 4H), 1.22-1.20 (m, 1H), 1.02-0.90 (m, 4H), 0.90-0.78 (m, 6H) ppm.

Synthesis of Cystamine Prodrugs: Linker-Payloads LP5, 6, 7 and LP8

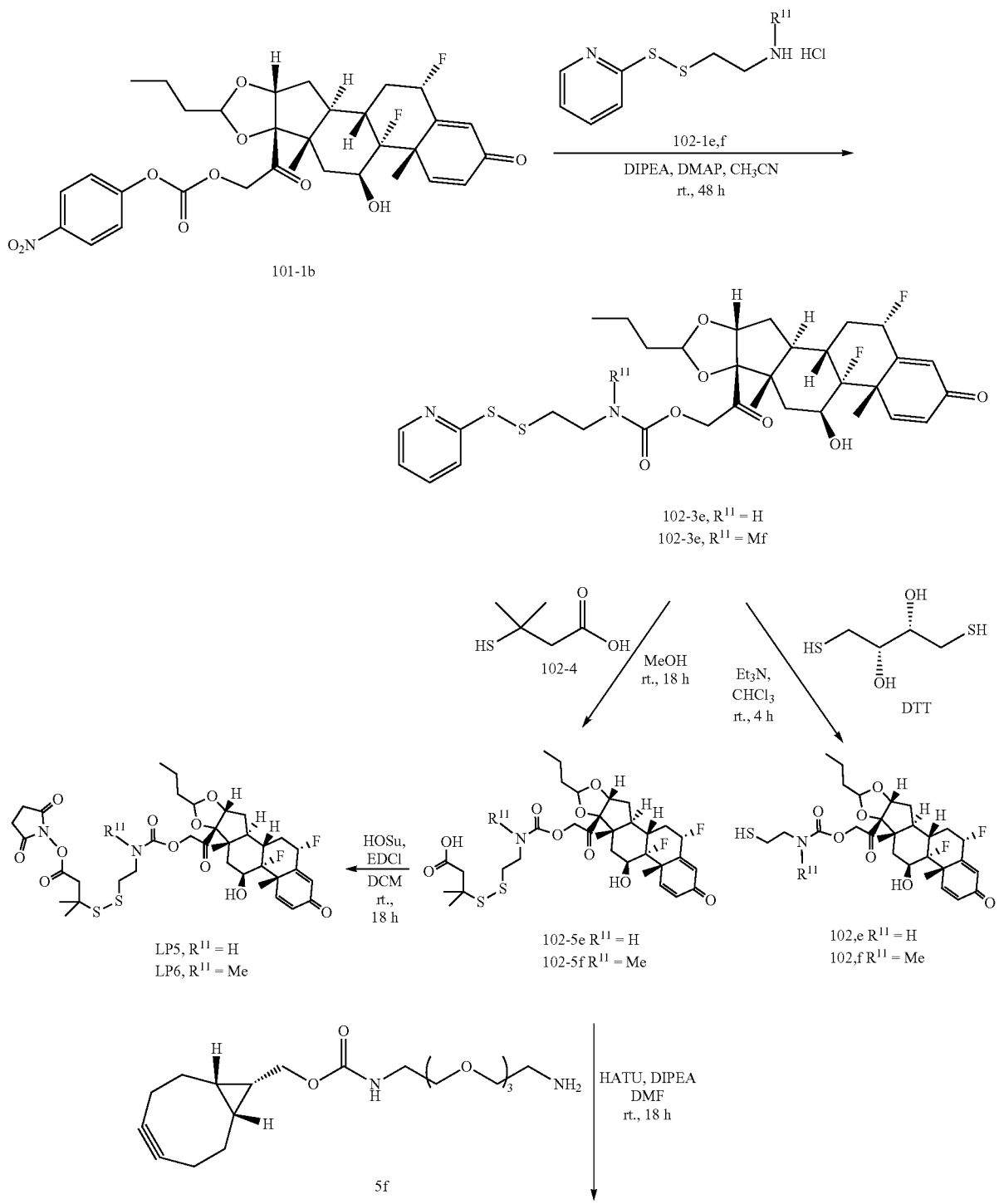

-continued

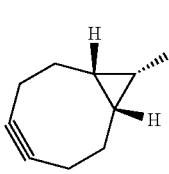 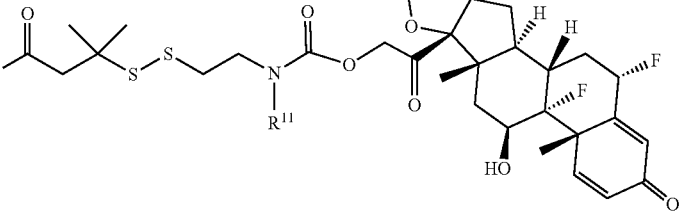

LP7, R[11] = H
LP8, R[11] = Me 2-(pyridin-2-yldisulfanyl)ethanamine hydrochloride (102-1e) was commercially available with CAS 83578-21-6. tert-butyl (2-mercaptoethyl)(methyl)carbamate (102-1f) was synthesized according to *Eur. J. Med. Chem.*, 2015, 95, 483-491.

endo-bicyclo[6.1.0]non-4-yn-9-ylmethyl N-(2-{2-[2-(2-aminoethoxy)ethoxy]ethoxy}ethyl)carbamate (5f) was synthesized according to WO2016168769. 2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-[2-(pyridin-2-yldisulfanyl)ethyl]carbamate (102-3e)

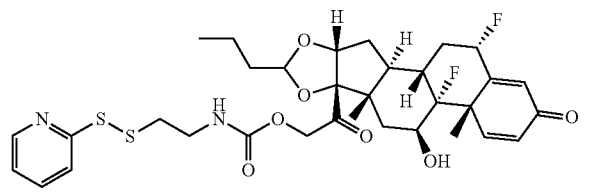

To a solution of compound 101-1b (0.54 g, 0.86 mmol) in acetonitrile (10 mL) were added DIPEA (0.22 g, 1.7 mmol), 102-1e (0.19 g, 0.86 mmol) and DMAP (10 mg, 86 μmol). The reaction mixture was stirred at RT for 48 hours until 101-1b was totally consumed according to LCMS. The mixture was then filtered and the filtrate was concentrated in vacuo. The residual oil was purified by silica gel column chromatography (20-50% ethyl acetate in hexane) to give compound 102-3e (0.47 g, 80% yield) as a white solid. ESI m/z: 679.2 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-[2-(pyridin-2-yldisulfanyl)ethyl]carbamate (102-3f)

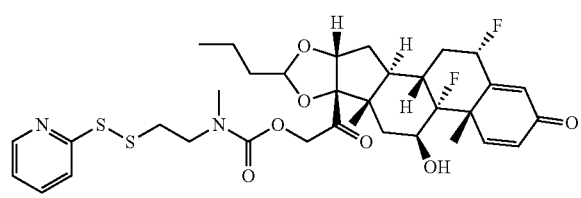

Following the similar procedure as 102-3e except substituting 102-1f for 102-1e, compound 102-3f (0.45 g, 75% yield) was obtained as a white solid. ESI m/z: 693.2 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-sulfanylethyl)carbamate (102e)

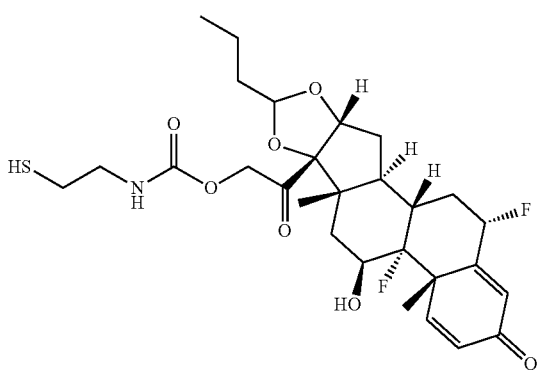 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCS)O1]

To a solution of compound 102-3e (1.4 g, 2.1 mmol) in chloroform (30 mL) were added triethylamine (0.82 mL, 5.9 mmol) and 1,4-dithiothreitol (Cleland's reagent, DTT) (1.2 g, 7.8 mmol). The reaction mixture was stirred at RT under nitrogen for 4 hours, which was monitored by LCMS. The resulting mixture was concentrated in vacuo. The residue was purified by silica gel column chromatography (50-70% ethyl acetate in hexane) to give compound 102e (0.95 g, 83% yield) as a white solid. ESI m/z: 570.2 (M+H)$^+$.

413

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-(2-sulfanylethyl)carbamate (102f)

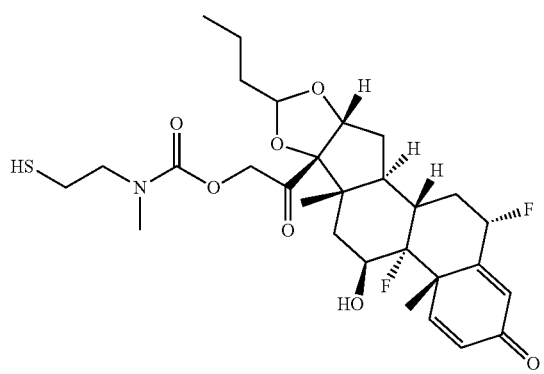 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCS)O1]

Following the similar procedure as 102e except substituting 102-3f for 102-3e, compound 102f (0.97 g, 83% yield) was obtained as a white solid. ESI m/z: 584.3 (M+H)$^+$.

3-({2-[({2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)amino]ethyl}disulfanyl)-3-methylbutanoic acid (102-5e)

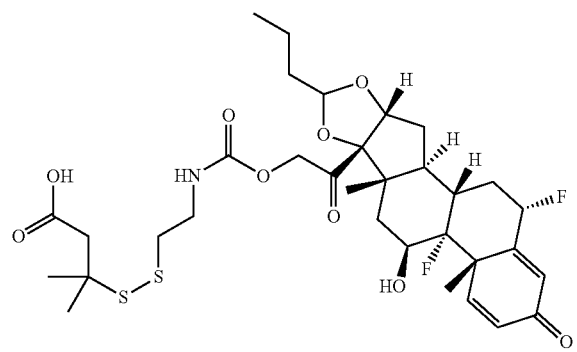 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)O)O1]

To a solution of compound 102-3e (0.68 g, 1.0 mmol) in methanol (5 mL) were added compound 102-4 (0.13 g, 1.0 mmol). The reaction mixture was stirred at RT for 18 hours, which was monitored by LCMS. The resulting mixture was then directly purified by prep-HPLC (method B) to give compound 102-5e (0.39 g, 55% yield) as a white solid. ESI m/z: 702.2 (M+H)$^+$.

414

3-({2-[({2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}disulfanyl)-3-methylbutanoic acid (102-5f)

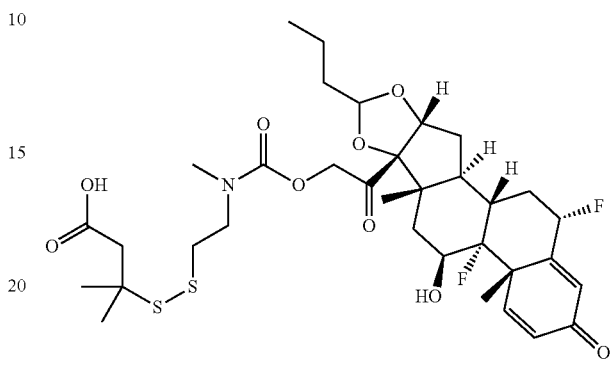

Following the similar procedure as 102-5e except substituting 102-3f for 102-3e, compound 102-5f (0.29 g, 40% yield) was obtained as a white solid. ESI m/z: 716.3 (M+H)$^+$.

2,5-Dioxopyrrolidin-1-yl 3-({2-[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)amino]ethyl}disulfanyl)-3-methylbutanoate (LP5)

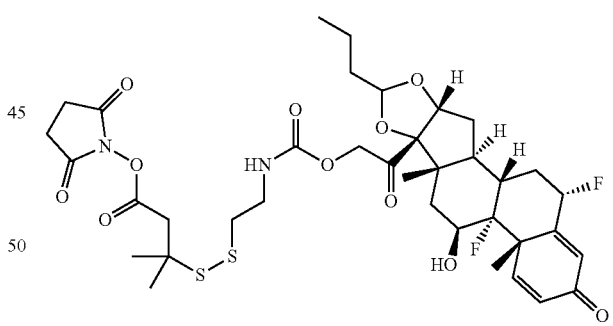

To a solution of compound 102-5e (0.20 g, 0.29 mmol) in DCM (10 mL) were added HOSu (73 mg, 0.64 mmol) and EDCI (0.12 g, 0.64 mmol), and the mixture was stirred at RT for 24 hours, which was monitored by LCMS. The resulting mixture was diluted with DCM (50 mL) and the organic solution was washed with water and brine, dried over anhydrous sodium sulfate and concentrated in vacuo. The residue was purified by prep-HPLC (method A) to give LP5 (85 mg, 37% yield) as colorless oil. ESI m/z: 799.3 (M+H)$^+$.

2,5-Dioxopyrrolidin-1-yl 3-({2-[({2-[((1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}disulfanyl)-3-methylbutanoate (LP6)

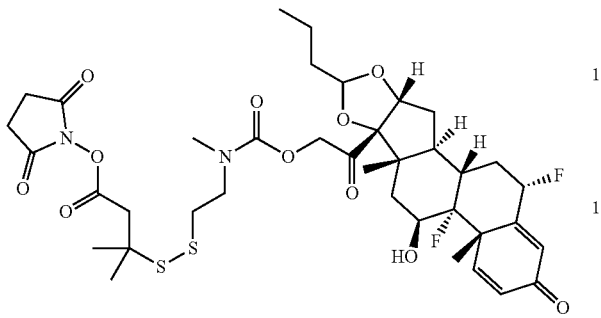

Following the similar procedure as LP5 except substituting 102-5f for 102-5e, compound LP6 (86 mg, 36% yield) was obtained as colorless oil. ESI m/z: 813.3 (M+H)$^+$.

endo-Bicyclo[6.1.0]non-4-yn-9-ylmethyl N-{2-[2-(2-{2-[3-({2-[({2-[((1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)amino]ethyl}disulfanyl)-3-methylbutanamido]ethoxy}ethoxy)ethoxy]ethyl}carbamate (LP7)

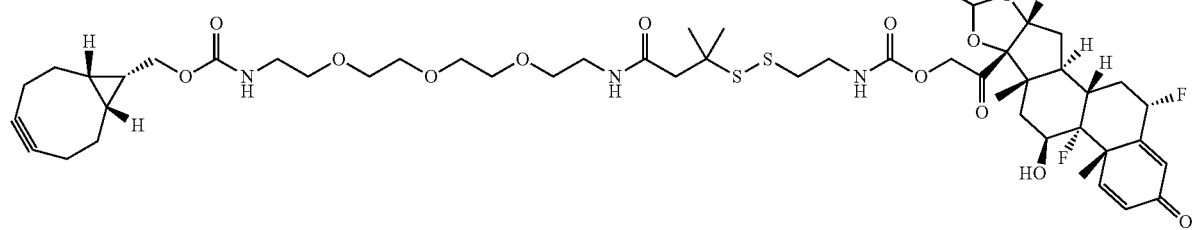

To a solution of compound 102-5e (0.20 g, 0.29 mmol) in DMF (10 mL) were added HATU (0.11 g, 0.29 mmol) and DIPEA (75 mg, 0.58 mmol). The reaction mixture was stirred at RT for 10 minutes before compound 5f (0.11 g, 0.29 mmol) was added into. The reaction mixture was stirred at RT for 18 hours, which was monitored by LCMS. The resulting mixture was then directly purified by prep-HPLC (method B) to give compound LP7 (0.16 g, 55% yield) as a white solid. ESI m/z: 526.7 (M/2+H)$^+$.

endo-Bicyclo[6.1.0]non-4-yn-9-ylmethyl N-{2-[2-(2-{2-[3-({2-[({2-[((1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}disulfanyl)-3-methylbutanamido]ethoxy}ethoxy)ethoxy]ethyl}carbamate (LP8)

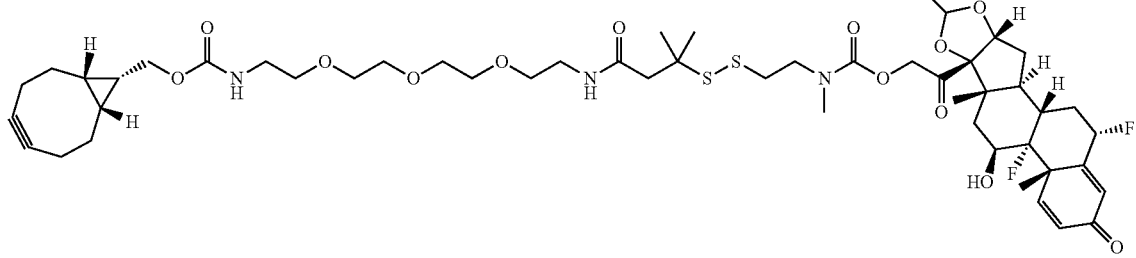

Following the similar procedure as LP7 except substituting 102-5f for 102-5e, compound LP8 (0.13 g, 41% yield) was obtained as a white solid. ESI m/z: 533.8 (M/2+H)$^+$.
Synthesis of AMO Linker-Payloads LP9-11
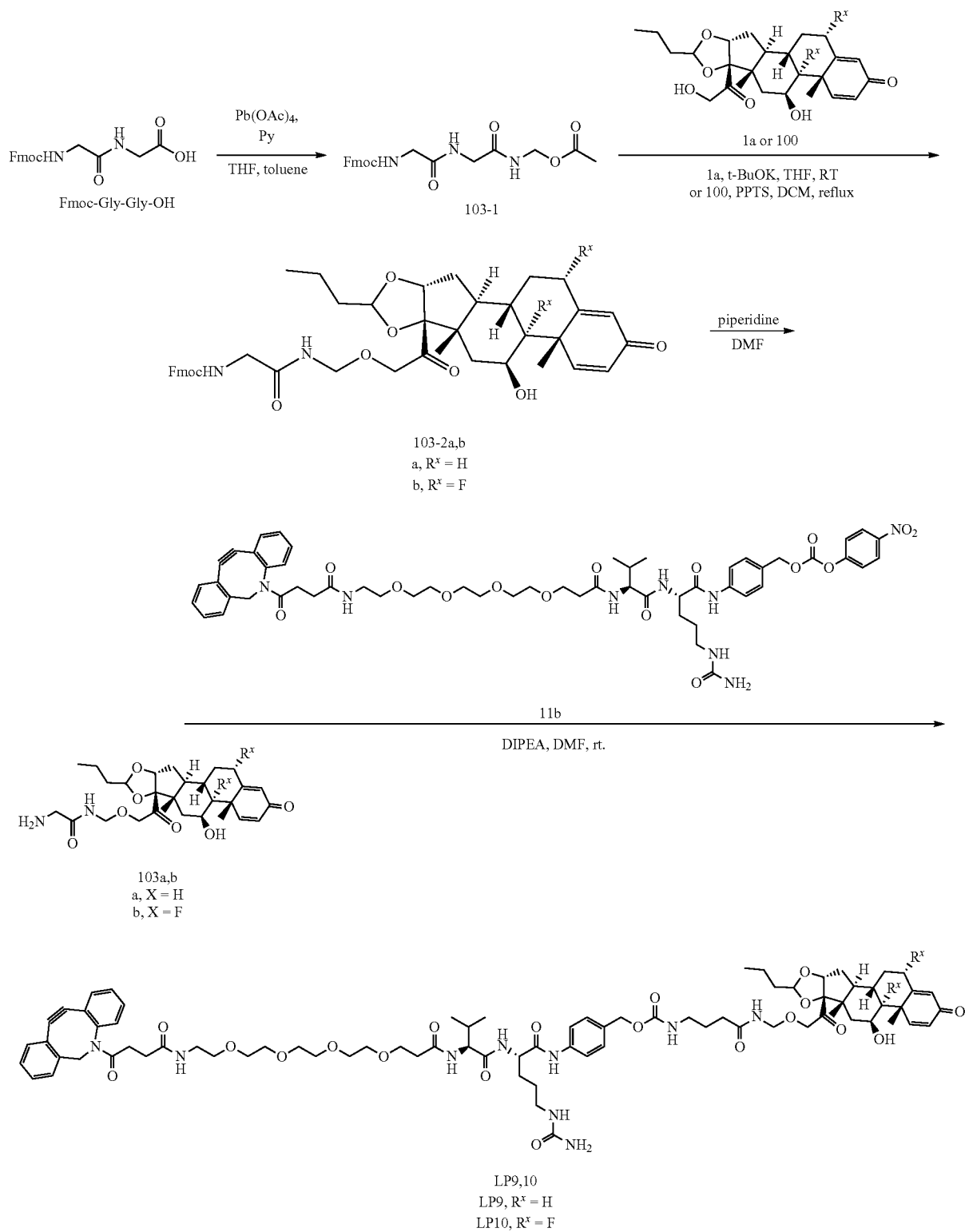

(2-(((9H-Fluoren-9-yl)methoxy)carbonylamino)acetamido)methyl acetate (103-1)

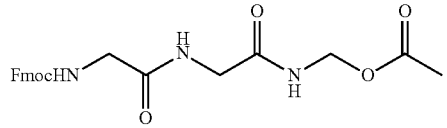

To a mixture of Fmoc-Gly-Gly-OH (4.3 g, 12 mmol) in THF (0.12 L) and toluene (40 mL) were added pyridine (1.2 mL, 15 mmol) and lead tetraacetate (6.8 g, 15 mmol). The reaction mixture was refluxed for 5 hours, which was monitored by LCMS. After cooled to RT, the reaction mixture was filtered through Celite to remove the insoluble material, and the filtrate was concentrated in vacuo. The residue was dissolved in ethyl acetate, and the solution was washed with water and brine. The organic solution was dried over sodium sulfate and concentrated in vacuo. The residue was purified by silica gel column chromatography (10% ethyl acetate in petroleum ether) to provide compound 103-1 (3.0 g, 67% yield) as a colorless solid. ESI m/z: 391 $(M+Na)^+$.

9H-Fluoren-9-ylmethyl N-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamate (103-2a)

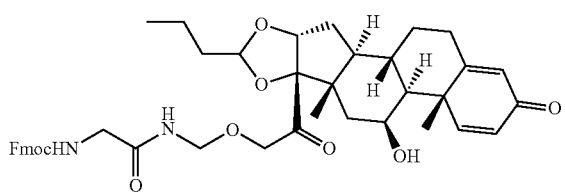

To a solution of compound 103-1 (0.37 g, 1.0 mmol) and budesonide 1a (1.3 g, 3.0 mmol) in THF (4 mL) was added potassium tert-butoxide (0.22 g, 2.0 mmol) at 0° C. The reaction mixture was stirred at RT for 15 minutes, which was monitored by TLC. The reaction solution was charged with ethyl acetate and water at 0° C., and extracted with ethyl acetate and chloroform. The combined organic solution was dried over sodium sulfate and concentrated in vacuo. The residue was purified by silica gel column chromatography (30-35% ethyl acetate in petroleum ether) to give compound 103-2a (0.19 g, 40% yield) as a white solid. ESI m/z: 739 $(M+H)^+$.

9H-Fluoren-9-ylmethyl N-{[1(2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamate (103-2b)

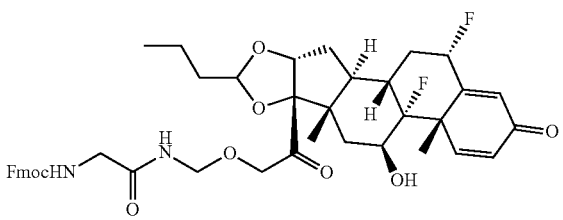

To a sealed tube were added a solution of compound 103-1 (0.30 g, 0.81 mmol) and compound 100 (0.38 g, 0.81 mmol) in DCM (4 mL) and pyridinium p-toluenesulfonate (21 mg, 81 μmol) at RT. The reaction tube was sealed and stirred at 50° C. for 24 hours, which was monitored by LCMS. After cooled, the reaction mixture was concentrated in vacuo and the residue was purified by prep-HPLC (method A) to give compound 103-2b (0.23 g, 37% yield) as a white solid. ESI m/z: 775 $(M+H)^+$.

2-Amino-N-({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)acetamide (103a)

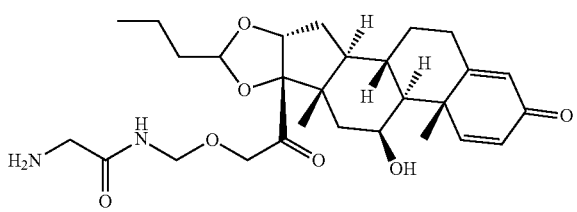

To a solution of compound 103-2a (0.10 g, 0.14 mmol) in DMF (2 mL) was added piperidine (35 mg, 0.41 mmol). The reaction mixture was stirred at RT for 2 hours until Fmoc was totally removed, which was monitored by LCMS. The resulting mixture was directly purified by reversed phase flash chromatography (0-100% acetonitrile in aq. TFA (0.05%)) to give compound 103a (50 mg, 70% yield) as a white solid. ESI m/z: 517.6 $(M+H)^+$.

2-Amino-N-({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)acetamide (103b)

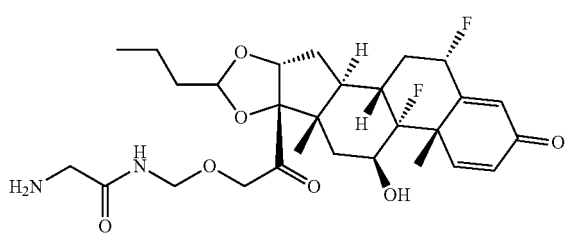

Following the similar procedure as 103a except substituting 103-2b for 103-2a, compound 103b (0.26 g, 65% yield) was obtained as a white solid. ESI m/z: 553.2 (M/2+H)+.

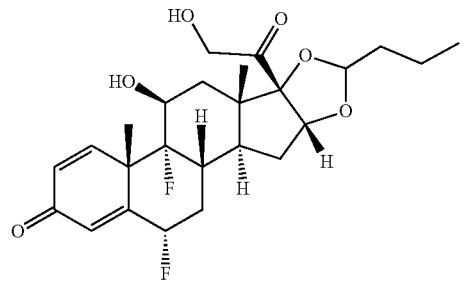 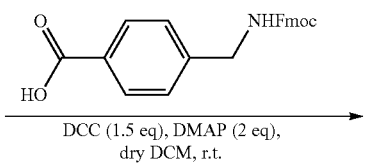

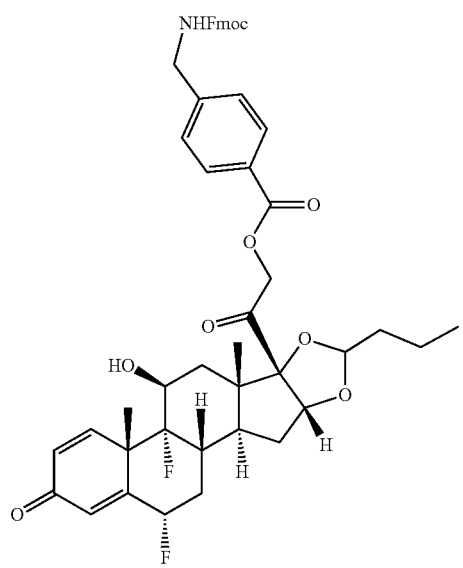 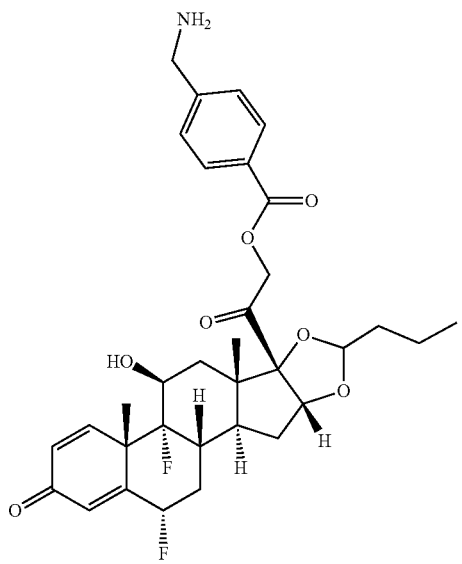

105b

Compound 105(b) was prepared according to the above procedure.

{4-[(2S)-2-[(2S)-2-[1-(4-{2-Azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{[({2-[(1S,2S,4R,8S,9S,11S,12S,13R)-11-hydroxy-9,13-dimethyl-16-oxo-6-propyl-5,7-dioxapentacyclo[10.8.0.0^{2,9}.0^{4,8}.0^{13,18}]icosa-14,17-dien-8-yl]-2-oxoethoxy}methyl)carbamoyl]methyl}carbamate (LP9)

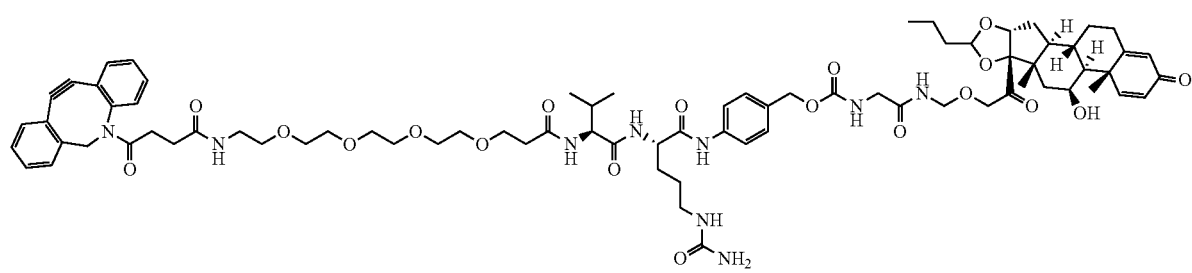

To a solution of compound 103a (15 mg, 29 µmol) in DMF (1.0 mL) were added compound 11b (30 mg, 28 µmol), HOBT (2.0 mg, 15 µmol) and DIPEA (7.7 mg, 60 µmol). The reaction mixture was stirred at RT for 2 hours, which was monitored by LCMS. The mixture was directly purified by prep-HPLC (method B) to give linker-payload LP9 (5.0 mg, 110% yield) as a white solid. ESI m/z: 729 (M/2+H)$^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamate (LP10)

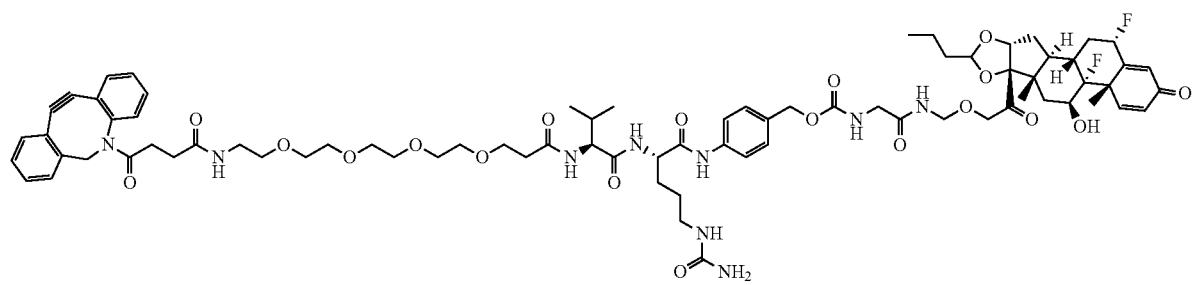

Following the similar procedure as LP9 except substituting 103b for 103a, linker-payload LP10 (23 mg, 58% yield) was obtained as a white solid. ESI m/z: 747.0 (M/2+H)$^+$; 513.8 (fragment cleaved by LCMS, piece cleaved at NHCH$_2$—O) $^1$HNMR (400 MHz, DMSO$_{d6}$) δ 10.02 (s, 1H), 8.80-8.72 (m, 1H), 8.15 (d, J=6.8 Hz, 1H), 7.89 (d, J=8.8 Hz, 1H), 7.80-7.75 (m, 1H), 7.68 (d, J=7.6 Hz, 1H), 7.64-7.58 (m, 3H), 7.54-7.22 (m, 9H), 6.29 (d, J=10.0 Hz, 1H), 6.10 (s, 1H), 6.04-5.96 (m, 1H), 5.78-4.10 (m, 15H), 3.66-3.54 (m, 5H), 3.54-3.42 (m, 13H), 3.32-3.26 (m, 2H), 3.20-2.50 (m, 7H), 2.42-2.20 (m, 4H), 2.05-1.90 (m, 4H), 1.85-1.25 (m, 15H), 0.90-0.80 (m, 13H) ppm.

Scheme 103B. Synthesis of Linker-payload LP11

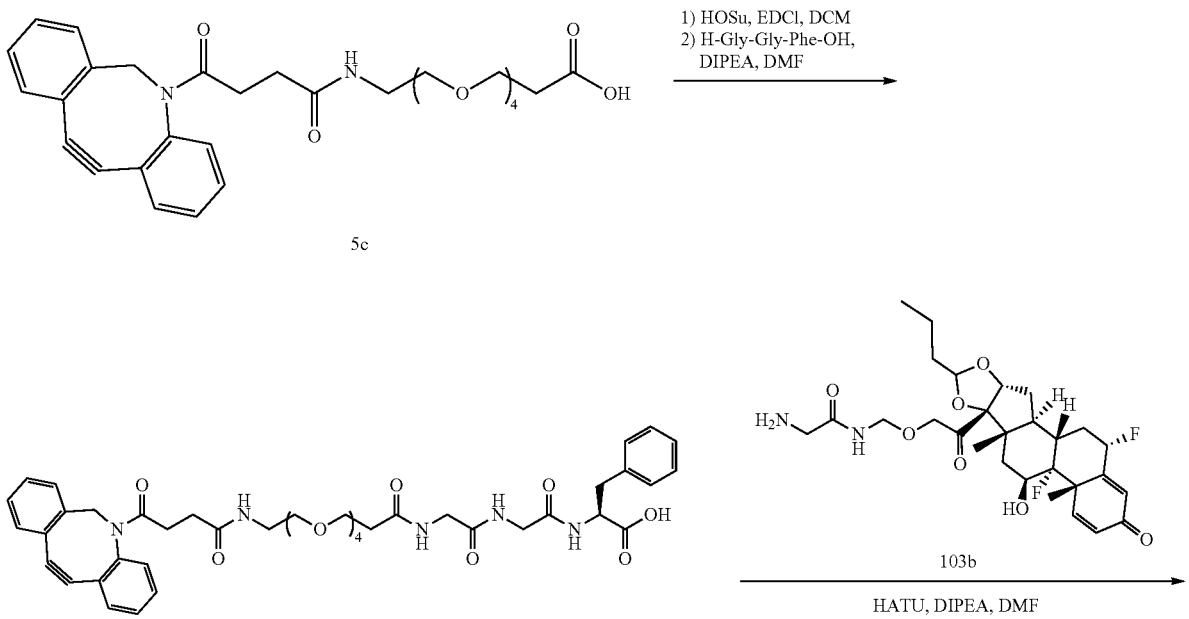

-continued

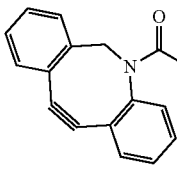 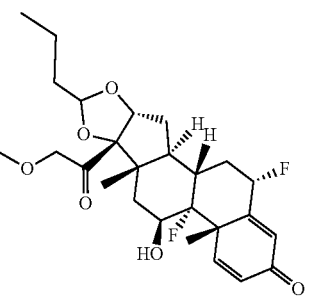

LP11

(2S)-2-(2-{2-[1-(4-{2-Azatricyclo[10.4.0.0^{4,9}]hexa-deca-1(12),4(9),5,7,13,15-hexaen-10-yn-2-yl}-4-oxobutanamido)-3,6,9,12-tetraoxapentadecan-15-amido]acetamido}acetamido)-3-phenylpropanoic acid (103-3)

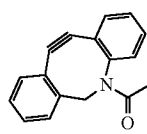

To a solution of compound 5c (0.16 g, 0.29 mmol) in DCM (20 mL) were added HOSu (73 mg, 0.64 mmol) and EDCI (0.12 g, 0.64 mmol). The mixture was stirred at RT for 24 hours until compound 5c was totally consumed according to LCMS. The resulting mixture was diluted with DCM (50 mL) and the organic solution was washed with water (50 mL) and brine (50 mL), dried with anhydrous sodium sulfate and concentrated in vacuo to give the OSu active ester (0.16 g, 84% yield) as colorless oil, which was used for next step directly.

To a solution of H-Gly-Gly-Phe-OH (10 mg, 36 μmol) in DMF (0.5 mL) were added the OSu active ester (23 mg, 36 μmol) obtained above and DIPEA (9.0 mg, 72 μmol). The reaction mixture was stirred at RT overnight. The mixture was directly purified by prep-HPLC (method B) to give compound 103-3 (15 mg, 51% yield) as a white solid. ESI m/z: 408.2 (M/2+H)+.

1-(4-{2-Azatricyclo[10.4.0.0^{4,9}]hexadeca-1(12),4(9),5,7,13,15-hexaen-10-yn-2-yl}-4-oxobutanamido)-N-{[({[(1S)-1-({[({2-[(19S)-12,19-difluoro-11-hydroxy-9,13-dimethyl-16-oxo-6-propyl-5,7-dioxapentacyclo[10.8.0.0^{2,9}.0^{4,8}.0^{13,18}]icosa-14,17-dien-8-yl]-2-oxoethoxy}methyl)carbamoyl]methyl}carbamoyl)-2-phenylethyl]carbamoyl}methyl)carbamoyl]methyl}-3,6,9,12-tetraoxapentadecan-15-amide (LP11)

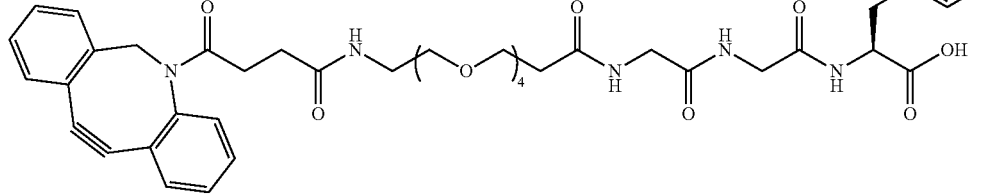

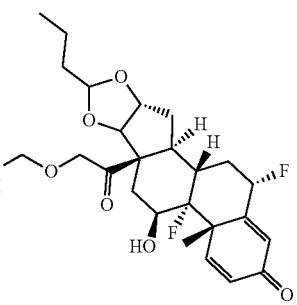

To a solution of compound 103-3 (15 mg, 18 µmol) in DMF (0.5 mL) were added HATU (14 mg, 36 µmol) and DIPEA (9.3 mg, 72 µmol). The reaction mixture was stirred at RT for 10 min before compound 103b (10 mg, 18 µmol) was added into the mixture. The reaction mixture was then stirred at RT overnight. The resulting mixture was directly purified by prep-HPLC (method B) to give linker-payload LP11 (5.0 mg, 20% yield) as a white solid. ESI m/z: 420.2 (M/3+H)$^+$.

Synthesis of Dipeptide Prodrug: Linker-Payload LP12

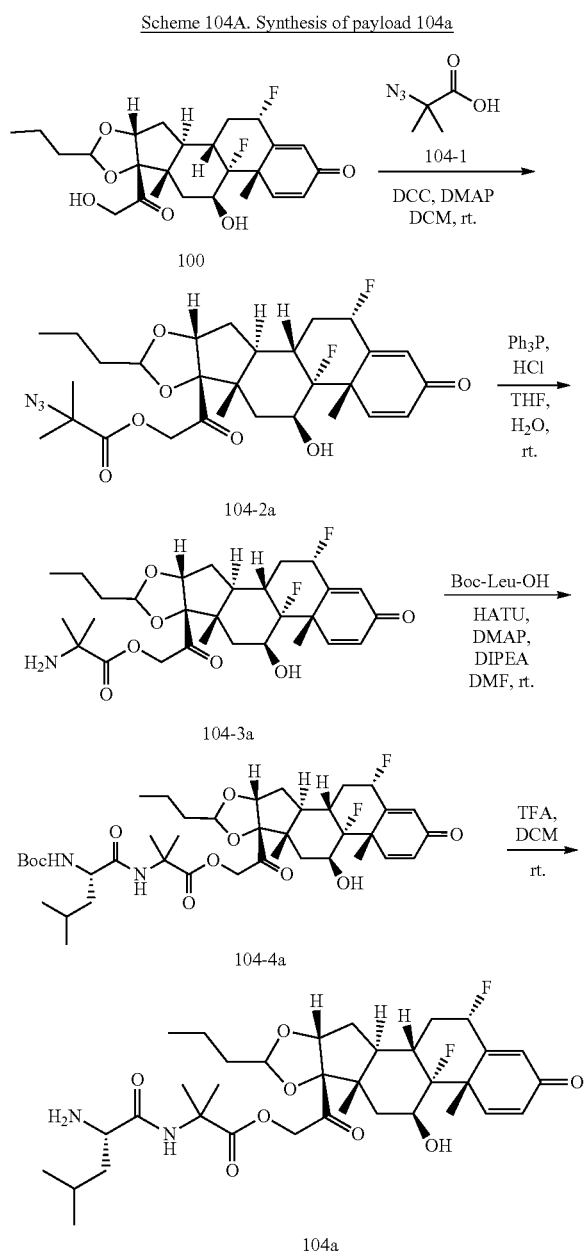

Alpha-Azidoisobutyric acid 104-1 was synthesized according to *Org. Lett.*, 2001, 3(5), 781-783.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-azido-2-methylpropanoate (104-2a)

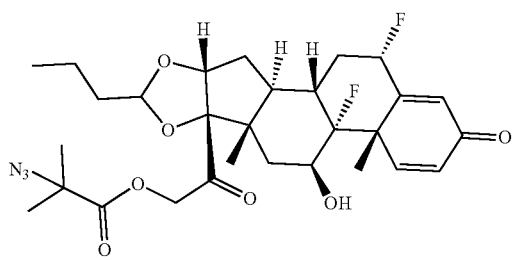

To a solution of compound 100 (0.10 g, 0.21 mmol) in DCM (30 mL) were added compound 104-1 (52 mg, 0.40 mmol), DCC (90 mg, 0.44 mmol) and DMAP (10 mg) and the mixture was stirred at RT overnight, which was monitored by LCMS. The resulting mixture was concentrated in vacuo and the residue was purified by prep-HPLC (method A) to give compound 104-2a (80 mg, 70% yield) as a white solid. ESI m/z: 578.3 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-amino-2-methylpropanoate (104-3a)

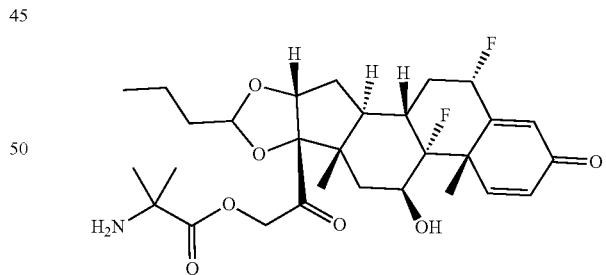

To a solution of compound 104-2a (75 mg, 0.15 mmol) in THF (5 mL) were added PPh$_3$ (0.15 g, 0.57 mmol), water (5 mL) and conc. HCl (1 drop), and the reaction mixture was stirred at RT overnight. The mixture was concentrated in vacuo and diluted with DMF. The precipitated was removed off by filtration. The filtrate was purified by prep-HPLC (method A) to give compound 104-3a (45 mg, 54% yield) as a white solid. ESI m/z: 552.3 (M+H)$^+$.

429

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,9}$.0$^{13,18}$]icosa-14,17-dien-8-yl]-2-oxoethyl 2-[(2S)-2-{[(tert-butoxy)carbonyl]amino}-4-methylpentanamido]-2-methylpropanoate (104-4a)

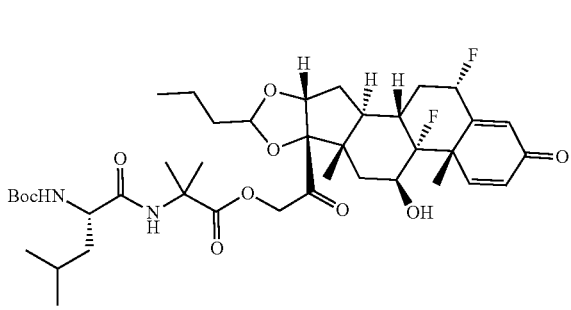

To a mixture of Boc-Leu-OH (20 mg, 87 µmol) and HATU (50 mg, 0.13 mmol) in DMF (3 mL) were added DIPEA (30 mg, 0.23 mmol), DMAP (2 mg) and compound 104-3a (30 mg, 54 µmol). The mixture was stirred at RT for an hour, which was monitored by LCMS. The mixture was directly purified by prep-HPLC (method A) to give compound 104-4a (25 mg, 55% yield) as a white solid. ESI m/z: 787.4 (M+Na)$^+$.

430

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-[(2S)-2-amino-4-methylpentanamido]-2-methylpropanoate (104a)

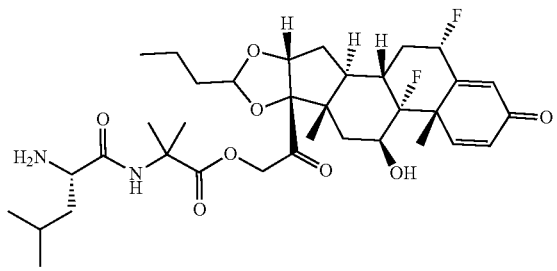

To a mixture of compound 104-4a (25 mg, 33 µmol) in DCM (1.5 mL) was added TFA (0.15 mL), and the mixture was stirred at RT for an hour until Boc was totally removed according to LCMS. The reaction mixture was concentrated in vacuo and the residue was purified by prep-HPLC (method A) to give compound 104a (13 mg, 61% yield) as a white solid. ESI m/z: 665.4 (M+H)$^+$. $^1$H NMR (400 MHz, DMSO$_{d6}$) δ 8.39 (s, 1H), 8.26 (s, 1H), 7.27 (d, J=10.0 Hz, 1H), 6.31 (d, J=10.1 Hz, 1H), 6.11 (s, 1H), 5.63 (t, J=24.2 Hz, 2H), 5.30-5.05 (m, 1H), 4.96 (d, J=17.7 Hz, 1H), 4.81-4.65 (m, 2H), 4.20 (s, 1H), 2.69-2.54 (m, 1H), 2.36-2.15 (m, 1H), 2.12-1.94 (m, 2H), 1.85-1.63 (m, 2H), 1.63-1.53 (m, 3H), 1.52-1.41 (m, 11H), 1.41-1.10 (m, 6H), 0.97-0.76 (m, 12H) ppm.

Scheme 104B. Synthesis of Linker-payload LP12

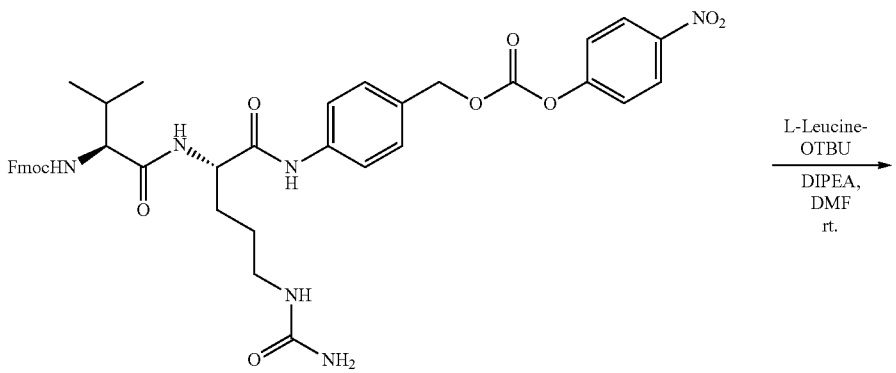

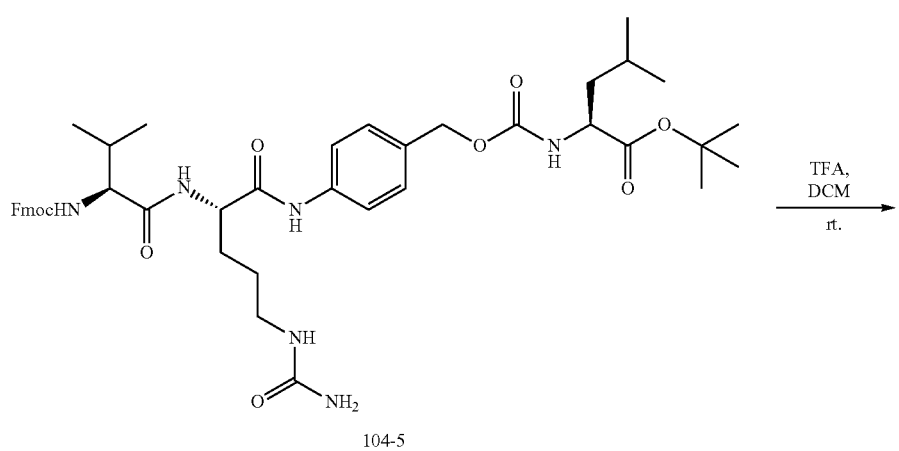

-continued
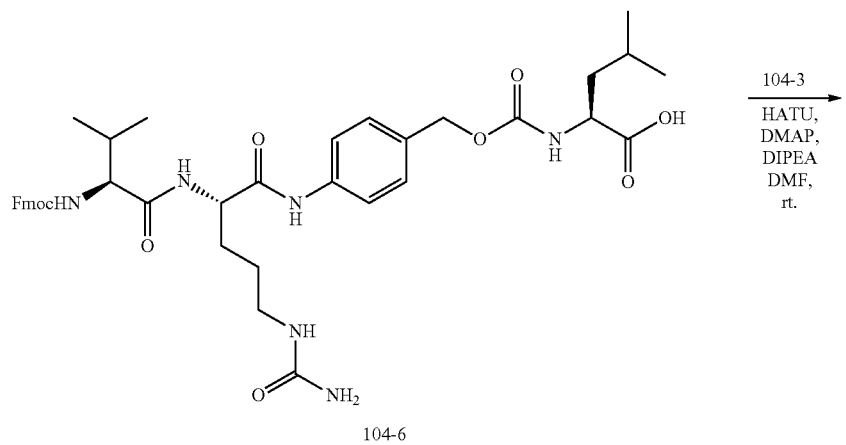
104-6
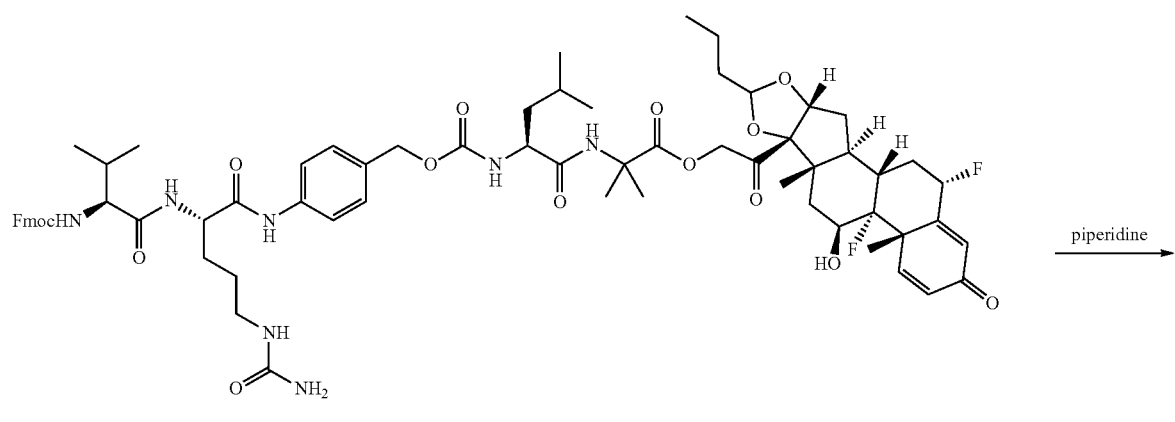
104-7a
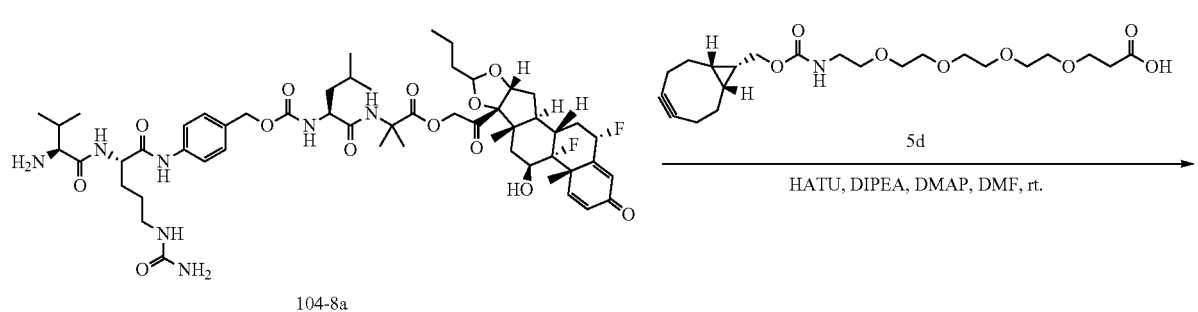
104-8a
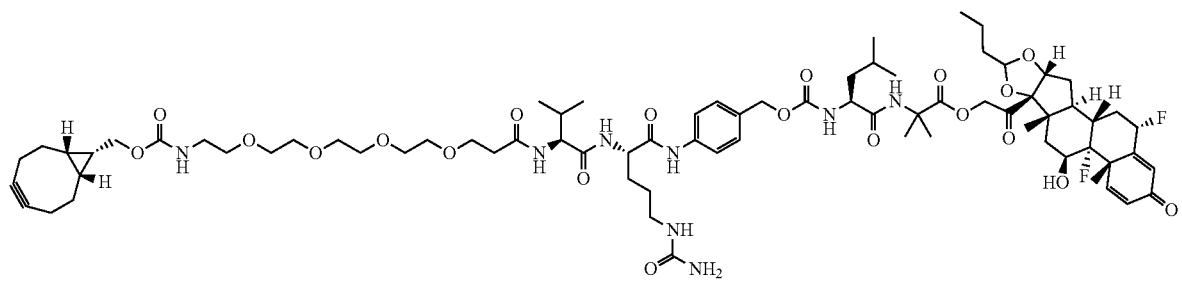
LP12

433 tert-Butyl (2S)-2-{[({4-[(2S)-5-(carbamoylamino)-2-[(2S)-2-{[(9H-fluoren-9-ylmethoxy)carbonyl]amino}-3-methylbutanamido]pentanamido]phenyl}methoxy)carbonyl]amino}-4-methylpentanoate (104-5)

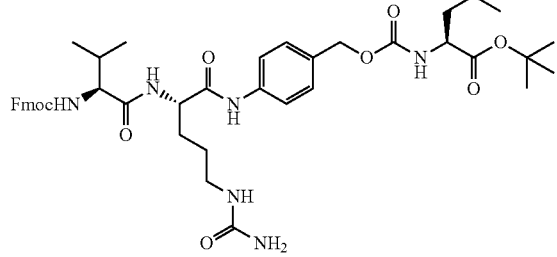

To a solution of compound 11b (0.30 g, 0.39 mmol) and H-Leu-OTBU-OH (0.14 g, 0.63 mmol) in DMF (3 mL) was added DIPEA (0.26 g, 2.0 mmol), and the reaction mixture was stirred at RT for 2 hours. The resulting mixture was directly purified by prep-HPLC (method A) to give compound 104-5 (0.11 g, 35% yield) as a white solid. ESI m/z: 815.4 (M+H)$^+$.

434

(2S)-2-{[({4-[(2S)-5-(Carbamoylamino)-2-[(2S)-2-{[(9H-fluoren-9-ylmethoxy)carbonyl]amino}-3-methylbutanamido]pentanamido]phenyl}methoxy)carbonyl]amino}-4-methylpentanoic acid (104-6)

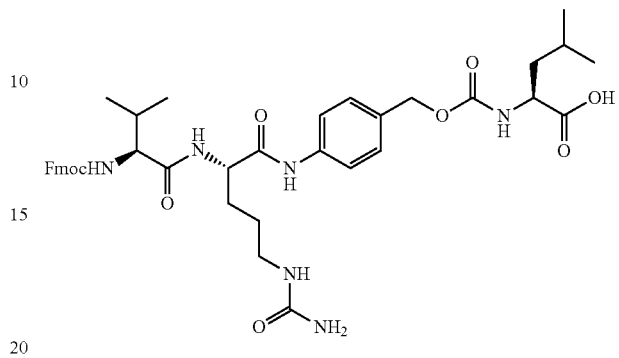

To a solution of compound 104-5 (25 mg, 31 μmol) in DCM (4 mL) was added TFA (0.8 mL) and the mixture was stirred at RT for 2 hours. The resulting mixture was concentrated in vacuo and the residue was purified by prep-HPLC (method A) to give compound 104-6 (15 mg, 67% yield) as a white solid. ESI m/z: 759.3 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,9}$.0$^{13,18}$]icosa-14,17-dien-8-yl]-2-oxoethyl 2-[(2S)-2-{[({4-[(2S)-5-(carbamoylamino)-2-[(2S)-2-{[(9H-fluoren-9-ylmethoxy)carbonyl]amino}-3-methylbutanamido]pentanamido]phenyl}methoxy)carbonyl]amino}-4-methylpentanamido]-2-methylpropanoate (104-7a)

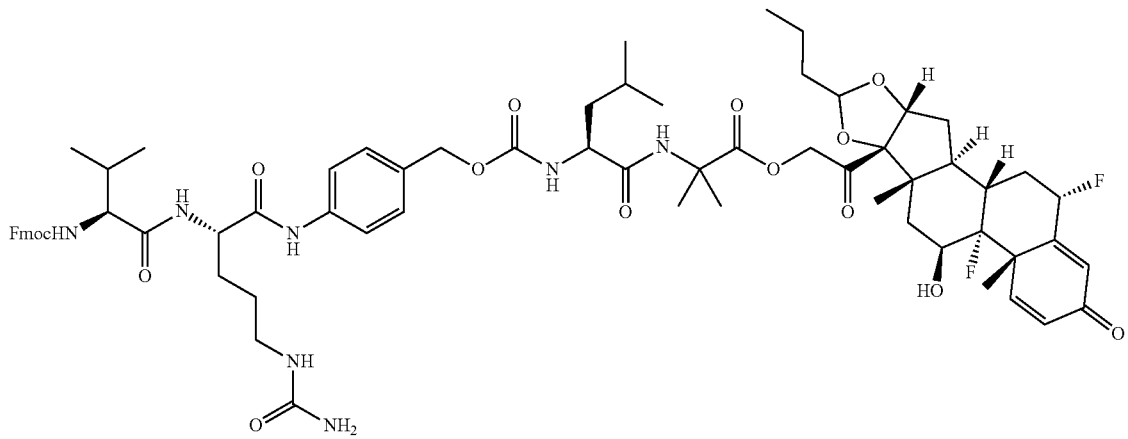

To a solution of compound 104-5 (20 mg, 26 μmol) and compound 104-3 (17 mg, 32 μmol) in DMF (2 mL) were added HATU (20 mg, 52 μmol), DIPEA (13 mg, 0.10 mmol) and DMAP (1 mg), and the reaction mixture was stirred at RT for an hour, which was monitored by LCMS. The resulting mixture was directly purified by prep-HPLC (method A) to give compound 104-7a (30 mg, 89% yield) as a white solid. ESI m/z: 1293 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl 2-[(2S)-2-{[({4-[(2S)-2-[(2S)-2-amino-3-methylbutanamido]-5-(carbamoylamino)pentanamido]phenyl}methoxy)carbonyl]amino}-4-methylpentanamido]-2-methylpropanoate (104-8a)

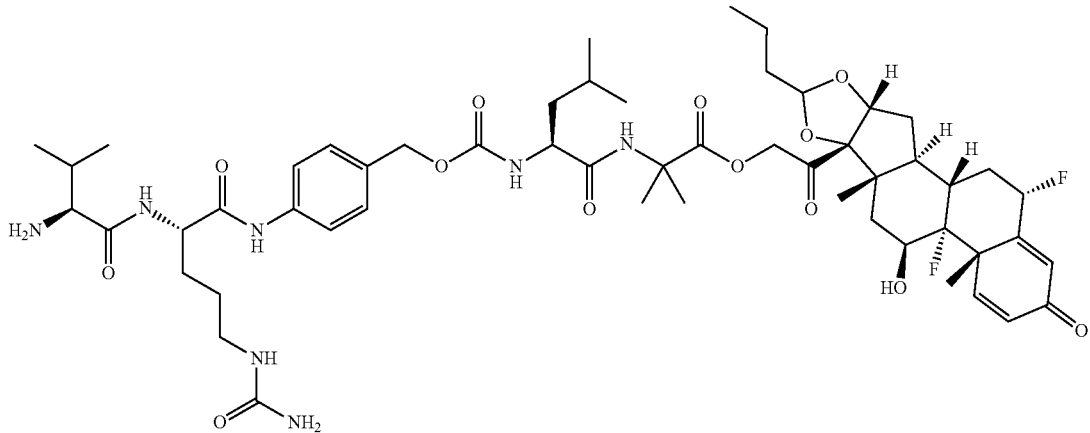 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](N)C(C)C)cc2)O1]

To a solution of compound 104-7a (25 mg, 19 μmol) in DMF (2 mL) was added piperidine (0.2 mL), and the mixture was stirred at RT for half an hour until Fmoc was totally removed according to LCMS. The reaction mixture was immediately purified by reversed phase flash chromatography (0-50% acetonitrile in aq. TFA (0.03%)) to give compound 104-8a (20 mg, 95% yield) as a white solid. ESI m/z: 1070.5 (M+H)⁺.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethyl 2-[(2S)-2-{[({4-[(2S)-2-[(2S)-2-[1-({[endo-bicyclo[6.1.0]non-4-yn-9-ylmethoxy]carbonyl}amino)-3,6,9,12-tetraoxapentadecan-15-amido]-3-methylbutanamido]-5-(carbamoylamino)pentanamido]phenyl}methoxy)carbonyl]amino}-4-methylpentanamido]-2-methylpropanoate (LP12)

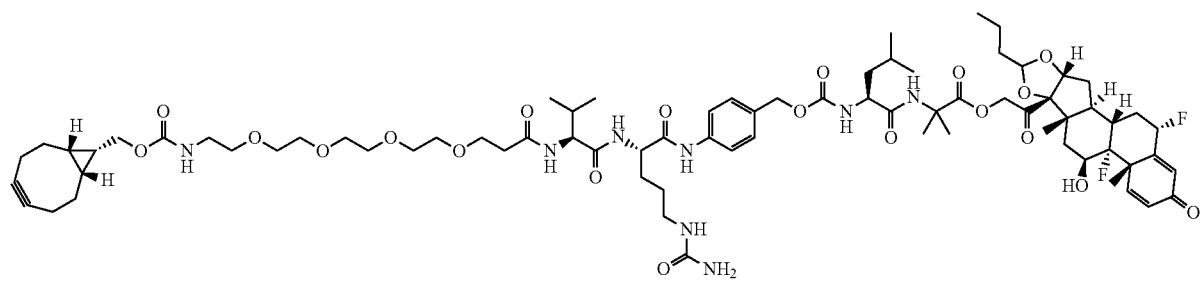 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1]

To a solution of compound 104-8a (20 mg, 26 μmol) and compound 5d (14 mg, 32 μmol) in DMF (2 mL) were added HATU (22 mg, 58 μmol), DIPEA (15 mg, 0.12 mmol) and DMAP (1 mg), and the reaction mixture was stirred at RT for 2 hours, which was monitored by LCMS. The resulting mixture was directly purified by prep-HPLC (method A) to give linker-payload LP12 (10 mg, 21% yield) as a white solid. ESI m/z: 747.6 (M/2+H)⁺. ¹H NMR (400 MHz, DMSO$_{d6}$) δ 9.97 (s, 1H), 8.35-8.25 (m, 1H), 8.11 (d, J=7.4 Hz, 1H), 7.87 (d, J=8.6 Hz, 1H), 7.58 (d, J=8.2 Hz, 2H), 7.34-7.18 (m, 4H), 7.17-7.04 (m, 1H), 6.30 (d, J=10.1 Hz, 1H), 6.11 (s, 1H), 6.03-5.90 (s, 1H), 5.72-5.50 (m, 2H), 5.41 (s, 2H), 5.34-3.91 (m, 12H), 3.66-3.38 (m, 15H), 3.15-2.88 (m, 4H), 2.73-2.53 (m, 1H), 2.50-2.45 (m, 1H), 2.41-2.31 (m, 1H), 2.30-1.90 (m, 9H), 1.83-1.62 (m, 2H), 1.63-1.17 (m, 27H), 0.92-0.77 (m, 20H) ppm.

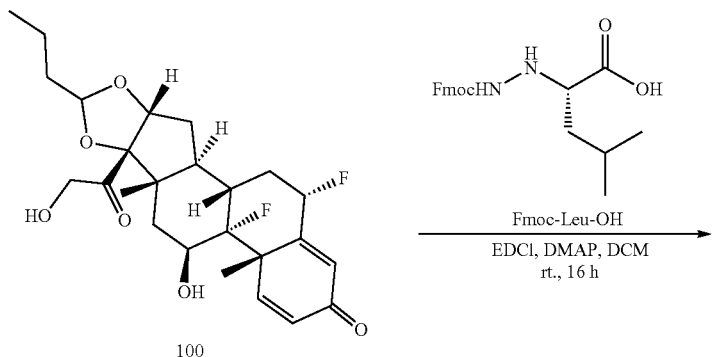
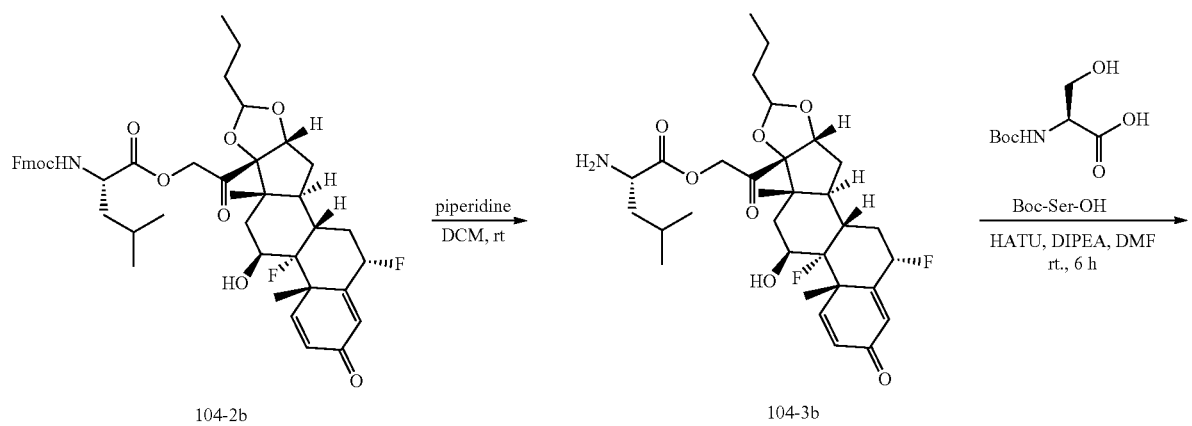
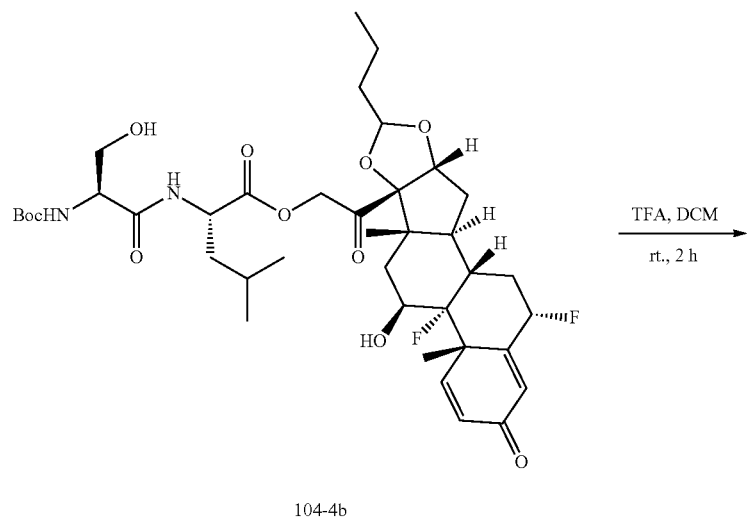

-continued
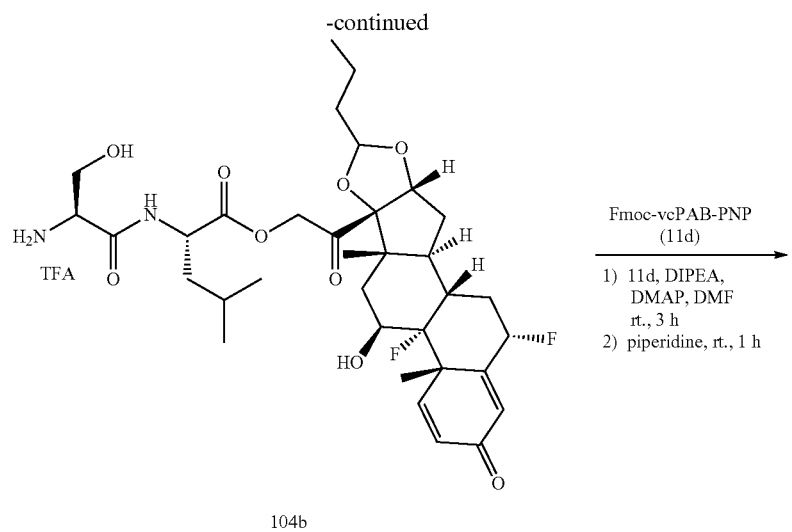
104b
Fmoc-vcPAB-PNP
(11d)
1) 11d, DIPEA, DMAP, DMF rt., 3 h
2) piperidine, rt., 1 h
Scheme 104C. Synthesis of Payload 104b and its linker-payload LP13
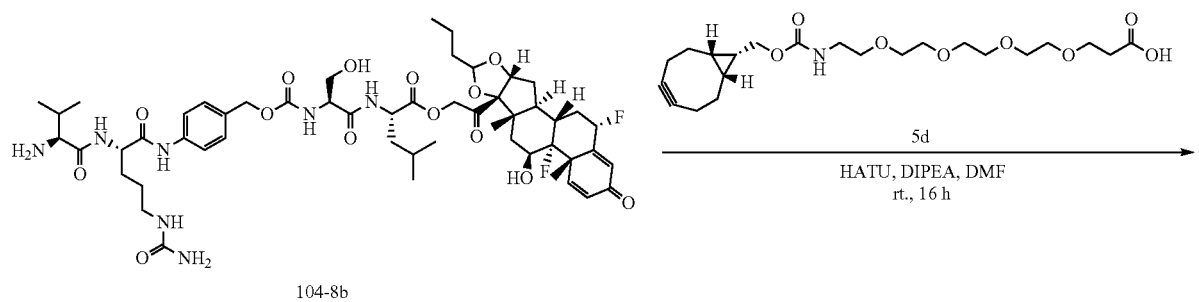
104-8b
5d
HATU, DIPEA, DMF
rt., 16 h
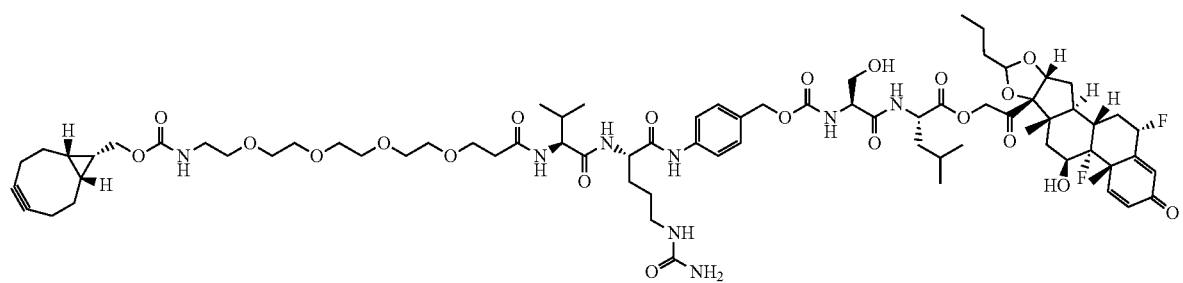
LP13

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-{[(9H-fluoren-9-ylmethoxy)carbonyl]amino}-4-methylpentanoate (104-2b)

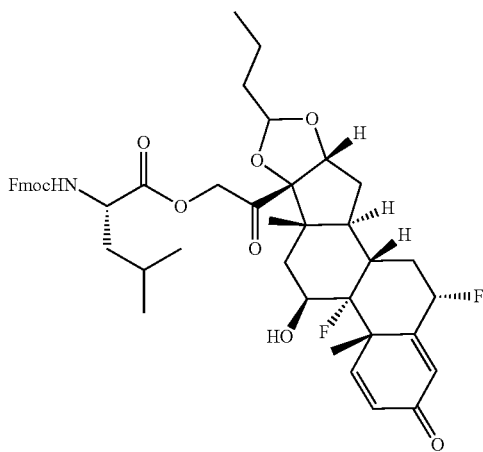

To a solution of compound 100 (0.47 g, 1.0 mmol) and Fmoc-Leu-OH (0.39 g, 1.1 mmol) in DCM (10 mL) were added EDCI (0.23 g, 1.2 mmol) and DMAP (12 mg, 0.10 mmol). The mixture was stirred at RT for 16 hours, which was monitored by LCMS. The resulting mixture was diluted with water (50 mL) and extracted with DCM (50 mL×2). The combined organic solution was dried over sodium sulfate and concentrated in vacuo. The residue was purified silica gel column chromatography (10-50% ethyl acetate in petroleum ether) to give compound 104-2b (0.52 g, 65% yield) as a white solid. ESI m/z: 802.4 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-amino-4-methylpentanoate (104-3b)

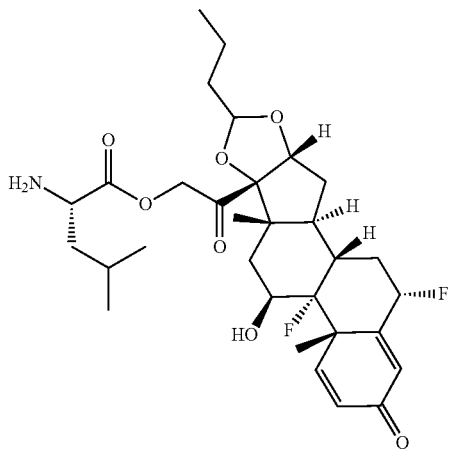 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@@H](N)CC(C)C)O1]

To a solution of compound 104-2b (0.50 g, 0.62 mmol) in DCM (9 mL) was added piperidine (1 mL) and the reaction mixture was stirred at RT for 30 minutes until Fmoc was totally removed according to LCMS. The resulting mixture was concentrated in vacuo. The residue was purified by silica gel column chromatography (5-10% methanol in DCM) to give compound 104-3b (0.32 g, 90% yield) as a white solid. ESI m/z: 580.3 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-{[(tert-butoxy)carbonyl]amino}-3-hydroxypropanamido]-4-methylpentanoate (104-4b)

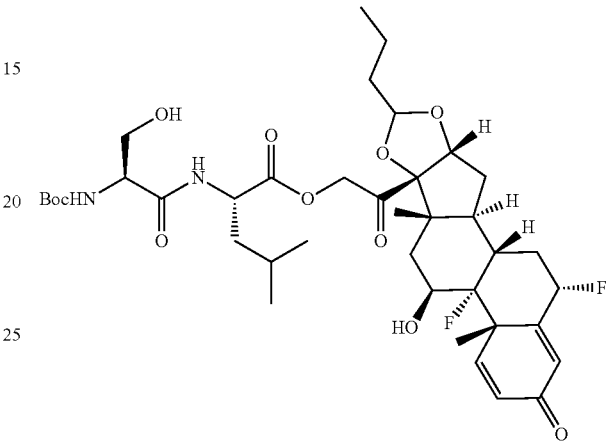

To a mixture of compound 104-3b (0.32 g, 0.55 mmol) and Boc-Ser-OH (0.14 g, 0.66 mmol) in DMF (3 mL) were added HATU (0.25 g, 0.66 mmol) and DIPEA (0.21 g, 1.6 mmol) at RT. The mixture was stirred at RT for 6 hours, which was monitored by LCMS. The resulting mixture was concentrated in vacuo, and the residue was purified silica gel column chromatography (10-50% ethyl acetate in petroleum ether) to give compound 104-4b (0.34 mg, 80% yield) as a white solid. ESI m/z: 767.4 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-amino-3-hydroxypropanamido]-4-methylpentanoate trifluoroacetic acid salt (104b)

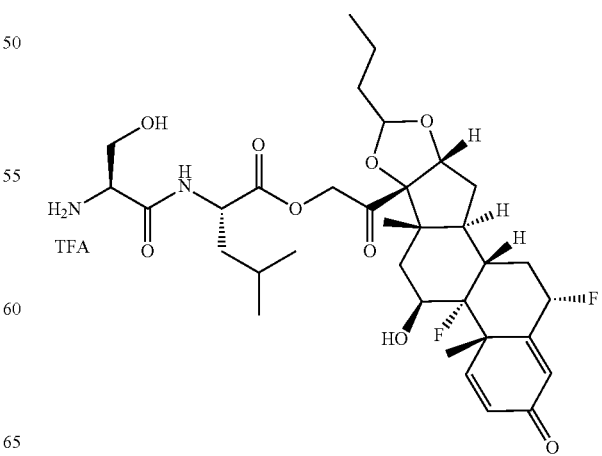

To a solution of compound 104-4b (0.34 g, 0.44 mmol) in DCM (5 mL) was added TFA (1 mL). The reaction mixture was stirred at RT for 2 hours until Boc was totally removed according to LCMS. The resulting mixture was concentrated and the residue (0.33 g, 95% yield) was pure enough for the next step. 100 mg of crude product was further purified by prep-HPLC (method A) to give compound 104b (80 mg, 80% yield) as a yellow solid. ESI m/z: 667.3 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-{[({4-[(2S)-2-[(2S)-2-amino-3-methylbutanamido]-5-(carbamoylamino)pentanamido]phenyl}methoxy)carbonyl]amino}-3-hydroxypropanamido]-4-methylpentanoate (104-8b)

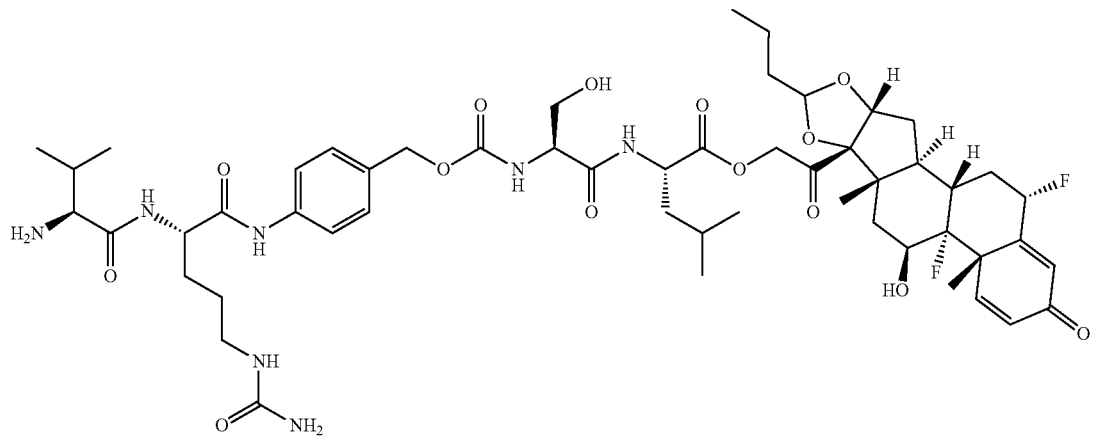 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](N)C(C)C)cc2)O1]

To a solution of crude compound 104b (0.10 g, 0.13 mmol) freshly obtained above in DMF (3 mL) were added Fmoc-vcPAB-PNP (11d) (0.12 g, 0.16 mmol), DMAP (16 mg, 0.13 mmol) and DIPEA (50 mg, 0.39 mmol) at RT. The mixture was stirred at RT for 3 hours until most of starting materials were consumed, which was monitored by LCMS. To the reaction mixture was then added piperidine (1 mL). After stirred at room temperature for an hour until the Fmoc was totally removed according to LCMS. The reaction mixture was directly purified by prep-HPLC (method B) to give compound 104-8b (28 mg, 20% yield) as a white solid. ESI m/z: 536.8 (M/2+H)$^+$.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-{[({4-[(2S)-2-[(2S)-2-[1-({[endo-bicyclo[6.1.0]non-4-yn-9-ylmethoxy]carbonyl}amino)-3,6,9,12-tetraoxapentadecan-15-amido]-3-methylbutanamido]-5-(carbamoylamino)pentanamido]phenyl}methoxy)carbonyl]amino}-3-hydroxypropanamido]-4-methylpentanoate (LP13)

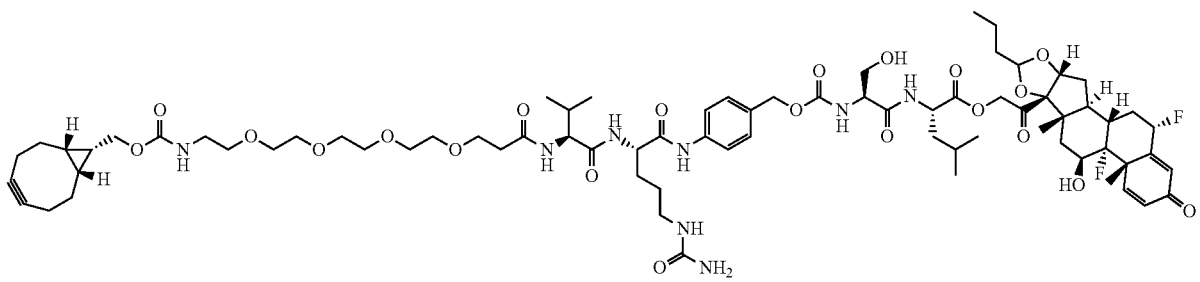 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1]

To a solution of compound 5d (10 mg, 22 μmol) in DMF (1 mL) were added HATU (9 mg, 22 μmol) and DIPEA (8.0 mg, 62 μmol) successively at RT. The mixture was stirred at RT for half an hour followed by the addition of a solution of compound 104-8b (20 mg, 19 μmol) in DMF (1 mL). The resulting mixture was stirred at RT for 2 hours until compound 104-8b was consumed, which was monitored by LCMS. After filtered through membrance, the filtrate was directly purified by prep-HPLC (method B) to give linker-payload LP13 (10 mg, 35% yield) as a white solid. ESI m/z: 748.4 $(M/2+H)^+$.

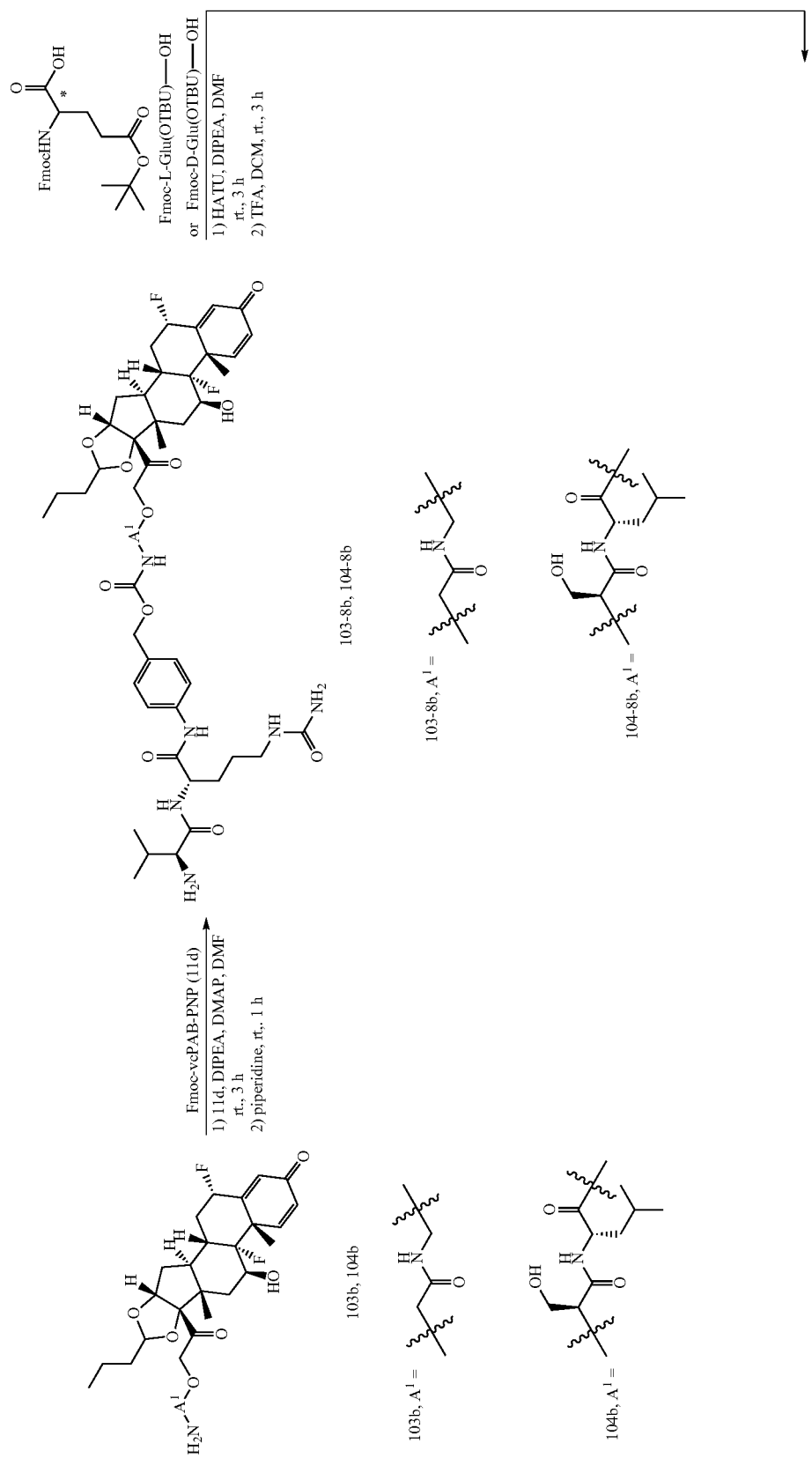

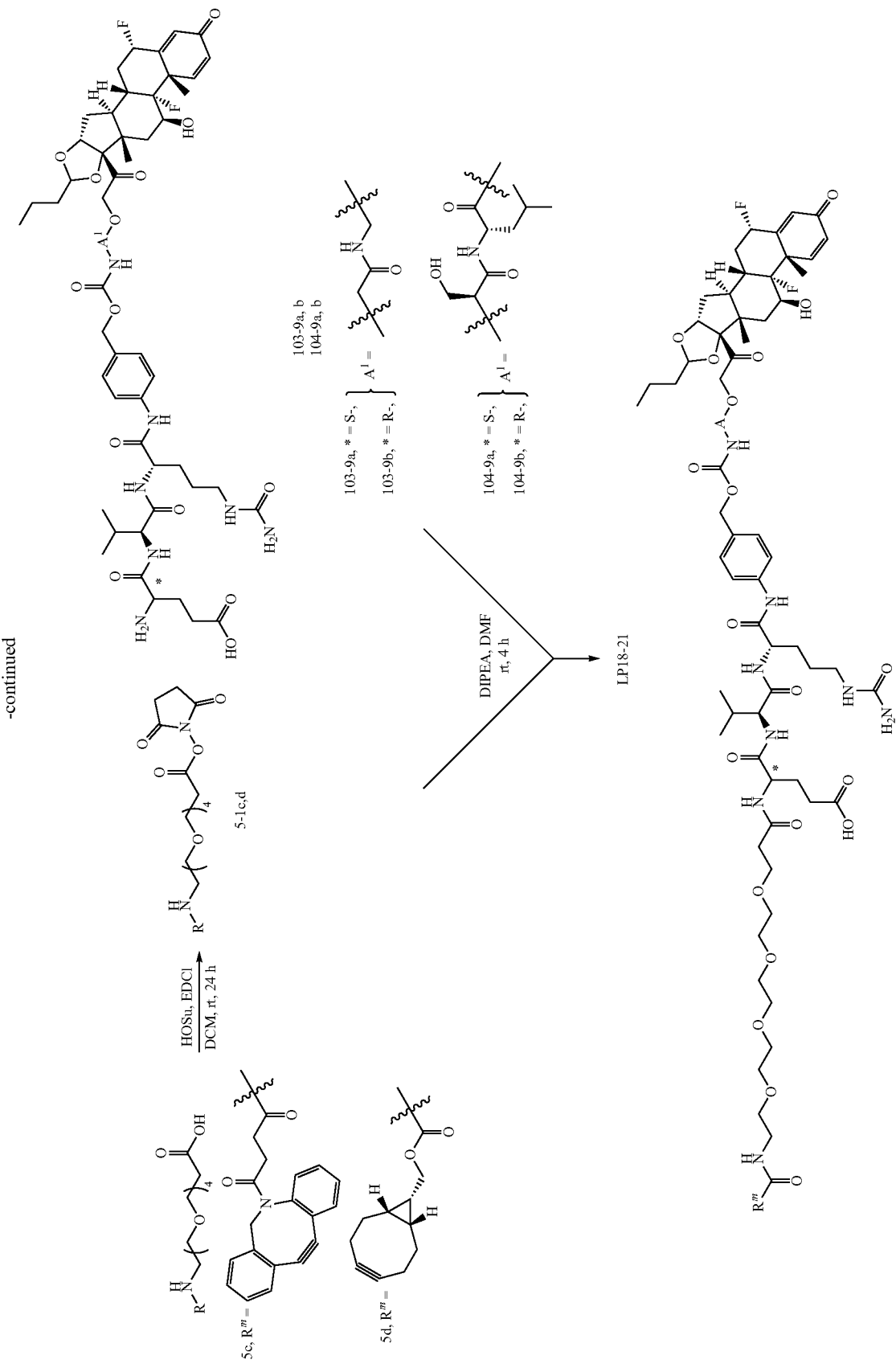

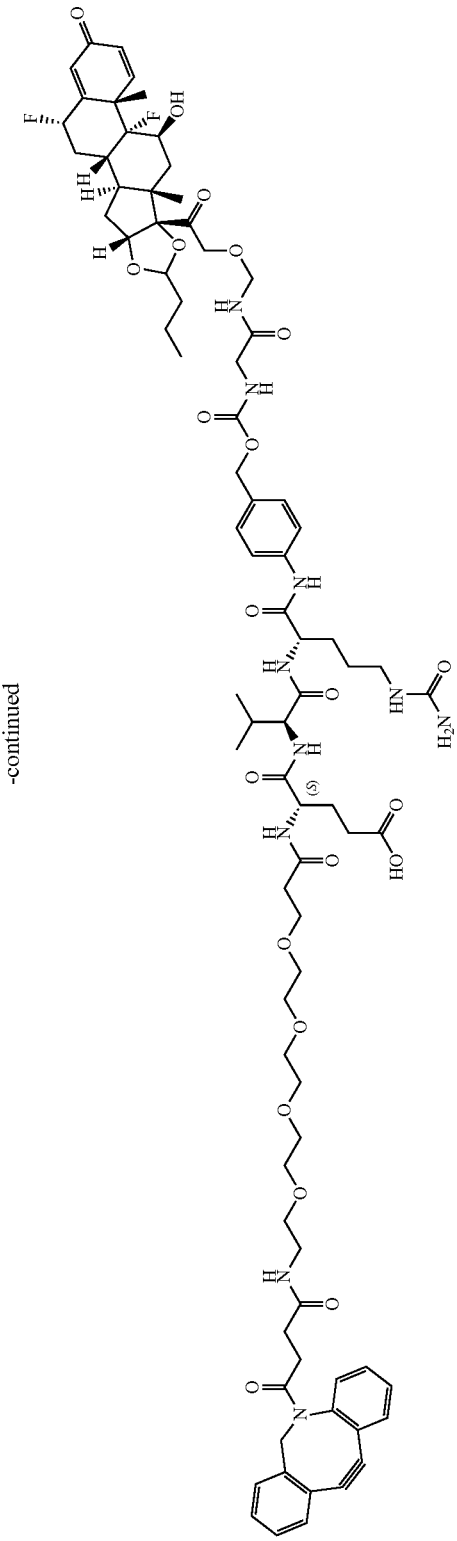
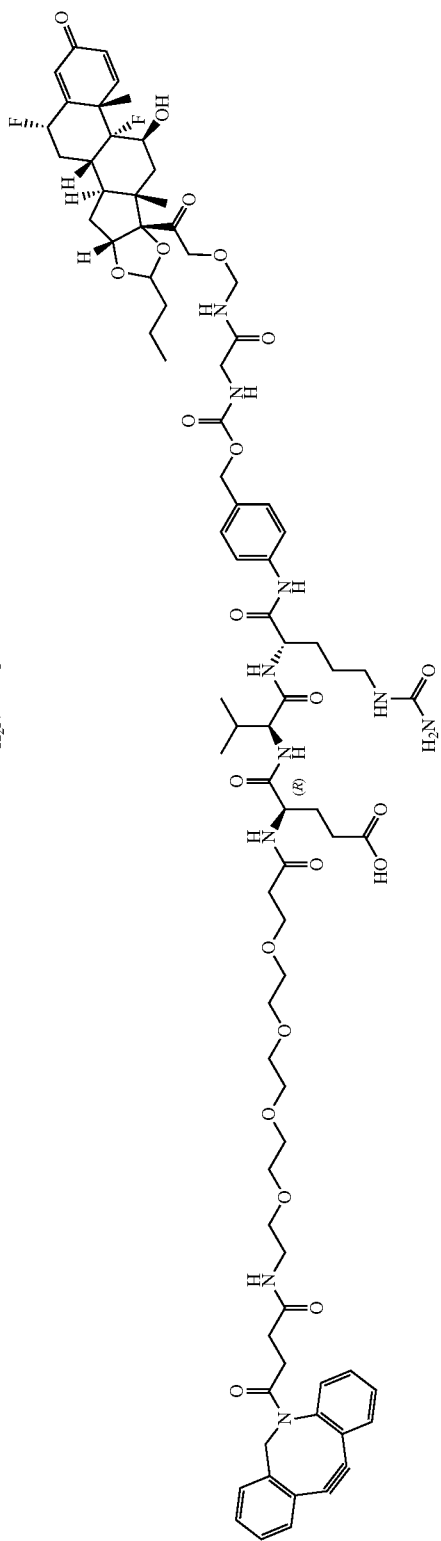

-continued
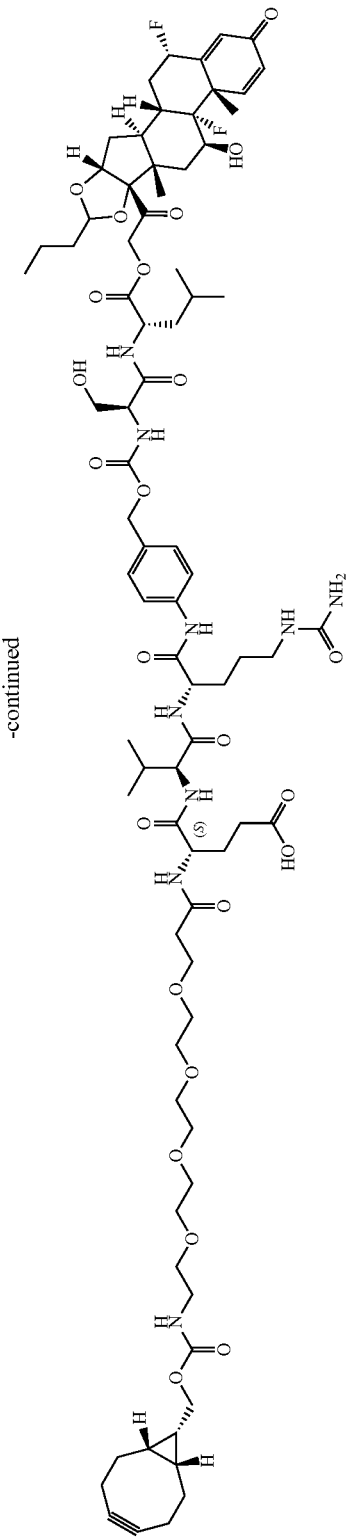
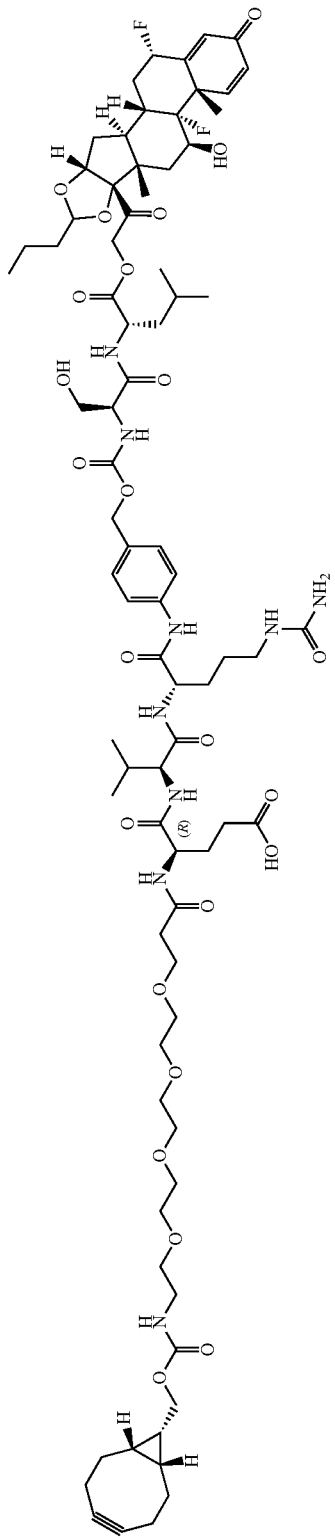

2,5-Dioxopyrrolidin-1(4-{-azatricyclo[10.4.0.0^{4,9}]hexadeca-1(12),4(9),5,7,13,15-hexaen-10-yn-2-yl}-4-oxobutanamido)-3,6,9,12-tetraoxapentadecan-15-oate (5-1c)

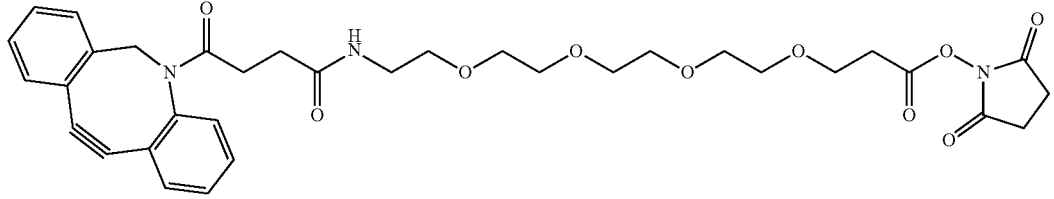 [SMILES: O=C(CCC(=O)N1Cc2ccccc2C#Cc2ccccc21)NCCOCCOCCOCCOCCC(=O)ON1C(=O)CCC1=O]

To a solution of compound 5c (160 mg, 0.290 mmol) in DCM (20 mL) were added HOSu (73.3 mg, 0.637 mmol) and EDCI (122 mg, 0.637 mmol), and the mixture was stirred at RT for 24 hours, which was monitored by LCMS. The reaction mixture was diluted with DCM (50 mL) and the organic layer was washed with water (50 mL) and brine, dried with anhydrous $Na_2SO_4$ and concentrated in vacuo to give compound 5-1c (159 mg, 84% yield) as colorless oil, which was used for the next step directly. ESI m/z: 650 $(M+H)^+$.

2,5-Dioxopyrrolidin-1-yl 1-[({endo-bicyclo[6.1.0]non-4-yn-9-ylmethoxy}carbonyl)amino]-3,6,9,12-tetraoxapentadecan-15-oate (5-1d)

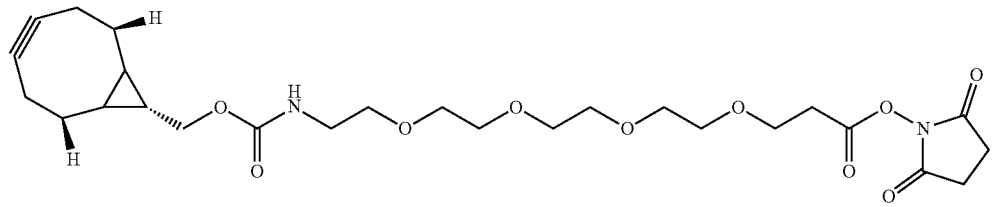

Following the similar procedure as 5-1c except substituting 5d for 5c, compound 5-1d (150 mg, 54% yield) was obtained as colorless oil, which was used for the next step directly without further purification. ESI m/z: 539 $(M+H)^+$.

{4-[(2S)-2-[(2S)-2-Amino-3-methylbutanamido]-5-(carbamoylamino)pentanamido]phenyl}methyl N-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0^{2,9}.0^{4,8}.0^{13,18}]icosa-14,17-dien-8-yl]-2-oxoethoxy}methyl)carbamoyl]methyl}carbamate (103-8b)

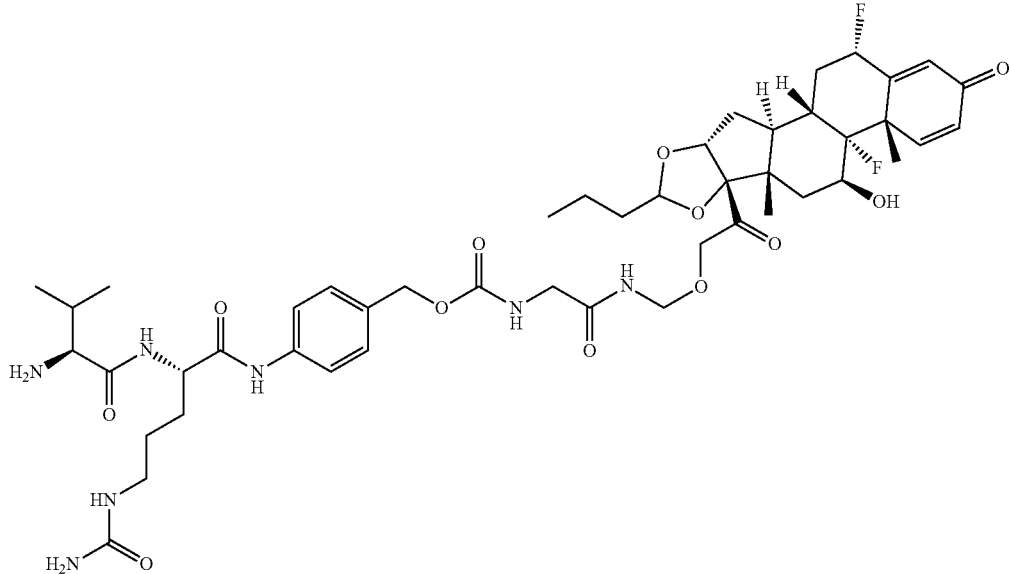 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COCNC(=O)CNC(=O)OCc2ccc(NC(=O)[C@H](CCCNC(N)=O)NC(=O)[C@@H](N)C(C)C)cc2)O1]

Following the similar procedure as 104-8b (see scheme 104C) except substituting 103b for 104b, compound 103-8b (28 mg, 20% yield) was obtained as a white solid. ESI m/z: 480 (M/2+H)⁺.

(4S)-4-Amino-4-{[(1S)-1-{[(1S)-4-(carbamoylamino)-1-[(4-{[({[({2-[(1S,2S,4R,8S,9S,11S,12R, 13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamoyl) oxy]methyl}phenyl)carbamoyl]butyl]carbamoyl}-2-methylpropyl]carbamoyl}butanoic acid (103-9a)

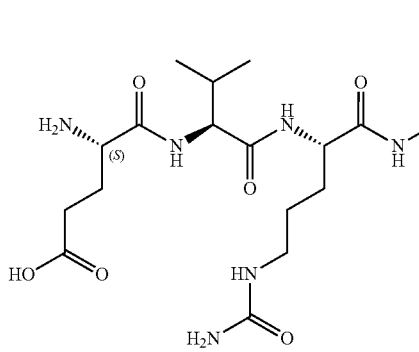
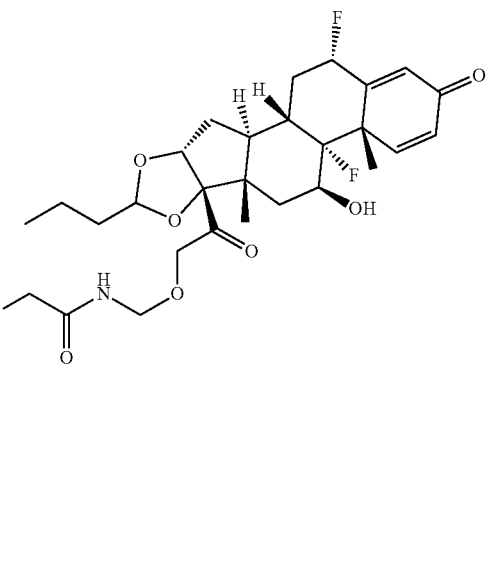

To a solution of compound Boc-L-Glu(OTBU)-OH (0.15 g, 0.50 mmol) in DMF (5 mL) were added HATU (0.19 g, 0.50 mmol) and DIPEA (0.13 g, 1.0 mmol). The reaction mixture was stirred at RT for 10 minutes, before compound 103-8b (0.48 g, 0.50 mmol) was added into the reaction mixture. The reaction mixture was then stirred at RT for 3 hours until 103-8b was totally consumed according to LCMS. The mixture was extracted with EtOAc, and the combined organic solution was washed with water, dried over anhydrous sodium sulfate and concentrated in vacuo. The residue was dissolved into DCM (10 mL). To the solution was added TFA (2 mL), and the reaction mixture was stirred at RT for 3 hours, which was monitored by LCMS. The reaction mixture was concentrated, and the residue was directly purified by prep-HPLC (method B) to give compound 103-9a (0.41 g, 75% yield) as a white solid. ESI m/z: 536.8 (M/2+H)⁺.

(4R)-4-Amino-4-{[(1S)-1-{[(1S)-4-(carbamoy-lamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamoyl)oxy]methyl}phenyl)carbamoyl]butyl]carbamoyl}-2-methylpropyl]carbamoyl}butanoic acid (103-9b)

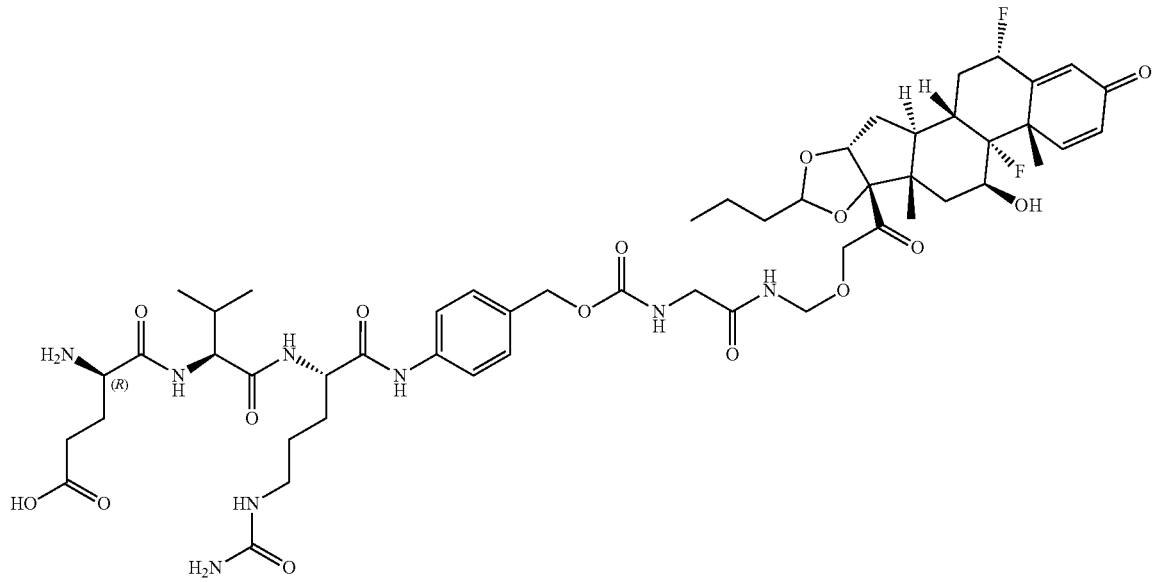

Following the similar procedure as 103-9a except substituting Boc-D-Glu(OTBU)-OH for Boc-L-Glu(OTBU)-OH, compound 103-9b (0.40 g, 74% yield) as a white solid. ESI m/z: 536.8 (M/2+H)$^+$.

(4S)-4-Amino-4-{[(1S)-1-{[(1S)-4-(carbamoy-lamino)-1-({4-[({[{[(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (104-9a)

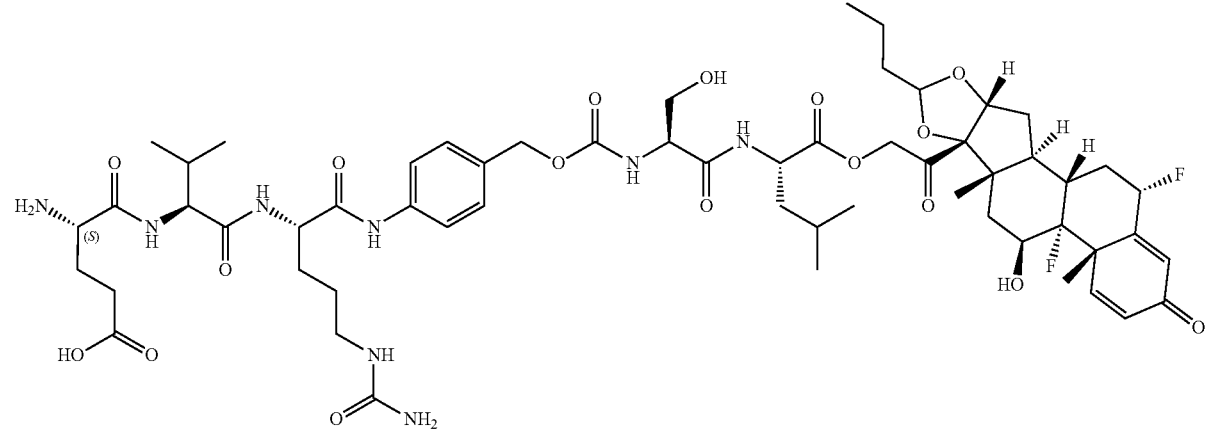

Following the similar procedure as 103-9a except substituting 104-8b for 103-8b, compound 104-9a (0.39 g, 65% yield) as a white solid. ESI m/z: 601.3 (M/2+H)+.

(4R)-4-Amino-4-{[(1S)-1-{[(1S)-4-(carbamoylamino)-1-({4-[({[(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (104-9b)

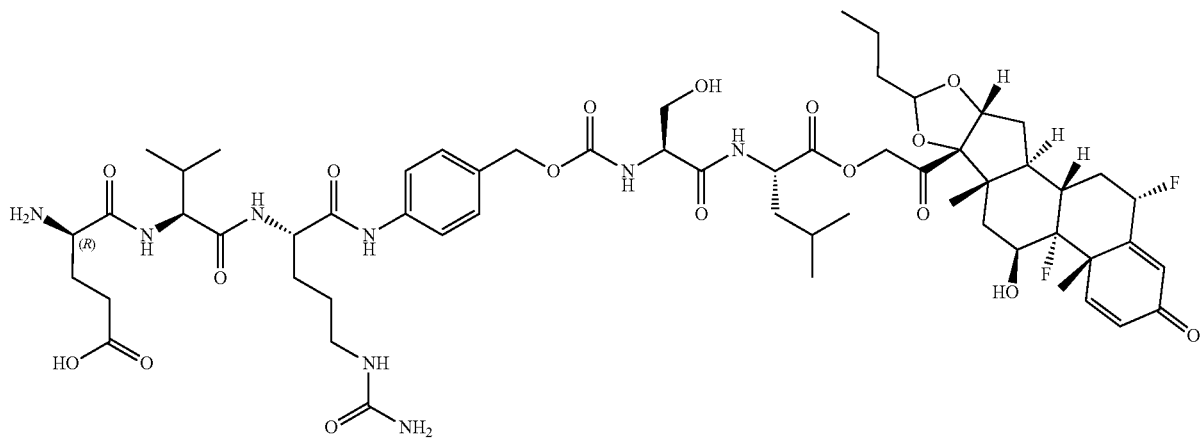

Following the similar procedure as 103-9a except substituting 104-8b for 103-8b, Boc-D-Glu(OTBU)-OH for Boc-L-Glu(OTBU)-OH, compound 104-9b (0.39 g, 65% yield) as a white solid. ESI m/z: 601.3 (M/2+H)+.

(4S)-4-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-4-{[(1S)-1-{[(1S)-4-(carbamoylamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}methyl)carbamoyl]methyl}carbamoyl)oxy]methyl}phenyl)carbamoyl]butyl]carbamoyl}-2-methylpropyl]carbamoyl}butanoic acid (LP18)

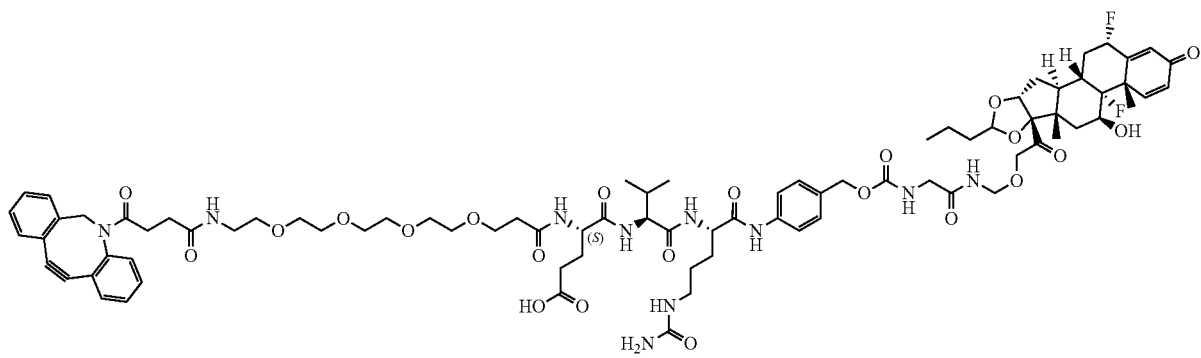

To a solution of compound 103-9a (57 mg, 53 μmol) in DMF (1 mL) were added compound 5-1c (36 mg, 56 μmol) and DIPEA (27 mg, 0.21 mmol). The reaction mixture was stirred at RT for 4 hours, which was monitored by LCMS. The resulting mixture was then directly purified by prep-HPLC (method B) to give compound LP18 (12 mg, 15% yield) as a white solid. ESI m/z: 811.4 (M/2+H)⁺.

(4R)-4-[1-(4-{2-Azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-4-{[(1S)-1-{[(1S)-4-(carbamoylamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}methyl)carbamoyl]methyl}carbamoyl)oxy]methyl}phenyl)carbamoyl]butyl]carbamoyl}-2-methylpropyl]carbamoyl}butanoic acid (LP19)

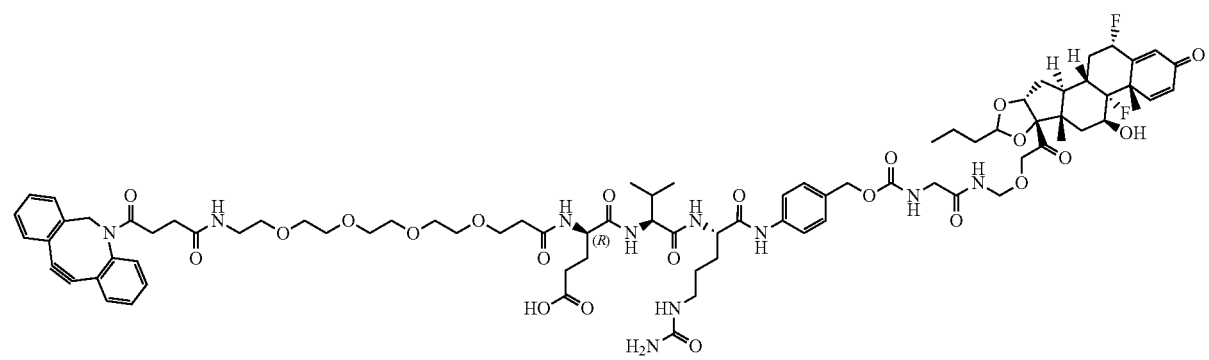

Following the similar procedure as LP18 except substituting 103-9b for 103-9a, compound LP19 (14 mg, 17% yield) as a white solid. ESI m/z: 811.4 (M/2+H)⁺.

(4S)-4-{1-[({endo-Bicyclo[6.1.0]non-4-yn-9-ylmethoxy}carbonyl)amino]-3,6,9,12-tetraoxapentadecan-15-amido}-4-{[(1S)-1-{[(1S)-4-(carbamoylamino)-1-({4-[([(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (LP20)

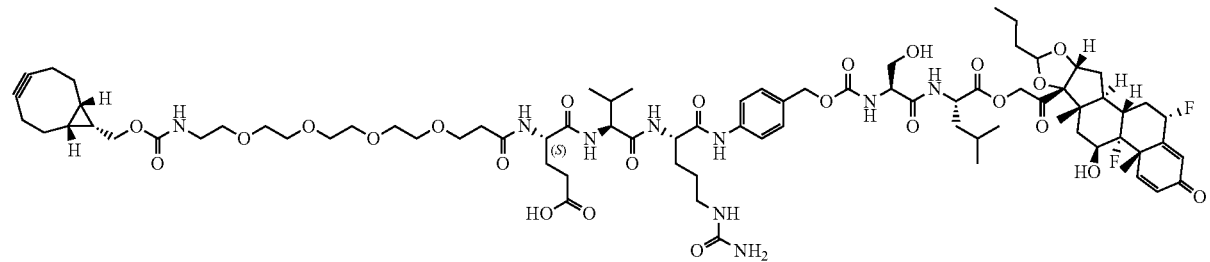

To a solution of compound 104-9a (64 mg, 53 μmol) in DMF (1 mL) were added compound 5-1d (30 mg, 56 μmol) and DIPEA (27 mg, 0.21 mmol). The reaction mixture was stirred at RT for 4 hours, which was monitored by LCMS. The resulting mixture was then directly purified by prep-HPLC (method B) to give compound LP20 (17 mg, 20% yield) as a white solid. ESI m/z: 813.0 (M/2+H)⁺.

(4R)-4-{1-[({endo-Bicyclo[6.1.0]non-4-yn-9-ylmethoxy}carbonyl)amino]-3,6,9,12-tetraoxapentadecan-15-amido}-4-{[(1S)-1-{[(1S)-4-(carbamoylamino)-1-({4-[({[(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (LP21)

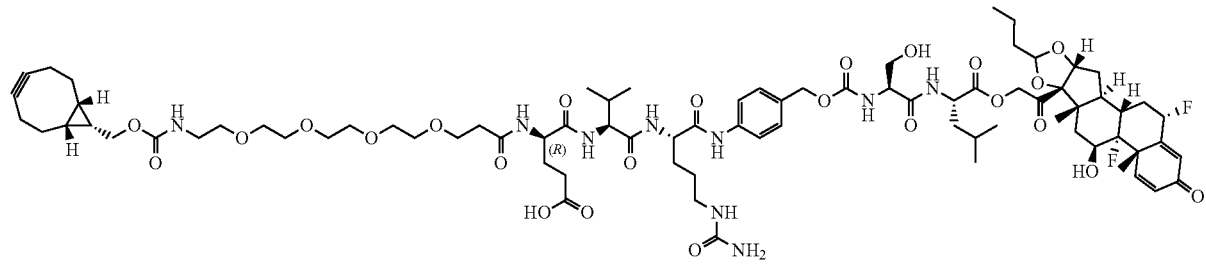

Following the similar procedure as LP20 except substituting 104-9b for 104-9a, compound LP21 (14 mg, 17% yield) as a white solid. ESI m/z: 813.0 (M/2+H)⁺.

Table 5a below presents linker payloads made using the methods described herein.

TABLE 5a
Examples of Linker-Payloads
| LP | Payload | Linker name | Structures |
|---|---|---|---|
| LP1 | 101a | DIBAC-suc-PEG4-vcPAB-MEDA-100 | 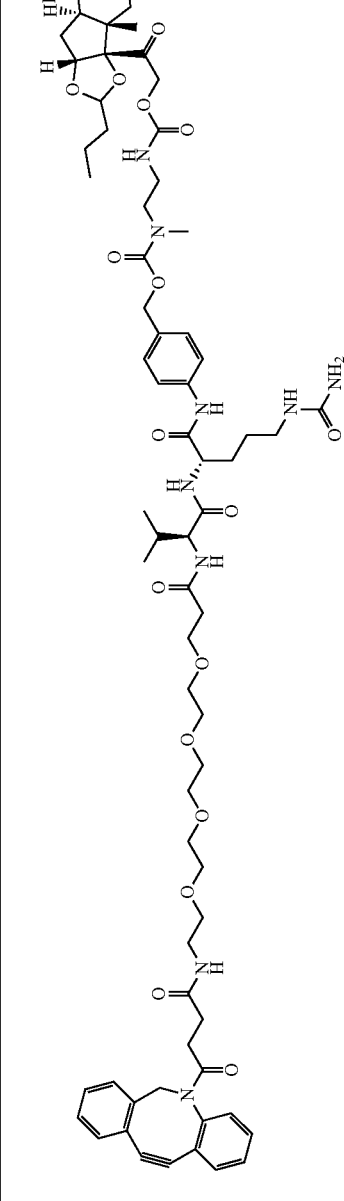 |
| LP2 | 101b | DIBAC-suc-PEG4-vcPAB-DMEDA-100 | 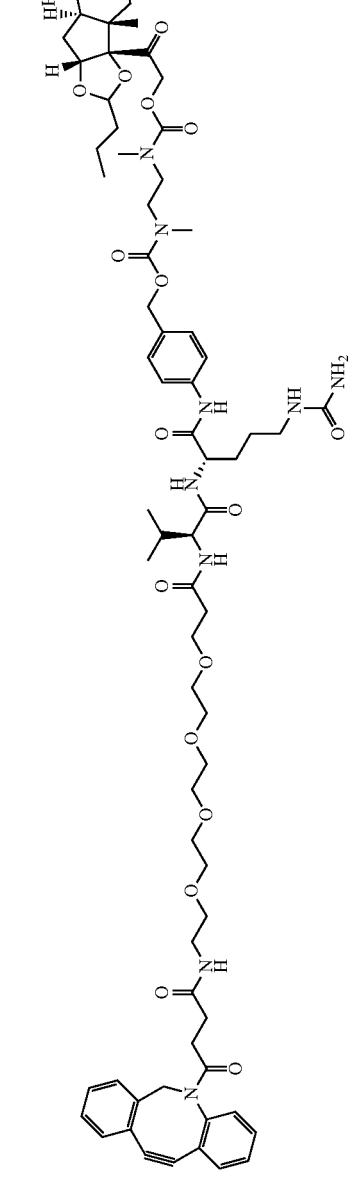 |

TABLE 5a-continued

Examples of Linker-Payloads

| LP | Payload | Linker name | Structures |
|---|---|---|---|
| LP3 | 101c | DIBAC-suc-PEG4-vcPAB-DEEDA-100 | 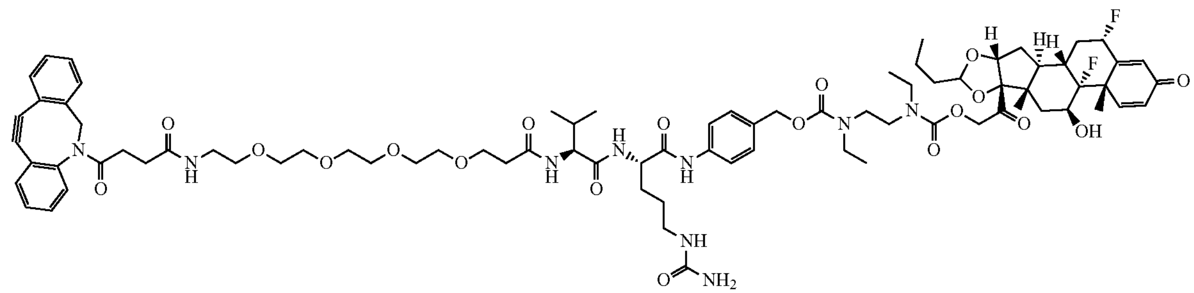 |
| LP4 | 101d | DIBAC-suc-PEG4-vcPAB-Pip-100 | 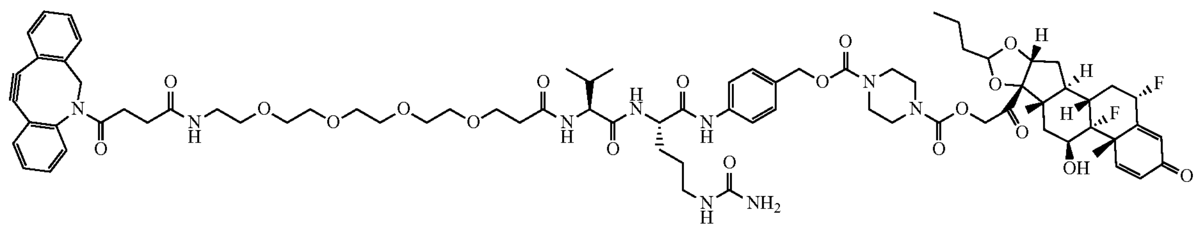 |
| LP5 | 102e | NHS-disulfide-SEA-100 | 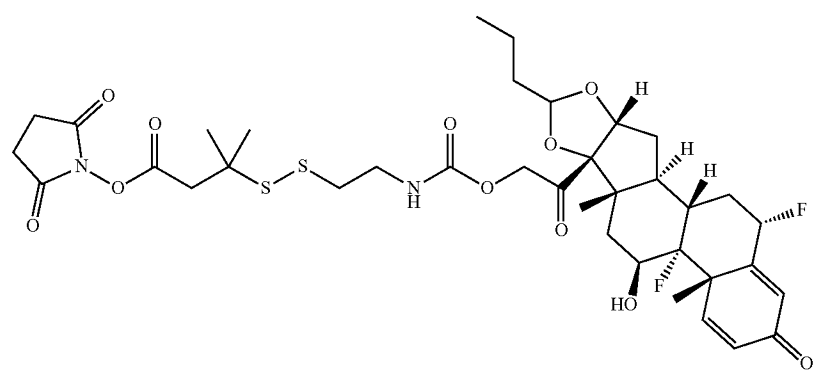 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)ON2C(=O)CCC2=O)O1] |

TABLE 5a-continued

Examples of Linker-Payloads

| LP | Payload | Linker name | Structures |
|---|---|---|---|
| LP6 | 102f | NHS-disulfide-SEMA-100 | 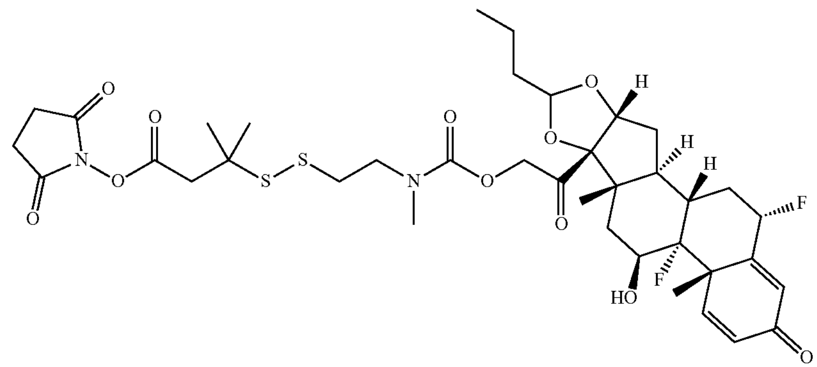 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)ON2C(=O)CCC2=O)O1] |
| LP7 | 102e | BCN-PEG3-disulfide-SEA-100 | 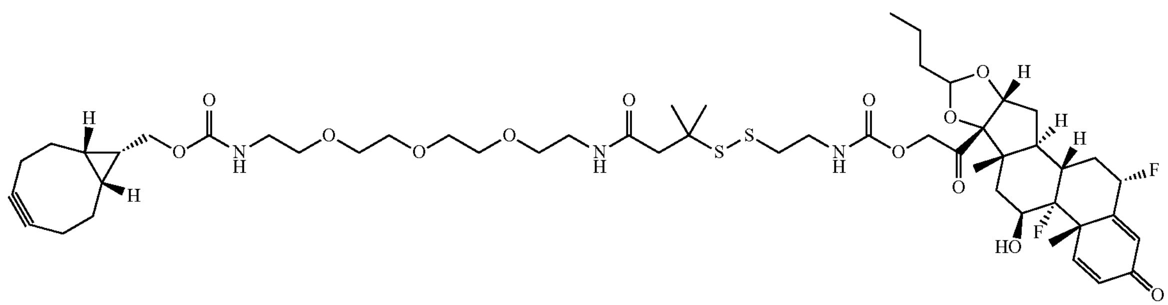 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)NCCOCCOCCOCCNC(=O)OC[C@@H]2[C@@H]3CCC#CCC[C@@H]32)O1] |
| LP8 | 102f | BCN-PEG3-disulfide-SEMA-100 | 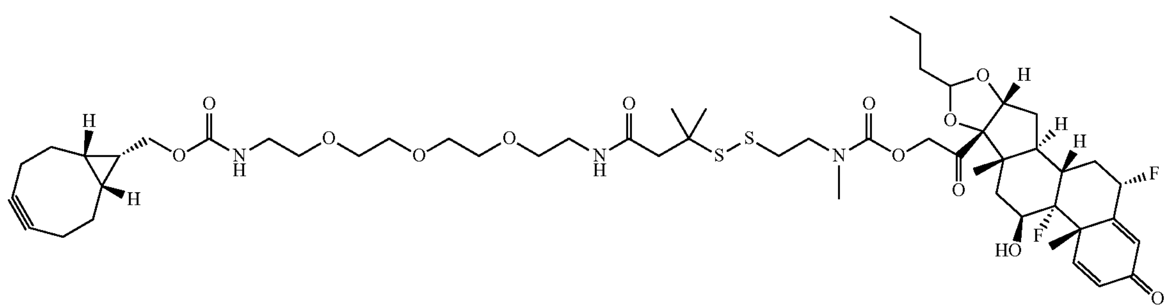 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)NCCOCCOCCOCCNC(=O)OC[C@@H]2[C@@H]3CCC#CCC[C@@H]32)O1] |

TABLE 5a-continued
Examples of Linker-Payloads
| LP | Payload | Linker name | Structures |
|---|---|---|---|
| LP9 | 103a | DIBAC-suc-PEG4-vcPAB-Gly-AMO-Bud | 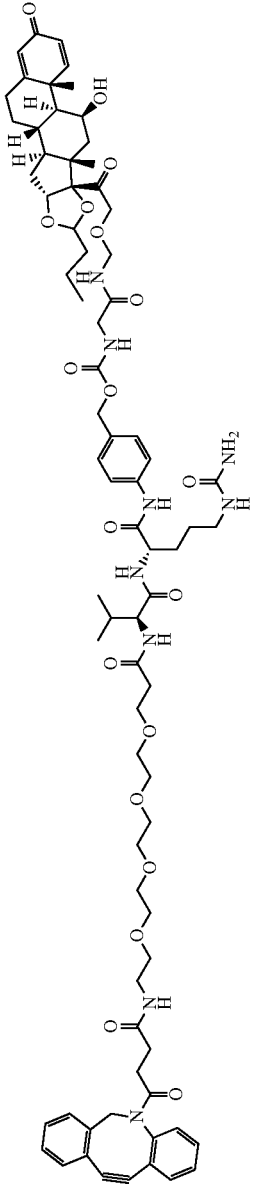 |
| LP10 | 103b | DIBAC-suc-PEG4-vcPAB-Gly-AMO-100 | 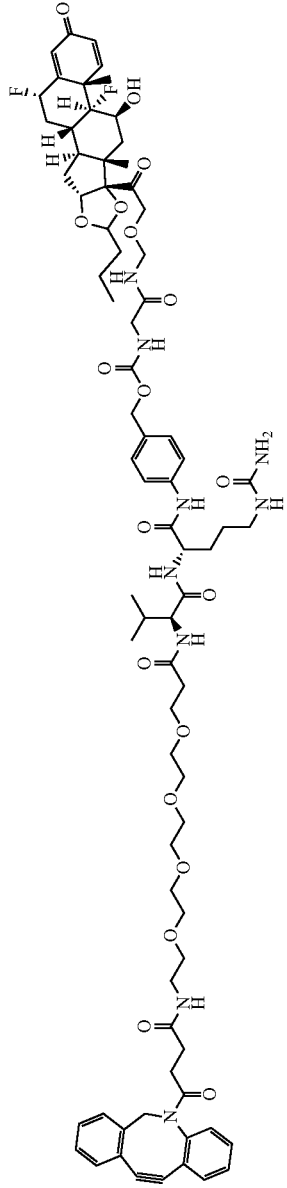 |
| LP11 | 103b | DIBAC-suc-PEG4-GGFG-AMO-100 | 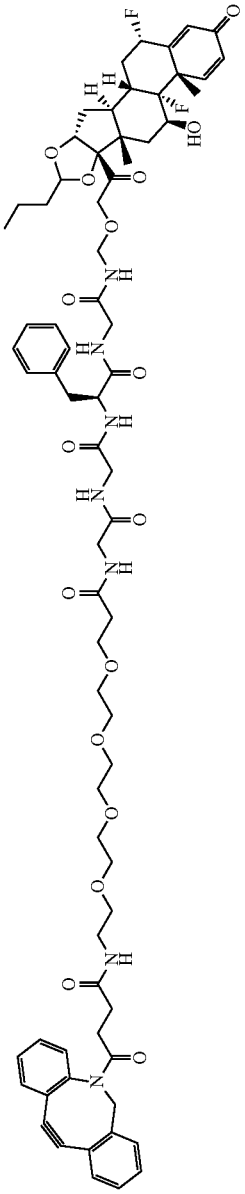 |

TABLE 5a-continued

Examples of Linker-Payloads

| LP | Payload | Linker name | Structures |
|---|---|---|---|
| LP12 | 104a | BCN-PEG4-vcPAB-Leu-Aib-100 | 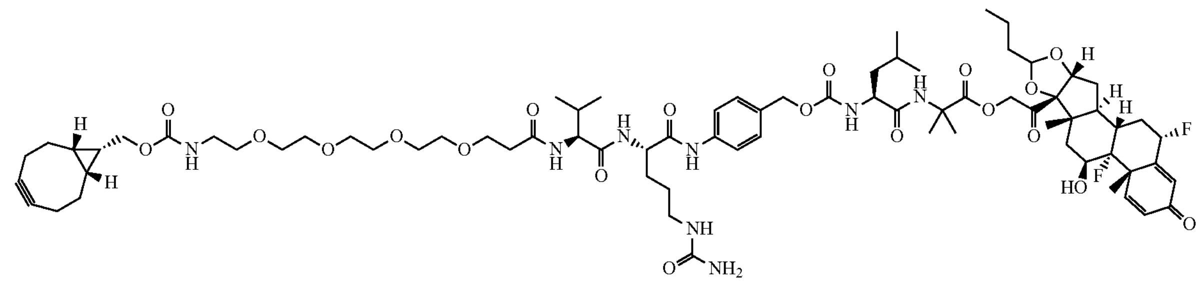 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1] |
| LP13 | 104b | BCN-PEG4-vcPAB-Ser-Leu-100 | 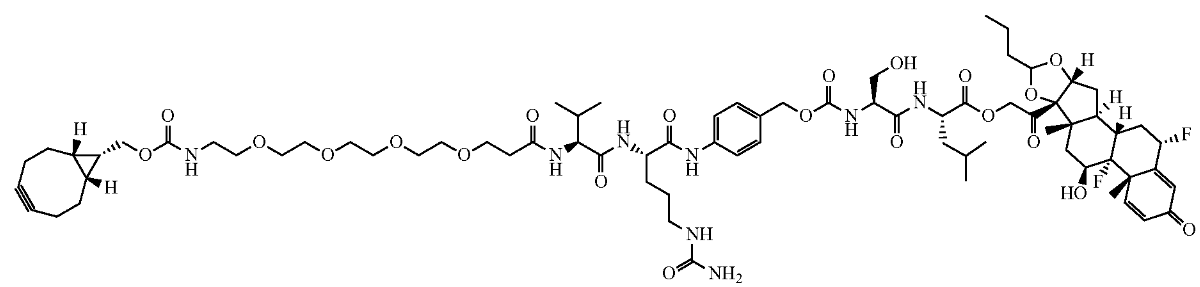 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1] |
| LP18 | 103b | DIBAC-suc-PEG4-EVC-PAB-Gly-AMO-100 | 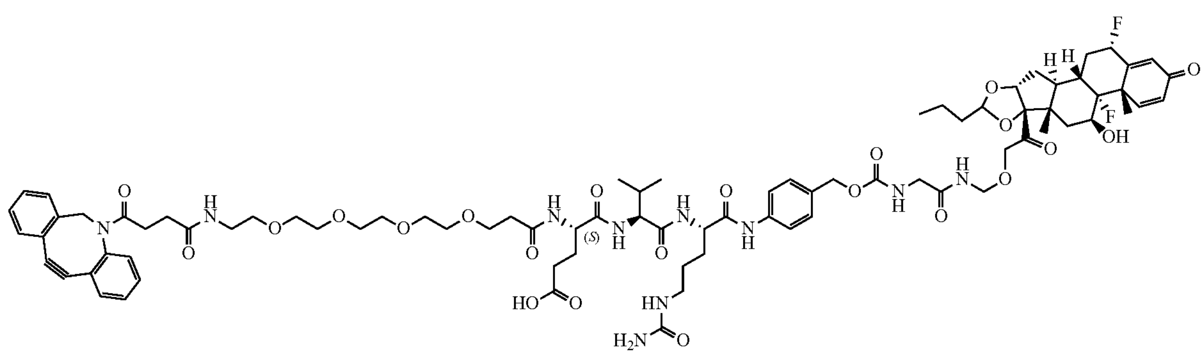 |

TABLE 5a-continued
Examples of Linker-Payloads
| LP | Payload | Linker name | Structures |
|---|---|---|---|
| LP19 | 103b | DIBAC-suc-PEG4-dEVC-PAB-Gly-AMO-100 | 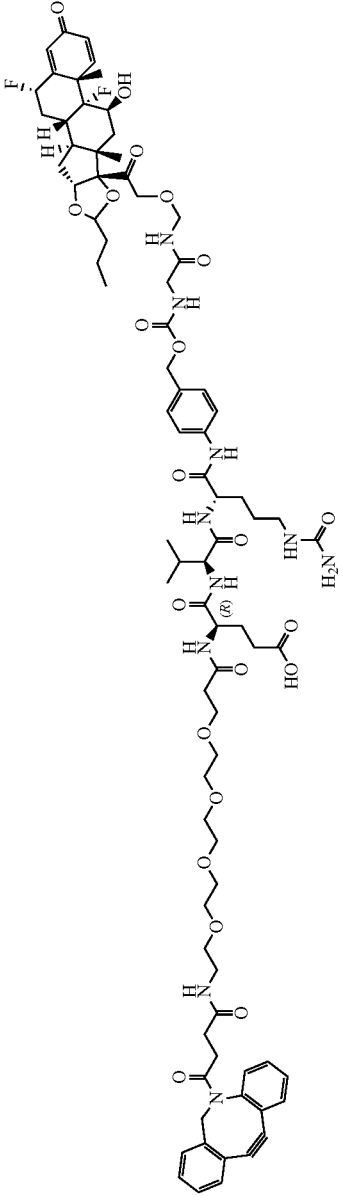 |
| LP20 | 104b | BCN-PEG4-EVC-PAB-Ser-Leu-100 | 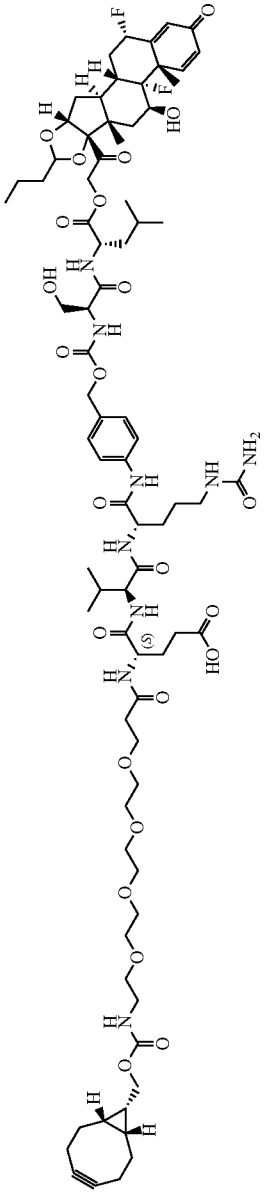 |
| LP21 | 104b | BCN-PEG4-dEVC-PAB-Ser-Leu-100 | 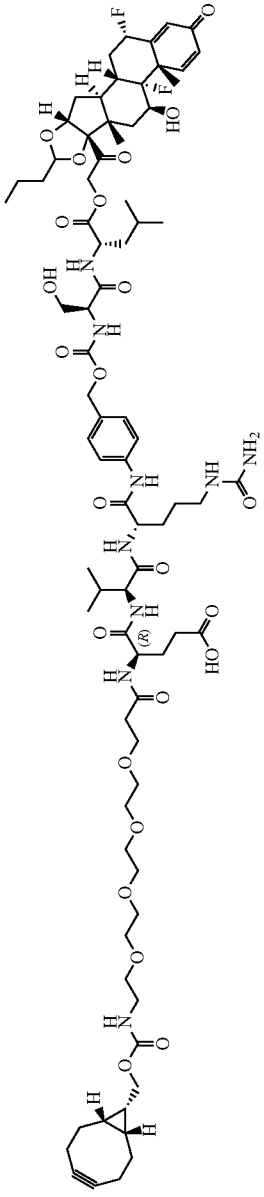 |

TABLE 6a

Characterization Data for Linker-Payloads

| LP | cLogP | MF | MW | HPLC purity (%) | MS (m/z) 100% | Highest m/z peak |
|---|---|---|---|---|---|---|
| LP1 | 4.26 | $C_{78}H_{101}F_2N_9O_{19}$ | 1506.71 | 95 | 753.9 (m/2 + H) | 753.9 (m/2 + H) |
| LP2 | 4.48 | $C_{79}H_{103}F_2N_9O_{19}$ | 1520.71 | 97 | 761.0 (m/2 + H) | 761.0 (m/2 + H) |
| LP3 | 5.20 | $C_{81}H_{107}F_2N_9O_{19}$ | 1548.76 | 95 | 775.0 (m/2 + H) | 775.0 (m/2 + H) |
| LP4 | 4.31 | $C_{79}H_{101}F_2N_9O_{19}$ | 1518.69 | 99 | 760.0 (m/2 + H) | 760.0 (m/2 + H) |
| LP5 | 3.40 | $C_{37}H_{48}F_2N_2O_{11}S_2$ | 798.91 | 99 | 799.3 (m + H) | 799.3 (m + H) |
| LP6 | 3.62 | $C_{38}H_{50}F_2N_2O_{11}S_2$ | 812.94 | 97 | 813.3 (m + H) | 813.3 (m + H) |
| LP7 | 5.20 | $C_{52}H_{75}F_2N_3O_{13}S_2$ | 1052.29 | 97 | 526.7 (m/2 + H) | 526.7 (m/2 + H) |
| LP8 | 5.42 | $C_{53}H_{77}F_2N_3O_{13}S_2$ | 1066.32 | 98 | 533.8 (m/2 + H) | 533.8 (m/2 + H) |
| LP9 | 3.65 | $C_{77}H_{101}N_9O_{19}$ | 1456.70 | 96 | 729.0 (m/2 + H) | 729.0 (m/2 + H) |
| LP10 | 3.35 | $C_{77}H_{99}F_2N_9O_{19}$ | 1492.68 | 95 | 513.8 (fragment) | 747.0 (m/2 + H) |
| LP11 | 1.96 | $C_{71}H_{87}F_2N_7O_{17}$ | 1348.51 | 95 | 450.2 (m/3 + H) | 675.2 (m/2 + H) |
| LP12 | 5.61 | $C_{76}H_{110}F_2N_8O_{20}$ | 1493.75 | 90 | 747.6 (m/2 + H) | 747.6 (m/2 + H) |
| LP13 | 4.13 | $C_{75}H_{108}F_2N_8O_{21}$ | 1495.70 | 95 | 748.4 (m/2 + H) | 748.4 (m/2 + H) |
| LP18 | 2.46 | $C_{82}H_{106}F_2N_{10}O_{22}$ | 1621.77 | 95 | 811 (m/2 + H) | 811 (m/2 + H) |
| LP19 | 2.46 | $C_{82}H_{106}F_2N_{10}O_{22}$ | 1621.77 | 95 | 811 (m/2 + H) | 811 (m/2 + H) |
| LP20 | 3.25 | $C_{80}H_{115}F_2N_9O_{24}$ | 1624.81 | 95 | 813 (m/2 + H) | 813 (m/2 + H) |
| LP21 | 3.25 | $C_{80}H_{115}F_2N_9O_{24}$ | 1624.81 | 95 | 813 (m/2 + H) | 813 (m/2 + H) |

Example 2

This Example demonstrates specific procedures for site-specific conjugation of an alkyne-linker-payload to antibody.

In this example, the site-specific conjugates is produced in two steps. The first step is MTG-based enzymatic attachment of a small molecule, such as azide-PEG3-amine (supra), to the antibody having a Q-tag (for example, WO2017/147542) (hereinafter "MTG-based" conjugation). The antibody having an N297Q mutation or N297D mutation has Q295/Q297 or Q295 that are espoused to be attached to the MTG for the enzymatic based site-specific conjugations, where Q295 and/or Q297 were defined as the Qtag. The second step employs the attachment of a linker-payload to the azido-functionalized antibody via a [2+3]cycloaddition, for example, the 1,3-dipolar cycloaddition between the azides and the cyclooctynes (aka copper-free click chemistry). See, Baskin, J. M; Prescher, J. A.; Laughlin, S. T.; Agard, N. J.; Chang, P. V.; Miller, I. A.; Lo, A.; Codelli, J. A.; Bertozzi, C. R. *PNAS* 2007, 104 (43), 16793-7, the entire contents of which are herein incorporated by reference in its entirety for all purposes. Where the reactive group (RG) is a DIBAC moiety, the conjugation is carried out with an azido-functionalized antibody via a [2+3] cycloaddition. This process provides the site-specific and stoichiometric conjugates.

ADC Conjugation Via [2+3] Click Reaction.

Step 1: Preparation of an Azido-Functionalized Antibody.

Aglycosylated human antibody IgG (IgG1, IgG4, etc.) or a human IgG1 isotype with N297Q mutation (EU numbering), in PBS (pH 6.5-8.0) is mixed with ≥200 molar equivalents of azido-dPEG$_3$-amine (MW=218.26 g/mol). The resulting solution is mixed with MTG (EC 2.3.2.13 from Zedira, Darmstadt, Germany, or Modernist Pantry [L #210115A]-ACTIVA TI contains Maltodextrin from Ajinomoto, Japan) (25 U/mL; 5 U MTG per mg of antibody) resulting in a final concentration of the antibody at 0.5-5 mg/mL, and the solution was then incubated at 37° C. for 4-24 h while gently shaking. The reaction is monitored by ESI-MS. Upon reaction completion, the excess amine and MTG are removed by SEC or protein A column chromatography, to generate the azido-functionalized antibody. This product is characterized by SDS-PAGE and ESI-MS. The azido-dPEG$_3$-amine added to two sites of the antibody resulting in a 204 Da increase for the 2DAR antibody-PEG$_3$-azide conjugate.

Step 2: Preparation of Site-Specific Conjugates of a Drug to an Antibody Using Click Chemistry Reactions.

The site-specific antibody drug conjugates with a human IgG (IgG1, IgG4, etc.) in Table 7 are prepared by a [2+3] click reaction between azido-functionalized antibodies and an alkyne containing linker-payload. The detailed conjugation procedure follows. A site-specific antibody conjugate with linker-payload (LP) is prepared by incubating mAb-PEG$_3$-N$_3$ (1-3 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for over 6 h. The progress of the reaction is monitored by ESI-MS and the absence of mAb-PEG$_3$-N$_3$ indicated the completion of the conjugation. The excess amount of the LP and organic solvent are removed by SEC via elution with PBS, or via protein A column chromatography via elution with acidic buffer followed by neutralization with Tris (pH8.0).

The final product is concentrated by ultra centrifugation and characterized by UV, SEC, SDS-PAGE and ESI-MS.

Example 3

This example demonstrates a method for making a non-site-specific conjugation of a drug to an antibody using a thiol-maleimide reaction.

Conjugation through antibody cysteines is performed in two steps using the methods described similar to those described in *Mol Pharm.* 2015 Jun. 1; 12(6):1863-71.

A monoclonal antibody (mAb, 10 mg/ml in 50 mM HEPES, 150 mM NaCl) at pH 7.5 is reduced with 1 mM dithiothreitol (0.006 mg per mg of antibody) or TCEP (2.5 molar equivalent to antibody) at 37° C. for 30 minutes. The concentration of the antibody was calculated based on the absorbance at 280 nm on Nanodrop (ThermoFisher Scientific) and an extinction coefficient of the antibody. After gel filtration (G-25, pH 4.5 sodium acetate), the LP compound in DMSO (10 mg/mL) is added to the reduced antibody, and the mixture was adjusted to pH 7.0 with 1 M HEPES (pH 7.4). The reaction is allowed to react for 3-14 hours. The resulting conjugate was purified by SEC. The DAR (UV) values are determined using the measured absorbances of the ncADC and the extinction coefficients of the antibody and LP compound.

Example 4

ADC Conjugation

In one example, site-specific conjugates are produced via Microbial transglutaminase (MTG EC 2.3.2.13, Zedira, Darmstadt, Germany) (herein "MTG-based") two-step conjugation of an N297Q or N297D mutated antibody. In the first step, the N297Q-mutated antibody is functionalized with azdio-$PEG_3$-amine via MTG based enzymatic reaction. See, e.g., International PCT Patent Application No. PCT/US17/19537 filed on Feb. 24, 2017, incorporated herein by reference in its entirety for all purposes. In the second step, an alkyne-functionalized linker-payload is attached to the azido-functionalized antibody via [2+3] 1, 3-dipolar cycloaddition reaction conjugated with an azido-functionalized antibody derived via [2+3] cyclization). This process provides site-specific and stoichiometric conjugates.

Example 5

The following example demonstrates a method for making an azido-functionalized antibody drug conjugate listed in Table 7.

or ESI-MS. Upon the completion, the excess amine and MTG were removed by Size Exclusion Chromatography (SEC) to generate the azido-functionalized antibody. This product was analyzed on SDS-PAGE and ESI-MS. The azido-$dPEG_3$-amine added to two sites—Q295 and Q297—of the antibody resulting in an 804 Da increase for the 4DAR aglycosylated antibody-$PEG_3$-azide conjugate.

The following example demonstrates a method for making a site-specific conjugations of a drug to an antibody using click chemistry reactions.

Site-specific aglycosylated antibody drug conjugates with a human IgG1 containing an N297Q mutation were prepared by a [2+3] click reaction between azido-functionalized antibodies with an alkyne containing linker-payload. Specifically, anti PRLR Ab-$PEG_3$-$N_3$ was conjugated to 2b, 2g, 2l, 2r, or 2s; and anti HER2 Ab-$PEG_3$-$N_3$ was conjugated to 2b, 2g, 2l, 2r, or 2s. These anti-HER2 antibody conjugates were synthesized to serve as isotype controls in the assays described herein. Hereinafter, for convenience, anti-HER2 antibodies are referred to as "isotype" antibodies.

The detailed conjugation procedure follows. A site-specific antibody conjugate with linker-payload (LP or 2) was prepared by incubating mAb-$PEG_3$-$N_3$ (1-3 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for over 6 h. The progress of the reaction was monitored by ESI-MS and the absence of mAb-$PEG_3$-

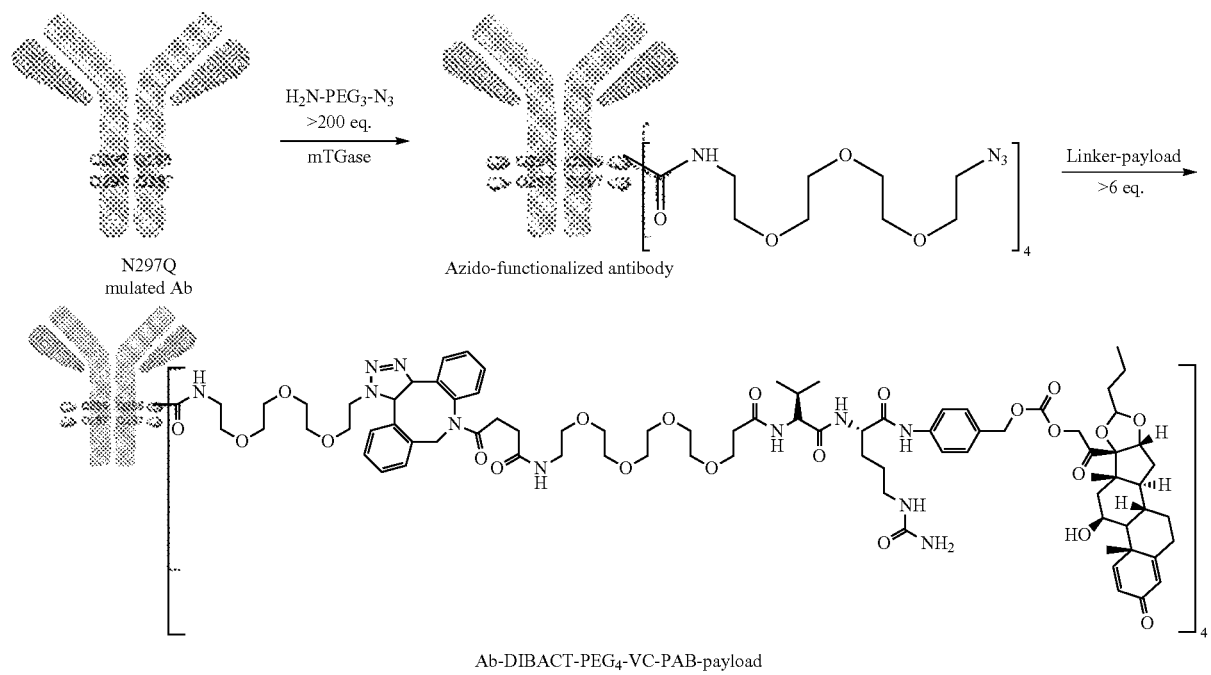

Ab-DIBACT-$PEG_4$-VC-PAB-payload

Aglycosylated antibody with a human IgG1 isotype in BupH™ (pH 7.6-7.8) was mixed with ≥200 molar equivalents of azido-$dPEG_3$-amine (MW. 218.26 g/mol). The resulting solution was mixed with transglutaminase (25 U/mL; 5 U MTG per mg of antibody) resulting in a final concentration of the antibody at 0.5-3 mg/mL, and the solution was then incubated at 37° C. for 4-24 hours while gently shaking. The reaction was monitored by SDS-PAGE $N_3$ indicated the completion of the conjugation. The excess amount of the LP and organic solvent were removed by SEC via elution with PBS, or via protein A column chromatography via elution with acidic buffer followed by neutralization with Tris (pH8.0). The purified conjugates were analyzed by SEC, SDS-PAGE, and ESI-MS. Shown in Table 7 is a list of the steroid antibody conjugates from the corresponding LPs, their molecular weights and ESI-DAR values In a specific example, the azido-functionalized antibody (1 mg) in 0.800 mL PBSg (PBS, 5% glycerol, pH 7.4) was treated with six molar equivalents of 2b (conc. 10 mg/mL in DMSO) for 6-12 hours at RT and the excess linker payload (LP) was removed by size exclusion chromatography (SEC, Superdex 200 HR, GE Healthcare). The final product was concentrated by ultra-centrifugation and characterized by UV, SEC, SDS-PAGE and ESI-MS.

Example 6

Characterization of ADCs

SDS-PAGE is used to analyze the integrity and purity of the ADCs.

In one method, SDS-PAGE running conditions include non-reduced and reduced samples (2-4 µg) along with BenchMark Pre-Stained Protein Ladder (Invitrogen, cat #10748-010; L #1671922) are loaded per lane in (1.0 mm×10 well) Novex 4-20% Tris-Glycine Gel and is run at 180 V, 300 mA, for 80 minutes. An non-reduced sample is prepared using Novex Tris-Glycine SDS buffer (2×) (Invitrogen, Cat #LC2676) and the reduced sample is prepared with SDS sample buffer (2×) containing 10% 2-mecapto-ethanol.

Molecular weights of the antibodies and ncADCs on SDS-PAGE are determined under non-reducing and reducing conditions. The mass shifts may not be obvious under non-reducing conditions due to relatively small percentages of mass changes. However, the masses of the heavy chains are increased from the naked antibodies to the azido-functionalized antibodies, and further to the ncADC conjugate. Cross-linked material may or may not be detected.

ADCs are analyzed for purity by Size Exclusion Chromatography (SEC)

To determine the purity of antibody drug conjugates, size exclusion chromatography is performed. Analytical SEC experiments are run using a Waters 600 instrument, on a Superdex 200 (1.0×30 cm) HR column, at flow rate of 0.80 mL/min using PBS pH 7.4, and monitored at λ280 nm using a Waters 2998 PDA. An analytic sample is composed of 200 µL PBS (pH 7.4) with 30-100 µL of test sample. Preparative SEC purifications are performed using an AKTA instrument from GE Healthcare, on Superdex 200 PG (2.6×60 cm) column, at a flow rate 2 mL/min eluting with PBSg at pH 7.4, and monitored at λ280 nm.

Antibody and ADC are analyzed by intact mass analysis by LC-ESI-MS, as described further below.

Measurement of intact mass for the ADC samples by LC-ESI-MS was performed to determine drug-payload distribution profile and to calculate the average DAR. Each testing sample (20-50 ng, 5 uL) was loaded onto an Acquity UPLC Protein BEH C4 column (10K psi, 300 Å, 1.7 µm, 75 µm×100 mm; Cat No. 186003810). After 3 min desalting, the protein was eluted and mass spectra were acquired by a Waters Synapt G2-Si mass spectrometer.

Summarized in Table 7 is a list of the budesonide-spacer-linker antibody conjugates from the corresponding LPs (2b, 2g, 2l, 2r, and 2s), their molecular weights of the naked antibodies, the azido-functionalized antibodies, the LPs, and the steroid ADCs, as well as the ESI-DAR values. In the table, Ab refers to an antibody, Ab-N$_3$ refers to an azido-functionalized antibody, and Ab-steroid conjugates refers to a non-cytotoxic steroid antibody conjugates with the corresponding LPs. As summarized in Table 7, most site-specific ADCs have ~4DAR.

TABLE 7

| | LP | Ab, Ab-N3, or Ab-Steroid conjugates | | |
|---|---|---|---|---|
| EX | MS m/z | Name | MW (Da) | DAR |
| | | Anti-PRLR Ab | 144602 | — |
| PEG$_3$-N$_3$ | 218.3 | Anti-PRLR Ab-N$_3$ | 145385 | 4 |
| 2b | 1369.7 | Anti-PRLR Ab-2b | 150894 | 4 |
| 2g | 1426.7 | Anti-PRLR Ab-2g | 151097 | 4 |
| 2l | 1373.7 | Anti-PRLR Ab-2l | 150884 | 4 |
| 2r | 729.8 | Anti-PRLR Ab-2r | 148330 | 4 |
| 2s | 809.8 | Anti-PRLR Ab-2s | 148623 | 4 |
| | | Anti-HER2 (Isotype) Ab | 145126 | — |
| PEG$_3$-N$_3$ | 218.3 | isotype Ab-N$_3$ | 145930 | 4 |
| 2b | 1369.7 | Isotype Ab-2b | 151439 | 3.8 |
| 2g | 1426.7 | isotype Ab-2g | 151652 | 4 |
| 2l | 1373.7 | Isotype Ab-2l | 151445 | 3.9 |
| 2r | 729.8 | Isotype Ab-2r | 148876 | 4 |
| 2s | 809.8 | Isotype Ab-2s | 149169 | 4 |

Example 7

A Glucocorticoid Receptor (GR) co-activator luciferase reporter cell based assay was used to analyze the GR activation by Budesonide and the steroids described herein as a function of time.

To generate the assay cell line, a HEK293 cell line was engineered to express human full length PRLR. Then such stable cell line was further transfected with pBIND-GR vector (Cat #E1581, Promega) and pGL4.35 [Luc2P/9× GAL4UAS/Hygro] vector (Cat #E1370, Promega) so that luciferase gene is transcribed upon steroid binding to GR. The resulting stable cell line is referred to herein as HEK293/PRLR/GRE-Luc.

The activity of steroids in the HEK293/PRLR/GRE-Luc cells was studied at 24, 48, and 72 hours of incubation after addition of the testing reagents. For this assay, 20,000 cells were seeded in 96-well plates in media containing DMEM supplemented with 10% FBS and penicillin/streptomycin (complete media) and grown overnight at 37° C. in 5% CO$_2$. To generate the dose response curves of the free steroids and/or their ncADCs, serially diluted reagents ranging from 100 nM to 5.1 pM were added to the cells and incubated for 24, 48, and 72 hours at 37° C. Luciferase activity was determined by addition of 100 uL of One-Glo™ reagent (Promega, Cat #E6130), incubating at room temperature for 5 minutes and relative light units (RLUs) were measured on a Victor luminometer (Perkin Elmer).

In a first assay run, anti-PRLR Ab ncADCs (Anti-PRLR Ab-2r, Anti-PRLR Ab-2s, and Anti-PRLR Ab-2b), Isotype Ab ncADCs (Isotpye Ab-2r, Isotype Ab-2s, and Isotype Ab-2b) and budesonide free payload were tested in the HEK293/PRLR/GRE-Luc cell based assay using the protocol described above with either 24, 48 or 72 hour-incubation in one assay run. In a second assay run, anti-PRLR Ab ncADCs (Anti-PRLR Ab-2b, Anti-PRLR Ab-2l, and Anti-PRLR Ab-2g), Isotype Ab ncADCs (Isotype Ab-2b, Isotype Ab-2l, and Isotype Ab-2g), antibodies alone (Anti-PRLR Ab and Isotype Ab), and budesonide free payload were tested in the HEK293/PRLR/GRE-Luc cell based assay using the protocol described above with 72 hour-incubation. The EC$_{50}$ values were determined from a four-parameter logistic equation over a 10-point response curve using GraphPad Prism. Delivery of the steroids will result in an activation of the Luc reporter in HEK293/PRLR/GRE-Luc cells.

Figure 1C:
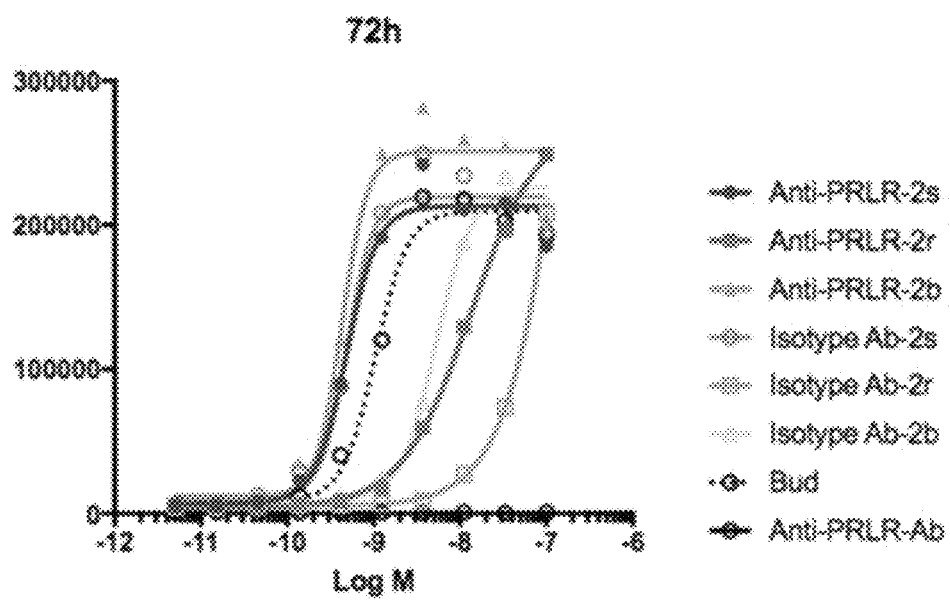

FIGS. 1A-C and Table 8 illustrate the results from the first assay run. As shown in FIGS. 1A-C, the anti-PRLR Ab-2b conjugate induced activation in the HEK293/PRLR/GRE-Luc cells at 24, 48, and 72 hours, with an $EC_{50}$ value less than ≤10 nM at all three time points and showed about >15 fold selectivity over the control Isotype-Ab-2b. The anti-PRLR Ab-2s conjugate induced activation in the HEK293/PRLR/GRE-Luc cells at 24, 48, and 72 hours, however, it did not demonstrate selectivity over the control isotype-2s. The anti-PRLR Ab-2r conjugate induced activation in the 293/PRLR/GRE-Luc cells with <5 fold selectivity at 24 and 48 hours, but had increased activation only at 72 hours with an $EC_{50}$ of 13.4 nM.

Figure 2:
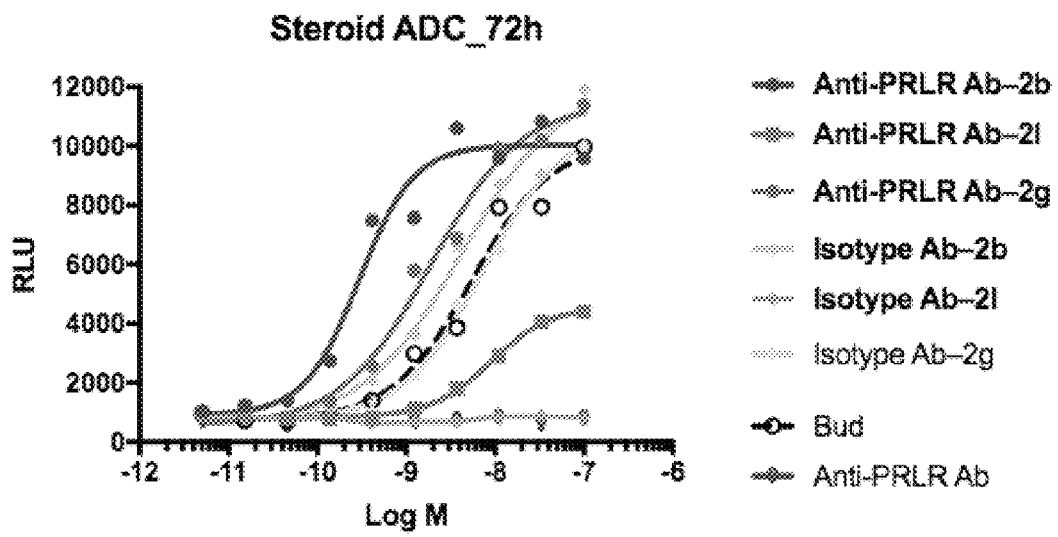

In the second assay run as shown in FIG. 2 and Table 9, the anti-PRLR Ab-2b conjugate induced activation in the HEK293/PRLR/GRE-Luc cells, having an $EC_{50}$ of 0.48 nM that and showed about 14 fold selectivity over the control Isotype-Ab-2b. The anti-PRLR Ab-2g conjugate induced activation in the HEK293/PRLR/GRE-Luc cells having an $EC_{50}$ of 1.9 nM with about 3.7 fold selectivity over the control Isotype-Ab-2g. The anti-PRLR Ab-2l conjugate induced activation in the HEK293/PRLR/GRE-Luc cells with an $EC_{50}$ of 8.98 nM, while Isotype-Ab-2l did not demonstrate activation in this assay.

TABLE 8

| | HEK293/PRLR/GRE-Luc cells | | |
|---|---|---|---|
| Molecule | $EC_{50}$ (24 hr) | $EC_{50}$ (48 hr) | $EC_{50}$ (72 hr) |
| Anti-PRLR Ab-2s | 0.9078 | 0.4239 | 0.4823 |
| Anti-PRLR Ab-2r | 34.98 | 18.33 | 13.35 |
| Anti-PRLR Ab-2b | 1.225 | 0.4674 | 0.4291 |
| Isotype Ab-2s | 1.461 | 0.6594 | 0.4904 |
| Isotype Ab-2r | 109.2 | 64.01 | 310.9 |
| Isotype Ab-2b | 15.04 | 8.201 | 5.243 |
| 1a | 0.5732 | 0.5679 | 1.043 |

TABLE 9

| Steroid ADCs | HEK293/PRLR/GRE-Luc cells $EC_{50}$ (nM) at 72 hours |
|---|---|
| Anti-PRLR Ab-2b | 0.29 |
| Anti-PRLR Ab-2l | 8.98 |
| Anti-PRLR Ab-2i | >90.9 |
| Anti-PRLR Ab-2g | 1.90 |
| Isotype Ab-2b | 4.16 |
| Isotype Ab-2l | NA |
| Isotype Ab-2i | NA |
| Isotype Ab-2g | 7.11 |
| Budesonide (1a) | 5.42 |
| Anti-PRLR Ab | NA |
| Isotype Ab | NA | where NA means not active

Example 8

This example describes a mouse model of LPS induced cytokine release.

The aim of this study is to evaluate the test compounds on inhibition of LPS-induced cytokine release in mice. Test compounds are administered 48 hr, 24 hr and 2 hr before LPS challenge, cytokine levels in blood samples including TNF-α and IL6 were measured at 2 hr and 4 hr time-points after LPS challenge.

Materials and Reagents

Lipopolysaccharide (LPS) derived from *E. coli* K12 can be purchased from Invivogen (San Diego, California, USA, cat #Tlrl-eklps), Dexamethasone can be purchased from ADAMAS (Emeryville, CA, USA, Cat #50-02-2). Mouse TNF-α ELISA kit can be purchased from ebioscience (ThermoFisher Scientific, Cat #88-7324). Mouse IL6 ELISA kit can be purchased from ebioscience (ThermoFisher Scientific, Cat #88-7064).

Experimental Methods

Animal Husbandry:

A total of 18 naive C57BL/6j mice are used in this study. The animals are male, with body weight of 18-20g at the initiation of the study. Animals are purchased from Shanghai Laboratory Animal Center, CAS (SLAC), and housed in ChemPartner's animal vivarium in a SPF environment. After arrival, animals are checked for health conditions including coat, extremities, orifices and abnormal signs in posture or movements, and acclimated to the environment for more than 7 days.

Animals are housed 3 mice per cage in IVC polycarbonate shoebox cages in SPF environment; the environment controls for the animal room are set to maintain a temperature of 20-26° C., humidity of 40-70%, and a 12-hour light/12-hour dark cycle.

Standard chow (SLAC-M01, from Shanghai Laboratories Animal Center) and purified water (filtered, municipal water quality) are provided ad libitum throughout the study period.

Experimental Procedures

Grouping: Animals are randomly allocated into 6 groups (A-F) before study initiation. Each group included 3 mice. Group A serve as naive control; Group B receive dexamethasone and served as positive control; Group C is treated with a test compound and Groups D-F are treated with a test compound.

Experimental Procedure

All mice receive LPS dissolved in PBS at a dose of 0.5 mpk by i.p injection. Mice in group A received PBS, mice in group B received Dex (5 mpk) and mice in group C received 4b (5 mpk) by ip injection, 2 hr prior to LPS challenge; Mice in group D, E and F received at a dose of 5 mpk by ip injection, 2 hr, 24 hr and 48 hr prior to LPS challenge, respectively.

Blood samples are collected at 2 hr and 4 hr time points post LPS challenge, into heparin containing tubes. Blood samples are centrifuged, and plasma samples are collected and stored at −80° C. before analysis.

The levels of TNFα in plasma are measured with ELISA kits following the standard procedures recommended by the manufacturer. Various PK parameters are measured (e.g. $T_{max}$, $C_{max}$, Terminal $t_{1/2}$, $AUC_{last}$, and $AUC_{INF}$).

Blood samples are collected at 2 hr and aa post LPS challenge; TNF-α levels in plasma are measured. Data are expressed as mean±SEM, *p<0.05, **p<0.01 vs Group A, by Oneway ANOVA analysis.

Example 9

Mouse Dendritic Cells

To determine the effect of a test compound on ex-vivo LPS-induced inflammatory immune responses, CD11c+ dendritic cells (DC) are isolated from the spleens of wild-type C57Bl/6 mice (Jackon Labs, Protocol #426.0). Splenic DCs are isolated using a Collagenase D digestion (400 U/mL collagenase D (Roche Cat #11088858001), 20 g/mL DNase I (Roche Cat #10104159001), 2% FCS in HEPES-buffered RPMI-1640) and incubated at 37° C. for 25 minutes. Post incubation, the splenic tissue is washed with RPMI-1640 and filtered through a 70 m filter, then red blood cell lysis is performed using ACK lysing buffer (Gibco Cat #A1049201) for 1 minute. The cell suspension is subsequently washed twice using RPMI-1640. Classical DCs are isolated from the mononuclear cell suspension using CD11c magnetic MicroBeads (Milteny Biotec Cat #130108338). In brief, the cell suspension is washed twice with autoMACS running buffer (Milteny Biotec Cat #130091221) prior to a 30-minute incubation at 4° C. with CD11c$^+$ MicroBeads, as per Milteny Biotec established protocols. CD11c$^+$ cells are isolated by positive selection, washed, suspended in complete-RPMI [RPMI-1640 (ThermoFisher Scientific, Cat #15140122) containing 10% of FBS (ThermoFisher Scientific, Cat #10082147) and 1% of penicillin-streptomycin (ThermoFisher Scientific, Cat #11875093)], and counted prior to culture at $2 \times 10^5$ cells per well. Control complete-RPMI, Compound of Formula (III) treated complete-RMPI (at 10 nM and 100 nM) or Dexamethasone (Sigma, Cat #D4902-25MG) treated complete-RMPI (at 10 nM and 100 nM) is added to the cells in a 96 well-culture dish. DC/Control, a test compound or Dexamethasone treated cells were incubated for 24 hours at 37° C. prior to stimulation with 10 ng/mL of LPS for 24 hours.

Human Dendritic Cells

To determine the effect of a test compound on ex-vivo LPS-induced inflammatory immune responses in human innate immune cells, CD14$^+$ monocytes (Lonza Cat #2W-400C) are isolated and cultured in the presence of complete-RPMI [RPMI-1640 (ThermoFisher Scientific, Cat #15140122) containing 10% of FBS (ThermoFisher Scientific, Cat #10082147) and 1% of penicillin-streptomycin (ThermoFisher Scientific, Cat #11875093)] supplemented with human IL4 (50 ng/mL) (Milteny Biotec, Cat #130-093-922) and human GM-CSF (100 ng/mL) (Milteny Biotec, Cat #130093866) for 7 days. The complete-RPMI with IL4 and GM-CSF is changed every three days. Two specific culture conditions are developed: Condition 1: Incubation of CD14$^+$ monocytes with control complete-RPMI, a test compound treated complete-RMPI (at 10 nM and 100 nM) or Dexamethasone (Sigma) treated complete-RMPI (at 10 nM and 100 nM) for the entire 7 day culture or Condition 2: Incubation of CD14$^+$ monocytes with control complete-RPMI for 5 days prior to incubation with Control complete-RMPI, a test compound treated complete-RMPI (at 10 nM and 100 nM) or Dexamethasone (Sigma, Cat #D4902-25MG) treated complete-RMPI (at 10 nM and 100 nM) until day 7. On day 7 the various experimental groups are stimulated with 10 ng/mL of LPS for 24 hours.

Measurement of Cytokines in the Supernatants 24 Hours Post-LPS Ex Vivo Challenge Supernatants are collected into 96-well round bottom tissue culture plates 24 hours post-LPS challenge and stored at −20° C. until further analysis. Cytokine concentrations in the supernatants are measured using a Pro-inflammatory Panel 1 (mouse) multiplex immunoassay kit (MesoScale Discovery, Cat #K15048D) according to manufacturer's instructions or Pro-inflammatory Panel 1 (human) multiplex immunoassay kit (MesoScale Discovery, Cat #K15049D). In brief, 50 μL/well of calibrators and samples (diluted in Diluent 1:2) are added to the plates pre-coated with capture antibodies and incubated at room temperature while shaking at 700 rpm for 2 hours. The plates are then washed 3 times with 1×PBS containing 0.05% (w/v) Tween-20, followed by the addition of 25 μL of Detection Antibody Solution diluted in Diluent 45. After 2-hour incubation at room temperature while shaking, the plates are washed 3 times, and 150 μL of 2× Read Buffer was added to each well. Electrochemiluminescence is immediately read on a MSD Spector® instrument. Data analysis is performed using GraphPad Prism™ software. Statistical significance within the groups is determined by one-way Anova with Turkey's multiple comparison post-test and standard error of mean (SEM±) calculated. Production of IL12p70, IL1β, IL6, KC-GRO and TNF-α by splenic CD11c$^+$ DCs are measured. Expression of IL12p70, IL1β, IL6, and TNF-α by human monocyte-derived DCs are measured.

Example 10

Plasma Stability of 103a

Plasma stability can be measured according to the following protocol.

Preheated 0.05 M sodium phosphate and 0.07 M NaCl buffer, pH 7.4:14.505 g/L $Na_2HPO_4\_12H_2O$, 1.483 g/L $NaH_2PO_4\_2H_2O$ and 4.095 g/L NaCl were dissolved in deionized water. The basic solution was then titrated with the phosphoric acid to pH 7.40 and stored refrigerated for up to 7 days. pH was checked on the day of experiment and adjusted if outside specification of 7.4+/−0.1.

Plasma preparation: frozen plasma were thawed by placing at 37° C. The plasma was centrifuged at 3,000 rpm for 8 minutes to remove clots, pipetted and the supernatant was pooled as the plasma to be used in the experiment. The pH of the plasma was checked and recorded and only used within the range of pH 7.4 to pH 8. If higher than pH 8, the plasma was discarded. The initial pH of the plasma was not adjusted to pH 7.4 with acid or by bubbling with $CO_2$. By using a 5% $CO_2$ incubator and PBS buffer, a pH of 7.4 was reached after a 4 hour equilibrium dialysis time. The plasma was put on ice until used.

Test compounds and reference compounds spiking solution. 0.5 mM test compounds spiking solution A: 10 μL of 10 mM test compounds stock solution was added to 190 μL DMSO. 0.02 mM spiking solution B: 40 μL of spiking solution A were added to 960 μL of 0.05 mM Sodium phosphate buffer with 0.5% BSA.

The plasma and spiking solution B were pre-warmed at 37° C. for 5 min. 10 μL of pre-warmed spiking solution B was added into the wells designated for all the time points (0, 0.25, 1, 8, 24 h). For 0-min, 400 μL of ACN containing IS was added to the wells of 0-min plate and then 90 μL of plasma was added. 90 μL of pre-warmed plasma was added into the wells designated for the time points (0.25, 1, 8, 24 h), and start timing. At 0.25, 1, 8, 24 h, 400 μL of ACN containing IS was added to the wells of corresponding plates, respectively, to stop the reaction. After quenching, the plates were shaken on a vibrator (IKA, MTS 2/4) for 10 min (600 rpm/min) and then centrifuged at 5594 g for 15 min (Thermo Multifuge×3R). 50 μL of the supernatant from each well was transferred into a 96-well sample plate containing 50 μL of ultra pure water (Millipore, ZMQS50F01) for LC/MS analysis.

The human plasma stability data for compound 103a is shown in the table below.

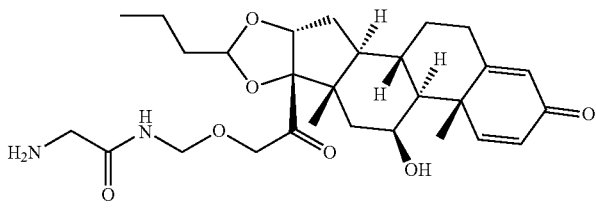

| Test Article | Percent Remaining (%) | | | | | $T_{1/2}$ (h) |
|---|---|---|---|---|---|---|
| | 0 h | 0.25 h | 1 h | 8 h | 24 h | |
| Procaine | 100.00 | BQL | BQL | BQL | BQL | <0.25 |
| 103a | 100.00 | 107.04 | 96.48 | 78.87 | 38.03 | 16.79 |
| | Area ratio | | | | | |
| Budesonide released from 103a | 0.054 | 0.052 | 0.042 | 0.047 | 0.049 | |

BQL: Below Quantitation Limit

Example 11 pH Stability of Linker-Payload

As the solubility of payload 103a,b and their linker-payloads LP9,10 are poor (<0.02 mg/mL aq. DMSO (20%)), the pH stability of these compounds was not tested. LP9 was quenched with CD-$N_3$ to give the following compound QLP9, which was water soluble and used for the pH stability test.

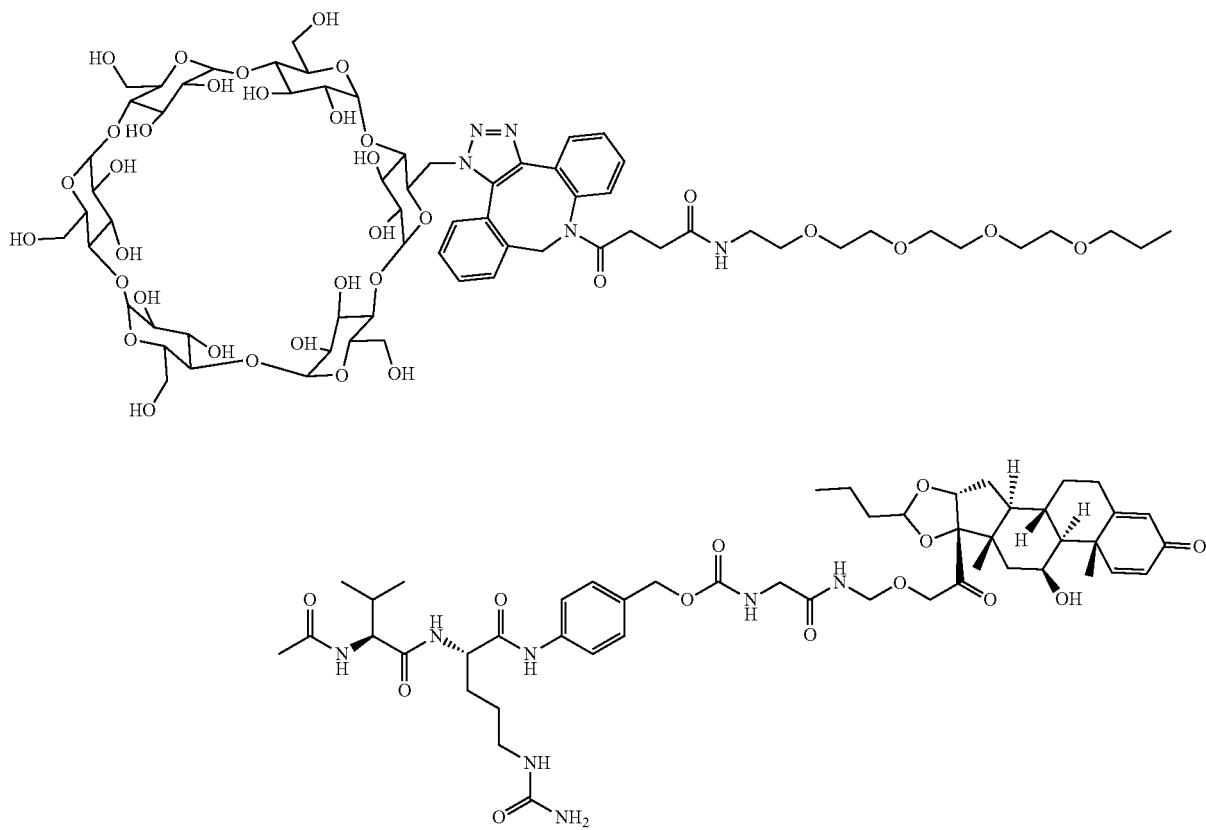

QLP9

Synthesis of compound QLP9: To a solution of LP9 (5 mg, 3.4 µmol) in DMF (1.0 mL) was added compound CD-N$_3$ (7.0 mg, 6.8 µmol). The reaction mixture was stirred at RT overnight, which was monitored by LCMS. The reaction mixture was directly purified by prep-HPLC to give compound QLP9 (5 mg, 60% yield) as a white solid. ESI m/z: 819.0 (M/3+H)$^+$.

pH Stability in buffers: The stability of QLP9 in DMSO, pH 5.0, 7.4 and 8.5 PBS buffers (containing 20% DMSO) was tested, and the compound was stable in those solutions after 7 days.

Example 12

Cell Based Glucocorticoid Receptor (GR) Luciferase Reporter Assay

A cell-based GR responsive luciferase reporter assay was used to test the GR agonist activity of compounds described herein. In this assay, the following materials were used.

| | Vendor information (where applicable)) |
|---|---|
| HEK293 cells | ATCC, cat# CRL-1573 |
| HEK293/UAS-Luc/pBIND GR Growth media: DME High Glucose, 10% FBS, 100 units/mL Penicillin, 100 µg/mL, Streptomycin, 53 µg/mL glutamine, 100 µg/mL hygromycin, 500 µg/mL G418 | |
| DME high glucose, 500 mL | Irvine Scientific #9033 |
| Fetal Bovine Serum | Saradigm # 1500-500 |
| Penicillin-Streptomycin L-glutamine Solution 100× | Gibco # 10378-016 |
| pGL4.35[luc2p/9XGAL 4UAS/Hygro] vector | Promega, cat# E137A |
| pBIND-GR vector, selection marker is neomycin | Promega, cat# E158A |
| Hygromycin-B 100 mg/mL | InvivoGen # ant-hg-5 |
| G418 100 mg/mL | GIBCO # 11811-098 |
| Nunclon delta 96 well microwell plate, sterile white, flat bottom | Thermo Scientific # 13610 |
| Assay media: Same as growth media | |
| DMSO Dianethyl sulfoxide, cell culture tested | ATCC. #4-x. |
| ONE Glo | Promega, Cat# E6130 |
| Instrument | Envision plate reader, Perkin Elmer |
| Dilution plates | Axygen Scientific, Cat# P-DW-11-C-S |
| Trypsin-EDTA | Millipore Cat# SM-2004-C |
| PBS 1 × without calcium and magnesium salts | Irvine Scientific # 9240 |
| Test compound 1a | Sigma/1278201/ RO36WO |
| Test compound 100 | |
| Test compound 105a | |
| Test compound 103a | |
| Test compound 103b | |
| Test compound Dexamethasone | Sigma/D1756-25MG/ BCBV3214 |

To generate the assay cell line, HEK293 cells were co-transfected with the pBind-GR (Promega, Cat #E158A) and pGL4.35 [Luc2P/9×GAL4UAS/Hygro] (Promega, Cat #E137A) vectors. The pBind-GR vector expresses a fusion protein consisting of the yeast Gal4DNA-binding domain and the GR ligand binding domain, that can bind to the Gal4 upstream activation sequence (UAS) in the luciferase expression vector and induce luciferase expression following GR agonist binding. The cells were selected for at least 2 weeks in G418+hygromycin. The resulting cell line is referred to as HEK293/UASLuc/pBIND-GR.

Cells were seeded into 96 well plates at 20,000 cells/well in assay media (DME high glucose supplemented with 1000 FBS, 100 units/mL Penicillin, 100 µg/mL Streptomycin, 53 µg/mL glutamine, 500 µg/mL G418, and 100 µg/mL Hygromycin) one day prior to assay. Three-fold serial dilutions of test compounds were prepared in 100% DMSO, transferred to fresh assay media, and added to the cells. The final DMSO concentration was held constant at 0.2%, and the test compound final concentrations ranged from 100 nM to 0.015 nM. The last well in the plate served as blank control containing only the assay media and 0.2% DMSO (untreated well) and was plotted as a continuation of the 3-fold serial dilution.

Forty-eight hours later, luciferase activity was determined after the addition of One-Glo™ reagent (Promega, Cat #E6130). Relative light units (RLUs) were measured on an Envision luminometer (PerkinElmer) and EC$_{50}$ values were determined using a four-parameter logistic equation over a 10-point dose response curve (GraphPad Prism). The signal to noise (S/N) was determined by taking the ratio of the highest RLU on the dose response curve to the RLU in the untreated wells.

As shown in the table below, EC$_{50}$ values ranged from 51.8 pM to 3.24 nM and S/N values ranged from 12.4 to 17.3. Test compound 100 was 5.6-fold more potent than 1a (budesonide) and 5.9-fold more potent than Dexamethasone. Spacer attachment to 1a to generate 103a resulted in EC$_{50}$ values comparable to 1a. Similarly, spacer attachment to 100 to generate 103b resulted in EC$_{50}$ values comparable to 100. Spacer attachment to 100 to generate 105a resulted in EC$_{50}$ values that were 2.7-fold less potent than 100. S/N values were comparable across all test compounds.

| Test Compound | EC$_{50}$ (M) | S/N |
|---|---|---|
| Dexamethasone | 3.24E−09 | 17.3 |
| 1a | 3.06E−10 | 15.3 |
| 103a | 4.84E−10 | 14.6 |
| 100 | 5.47E−11 | 14.5 |
| 103b | 5.18E−11 | 16.6 |
| 105b | 1.49E−10 | 12.4 |

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A Compound of Formula (III)

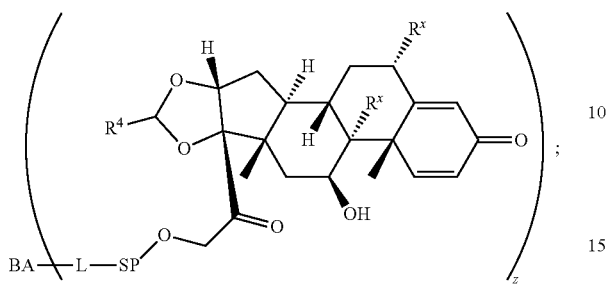

(III)

or a pharmaceutically acceptable salt, solvate, or stereoisomer thereof, wherein $R^4$ is alkyl, aryl, arylalkyl, or an N-containing heterocycloalkyl; and either (a) or (b):

a) both $R^x$ are hydrogen; and

SP is —C(O)—$C_1$-$C_{10}$-alkylene-C(O)—; —C(O)—N($C_{1-6}$-alkyl)-$C_1$-$C_{10}$-alkylene-$X^1$- where $X^1$ is attached to L; —C(O)—N(H)—($C_1$-$C_{10}$-alkylene)-S— where sulfur is attached to L; —C(O)—N($C_{1-6}$-alkyl)-($C_1$-$C_{10}$-alkylene)-S— where sulfur is attached to L;

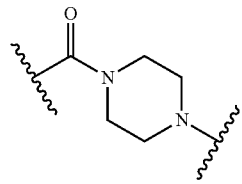 [SMILES: *C(=O)N1CCN(*)CC1]

where the piperazine nitrogen is attached to L;
—$CH_2$—NH— where nitrogen is attached to L;

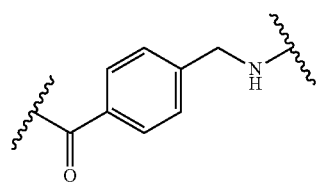 [SMILES: *NCc1ccc(C(*)=O)cc1]

where the nitrogen is attached to L;
—C(O)—N($R^5$)—$C_1$-$C_{10}$-alkylene-C(O)NH-$X^2$- where $X^2$ is attached to L; or,

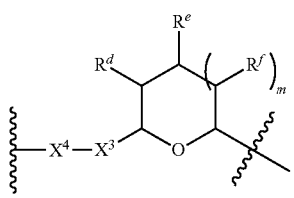

where $X^4$ is attached to L; or b) both $R^x$ are fluoro; and

SP is —C(O)—$C_1$-$C_{10}$-alkylene-C(O)—; —C(O)—N($C_{1-6}$-alkyl)-$C_1$-$C_{10}$-alkylene-$X^{1b}$- where $X^{1b}$ is attached to L; —C(O)—N(H)—($C_1$-$C_{10}$-alkylene)-$X^{1b}$- where $X^{1b}$ is attached to L;

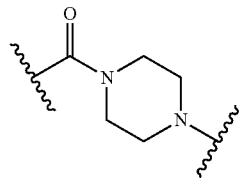 [SMILES: *C(=O)N1CCN(*)CC1]

where the piperazine nitrogen is attached to L;
—$CH_2$—NH— where nitrogen is attached to L;

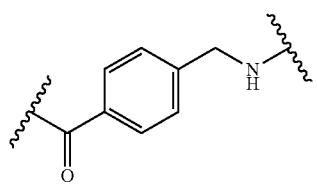 [SMILES: *NCc1ccc(C(*)=O)cc1]

where the nitrogen is attached to L;
—C(O)—N($R^5$)—($C_1$-$C_{10}$-alkylene)-C(O)NH-$X^2$- where $X^2$ is attached to L; or,

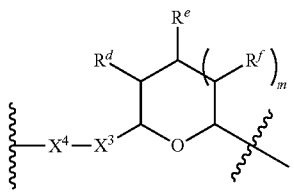

where $X^4$ is attached to L;

$X^1$ is —N($C_{1-6}$-alkyl)-;

$X^{1b}$ is —S—, —NH—, or —N($C_{1-6}$-alkyl)-;

$X^2$ is —NH—;

$X^3$ is —$CH_2$—, —$CH_2$—O—($C_1$-$C_{10}$-alkylene)-C(O)— where the C(O) is attached to $X^4$, or —C(O)—;

$X^4$ is —O—;

$R^5$ is hydrogen, —OH, —$OCH_3$, or $C_{1-6}$-alkyl;

$R^d$, $R^e$, and $R^f$ are independently hydrogen, —OH, hydroxyalkyl, alkoxycarbonyl, —C(O)OH, or —$CH_2OR^g$, where each $R^g$ is independently —$CH_2$C(O)OH or —$CH_2$C(O)O(alkyl);

m is zero or one;

z is an integer selected from one to thirty, inclusive;

L is a linker; and

BA is a binding agent.

2. The Compound of claim 1, where $R^4$ is linear or branched alkyl.

3. The Compound of claim 1, where $R^4$ is in the (R)-configuration.

4. The Compound of claim 1, where either (a) or (b):

a) both $R^x$ are hydrogen; and

SP is —C(O)—$C_1$-$C_{10}$-alkylene-C(O)—; —C(O)—N($C_{1-6}$-alkyl)-$C_1$-$C_{10}$-alkylene-$X^1$- where $X^1$ is attached to L; —C(O)—N(H)—($C_1$-$C_{10}$-alkylene)-S— where sulfur is attached to L;

—C(O)—N($C_{1-6}$-alkyl)-($C_1$-$C_{10}$-alkylene)-S— where sulfur is attached to L;

—C(O)—N($R^5$)-$C_1$-$C_{10}$-alkylene-C(O)NH-$X^2$- where $X^2$ is attached to L; or,

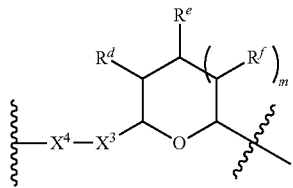

where $X^4$ is attached to L; or b) both $R^x$ are fluoro; and

SP is —C(O)—N($C_{1-6}$-alkyl)-$C_1$-$C_{10}$-alkylene-$X^{1b}$- where $X^{1b}$ is attached to L; —C(O)—N(H)—($C_1$-$C_{10}$-alkylene)-$X^{1b}$- where $X^{1b}$ is attached to L;

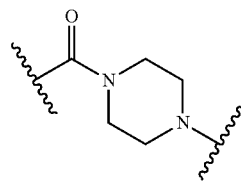 [SMILES: *C(=O)N1CCN(*)CC1]

where the piperazine nitrogen is attached to L; or,

—C(O)—N($R^5$)—($C_1$-$C_{10}$-alkylene)-C(O)NH-$X^2$- where $X^2$ is attached to L.

5. The Compound of claim 1, where both $R^x$ are hydrogen.

6. The Compound of claim 1, where both $R^x$ are fluoro.

7. The Compound of claim 1, where both $R^x$ are hydrogen or both $R^x$ are fluoro and SP is

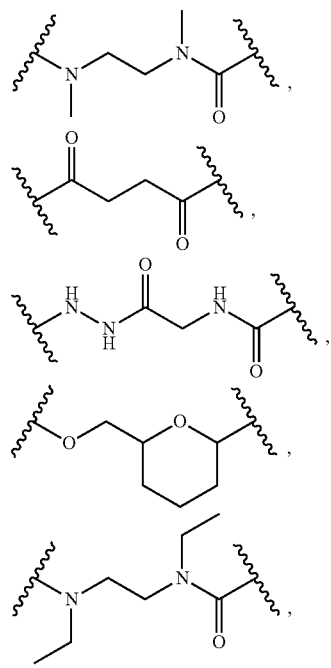

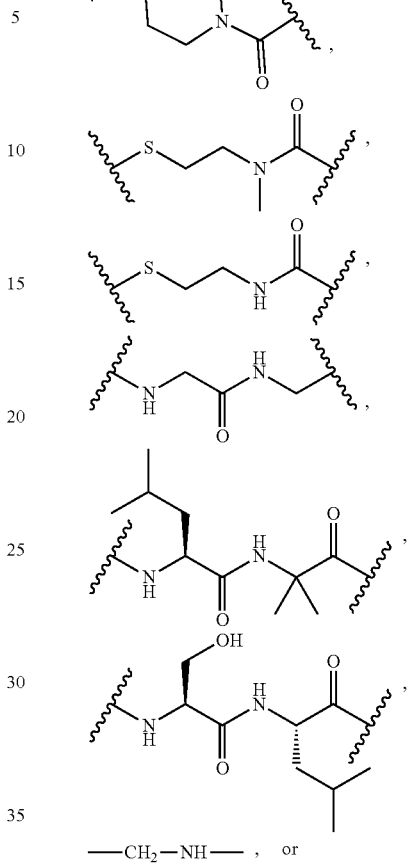

—$CH_2$—NH—, or

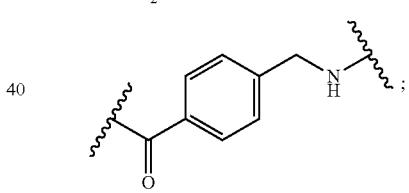

or both $R^x$ are fluoro and SP is

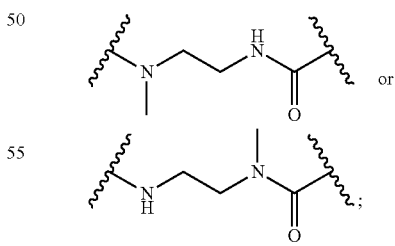

and where the left side point of attachment in the above SP structures is attached to L.

8. The Compound of Formula (III) of claim 1, where z is selected from two to four, inclusive.

9. The Compound of Formula (III) of claim 1, where BA comprises an antibody or antigen binding fragment thereof having the following structure

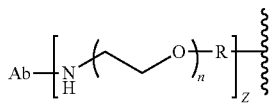

where Ab is a monoclonal antibody, polyclonal antibody, antibody fragment, or bispecific antibody; R is $C_{2-4}$-alkylene; and n is an integer selected from two to four, inclusive.

10. The Compound of Formula (III) of claim 1, where BA comprises an antibody or antigen binding fragment thereof that binds macrophage scavenger receptor 1 (MSR1).

11. The Compound of Formula (III) of claim 1, where L is
-$L^1$-$L^2$-$(L^3)_{0-1}$-, where $L^1$ is attached to BA and $L^3$ is attached to SP; and
where $L^1$ is a reactive group residue; $L^2$ is connecting linker; and $L^3$, when present, is a self-immolative linker; and
$L^1$ is selected from

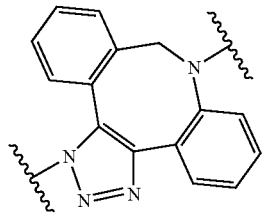 [SMILES: *N1Cc2ccccc2-c2c(nnn2*)-c2ccccc21]

or a regioisomer or mixture of isomers thereof;

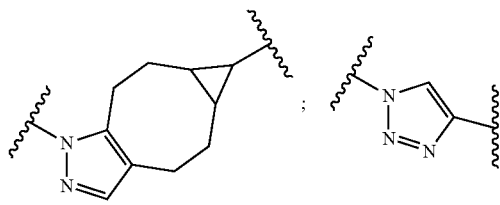 [SMILES: *C1C2CCc3cnn(*)c3CCC12 ; *c1cn(*)nn1]

or a regioisomer or mixture of isomers thereof,

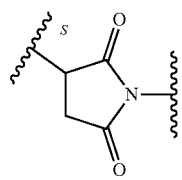

or a stereoisomer or mixture of stereoisomers thereof, where S refers to the sulfur atom on a cysteine residue through which the reactive group residue is attached to BA; and

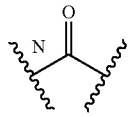

where N refers to the nitrogen atom on a lysine residue through which the reactive group residue is attached to BA.

12. The Compound of claim 1, where L is -$L^1$-$L^2$-$(L^3)_{0-1}$-; and (a), (b), or (c):

(a) where $L^3$ is

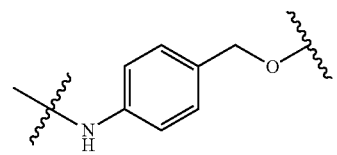 [SMILES: *Nc1ccc(CO*)cc1]

where the —NH— group is attached to $L^2$, when SP is —C(O)—$C_1$-$C_{10}$-alkylene-C(O)—; or (b) $L^3$ is

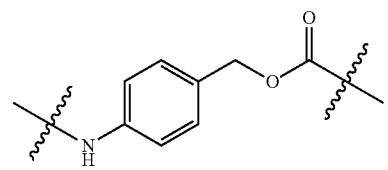 [SMILES: *Nc1ccc(COC(*)=O)cc1]

where the —NH— group is attached to $L^2$, when SP is
—C(O)—N($C_{1-3}$-alkyl)-$C_1$-$C_{10}$-alkylene-$X^1$-;
—C(O)—N($C_{1-3}$-alkyl)-$C_1$-$C_{10}$-alkylene-$X^{1b}$- where $X^{1b}$ is —NH— or —N($C_{1-6}$-alkyl)-;
—C(O)—N(H)—($C_1$-$C_{10}$-alkylene)-$X^{1b}$- where $X^{1b}$ is —NH— or —N($C_{1-6}$-alkyl)-;

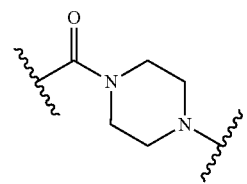

or
—C(O)—N($R^5$)-$C_1$-$C_{10}$-alkylene-C(O)NH—$X^2$-; or (c) $L^3$ in the Compound of Formula (III) is absent; wherein $L^1$ is a reactive group residue and $L^2$ is connecting linker.

13. The Compound of claim 1, where L is -$L^1$-$L^2$-$(L^3)_{0-1}$-; and
where $L^2$ comprises PEG, a di-peptide residue, a tripeptide residue, a tetrapeptide residue, a pentapeptide residue, —C(O)CH$_2$CH$_2$C(O)—, a cyclodextrin (CD) residue, or —CH$_2$CH$_2$CH$_2$CH$_2$CH$_2$C(O)—, or any combination thereof and wherein $L^1$ is a reactive group residue and $L^3$, when present, is a self-immolative linker.

14. The Compound of claim 1, where L is -$L^1$-$L^2$-$(L^3)_{0-1}$-; and where $L^2$ comprises
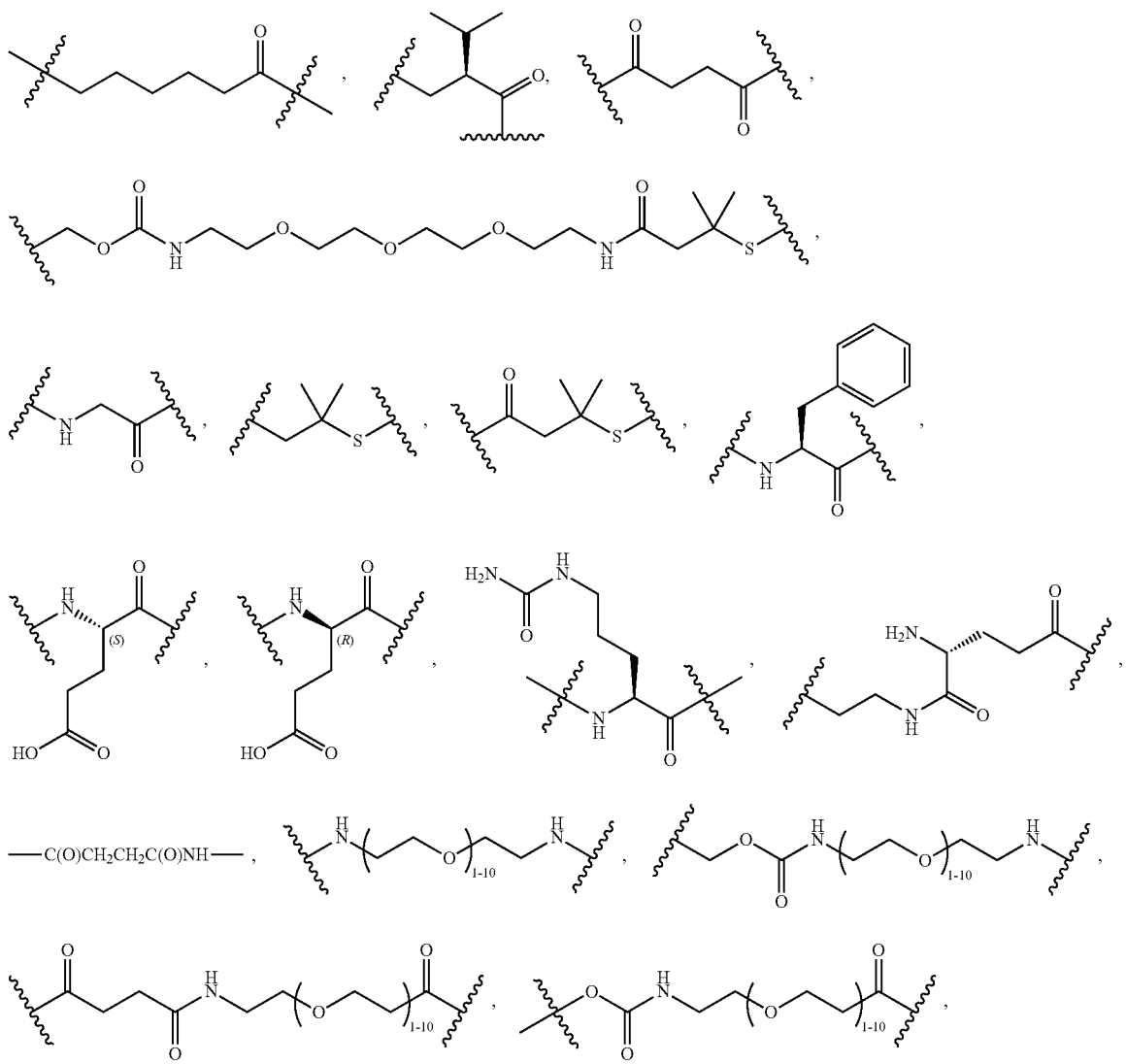
or a cyclodextrin residue (CD); or any combination thereof and wherein $L^1$ is a reactive group residue and $L^3$, when present, is a self-immolative linker.
15. The Compound of claim 1, where L is -$L^1$-$L^2$-$(L^3)_{0-1}$-; and where -$L^2$-$(L^3)_{0-1}$- comprises
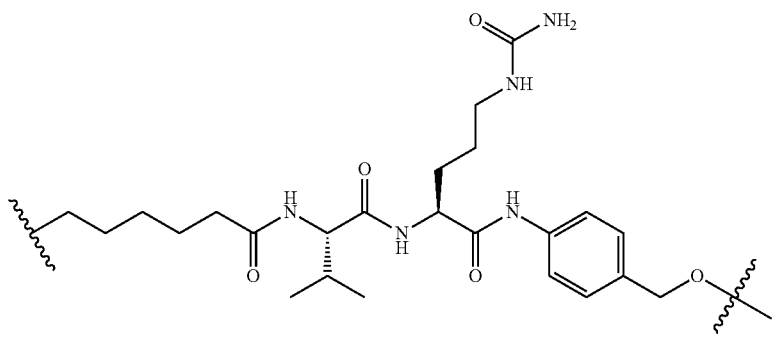

513
514
-continued
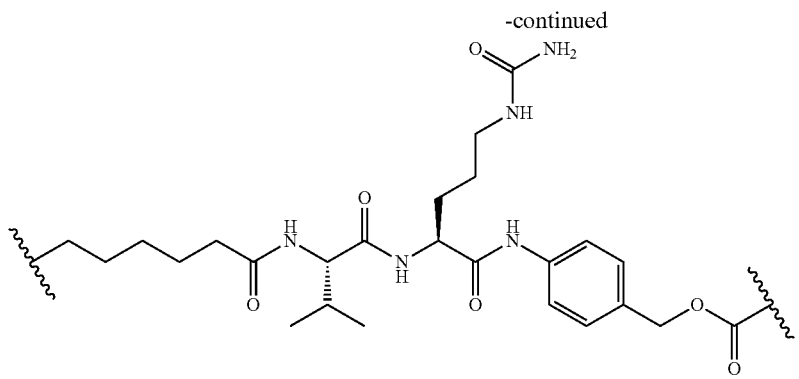
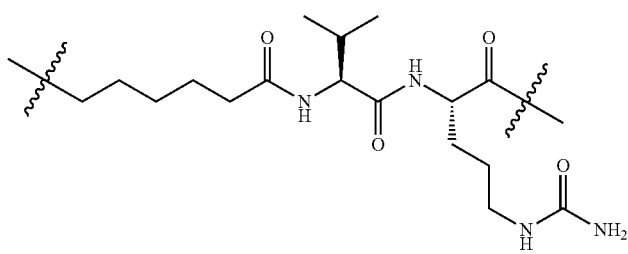
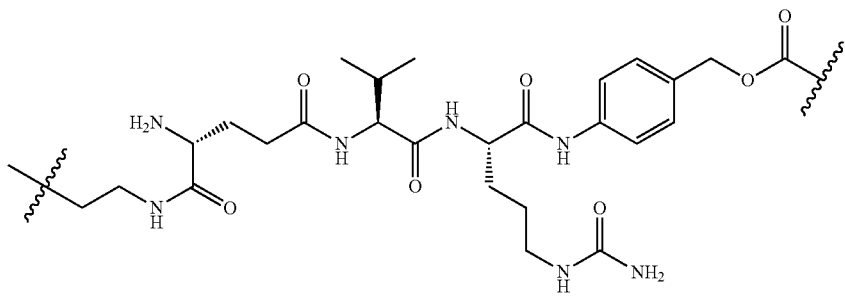
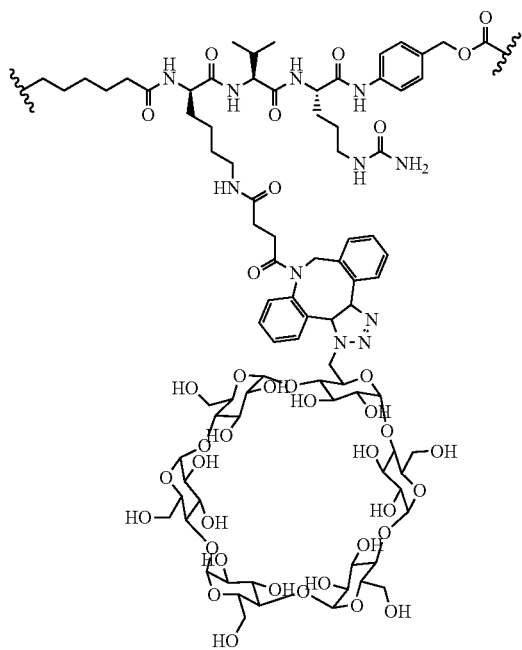

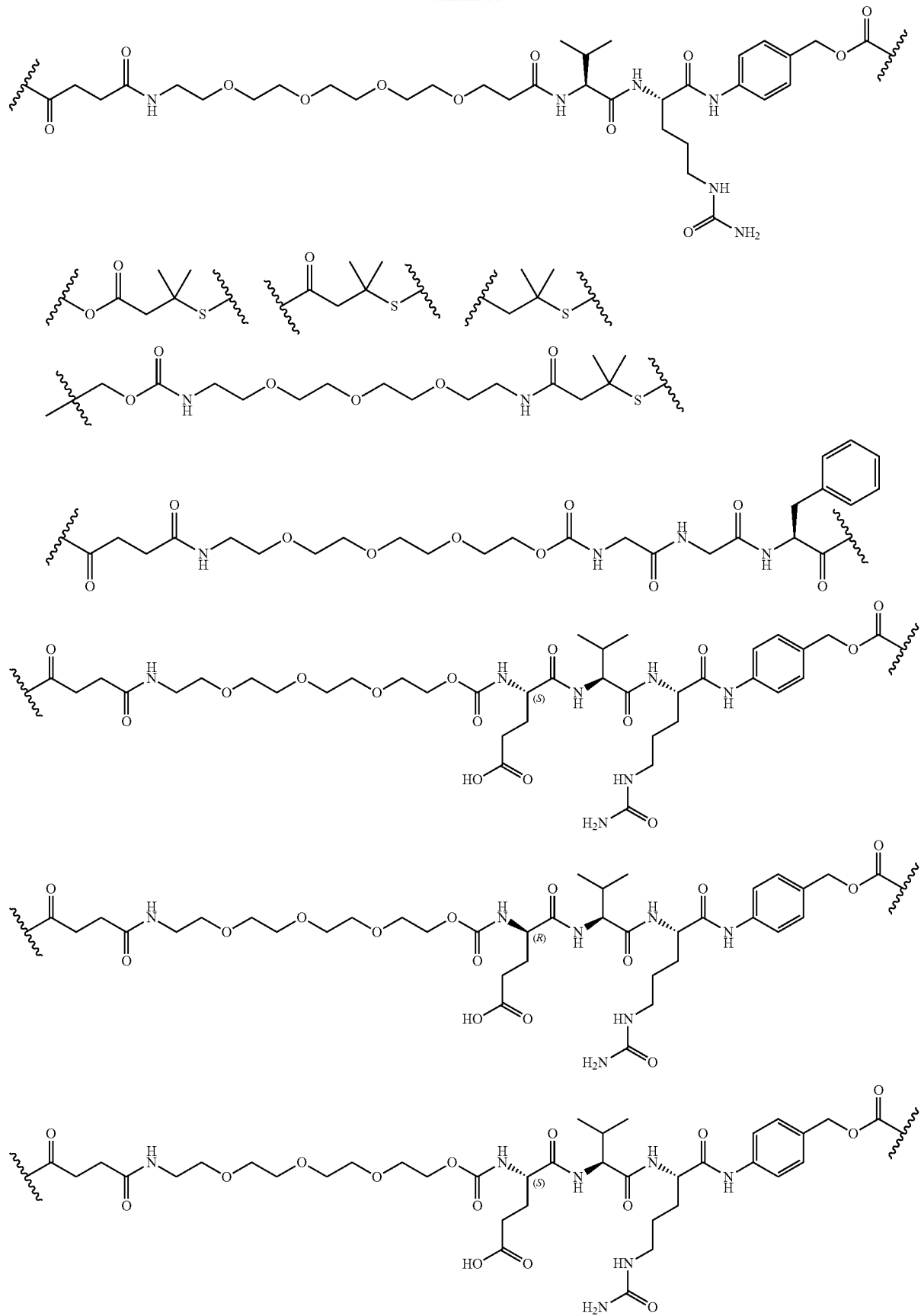

-continued
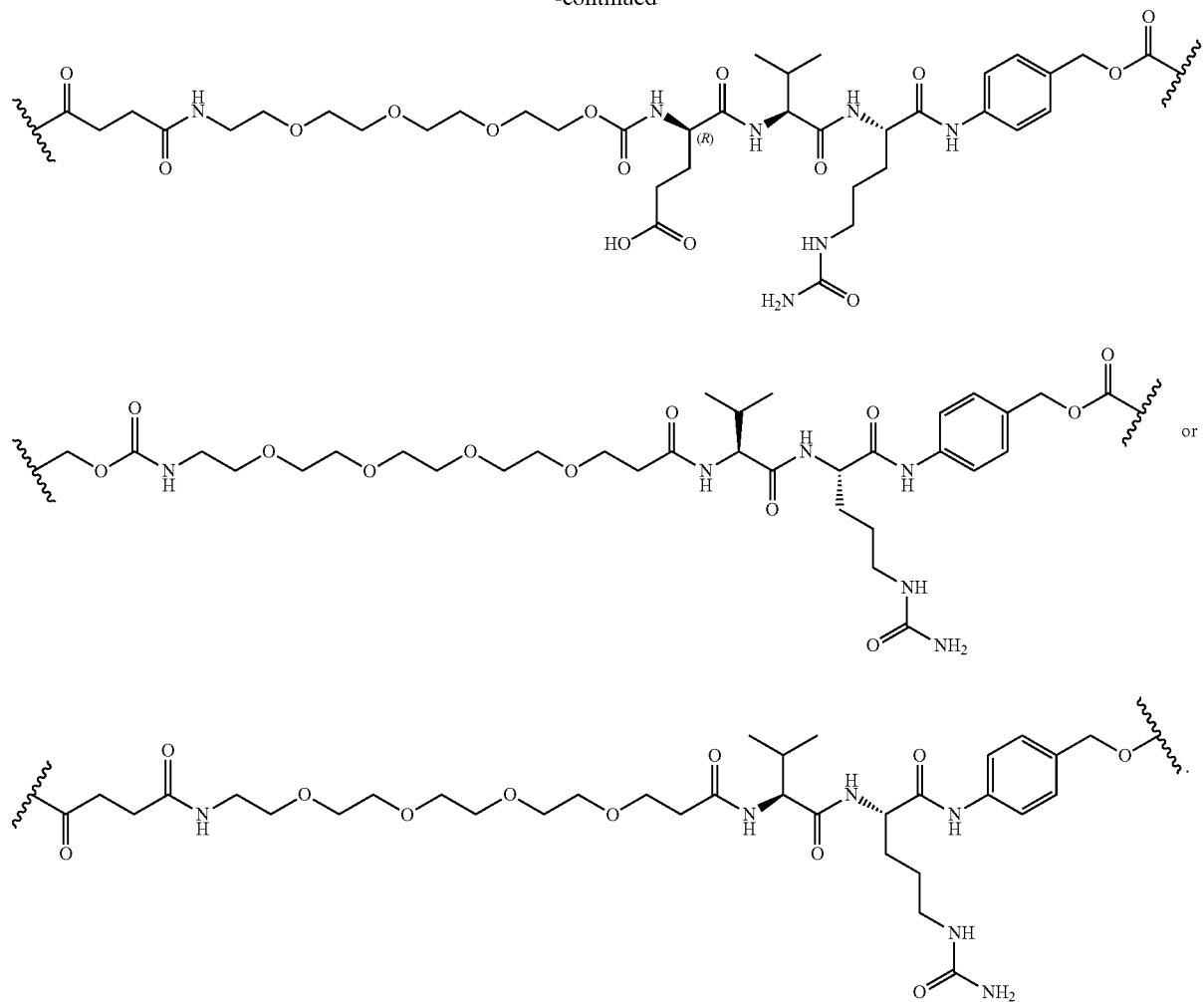
and wherein L¹ is a reactive group residue.
16. The compound of claim 1, wherein the compound is
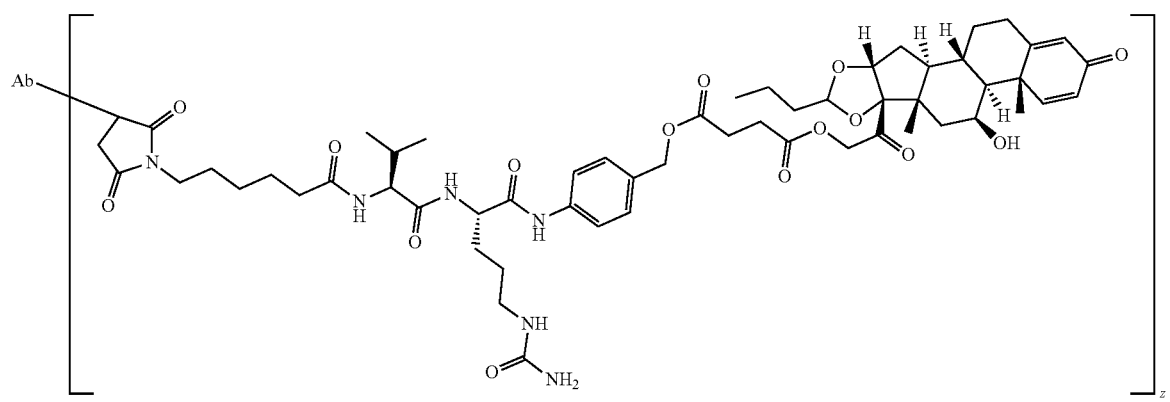
wherein the linker-payload is connected to Ab through a side chain of a cysteine residue; or a stereoisomer or mixture of stereoisomers thereof;

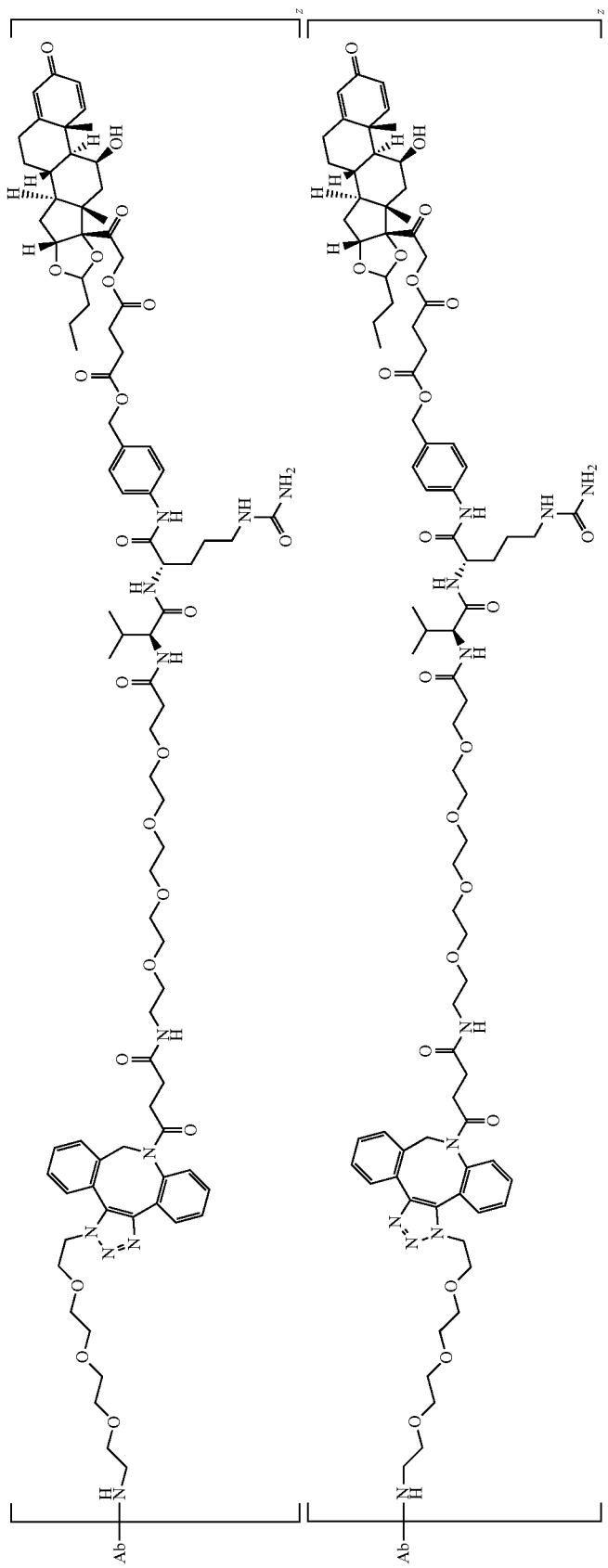

or a mixture thereof;
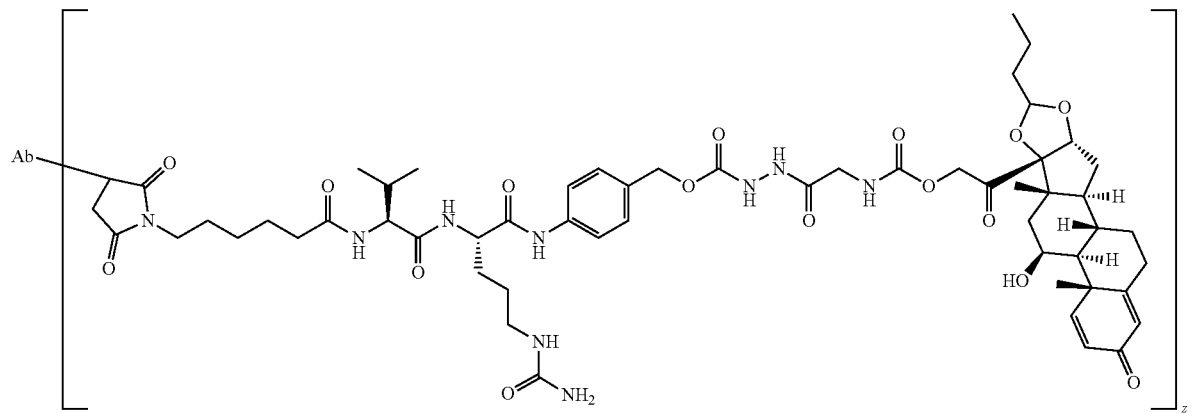
wherein the linker-payload is connected to Ab through a side chain of a cysteine residue; or a stereoisomer or mixture of stereoisomers thereof;
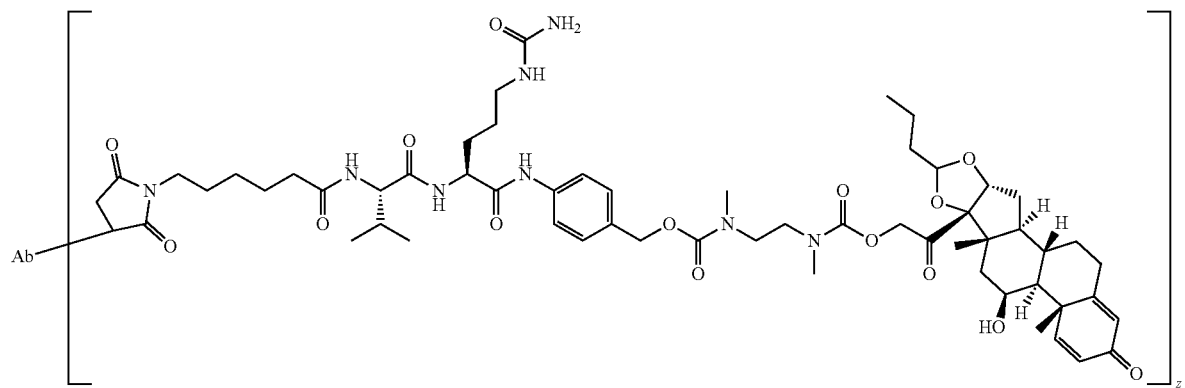
wherein the linker-payload is connected to Ab through a side chain of a cysteine residue; or a stereoisomer or mixture of stereoisomers thereof;
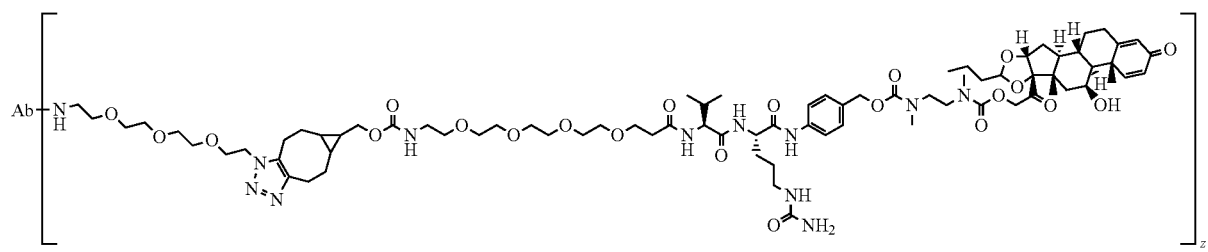

-continued
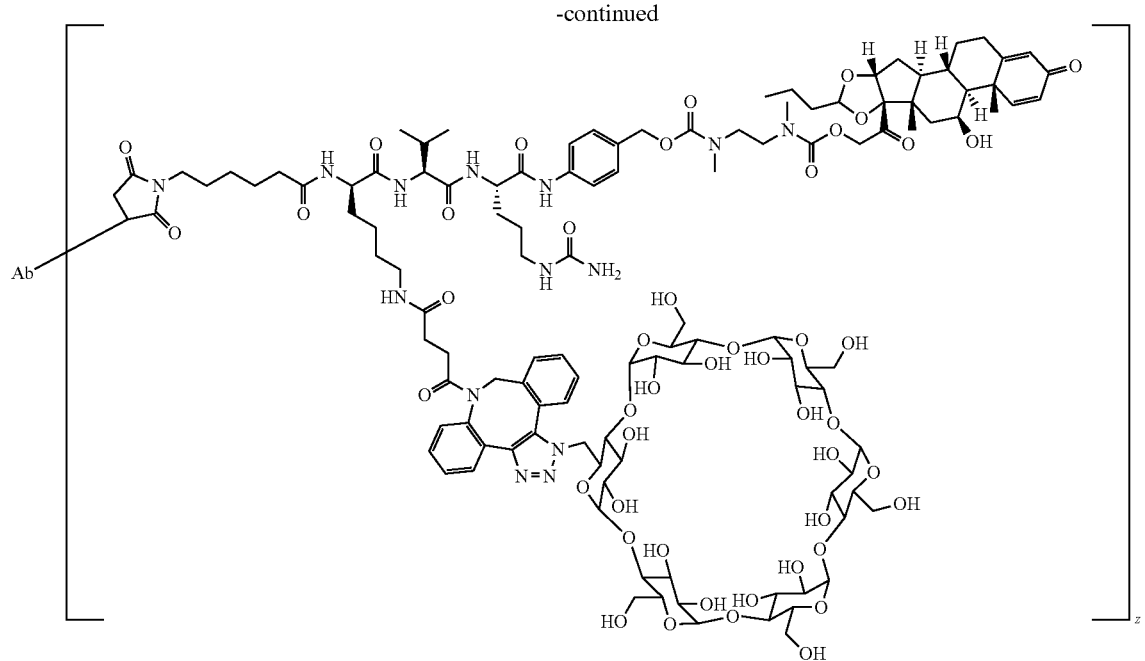
wherein the linker-payload is connected to Ab through a side chain of a cysteine residue;
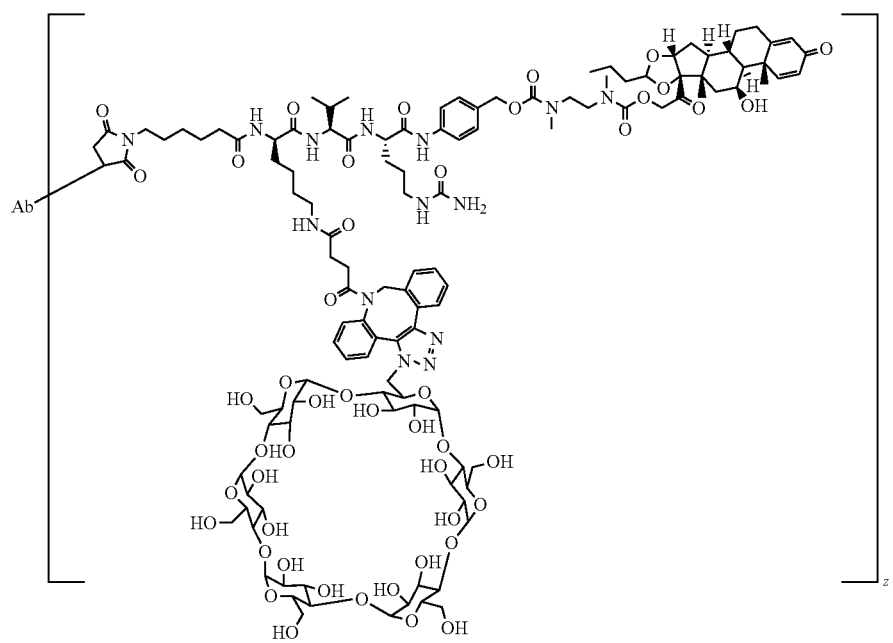
wherein the linker-payload is connected to Ab through a side chain of a cysteine residue; or a mixture thereof;

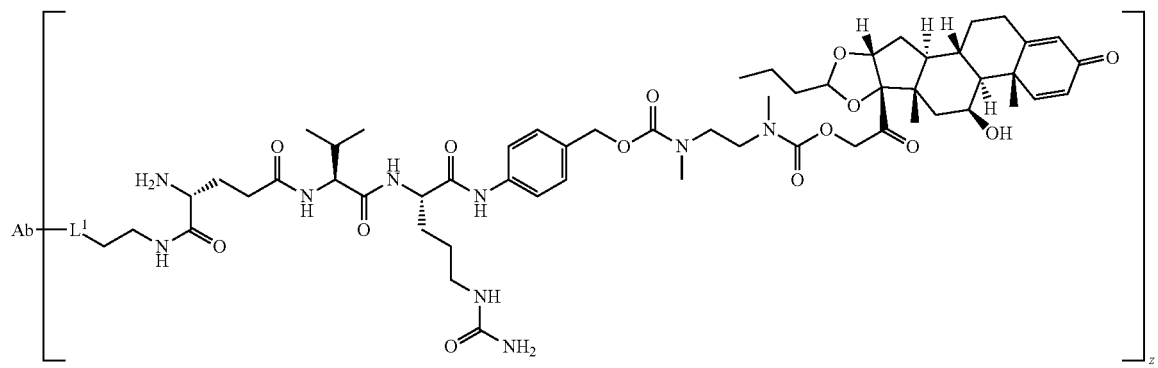

where L¹ is a reactive group residue comprising a triazole moiety;

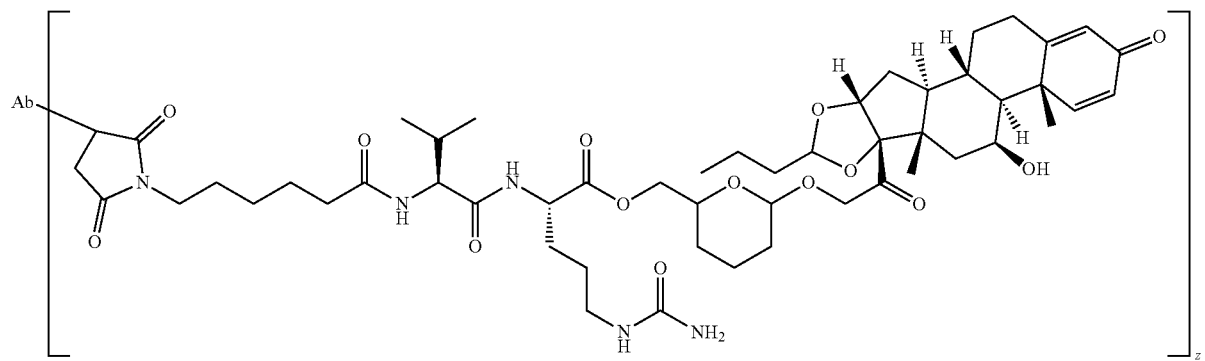

wherein the linker-payload is connected to Ab through a side chain of a cysteine residue; or a stereoisomer or mixture of stereoisomers thereof;

where BA comprises an antibody or antigen binding fragment thereof having the following structure

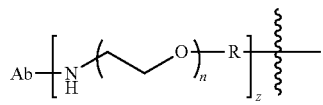

where Ab is a monoclonal antibody, polyclonal antibody, antibody fragment, or bispecific antibody; R is $C_{2-4}$-alkylene; and n is an integer selected from two to four, inclusive.

17. The Compound of claim 1, according to one of the following formulae

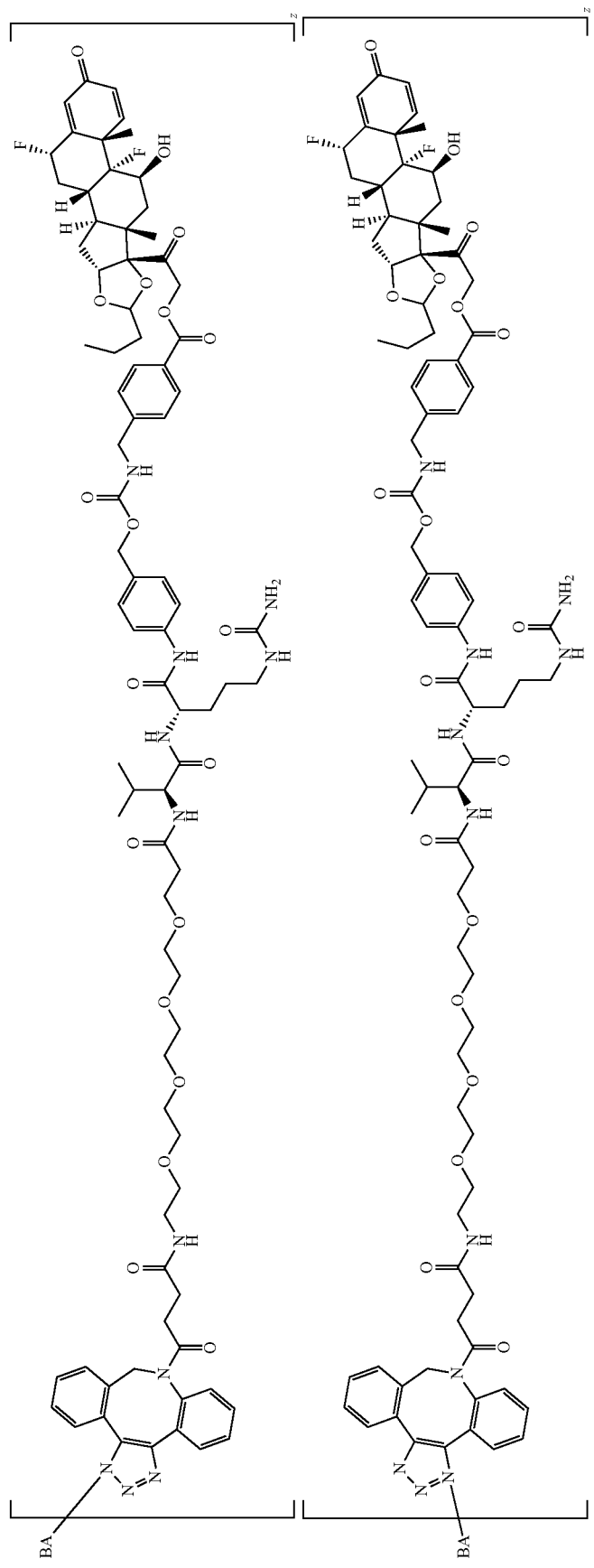

or a mixture thereof,

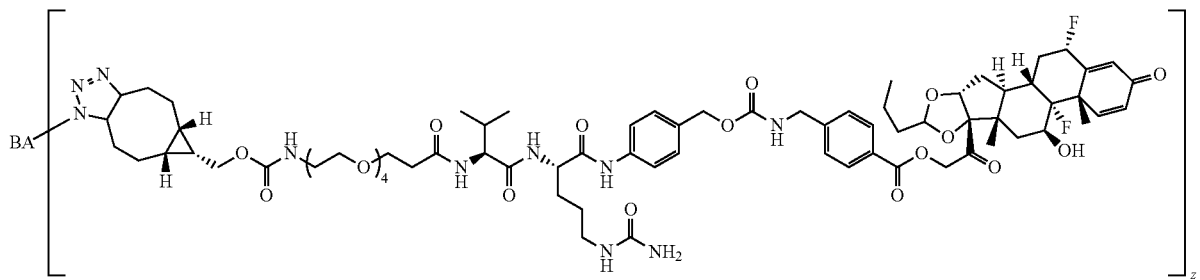

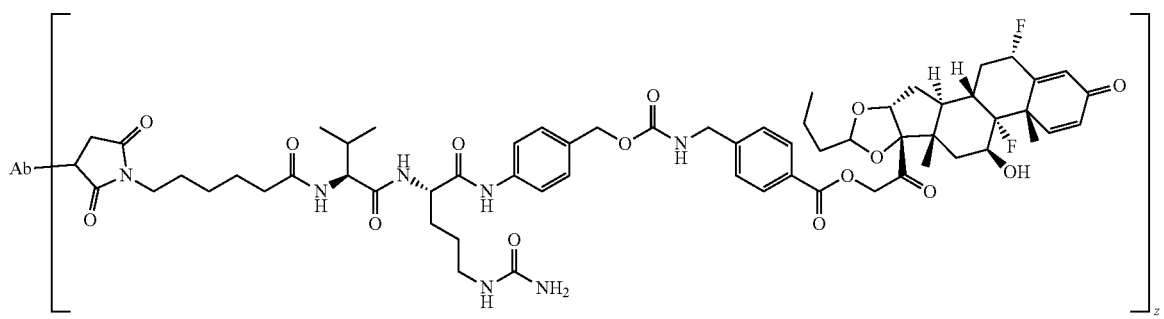

wherein the linker-payload is connected to Ab through a side chain of a cysteine residue;

where BA comprises an antibody or antigen binding fragment thereof having the following structure

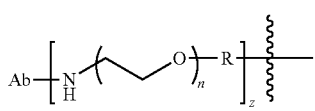

where Ab is a monoclonal antibody, polyclonal antibody, antibody fragment, or bispecific antibody;
R is $C_{2-4}$-alkylene;
n is an integer selected from two to four, inclusive; and
z is an integer from one to four.

18. A method for treating a disease, disorder, or condition associated with glucocorticoid receptor signaling comprising administering to a patient having said disease, disorder, or condition a therapeutically effective amount of a Compound of Formula (III) of claim 1.

19. The Compound of claim 1, where L is
    $-L^1-L^2-(L^3)_{0-1}-$; SP is $-C(O)-C_1-C_{10}$-alkylene-$C(O)-$;
    $L^3$ is

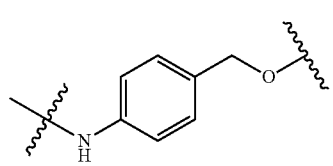 [SMILES: *Nc1ccc(CO*)cc1]

where the —NH— group is attached to $L^2$, $L^1$ is a reactive group residue, and $L^2$ is a connecting linker.

20. The Compound of claim 1, selected from the group consisting of

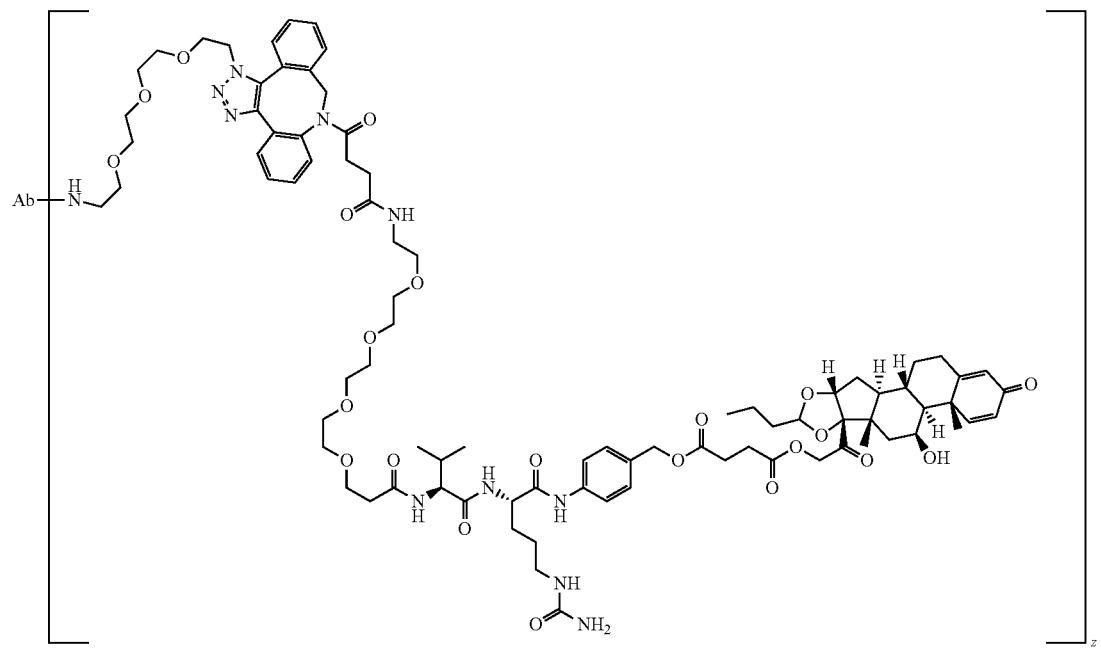

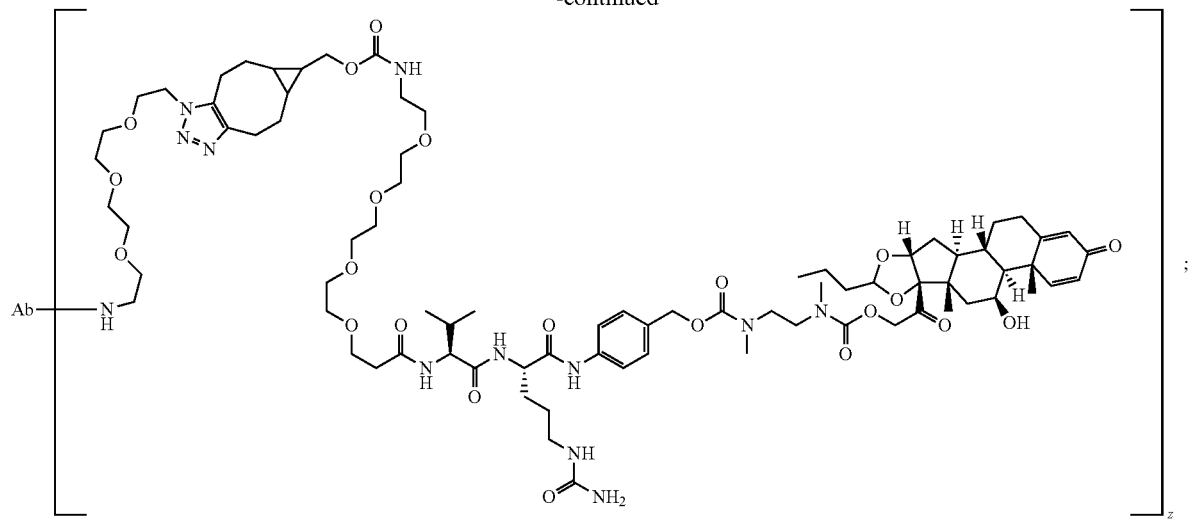
wherein Ab is an antibody or an antigen binding fragment thereof; and
z is an integer from one to four.
21. The Compound of claim 1, selected from the group consisting of
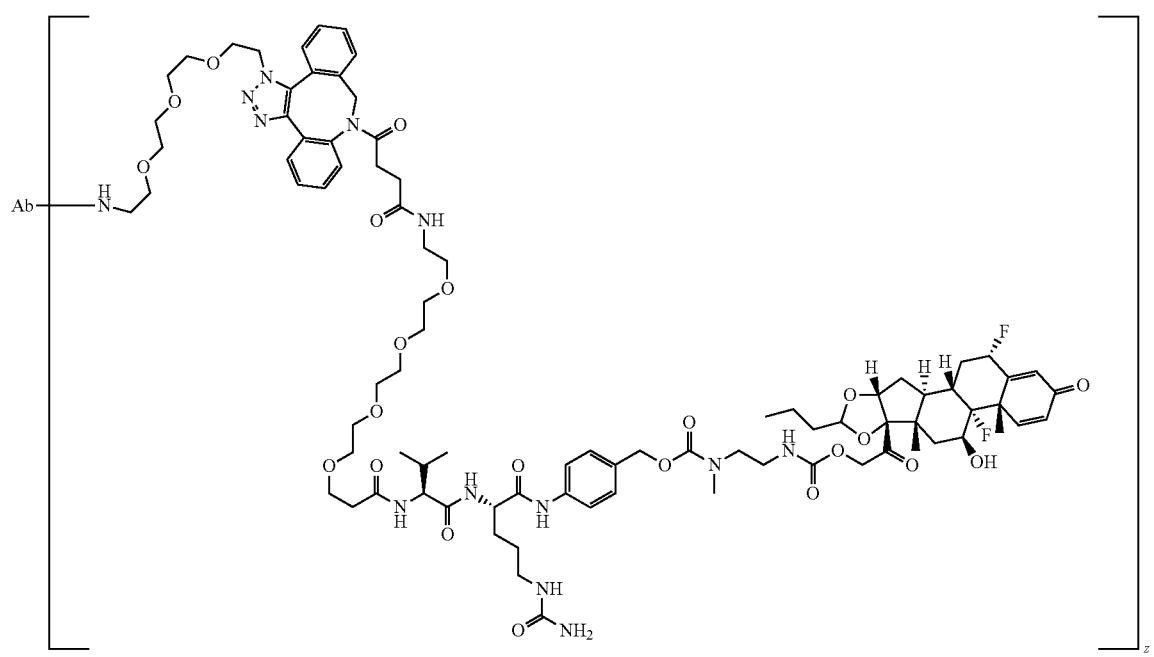

535
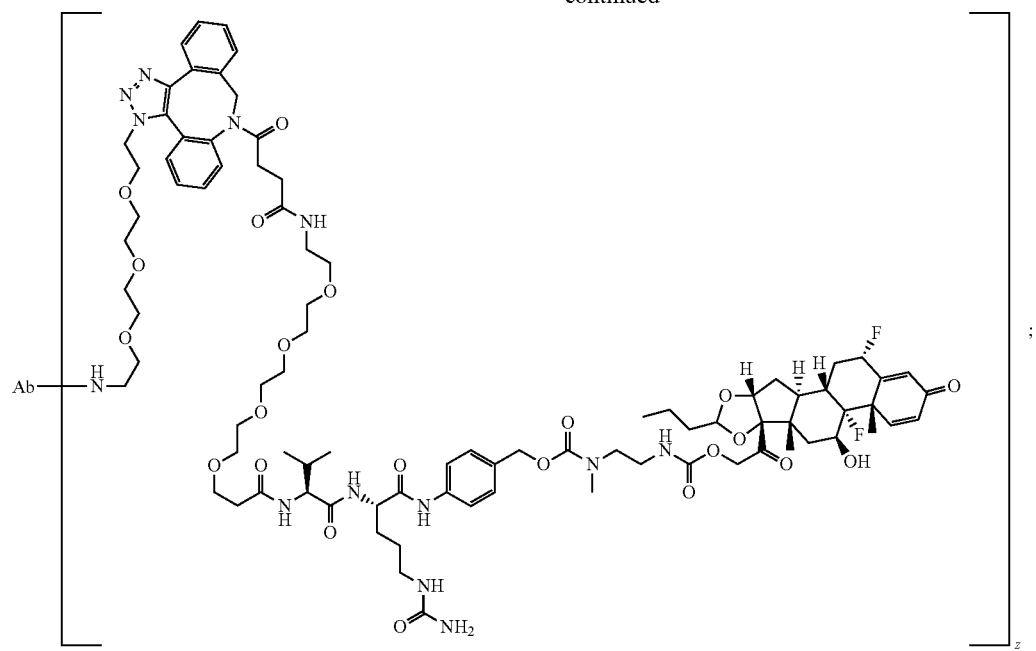
536
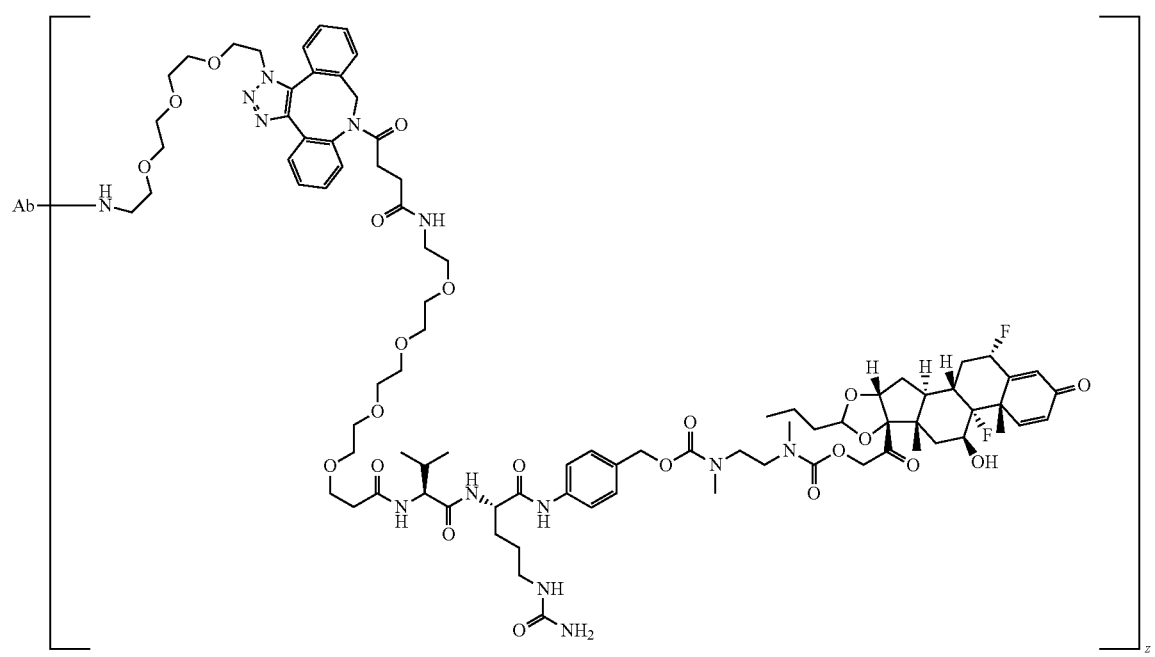

537
538
-continued
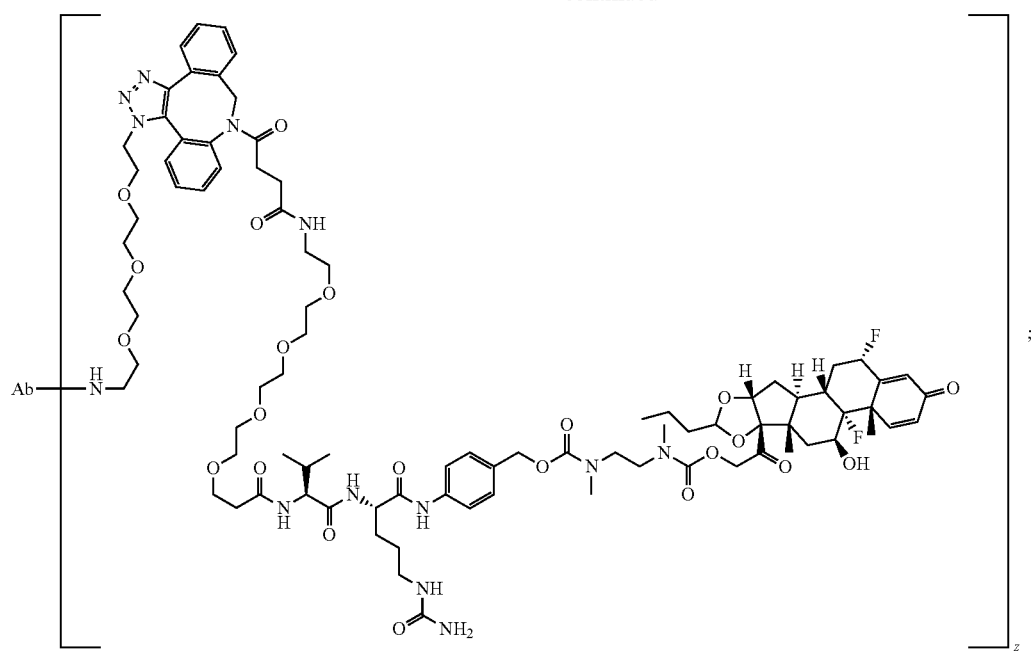
;
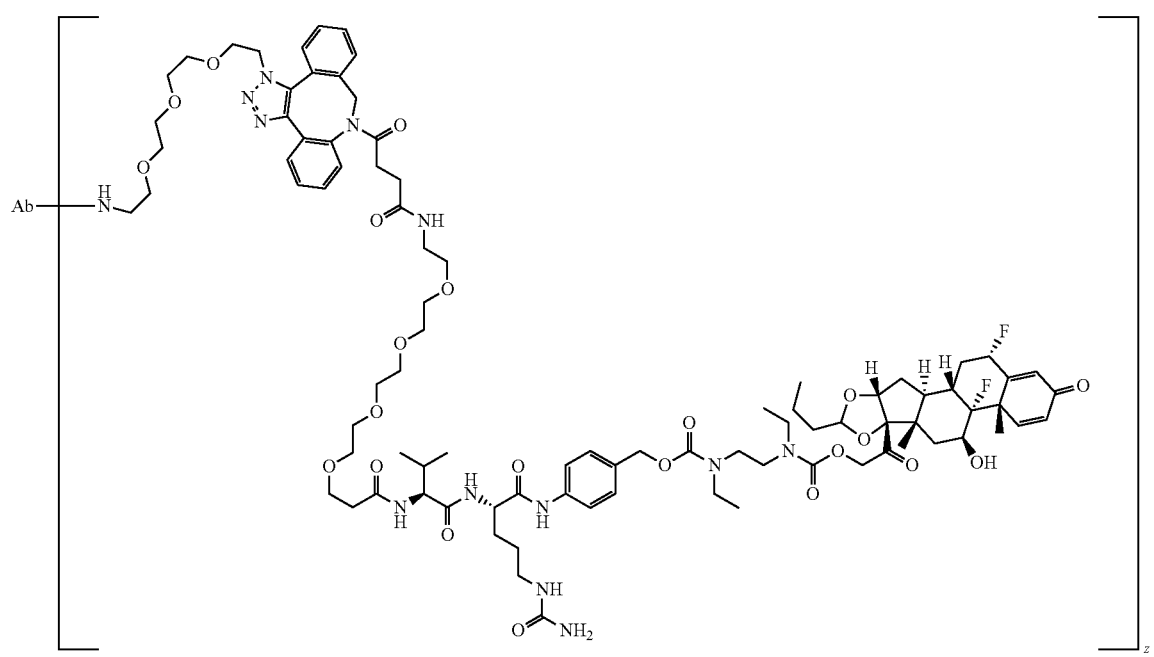

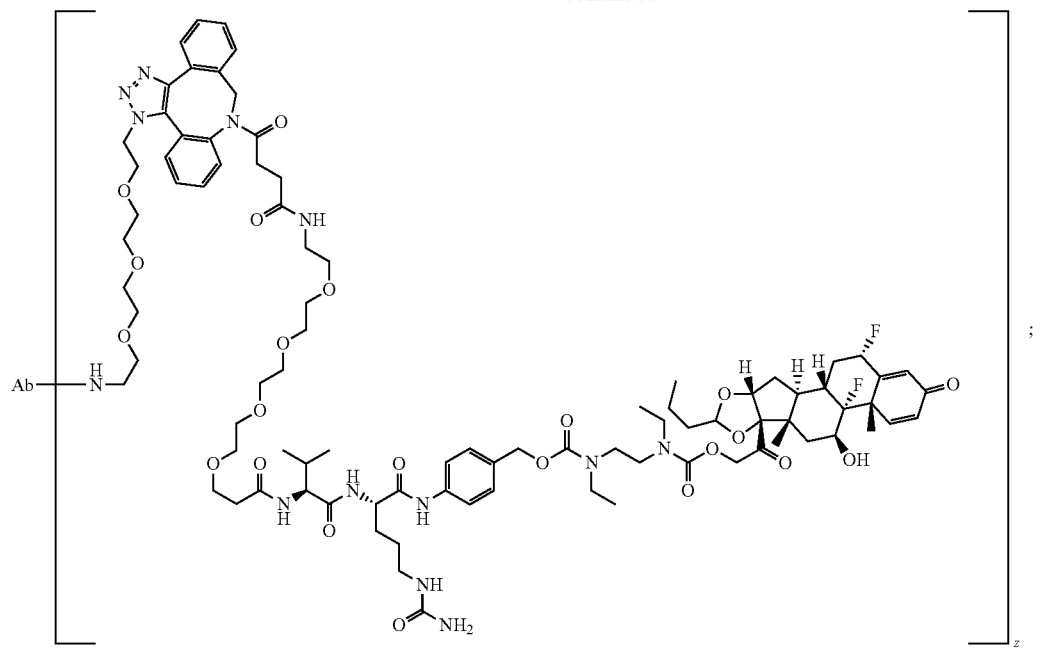
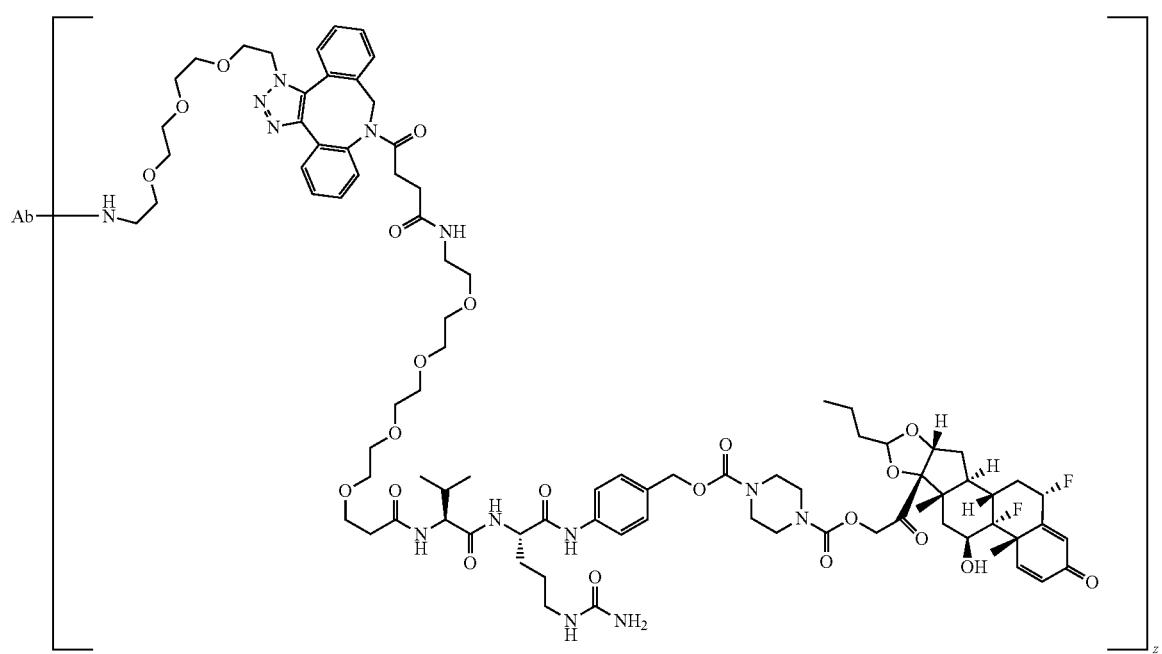

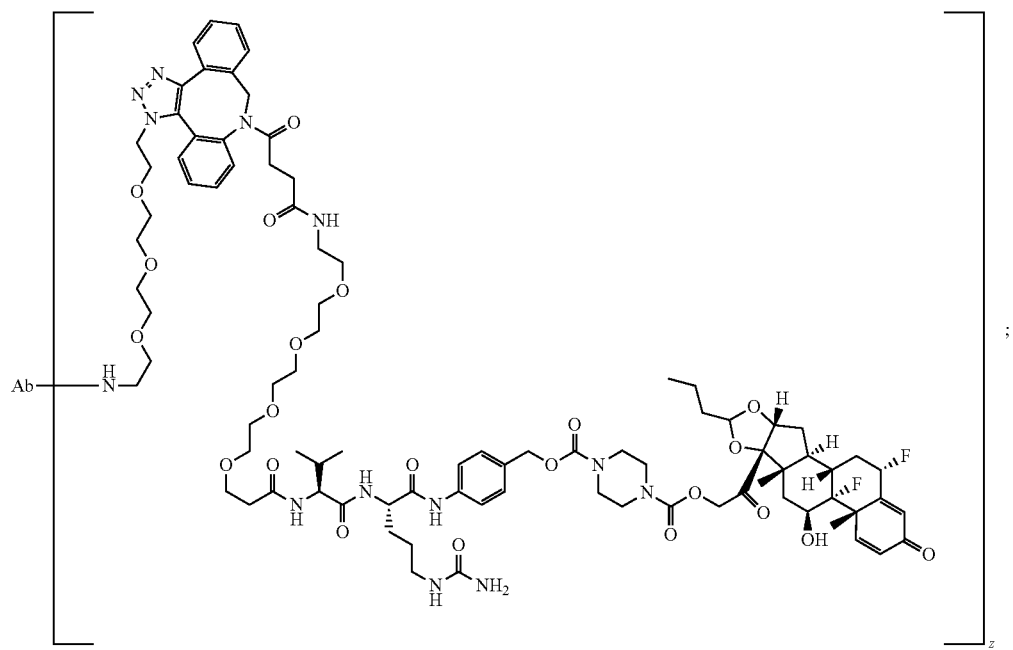
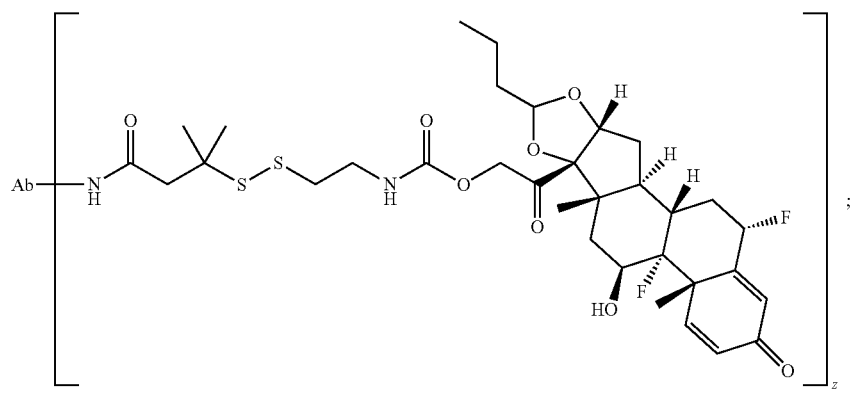
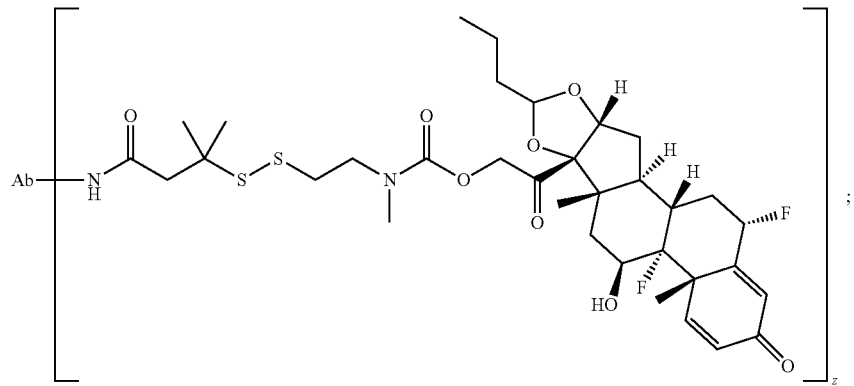

543
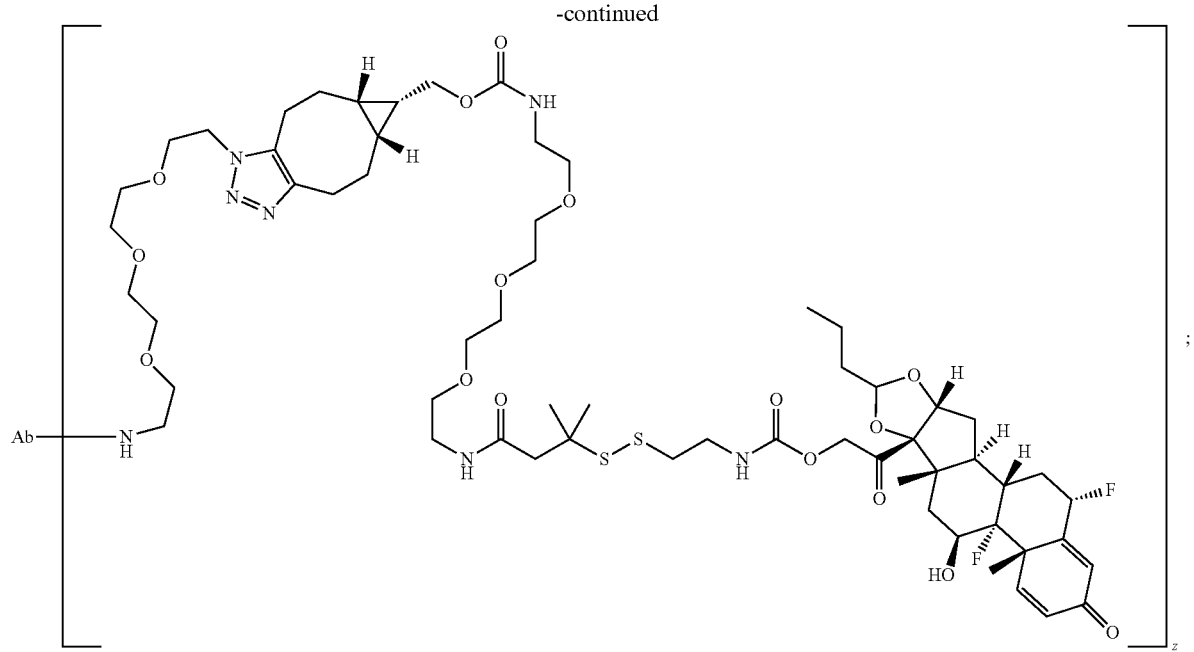
544
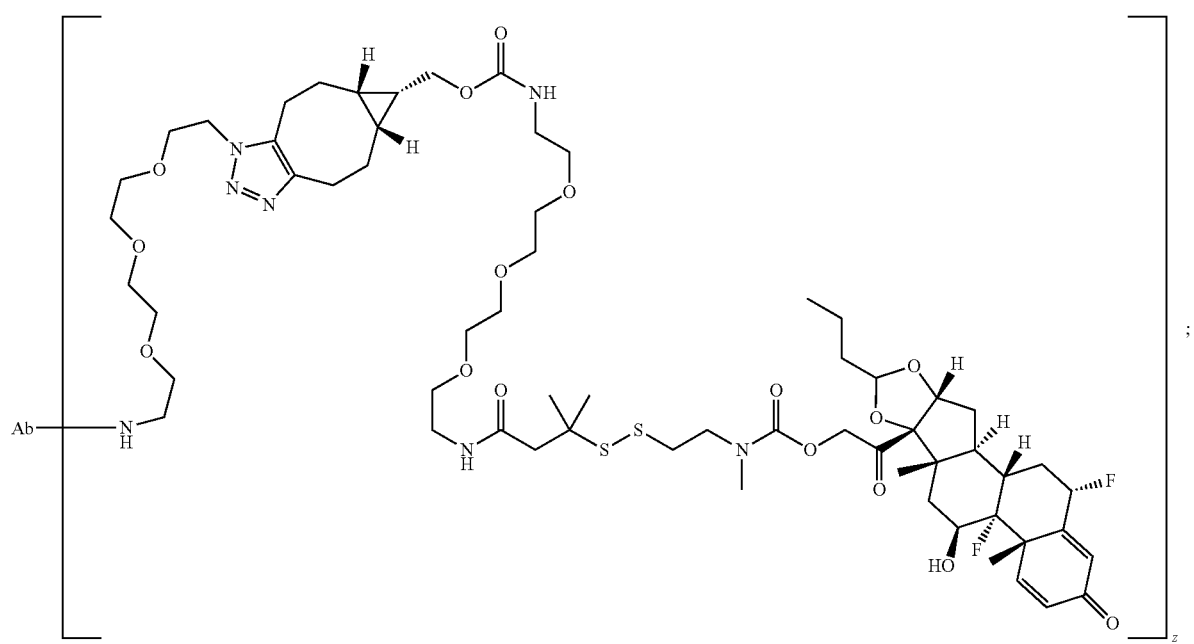

545
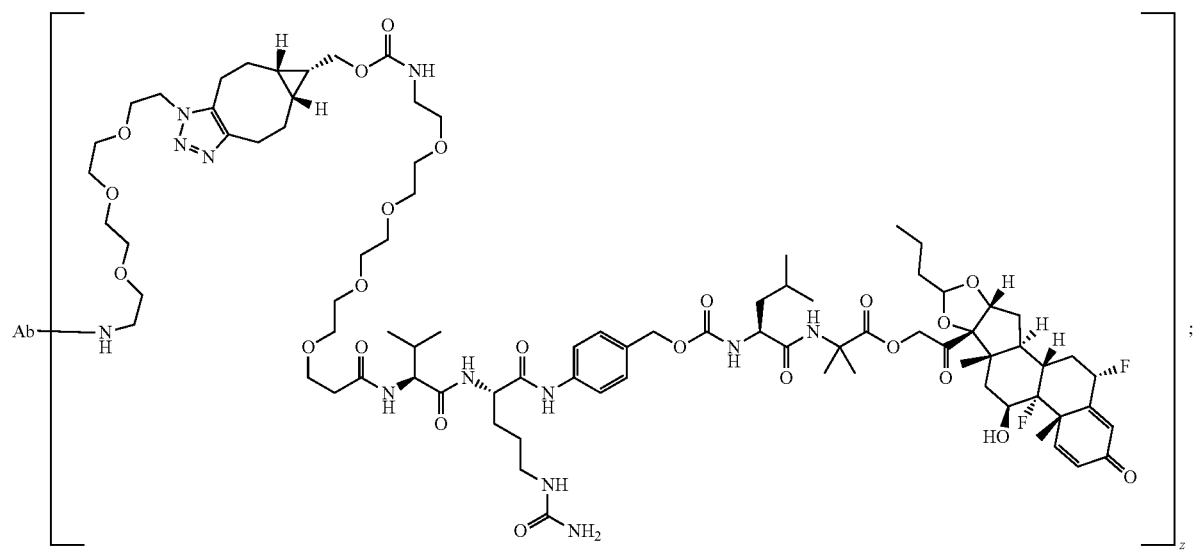
546
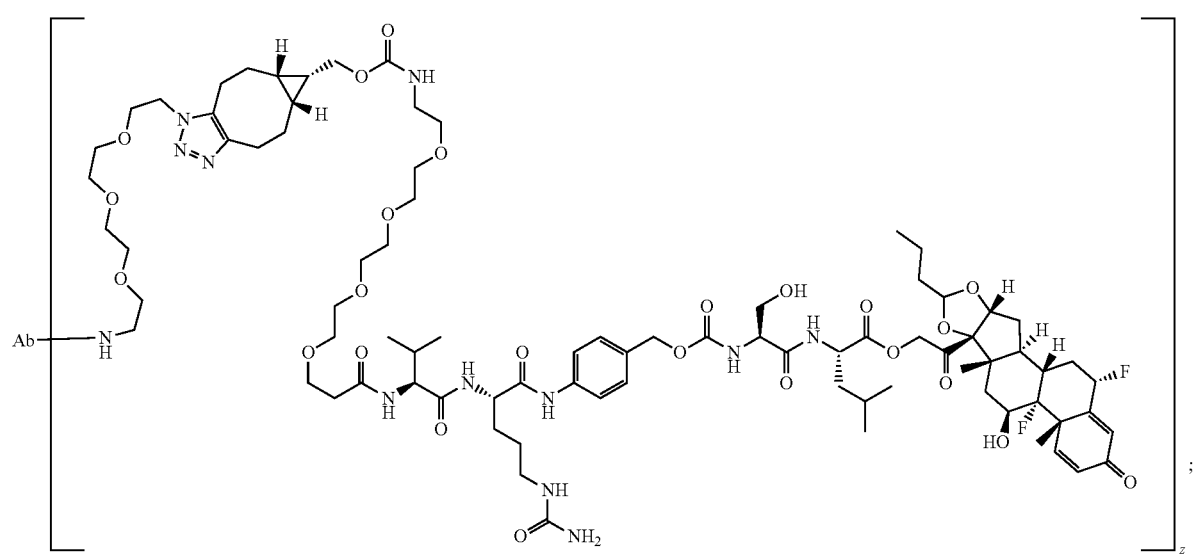

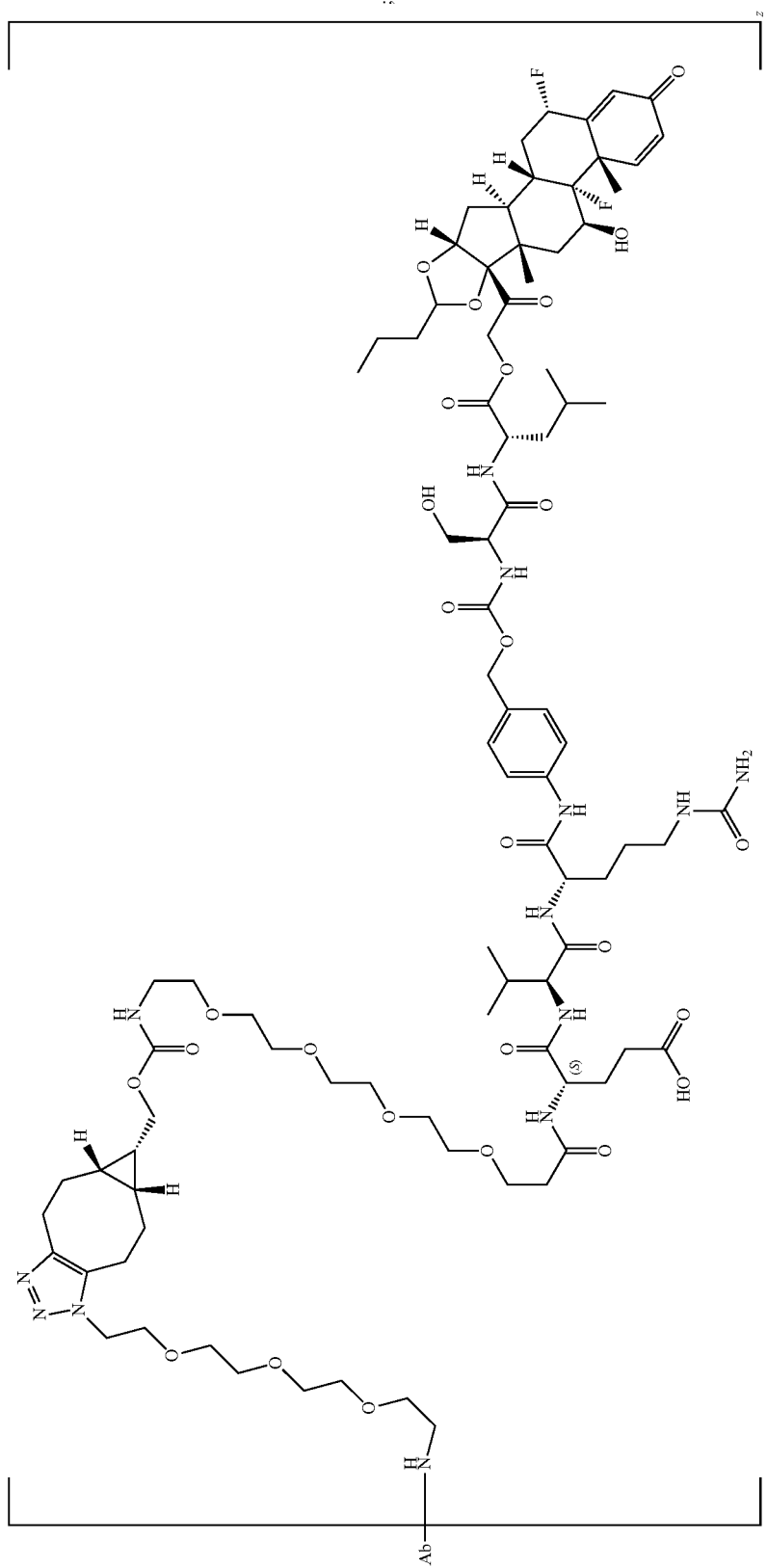

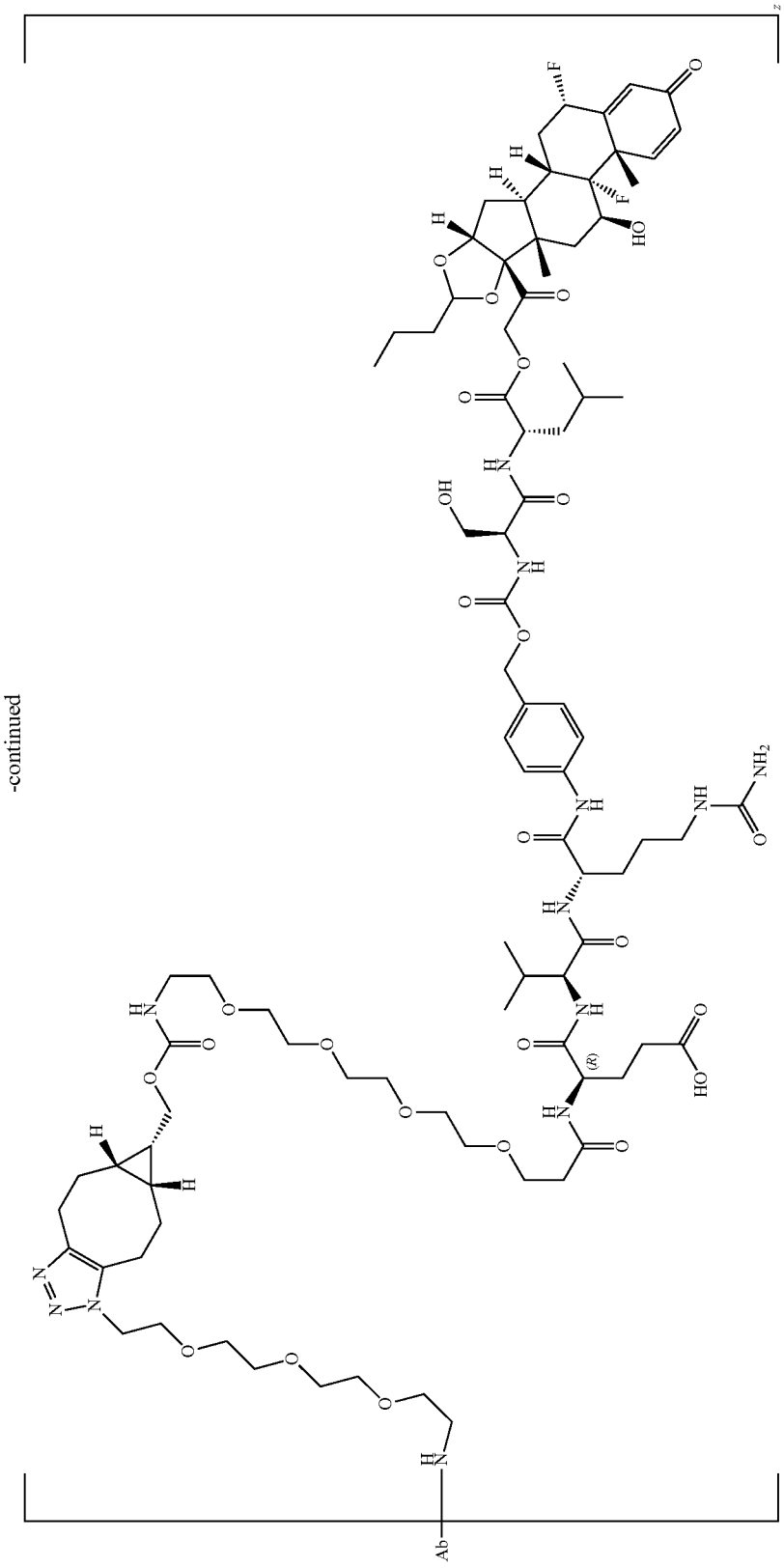

wherein Ab is an antibody or an antigen binding fragment thereof; and z is an integer from one to four.

* * * * *

SEQUENCE LISTING

<160> NUMBER OF SEQ ID NOS: 25

<210> SEQ ID NO 1
<211> LENGTH: 357
<212> TYPE: DNA

```
<213> ORGANISM: Artificial Sequence
<220> FEATURE:
<223> OTHER INFORMATION: Synthetic

<400> SEQUENCE: 1
caggtgcagc tgcaggagtc gggcccagga ctggtgaagc cttcggagac cctgtccctc      60
acctgcactg tcactggtgg ctccatcagt aggaactact ggagttggat ccggcagccc     120
ccagggaagg gactggaatg gattggatat atctattaca gtgggagtat cgactacaat     180
ccctccctca agagtcgagt caccatatca gtagacacgt ccaagaacca gttctccctg     240
aagctgagtt ctatgaccgc tgcggacacg gccgtatact actgtgcgag agatcggtgg     300
aactggaaat acggtatgga cgtctggggc caagggacca cggtcatcgt ctcgtca       357

<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Gln Val Gln Leu Gln Glu Ser Gly Pro Gly Leu Val Lys Pro Ser Glu
1               5                   10                  15

Thr Leu Ser Leu Thr Cys Thr Val Thr Gly Gly Ser Ile Ser Arg Asn
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Ile Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Arg Trp Asn Trp Lys Tyr Gly Met Asp Val Trp Gly Gln Gly
            100                 105                 110

Thr Thr Val Ile Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggtggctcca tcagtaggaa ctac                                             24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Gly Ser Ile Ser Arg Asn Tyr
1               5

<210> SEQ ID NO 5
```

```
<211> LENGTH: 21
<212> TYPE: DNA
<213> ORGANISM: Artificial Sequence
<220> FEATURE:
<223> OTHER INFORMATION: Synthetic

<400> SEQUENCE: 5
atctattaca gtgggagtat c                                              21

<210> SEQ ID NO 6
<211> LENGTH: 7
<212> TYPE: PRT
<213> ORGANISM: Artificial Sequence
<220> FEATURE:
<223> OTHER INFORMATION: Synthetic

<400> SEQUENCE: 6

Ile Tyr Tyr Ser Gly Ser Ile
1               5

<210> SEQ ID NO 7
<211> LENGTH: 39
<212> TYPE: DNA
<213> ORGANISM: Artificial Sequence
<220> FEATURE:
<223> OTHER INFORMATION: Synthetic

<400> SEQUENCE: 7
gcgagagatc ggtggaactg gaaatacggt atggacgtc                           39

<210> SEQ ID NO 8
<211> LENGTH: 13
<212> TYPE: PRT
<213> ORGANISM: Artificial Sequence
<220> FEATURE:
<223> OTHER INFORMATION: Synthetic

<400> SEQUENCE: 8

Ala Arg Asp Arg Trp Asn Trp Lys Tyr Gly Met Asp Val
1               5                   10

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9
gaaattgtgt tgacgcagtc tccaggcacc ctgtctttgt ctccagggga aagagccacc     60
ctctcctgca gggccagtca gactgttaga acaactact  tagcctggta ccaccagaaa    120
cctggccagg ctcccaggct cctcatctat ggtgcatcca gcaggccac  tggcatccca    180 gacaggttca gtggcagtgg gtctgggaca gacttcactc tcaccatcag cagactggag    240
cctgaagatt ttacagtgta ttactgtcac cagtatggta actcaccttg gacgttcggc    300
caagggacca aaatggaaat caaacga                                       327

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Arg Asn Asn
            20                  25                  30

Tyr Leu Ala Trp Tyr His Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Thr Val Tyr Tyr Cys His Gln Tyr Gly Asn Ser Pro
                85                  90                  95

Trp Thr Phe Gly Gln Gly Thr Lys Met Glu Ile Lys Arg
            100                 105
```

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
cagactgtta gaaacaacta c                                              21

<210> SEQ ID NO 12
<211> LENGTH: 7
<212> TYPE: PRT
<213> ORGANISM: Artificial Sequence
<220> FEATURE:
<223> OTHER INFORMATION: Synthetic

<400> SEQUENCE: 12

Gln Thr Val Arg Asn Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 ggtgcatcc                                                             9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Gly Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caccagtatg gtaactcacc ttggacg                                27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

His Gln Tyr Gly Asn Ser Pro Trp Thr
1               5

<210> SEQ ID NO 17
<211> LENGTH: 115
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Arg Asn Tyr
            20                  25                  30

Gly Met Gln Trp Val Arg Gln Gly Pro Gly Lys Gly Leu Glu Trp Val
        35                  40                  45

Thr Leu Ile Ser Phe Asp Gly Asn Asp Lys Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Thr Glu Asp Thr Ala Val Tyr Tyr Cys
                85                  90                  95

Ala Arg Gly Gly Asp Phe Asp Tyr Trp Gly Gln Gly Thr Leu Val Thr
            100                 105                 110

Val Ser Ser
        115

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Gly Phe Thr Phe Arg Asn Tyr Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Ile Ser Phe Asp Gly Asn Asp Lys
1               5

```
<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Ala Arg Gly Gly Asp Phe Asp Tyr
1               5

<210> SEQ ID NO 21
<211> LENGTH: 108
<212> TYPE: PRT
<213> ORGANISM: Artificial Sequence
<220> FEATURE:
<223> OTHER INFORMATION: Synthetic

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Lys Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu His Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Met
                85                  90                  95

Tyr Thr Phe Gly Gln Gly Thr Lys Leu Glu Ile Lys
            100                 105

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Gln Asp Ile Arg Lys Asp
1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic

<400> SEQUENCE: 23

Ala Ala Ser
1

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24
```

```
Leu Gln His Asn Ser Tyr Pro Met Tyr Thr
1               5                   10
```

<210> SEQ ID NO 25
<211> LENGTH: 267
<212> TYPE: PRT
<213> ORGANISM: Artificial Sequence
<220> FEATURE:
<223> OTHER INFORMATION: Synthetic

<400> SEQUENCE: 25

```
Met His Arg Pro Arg Arg Gly Thr Arg Pro Pro Leu Ala Leu
1               5                   10                  15

Leu Ala Ala Leu Leu Ala Ala Arg Gly Ala Asp Ala Gln Leu Pro
                20                  25                  30

Pro Gly Lys Pro Glu Ile Phe Lys Cys Arg Ser Pro Asn Lys Glu Thr
                35                  40                  45

Phe Thr Cys Trp Trp Arg Pro Gly Thr Asp Gly Leu Pro Thr Asn
50                  55                              60

Tyr Ser Leu Thr Tyr His Arg Glu Gly Glu Thr Leu Met His Glu Cys
65                  70                  75                  80

Pro Asp Tyr Ile Thr Gly Gly Pro Asn Ser Cys His Phe Gly Lys Gln
                85                  90                  95

Tyr Thr Ser Met Trp Arg Thr Tyr Ile Met Met Val Asn Ala Thr Asn
                100                 105                 110

Gln Met Gly Ser Ser Phe Ser Asp Glu Leu Tyr Val Asp Val Thr Tyr
                115                 120                 125

Ile Val Gln Pro Asp Pro Pro Leu Glu Leu Ala Val Glu Val Lys Gln
                130                 135                 140

Pro Glu Asp Arg Lys Pro Tyr Leu Trp Ile Lys Trp Ser Pro Pro Thr
145                 150                 155                 160

Leu Ile Asp Leu Lys Thr Gly Trp Phe Thr Leu Leu Tyr Glu Ile Arg
                165                 170                 175

Leu Lys Pro Glu Lys Ala Ala Glu Trp Glu Ile His Phe Ala Gly Gln
                180                 185                 190

Gln Thr Glu Phe Lys Ile Leu Ser Leu His Pro Gly Gln Lys Tyr Leu
                195                 200                 205

Val Gln Val Arg Cys Lys Pro Asp His Gly Tyr Trp Ser Ala Trp Ser
                210                 215                 220

Pro Ala Thr Phe Ile Gln Ile Pro Ser Asp Phe Thr Met Asn Asp Glu
225                 230                 235                 240

Gln Lys Leu Ile Ser Glu Glu Asp Leu Gly Gly Glu Gln Lys Leu Ile
                245                 250                 255

Ser Glu Glu Asp Leu His His His His His
                260                 265
```